United States Patent
Soneda et al.

(10) Patent No.: US 8,536,197 B2
(45) Date of Patent: Sep. 17, 2013

(54) IMIDAZOLE CARBONYL COMPOUND

(75) Inventors: Tsuyoshi Soneda, Kanagawa (JP); Hiroshi Takeshita, Chiba (JP); Yoshiko Kagoshima, Tokyo (JP); Yuko Yamamoto, Tokyo (JP); Takafumi Hosokawa, Tokyo (JP); Toshiyuki Konosu, Kanagawa (JP); Nobuhisa Masuda, Tokyo (JP); Takuya Uchida, Tokyo (JP); Issei Achiwa, Chiba (JP); Junichi Kuroyanagi, Chiba (JP); Tetsunori Fujisawa, Tokyo (JP); Aki Yokomizo, Chiba (JP); Tetsuji Noguchi, Tokyo (JP)

(73) Assignee: Daiichi Sankyo Company, Limited, Chuo-ku (JP)

( * ) Notice: Subject to any disclaimer, the term of this patent is extended or adjusted under 35 U.S.C. 154(b) by 116 days.

(21) Appl. No.: 12/811,004

(22) PCT Filed: Dec. 26, 2008

(86) PCT No.: PCT/JP2008/073686
§ 371 (c)(1),
(2), (4) Date: Jun. 28, 2010

(87) PCT Pub. No.: WO2009/084614
PCT Pub. Date: Jul. 9, 2009

(65) Prior Publication Data
US 2010/0311966 A1    Dec. 9, 2010

(30) Foreign Application Priority Data
Dec. 27, 2007    (JP) .................................. 2007-337693

(51) Int. Cl.
C07D 417/04    (2006.01)
C07D 401/12    (2006.01)
A61K 31/4164    (2006.01)
A61K 31/4178    (2006.01)

(52) U.S. Cl.
USPC .......................................... 514/326; 546/211

(58) Field of Classification Search
USPC .......................................... 546/211; 514/326
See application file for complete search history.

(56) References Cited

U.S. PATENT DOCUMENTS

| | | |
|---|---|---|
| 4,179,277 A | 12/1979 | Beck |
| 4,369,186 A * | 1/1983 | Beck et al. ................. 504/275 |
| 4,602,095 A | 7/1986 | Zanno |
| 4,772,617 A * | 9/1988 | Archibald et al. ............ 514/323 |
| 5,082,847 A | 1/1992 | Pascal |
| 5,318,975 A | 6/1994 | Lis |

FOREIGN PATENT DOCUMENTS

| | | |
|---|---|---|
| EP | 0 585 500 A1 | 3/1994 |
| GB | 2184444 A * | 6/1987 |
| WO | 2005/009966 A1 | 2/2005 |
| WO | 2005026149 A1 | 3/2005 |
| WO | 2005/105802 A1 | 11/2005 |
| WO | 2006/047277 A2 | 5/2006 |
| WO | 2006/066790 A1 | 6/2006 |
| WO | 2006087543 A1 | 8/2006 |
| WO | 2006087544 A2 | 8/2006 |
| WO | 2006087548 A2 | 8/2006 |
| WO | 2006092599 A2 | 9/2006 |
| WO | 2006092608 A1 | 9/2006 |
| WO | 2007071965 A2 | 6/2007 |
| WO | 2008/075196 A1 | 6/2008 |

OTHER PUBLICATIONS

International Search Report mailed Feb. 3, 2009, issued in corresponding Application No. PCT/JP2008/073686, filed Dec. 26, 2008.
Diriam, J.P., et al., "Synthesis of Some Dihydroxyphenyl 4,5-Dichloroimidazol-2-yl Ketones: Compounds Related to Pyoluteorin," Journal of Organic Chemistry 47(11):2196-2199, May 1982.
Papadopoulos, E.P., "Reactions of Imidazoles With Isocyanates at Elevated Temperature," Journal of Organic Chemistry 42(24):3925-3929, Nov. 1977.
Regel, E., and K.-H. Büchel, "C-Acylierung von 5 Gliedrigen N-Heterocyclen, I. Acylierung an C-2 von Imidazolen und Benzimadazolen (C-Acylation of 5-Membered N-Heterocycles, I. Acylation at C-2 of Imidazoles and Benzimidazoles)," Justus Liebigs Annalen der Chemie 1977(1):145-158, Feb. 1977.
Extended European Search Report mailed May 11, 2011, issued in corresponding European Patent Application No. EP 08 86 7971.7, filed Dec. 26, 2008, 13 pages.

* cited by examiner

*Primary Examiner* — Kahsay Habte
(74) *Attorney, Agent, or Firm* — Christensen O'Connor Johnson Kindness PLLC

(57) ABSTRACT

An antibiotic compound having a novel mechanism of action, weak cytotoxicity, high solubility in water, effective in inhibiting both DNA gyrase GyrB and topoisomerase IV ParE subunits, and having antibacterial activity.

12 Claims, No Drawings

IMIDAZOLE CARBONYL COMPOUND

TECHNICAL FIELD

The present invention relates to compounds that exhibit antibacterial activity, production processes thereof, pharmaceutical compositions comprising the compounds as an active ingredient, and use of the compounds as pharmaceutical agents. Particularly, the present invention relates to compounds useful for the treatment of bacterial infectious disease in a warm-blooded animal (e.g., a human) and production and use of pharmaceutical agents used in the treatment of bacterial infectious disease in a warm-blooded animal (e.g., a human).

BACKGROUND ART

The problem of bacterial resistance to antibacterial agents has been threatening humans over many years. Examples of such difficult-to-treat resistant bacteria include methicillin-resistant *Staphylococcus aureus* (MRSA), penicillin-resistant *Streptococcus pneumoniae* (PRSP), and vancomycin-resistant *Enterococcus* (VRE). As existing antibacterial agents such as β-lactam, quinolone, and macrolide agents are used clinically, the number of bacteria resistant thereto goes on increasing. On the other hand, the total number of novel antibacterial agents launched has been decreasing since the late 1980s. The problem of bacterial resistance to antibacterial agents is considered as a more critical issue than ever before (Nathan, C. 2004, Nature 431: 899-902). For overcoming the threat of an increasing number of resistant bacteria, there is a need to develop novel antibacterial agents, particularly, antibacterial agents having a novel mechanism of action effective even for various resistant bacteria.

Among bacterial infectious diseases, community-acquired respiratory infection occurs with the highest frequency, which is mainly caused by bacteria including a gram-positive bacterium *Streptococcus pneumoniae* and a gram-negative bacterium *Haemophilus influenzae*. Gram-positive bacteria have only a cytoplasmic membrane consisting of a phospholipid bilayer, whereas gram-negative bacteria have, in addition to a cytoplasmic membrane (inner membrane), an outer membrane consisting of an asymmetric bilayer of lipopolysaccharide and phospholipid and therefore exhibit resistance to many antibacterial agents. Only some antibacterial agents used clinically exhibit effectiveness for both *Streptococcus pneumoniae* and *Haemophilus influenzae*. Most novel drugs launched from the 21st century and novel drug candidates under clinical tests are effective only for the gram-positive bacterium and are inferior in effectiveness for *Haemophilus influenzae*. There is a demand to develop a novel antibacterial agent that is effective for both *Streptococcus pneumoniae* and *Haemophilus influenzae* and is applicable to community-acquired respiratory infection.

Deoxyribonucleic acid (DNA) gyrase is one kind of type II topoisomerase which regulates the topological state of intracellular DNA (Champoux, J. J., 2001, Ann. Rev. Biochem. 70: 369-413). The type II topoisomerase modifies DNA topology by catalyzing a series of reactions through which a DNA duplex is transiently nicked by use of free energy generated as a result of hydrolysis of adenosine triphosphate (ATP); a strand is passed through the nick; and the nicked DNA is reannealed. The DNA gyrase regulates the supercoiling of DNA and relieves topological stress caused by the unwinding of a parent DNA duplex during the replication process. The DNA gyrase is an enzyme essential for growth to be conserved in bacteria and is characterized, among topoisomerases, in the ability to introduce a negative supercoil to DNA.

The DNA gyrase is a protein tetramer consisting of two A subunits (GyrA) and two B subunits (GyrB). GyrB consists of an amino-terminal domain having ATP hydrolytic activity and a carboxy-terminal domain which interacts with GyrA and DNA. The supercoiling reaction is initiated by ATP binding to GyrB. Subsequently, the ATP is hydrolyzed during this reaction. This ATP binding and the subsequent hydrolysis cause a change in the higher-order structure of the DNA-bound gyrase. This is essential for the activity of DNA gyrase.

In contrast to DNA gyrase, eukaryotic type II topoisomerase is a homodimer that is capable of relaxing negative and positive supercoils but not capable of introducing a negative supercoil. Ideally, an antibacterial agent based on the inhibition of bacterial DNA gyrase is selective for this enzyme and has no or relatively weak inhibitory activity against eukaryotic type II topoisomerase.

Another bacterial type II topoisomerase is referred to as topoisomerase IV, which is mainly involved in the segregation of catenated closed circular chromosomes produced during replication. The topoisomerase IV is a protein tetramer consisting of two ParC subunits and two ParE subunits. ParE consists of an amino-terminal domain having ATP hydrolytic activity and a carboxy-terminal domain which interacts with ParC. These subunits ParC and ParE are highly homologous to GyrA and GyrB, respectively. The hydrolysis of ATP is required for getting the enzyme back into the initial state and restarting catalytic cycles. TopoIV is highly conserved in bacteria and is essential for bacterial replication (Drlica, K. and Zhao, X., 1997, Microbiol. Mol. Biol. Rev. 61: 377-392).

DNA gyrase is targeted by quinolone antibacterial agents. Quinolone binds to GyrA to form a tripartite complex of quinolone, DNA gyrase, and DNA. This agent induces cell death by inhibiting DNA replication in this way. Moreover, some members in this class of antibacterial agents also inhibit topoisomerase IV. As a result, these compounds differ in their primary targets among bacterial species and among the compounds. Although the quinolone agents are effective antibacterial agents, they increasingly raise the problem of resistance caused by the mutation of the targets (DNA gyrase and topoisomerase IV) in several kinds of organisms such as *Staphylococcus aureus* and *Streptococcus pneumoniae* (Hooper, D. C., 2002, Lancet Infectious Diseases 2: 530-538). In addition, the quinolone antibacterial agents have been confirmed to have adverse reactions (joint or cartilage disorders) in immature animals and are thus prevented from being used in children (Lipsky, B. A. and Baker, C. A., 1999, Clin. Infect. Dis. 28: 352-364). Examples of other adverse reactions of the quinolone antibacterial agents include cardiotoxicity (prolonged QT interval), decreased blood sugar levels, photosensitivity, and convulsion caused by combined use with a non-steroidal anti-inflammatory agent.

Many conventional quinolones inhibit topoisomerase IV more strongly than DNA gyrase in many gram-positive bacteria and inhibit DNA gyrase more strongly than topoisomerase IV in many gram-negative bacteria. Some novel quinolones exhibit more equally balanced inhibitory activity against DNA gyrase and topoisomerase IV in one bacterial species. More highly sensitive intracellular (primary target) enzymes become resistant to quinolones as a result of a point mutation. However, a quinolone that equally inhibits DNA gyrase and topoisomerase IV inhibits a secondary target enzyme even if its primary target enzyme is mutated; thus the resistance level is low and limited (Hooper, D. C., 2000, Clin Infect Dis. 31: S24-S28). DNA gyrase and topoisomerase IV are highly homologous in their amino acid sequences. Compounds targeting bacterial type II topoisomerase have the potential to inhibit both these two targets in the cell.

There exist several kinds of known natural products that compete with ATP for binding to GyrB and inhibit DNA gyrase (Maxwell, A. and Lawson, D. M., 2003, Curr. Topics in Med. Chem. 3: 283-303). Coumarin antibacterial agents are natural products isolated from the genus *Streptomyces*. Examples thereof include novobiocin, clorobiocin, and coumermycin A1. Although these compounds are potent inhibitors for DNA gyrase, they have toxicity to eukaryotes and low permeability into the bodies of gram-negative bacteria and therefore have low efficacy in clinical application (Maxwell, A., 1997, Trends Microbiol. 5: 102-109). Examples of other natural products targeting GyrB include cyclothialidine isolated from *Streptomyces filipinensis* (Watanabe, J. et al., 1994, J. Antibiot. 47: 32-36) and cinodine isolated from the genus *Nocardia* (Martin, J. H. et al., 1978, J. Antibiot. 31: 398-404). Cyclothialidine is an inadequate antibacterial agent that exhibits activity against only a limited number of bacteria (Nakada, N. et al., 1993, Antimicrob. Agents Chemother. 37: 2656-2661). Cinodine has strong toxicity to eukaryotes and is therefore impossible to use clinically (Ellestad, G. A., 2006, Journal of Medicinal Chemistry. 49: 6627-6634). There is a demand to acquire a novel effective GyrB inhibitor that overcomes the disadvantages of these known natural products. Such an inhibitor is an interesting antibacterial agent candidate that is effective even against the spread of resistant bacteria, which besets the existing antibacterial agents.

In developing antibiotics having a novel mechanism of action, synthetic inhibitors targeting the DNA gyrase GyrB subunit are known in the art. Patent Publication Nos. WO 2005/026149, WO 2006/087543, WO 2006/087544, WO 2006/087548, WO 2006/092599, and WO 2006/092608 describe pyrrole derivatives having antibacterial activity. Patent Publication No. WO 2007/071965 describes bicyclic heteroaromatic compounds. These compounds had the problems of insufficient activity, cytotoxicity, low solubility in water, and the production of electrophilic reactive metabolites.

Patent Document 1: WO 2005/026149
Patent Document 2: WO 2006/087543
Patent Document 3: WO 2006/087544
Patent Document 4: WO 2006/087548
Patent Document 5: WO 2006/092599
Patent Document 6: WO 2006/092608
Patent Document 7: WO 2007/071965

DISCLOSURE OF THE INVENTION

Problems to be Solved by the Invention

To develop an antibiotic having a novel mechanism of action, the present inventors have searched for a compound that has weak cytotoxicity, the physical property of high solubility in water, the effect of inhibiting both DNA gyrase GyrB and topoisomerase IV ParE subunits, and sufficient antibacterial activity. As a result, the present inventors have completed the present invention by finding that compounds of the present invention represented by the general formula (1), pharmacologically acceptable salts thereof, and hydrates thereof have desirable properties.

The present invention provides a pharmaceutical composition (particularly, a preventive or therapeutic composition for infectious disease) comprising a compound represented by the formula (1), a pharmacologically acceptable salt thereof, or a hydrate thereof as an active ingredient, use of the compound represented by the formula (1), a pharmacologically acceptable salt thereof, or a hydrate thereof for producing a pharmaceutical composition (particularly, a preventive or therapeutic composition for infectious disease), and a method for preventing or treating disease (particularly, infectious disease), comprising administering a pharmacologically effective amount of the compound represented by the general formula (1), a pharmacologically acceptable salt thereof, or a hydrate thereof to a warm-blooded animal (particularly, a human).

Means for Solving the Problems

Specifically, the present invention provides:
(1) A compound represented by the formula (1), a pharmacologically acceptable salt thereof, or a hydrate thereof:

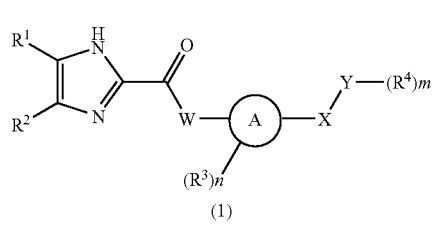

[Formula 1]

(1)

wherein
$R^1$ and $R^2$ are each independently selected from a hydrogen atom, a nitro group, a hydroxy group, a halogen atom, a cyano group, a ($C_1$-$C_4$) alkyl group, a ($C_1$-$C_4$) alkoxy group, a ($C_2$-$C_4$) alkenyl group, a ($C_2$-$C_4$) alkynyl group, a —CO($C_1$-$C_4$) alkyl group, a —S(O)$_a$($C_1$-$C_4$) alkyl group (wherein a is 0, 1, or 2), and a ($C_3$-$C_6$) cycloalkyl group, and $R^1$ and $R^2$ may each independently be substituted at their respective carbon atoms with one or more halogen atom(s), cyclopropyl group(s), cyclobutyl group(s), and/or ($C_1$-$C_4$) alkoxy group(s);
W represents a single bond, —O—, —NR$^5$—, NR$^5$CH$_2$—, or —C(R$^6$)(R$^7$)—;
ring A represents a hydrocarbon ring group or a heterocyclic ring group;
X represents a single bond, —O—, —NR$^8$—, —C(R$^9$)(R$^{10}$)—, —C(O)—, —S(O)$_p$— (wherein p is an integer of 0, 1, or 2), —C(O)NR$^{11}$—, —NR$^{12}$C(O)—, —S(O)$_2$NR$^{13}$—, or —NR$^{14}$S(O)$_2$—;
Y represents a single bond, a hydrocarbon ring group, or a heterocyclic ring group;
$R^3$ and $R^4$ are each independently selected from the following substituents: the substituents are a hydrogen atom, a halogen atom, a nitro group, a cyano group, an oxo group, a hydroxy group, a trifluoromethoxy group, an amino group, a carboxy group, a carbamoyl group, a mercapto group, a sulfamoyl group, a sulfo group, a formyl group, an ureido group, a hydroxyiminomethyl group, a ($C_1$-$C_4$) alkoxyiminomethyl group, an N-hydroxyformamide group, a ($C_1$-$C_4$) alkylhydrazino group, a hydrazinocarbonyl group, an N-hydroxyethanimidoyl group, a ($C_1$-$C_4$) alkyl group, a ($C_2$-$C_4$) alkenyl group, a ($C_2$-$C_4$) alkynyl group, a ($C_1$-$C_4$) alkoxy group, —CO($C_1$-$C_4$) alkyl, —OC(O)($C_1$-$C_4$) alkyl, —NH($C_1$-$C_4$) alkyl, —N[di($C_2$-$C_4$) alkyl], —NHC(O)($C_1$-$C_4$) alkyl, —C(O)NH($C_1$-$C_4$) alkyl, —C(O)N[di($C_1$-$C_4$) alkyl], —C(O)NH($C_1$-$C_4$) alkoxy, —NHC(O)NH($C_1$-$C_4$) alkyl, —NHC(O)N[di($C_1$-$C_4$) alkyl], —C(O)N[($C_1$-$C_4$) alkyl][($C_1$-$C_4$) alkoxy], —S(O)$_a$($C_1$-$C_4$) alkyl (wherein a is 0, 1, or 2), —C(O)(C$_1$-C$_4$) alkoxy, —OC(O)(C$_1$-C$_4$) alkoxy, —NHC(O)(C$_1$-C$_4$) alkoxy, —S(O)$_2$NH(C$_1$-C$_4$) alkyl, —S(O)$_2$N [di(C$_1$-C$_4$) alkyl], —NHSO$_2$(C$_1$-C$_4$) alkyl, —C(O)NHSO$_2$(C$_1$-C$_4$) alkyl, —C(O)NHNH(C$_1$-C$_4$) alkyl, —C(O)NHN[di(C$_1$-C$_4$) alkyl], =CH(C$_1$-C$_4$) alkyl, =C[di(C$_1$-C$_4$) alkyl], =N(C$_1$-C$_4$) alkoxy, =NN[di(C$_1$-C$_4$) alkyl], —R$^{15}$-hydrocarbon ring, and —R$^{16}$-heterocyclic ring, and R$^3$ and R$^4$ may each independently be substituted with one or more R$^{17}$ moiety/moieties);

R$^5$, R$^6$, R$^7$, R$^8$, R$^{10}$, R$^{11}$, R$^{12}$, R$^{13}$, and R$^{14}$ each independently represent a hydrogen atom or a (C$_1$-C$_4$) alkyl group, wherein the (C$_1$-C$_4$) alkyl group may be substituted with R$^{17}$;

n is an integer of 0, 1, 2, 3, or 4, wherein a plurality of R$^3$ moieties are the same or different;

m is an integer of 0, 1, 2, 3, or 4, wherein a plurality of R$^4$ moieties are the same or different;

R$^{17}$ is selected from an azide group, a halogen atom, a nitro group, a cyano group, an oxo group, a hydroxy group, a trifluoromethoxy group, an amino group, a carboxy group, a carbamoyl group, a mercapto group, a sulfamoyl group, a (C$_1$-C$_4$) alkyl group, a (C$_2$-C$_4$) alkenyl group, a (C$_2$-C$_4$) alkynyl group, a (C$_1$-C$_4$) alkoxy group, a —OC(C$_1$-C$_4$) alkyl group, a —OC(O)(C$_1$-C$_4$) alkyl group, —OC(O)(C$_1$-C$_4$) alkoxy, a —NH(C$_1$-C$_4$) alkyl group, a —N[di(C$_1$-C$_4$) alkyl] group, a —NHC(O)(C$_1$-C$_4$) alkyl group, —C(O)NH(C$_1$-C$_4$) alkyl, —C(O)N[di(C$_1$-C$_4$) alkyl], —C(O)NH(C$_1$-C$_4$) alkoxy, —NHC(O)NH(C$_1$-C$_4$) alkyl, —NHC(O)N[di(C$_1$-C$_4$) alkyl], —C(O)N[(C$_1$-C$_4$) alkyl][(C$_1$-C$_4$) alkoxy], —S(O)$_a$(C$_1$-C$_4$) alkyl (wherein a is 0, 1, or 2), —C(O)(C$_1$-C$_4$) alkoxy, —S(O)$_2$NH(C$_1$-C$_4$) alkyl, —S(O)$_2$N[di(C$_1$-C$_4$) alkyl], —NHS(O)$_2$(C$_1$-C$_4$) alkyl, —NHC(O) (C$_1$-C$_4$) alkoxy, =CH(C$_1$-C$_4$) alkyl, =C[di(C$_1$-C$_4$) alkyl], =N(C$_1$-C$_4$) alkoxy, =NN[di(C$_1$-C$_4$) alkyl], —R$^{18}$-hydrocarbon ring, and —R$^{19}$-heterocyclic ring, and R$^{17}$ moieties may each independently be substituted with one or more R$^{20}$ moiety/moieties;

R$^{15}$, R$^{16}$, R$^{18}$, and R$^{19}$ are each independently selected from a single bond, a double bond, —C(R$^{21}$)(R$^{22}$)—, —O—, —N(R$^{23}$)—, —C(O)—, —N(R$^{24}$)C(O)—, —C(O)N(R$^{25}$)—, —S(O)$_p$— (wherein p is an integer of 0, 1, or 2), —S(O)$_2$N(R$^{26}$)—, —N(R$^{27}$)S(O)$_2$—, —O(CO)O—, —C(R$^{28}$)=, and —N=, wherein R$^{21}$, R$^{22}$, R$^{23}$, R$^{24}$, R$^{25}$, R$^{26}$, R$^{27}$, and R$^{28}$ are each independently selected from a hydrogen atom and a (C$_1$-C$_4$) alkyl group; and R$^{20}$ is selected from a halogen atom, a nitro group, a cyano group, an oxo group, a hydroxy group, a trifluoromethoxy group, a trifluoromethyl group, an amino group, a carboxy group, a carbamoyl group, a mercapto group, a sulfamoyl group, a methyl group, an ethyl group, a vinyl group, a methoxy group, an ethoxy group, an acetyl group, an acetoxy group, a methylamino group, an ethylamino group, a dimethylamino group, a diethylamino group, —N(methyl)(ethyl), —NHC(O)-methyl, —C(O)NH-methyl, —C(O)NH-ethyl, —C(O)N[di(methyl)], —C(O)N[di(ethyl)], —C(O)N[(methyl)(ethyl)], a methylthio group, an ethylthio group, —S(O)-methyl, —S(O)-ethyl, —S(O)$_2$-methyl, —S(O)$_2$-ethyl, a methoxycarbonyl group, an ethoxycarbonyl group, —S(O)$_2$NH-methyl, —S(O)$_2$NH-ethyl, —S(O)$_2$N[di(methyl)], —S(O)$_2$N[di(ethyl)], and —S(O)$_2$N[(methyl)(ethyl)].

(2) The compound according to (1), a pharmacologically acceptable salt thereof, or a hydrate thereof, wherein W is a single bond.

(3) The compound according to (1), a pharmacologically acceptable salt thereof, or a hydrate thereof, wherein W is —NR$^5$—.

(4) The compound according to any one of (1) to (3), a pharmacologically acceptable salt thereof, or a hydrate thereof, wherein the ring A is a hydrocarbon ring.

(5) The compound according to any one of (1) to (3), a pharmacologically acceptable salt thereof, or a hydrate thereof, wherein the ring A is a heterocyclic ring.

(6) The compound according to any one of (1) to (3), a pharmacologically acceptable salt thereof, or a hydrate thereof, wherein the hydrocarbon ring is an indan ring, a benzene ring, a cyclohexane ring, or a cyclohexene ring.

(7) The compound according to any one of (1) to (3), a pharmacologically acceptable salt thereof, or a hydrate thereof, wherein the heterocyclic ring is an azetidine ring, a pyrrolidine ring, a piperidine ring, an azepane ring, a thiazole ring, an oxazole ring, an imidazole ring, a pyrazole ring, a pyridine ring, a pyrimidine ring, a quinoline ring, an isoquinoline ring, a quinazoline ring, a benzoxazole ring, an oxazolopyridine ring, an oxazolopyrimidine ring, a benzimidazole ring, an imidazolopyridine ring, an imidazolopyrimidine ring, a pyrazolopyridine ring, a pyrazolopyrimidine ring, a thienopyridine ring, a thienopyrimidine ring, a benzothiophene ring, a thiazolopyridine ring, a thiazolopyrimidine ring, or a benzothiazole ring.

(8) The compound according to any one of (1) to (3), a pharmacologically acceptable salt thereof, or a hydrate thereof, wherein the ring A is an indan ring, a benzene ring, a cyclohexane ring, or a cyclohexene ring.

(9) The compound according to any one of (1) to (3), a pharmacologically acceptable salt thereof, or a hydrate thereof, wherein the ring A is an azetidine ring, a pyrrolidine ring, or a piperidine ring.

(10) The compound according to any one of claims 1 to 9, a pharmacologically acceptable salt thereof, or a hydrate thereof, wherein X is selected from a single bond, —CH$_2$—, and —C(O)—.

(11) The compound according to any one of claims 1 to 10, a pharmacologically acceptable salt thereof, or a hydrate thereof, wherein Y is selected from a single bond, a phenyl group, and a heterocyclic ring group.

(12) The compound according to any one of claims 1 to 10, a pharmacologically acceptable salt thereof, or a hydrate thereof, wherein Y is selected from a single bond, a phenyl group, a thiazolyl group, an oxazolyl group, an imidazolyl group, a pyrazolyl group, a quinolinyl group, an isoquinolinyl group, a quinazolyl group, a benzoxazolyl group, an oxazolopyridyl group, an oxazolopyrimidinyl group, a benzimidazolyl group, an imidazolopyridyl group, an imidazolopyrimidinyl group, a pyrazolopyridyl group, a pyrazolopyrimidinyl group, a thiazolopyridyl group, a thiazolopyrimidinyl group, a benzothiazolyl group, a pyrimidinyl group, and a pyridyl group.

(13) A compound represented by the formula (1) selected from the following, or a pharmacologically acceptable salt thereof:

cis(±)-2-(4-{[(4-chloro-5-methyl-1H-imidazol-2-yl)carbonyl]amino}-3-methoxypiperidin-1-yl)-1,3-benzothiazole-7-carboxylic acid, cis(±)-2-(4-{[(4-chloro-5-ethyl-1H-imidazol-2-yl)carbonyl]amino}-3-methoxypiperidin-1-yl)-1,3-benzothiazole-7-carboxylic acid, cis(±)-2-(4-{[(4-chloro-5-ethyl-1H-imidazol-2-yl)carbonyl]amino}-3-methoxypiperidin-1-yl)-4-ethyl-1,3-thiazole-5-carboxylic acid, cis(±)-2-(4-{[(4-chloro-5-ethyl-1H-imidazol-2-yl)carbonyl]amino}-3-methoxypiperidin-1-yl)-4-vinyl-1,3-thiazole-5-carboxylic acid, cis(±)-2-(4-{[(4-chloro-5-methyl-1H-imidazol-2-yl)carbonyl]amino}-3-methoxypiperidin-1-yl)-4-ethyl-1,3-thiazole-5-carboxylic acid, cis(±)-2-(4-{[(4-chloro-5-ethyl-1H-imidazol-2-yl)carbonyl]amino}-3-ethoxypiperidin-1-yl)-1,3-benzothiazole-7-carboxylic acid, cis(±)-2-(4-{[(4-chloro-5-ethyl-1H-imidazol-2-yl)carbonyl]amino}-3-methoxypiperidin-1-yl)-4-(methylcarbamoyl)-1,3-thiazole-5-carboxylic acid, cis(±)-2-(4-{[(4-chloro-5-ethyl-1H-imidazol-2-yl)carbonyl]amino}-3-methoxypiperidin-1-yl)-4-[(methoxyethyl)carbamoyl]-1,3-thiazole-5-carboxylic acid, cis(±)-2-(4-{[(4-chloro-5-ethyl-1H-imidazol-2-yl)carbonyl]amino}-3-(2,2-difluoroethoxy)piperidin-1-yl)-4-methyl-1,3-thiazole-5-carboxylic acid, cis(±)-2-(4-{[(4-chloro-5-ethyl-1H-imidazol-2-yl)carbonyl]amino}-3-propoxypiperidin-1-yl)-1,3-benzothiazole-7-carboxylic acid, cis(±)-2-(4-{[(4-chloro-5-ethyl-1H-imidazol-2-yl)carbonyl]amino}-3-methoxypiperidin-1-yl)-4-acetyl-1,3-thiazole-5-carboxylic acid, 2-[(3S,4R)-4-{[(4-chloro-5-ethyl-1H-imidazol-2-yl)carbonyl]amino}-3-methoxypiperidin-1-yl]-4-methyl-1,3-thiazole-5-carboxylic acid, cis(±)-2-(4-{[(4-chloro-5-ethyl-1H-imidazol-2-yl)carbonyl]amino}-3-ethoxypiperidin-1-yl)-4-acetyl-1,3-thiazole-5-carboxylic acid, cis(±)-2-(4-{[(4-chloro-5-ethyl-1H-imidazol-2-yl)carbonyl]amino}-3-(2,2-difluoropropoxy)piperidin-1-yl)-4-methyl-1,3-thiazole-5-carboxylic acid, cis(±)-2-(4-{[(4-chloro-5-ethyl-1H-imidazol-2-yl)carbonyl]amino}-3-ethoxypiperidin-1-yl)-4-[(methoxyethyl)carbamoyl]-1,3-thiazole-5-carboxylic acid, cis(±)-2-(4-{[(4-chloro-5-ethyl-1H-imidazol-2-yl)carbonyl]amino}-3-methoxypiperidin-1-yl)-4-(dimethylcarbamoyl)-1,3-thiazole-5-carboxylic acid, cis(±)-2-(4-{[(4-chloro-5-ethyl-1H-imidazol-2-yl)carbonyl]amino}-3-propoxypiperidin-1-yl)-4-[(methoxyethyl)carbamoyl]-1,3-thiazole-5-carboxylic acid, cis(±)-2-(4-{[(4-chloro-5-ethyl-1H-imidazol-2-yl)carbonyl]amino}-3-propoxypiperidin-1-yl)-4-(methylcarbamoyl)-1,3-thiazole-5-carboxylic acid, cis(±)-2-(4-{[(4-chloro-5-ethyl-1H-imidazol-2-yl)carbonyl]amino}-3-ethoxypiperidin-1-yl)-4-(ethylcarbamoyl)-1,3-thiazole-5-carboxylic acid, cis(±)-2-(4-{[(4-chloro-5-ethyl-1H-imidazol-2-yl)carbonyl]amino}-3-ethoxypiperidin-1-yl)-4-(isopropylcarbamoyl)-1,3-thiazole-5-carboxylic acid, cis(±)-2-[3-(butylamino)-4-{[(4-chloro-5-ethyl-1H-imidazol-2-yl)carbonyl]amino}piperidin-1-yl]-1,3-benzothiazole-7-carboxylic acid, cis(±)-2-(4-{[(4-chloro-5-ethyl-1H-imidazol-2-yl)carbonyl]amino}-3-ethoxypiperidin-1-yl)-4-[(2-fluoroethyl)carbamoyl]-1,3-thiazole-5-carboxylic acid, 2-((3R*,4S*)-4-{[(4-chloro-5-ethyl-1H-imidazol-2-yl)carbonyl]amino}-3-ethoxypiperidin-1-yl)-4-[(2-methoxy-1-methylethyl)carbamoyl]-1,3-thiazole-5-carboxylic acid, cis(±)-2-(4-{[(4-chloro-5-ethyl-1H-imidazol-2-yl)carbonyl]amino}-3-ethoxypiperidin-1-yl)-4-[(2-ethoxyethyl)carbamoyl]-1,3-thiazole-5-carboxylic acid, cis(±)-2-(4-{[(4-chloro-5-ethyl-1H-imidazol-2-yl)carbonyl]amino}-3-isopropoxypiperidin-1-yl)-4-(2-methoxyethylcarbamoyl)-1,3-thiazole-5-carboxylic acid, cis(±)-2-(4-{[(4-chloro-5-ethyl-1H-imidazol-2-yl)carbonyl]amino}-3-[(cyclopropylmethyl)amino]piperidin-1-yl)-1,3-benzothiazole-7-carboxylic acid, cis(±)-2-[4-{[(4-chloro-5-ethyl-1H-imidazol-2-yl)carbonyl]amino}-3-(pentylamino)piperidin-1-yl]-1,3-benzothiazole-7-carboxylic acid, cis(±)-2-[4-{[(4-chloro-5-ethyl-1H-imidazol-2-yl)carbonyl]amino}-3-(cyclopentylamino)piperidin-1-yl]-1,3-benzothiazole-7-carboxylic acid, cis(±)-2-(4-{[(4-chloro-5-ethyl-1H-imidazol-2-yl)carbonyl]amino}-3-[(3-methylbutyl)amino]piperidin-1-yl)-1,3-benzothiazole-7-carboxylic acid, cis(±)-2-[4-{[(4-chloro-5-ethyl-1H-imidazol-2-yl)carbonyl]amino}-3-(cyclobutylamino)piperidin-1-yl]-1,3-benzothiazole-7-carboxylic acid, and 2-{(3S,4R)-4-{[(4-chloro-5-ethyl-1H-imidazol-2-yl)carbonyl]amino}-3-[(1-ethylpropyl)amino]piperidin-1-yl}-1,3-benzothiazole-7-carboxylic acid.

(14) The compound according to any one of (1) to (13), a pharmacologically acceptable salt thereof, or a hydrate thereof, which is intended for use in a method for therapeutically treating a human or animal body.

(15) A pharmaceutical agent comprising a compound according to any one of (1) to (13), a pharmacologically acceptable salt thereof, or a hydrate thereof.

(16) Use of a compound according to any one of (1) to (13), a pharmacologically acceptable salt thereof, or a hydrate thereof for producing a pharmaceutical agent.

(17) A bacterial DNA gyrase inhibitor comprising a compound according to any one of (1) to (13), a pharmacologically acceptable salt thereof, or a hydrate thereof.

(18) An antibacterial agent comprising a compound according to any one of (1) to (13), a pharmacologically acceptable salt thereof, or a hydrate thereof.

(19) A therapeutic agent for infectious disease comprising a compound according to any one of (1) to (13), a pharmacologically acceptable salt thereof, or a hydrate thereof.

(20) A method for producing an antibacterial effect in a warm-blooded animal (e.g., a human) in need of treatment which produces an antibacterial effect, the method comprising administering an effective amount of a compound according to any one of (1) to (13), a pharmacologically acceptable salt thereof, or a hydrate thereof to the animal.

(21) A method for inhibiting bacterial DNA gyrase in a warm-blooded animal (e.g., a human) in need of treatment which inhibits bacterial DNA gyrase, the method comprising administering an effective amount of a compound according to any one of (1) to (13), a pharmacologically acceptable salt thereof, or a hydrate thereof to the animal.

(22) A method for treating bacterial infection in a warm-blooded animal (e.g., a human) in need of treatment of bacterial infection, the method comprising administering an effective amount of a compound according to any one of (1) to (13), a pharmacologically acceptable salt thereof, or a hydrate thereof to the animal.

(23) The compound according to any one of (1) to (13), a pharmacologically acceptable salt thereof, or a hydrate thereof, which is intended for use as a pharmaceutical agent.

(24) Use of a compound according to any one of (1) to (13), a pharmacologically acceptable salt thereof, or a hydrate thereof in the production of a pharmaceutical agent used for producing an antibacterial effect in a warm-blooded animal (e.g., a human).

(25) Use of a compound according to any one of (1) to (13), a pharmacologically acceptable salt thereof, or a hydrate thereof in the production of a pharmaceutical agent used for inhibiting bacterial DNA gyrase in a warm-blooded animal (e.g., a human).

(26) Use of a compound according to any one of (1) to (13), a pharmacologically acceptable salt thereof, or a hydrate thereof in the production of a pharmaceutical agent used for treating bacterial infection in a warm-blooded animal (e.g., a human).

(27) The compound according to any one of (1) to (13), a pharmacologically acceptable salt thereof, or a hydrate thereof, which is intended for use for producing an antibacterial effect in a warm-blooded animal (e.g., a human).

(28) The compound according to any one of (1) to (13), a pharmacologically acceptable salt thereof, or a hydrate thereof, which is intended for use for inhibiting bacterial DNA gyrase in a warm-blooded animal (e.g., a human).

(29) The compound according to any one of (1) to (13), a pharmacologically acceptable salt thereof, or a hydrate thereof, which is intended for use for treating bacterial infection in a warm-blooded animal (e.g., a human).

(30) A pharmaceutical composition comprising a compound according to any one of (1) to (13), a pharmacologically acceptable salt thereof, or a hydrate thereof, and a pharmaceutically acceptable diluent or carrier.

(31) A pharmaceutical composition intended for use for producing an antibacterial effect in a warm-blooded animal (e.g., a human), the pharmaceutical composition comprising a compound according to any one of (1) to (13), a pharmacologically acceptable salt thereof, or a hydrate thereof, together with a pharmaceutically acceptable excipient or carrier.

(32) A pharmaceutical composition intended for use for inhibiting bacterial DNA gyrase in a warm-blooded animal (e.g., a human), the pharmaceutical composition comprising a compound according to any one of (1) to (13), a pharmacologically acceptable salt thereof, or a hydrate thereof, together with a pharmaceutically acceptable excipient or carrier.

(33) A pharmaceutical composition intended for use for treating bacterial infection in a warm-blooded animal (e.g., a human), the pharmaceutical composition comprising a compound according to any one of (1) to (13), a pharmacologically acceptable salt thereof, or a hydrate thereof, together with a pharmaceutically acceptable excipient or carrier.

Advantages of the Invention

An imidazole carbonyl compound of the present invention represented by the general formula (1) is useful as a pharmaceutical agent, particularly, a preventive and/or therapeutic agent for infectious disease, which has the effect of inhibiting both bacterial DNA gyrase GyrB and topoisomerase IV ParE subunits, is excellent in sufficient antibacterial activity, and has weak cytotoxicity and the physical property of high solubility in water.

Best Mode for Carrying out the Invention

In the present specification, the term "alkyl" encompasses both linear and branched alkyl groups. However, an individual alkyl group, for example, propyl, described herein refers to only the linear form.

A similar rule is also applied to other generic names. The term "alkyl" advantageously means a chain having 1 to 6 carbon atoms, preferably 1 to 4 carbon atoms, unless otherwise specified. In the present specification, all the terms "alkenyl", "alkynyl", and "cycloalkenyl" encompass regioisomers and geometric isomers.

In the present specification, the term "alkoxy" means such an alkyl group as defined above linked to an oxygen atom. When arbitrary substituents are selected from 0, 1, 2, or 3 kinds of groups, this definition naturally encompasses all substituents being selected from any one kind of these specified groups or substituents being selected from two or more kinds of the specified groups. A similar rule is applied to substituents selected from 0, 1, or 2 kinds of groups; 1, 2, or 3 kinds of substituents; and 1 or 2 kinds of groups.

The hydrocarbon ring group refers to a hydrocarbon ring having a monovalent or divalent bond. The term "hydrocarbon ring" refers to a saturated, partially saturated, or unsaturated monocyclic or bicyclic carbon ring containing 3 to 12 carbon atoms, wherein a —$CH_2$— group may optionally be substituted with —C(O)—. Preferably, the hydrocarbon ring is a monocyclic carbon ring containing 5 to 6 atoms or a bicyclic carbon ring containing 9 or 10 atoms. Preferred specific examples thereof include a cyclopropane ring, a cyclobutane ring, a cyclopentane ring, an oxocyclopentane ring, a cyclopentene ring, a cyclohexane ring, a cyclohexene ring, a benzene ring, an indan ring, an oxoindan ring, an indene ring, a tetralin ring, and a naphthalene ring.

The heterocyclic ring group refers to a heterocyclic ring having a monovalent or divalent bond. The term "heterocyclic ring" refers to an optionally substituted, saturated or unsaturated monocyclic or bicyclic ring containing 3 to 12 atoms (of them, 1, 2, 3, or 4 ring atoms are selected from nitrogen, sulfur, and oxygen and may be linked carbon, nitrogen, sulfur, or oxygen, unless otherwise specified), wherein a —$CH_2$— group may optionally be substituted with —C(O)—; a sulfur atom in the ring may optionally be oxidized to form an S-oxide; and a nitrogen atom in the ring may optionally be oxidized to form an N-oxide. Specific examples of the heterocyclic ring include an azetidine ring, a morpholine ring, a piperidine ring, a pyridine ring, a pyridyl-N-oxide ring, a pyran ring, a pyrrole ring, an imidazoline ring, a thiazole ring, a thiophene ring, a dioxolane ring, a thiadiazole ring, a piperazine ring, an isothiazole ring, a thiazolidine ring, a triazole ring, a tetrazole ring, an azepane ring, a pyrrolidine ring, an oxazolidine ring, an isoxazolone ring, a thiomorpholine ring, a homopiperazine ring, a 3,5-k dioxopiperidine ring, a pyrazolone ring, a tetrahydropyran ring, a tetrahydrothiopyran ring, a 1-oxotetrahydrothiopyran ring, a 1,1-dioxotetrahydrothiopyran ring, a pyrimidine ring, a pyrazine ring, a pyridazine ring, a pyrazole ring, a pyrazoline ring, an isoxazole ring, a 4-oxopyrrolidine ring, a 2-oxopyrrolidine ring, a 4-oxothiazolidine ring, a furan ring, a thiophene ring, an oxazole ring, an oxadiazole ring, a quinoline ring, and a benzothiazole ring.

Preferably, the heterocyclic ring group is an azetidine ring group, a morpholine ring group, a pyrrolidine ring group, a piperidine ring group, a pyridine ring group, a pyran ring group, a pyrrole ring group, an imidazole ring group, a thiazole ring group, a thiophene ring group, a thiadiazole ring group, a piperazine ring group, an isothiazolidine ring group, a 1,2,4-triazole ring group, a tetrazole ring group, an azepane ring group, a pyrrolidine ring group, a thiomorpholine ring group, a pyrroline ring group, a homopiperazine ring group, a 3,5-dioxopiperidine ring group, a pyrimidine ring group, a pyrazine ring group, a pyridazine ring group, a pyrazole ring group, a pyrazoline ring group, an isoxazole ring group, a 4-oxopyrrolidine ring group, a 2-oxopyrrolidine ring group, a 4-oxothiazolidine ring group, a furan ring group, a thiophene ring group, an oxazole ring group, a 1,3,4-oxadiazole ring group, a 1,2,4-oxadiazole ring group, a quinoline ring group, or a benzothiazole ring group.

More preferably, the heterocyclic ring group is an azetidine ring group, a piperidine ring group, a pyrimidine ring group, a pyridine ring group, an oxazole ring group, a thiazole ring group, a quinoline ring group, or a benzothiazole ring group.

The halogen atom is, for example, a fluorine, chlorine, bromine, or iodine atom.

The ($C_1$-$C_4$) alkyl is, for example, methyl, ethyl, propyl, butyl, 1-methylethyl, 1,1-dimethylethyl, 1-methylpropyl, or 2-methylpropyl.

The ($C_1$-$C_4$) alkoxy is, for example, methoxy, ethoxy, propoxy, 1-methylethoxy, butoxy, 2-methylpropoxy, 1,1-dimethylethylethoxy, or 1-methylpropoxy.

Examples of the ($C_2$-$C_4$) alkenyl include vinyl, propenyl, allyl, but-2-enyl, and but-3-enyl.

Examples of the ($C_2$-$C_4$) alkynyl include ethynyl, prop-2-ynyl, but-2-ynyl, and but-3-ynyl.

Examples of the ($C_3$-$C_6$) cycloalkyl include cyclopropyl, cyclobutyl, cyclopentyl, and cyclohexyl.

Hereinafter, $R^1$ to $R^4$, W, ring A, X, Y, m, and n will be illustrated specifically.

Specific examples of $R^1$ and $R^2$ each independently include a hydrogen atom, a nitro group, a hydroxy group, a fluorine atom, a chlorine atom, a bromine atom, an iodine atom, a cyano group, a methyl group, an ethyl group, a propyl group, a butyl group, a 1-methylethyl group, a 1,1-dimethylethyl group, a 1-methylpropyl group, a trifluoromethyl group, a 2-methylpropyl group, a methoxy group, a methoxymethyl group, an ethoxy group, a propoxy group, a butoxy group, a vinyl group, a propenyl group, an allyl group, a but-2-enyl group, a but-3-enyl group, an ethynyl group, a prop-2-ynyl group, a but-2-ynyl group, a but-3-ynyl group, an acetyl group, —CO-ethyl, —CO-propyl, —CO-butyl, —CO-1-methylethyl, —CO-1,1-dimethylethyl, —CO-1-methylpropyl, —CO-2-methylpropyl, —S-methyl, —S-ethyl, —S-propyl, —S-butyl, —S-1-methylethyl, —S-1,1-dimethylethyl, —S-1-methylpropyl, —S-2-methylpropyl, —S(O)-methyl, —S(O)-ethyl, —S(O)-propyl, —S(O)-butyl, —S(O)-1-methylethyl, —S(O)-1,1-dimethylethyl, —S(O)-1-methylpropyl, —S(O)-2-methylpropyl, —S(O)$_2$-methyl, —S(O)$_2$-ethyl, —S(O)$_2$-propyl, —S(O)$_2$-butyl, —S(O)$_2$-1-methylethyl, —S(O)$_2$-1,1-dimethylethyl, —S(O)$_2$-1-methylpropyl, —S(O)$_2$-2-methylpropyl, a cyclopropyl group, a cyclobutyl group, a cyclopentyl group, and a cyclohexyl group. Preferably, $R^1$ and $R^2$ are each independently a hydrogen atom, a methyl group, an ethyl group, a propyl group, a 1-methylethyl group, a methoxymethyl group, a trifluoromethyl group, —S-methyl, a chlorine atom, a bromine atom, or an iodine atom, more preferably a methyl group, an ethyl group, a chlorine atom, or a bromine atom.

Specific examples of $R^3$ and $R^4$ each independently include a hydrogen atom, a fluorine atom, a chlorine atom, a bromine atom, an iodine atom, a nitro group, a cyano group, an oxo group, a hydroxy group, an acetyl group, a fluoromethyl group, a trifluoromethyl group, a hydroxymethyl group, a trifluoromethoxy group, an amino group, a carboxy group, a carbamoyl group, a mercapto group, a sulfamoyl group, a sulfo group, a formyl group, an ureido group, a hydroxyiminomethyl group, a methoxyiminomethyl group, an ethoxyiminomethyl group, a propoxyiminomethyl group, a butoxyiminomethyl group, an N-hydroxyformamide group, a methylhydrazino group, an ethylhydrazino group, a propylhydrazino group, a butylhydrazino group, a 1-methylethylhydrazino group, a 1,1-dimethylethylhydrazino group, a 1-methylpropylhydrazino group, a 2-methylpropylhydrazino group, a hydrazinocarbonyl group, an N-hydroxyethanimidoyl group, a methyl group, a cyclopropylmethyl group, an ethyl group, a propyl group, butyl group, a pentyl group, a hexyl group, a 1-methylethyl group, a 1,1-dimethylethyl group, a 1-methylpropyl group, a 2-methylpropyl group, a 1-ethylpropyl group, a 3-methylbutyl group, a vinyl group, a propenyl group, an allyl group, a but-2-enyl group, a but-3-enyl group, an ethynyl group, a prop-2-ynyl group, a but-2-ynyl group, a but-3-ynyl group, a methoxy group, an ethoxy group, a 1-methylethoxy group, a 1,1-dimethylethoxy group, a 2-difluoroethoxy group, a 2-fluoroethoxy group, a propoxy group, a 1-ethylpropoxy group, a 3-fluoropropoxy group, a 2-difluoropropoxy group, a butoxy group, a 2-methylpropoxy group, a 3-methylbutoxy group, a benzyloxy group, a carboxymethyl group, a 2-carboxyethyl group, a 5-carboxy-4-methyl-1,3-thiazolyl group, a 1-carboxy-cyclopropyl group, —CO-Et, —CO-propyl, —CO-butyl, —CO-1-methylethyl, —CO-1,1-dimethylethyl, —CO-1-methylpropyl, —CO-2-methylpropyl, —CO-Ph, —OC(O)-methyl, —OC(O)-ethyl, —OC(O)-propyl, —OC(O)-butyl, —OC(O)-1-methylethyl, —OC(O)-1,1-dimethylethyl, —OC(O)-1-methylpropyl, —OC(O)-2-methylpropyl, —NHMe, —NHEt, —NH-propyl, —NH-cyclopropyl, —NH-cyclopropylmethyl, —NH-butyl, —NHCH(Me)$_2$, —NH-1,1-dimethylethyl, —NH-1-methylpropyl, —NH-2-methylpropyl, —NHCH(Et)$_2$, —NH-3-methylbutyl, —NH-pentyl, —NH-hexyl, —NH-benzyl, —NH-cyclobutyl, —NH-cyclopentyl, —NMe$_2$, —N[methyl][ethyl], —N[ethyl]$_2$, —N[methyl][propyl], —N[propyl]$_2$, —N[butyl]$_2$, —N[methyl][1-methylethyl], —N[1-methylethyl]$_2$, —N[1,1-dimethylethyl]$_2$, —N[1-methylpropyl]$_2$, —N[2-methylpropyl]$_2$, —NHAc, —NHC(O)-ethyl, —NHC(O)-propyl, —NHC(O)-butyl, —NHC(O)-1-methylethyl, —NHC(O)-1,1-dimethylethyl, —NHC(O)-1-methylpropyl, —NHC(O)-2-methylpropyl, —C(O)NHMe, —C(O)NHEt, —C(O)NH-propyl, —C(O)NH-butyl, —C(O)NHCH(Me)$_2$, —C(O)NH-1,1-dimethylethyl, —C(O)NH-1-methylpropyl, —C(O)NH-2-methylpropyl, —C(O)NH-Ph, —C(O)NH-cyclopropyl, a piperidin-4-ylcarbamoyl group, —C(O)NHCH$_2$COOH, —C(O)NH(CH$_2$)$_2$F, —C(O)NH(CH$_2$)$_2$Nme$_2$, —C(O)NH(CH$_2$)$_2$NEt$_2$-C(O)NH(CH$_2$)$_2$NHAo, —C(O)NH(CH$_2$)$_2$OMe, —C(O)NH(CH$_2$)$_2$OEt, —C(O)NH(CH$_2$)$_2$CN, —C(O)NHCH(Me) CH$_2$OH, —C(O)NHCH(Me) CH$_2$OMe, —C(O)NHCH$_2$CHF$_2$, —C(O)NH-2-methylpropyl, —C(O)NMe$_2$, —C(O)N[methyl][ethyl], —C(O)N[ethyl]$_2$, —C(O)N[methyl][propyl], —C(O)N[methyl][1-methylethyl], —C(O)N[propyl]$_2$, —C(O)N[butyl]$_2$, —C(O)N[1-methylethyl]$_2$, —C(O)N[1,1-dimethylethyl]$_2$, —C(O)N[1-methylpropyl]$_2$, —C(O)N[2-methylpropyl]$_2$, a 4-methylpiperazin-1-ylcarbonyl group, —C(O)NH-OMe, —C(O)NH-ethoxy, —C(O)NH-propoxy, —C(O)NH-butoxy, —NHC(O)NH-methyl, —NHC(O)NH-ethyl, —NHC(O)NH-propyl, —NHC(O)NH-butyl, —NHC(O)NH-1-methylethyl, —NHC(O)NH-1,1-dimethylethyl, —NHC(O)NH-1-methylpropyl, —NHC(O)NH-2-methylpropyl, —NHC(O)N[methyl]$_2$, —NHC(O)N[ethyl]$_2$, —NHC(O)N[propYl]$_2$, —NHC(O)N[butyl]$_2$, —NHC(O)N[1-methylethyl]$_2$, —NHC(O)N[1,1-dimethylethyl]$_2$, —NHC(O)N[1-methylpropyl]$_2$, —NHC(O)N[2-methylpropyl]$_2$, —C(O)N[methyl][methoxy], —C(O)N[ethyl][methoxy], —C(O)N[propyl][methoxy], —C(O)N[butyl][methoxy], —C(O)N[1-methylethyl][methoxy], —C(O)N[1,1-dimethylethyl][methoxy], —C(O)N[1-methylpropyl][methoxy], —C(O)N[2-methylpropyl][methoxy], —C(O)N[methyl][ethoxy], —C(O)N[ethyl][ethoxy], —C(O)N[propyl][ethoxy], —C(O)N[butyl][ethoxy], —C(O)N[1-methylethyl][ethoxy], —C(O)N[1,1-dimethylethyl][ethoxy], —C(O)N[1-methylpropyl][ethoxy], —C(O)N[2-methylpropyl][ethoxy], —C(O)N[methyl][propoxy], —C(O)N[ethyl][propoxy], —C(O)N[propyl][propoxy], —C(O)N[butyl][propoxy], —C(O)N[1-methylethyl][propoxy], —C(O)N[1,1-dimethylethyl][propoxy], —C(O)N[1-methylpropyl][propoxy], —C(O)N[2-methylpropyl][propoxy], —C(O)N[methyl][butoxy], —C(O)N[ethyl][butoxy], —C(O)N[propyl][butoxy], —C(O)N[butyl][butoxy], —C(O)N[1-methylethyl][butoxy], —C(O)N[1,1-dimethylethyl][butoxy], —C(O)N[1-methylpropyl][butoxy], —C(O)N[2-methylpropyl][butoxy], —S-methyl, —S-ethyl, —S-propyl, —S-butyl, —S-1-methylethyl, —S-1,1-dimethylethyl, —S-1-methylpropyl, —S-2-methylpropyl, —S(O)-methyl, —S(O)-ethyl, —S(O)-propyl, —S(O)-butyl, —S(O)-1-methylethyl, —S(O)-1,1-dimethylethyl, —S(O)-1-methylpropyl, —S(O)-2-methylpropyl, —S(O)$_2$-methyl, —S(O)$_2$-ethyl, —S(O)$_2$-propyl, —S(O)$_2$-butyl, —S(O)$_{2-1}$-methylethyl, —S(O)$_2$-1,1-dimethylethyl, —S(O)$_2$-1-methylpropyl, —S(O)$_2$-2-methylpropyl, a methoxycarbonyl group, an ethoxycarbonyl group, —C(O)-propoxy, —C(O)-butoxy, —C(O)(1,1-dimethylethoxy), —OC(O)-methoxy, —OC(O)-ethoxy, —OC(O)-propoxy, —OC(O)-butoxy, —NHC(O)-methoxy, —NHC(O)-ethoxy, —NHC(O)-propoxy, —NHC(O)-butoxy, —NHC(O)-benzyloxy, —S(O)$_2$NH-methyl, —S(O)$_2$NH-ethyl, —S(O)$_2$NH-propyl, —S(O)$_2$NH-butyl, —S(O)$_2$NH-1-methylethyl, —S(O)$_2$NH-1,1-dimethylethyl, —S(O)$_2$NH-1-methylpropyl, —S(O)$_2$NH-2-methylpropyl, —S(O)$_2$N[methyl]$_2$, —S(O)$_2$N[ethyl]$_2$r —S(O)$_2$N[propyl]$_2$, —S(O)$_2$N[butyl]$_2$, —S(O)$_2$N[1-methylethyl]$_2$, —S(O)$_2$N[1,1-dimethylethyl]$_2$, —S(O)$_2$N[1-methylpropyl]$_2$, —S(O)$_2$N[2-methylpropyl]$_2$, —NHSO$_2$-methyl, —NHSO$_2$-ethyl, —NHSO$_2$-propyl, —NHSO$_2$-butyl, —NHSO$_2$-1-methylethyl, —NHSO$_2$-1,1-dimethylethyl, —NHSO$_2$-1-methylpropyl, —NHSO$_2$-2-methylpropyl, —C(O)NHSO$_2$-methyl, —C(O)NHSO$_2$-ethyl, —C(O)NHSO$_2$-propyl, —C(O)NHSO$_2$-butyl, —C(O)NHSO$_2$-1-methylethyl, —C(O)NHSO$_2$-1,1-dimethylethyl, —C(O)NHSO$_2$-1-methylpropyl, —C(O)NHSO$_2$-2-methylpropyl, —C(O)NHNH-methyl, —C(O)NHNH-ethyl, —C(O)NHNH-propyl, —C(O)NHNH-butyl, —C(O)NHNH-1-methylethyl, —C(O)NHNH-1,1-dimethylethyl, —C(O)NHNH-1-methylpropyl, —C(O)NHNH-2-methylpropyl, —C(O)NHN[methyl]$_2$, —C(O)NHN[ethyl]$_2$, —C(O)NHN[propyl]$_2$, —C(O)NHN[butyl]$_2$, —C(O)NHN[1-methylethyl]$_2$, —C(O)NHN[1,1-dimethylethyl]$_2$, —C(O)NHN[1-methylpropyl]$_2$, —C(O)NHN[2-methylpropyl]$_2$, =CH-methyl, =CH-ethyl, =CH-propyl, =CH-butyl, =CH-1-methylethyl, =CH-1,1-dimethylethyl, =CH-1-methylpropyl, =CH-2-methylpropyl, =C[methyl]$_2$, =C[ethyl]$_2$, =C[propyl]$_2$, =C[butyl]$_2$, =C[1-methylethyl]$_2$, =C[1,1-dimethylethyl]$_2$, =C[1-methylpropyl]$_2$, =C[2-methylpropyl]$_2$, =N-methoxy, =N-ethoxy, =N-propoxy, =N-butoxy, =NN[methyl]$_2$, =NN[ethyl]$_2$, =NN[propyl]$_2$, =NN[butyl]$_2$, =NN[1-methylethyl]$_2$, =NN[1,1-dimethylethyl]$_2$, =NN[1-methylpropyl]$_2$, =NN[2-methylpropyl]$_2$, a tetrahydro-2H-pyran-4-ylamino group, a (1E)-3-(methoxyamino)-3-oxoprop-1-en-1-yl group, a (E)-2-carboxyethenyl group, a (E)-2-(4-carboxyphenyl)ethenyl group, a (E)-2-(2-fluoro-4-carboxyphenyl)ethenyl group, a (E)-2-(2-methoxy-4-carboxyphenyl)ethenyl group, a (1E)-N-methoxyethanimidoyl group, a (1Z)—N-methoxyethanimidoyl group, a (Z)-[3-(carboxymethyl)-2,4-dioxo-1,3-thiazolidin-5-ylidene]methyl group, a (Z)-(2,4-dioxo-1,3-thiazolidin-5-ylidene)methyl group, a (1-acetoxy)ethoxycarbonyl group, a (1,1-dimethylpropionyloxy)methoxycarbonyl group, a 1-[(2-propoxy)carbonyloxy]ethoxycarbonyl group, a 1-(cyclohexyloxycarboxy)ethoxycarbonyl group, a cyclopropane ring group, a cyclobutane ring group, a cyclopentane ring group, an oxocyclopentane ring group, a cyclopentene ring group, a cyclohexane ring group, a cyclohexene ring group, a benzene ring group, an indan ring group, an oxoindan ring group, an indene ring group, a tetralone ring group, a naphthalene ring group, an azetidine ring group, a morpholine ring group, a piperidine ring group, a pyridine ring group, a pyridyl-N-oxide ring group, a pyran ring group, a pyrrole ring group, an imidazoline ring group, a thiazole ring group, a thiophene ring group, a dioxolane ring group, a thiadiazole ring group, a piperazine ring group, an isothiazole ring group, a thiazolidine ring group, a triazole ring group, a tetrazole ring group, an azepane ring group, a pyrrolidine ring group, an oxazolidine ring group, an isoxazolone ring group, a thiomorpholine ring group, a pyrrole ring group, a homopiperazine ring group, a 3,5-dioxopiperidine ring group, a pyrazolone ring group, a tetrahydropyran ring group, a tetrahydrothiopyran ring group, a 1-oxotetrahydrothiopyran ring group, a 1,1-dioxotetrahydrothiopyran ring group, a pyrimidine ring group, a pyrazine ring group, a pyridazine ring group, a pyrazole ring group, a pyrazoline ring group, an isoxazole ring group, a 4-oxopyrrolidine ring group, a 2-oxopyrrolidine ring group, a 4-oxothiazolidine ring group, a furan ring group, a thiophene ring group, an oxazole ring group, an oxadiazole ring group, a quinoline ring group, and a benzothiazole ring group.

Of them, a group having a divalent bond may be bonded when ring A or Y is a saturated or partially saturated hydrocarbon ring or heterocyclic ring or is even an aromatic ring, which must however be, for example, an indene ring or 7H-cyclopenta[c]pyridine ring.

Preferably, $R^3$ is a hydrogen atom, a fluorine atom, a chlorine atom, a methyl group, an ethyl group, a methoxy group, an ethoxy group, a 2-difluoroethoxy group, a 2-fluoroethoxy group, a 1-methylethoxy group, a propoxy group, a 2-methylpropoxy group, a 2-difluoropropoxy group, a 3-fluoropropoxy group, —NHEt, —NHCH(Et)$_2$, —NHCH(Me)$_2$, —NH-propyl, —NH-butyl, —NH-2-methylpropyl, —NH-3-methylbutyl, —NH-pentyl, —NH-hexyl, —NMe$_2$, —NH-benzyl, —NHC(O)-benzyloxy, —NH-cyclobutyl, —NH-cyclopentyl, —NH-cyclopropyl, —NH-cyclopropylmethyl, a pyrrolidine ring group, a tetrahydro-2H-pyran-4-ylamino group, a benzyloxy group, a 3-methylbutoxy group, or a butoxy group. More preferred examples of $R^3$ include a chlorine atom, an ethyl group, a methoxy group, an ethoxy group, a 2-fluoroethoxy group, a 2-difluoroethoxy group, a 1-methylethoxy group, a propoxy group, a 2-methylpropoxy group, a 2-difluoropropoxy group, a 3-fluoropropoxy group, —NH-2-methylpropyl, —NHCH(Et)$_2$, —NH-3-methylbutyl, —NH-butyl, —NH-pentyl, —NH-hexyl, —NH-benzyl, —NH-cyclobutyl, —NH-cyclopentyl, —NH-cyclopropylmethyl, and a butoxy group.

Preferably, $R^4$ is a hydrogen atom, a chlorine atom, an oxo group, a methyl group, a fluoromethyl group, a trifluoromethyl group, an ethyl group, a vinyl group, a 1-methylethyl group, a butyl group, a propyl group, a methoxy group, a 1,1-dimethylethoxy group, a hydroxymethyl group, a carboxy group, an acetyl group, a 1-carboxy-cyclopropyl group, a carboxymethyl group, a 2-carboxyethyl group, a 5-carboxy-4-methyl-1,3-thiazolyl group, —CO-Et, a carbamoyl group, —C(O)NHMe, —C(O)NHEt, —C(O)NHCH(Me)$_2$, —C(O)NH-Ph, —C(O)NH-cyclopropyl, a (1E)-N-methoxyethanimidoyl group, a (1Z)—N-methoxyethanimidoyl group, —C(O)NH-OMe, —C(O)NMe$_2$, a methoxycarbonyl group, an ethoxycarbonyl group, —C(O)(1,1-dimethylethoxy), —C(O)-Ph, a (1E)-3-(methoxyamino)-3-oxoprop-1-en-1-yl group, —C(O)NH(CH$_2$)$_2$F, —C(O)NH(CH$_2$)$_2$Nme$_2$, —C(O)NH(CH$_2$)$_2$NHAc, —C(O)NH(CH$_2$)$_2$OMe —C(O)NH(CH$_2$)$_2$OEt, —C(O)NHCH(Me)CH$_2$OH, —C(O)NHCH(Me)CH$_2$OMe, —C(O)NHCH$_2$COOH, —C(O)NH(CH$_2$)$_2$NEt$_2$, —C(O)NHCH$_2$CHF$_2$, —C(O)NH(CH$_2$)$_2$CN, a 4-methylpiperazin-1-ylcarbonyl group, a methoxyiminomethyl group, a piperidin-4-ylcarbamoyl group, a (E)-2-carboxyethenyl group, a (E)-2-(4-carboxyphenylethenyl) group, a (E)-2-(2-fluoro-4-carboxyphenyl)ethenyl group, a (E)-2-(2-methoxy-4-carboxyphenyl)ethenyl group, —NHAc, a tetrazole ring group, a (Z)-(2,4-dioxo-1,3-thiazolidin-5-ylidene)

methyl group, or a (Z)-[3-(carboxymethyl)-2,4-dioxo-1,3-thiazolidin-5-ylidene]methyl group.

More preferably, $R^4$ is a hydrogen atom, an oxo group, a methyl group, an ethyl group, a vinyl group, a 1-methylethyl group, a propyl group, a butyl group, an acetyl group, a carbamoyl group, —C(O)NHMe, —C(O)NHEt, —C(O)NHCH(Me)$_2$, —C(O)NH-cyclopropyl, —C(O)NMe$_2$, —C(O)NH(CH$_2$)$_2$F, —C(O)NH(CH$_2$)$_2$OMe, —C(O)NH(CH$_2$)$_2$OEt —C(O)NHCH(Me)CH$_2$OMe, —C(O)NHCH$_2$CHF$_2$, —C(O)NH(CH$_2$)$_2$CN, a carboxy group, a (1E)-3-(methoxyamino)-3-oxoprop-1-en-1-yl group, or a (Z)-(2,4-dioxo-1,3-thiazolidin-5-ylidene)methyl group.

Specific examples of $R^5$, $R^6$, $R^7$, $R^8$, $R^9$, $R^{10}$, and $R^{11}$ each independently include a hydrogen atom, a methyl group, an ethyl group, a 2-methoxyethyl group, a propyl group, a butyl group, a 1-methylethyl group, a 1,1-dimethylethyl group, a 1-methylpropyl group, and a 2-methylpropyl group.

Specific examples of m and n each independently include an integer of 0, 1, 2, 3, or 4. Preferably, m is an integer of 0, 1, 2, or 4, and n is an integer of 0 or 1. More preferably, m is an integer of 1 or 2, and n is an integer of 1.

Specific examples of W include a single bond, —O—, —NH—, —N[methyl]-, —N[ethyl]-, —N[(CH$_2$)$_2$OMe]—, —N[propyl]-, —N[butyl]-, —N[1-methylethyl]-, —N[1,1-dimethylethyl]-, —N[1-methylpropyl]-, —N[2-methylpropyl]-, —CH$_2$—, —C(H)(methyl)-, —C(H)(ethyl)-, —C(H)(propyl)-, —C(H)(butyl)-, —C(H)(1-methylethyl)-, —C(H)(1,1-dimethylethyl)-, —C(H)(1-methylpropyl)-, —C(H)(2-methylpropyl)-, —C(methyl)(methyl)-, —C(methyl)(ethyl)-, —C(methyl)(propyl)-, —C(methyl)(butyl)-, —C(methyl)(1-methylethyl)-, —C(methyl)(1,1-dimethylethyl)-, —C(methyl)(1-methylpropyl)-, —C(methyl)(2-methylpropyl)-, —C(ethyl)(ethyl)-, —C(ethyl)(propyl)-, —C(ethyl)(butyl)-, —C(ethyl)(1-methylethyl)-, —C(ethyl)(1,1-dimethylethyl)-, —C(ethyl)(1-methylpropyl)-, —C(ethyl)(2-methylpropyl)-, —C(propyl)(propyl)-, —C(propyl)(butyl)-, —C(propyl)(1-methylethyl)-, —C(propyl)(1,1-dimethylethyl)-, —C(propyl)(1-methylpropyl)-, —C(propyl)(2-methylpropyl)-, —C(butyl)(butyl)-, —C(butyl)(1-methylethyl)-, —C(butyl)(1,1-dimethylethyl)-, —C(butyl)(1-methylpropyl)-, —C(butyl)(2-methylpropyl)-, —C(1-methylethyl)(1-methylethyl)-, —C(1-methylethyl)(1,1-dimethylethyl)-, —C(1-methylethyl)(1-methylpropyl)-, —C(1-methylethyl)(2-methylpropyl)-, —C(1,1-dimethylethyl)(1,1-dimethylethyl)-, —C(1,1-dimethylethyl)(1-methylpropyl)-, —C(1,1-dimethylethyl)(2-methylpropyl)-, —C(1-methylpropyl)(1-methylpropyl)-, —C(1-methylpropyl)(2-methylpropyl)-, and —C(2-methylpropyl)(2-methylpropyl)-. Preferably, W is a single bond, —NH—, —N[methyl]-, —N[(CH$_2$)$_2$OMe]—, —N[propyl]-, or —N[butyl]-. More preferably, W is a single bond, —NH—, —N[propyl]-, or —N[butyl]-.

Specific examples of ring A include a cyclopropane ring, a cyclobutane ring, a cyclopentane ring, an oxocyclopentane ring, a cyclopentene ring, a cyclohexane ring, a cyclohexene ring, a benzene ring, an indan ring, an oxoindan ring, an indene ring, a tetralone ring, a naphthalene ring, an azetidine ring, a morpholine ring, a piperidine ring, a pyridine ring, a 1,2,3,4-tetrahydropyridine ring, a pyridyl-N-oxide ring, a pyran ring, a pyrrole ring, an imidazoline ring, a thiazole ring, a thiophene ring, a dioxolane ring, a thiadiazole ring, a piperazine ring, an isothiazole ring, an isoindole ring, a thiazolidine ring, a triazole ring, a tetrazole ring, an azepane ring, a pyrrolidine ring, an oxazolidine ring, a benzoxazine ring, an isoxazolone ring, a thiomorpholine ring, a pyrrole ring, a homopiperazine ring, a 3,5-dioxopiperidine ring, a pyrazolone ring, a tetrahydropyran ring, a tetrahydrothiopyran ring, a 1-oxotetrahydrothiopyran ring, a 1,1-dioxotetrahydrothiopyran ring, a pyrimidine ring, a pyrazine ring, a pyridazine ring, a pyrazole ring, a pyrazoline ring, an isoxazole ring, a 4-oxopyrrolidine ring, a 2-oxopyrrolidine ring, a 4-oxothiazolidine ring, a 4,5,6,7-tetrahydro-2H-indazole ring, a 4,5,6,7-tetrahydro-1H-indazole ring, a 2,6-diazabicyclo[3.2.0] heptane ring, a furan ring, a benzothiophene ring, a 2H-chromene ring, an oxazole ring, an oxadiazole ring, a quinoline ring, a 1,2,3,4-tetrahydropyridine ring, and a benzothiazole ring.

Preferably, the ring A is a benzene ring, a cyclohexane ring, a cyclohexene ring, an azetidine ring, a benzoxazine ring, an indan ring, a 4,5,6,7-tetrahydro-2H-indazole ring, a 4,5,6,7-tetrahydro-1H-indazole ring, a 2,6-diazabicyclo[3.2.0]heptane ring, a benzothiophene ring, a 2H-chromene ring, a 1,2,3,4-tetrahydropyridine ring, a piperidine ring, a pyrrolidine ring, or an isoindole ring, more preferably, a piperidine ring, a benzene ring, a 4,5,6,7-tetrahydro-1H-indazole ring, a 2,6-diazabicyclo[3.2.0]heptane ring, a cyclohexene ring, a benzothiophene ring, a 1,2,3,4-tetrahydropyridine ring, or an azetidine ring.

Specific examples of X include a single bond, —O—, —NH—, —N(methyl)-, —N(ethyl)-, —N(propyl)-, —N(butyl)-, —N(1-methylethyl)-, —N(1,1-dimethylethyl)-, —N(1-methylpropyl)-, —N(2-methylpropyl)-, —CH$_2$—, —C(H)(methyl)-, —C(H)(ethyl)-, —C(H)(propyl)-, —C(H)(butyl)-, —C(H)(1-methylethyl)-, —C(H)(1,1-dimethylethyl)-, —C(H)(1-methylpropyl)-, —C(H)(2-methylpropyl)-, —C(methyl)(methyl)-, —C(methyl)(ethyl)-, —C(methyl)(propyl)-, —C(methyl)(butyl)-, —C(methyl)(1-methylethyl)-, —C(methyl)(1,1-dimethylethyl)-, —C(methyl)(1-methylpropyl)-, —C(methyl)(2-methylpropyl)-, —C(ethyl)(ethyl)-, —C(ethyl)(propyl)-, —C(ethyl)(butyl)-, —C(ethyl)(1-methylethyl)-, —C(ethyl)(1,1-dimethylethyl)-, —C(ethyl)(1-methylpropyl)-, —C(ethyl)(2-methylpropyl)-, —C(propyl)(propyl)-, —C(propyl)(butyl)-, —C(propyl)(1-methylethyl)-, —C(propyl)(1,1-dimethylethyl)-, —C(propyl)(1-methylpropyl)-, —C(propyl)(2-methylpropyl)-, —C(butyl)(butyl)-, —C(butyl)(1-methylethyl)-, —C(butyl)(1,1-dimethylethyl)-, —C(butyl)(1-methylpropyl)-, —C(butyl)(2-methylpropyl)-, —C(1-methylethyl)(1-methylethyl)-, —C(1-methylethyl)(1,1-dimethylethyl)-, —C(1-methylethyl)(1-methylpropyl)-, —C(1-methylethyl)(2-methylpropyl)-, —C(1,1-dimethylethyl)(1,1-dimethylethyl)-, —C(1,1-dimethylethyl)(1-methylpropyl)-, —C(1,1-dimethylethyl)(2-methylpropyl)-, —C(1-methylpropyl)(1-methylpropyl)-, —C(1-methylpropyl)(2-methylpropyl)-, —C(2-methylpropyl)(2-methylpropyl)-, —C(O)—, —S—, —S(O)—, —S(O)$_2$—, —C(O)NH—, —C(O)N(methyl)-, —C(O)N(ethyl)-, —C(O)N(propyl)-, —C(O)N(butyl)-, —C(O)N(1-methylethyl)-, —C(O)N(1,1-dimethylethyl)-, —C(O)N(1-methylpropyl)-, —C(O)N(2-methylpropyl)-, —NHC(O)—, —N(methyl)C(O)—, —N(ethyl)C(O)—, —N(propyl)C(O)—, —N(butyl)C(O)—, —N(1-methylethyl)C(O)—, —N(1,1-dimethylethyl)C(O)—, —N(1-methylpropyl)C(O)—, —N(2-methylpropyl)C(O)—, —S(O)$_2$NH—, —S(O)$_2$N(methyl)-, —S(O)$_2$N(ethyl)-,)—S(O$_2$N(propyl)-, —S(O)$_2$N(butyl)-, —S(O)$_2$N(1-methylethyl)-, —S(O)$_2$N(1,1-dimethylethyl)-, —S(O)$_2$N(1-methylpropyl)-, —S(O)$_2$N(2-methylpropyl)-, —NHS(O)$_2$—, —N(methyl)S(O)$_2$—, —N(ethyl)S(O)$_2$—, —N(propyl)S(O)$_2$—, —N(butyl)S(O)$_2$—, —N(1-methylethyl)S(O)$_2$—, —N(1,1-dimethylethyl)S(O)$_2$—, —N(1-methylpropyl)S(O)$_2$—, and —N(2-methylpropyl)S(O)$_2$—. Preferably, X is a single bond, —NHC(O)—, —CH$_2$—, or —C(O)—. More preferably, X is a single bond, —CH$_2$—, or —C(O)—.

Specific examples of Y include a single bond, a cyclopropane ring group, a cyclobutane ring group, a cyclopentane ring group, an oxocyclopentane ring group, a cyclopentene ring group, a cyclohexane ring group, a cyclohexene ring group, a benzene ring group, an indan ring group, an oxoindan ring group, an indene ring group, a tetralone ring group, a naphthalene ring group, an azetidine ring group, a morpholine ring group, a piperidine ring group, a pyridine ring group, a pyridyl-N-oxide ring group, a pyran ring group, a pyrrole ring group, an imidazoline ring group, a thiazole ring group, a thiophene ring group, a dioxolane ring group, a thiadiazole ring group, a piperazine ring group, an isothiazole ring group, a thiazolidine ring group, a triazole ring group, a tetrazole ring group, an azepane ring group, a pyrrolidine ring group, an oxazolidine ring group, an isoxazolone ring group, a thiomorpholine ring group, a pyrrole ring group, a homopiperazine ring group, a 3,5-dioxopiperidine ring group, a pyrazolone ring group, a tetrahydropyran ring group, a tetrahydrothiopyran ring group, a 1-oxotetrahydrothiopyran ring group, a 1,1-dioxotetrahydrothiopyran ring group, a pyrimidine ring group, a pyrazine ring group, a pyridazine ring group, a pyrazole ring group, a pyrazoline ring group, an isoxazole ring group, a 4-oxopyrrolidine ring group, a 2-oxopyrrolidine ring group, a 4-oxothiazolidine ring group, a furan ring group, a thiophene ring group, an oxazole ring group, a benzoxazole ring group, a benzimidazole ring group, an oxadiazole ring group, a quinoline ring group, a 1,4-dihydroquinoline ring group, a 5,6-dihydro-4H-pyrrolo[3,4-d][1,3]thiazole ring group, a 1,2-dihydropyridine ring group, and a benzothiazole ring group. Preferably, Y is a single bond, a benzene ring group, a cyclopropane ring group, a pyrrolidine ring group, an oxazole ring group, a benzoxazole ring group, a benzimidazole ring group, a thiazole ring group, a thiadiazole ring group, a thiophene ring group, a tetrazole ring group, a 1,4-dihydroquinoline ring group, a benzothiazole ring group, a pyrimidine ring group, a 5,6-dihydro-4H-pyrrolo[3,4-d][1,3]thiazole ring group, a 1,2-dihydropyridine ring group, or a pyridine ring group. More preferably, Y is a benzothiazole ring group, a thiazole ring group, or a benzene ring group.

When a compound of the present invention represented by the general formula (I) has a basic group such as an amino group, a "pharmacologically acceptable salt thereof" can be formed by reacting the compound with an acid. Alternatively, when a compound of the present invention represented by the general formula (I) has an acidic group such as a carboxyl group, a "pharmacologically acceptable salt thereof" can be formed by reacting the compound with a base. Thus, these salts will be shown below.

Preferred examples of the salt based on a basic group include: inorganic acid salts such as hydrohalides (e.g., hydrochloride, hydrobromide, and hydroiodide), nitrate, perchlorate, sulfate, and phosphate; organic acid salts such as lower alkanesulfonates (e.g., methanesulfonate, trifluoromethanesulfonate, and ethanesulfonate), arylsulfonates (e.g., benzenesulfonate and p-toluenesulfonate), acetate, malate, fumarate, succinate, citrate, ascorbate, tartrate, oxalate, and maleate; and amino acid salts such as glycine salt, lysine salt, arginine salt, ornithine salt, glutamate, and aspartate.

On the other hand, preferred examples of the salt based on an acidic group include: metal salts such as alkali metal salts (e.g., sodium salt, potassium salt, and lithium salt), alkaline earth metal salts (e.g., calcium salt and magnesium salt), aluminum salt, and iron salt; amine salts such as inorganic salts (ammonium salt) and organic salts (e.g., t-octylamine salt, dibenzylamine salt, morpholine salt, glucosamine salt, phenylglycine alkyl ester salt, ethylenediamine salt, N-methylglucamine salt, guanidine salt, diethylamine salt, triethylamine salt, dicyclohexylamine salt, N,N'-dibenzylethylenediamine salt, chloroprocaine salt, procaine salt, diethanolamine salt, N-benzylphenethylamine salt, piperazine salt, tetramethylammonium salt, and tris(hydroxymethyl)aminomethane salt); and amino acid salts such as glycine salt, lysine salt, arginine salt, ornithine salt, glutamate, and aspartate.

When a compound of the present invention represented by the general formula (I) or the pharmacologically acceptable salt thereof has an asymmetric carbon atom in the molecule, stereoisomers with an R or S configuration are included. Each of these stereoisomers and all mixtures of the stereoisomers at arbitrary ratios are also encompassed by the present invention. Such stereoisomers can be prepared, for example, by synthesizing the compound (I) using an optically resolved starting compound or by optically resolving the synthesized compound (I) by a usual optical resolution or separation method, as desired.

The compound of the present invention represented by the general formula (I) or the pharmacologically acceptable salt thereof includes optical isomers. Each of these optical isomers and all mixtures of these optical isomers are also encompassed by the present invention.

The compound of the present invention represented by the general formula (I) or the pharmacologically acceptable salt thereof, when left in the air or recrystallized, may absorb water to associate with adsorbed water or to form a hydrate. Such water-containing compounds and salts are also encompassed by the present invention.

According to a further aspect, the present invention provides a compound represented by the formula (1) or a pharmacologically acceptable salt thereof, which is intended for use in a method for therapeutically treating a human or animal body.

We have found that compounds of the present invention inhibit bacterial DNA gyrase and are therefore important for antibacterial effects.

According to a further aspect, the present invention provides a method for producing an antibacterial effect in a warm-blooded animal (e.g., a human) in need of treatment which produces an antibacterial effect. This method comprises administering an effective amount of a compound of the present invention or a pharmacologically acceptable salt thereof to the animal.

According to a further aspect, the present invention provides a method for inhibiting bacterial DNA gyrase in a warm-blooded animal (e.g., a human) in need of treatment which produces an antibacterial effect. This method comprises administering an effective amount of a compound represented by the formula (1) as defined above or a pharmacologically acceptable salt thereof to the animal.

According to a further aspect, the present invention provides a method for treating bacterial infection in a warm-blooded animal (e.g., a human) in need of treatment of bacterial infection. This method comprises administering an effective amount of a compound represented by the formula (1) as defined above or a pharmacologically acceptable salt thereof to the animal.

A further aspect of the present invention provides a compound represented by the formula (1) or a pharmacologically acceptable salt thereof, which is intended for use as a pharmaceutical agent.

The pharmaceutical agent is appropriately an antibacterial agent.

In a convenient embodiment, this is a compound represented by the formula (1) or a pharmacologically acceptable salt thereof, which is intended for use as a pharmaceutical agent for producing an antibacterial effect in a warm-blooded animal (e.g., a human).

In another convenient embodiment, this is a compound represented by the formula (1) or a pharmacologically acceptable salt thereof, which is intended for use as a pharmaceutical agent for inhibiting bacterial DNA gyrase in a warm-blooded animal (e.g., a human).

Particularly, this is a compound represented by the formula (1) or a pharmacologically acceptable salt thereof, which is intended for use as a pharmaceutical agent for treating bacterial infection in a warm-blooded animal (e.g., a human).

According to a further aspect, the present invention provides use of a compound represented by the formula (1) or a pharmacologically acceptable salt thereof in the production of a pharmaceutical agent used for producing antibacterial effect in a warm-blooded animal (e.g., a human).

According to a further aspect, the present invention provides use of a compound represented by the formula (1) or a pharmacologically acceptable salt thereof in the production of a pharmaceutical agent used for inhibiting bacterial DNA gyrase in a warm-blooded animal (e.g., a human).

Thus, according to a further aspect, the present invention provides use of a compound represented by the formula (1) or a pharmacologically acceptable salt thereof in the production of a pharmaceutical agent used for treating bacterial infection in a warm-blooded animal (e.g., a human).

According to a further aspect, the present invention provides a compound represented by the formula (1) or a pharmacologically acceptable salt thereof, which is intended for use for producing an antibacterial effect in a warm-blooded animal (e.g., a human).

According to a further aspect, the present invention provides a compound represented by the formula (1) or a pharmacologically acceptable salt thereof, which is intended for use for inhibiting bacterial DNA gyrase in a warm-blooded animal (e.g., a human).

Thus, according to a further aspect, the present invention provides a compound represented by the formula (1) or a pharmacologically acceptable salt thereof, which is intended for use for treating bacterial infection in a warm-blooded animal (e.g., a human).

The compound represented by the formula (1) or a pharmacologically acceptable salt is used for therapeutically (including preventively) treating a mammal such as a human, particularly, in the treatment of infection (which will be mentioned later in this chapter in relation to the compound or pharmaceutical composition of the present invention). For this purpose, the compound or the salt is usually prepared into a pharmaceutical composition according to standard pharmaceutical practice.

Therefore, in an additional aspect, the present invention provides a pharmaceutical composition comprising the compound represented by the formula (1) or a pharmacologically acceptable salt thereof and a pharmaceutically acceptable diluent or carrier.

According to a further aspect, the present invention provides a pharmaceutical composition intended for use for inhibiting bacterial DNA gyrase in a warm-blooded animal (e.g., a human), the pharmaceutical composition comprising a compound represented by the formula (1) as defined above or a pharmacologically acceptable salt thereof, together with a pharmaceutically acceptable excipient or carrier.

According to a further aspect, the present invention provides a pharmaceutical composition intended for use for treating bacterial infection in a warm-blooded animal (e.g., a human), the pharmaceutical composition comprising a compound represented by the formula (1) as defined above or a pharmacologically acceptable salt thereof, together with a pharmaceutically acceptable excipient or carrier.

The composition of the present invention may be in a form suitable for oral use (e.g., tablets, lozenges, hard or soft capsules, aqueous or oily suspensions, emulsions, dispersible powders or granules, syrups, and elixirs), topical use (e.g., creams, ointments, gels, and aqueous or oily solutions or suspensions), administration by an inhalation method (e.g., finely grained powders and liquid aerosols), administration by an aeration method (e.g., pulverized powders), or parenteral administration (e.g., sterile aqueous or oily solutions for intravenous, hypodermic, or intramuscular administration and suppositories for rectal administration).

The compositions of the present invention can also be obtained by conventional approaches using conventional pharmaceutical excipients well known in the art.

Thus, the compositions intended for oral use may contain, for example, one or more coloring agent(s), sweetener(s), corrigent(s), and/or preservative(s).

Examples of the pharmaceutically acceptable excipients suitable for tablet preparation include: inert diluents, for example, lactose, sodium carbonate, calcium phosphate, and calcium carbonate; granulating agents and disintegrants, for example, corn starch and alginic acid; binders, for example, starch; lubricants, for example, magnesium stearate, stearic acid, and talc; preservatives, for example, ethyl p-hydroxybenzoate and propyl p-hydroxybenzoate; and antioxidants, for example, ascorbic acid.

The prepared tablets may be uncoated or may be coated for altering their disintegration, and subsequent enteral absorption of the active ingredient, or for improving their stability and/or appearance. In both cases, conventional coating agents and approaches well known in the art are used.

The compositions intended for oral use may be in the form of a hard gelatin capsule. In this case, the active ingredient is mixed with an inert solid diluent, for example, calcium carbonate, calcium phosphate, or kaolin. Alternatively, for use as a soft gelatin capsule, the active ingredient is mixed with water or oil, for example, peanut oil, liquid paraffin, or olive oil.

The aqueous suspensions generally comprise the active ingredient in a pulverized form, together with one or more suspending agent(s), for example, sodium carboxymethylcellulose, methylcellulose, hydroxypropylmethylcellulose, sodium alginate, polyvinylpyrrolidone, tragacanth gum, and gum arabic; and dispersant(s) or wetting agent(s), for example, lecithin, condensation products of alkylene oxides and fatty acids (e.g., polyoxyethylene stearate), condensation products of ethylene oxide and long-chain aliphatic alcohols (e.g., heptadecaethylene oxycetanol), condensation products of ethylene oxide and partial esters derived from fatty acids and hexitols (e.g., polyoxyethylene sorbitol monooleate), and condensation products of ethylene oxide and partial esters derived from fatty acids and hexitol anhydrides (e.g., polyethylene sorbitan monooleate).

The aqueous suspensions may also contain one or more preservative(s) (e.g., ethyl p-hydroxybenzoate and propyl p-hydroxybenzoate), antioxidant(s) (e.g., ascorbic acid), coloring agent(s), corrigent(s), and/or sweetener(s) (e.g., sucrose, saccharine, and aspartame).

The oily suspensions may be prepared by suspending the active ingredient in a plant oil (e.g., peanut oil, olive oil, sesame oil, or coconut oil) or a mineral oil (e.g., liquid paraffin). The oily suspensions may also contain a thickener such as beeswax, solid paraffin, or cetyl alcohol. To provide palatable oral preparations, such sweetener(s) and corrigent(s) as described above may be added thereto. These compositions may be stored by adding thereto an antioxidant such as ascorbic acid.

The dispersible powders and granules suitable for producing aqueous suspensions by the addition of water generally comprise the active ingredient, together with a dispersant or wetting agent, a suspending agent, and one or more preservative(s). Appropriate dispersants or wetting agents and suspending agents are already shown above. Moreover, additional excipients such as sweeteners, corrigents, and coloring agents may be contained therein.

Moreover, the pharmaceutical compositions of the present invention may be in the form of a water-in-oil emulsion. The oil phase can be a plant oil (e.g., olive oil or peanut oil) or a mineral oil (e.g., liquid paraffin), or any mixture thereof. Appropriate emulsifying agents can be, for example, naturally existing gums (e.g., gum arabic and tragacanth gum), naturally existing phosphatides (e.g., soybean and lecithin), esters or partial esters derived from fatty acids and hexitol anhydrides (e.g., sorbitan monooleate), and condensation products of the partial esters and ethylene oxide (e.g., polyoxyethylene sorbitan monolaurate). The emulsions may also contain a sweetener, a corrigent, and a preservative.

The syrups and the elixirs may be prepared together with a sweetener such as glycerol, propylene glycol, sorbitol, aspartame, or sucrose and may contain a demulcent, a preservative, a corrigent, and/or a coloring agent.

The present pharmaceutical compositions may be in the form of a sterile injectable aqueous or oily suspension. These suspensions may be prepared according to known approaches using one or more of the appropriate dispersants or wetting agents and suspending agents described above.
Moreover, the sterile injectable formulations may be sterile injectable solutions or suspensions in a nontoxic, parenterally acceptable diluent or solvent and are, for example, 1,3-butanediol solutions.

The compositions for use in administration by an inhalation method may be in the form of a conventional pressurized aerosol that is adjusted to distribute the active ingredient either as an aerosol containing pulverized solid or as an aerosol containing liquid droplets. Conventional aerosol propellants such as volatile fluorinated hydrocarbons or hydrocarbons may be used. An aerosol apparatus is appropriately adjusted to distribute a constant amount of the active ingredient.

For further information about preparation, the readers can refer to the chapter 25.2 in vol. 5 of Comprehensive Medicinal Chemistry (Corwin Hansch; editor in chief), Pergamon Press, 1990.

The amount of the active ingredient contained together with one or more excipient(s) for producing one dosage form is inevitably predicted to vary according to the host to be treated and the particular administration route. For example, a preparation intended for oral administration to a human is generally predicted to comprise, for example, 0.5 mg to 2 g of the active ingredient formulated together with an appropriate and convenient amount of excipient(s). In this context, the amount of the excipients can vary within the range of approximately 5 to approximately 98% by weight of the total weight of the composition. A unit dosage form is generally predicted to comprise approximately 1 mg to approximately 500 mg of the active ingredient. For further information about administration routes and dose schedules, the readers can refer to the chapter 25.3 in vol. 5 of Comprehensive Medicinal Chemistry (Corwin Hansch; editor in chief), Pergamon Press, 1990.

The pharmaceutical compositions of the present invention may also comprise, in addition to a compound of the present invention, one or more known agent(s) selected from other clinically useful antibacterial agents (e.g., macrolide, quinolone, β-lactam, and aminoglycoside agents) and/or other anti-infective agents (e.g., anti-fungal triazoles and amphotericin) or may be coadministered with these agents (simultaneously, continuously, or separately). Examples of these known agents include carbapenems, for example, meropenem and imipenem. Use of these agents can expand the therapeutic effectiveness of the pharmaceutical compositions of the present invention. The compounds of the present invention may also comprise a bactericidal/permeability-increasing protein (BPI) product or an efflux pump inhibitor for improving their activity against gram-negative bacteria and bacterial resistance to the antibacterial agent, or may be coadministered with these agents.

As described above, the magnitude of the dose necessary for the therapeutic or preventive treatment of a particular condition is inevitably predicted to vary according to the host to be treated, the administration route, and the severity of disease to be treated. Preferably, the daily dose is used within the range of 1 to 50 mg/kg. However, the daily dose is inevitably predicted to vary according to the host to be treated, the particular administration route, and the severity of the disease to be treated. Thus, the optimum dose may be determined by any general practitioner that provides treatment to the patient.

Moreover, the compounds represented by the formula (1) and the pharmacologically acceptable salts thereof are useful not only for use in therapeutic agents but also as pharmacological tools for development and standardization of in-vitro and in-vivo test systems for evaluating the effect of a DNA gyrase inhibitor in experimental animals (e.g., cats, dogs, rabbits, monkeys, rats, or mice) as part of a search for novel therapeutic agents.

Alternative preferred embodiments of the compounds of the present invention described herein are also applied to the aspects of additional pharmaceutical compositions, processes, methods, uses, and production of pharmaceutical agents other than those described above.

The present invention provides synthesis methods for producing the compounds represented by the formula (1) or the pharmacologically acceptable salts thereof.
Synthesis Method 1)
A compound represented by the formula (1) wherein W is —C($R^6$)($R^7$)— is converted from a compound represented by the formula (2):

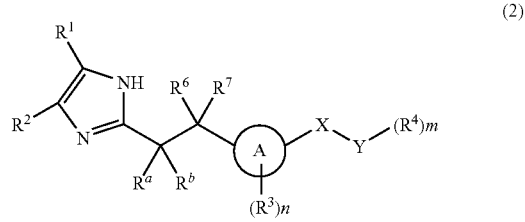

wherein $R^a$ is cyano, and $R^b$ is dimethylamino or diethylamino; or $R^a$ and $R^b$ are each independently selected from —S($C_1$-$C_4$) alkyl groups; or $R^a$ and $R^b$ may together form a 1,3-dithiane ring or a 1,3-dithiolane ring.
Synthesis Method 2)
A compound represented by the formula (1) wherein W is —O— is synthesized from a compound represented by the formula (3):

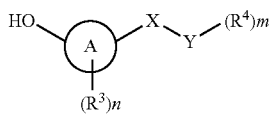
(3)

and a carboxylic acid represented by the formula (4):

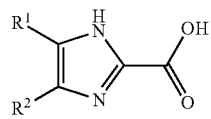
(4)

Synthesis Method 3)
A compound represented by the formula (1) wherein W is —N(R$^5$) is synthesized from a compound represented by the formula (5):

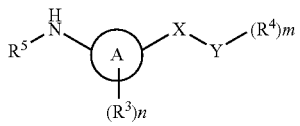
(5)

and the carboxylic acid represented by the formula (4) or an activated derivative thereof.

Synthesis Method 4)
A compound represented by the formula (1) wherein W is —C(R$^6$)(R$^7$)— is synthesized from a compound represented by the formula (6):

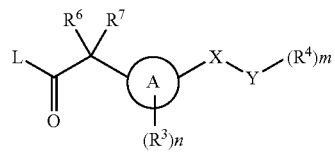
(6)

wherein L is a group which may be substituted, and a compound represented by the formula (7):

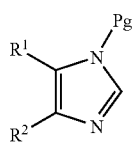
(7)

wherein Pg is a protecting group.

Synthesis Method 5)
A compound represented by the formula (1) wherein W is —C(R$^6$)(R$^7$)— is synthesized from a compound represented by the formula (8):

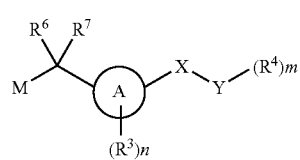
(8)

wherein M is an organometal species, and a compound represented by the formula (9):

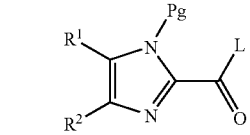
(9)

wherein L is a group which may be substituted, and Pg is a protecting group.

Synthesis Method 6)
A compound represented by the formula (1) wherein W is a single bond is synthesized from a compound represented by the formula (10):

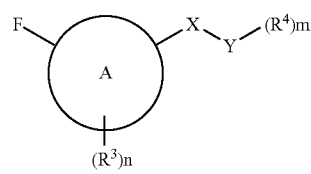
(10)

wherein F is hydrogen or an organometal species, and the carboxylic acid represented by the formula (4) or an activated derivative thereof.

Synthesis Method 7)
A compound represented by the formula (1) is synthesized from a compound represented by the formula (11):

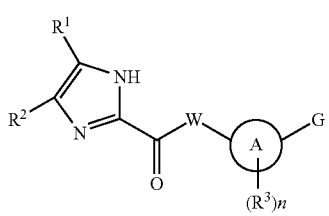
(11)

wherein G is an organometal species or hydrogen, and a compound represented by the formula (12):

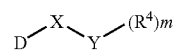
(12)

wherein D is a group which may be substituted.

Synthesis Method 8)
A compound represented by the formula (1) wherein X is —C(O)— is synthesized from the compound represented by the formula (11):

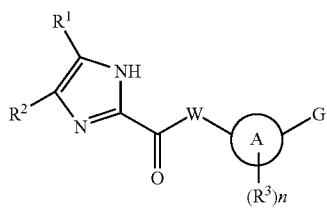

wherein G is hydrogen or an organometal species, and a carboxylic acid represented by the formula (13):

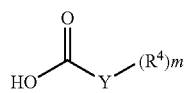

or an activated derivative thereof.

Synthesis Method 9)
Conversion From The Compound Represented By The Formula (1) To Another Compound Represented By The Formula (1)

Synthesis Method 10)
Conversion To The Compound Represented By The Formula (1) By Removal Of The Protecting Group Synthesis Method 11)
Conversion To A Pharmacologically Acceptable Salt Containing The Compound Represented By The Formula (1)

Description of Abbreviations

L represents a group which may be substituted and encompasses halo as an appropriate example, and examples thereof include chloro, bromo, pentafluorophenoxy, and 2,5-oxopyrrolidin-1-yloxy.

D represents a group which may be substituted and encompasses halo as an appropriate example, and examples thereof include chloro, bromo, iodo, p-toluenesulfonyloxy, and methanesulfonyloxy.

Pg represents a protecting group for the functional group and encompasses trimethylsilylethoxymethyl or benzyloxycarbonyl as an appropriate example, and examples thereof include methoxymethyl, tetrahydropyranyl, and t-butyloxycarbonyl.

M encompasses an organocopper compound as an appropriate example, and examples thereof include copper lithium, organozinc compounds, zinc, and Grignard reagents (e.g., magnesium chloride).

F represents a group which may be substituted and encompasses hydrogen or an organocopper compound as an appropriate example, and examples thereof include copper lithium, organozinc compounds, zinc, and Grignard reagents (e.g., magnesium chloride).

G represents a group which may be substituted and encompasses hydrogen or an organoboron compound as an appropriate example, and examples thereof include —B(OR$^a$)$_2$ (wherein R$^a$ is hydrogen or C$_2$-C$_4$ alkyl), organocopper compounds (e.g., copper lithium), organozinc, zinc, Grignard reagents (e.g., magnesium chloride), and organotin compounds (e.g., trimethyltin and tributyltin).

Special reaction conditions for the reactions will be shown below.

Synthesis Method 1)
Conversion Of The Compound Represented By The Formula (1) Wherein W Is —C(R)(R$^7$)— From The Compound Represented By The Formula (2)

For The Case Where R$^a$ Is Cyano, And R$^b$ Is Dimethylamino Or Diethylamino

For example, the compound represented by the formula (2) is treated in an appropriate solvent, for example, aqueous methanol, at room temperature in the presence of a base such as sodium hydroxide.

For The Case Where R$^a$ And R$^b$ Are Each Independently Selected from —S(C$_1$-C$_4$) Alkyl Groups; Or R$^a$ And R$^b$ Together Form A 1,3-Dithiane Ring Or A 1,3-Dithiolane Ring For example, the compound represented by the formula (2) is treated in an appropriate solvent, for example, methanol, ethanol, or acetone, in the range of room temperature to reflux temperature in the presence of a mercury salt, copper salt, or silver salt such as mercury (II) perchlorate, copper (II) chloride, silver nitrate, or silver oxide.

The compound represented by the formula (2) is synthesized according to scheme 1.

Scheme 1

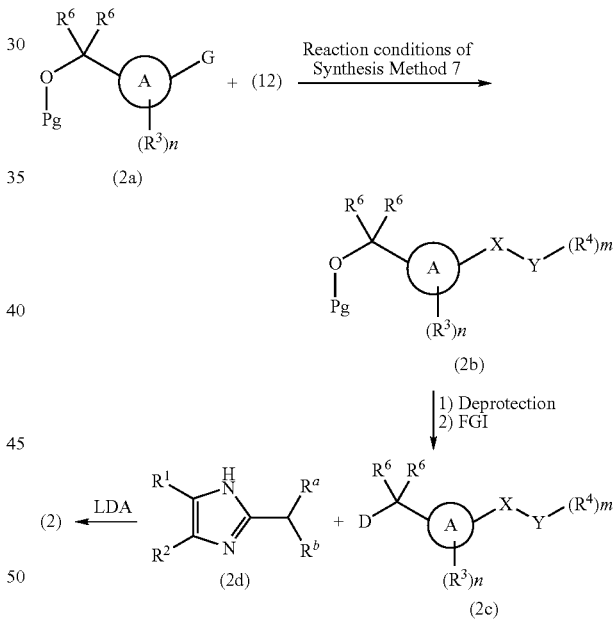

wherein Pg is a protecting group for a hydroxyl group and is defined above as a protecting group for the functional group; and D is defined above as a group which may be substituted.

The deprotection of the hydroxyl group is well known in the art.

FGI means functional group interconversion. The interconversion from the hydroxyl group to the group D in the scheme is well known in the art and can be practised by those skilled in the art.

The compounds represented by the formula (2a) or (2b) are compounds known in documents or compounds synthesized by standard synthesis methods well known in the art.

Synthesis Method 2)

The compound represented by the formula (3) and the compound represented by the formula (4) can be reacted in an appropriate solvent, for example, methylene chloride, THF, or diethyl ether, in the presence of a condensing agent such as dicyclohexylcarbodiimide or 1-ethyl-3-(3-dimethylaminopropyl)carbodiimide hydrochloride (EDCI).

The compound represented by the formula (3) is synthesized according to scheme 2.

Scheme 2

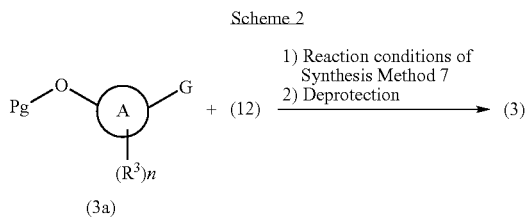

(3a)

wherein Pg is a protecting group for a hydroxyl group and is defined above as a protecting group for the functional group.

The deprotection of the hydroxyl group is described in documents well known in the art.

The compounds represented by the formula (3a) or (4) are commercially available compounds, compounds known in documents, or compounds synthesized by standard synthesis methods well known in the art.

Synthesis Method 3)

The compound represented by the formula (5) and the compound represented by the formula (4) can be condensed in the presence of an appropriate condensing agent.

A standard peptide coupling reagent known in the art can be used as an appropriate coupling reagent. Alternative examples of the coupling reagent include carbonyldiimidazole, dicyclohexyl-carbodiimide, and 1-ethyl-3-(3-dimethylaminopropyl)carbodiimide hydrochloride (EDCI). The reaction may be performed optionally in the presence of a catalyst (e.g., 1-hydroxy-benzotriazole, HOBT, dimethylaminopyridine, or 4-pyrrolidinopyridine) and optionally in the presence of a base (e.g., triethylamine, di-isopropylethylamine, pyridine, or 2,6-di-alkyl-pyridine (e.g., 2,6-lutidine or 2,6-di-tert-butylpyridine)).

Examples of an appropriate solvent include dimethylacetamide, methylene chloride, toluene, N-methylpyrrolidone, tetrahydrofuran, and dimethylformamide.

The coupling reaction is performed in the temperature range of −40° C. to 40° C.

Appropriate examples of the activated derivative of the acid include acid halides, for example, acid chlorides. Alternative examples thereof include active esters, for example, pentafluorophenyl esters. The reaction of these types of compounds with amines is well known in the art. For example, they can be reacted in an appropriate solvent (e.g., such a solvent as described above) in the presence of a base (e.g., such a base as described above).

Such a reaction is performed in the temperature range of −40° C. to 40° C.

The compound represented by the formula (5) is synthesized according to scheme 3.

Scheme 3

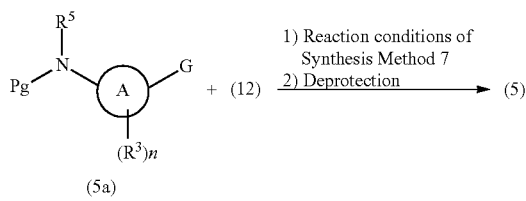

(5a)

wherein Pg is a protecting group for the amino group and is defined above as a protecting group for the functional group. Those skilled in the art can understand here that an appropriate protecting group needs to be introduced when $R^5$ is hydrogen.

The deprotection of the amino group is described in documents well known in the art.

The compounds represented by the formula (5a) are commercially available compounds, compounds known in documents, or compounds synthesized by standard synthesis methods well known in the art.

Synthesis Method 4)

The compound represented by the formula (6) and the compound represented by the formula (7) can be reacted in the range of −80° C. to 0° C. in an appropriate solvent, for example, THF or diethyl ether, in the presence of an alkyl lithium such as butyl lithium.

The compound represented by the formula (6) is synthesized according to scheme 4.

Scheme 4

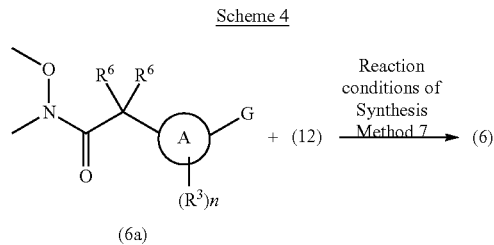

(6a)

The compounds represented by the formula (6a) or (7) are commercially available compounds, compounds known in documents, or compounds synthesized by standard synthesis methods well known in the art.

Synthesis Method 5)

The compound represented by the formula (8) and the compound represented by the formula (9) can be reacted in the range of −80° C. to 0° C. in an appropriate aprotic solvent, for example, THF or diethyl ether.

The compound represented by the formula (8) is synthesized from a compound represented by the formula (2c) under standard conditions well known in the art. For example, the compound represented by the formula (8) wherein M is an organocopper compound can be synthesized according to scheme 5.

Scheme 5

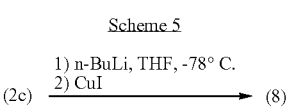

The compounds represented by the formula (9) are commercially available compounds, compounds known in documents, or compounds synthesized by standard synthesis methods well known in the art.
Synthesis Method 6)
Reaction Between The Compound Represented By The Formula (10) And The Compound Represented By The Formula (4) For The Case Where F In The Compound Represented By The Formula (10) Is Bound To A Nitrogen Atom
F in the compound represented by the formula (10) is hydrogen, and the compound represented by the formula (10) and the compound represented by the formula (4) can be reacted under the reaction conditions of Synthesis Method 3).

For The Case Where F In The Compound Represented By The Formula (10) Is Bound To A Carbon Atom
F in the compound represented by the formula (10) is an organometal species and encompasses an organocopper compound as an appropriate organometal compound. For example, the compound represented by the formula (10) wherein F is an organocopper compound can be synthesized with reference to the scheme 5. For example, the compound represented by the formula (10) and the activated derivative (e.g., acid chloride) of the carboxylic acid represented by the formula (4) can be reacted in the range of −80° C. to 0° C. in an appropriate aprotic solvent, for example, THF or diethyl ether.
Synthesis Method 7)
Reaction Between The Compound Represented By The Formula (11) And The Compound Represented By The Formula (12) For The Case Where G In The Compound Represented By The Formula (11) Is Bound To A Nitrogen Atom
G in the compound represented by the formula (11) is hydrogen, and the compound represented by the formula (11) and the compound represented by the formula (12) can be reacted in an appropriate solvent, for example, dioxane, DMF, or dimethylaminoacetamide, in the presence of a base such as triethylamine, diisopropylethylamine, or cesium carbonate and optionally in the presence of a catalyst such as copper (I) iodide or palladium (II) acetate under heating conditions or using a microwave irradiation reactor.
For The Case Where G In The Compound Represented By The Formula (11) Is Bound To A Carbon Atom
G in the compound represented by the formula (11) is an organometal species and encompasses an organoboron compound as an appropriate organometal compound. Examples thereof include —B(OR$^a$)$_2$ (wherein R$^a$ is hydrogen or C$_1$-C$_4$ alkyl), organocopper compounds (e.g., copper lithium), organozinc, zinc, Grignard reagents (e.g., magnesium chloride), and organotin compounds (e.g., trimethyltin and tributyltin). The compound represented by the formula (11) and the compound represented by the formula (12) can be reacted in an appropriate solvent, for example, dioxane, THF, toluene, or DMF, optionally in the presence of a base such as cesium carbonate or sodium carbonate, in the presence of a catalyst such as tetrakis(triphenylphosphine)palladium, and optionally in the presence of water under heating conditions or using a microwave irradiation reactor.

The compound represented by the formula (11) is synthesized according to scheme 6.

Scheme 6

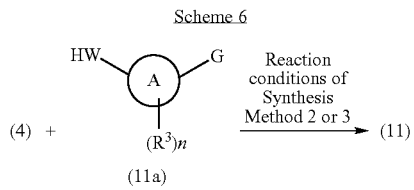

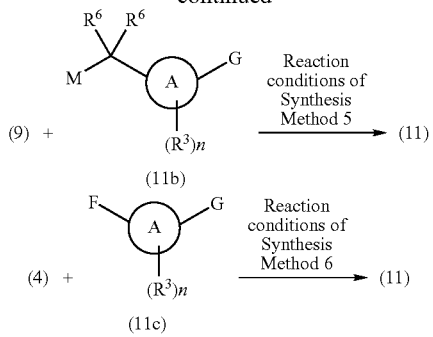

wherein M is defined above as an organometal species. The compounds represented by the formula (11a), (11b), (11c), or (12) are commercially available compounds, compounds known in documents, or compounds synthesized by standard synthesis methods well known in the art.
Synthesis Method 8)
Reaction Between The Compound Represented By The Formula (11) And The Compound Represented By The Formula (13) For The Case Where G In The Compound Represented By The Formula (11) Is Bound To A Nitrogen Atom
G in the compound represented by the formula (11) is hydrogen, and the compound represented by the formula (11) and the compound represented by the formula (13) can be reacted under the conditions of Synthesis Method 3).
For The Case Where G In The Compound Represented By The Formula (11) Is Bound To A Carbon Atom
G in the compound represented by the formula (11) is an organometal species and encompasses an organocopper compound as an appropriate organometal compound. For example, the compound represented by the formula (11) wherein G is an organocopper compound can be synthesized with reference to the scheme 5. Moreover, the compound represented by the formula (13) can be converted to an acid chloride by a standard synthesis method known in the art. For example, the compound represented by the formula (11) and the acid chloride converted from the compound represented by the formula (13) can be reacted in the range of −80° C. to 0° C. in an appropriate aprotic solvent, for example, THF or diethyl ether.

In this context, the compounds represented by the formula (13) are commercially available compounds, compounds known in documents, or compounds synthesized by standard synthesis methods well known in the art.

A synthesis method for producing the pharmacologically acceptable salt is within the skill routinely used by usual organic chemists.

Of course, substituents for various predetermined rings in the compound of the present invention may be introduced through standard aromatic substitution reaction either prior to the synthesis methods or immediately thereafter such that they are contained in the embodiments of the synthesis methods of the present invention. Alternatively, these substituents may be formed by the conventional modification of the functional groups.

Reagents used for introducing such substituents for rings are either commercially available or produced by synthesis methods known in the art.

A certain compound represented by the formula (1) can be converted to another compound represented by the formula (1).

Examples of such reaction and modification include introduction of substituents through aromatic substitution reaction, reduction of substituents, alkylation of substituents, oxidation of substituents, esterification of substituents, amination of substituents, and formation of heteroaryl rings. Reagents and reaction conditions for such approaches are well known in the chemical field.

Examples of the particular aromatic substitution reaction include introduction of alkoxide, diazotization reaction, and introduction of thiol, alcohol, or halogen groups. Examples of the modification include oxidation of alkylthio into alkylsulfinyl or alkylsulfonyl.

Skilled organic chemists can presumably obtain necessary starting materials and products by using reference documents described below, Examples described therein, information contained in Examples described herein, and information referred to in these Examples and adjusting them.

When starting materials necessary for such approaches as described above are not commercially available, they may be formed by an approach selected from standard organic chemical techniques, techniques similar to the synthesis of structurally similar known compounds, and techniques similar to approaches described in the procedures described above or in Examples.

It should be noted that many starting materials for the synthesis methods are commercially available and/or have been reported widely in scientific documents or can be formed from commercially available products by appropriately using synthesis methods reported in scientific documents. As a general guide to reaction conditions or reagents, further see Advanced Organic Chemistry, vol. 4 (Jerry March, ed., published by John Wiley and Sons, 1992).

Of course, for some of the reactions described herein, the protection of every highly reactive group in the compound is also predicted to be required or desired in some cases.

The case where such protection is required or desired is known as a method suitable for such protection by those skilled in the art.

Conventional protecting groups can be used according to standard techniques (for the illustrative purpose, see T. W. Greene, Protective Groups in Organic Synthesis, John Wiley and Sons, 1991).

Examples of the protecting groups suitable for the hydroxy group include acyl groups, for example, alkanoyl groups (e.g., acetyl), aroyl groups (e.g., benzoyl), silyl groups (e.g., trimethylsilyl), and arylmethyl groups (e.g., benzyl).

Deprotection conditions for the protecting groups are inevitably predicted to vary according to the selection of the protecting groups.

Thus, for example, acyl groups such as alkanoyl or aroyl groups may be removed, for example, by hydrolysis with an appropriate base such as an alkali metal hydroxide (e.g., lithium hydroxide or sodium hydroxide).

Alternatively, silyl groups such as trimethylsilyl may be removed using, for example, fluoride or an aqueous acid solution; or arylmethyl groups such as a benzyl group may be removed, for example, by the addition of hydrogen in the presence of a palladium-supported catalyst (e.g., active carbon).

Examples of the protecting groups suitable for the amino group include acyl groups, for example, alkanoyl groups (e.g., acetyl), alkoxycarbonyl groups (e.g., methoxycarbonyl, ethoxycarbonyl, and t-butoxycarbonyl), arylmethoxycarbonyl groups (e.g., benzyloxycarbonyl), and aroyl groups (e.g., benzoyl).

Deprotection conditions for the protecting groups inevitably vary according to the selection of the protecting groups.

Thus, for example, acyl groups such as alkanoyl or alkoxycarbonyl groups or aroyl groups may be removed, for example, by hydrolysis with an appropriate base such as an alkali metal hydroxide (e.g., lithium hydroxide or sodium hydroxide).

Alternatively, alkoxycarbonyl groups (e.g., a t-butoxycarbonyl group) may be removed, for example, by treatment with an appropriate acid such as hydrochloric acid, sulfuric acid, phosphoric acid, or trifluoroacetic acid. Arylmethoxycarbonyl groups (e.g., a benzyloxycarbonyl group) may be removed, for example, by the addition of hydrogen in the presence of a palladium-supported catalyst (e.g., active carbon) or by treatment with a Lewis acid, for example, boron tris(trifluoroacetate).

Moreover, examples of the protecting groups suitable for the primary amino group include a phthaloyl group, which may be removed by treatment with an alkylamine (e.g., dimethylaminopropylamine or 2-hydroxyethylamine) or hydrazine.

Examples of the protecting groups suitable for the carboxyl group include esterifiable substituents, for example, methyl, ethyl, t-butyl, and benzyl groups. Deprotection conditions for the protecting groups are inevitably predicted to vary according to the selection of the protecting groups.

Thus, for example, a methyl ester or ethyl ester group may be removed, for example, by hydrolysis with an appropriate base such as sodium hydroxide. For example, a t-butyl ester group may be removed, for example, by treatment with an organic acid such as trifluoroacetic acid. A benzyl ester group may be removed, for example, by the addition of hydrogen in the presence of a palladium-supported catalyst (e.g., active carbon).

These protecting groups may be removed at any convenient stage of synthesis using conventional techniques well known in the chemical field. Alternatively, the protecting groups may be removed in subsequent reaction steps or during workup.

The removal of every protecting group and the formation of the pharmacologically acceptable salt are within the ability of usual organic chemists to use standard techniques.

Further information about these steps is described above.

When an optically active form of the compound of the present invention is required, this form may be obtained by subjecting an optically active starting material (e.g., formed by asymmetric derivatization in an appropriate reaction step) to any one of the approaches described above; or by resolving a racemic form of the present compound or an intermediate thereof using standard procedures; or by separating a diastereoisomer, if formed, by chromatography.

Moreover, enzymatic techniques can also be useful in the production of the optically active compound and/or intermediate.

Likewise, when a pure regioisomer of the compound of the present invention is required, this isomer may be obtained by subjecting a pure regioisomer as a starting material to any one of the approaches described above or by resolving a mixture of regioisomers or intermediates thereof using standard procedures.

EXAMPLES

The present invention will be described in more detail below with reference to Examples, Reference Examples and Test Examples; however, the scope of the present invention is not limited thereto.

Example 1 cis(±)-2-(4-{[(4-Chloro-5-ethyl-1H-imidazol-2-yl)carbonyl]amino}-3-methoxypiperidin-1-yl)-1,3-benzothiazole-7-carboxylic acid (Exemplified Compound No. 1)

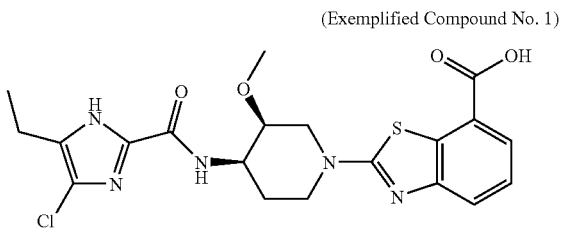 [SMILES: CCc1[nH]c(C(=O)N[C@@H]2CCN(c3nc4cccc(C(=O)O)c4s3)C[C@@H]2OC)nc1Cl]

(1a) 1-Amino-butan-2-one hydrochloride

The compound was synthesized according to the method described in the following document.
Synlett., 11, 2004, 2031-2033

(1b) Ethyl 5-ethyl-1H-imidazole-2-carboxylate

Sodium acetate (9.3 g, 113.4 mmol) was added to a solution of 1-amino-butan-2-one hydrochloride (3.41 g, 27.60 mmol) and ethyl imino(methylthio)acetate tetrafluoroborate (7.45 g, 31.84 mmol) synthesized according to the method described in the document (J. Med. Chem., 38, 1995, 2196-2201) in acetic acid (120 mL), and the mixture was stirred at 100° C. for four hours. The reaction solution was concentrated under reduced pressure and then saturated aqueous sodium bicarbonate solution was added to the reaction solution, followed by extraction with ethyl acetate. Then, the organic layer was washed with brine and dried over anhydrous sodium sulfate. Following concentration under reduced pressure, the residue was purified by silica gel column chromatography (elution solvent: hexane/ethyl acetate=5/1, 2/1, 1/2) to obtain 3.35 g of the title compound as a pale yellow solid (72%).

$^1$H NMR spectrum (400 MHz, CDCl$_3$) δ ppm: 1.28 (3H, t, J=7.66 Hz), 1.42 (3H, t, J=7.15 Hz), 2.70 (2H, q, J=7.66 Hz), 4.42 (2H, q, J=7.15 Hz), 6.96 (1H, s).

(1c) Ethyl 4-chloro-5-ethyl-1H-imidazole-2-carboxylate

NCS (3.15 g, 23.59 mmol) was added to a solution of ethyl 5-ethyl-1H-imidazole-2-carboxylate obtained in Example (1b) (3.35 g, 19.92 mmol) in chloroform (100 mL), and the mixture was stirred at room temperature for 28 hours. Saturated aqueous sodium bicarbonate solution was added to the reaction solution, followed by extraction with chloroform. Then, the organic layer was washed with brine and dried over anhydrous sodium sulfate. Following concentration under reduced pressure, the residue was purified by silica gel column chromatography (elution solvent: hexane/ethyl acetate=4/1, 3/1) to obtain 1.81 g of the title compound as a pale yellow solid (45%).

$^1$H NMR spectrum (400 MHz, CDCl$_3$) δ ppm: 1.27 (3H, t, J=7.61 Hz), 1.41 (3H, t, J=7.12 Hz), 2.71 (2H, q, J=7.61 Hz), 4.42 (2H, q, J=7.12 Hz), 10.46 (1H, s).

(1d) 4-Chloro-5-ethyl-1H-imidazole-2-carboxylic acid

Ethyl 4-chloro-5-ethyl-1H-imidazole-2-carboxylate obtained in Example (1c) (0.52 g, 2.56 mmol) was dissolved in methanol (8 mL) and dichloromethane (2 mL), and the solution was slowly added dropwise to a 3 N aqueous lithium hydroxide solution (3.5 mL, 10.5 mmol) heated to 70° C. Following stirring at that temperature for 40 minutes, the reaction solution was concentrated under reduced pressure and 1 N hydrochloric acid was added dropwise until the pH was 7. Thereafter, purification by reverse phase silica gel column chromatography (elution solvent: distilled water) gave 0.48 g of the title compound as a white solid (100%).

$^1$H NMR spectrum (400 MHz, DMSO-d$_6$) δ ppm: 1.10 (3H, t, J=7.32 Hz), 2.44-2.51 (2H, m).

(1e) tert-Butyl cis(±)-4-amino-3-methoxypiperidine-1-carboxylate

The compound was synthesized according to the method described in the following document.
WO 2006/087543 A1

(1f) Ethyl 2-bromo-1,3-benzothiazole-7-carboxylate

The compound was synthesized according to the method described in the following document.
WO 2006/087543 A1

(1g) tert-Butyl cis(±)-4-{[(4-chloro-5-ethyl-1H-imidazol-2-yl)carbonyl]amino}-3-methoxypiperidine-1-carboxylate WSC hydrochloride (580 mg, 3.02 mmol) and DMAP (125 mg, 1.02 mmol) were added to a solution of tert-butyl cis(±)-4-amino-3-methoxypiperidine-1-carboxylate obtained in Example (1e) (230 mg, 0.99 mmol) and ethyl 4-chloro-5-ethyl-1H-imidazole-2-carboxylate obtained in Example (1d) (85 mg, 0.49 mmol) in DMA (5 mL), and the mixture was stirred at room temperature for three hours. Dilute hydrochloric acid was added to the reaction solution, followed by extraction with ethyl acetate. Then, the organic layer was washed with water, saturated aqueous sodium bicarbonate solution and brine, and dried over anhydrous sodium sulfate. Following concentration under reduced pressure, the residue was purified by silica gel column chromatography (elution solvent: hexane/ethyl acetate=1/1, ethyl acetate) to obtain 117 mg of the title compound as a pale yellow solid (62%).

$^1$H NMR spectrum (400 MHz, CDCl$_3$) δ ppm: 1.26 (3H, t, J=7.62 Hz), 1.47 (9H, s), 1.57-1.70 (1H, m), 1.78-1.92 (1H, m), 2.68 (2H, q, J=7.62 Hz), 2.74-2.84 (2H, m), 3.33-3.39 (2H, m), 3.41 (3H, s), 4.05-4.50 (2H, m), 7.44-7.52 (1H, m), 11.27 (1H, s).

(1h) Ethyl cis(±)-2-(4-{[(4-chloro-5-ethyl-1H-imidazol-2-yl)carbonyl]amino}-3-methoxypiperidin-1-yl)-1,3-benzothiazole-7-carboxylate tert-Butyl cis(±)-4-{[(4-chloro-5-ethyl-1H-imidazol-2-yl)carbonyl]amino}-3-methoxypiperidine-1-carboxylate obtained in Example (1g) (117 mg, 0.30 mmol) was dissolved in methanol (2 mL). A 4 N hydrochloric acid/ethyl acetate solution (5 mL) was added, and the mixture was stirred at room temperature for one hour. Following concentration under reduced pressure, the residue was dissolved in DMF (3 mL).

Diisopropylethylamine (0.32 mL, 1.84 mmol) and ethyl 2-bromo-1,3-benzothiazole-7-carboxylate obtained in Example (1f) (87 mg, 0.30 mmol) were added, and the mixture was stirred at 70° C. for two hours. Dilute hydrochloric acid was added to the reaction solution, followed by extraction with ethyl acetate. The organic layer was washed with water, saturated aqueous sodium bicarbonate solution and brine, and dried over anhydrous sodium sulfate. Following concentration under reduced pressure, the residue was purified by silica gel column chromatography (elution solvent: hexane/ethyl acetate=5/1, ethyl acetate) to obtain 97 mg of the title compound as a pale yellow solid (65%).

$^1$H NMR spectrum (400 MHz, CDCl$_3$) δ ppm: 1.28 (3H, t, J=7.57 Hz), 1.44 (3H, t, J=7.12 Hz), 1.82-1.88 (1H, m), 2.05-2.16 (1H, m), 2.70 (2H, q, J=7.57 Hz), 3.20-3.33 (2H, m), 3.45 (3H, s), 3.55 (1H, br s), 4.23-4.34 (2H, m), 4.45 (2H, q, J=7.12 Hz), 4.58-4.67 (1H, m), 7.31-7.41 (1H, m), 7.53 (1H, d, J=9.03 Hz), 7.70 (1H, dd, J=7.93, 1.10 Hz), 7.74-7.83 (1H, m), 11.33 (1H, s).

(1i) cis(±)-2-(4-{[(4-Chloro-5-ethyl-1H-imidazol-2-yl)carbonyl]amino}-3-methoxypiperidin-1-yl)-1,3-benzothiazole-7-carboxylic acid Ethyl cis(±)-2-(4-{[(4-chloro-5-ethyl-1H-imidazol-2-yl)carbonyl]amino}-3-methoxypiperidin-1-yl)-1,3-benzothiazole-7-carboxylate obtained in Example (1h) (95 mg, 0.19 mmol) was dissolved in methanol (5 mL) and dichloromethane (2 mL). A 2 N aqueous lithium hydroxide solution (3 mL) was added, and the mixture was stirred at 70° C. for 1.5 hours. The organic solvent was evaporated under reduced pressure and 1 N hydrochloric acid was added until the pH of the solution was about 4. The resulting solid was collected by filtration and washed with distilled water to obtain 75 mg of the title compound as a white solid (84%).

$^1$H NMR spectrum (400 MHz, DMSO-$d_6$) δ ppm: 1.14 (3H, t, J=7.56 Hz), 1.68-1.77 (1H, m), 1.85-1.99 (1H, m), 2.55 (2H, q, J=7.56 Hz), 3.35-3.45 (5H, m), 3.60 (1H, br s), 4.07-4.17 (1H, m), 4.20-4.30 (1H, m), 4.36-4.48 (1H, m), 7.36-7.43 (1H, m), 7.63-7.71 (3H, m), 13.38 (1H, br s), 13.48 (1H, br s).

mass spectrum (ESI): m/z 464 (M+H)$^+$.

Example 2 cis(±)-2-(4-{[(4,5-Dibromo-1H-imidazol-2-yl)carbonyl]amino}-3-methoxypiperidin-1-yl)-1,3-thiazole-5-carboxylic acid (Exemplified Compound No. 2)

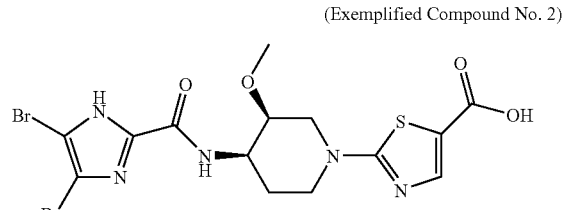

(2a) 4,5-Dibromoimidazole-2-carboxylic acid

The compound was synthesized according to the method described in the following document.

J. Heterocycle. Chem., 17, 1980, 409-411

(2b) tert-Butyl cis(±)-4-{[(4,5-dibromo-1H-imidazol-2-yl)carbonyl]amino}-3-methoxypiperidine-1-carboxylate The same operation as in Example (1g) was performed using tert-butyl cis(±)-4-amino-3-methoxypiperidine-1-carboxylate obtained by the method described in Example (1e) (300 mg, 1.30 mmol), 4,5-dibromoimidazole-2-carboxylic acid obtained in Example (2a) (300 mg, 1.11 mmol), WSC hydrochloride (460 mg, 2.40 mmol) and DMAP (50 mg, 0.41 mmol), to obtain 384 mg of the title compound as a white solid (72%).

$^1$H NMR spectrum (400 MHz, CDCl$_3$) δ ppm: 1.48 (9H, s), 1.68-1.71 (1H, m), 1.86-1.93 (1H, m), 2.72-2.85 (2H, m), 3.39-3.42 (1H, m), 3.42 (3H, s), 4.18-4.21 (2H, m), 4.37-4.44 (1H, m), 7.55 (1H, brs).

(2c) Ethyl cis(±)-2-(4-{[(4,5-dibromo-1H-imidazol-2-yl)carbonyl]amino}-3-methoxypiperidin-1-yl)-1,3-thiazole-5-carboxylate The same operation as in Example (1h) was performed using tert-butyl cis(±)-4-{[(4,5-dibromo-1H-imidazol-2-yl)carbonyl]amino}-3-methoxypiperidine-1-carboxylate obtained in Example (2b) (384 mg, 0.80 mmol), a 4 N hydrochloric acid/ethyl acetate solution (8 ml), diisopropylethylamine (0.7 mL, 4.02 mmol) and ethyl 2-bromo-1,3-thiazole-5-carboxylate (0.15 mL, 1.00 mmol), to obtain 249 mg of the title compound as an orange solid substance (58%).

$^1$H NMR spectrum (400 MHz, DMSO-$d_6$) δ ppm: 1.25 (3H, t, J=7.05 Hz), 1.67-1.71 (1H, m), 1.87-1.92 (1H, m), 3.32 (3H, s), 3.59 (1H, brs), 3.93-4.05 (2H, m), 4.21 (2H, q, J=7.05 Hz), 4.21-4.25 (2H, m), 4.31-4.36 (1H, m), 7.82 (1H, s), 7.87 (1H, d, J=8.20 Hz).

(2d) cis(±)-2-(4-{[(4,5-Dibromo-1H-imidazol-2-yl)carbonyl]amino}-3-methoxypiperidin-1-yl)-1,3-thiazole-5-carboxylic acid The same operation as in Example (1i) was performed using ethyl cis(±)-2-(4-{[(4,5-dibromo-1H-imidazol-2-yl)carbonyl]amino}-3-methoxypiperidin-1-yl)-1,3-thiazole-5-carboxylate obtained in Example (2c) (249 mg, 0.46 mmol) and a 2 N aqueous lithium hydroxide solution (10 mL), to obtain 164 mg of the title compound as a white solid (69%).

$^1$H NMR spectrum (400 MHz, DMSO-$d_6$) δ ppm: 1.67-1.70 (1H, m), 1.85-1.93 (1H, m), 3.29-3.34 (2H, m), 3.33 (3H, s), 3.58 (1H, brs), 3.91-3.94 (1H, m), 4.19-4.23 (1H, m), 4.30-4.33 (1H, m), 7.74 (1H, s), 7.83 (1H, d, J=8.20 Hz), 12.61 (1H, brs).

mass spectrum (FAB): m/z 510 (M+H)$^+$.

Example 3 cis(±)-{4-[(1H-Imidazol-2-ylcarbonyl)amino]-3-methoxypiperidin-1-yl}-1,3-thiazole-5-carboxylic acid (Exemplified Compound No. 3)

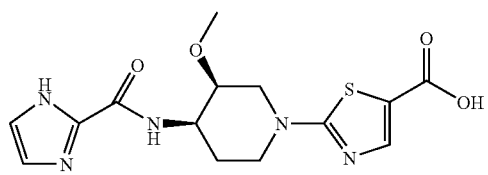

(3a) 1H-Imidazol-2-carboxylic acid

The compound was synthesized according to the method described in the following document.

J. Org. Chem., 60, 1995, 1090-1092

(3b) tert-Butyl cis(±)-4-[(1H-imidazol-2-ylcarbonyl)amino]-3-methoxypiperidine-1-carboxylate The same operation as in Example (1g) was performed using tert-butyl cis(±)-4-amino-3-methoxypiperidine-1-carboxylate obtained by the method described in Example (1e) (0.20 g, 0.87 mmol), 1H-imidazole-2-carboxylic acid obtained in Example (3a) (91 mg, 0.81 mmol), WSC hydrochloride (0.36 g, 1.88 mmol) and DMAP (10 mg, 0.083 mmol), to obtain 138 mg of the title compound as a white solid (58%).

$^1$H NMR spectrum (400 MHz, CDCl$_3$) δ ppm: 1.47 (9H, s), 1.80-1.93 (1H, m), 2.04-2.17 (1H, m), 2.72-3.01 (2H, m), 3.35-3.41 (1H, m), 3.42 (3H, s), 3.97-4.20 (2H, m), 4.33-4.56 (1H, m), 7.15-7.16 (2H, m), 7.60 (1H, brs).

(3c) Ethyl cis(±)-{4-[(1H-imidazol-2-ylcarbonyl)amino]-3-methoxypiperidin-1-yl}-1,3-thiazole-5-carboxylate The same operation as in Example (1h) was performed using tert-butyl cis(±)-4-[(1H-imidazol-2-ylcarbonyl)amino]-3-methoxypiperidine-1-carboxylate obtained in Example (3b) (135 mg, 0.42 mmol), a 4 N hydrochloric acid/ethyl acetate solution (7 ml), diisopropylethylamine (0.3 mL, 1.72 mmol) and ethyl 2-bromo-1,3-thiazole-5-carboxylate (0.06 mL, 0.41 mmol), to obtain 67 mg of the title compound as an orange solid substance (43%).

¹H NMR spectrum (400 MHz, DMSO-d₆) δ ppm: 1.25 (3H, t, J=7.07 Hz), 1.67-1.77 (1H, m), 1.78-1.90 (1H, m), 3.28-3.41 (2H, m), 3.34 (3H, s), 3.58 (1H, br s), 3.90-3.99 (1H, m), 4.20-4.28 (1H, m), 4.21 (2H, q, J=7.07 Hz), 4.31-4.41 (1H, m), 7.04 (1H, br s), 7.29 (1H, br s), 7.68 (1H, d, J=8.78 Hz), 7.82 (1H, s), 13.13 (1H, br s).

(3d) cis(±)-{4-[(1H-Imidazol-2-ylcarbonyl)amino]-3-methoxypiperidin-1-yl}-1,3-thiazole-5-carboxylic acid The same operation as in Example (1i) was performed using ethyl cis(±)-{4-[(1H-imidazol-2-ylcarbonyl)amino]-3-methoxypiperidin-1-yl}-1,3-thiazole-5-carboxylate obtained in Example (3c) (67 mg, 0.18 mmol) and a 2 N aqueous lithium hydroxide solution (4 mL), to obtain 45 mg of the title compound as a white solid (71%).

¹H NMR spectrum (400 MHz, DMSO-d₆) δ ppm: 1.64-1.74 (1H, m), 1.77-1.89 (1H, m), 3.10-3.21 (2H, m), 3.34 (3H, s), 3.53 (1H, br s), 3.76-3.86 (1H, m), 4.11-4.25 (2H, m), 7.03 (1H, br s), 7.13 (1H, s), 7.28 (1H, br s), 7.65 (1H, d, J=8.54 Hz), 13.12 (1H, br s).

mass spectrum (FAB): m/z 352 (M+H)⁺.

Example 4 cis(±)-(3-Methoxy-4-{[(4-methyl-1H-imidazol-2-yl)carbonyl]amino}piperidin-1-yl)-1,3-thiazole-5-carboxylic acid and cis(±)-(3-methoxy-4-{[(5-methyl-1H-imidazol-2-yl)carbonyl]amino}piperidin-1-yl)-1,3-thiazole-5-carboxylic acid (Exemplified Compound No. 4)

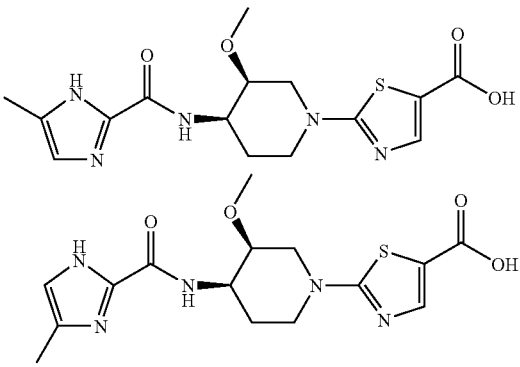

(4a) 1-{[2-(Trimethylsilyl)ethoxy]methyl}-4-methylimidazole and 1-{[2-(trimethylsilyl)ethoxy]methyl}-5-methylimidazole The compounds were synthesized according to the method described in the following document.

J. Org. Chem., 38, 1973, 1437-1438

(4b) Ethyl 4-methyl-1-{[2-(trimethylsilyl)ethoxy]methyl}-1H-imidazole-2-carboxylate and ethyl 5-methyl-1-{[2-(trimethylsilyl)ethoxy]methyl}-1H-imidazole-2-carboxylate A solution of the about 1:1 mixture of 1-{[2-(trimethylsilyl)ethoxy]methyl}-4-methylimidazole and 1-{[2-(trimethylsilyl)ethoxy]methyl}-5-methylimidazole obtained in Example (4a) (1.93 g, 9.01 mmol) in THF (50 mL) was cooled to −78° C. A n-butyllithium/1.58 M hexane solution (6 mL, 9.48 mmol) was added dropwise and the mixture was stirred for one hour. Thereafter, ethyl chloroformate (1 mL, 10.46 mmol) was added, and the mixture was heated to room temperature and further stirred for one hour. Brine was added to the reaction solution, followed by extraction with ethyl acetate. Then, the organic layer was washed with brine and dried over anhydrous sodium sulfate. Following concentration under reduced pressure, the residue was purified by silica gel column chromatography (elution solvent: hexane/ethyl acetate=3/1, 2/1, 1/1) to obtain 0.50 g of the title compound as an about 1:1 mixture and as a pale yellow oily substance (20%).

¹H NMR spectrum (400 MHz, CDCl₃) δ ppm: −0.01 (9H×½, s), 0.00 (9H×½, s), 0.86-1.00 (2H, m), 1.44 (3H, t, J=7.07 Hz), 2.30 (3H×½, s), 2.35 (3H×½, s), 3.55-3.60 (2H, m), 4.39-4.46 (2H, m), 5.76 (2H×½, s), 5.83 (2H×½, s), 6.97 (1H×½, s), 7.02 (1H×½, s).

(4c) tert-Butyl cis(±)-3-methoxy-4-{[(4-methyl-1-{[2-(trimethylsilyl)ethoxy]methyl}-1H-imidazol-2-yl)carbonyl]amino}piperidine-1-carboxylate and tert-butyl cis(±)-3-methoxy-4-{[(5-methyl-1-{[2-(trimethylsilyl)ethoxy]methyl}-1H-imidazol-2-yl)carbonyl]amino}piperidine-1-carboxylate The about 1:1 mixture of ethyl 4-methyl-1-{[2-(trimethylsilyl)ethoxy]methyl}-1H-imidazole-2-carboxylate and ethyl 5-methyl-1-{[2-(trimethylsilyl)ethoxy]methyl}-1H-imidazole-2-carboxylate obtained in Example (4b) (0.35 g, 1.23 mmol) was dissolved in methanol (8 ml). A 1 N aqueous sodium hydroxide solution (8 mL, 8 mmol) was added, and the mixture was stirred at room temperature for one hour. The reaction solution was concentrated under reduced pressure and 1 N hydrochloric acid was added dropwise until the pH was 7. Thereafter, purification by reverse phase silica gel column chromatography (elution solvent: distilled water, acetonitrile/distilled water: 3/7) gave 0.12 g of carboxylic acid. The resulting carboxylic acid (0.12 g, 0.48 mmol) and tert-butyl cis(±)-4-amino-3-methoxy piperidine-1-carboxylate obtained by the method described in Example (1e) (0.20 g, 0.87 mmol) were dissolved in dichloromethane. WSC hydrochloride (0.19 g, 0.99 mmol), triethylamine (0.2 mL, 1.43 mmol) and DMAP (10 mg, 0.083 mmol) were added, and the mixture was stirred at room temperature for 2.5 hours. Dilute hydrochloric acid was added to the reaction solution, followed by extraction with dichloromethane. Then, the organic layer was washed with saturated aqueous sodium bicarbonate solution and brine, and dried over anhydrous sodium sulfate. Following concentration under reduced pressure, the residue was purified by silica gel column chromatography (elution solvent: hexane/ethyl acetate=5/1, 1/1) to obtain 92 mg of the title compound as an about 3:1 mixture and as a pale yellow oily substance (16%).

¹H NMR spectrum (400 MHz, CDCl₃) δ ppm: −0.04 (9H×¼, s), −0.02 (9H×¾, s), 0.86-0.94 (2H, m), 1.47 (9H×¾, s), 1.60 (9H×¼, s), 1.62-1.71 (1H, m), 1.78-1.92 (1H, m), 2.23 (3H×¾, s), 2.31 (3H×¼, s), 3.32-3.40 (2H, m), 3.41 (3H×¼, s), 3.43 (3H×¾, s), 3.53-3.61 (3H, m), 4.07-4.52 (3H, m), 5.81 (2H×¾, s), 5.91 (2H×¼, s), 6.80 (1H×¼, s), 6.92 (1H×¾, s), 7.70 (1H, brs).

(4d) Ethyl cis(±)-(3-methoxy-4-{[(4-methyl-1H-imidazol-2-yl)carbonyl]amino}piperidin-1-yl)-1,3-thiazole-5-carboxylate and ethyl cis(±)-(3-methoxy-4-{[(5-methyl-1H-imidazol-2-yl)carbonyl]amino}piperidin-1-yl)-1,3-thiazole-5-carboxylate The same operation as in Example (1h) was performed using the about 3:1 mixture of tert-butyl cis(±)-3-methoxy-4-{[(4-methyl-1-{[2-(trimethylsilyl)ethoxy]methyl}-1H-imidazol-2-yl)carbonyl]amino}piperidine-1-carboxylate and tert-butyl cis(±)-3-methoxy-4-{[(5-methyl-1-{[2-(trimethylsilyl)ethoxy]methyl}-1H-imidazol-2-yl)carbonyl]amino}piperidine-1-carboxylate obtained in Example (4c)

(90 mg, 0.19 mmol), a 4 N hydrochloric acid/ethyl acetate solution (4 ml, 16 mmol), diisopropylethylamine (0.14 mL, 0.80 mmol) and ethyl 2-bromo-1,3-thiazole-5-carboxylate (0.045 mL, 0.30 mmol), to obtain 80 mg of the title compound as an about 3:1 mixture and as a yellow oily substance (80%).

$^1$H NMR spectrum (400 MHz, CDCl$_3$) δ ppm: −0.03 (9H× ¼, s), −0.02 (9H×¾, s), 0.86-0.96 (2H, m), 1.34 (3H, t, J=7.11 Hz), 1.55-1.58 (1H, m), 1.78-1.87 (1H, m), 2.23 (3H, s), 2.32 (3H×¾, s), 3.12-3.19 (1H×¼, m), 3.20-3.30 (1H, m), 3.43 (3H×¼, s), 3.44 (3H×¾, s), 3.52-3.62 (3H, m), 3.93-4.02 (1H, m), 4.21-4.31 (1H, m), 4.29 (2H, q, J=7.11 Hz), 4.49-4.58 (1H, m), 5.82 (2H×¾, s), 5.90 (2H×¼, s), 6.81 (1H×¼, s), 6.93 (1H×¾, s), 7.68-7.78 (1H, m), 7.84 (1H, s).

(4e) cis(±)-(3-Methoxy-4-{[(4-methyl-1H-imidazol-2-yl)carbonyl]amino}piperidin-1-yl)-1,3-thiazole-5-carboxylic acid and cis(±)-(3-methoxy-4-{[(5-methyl-1H-imidazol-2-yl)carbonyl]amino}piperidin-1-yl)-1,3-thiazole-5-carboxylic acid The about 3:1 mixture of ethyl cis(±)-(3-methoxy-4-{[(4-methyl-1H-imidazol-2-yl)carbonyl]amino}piperidin-1-yl)-1,3-thiazole-5-carboxylate and ethyl cis(±)-(3-methoxy-4-{[(5-methyl-1H-imidazol-2-yl)carbonyl]amino}piperidin-1-yl)-1,3-thiazole-5-carboxylate obtained in Example (4d) (79 mg, 0.15 mmol) was dissolved in ethanol (1 mL). A 4 N hydrochloric acid/ethyl acetate solution (5 mL, 20 mmol) was added, and the mixture was heated under reflux for four hours. The reaction solution was concentrated under reduced pressure, diluted with dichloromethane, washed with saturated aqueous sodium bicarbonate solution and brine, and dried over anhydrous sodium sulfate. Following concentration under reduced pressure, the residue was dissolved in methanol (5 mL) and dichloromethane (2 mL). The solution was subjected to the same operation as in Example (1i) using a 2 N aqueous lithium hydroxide solution (4 mL, 8 mmol), to obtain 42 mg of the title compound as an about 3:2 mixture and as a white solid (77%).

$^1$H NMR spectrum (400 MHz, DMSO-d$_6$) δ ppm: 1.70-1.86 (2H, m), 2.14 (3H×⅖, s), 2.18 (3H×⅗, s), 3.26-3.40 (2H, m), 3.31 (3H, s), 3.57 (1H, br s), 3.88-3.97 (1H, m), 4.16-4.40 (2H, m), 6.73 (1H×⅖, s), 6.99 (1H×⅗, s), 7.52-7.62 (1H, m), 7.73 (1H, s), 12.55-12.68 (1H, m), 12.75-12.90 (1H, m).

mass spectrum (FAB): m/z 366 (M+H)$^+$.

Example 5 cis(±)-2-(4-{[(4-Chloro-5-methyl-1H-imidazol-2-yl)carbonyl]amino}-3-methoxypiperidin-1-yl)-1,3-thiazole-5-carboxylic acid (Exemplified Compound No. 5)

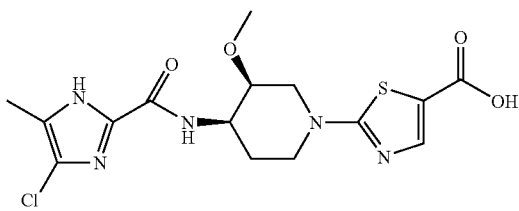

(5a) Ethyl 5-methyl-1H-imidazole-2-carboxylate

The compound was synthesized according to the method described in the following document.

J. Org. Chem., 38, 1973, 1437-1438

(5b) Ethyl 4-chloro-5-methyl-1H-imidazole-2-carboxylate

The same operation as in Example (1c) was performed using ethyl 5-methyl-1H-imidazole-2-carboxylate obtained in Example (5a) (0.50 g, 3.23 mmol) and NCS (0.44 g, 3.25 mmol), to obtain 0.50 g of the title compound as a white solid (82%).

$^1$H NMR spectrum (400 MHz, CDCl$_3$) δ ppm: 1.41 (3H, t, J=7.15 Hz), 2.32 (3H, s), 4.42 (2H, q, J=7.15 Hz), 10.53 (1H, br s).

(5c) 4-Chloro-5-methyl-1H-imidazole-2-carboxylic acid

The same operation as in Example (1d) was performed using ethyl 4-chloro-5-methyl-1H-imidazole-2-carboxylate obtained in Example (5b) (0.50 g, 2.65 mmol) and a 3 N aqueous lithium hydroxide solution (4 mL), to obtain 0.35 g of the title compound as a white solid (82%).

$^1$H NMR spectrum (400 MHz, DMSO-d$_6$) δ ppm: 2.21 (3H, s), 10.02 (1H, brs).

(5d) Ethyl cis(±)-2-(4-amino-3-methoxypiperidin-1-yl)-1,3-thiazole-5-carboxylate The same operation as in Example (1h) was performed using tert-butyl cis(±)-4-amino-3-methoxypiperidine-1-carboxylate obtained by the method described in Example (1e) (3.00 g, 13.03 mmol), a 4 N hydrochloric acid/ethyl acetate solution (120 ml, 480 mmol), diisopropylethylamine (13 mL, 78.16 mmol) and ethyl 2-bromo-4-methyl-1,3-thiazole-5-carboxylate (3.23 g, 13.68 mmol), to obtain 2.41 g of the title compound as a yellow oily substance (65%).

$^1$H NMR spectrum (400 MHz, CD$_3$OD) δ ppm: 1.32 (3H, t, J=7.20 Hz), 1.66-1.85 (2H, m), 2.96-3.03 (1H, m), 3.20-3.26 (2H, m), 3.42 (3H, s), 3.42-3.46 (1H, m), 3.89-3.99 (1H, m), 4.23-4.38 (3H, m), 7.77 (1H, s).

(5e) Ethyl cis(±)-2-(4-{[(4-chloro-5-methyl-1H-imidazol-2-yl)carbonyl]amino}-3-methoxypiperidin-1-yl)-1,3-thiazole-5-carboxylate The same operation as in Example (1g) was performed using ethyl cis(±)-2-(4-amino-3-methoxypiperidin-1-yl)-1,3-thiazole-5-carboxylate obtained in Example (5d) (0.21 g, 0.73 mmol), 4-chloro-5-methyl-1H-imidazole-2-carboxylic acid obtained in Example (5c) (0.10 g, 0.64 mmol), WSC hydrochloride (0.27 g, 1.41 mmol) and DMAP (10 mg, 0.083 mmol), to obtain 54 mg of the title compound as a pale yellow solid (20%).

$^1$H NMR spectrum (400 MHz, CDCl$_3$) δ ppm: 1.34 (3H, t, J=7.12 Hz), 1.78-1.86 (1H, m), 1.99-2.13 (1H, m), 2.30 (3H, s), 3.11-3.17 (1H, m), 3.20-3.30 (1H, m), 3.42 (3H, s), 3.53 (1H, br s), 3.95-4.04 (1H, m), 4.22-4.32 (1H, m), 4.30 (2H, q, J=7.12 Hz), 4.52-4.60 (1H, m), 7.43-7.49 (1H, m), 7.84 (1H, s), 11.01 (1H, br s).

(5f) cis(±)-2-(4-{[(4-Chloro-5-methyl-1H-imidazol-2-yl)carbonyl]amino}-3-methoxypiperidin-1-yl)-1,3-thiazole-5-carboxylic acid The same operation as in Example (1i) was performed using ethyl cis(±)-2-(4-{[(4-chloro-5-methyl-1H-imidazol-2-yl)carbonyl]amino}-3-methoxypiperidin-1-yl)-1,3-thiazole-5-carboxylate obtained in Example (5e) (54 mg, 0.12 mmol) and a 2 N aqueous lithium hydroxide solution (2 mL), to obtain 11 mg of the title compound as a white solid (22%).

$^1$H NMR spectrum (400 MHz, DMSO-d$_6$) δ ppm: 1.65-1.74 (2H, m), 1.81-1.94 (2H, m), 2.16 (3H, s), 3.30-3.34 (1H, m), 3.32 (3H, s), 3.57 (1H, br s), 3.87-3.97 (1H, m), 4.17-4.38 (2H, m), 7.66 (1H, d, J=8.54 Hz), 7.72 (1H, s), 13.35 (1H, br s).

mass spectrum (FAB): m/z 400 (M+H)$^+$.

Example 6 cis(±)-2-(4-{[(4-Chloro-5-methyl-1H-imidazol-2-yl)carbonyl]amino}-3-methoxypiperidin-1-yl)-N-methoxy-1,3-thiazole-5-carboxamide (Exemplified Compound No. 6)

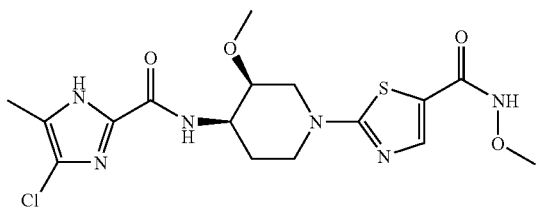

(6a) cis(±)-2-(4-{[(4-Chloro-5-methyl-1H-imidazol-2-yl)carbonyl]amino}-3-methoxypiperidin-1-yl)-N-methoxy-1,3-thiazole-5-carboxamide The same operation as in Example (1g) was performed using cis(±)-2-(4-{[(4-chloro-5-methyl-1H-imidazol-2-yl)carbonyl]amino}-3-methoxypiperidin-1-yl)-1,3-thiazole-5-carboxylic acid obtained by the method described in Example (5f) (17 mg, 0.045 mmol), O-methylhydroxylamine (15 mg, 0.18 mmol), WSC hydrochloride (0.46 g, 0.24 mmol) and DMAP (5 mg, 0.042 mmol), to obtain 3.5 mg of the title compound as a white solid (18%).

$^1$H NMR spectrum (400 MHz, CDCl$_3$) δ ppm: 1.78-1.87 (1H, m), 1.98-2.11 (1H, m), 2.30 (3H, s), 3.12-3.18 (1H, m), 3.20-3.30 (1H, m), 3.42 (3H, s), 3.53 (1H, br s), 3.83 (3H, s), 3.96-4.04 (1H, m), 4.22-4.32 (1H, m), 4.52-4.62 (1H, m), 7.26 (0H, s), 7.43-7.50 (1H, m), 7.88 (1H, s), 8.29 (1H, br s), 10.87 (1H, br s).

mass spectrum (ESI): m/z 429 (M+H)$^+$.

Example 7 cis(±)-2-(4-{[(4,5-Dichloro-1H-imidazol-2-yl)carbonyl]amino}-3-methoxypiperidin-1-yl)-1,3-thiazole-5-carboxylic acid (Exemplified Compound No. 7)

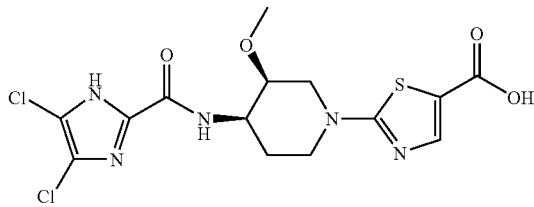

(7a) 2-Bromo-4,5-dichloro-1-[[2-(trimethylsilyl)ethoxy]methyl]-1H-imidazole

2-Bromo-4,5-dichloro-1H-imidazole (1.1 g, 5.09 mmol) was dissolved in THF (30 mL), and sodium hydride (0.29 g, 6.65 mmol) was added under ice-cooling, followed by stirring for 15 minutes.

2-(Chloromethoxy)ethyltrimethylsilane (1 mL, 5.65 mmol) was added to the reaction solution, and the mixture was heated to room temperature and stirred for 40 minutes. Aqueous ammonium chloride solution was added to the reaction solution, followed by extraction with ethyl acetate. Then, the organic layer was washed with saturated aqueous sodium bicarbonate solution and brine, and dried over anhydrous sodium sulfate. Following concentration under reduced pressure, the residue was purified by silica gel column chromatography (elution solvent: hexane/ethyl acetate=20/1, 10/1) to obtain 1.76 g of the title compound as a pale yellow oily substance (100%).

$^1$H NMR spectrum (400 MHz, CDCl$_3$) δ ppm: 0.00 (9H, s), 0.93 (2H, t, J=8.23 Hz), 3.60 (2H, t, J=8.23 Hz), 5.29 (2H, s).

(7b) Ethyl 4,5-dichloro-1-{[2-(trimethylsilyl)ethoxy]methyl}-1H-imidazole-2-carboxylate The same operation as in Example (4b) was performed using 2-bromo-4,5-dichloro-1-{[2-(trimethylsilyl)ethoxy]methyl}-1H-imidazole obtained in Example (7a) (0.95 g, 2.55 mmol), a n-butyllithium/1.58 M hexane solution (1.9 mL, 3.00 mmol) and ethyl cyanoformate (0.33 mL, 3.34 mmol), to obtain 0.59 g of the title compound as a pale yellow oily substance (67%).

$^1$H NMR spectrum (400 MHz, CDCl$_3$) δ ppm: 0.01 (9H, s), 0.90-0.99 (2H, m), 1.46 (3H, t, J=7.17 Hz), 3.61-3.68 (2H, m), 4.47 (2H, q, J=7.17 Hz), 5.87 (2H, s).

(7c) Ethyl 4,5-dichloroimidazole-2-carboxylate

Ethyl 4,5-dichloro-1-{[2-(trimethylsilyl)ethoxy]methyl}-1H-imidazole-2-carboxylate obtained in Example (7b) (0.61 g, 1.79 mmol) was dissolved in ethanol (3 mL). A 4 N hydrochloric acid/ethyl acetate solution (15 mL) was added, and the mixture was heated under reflux for one hour. The reaction solution was concentrated under reduced pressure, diluted with ethyl acetate, washed with brine and dried over anhydrous sodium sulfate. Following concentration under reduced pressure, the residue was purified by silica gel column chromatography (elution solvent: hexane/ethyl acetate=10/1, 1/1) to obtain 0.24 g of the title compound as a pale yellow oily substance (65%).

mass spectrum (FAB): m/z 210 (M+H)$^+$.

(7d) 4,5-Dichloroimidazole-2-carboxylic acid

The same operation as in Example (1d) was performed using ethyl 4,5-dichloroimidazole-2-carboxylate obtained in Example (7c) (0.24 g, 1.16 mmol) and a 2 N aqueous lithium hydroxide solution (5 mL), to obtain 0.16 g of the title compound as a white solid (76%).

mass spectrum (FAB): m/z 181 (M+H)$^+$.

(7e) Ethyl cis(±)-2-(4-{[(4,5-dichloro-1H-imidazol-2-yl)carbonyl]amino}-3-methoxypiperidin-1-yl)-1,3-thiazole-5-carboxylate The same operation as in Example (1g) was performed using ethyl cis(±)-2-(4-amino-3-methoxypiperidin-1-yl)-1,3-thiazole-5-carboxylate obtained by the method described in Example (5d) (0.23 g, 0.81 mmol), 4,5-dichloroimidazole-2-carboxylic acid obtained in Example (7d) (84 mg, 0.46 mmol), WSC hydrochloride (0.24 g, 1.25 mmol) and DMAP (10 mg, 0.083 mmol), to obtain 49 mg of the title compound as a pale yellow solid (24%).

$^1$H NMR spectrum (400 MHz, CDCl$_3$) δ ppm: 1.34 (3H, t, J=7.12 Hz), 1.79-1.88 (1H, m), 1.99-2.10 (1H, m), 3.10-3.17 (1H, m), 3.20-3.30 (1H, m), 3.43 (3H, s), 3.53 (1H, br s), 3.94-4.04 (1H, m), 4.23-4.32 (1H, m), 4.30 (2H, q, J=7.12 Hz), 4.52-4.61 (1H, m), 7.48 (1H, d, J=8.79 Hz), 7.84 (1H, s).

(7f) cis(±)-2-(4-{[(4,5-Dichloro-1H-imidazol-2-yl)carbonyl]amino}-3-methoxypiperidin-1-yl)-1,3-thiazole-5-carboxylic acid The same operation as in Example (1i) was performed using ethyl cis(±)-2-(4-{[(4,5-dichloro-1H-imidazol-2-yl)carbonyl]amino}-3-methoxypiperidin-1-yl)-1,3-thiazole-5-carboxylate obtained in Example (7e) (49 mg, 0.11 mmol) and a 2 N aqueous lithium hydroxide solution (2 mL), to obtain 18 mg of the title compound as a white solid (38%).

¹H NMR spectrum (400 MHz, DMSO-d₆) δ ppm: 1.63-1.73 (1H, m), 1.80-1.93 (1H, m), 3.27-3.36 (2H, m), 3.30 (3H, s), 3.56 (3H, br s), 3.87-3.98 (1H, m), 4.15-4.25 (1H, m), 4.27-4.38 (1H, m), 7.70-7.77 (1H, m), 7.74 (1H, s).

mass spectrum (ESI): m/z 421 (M+H)⁺.

Example 8 cis(±)-2-(4-{[(4-Chloro-5-methyl-1H-imidazol-2-yl)carbonyl]amino}-3-methoxypiperidin-1-yl)-1,3-benzothiazole-7-carboxylic acid (Exemplified Compound No. 8)

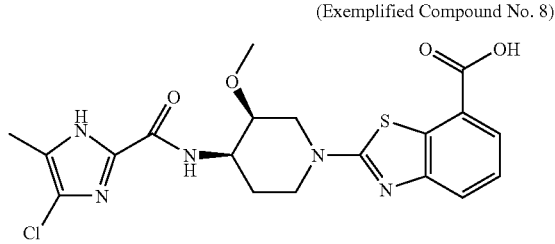 [SMILES: CO[C@H]1CN(c2nc3cccc(C(=O)O)c3s2)CC[C@H]1NC(=O)c1nc(Cl)c(C)[nH]1]

(8a) tert-Butyl cis(±)-4-{[(4-chloro-5-methyl-1H-imidazol-2-yl)carbonyl]amino}-3-methoxypiperidine-1-carboxylate The same operation as in Example (1g) was performed using tert-butyl cis(±)-4-amino-3-methoxypiperidine-1-carboxylate obtained by the method described in Example (1e) (1 g, 4.34 mmol), 4-chloro-5-methyl-1H-imidazole-2-carboxylic acid obtained by the method described in Example (5c) (0.35 g, 2.17 mmol), WSC hydrochloride (1.25 g, 6.52 mmol) and HOBT (0.30 g, 2.22 mmol), to obtain 0.68 g of the title compound as a white solid (84%).

¹H NMR spectrum (400 MHz, CDCl₃) δ ppm: 1.47 (9H, s), 1.57-1.70 (1H, m), 1.78-1.92 (1H, m), 2.30 (3H, s), 2.74-2.84 (2H, m), 3.35-3.39 (2H, m), 3.42 (3H, s), 4.05-4.50 (2H, m), 7.44-7.52 (1H, m), 11.25 (1H, s).

(8b) Ethyl cis(±)-2-(4-{[(4-chloro-5-methyl-1H-imidazol-2-yl)carbonyl]amino}-3-methoxypiperidin-1-yl)-1,3-benzothiazole-7-carboxylate The same operation as in Example (1h) was performed using tert-butyl cis(±)-4-{[(4-chloro-5-methyl-1H-imidazol-2-yl)carbonyl]amino}-3-methoxypiperidine-1-carboxylate obtained in Example (8a) (48 mg, 0.13 mmol), a 4 N hydrochloric acid/ethyl acetate solution (4 mL), diisopropylethylamine (0.1 mL, 0.52 mmol) and ethyl 2-bromo-1,3-benzothiazole-7-carboxylate obtained by the method described in Example (1f) (42 mg, 0.15 mmol), to obtain 38 mg of the title compound as an orange solid substance (61%).

¹H NMR spectrum (400 MHz, CDCl₃) δ ppm: 1.44 (3H, t, J=7.11 Hz), 1.80-1.89 (1H, m), 2.01-2.14 (1H, m), 2.30 (3H, s), 3.20-3.34 (2H, m), 3.46 (3H, s), 3.55 (1H, br s), 4.21-4.34 (2H, m), 4.45 (2H, q, J=7.11 Hz), 4.57-4.68 (1H, m), 7.34-7.44 (2H, m), 7.69 (1H, d, J=7.80 Hz), 7.79 (2H, d, J=8.05 Hz), 10.42 (1H, br s).

(8c) cis(±)-2-(4-{[(4-Chloro-5-methyl-1H-imidazol-2-yl)carbonyl]amino}-3-methoxypiperidin-1-yl)-1,3-benzothiazole-7-carboxylic acid The same operation as in Example (1i) was performed using ethyl cis(±)-2-(4-{[(4-chloro-5-methyl-1H-imidazol-2-yl)carbonyl]amino}-3-methoxypiperidin-1-yl)-1,3-benzothiazole-7-carboxylate obtained in Example (8b) (38 mg, 0.079 mmol) and a 4 N aqueous lithium hydroxide solution (2 mL), to obtain 21 mg of the title compound as a white solid (59%).

¹H NMR spectrum (400 MHz, DMSO-d₆) δ ppm: 1.67-1.83 (1H, m), 1.87-2.02 (1H, m), 2.16 (3H, s), 3.26-3.54 (2H, m), 3.38 (3H, s), 3.57-3.67 (1H, m), 4.06-4.57 (3H, m), 7.36-7.48 (1H, m), 7.61-7.77 (3H, m), 13.29-13.51 (1H, m).

mass spectrum (ESI): m/z 450 (M+H)⁺.

Example 9 cis(±)-2-(4-{[5-Ethyl-1H-imidazol-2-yl)carbonyl]amino}-3-methoxypiperidin-1-yl)-1,3-thiazole-5-carboxylic acid (Exemplified Compound No. 9)

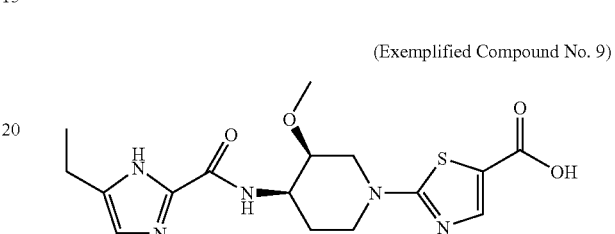

(9a) 5-Ethyl-1H-imidazole-2-carboxylic acid

The same operation as in Example (1d) was performed using ethyl 5-ethyl-1H-imidazole-2-carboxylate obtained by the method described in Example (1b) (0.15 g, 0.89 mmol) and a 2 N aqueous lithium hydroxide solution (2 mL), to obtain 0.12 g of the title compound as a white solid (100%).

¹H NMR spectrum (400 MHz, DMSO-d₆) δ ppm: 1.28 (3H, t, J=7.66 Hz), 2.70 (2H, q, J=7.66 Hz), 10.01 (1H, br s).

(9b) Ethyl cis(±)-2-(4-{[(5-ethyl-1H-imidazol-2-yl)carbonyl]amino}-3-methoxypiperidin-1-yl)-1,3-thiazole-5-carboxylate The same operation as in Example (1g) was performed using ethyl cis(±)-2-(4-amino-3-methoxypiperidin-1-yl)-1,3-thiazole-5-carboxylate obtained by the method described in Example (5d) (0.21 g, 0.73 mmol), 5-ethyl-1H-imidazole-2-carboxylic acid obtained in Example (9a) (82 mg, 0.44 mmol), WSC hydrochloride (0.53 g, 2.76 mmol) and DMAP (0.12 g, 0.94 mmol), to obtain 107 mg of the title compound as a pale yellow solid (60%).

¹H NMR spectrum (400 MHz, CDCl₃) δ ppm: 1.23-1.30 (3H, m), 1.34 (3H, t, J=7.07 Hz), 1.80-1.88 (1H, m), 2.01-2.07 (1H, m), 2.61-2.72 (2H, m), 3.11-3.18 (1H, m), 3.22-3.32 (1H, m), 3.43 (3H, s), 3.54 (1H, br s), 3.95-4.04 (1H, m), 4.24-4.35 (1H, m), 4.29 (2H, q, J=7.07 Hz), 4.50-4.60 (1H, m), 6.84-6.91 (1H, m), 7.52-7.59 (1H, m), 7.84 (1H, s), 10.42-10.63 (1H, m).

(9c) cis(±)-2-(4-{[5-Ethyl-1H-imidazol-2-yl)carbonyl]amino}-3-methoxypiperidin-1-yl)-1,3-thiazole-5-carboxylic acid The same operation as in Example (1i) was performed using ethyl cis(±)-2-(4-{[(5-ethyl-1H-imidazol-2-yl)carbonyl]amino}-3-methoxypiperidin-1-yl)-1,3-thiazole-5-carboxylate obtained in Example (9b) (106 mg, 0.26 mmol) and a 2 N aqueous lithium hydroxide solution (2 mL) to obtain 63 mg of the title compound as a white solid (64%).

¹H NMR spectrum (400 MHz, DMSO-d₆) δ ppm: 1.12-1.21 (3H, m), 1.66-1.76 (1H, m), 1.78-1.90 (1H, m), 2.51-2.60 (2H, m), 3.29-3.37 (2H, m), 3.34 (3H, s), 3.57 (1H, br s), 3.88-3.98 (1H, m), 4.18-4.40 (2H, m), 6.73-7.02 (1H, m), 7.54-7.60 (1H, m), 7.74 (1H, s), 12.52-12.63 (1H, m), 12.80-12.92 (1H, m).

mass spectrum (FAB): m/z 380 (M+H)⁺.

Example 10 cis(±)-2-(4-{[(5-Ethyl-1H-imidazol-2-yl)carbonyl]amino}-3-methoxypiperidin-1-yl)-1,3-benzothiazole-7-carboxylic acid (Exemplified Compound No. 10)

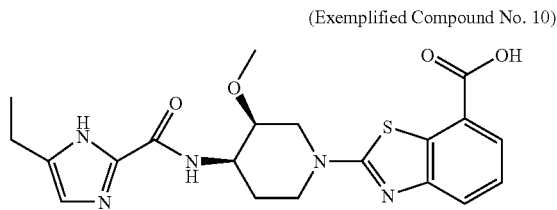 [SMILES: CCc1cnc(C(=O)N[C@@H]2CCN(c3nc4cccc(C(=O)O)c4s3)C[C@@H]2OC)[nH]1]

(10a) tert-Butyl cis(±)-4-{[(5-ethyl-1H-imidazol-2-yl)carbonyl]amino}-3-methoxypiperidine-1-carboxylate The same operation as in Example (1g) was performed using tert-butyl cis(±)-4-amino-3-methoxypiperidine-1-carboxylate obtained by the method described in Example (1e) (0.20 g, 0.87 mmol), 5-ethyl-1H-imidazole-2-carboxylic acid obtained in Example (1b) (85 mg, 0.44 mmol), WSC hydrochloride (0.55 g, 2.87 mmol) and DMAP (115 mg, 0.94 mmol), to obtain 85 mg of the title compound as a pale yellow solid (55%).

$^1$H NMR spectrum (400 MHz, CDCl$_3$) δ ppm: 1.24-1.30 (3H, m), 1.47 (9H, s), 1.64-1.72 (1H, m), 1.78-1.92 (1H, m), 2.60-2.72 (2H, m), 3.34-3.44 (5H, m), 4.10-4.22 (2H, m), 4.35-4.54 (2H, m), 6.83-6.89 (1H, m), 7.48-7.59 (1H, m), 10.27-10.50 (1H, m).

(10b) Ethyl cis(±)-2-(4-{[5-Ethyl-1H-imidazol-2-yl)carbonyl]amino}-3-methoxypiperidin-1-yl)-1,3-benzothiazole-7-carboxylate The same operation as in Example (1h) was performed using tert-butyl cis(±)-4-{[(5-ethyl-1H-imidazol-2-yl)carbonyl]amino}-3-methoxypiperidine-1-carboxylate obtained in Example (10a) (84 mg, 0.24 mmol), a 4 N hydrochloric acid/ethyl acetate solution (3 ml), diisopropylethylamine (0.25 mL, 1.43 mmol) and ethyl 2-bromo-1,3-benzothiazole-7-carboxylate obtained by the method described in Example (1f) (71 mg, 0.24 mmol), to obtain 65 mg of the title compound as a yellow solid substance (58%).

$^1$H NMR spectrum (400 MHz, CDCl$_3$) δ ppm: 1.23-1.32 (3H, m), 1.44 (3H, t, J=7.18 Hz), 1.83-1.91 (1H, m), 2.02-2.19 (1H, m), 2.60-2.73 (2H, m), 3.22-3.36 (2H, m), 3.46 (3H, s), 3.57 (1H, br s), 4.21-4.37 (2H, m), 4.45 (2H, q, J=7.18 Hz), 4.56-4.66 (1H, m), 6.83-6.92 (1H, m), 7.33-7.39 (1H, m), 7.52-7.59 (1H, m), 7.69 (1H, d, J=8.06 Hz), 7.78 (1H, dd, J=7.81, 0.98 Hz), 10.20-10.37 (1H, m).

(10c) cis(±)-2-(4-{[5-Ethyl-1H-imidazol-2-yl)carbonyl]amino}-3-methoxypiperidin-1-yl)-1,3-benzothiazole-7-carboxylic acid The same operation as in Example (1i) was performed using ethyl cis(±)-2-(4-{[5-ethyl-1H-imidazol-2-yl)carbonyl]amino}-3-methoxypiperidin-1-yl)-1,3-benzothiazole-7-carboxylate obtained in Example (10b) (65 mg, 0.14 mmol) and a 2 N aqueous lithium hydroxide solution (2 mL, 4 mmol), to obtain 38 mg of the title compound as a pale yellow solid (62%).

$^1$H NMR spectrum (400 MHz, DMSO-d$_6$) δ ppm: 1.17 (3H, t, J=7.56 Hz), 1.71-1.80 (1H, m), 1.84-1.90 (1H, m), 2.52-2.60 (2H, m), 3.28-3.46 (2H, m), 3.38 (3H, s), 3.60 (1H, br s), 4.07-4.17 (1H, m), 4.21-4.31 (1H, m), 4.37-4.50 (1H, m), 6.84-7.00 (1H, m), 7.36-7.43 (1H, m), 7.61-7.71 (3H, m), 13.47 (1H, br s).

mass spectrum (ESI): m/z 430 (M+H)$^+$.

Example 11 cis(±)-2-(4-{[(4-Chloro-5-ethyl-1H-imidazol-2-yl)carbonyl]amino}-3-methoxypiperidin-1-yl)-1,3-thiazole-5-carboxylic acid (Exemplified Compound No. 11)

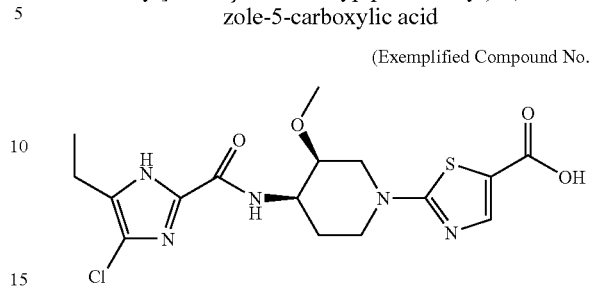

(11a) Ethyl cis(±)-2-(4-{[(4-Chloro-5-ethyl-1H-imidazol-2-yl)carbonyl]amino}-3-methoxypiperidin-1-yl)-1,3-thiazole-5-carboxylate The same operation as in Example (1g) was performed using ethyl cis(±)-2-(4-amino-3-methoxypiperidin-1-yl)-1,3-thiazole-5-carboxylate obtained by the method described in Example (5d) (0.22 g, 0.77 mmol), 4-chloro-5-ethyl-1H-imidazole-2-carboxylic acid obtained by the method described in Example (1d) (85 mg, 0.49 mmol), WSC hydrochloride (0.56 g, 2.92 mmol) and DMAP (0.13 g, 1.02 mmol), to obtain 0.15 g of the title compound as a pale yellow solid (71%).

$^1$H NMR spectrum (400 MHz, CDCl$_3$) δ ppm: 1.26 (3H, t, J=7.56 Hz), 1.34 (3H, t, J=7.19 Hz), 1.75-1.86 (1H, m), 2.03-2.09 (1H, m), 2.69 (2H, q, J=7.56 Hz), 3.09-3.17 (1H, m), 3.19-3.31 (1H, m), 3.42 (3H, s), 3.52 (1H, brs), 3.95-4.05 (1H, m), 4.22-4.34 (3H, m), 4.51-4.61 (1H, m), 7.41-7.49 (1H, m), 7.84 (1H, s), 10.71 (1H, s).

(11b) cis(±)-2-(4-{[(4-Chloro-5-ethyl-1H-imidazol-2-yl)carbonyl]amino}-3-methoxypiperidin-1-yl)-1,3-thiazole-5-carboxylic acid The same operation as in Example (1i) was performed using ethyl cis(±)-2-(4-{[(4-chloro-5-ethyl-1H-imidazol-2-yl)carbonyl]amino}-3-methoxypiperidin-1-yl)-1,3-thiazole-5-carboxylate obtained in Example (11a) (0.15 g, 0.34 mmol) and a 2 N aqueous lithium hydroxide solution (2 mL), to obtain 0.12 g of the title compound as a white solid (87%).

$^1$H NMR spectrum (400 MHz, DMSO-d$_6$) δ ppm: 1.14 (3H, t, J=7.57 Hz), 1.64-1.73 (1H, m), 1.85-1.91 (1H, m), 2.52-2.60 (2H, m), 3.28-3.36 (2H, m), 3.32 (3H, s), 3.58 (1H, br s), 3.88-3.97 (1H, m), 4.18-4.26 (1H, m), 4.29-4.38 (1H, m), 7.65-7.70 (1H, m), 7.74 (1H, s), 13.37 (1H, br s).

mass spectrum (FAB): m/z 414 (M+H)$^+$.

Example 12 cis(±)-2-(4-{[(4-Chloro-5-methyl-1H-imidazol-2-yl)carbonyl]amino}-3-methoxypiperidin-1-yl)-4-methyl-1,3-thiazole-5-carboxylic acid (Exemplified Compound No. 12)

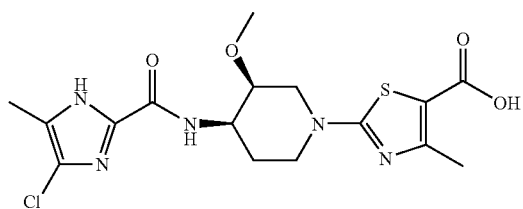

(12a) Ethyl cis(±)-2-(4-{[(4-chloro-5-methyl-1H-imidazol-2-yl)carbonyl]amino}-3-methoxypiperidin-1-yl)-4-methyl-1,3-thiazole-5-carboxylate The same operation as in Example (1h) was performed using tert-butyl cis(±)-4-{[(4-chloro-5-methyl-1H-imidazol-2-yl)carbonyl]amino}-3-methoxypiperidine-1-carboxylate obtained by the method described in Example (8a) (42 mg, 0.11 mmol), a 4 N hydrochloric acid/ethyl acetate solution (4 ml), diisopropylethylamine (0.1 mL, 0.57 mmol) and ethyl 2-bromo-4-methyl-1,3-thiazole-5-carboxylate (40 mg, 0.16 mmol), to obtain 33 mg of the title compound as a yellow solid substance (66%).

$^1$H NMR spectrum (400 MHz, CDCl$_3$) δ ppm: 1.33 (3H, t, J=7.19 Hz), 1.74-1.84 (1H, m), 2.00-2.05 (1H, m), 2.29 (3H, s), 2.54 (3H, s), 3.06-3.14 (1H, m), 3.16-3.25 (1H, m), 3.42 (3H, s), 3.51 (1H, br s), 3.95-4.04 (1H, m), 4.21-4.28 (3H, m), 4.46-4.55 (1H, m), 7.38-7.45 (1H, m), 10.32-10.46 (1H, m).

(12b) cis(±)-2-(4-{[(4-Chloro-5-methyl-1H-imidazol-2-yl)carbonyl]amino}-3-methoxypiperidin-1-yl)-4-methyl-1,3-thiazole-5-carboxylic acid The same operation as in Example (1i) was performed using ethyl cis(±)-2-(4-{[(4-chloro-5-methyl-1H-imidazol-2-yl)carbonyl]amino}-3-methoxypiperidin-1-yl)-4-methyl-1,3-thiazole-5-carboxylate obtained in Example (12a) (32 mg, 0.072 mmol) and a 2 N aqueous lithium hydroxide solution (2 mL), to obtain 24 mg of the title compound as a white solid (80%).

$^1$H NMR spectrum (400 MHz, DMSO-d$_6$) δ ppm: 1.63-1.72 (1H, m), 1.77-1.92 (1H, m), 2.16 (3H, s), 2.41 (3H, s), 3.22-3.36 (2H, m), 3.32 (3H, s), 3.56 (1H, brs), 3.87-3.98 (1H, m), 4.17-4.27 (2H, m), 7.65 (1H, d, J=8.29 Hz), 12.39 (1H, br s), 13.35 (1H, br s).

mass spectrum (ESI): m/z 414 (M+H)$^+$.

Example 13

Ethyl cis(±)-2-(4-{[(4-chloro-5-ethyl-1H-imidazol-2-yl)carbonyl]amino}-3-methoxypiperidin-1-yl)-4-methyl-1,3-thiazole-5-carboxylate (Exemplified Compound No. 13)

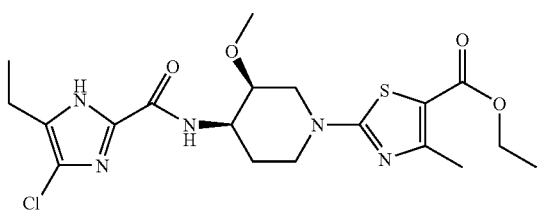

(13a) Ethyl cis(±)-2-(4-{[(4-chloro-5-ethyl-1H-imidazol-2-yl)carbonyl]amino}-3-methoxypiperidin-1-yl)-4-methyl-1,3-thiazole-5-carboxylate The same operation as in Example (1h) was performed using tert-butyl cis(±)-4-{[(4-chloro-5-ethyl-1H-imidazol-2-yl)carbonyl]amino}-3-methoxypiperidine-1-carboxylate obtained by the method described in Example (1g) (57 mg, 0.15 mmol), a 4 N hydrochloric acid/ethyl acetate solution (3 ml), diisopropylethylamine (0.1 mL, 0.57 mmol) and ethyl 2-bromo-4-methyl-1,3-thiazole-5-carboxylate (45 mg, 0.18 mmol), to obtain 52 mg of the title compound as a yellow solid substance (78%).

$^1$H NMR spectrum (400 MHz, CDCl$_3$) δ ppm: 1.27 (3H, t, J=7.66 Hz), 1.33 (3H, t, J=7.19 Hz), 1.72-1.81 (1H, m), 1.97-2.11 (1H, m), 2.54 (3H, s), 2.69 (2H, q, J=7.66 Hz), 3.06-3.13 (1H, m), 3.14-3.24 (1H, m), 3.42 (3H, s), 3.51 (1H, br s), 3.96-4.06 (1H, m), 4.21-4.31 (3H, m), 4.46-4.56 (1H, m), 7.54 (1H, d, J=9.02 Hz), 11.61 (1H, br s).

mass spectrum (ESI): m/z 456 (M+H)$^+$

Example 14 cis(±)-2-(4-{[(4-Chloro-5-ethyl-1H-imidazol-2-yl)carbonyl]amino}-3-methoxypiperidin-1-yl)-4-methyl-1,3-thiazole-5-carboxylic acid (Exemplified Compound No. 14)

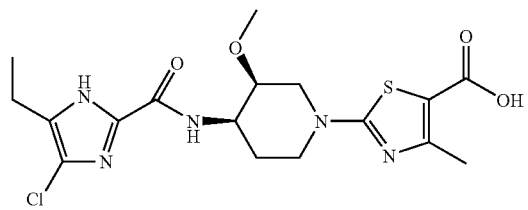

(14a) cis(±)-2-(4-{[(4-Chloro-5-ethyl-1H-imidazol-2-yl)carbonyl]amino}-3-methoxypiperidin-1-yl)-4-methyl-1,3-thiazole-5-carboxylic acid The same operation as in Example (1i) was performed using ethyl cis(±)-2-(4-{[(4-chloro-5-ethyl-1H-imidazol-2-yl)carbonyl]amino}-3-methoxypiperidin-1-yl)-4-methyl-1,3-thiazole-5-carboxylate obtained by the method described in Example (13a) (52 mg, 0.12 mmol) and a 2 N aqueous lithium hydroxide solution (2 mL), to obtain 32 mg of the title compound as a white solid (65%).

$^1$H NMR spectrum (400 MHz, DMSO-d$_6$) δ ppm: 1.14 (3H, t, J=7.56 Hz), 1.62-1.72 (1H, m), 1.81-1.87 (1H, m), 2.41 (3H, s), 2.55 (2H, q, J=7.56 Hz), 3.22-3.36 (2H, m), 3.34 (3H, s), 3.56 (1H, br s), 3.86-3.98 (1H, m), 4.15-4.29 (2H, m), 7.64 (1H, d, J=8.54 Hz), 12.38 (1H, br s), 13.36 (1H, br s).

mass spectrum (ESI): m/z 428 (M+H)$^+$.

Example 15 cis(±)-2-(4-{[(5-Ethyl-4-methyl-1H-imidazol-2-yl)carbonyl]amino}-3-methoxypiperidin-1-yl)-1,3-thiazole-5-carboxylic acid (Exemplified Compound No. 15)

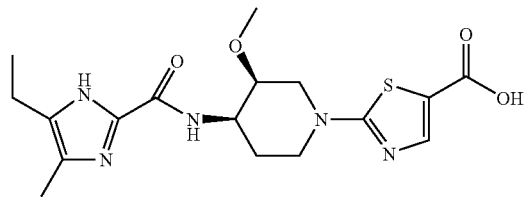

(15a) 2-Bromo-pentan-3-one

The compound was synthesized according to the method described in the following document.

J. Org. Chem., 40, 1975, 1294-1298 (15b) 2-(1-Methyl-2-oxobutyl)-1H-isoindole-1,3(2H)-dione 2-Bromo-pentan-3-one obtained in Example (15a) (8.47 g, 35.57 mmol) was dissolved in DMF (120 mL). Potassium phthalimide (6.9 g, 37.25 mmol) was added, and the mixture was stirred at room temperature for 10 hours. Ethyl acetate was added to the reaction solution, and the organic layer was washed with 1 N hydrochloric acid and brine, and dried over anhydrous sodium sulfate.

Following concentration under reduced pressure, the residue was washed with hexane to obtain 6.5 g of the title compound as a white solid (79%).

$^1$H NMR spectrum (400 MHz, CDCl$_3$) δ ppm: 1.08 (3H, t, J=7.19 Hz), 1.68 (3H, d, J=7.32 Hz), 2.45-2.56 (2H, m), 4.82 (1H, q, J=7.32 Hz), 7.74-7.80 (2H, m), 7.84-7.92 (2H, m).

(15c) 2-Amino-pentan-3-one hydrochloride 2-(1-Methyl-2-oxobutyl)-1H-isoindole-1,3(2H)-dione obtained in Example (15b) (2.3 g, 9.95 mmol) was dissolved in acetic acid (20 mL). 6 N hydrochloric acid (20 mL) was added, and the mixture was heated under reflux for seven hours. The reaction solution was left to stand overnight and the precipitated phthalic acid was separated by filtration. The filtrate was concentrated under reduced pressure to obtain the title compound as a white solid. The resulting compound was used for the next reaction without purification.

(15d) Ethyl 5-ethyl-4-methyl-1H-imidazole-2-carboxylate

The same operation as in Example (1b) was performed using 2-amino-pentan-3-one hydrochloride obtained in Example (15c) (about 10 mmol) and ethyl imino(methylthio) acetate tetrafluoroborate obtained according to a method known in the literature (J. Med. Chem., 38, 1995, 2196-2201) (about 10 mmol), to obtain 1.1 g of the title compound as a yellow solid (60%).

$^1$H NMR spectrum (400 MHz, CDCl$_3$) δ ppm: 1.23 (3H, t, J=7.56 Hz), 1.41 (3H, t, J=7.17 Hz), 2.24 (3H, s), 2.61 (2H, br s), 4.41 (2H, q, J=7.17 Hz), 9.88 (1H, br s).

(15e) 5-Ethyl-4-methyl-1H-imidazole-2-carboxylic acid

The same operation as in Example (1d) was performed using ethyl 5-ethyl-4-methyl-1H-imidazole-2-carboxylate obtained in Example (15d) (0.30 g, 1.66 mmol) and a 3 N aqueous lithium hydroxide solution (2.5 mL), to obtain 0.26 g of the title compound as a white solid (100%).

$^1$H NMR spectrum (400 MHz, DMSO-d$_6$) δ ppm: 1.12 (3H, t, J=7.44 Hz), 2.13 (3H, s), 2.50-2.54 (2H, m).

(15f) tert-Butyl cis(±)-4-{[(5-ethyl-4-methyl-1H-imidazol-2-yl)carbonyl]amino}-3-methoxypiperidine-1-carboxylate The same operation as in Example (1g) was performed using tert-butyl cis(±)-4-amino-3-methoxypiperidine-1-carboxylate obtained by the method described in Example (1e) (0.77 g, 3.32 mmol), 5-ethyl-4-methyl-1H-imidazole-2-carboxylic acid obtained in Example (15e) (0.26 g, 1.66 mmol), WSC hydrochloride (1.85 g, 9.65 mmol) and DMAP (0.2 g, 1.64 mmol), to obtain 0.43 g of the title compound as a white foamy substance (70%).

$^1$H NMR spectrum (400 MHz, CDCl$_3$) δ ppm: 1.19-1.28 (3H, m), 1.47 (9H, s), 1.58-1.71 (1H, m), 1.78-1.92 (1H, m), 2.19 (3H, s), 2.48-2.66 (2H, m), 3.34-3.44 (2H, m), 3.41 (3H, s), 3.97-4.25 (3H, m), 4.33-4.56 (1H, m), 7.41-7.51 (1H, m), 10.21-10.38 (1H, m).

(15g) Ethyl cis(±)-2-(4-{[(5-ethyl-4-methyl-1H-imidazol-2-yl)carbonyl]amino}-3-methoxypiperidin-1-yl)-1,3-thiazole-5-carboxylate The same operation as in Example (1h) was performed using tert-butyl cis(±)-4-{[(5-ethyl-4-methyl-1H-imidazol-2-yl)carbonyl]amino}-3-methoxypiperidine-1-carboxylate obtained in Example (15f) (0.11 g, 0.26 mmol), a 4 N hydrochloric acid/ethyl acetate solution (2 mL), diisopropylethylamine (0.2 mL, 1.15 mmol) and ethyl 2-bromo-1,3-thiazole-5-carboxylate (0.05 mL, 0.33 mmol), to obtain 97 mg of the title compound as a yellow solid (79%).

$^1$H NMR spectrum (400 MHz, CDCl$_3$) δ ppm: 1.26 (3H, t, J=7.07 Hz), 1.34 (3H, t, J=7.07 Hz), 1.78-1.87 (1H, m), 2.00-2.09 (1H, m), 2.18-2.26 (3H, m), 2.50-2.65 (2H, m), 3.12-3.19 (1H, m), 3.20-3.30 (1H, m), 3.42 (3H, s), 3.54 (1H, br s), 3.95-4.03 (1H, m), 4.23-4.33 (1H, m), 4.29 (3H, q, J=7.07 Hz), 4.50-4.57 (1H, m), 7.42-7.49 (1H, m), 7.84 (1H, s), 10.00-10.13 (1H, m).

(15h) cis(±)-2-(4-{[(5-Ethyl-4-methyl-1H-imidazol-2-yl)carbonyl]amino}-3-methoxypiperidin-1-yl)-1,3-thiazole-5-carboxylic acid The same operation as in Example (1i) was performed using ethyl cis(±)-2-(4-{[(5-ethyl-4-methyl-1H-imidazol-2-yl)carbonyl]amino}-3-methoxypiperidin-1-yl)-1,3-thiazole-5-carboxylate obtained in Example (15g) (95 mg, 0.19 mmol) and a 2 N aqueous lithium hydroxide solution (3 mL), to obtain 64 mg of the title compound as a white solid (72%).

$^1$H NMR spectrum (400 MHz, DMSO-d$_6$) δ ppm: 1.10 (3H, t, J=7.44 Hz), 1.66-1.75 (1H, m), 1.77-1.87 (1H, m), 2.05-2.16 (3H, m), 2.46-2.55 (2H, m), 3.28-3.37 (2H, m), 3.34 (3H, s), 3.56 (1H, br s), 3.88-3.97 (1H, m), 4.18-4.23 (1H, m), 4.29-4.40 (1H, m), 7.41-7.51 (1H, m), 7.74 (1H, s), 12.57-12.67 (2H, m).

mass spectrum (ESI): m/z 394 (M+H)$^+$.

Example 16 cis(±)-2-(4-{[(5-Ethyl-4-methyl-1H-imidazol-2-yl)carbonyl]amino}-3-methoxypiperidin-1-yl)-1,3-benzothiazole-7-carboxylic acid (Exemplified Compound No. 16)

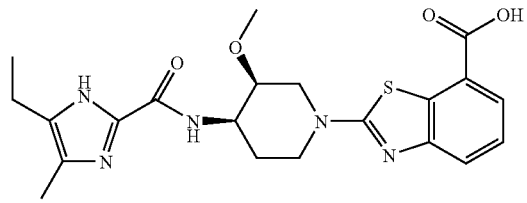

(16a) Ethyl cis(±)-2-(4-{[(5-ethyl-4-methyl-1H-imidazol-2-yl)carbonyl]amino}-3-methoxypiperidin-1-yl)-1,3-benzothiazole-7-carboxylate The same operation as in Example (1h) was performed using tert-butyl cis(±)-4-{[(5-ethyl-4-methyl-1H-imidazol-2-yl)carbonyl]amino}-3-methoxypiperidine-1-carboxylate obtained by the method described in Example (15f) (0.11 g, 0.26 mmol), a 4 N hydrochloric acid/ethyl acetate solution (2 mL), diisopropylethylamine (0.2 mL, 1.15 mmol) and ethyl 2-bromo-1,3-benzothiazole-7-carboxylate obtained by the method described in Example (1f) (88 mg, 0.31 mmol), to obtain 80 mg of the title compound as a yellow solid (58%).

$^1$H NMR spectrum (400 MHz, CDCl$_3$) δ ppm: 1.21-1.28 (3H, m), 1.44 (3H, t, J=7.14 Hz), 1.81-1.90 (1H, m), 2.03-2.28 (4H, m), 2.48-2.68 (2H, m), 3.22-3.37 (2H, m), 3.46 (3H, s), 3.57 (1H, br s), 4.19-4.36 (2H, m), 4.45 (2H, q, J=7.14 Hz), 4.54-4.64 (1H, m), 7.33-7.39 (1H, m), 7.43-7.54 (1H, m), 7.69 (1H, dd, J=7.80, 1.04 Hz), 7.78 (1H, dd, J=7.68, 1.04 Hz), 10.05-10.21 (1H, m).

(16b) cis(±)-2-(4-{[(5-Ethyl-4-methyl-1H-imidazol-2-yl)carbonyl]amino}-3-methoxypiperidin-1-yl)-1,3-benzothiazole-7-carboxylic acid The same operation as in Example (1i) was performed using ethyl cis(±)-2-(4-{[(5-ethyl-4-methyl-1H-imidazol-2- yl)carbonyl]amino}-3-methoxypiperidin-1-yl)-1,3-benzothiazole-7-carboxylate obtained in Example (16a) (78 mg, 0.17 mmol) and a 2 N aqueous lithium hydroxide solution (2 mL), to obtain 36 mg of the title compound as a white solid (49%).

$^1$H NMR spectrum (400 MHz, DMSO-$d_6$) δ ppm: 1.22 (3H, t, J=7.56 Hz), 1.33 (3H, t, J=7.07 Hz), 1.76-1.85 (1H, m), 1.98-2.10 (1H, m), 2.16-2.28 (3H, m), 2.54 (3H, s), 2.62 (2H, q, J=7.56 Hz), 3.09-3.15 (1H, m), 3.18-3.25 (1H, m), 3.43 (3H, s), 3.52 (1H, br s), 3.95-4.03 (1H, m), 4.21-4.31 (3H, m), 4.46-4.53 (1H, m), 7.41-7.49 (1H, m), 9.95-10.07 (1H, m).

mass spectrum (ESI): m/z 444 (M+H)$^+$.

Example 17 cis(±)-2-(4-{[(5-Ethyl-4-methyl-1H-imidazol-2-yl)carbonyl]amino}-3-methoxypiperidin-1-yl)-4-methyl-1,3-thiazole-5-carboxylic acid (Exemplified Compound No. 17)

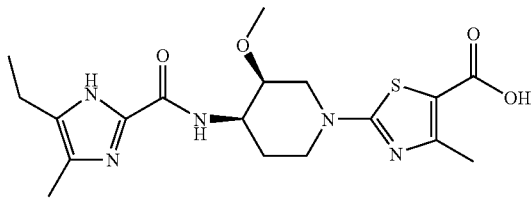

(17a) Ethyl cis(±)-2-(4-{[(5-ethyl-4-methyl-1H-imidazol-2-yl)carbonyl]amino}-3-methoxypiperidin-1-yl)-4-methyl-1,3-thiazole-5-carboxylate The same operation as in Example (1h) was performed using tert-butyl cis(±)-4-{[(5-ethyl-4-methyl-1H-imidazol-2-yl)carbonyl]amino}-3-methoxypiperidine-1-carboxylate obtained by the method described in Example (15f) (0.11 g, 0.26 mmol), a 4 N hydrochloric acid/ethyl acetate solution (2 mL), diisopropylethylamine (0.2 mL, 1.15 mmol) and ethyl 2-bromo-4-methyl-1,3-thiazole-5-carboxylate (83 mg, 0.33 mmol), to obtain 78 mg of the title compound as a yellow solid (61%).

$^1$H NMR spectrum (400 MHz, CDCl$_3$) δ ppm: 1.22 (3H, t, J=7.56 Hz), 1.33 (3H, t, J=7.07 Hz), 1.76-1.85 (1H, m), 1.98-2.10 (1H, m), 2.16-2.28 (3H, m), 2.54 (3H, s), 2.62 (2H, q, J=7.56 Hz), 3.09-3.15 (1H, m), 3.18-3.25 (1H, m), 3.43 (3H, s), 3.52 (1H, br s), 3.95-4.03 (1H, m), 4.21-4.31 (3H, m), 4.46-4.53 (1H, m), 7.41-7.49 (1H, m), 9.95-10.07 (1H, m).

(17b) cis(±)-2-(4-{[(5-Ethyl-4-methyl-1H-imidazol-2-yl)carbonyl]amino}-3-methoxypiperidin-1-yl)-4-methyl-1,3-thiazole-5-carboxylic acid The same operation as in Example (1i) was performed using ethyl cis(±)-2-(4-{[(5-ethyl-4-methyl-1H-imidazol-2-yl)carbonyl]amino}-3-methoxypiperidin-1-yl)-4-methyl-1,3-thiazole-5-carboxylate obtained in Example (17a) (75 mg, 0.17 mmol) and a 2 N aqueous lithium hydroxide solution (2 mL), to obtain 60 mg of the title compound as a white solid (85%).

$^1$H NMR spectrum (400 MHz, DMSO-$d_6$) δ ppm: 1.10 (3H, t, J=7.56 Hz), 1.69 (1H, s), 1.81-1.85 (1H, m), 2.06-2.12 (3H, m), 2.40 (3H, s), 2.46-2.53 (2H, m), 3.26-3.37 (2H, m), 3.34 (3H, s), 3.90 (1H, br s), 4.12-4.32 (2H, m), 7.37-7.49 (1H, m), 12.33-12.43 (1H, m), 12.58-12.67 (1H, m).

mass spectrum (ESI): m/z 408 (M+H)$^+$.

Example 18 cis(±)-2-(4-{[(4-Chloro-5-methyl-1H-imidazol-2-yl)carbonyl]amino}-3-ethoxypiperidin-1-yl)-1,3-thiazole-5-carboxylic acid (Exemplified Compound No. 18)

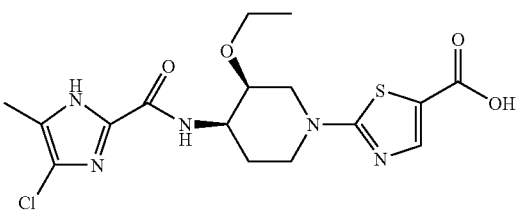

(18a) tert-Butyl cis(±)-4-amino-3-ethoxypiperidine-1-carboxylate

The compound was synthesized according to the method described in the following document.

WO 2006/087543 A1

(18b) tert-Butyl cis(±)-4-{[(4-chloro-5-methyl-1H-imidazol-2-yl)carbonyl]amino}-3-ethoxypiperidine-1-carboxylate The same operation as in Example (1g) was performed using tert-butyl cis(±)-4-amino-3-ethoxypiperidine-1-carboxylate obtained in Example (18a) (0.34 g, 1.37 mmol), 4-chloro-5-methyl-1H-imidazole-2-carboxylic acid obtained by the method described in Example (5c) (0.16 g, 0.91 mmol), WSC hydrochloride (1.18 g, 6.15 mmol) and DMAP (0.12 g, 0.94 mmol), to obtain 0.23 g of the title compound as a pale yellow solid (43%).

$^1$H NMR spectrum (400 MHz, CDCl$_3$) δ ppm: 1.17-1.29 (3H, m), 1.47 (9H, s), 1.56-1.69 (1H, m), 1.81-1.95 (1H, m), 2.28 (3H, s), 2.68-2.90 (2H, m), 3.40 (2H, m), 3.68-3.81 (1H, m), 4.00-4.51 (3H, m), 7.39-7.50 (1H, m), 10.93 (1H, brs).

(18c) Ethyl cis(±)-2-(4-{[(4-chloro-5-methyl-1H-imidazol-2-yl)carbonyl]amino}-3-ethoxypiperidin-1-yl)-1,3-thiazole-5-carboxylate The same operation as in Example (1h) was performed using tert-butyl cis(±)-4-{[(4-chloro-5-methyl-1H-imidazol-2-yl)carbonyl]amino}-3-ethoxypiperidine-1-carboxylate obtained in Example (18b) (82 mg, 0.21 mmol), a 4 N hydrochloric acid/ethyl acetate solution (5 ml), diisopropylethylamine (0.2 mL, 1.15 mmol) and ethyl 2-bromo-1,3-thiazole-5-carboxylate (0.004 mL, 0.27 mmol), to obtain 79 mg of the title compound as a yellow solid substance (85%).

$^1$H NMR spectrum (400 MHz, CDCl$_3$) δ ppm: 1.15 (3H, t, J=6.95 Hz), 1.34 (3H, t, J=7.17 Hz), 1.76-1.84 (1H, m), 2.02-2.14 (1H, m), 2.30 (3H, s), 3.13-3.20 (1H, m), 3.20-3.29 (1H, m), 3.39-3.49 (1H, m), 3.62 (1H, brs), 3.68-3.78 (1H, m), 3.98-4.06 (1H, m), 4.20-4.34 (1H, m), 4.30 (2H, q, J=7.17 Hz), 4.41-4.51 (OH, m), 7.43 (1H, d, J=9.02 Hz), 7.84 (1H, s), 10.65 (1H, br s).

(18d) cis(±)-2-(4-{[(4-Chloro-5-methyl-1H-imidazol-2-yl)carbonyl]amino}-3-ethoxypiperidin-1-yl)-1,3-thiazole-5-carboxylic acid The same operation as in Example (1i) was performed using ethyl cis(±)-2-(4-{[(4-chloro-5-methyl-1H-imidazol-2-yl)carbonyl]amino}-3-ethoxypiperidin-1-yl)-1,3-thiazole-5-carboxylate obtained in Example (18c) (78 mg, 0.18 mmol) and a 2 N aqueous lithium hydroxide solution (2 mL), to obtain 50 mg of the title compound as a pale yellow solid (68%).

¹H NMR spectrum (400 MHz, DMSO-d₆) δ ppm: 1.04 (3H, t, J=6.95 Hz), 1.65-1.74 (1H, m), 1.84-1.90 (1H, m), 2.16 (3H, s), 3.25-3.48 (3H, m), 3.58-3.67 (2H, m), 3.92-4.04 (1H, m), 4.14-4.27 (2H, m), 7.64 (1H, d, J=8.29 Hz), 7.73 (1H, s), 12.59 (1H, br s), 13.34 (1H, brs).

mass spectrum (ESI): m/z 414 (M+H)⁺.

Example 19 cis(±)-2-(4-{[(4-Chloro-5-methyl-1H-imidazol-2-yl)carbonyl]amino}-3-ethoxypiperidin-1-yl)-4-methyl-1,3-thiazole-5-carboxylic acid (Exemplified Compound No. 19)

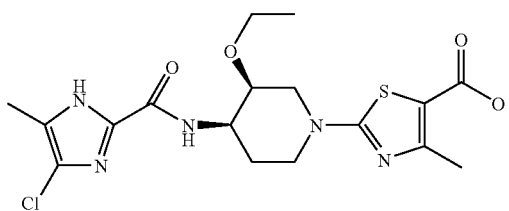

(19a) Ethyl cis(±)-2-(4-{[(4-chloro-5-methyl-1H-imidazol-2-yl)carbonyl]amino}-3-ethoxypiperidin-1-yl)-4-methyl-1,3-thiazole-5-carboxylate The same operation as in Example (1h) was performed using tert-butyl cis(±)-4-{[(4-chloro-5-methyl-1H-imidazol-2-yl)carbonyl]amino}-3-ethoxypiperidine-1-carboxylate obtained by the method described in Example (18b) (82 mg, 0.21 mmol), a 4 N hydrochloric acid/ethyl acetate solution (5 mL), diisopropylethylamine (0.2 mL, 1.15 mmol) and ethyl 2-bromo-4-methyl-1,3-thiazole-5-carboxylate (58 mg, 0.23 mmol), to obtain 74 mg of the title compound as a yellow solid (76%).

¹H NMR spectrum (400 MHz, CDCl₃) δ ppm: 1.16 (3H, t, J=6.95 Hz), 1.33 (3H, t, J=7.07 Hz), 1.74-1.83 (1H, m), 2.01-2.12 (1H, m), 2.29 (3H, s), 2.54 (3H, s), 3.08-3.26 (2H, m), 3.39-3.47 (1H, m), 3.61 (1H, br s), 3.70-3.78 (1H, m), 3.96-4.06 (1H, m), 4.19-4.30 (3H, m), 4.36-4.45 (1H, m), 7.40-7.47 (1H, m), 10.75 (1H, br s).

(19b) cis(±)-2-(4-{[(4-Chloro-5-methyl-1H-imidazol-2-yl)carbonyl]amino}-3-ethoxypiperidin-1-yl)-4-methyl-1,3-thiazole-5-carboxylic acid The same operation as in Example (1i) was performed using ethyl cis(±)-2-(4-{[(4-chloro-5-methyl-1H-imidazol-2-yl)carbonyl]amino}-3-ethoxypiperidin-1-yl)-4-methyl-1,3-thiazole-5-carboxylate obtained in Example (19a) (70 mg, 0.15 mmol) and a 2 N aqueous lithium hydroxide solution (2 mL), to obtain 31 mg of the title compound as a white solid (47%).

¹H NMR spectrum (400 MHz, DMSO-d₆) δ ppm: 1.04 (3H, t, J=7.08 Hz), 1.61-1.72 (1H, m), 1.78-1.92 (1H, m), 2.16 (3H, s), 2.40 (3H, s), 3.22-3.47 (3H, m), 3.59-3.65 (2H, m), 3.91-4.01 (1H, m), 4.09-4.22 (2H, m), 7.62 (1H, d, J=8.54 Hz), 13.34 (1H, br s).

mass spectrum (ESI): m/z 428 (M+H)⁺.

Example 20 cis(±)-2-(4-{[(4-Chloro-5-methyl-1H-imidazol-2-yl)carbonyl]amino}-3-propoxypiperidin-1-yl)-1,3-thiazole-5-carboxylic acid (Exemplified Compound No. 20)

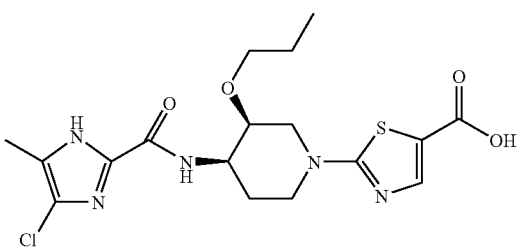

(20a) tert-Butyl cis(±)-4-amino-3-propoxypiperidine-1-carboxylate

The compound was synthesized according to the method described in the following document.

WO 2006/087543 A1

(20b) tert-Butyl cis(±)-4-{[(4-chloro-5-methyl-1H-imidazol-2-yl)carbonyl]amino}-3-propoxypiperidine-1-carboxylate The same operation as in Example (1g) was performed using tert-butyl cis(±)-4-amino-3-propoxypiperidine-1-carboxylate obtained in Example (20a) (0.22 g, 0.85 mmol), 4-chloro-5-methyl-1H-imidazole-2-carboxylic acid obtained by the method described in Example (5c) (0.11 g, 0.64 mmol), WSC hydrochloride (0.63 g, 3.28 mmol) and DMAP (84 mg, 0.69 mmol), to obtain 0.15 g of the title compound as a pale yellow solid (60%).

¹H NMR spectrum (400 MHz, CDCl₃) δ ppm: 0.90-0.99 (3H, m), 1.46 (9H, s), 1.57-1.67 (3H, m), 1.80-1.95 (1H, m), 2.28 (3H, s), 2.65-2.93 (2H, m), 3.22-3.31 (1H, m), 3.45 (1H, br s), 3.64 (1H, br s), 3.95-4.46 (3H, m), 7.40-7.51 (1H, m), 10.98 (1H, br s).

(20c) Ethyl cis(±)-2-(4-{[(4-chloro-5-methyl-1H-imidazol-2-yl)carbonyl]amino}-3-propoxypiperidin-1-yl)-1,3-thiazole-5-carboxylate The same operation as in Example (1h) was performed using tert-butyl cis(±)-4-{[(4-chloro-5-methyl-1H-imidazol-2-yl)carbonyl]amino}-3-propoxypiperidine-1-carboxylate obtained in Example (20b) (76 mg, 0.19 mmol), a 4 N hydrochloric acid/ethyl acetate solution (3 ml), diisopropylethylamine (0.15 mL, 0.86 mmol) and ethyl 2-bromo-1,3-thiazole-5-carboxylate (0.004 mL, 0.27 mmol), to obtain 65 mg of the title compound as a yellow solid substance (74%).

¹H NMR spectrum (400 MHz, CDCl₃) δ ppm: 0.86 (3H, t, J=7.44 Hz), 1.34 (3H, t, J=7.13 Hz), 1.49-1.60 (2H, m), 1.79-1.88 (1H, m), 2.05-2.16 (1H, m), 2.29 (3H, s), 3.14-3.36 (3H, m), 3.59-3.67 (2H, m), 3.96-4.06 (1H, m), 4.20-4.34 (1H, m), 4.30 (2H, q, J=7.13 Hz), 4.43-4.52 (1H, m), 7.50 (1H, d, J=8.78 Hz), 7.84 (1H, s), 11.33 (1H, br s).

(20d) cis(±)-2-(4-{[(4-Chloro-5-methyl-1H-imidazol-2-yl)carbonyl]amino}-3-propoxypiperidin-1-yl)-1,3-thiazole-5-carboxylic acid The same operation as in Example (1i) was performed using ethyl cis(±)-2-(4-{[(4-chloro-5-methyl-1H-imidazol-2-yl)carbonyl]amino}-3-propoxypiperidin-1-yl)-1,3-thiazole-5-carboxylate obtained in Example (20c) (60 mg, 0.13 mmol) and a 2 N aqueous lithium hydroxide solution (2 mL), to obtain 43 mg of the title compound as a pale yellow solid (76%).

$^1$H NMR spectrum (400 MHz, DMSO-d$_6$) δ ppm: 0.80 (3H, t, J=7.44 Hz), 1.38-1.49 (2H, m), 1.64-1.74 (1H, m), 1.81-1.96 (1H, m), 2.15 (3H, s), 3.28-3.35 (3H, m), 3.50-3.59 (1H, m), 3.66 (1H, br s), 3.89-4.00 (1H, m), 4.16-4.26 (2H, m), 7.63 (1H, d, J=8.54 Hz), 7.73 (1H, s), 12.58 (1H, br s), 13.33 (1H, br s).

mass spectrum (ESI): m/z 428 (M+H)$^+$.

Example 21 cis(±)-2-(4-{[(4-Chloro-5-methyl-1H-imidazol-2-yl)carbonyl]amino}-3-propoxypiperidin-1-yl)-4-methyl-1,3-thiazole-5-carboxylic acid (Exemplified Compound No. 21)

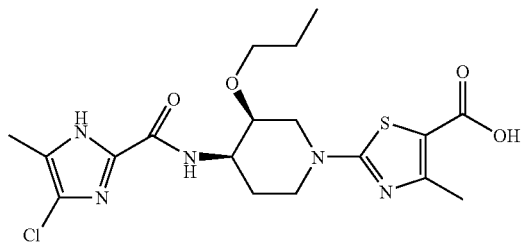

(21a) Ethyl cis(±)-2-(4-{[(4-chloro-5-methyl-1H-imidazol-2-yl)carbonyl]amino}-3-propoxypiperidin-1-yl)-4-methyl-1,3-thiazole-5-carboxylate The same operation as in Example (1h) was performed using tert-butyl cis(±)-4-{[(4-chloro-5-methyl-1H-imidazol-2-yl)carbonyl]amino}-3-propoxypiperidine-1-carboxylate obtained by the method described in Example (20b) (76 mg, 0.19 mmol), a 4 N hydrochloric acid/ethyl acetate solution (3 ml), diisopropylethylamine (0.15 mL, 0.86 mmol) and ethyl 2-bromo-4-methyl-1,3-thiazole-5-carboxylate (63 mg, 0.25 mmol), to obtain 79 mg of the title compound as a yellow solid (89%).

$^1$H NMR spectrum (400 MHz, CDCl$_3$) δ ppm: 0.86 (3H, t, J=7.44 Hz), 1.33 (3H, t, J=7.07 Hz), 1.49-1.62 (2H, m), 1.76-1.81 (1H, m), 2.04-2.18 (1H, m), 2.29 (3H, s), 2.53 (3H, s), 3.10-3.35 (3H, m), 3.60-3.67 (2H, m), 3.95-4.06 (1H, m), 4.20-4.29 (3H, m), 4.40-4.50 (1H, m), 7.51 (1H, d, J=8.78 Hz), 11.40 (1H, br s).

(21b) cis(±)-2-(4-{[(4-Chloro-5-methyl-1H-imidazol-2-yl)carbonyl]amino}-3-propoxypiperidin-1-yl)-4-methyl-1,3-thiazole-5-carboxylic acid The same operation as in Example (1i) was performed using ethyl cis(±)-2-(4-{[(4-chloro-5-methyl-1H-imidazol-2-yl)carbonyl]amino}-3-propoxypiperidin-1-yl)-4-methyl-1,3-thiazole-5-carboxylate obtained in Example (21a) (75 mg, 0.16 mmol) and a 2 N aqueous lithium hydroxide solution (2.5 mL), to obtain 56 mg of the title compound as a white solid (80%).

$^1$H NMR spectrum (400 MHz, DMSO-d$_6$) δ ppm: 0.81 (3H, t, J=7.44 Hz), 1.39-1.46 (2H, m), 1.64-1.73 (1H, m), 1.80-1.93 (1H, m), 2.15 (3H, s), 2.40 (3H, s), 3.22-3.36 (3H, m), 3.51-3.59 (1H, m), 3.62-3.67 (1H, m), 3.88-4.00 (1H, m), 4.12-4.24 (2H, m), 7.62 (1H, d, J=8.54 Hz), 12.37 (1H, br s), 13.33 (1H, br s).

mass spectrum (ESI): m/z 442 (M+H)$^+$.

Example 22 cis(±)-2-(4-{[(4-Chloro-5-ethyl-1H-imidazol-2-yl)carbonyl]amino}-3-methoxypiperidin-1-yl)-4-ethyl-1,3-thiazole-5-carboxylic acid (Exemplified Compound No. 22)

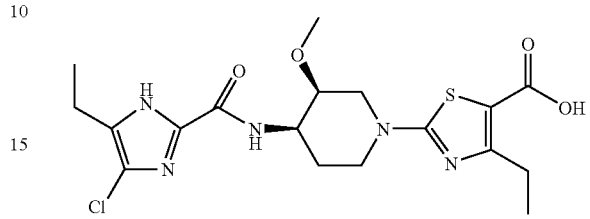

(22a) Methyl 2-chloro-3-oxo-pentanoate

The compound was synthesized according to the method described in the following document.

U.S. Pat. No. 5,925,792 A1

(22b) Methyl 2-amino-4-ethyl-1,3-thiazole-5-carboxylate

Methyl 2-chloro-3-oxo-pentanoate obtained in Example (22a) (1.91 g, 11.57 mmol) was dissolved in ethanol (50 mL). Thiourea (0.77 g, 10.09 mmol) was added, and the mixture was heated under reflux for 1.5 hours. The reaction solution was concentrated under reduced pressure, diluted with ethyl acetate, washed with saturated aqueous sodium bicarbonate solution and brine, and dried over anhydrous sodium sulfate. Following concentration under reduced pressure, the residue was washed with hexane/ethyl acetate: 5/1 to obtain 1.78 g of the title compound as a pale yellow solid (95%).

$^1$H NMR spectrum (400 MHz, CDCl$_3$) δ ppm: 1.23 (3H, t, J=7.53 Hz), 2.97 (2H, q, J=7.53 Hz), 3.80 (3H, s), 5.44 (2H, br s).

(22c) Methyl 2-bromo-4-ethyl-1,3-thiazole-5-carboxylate

Methyl 2-amino-4-ethyl-1,3-thiazole-5-carboxylate obtained in Example (22b) (0.5 g, 2.68 mmol) was suspended in acetonitrile (25 mL). Copper bromide (0.9 g, 4.03 mmol) and tert-butyl nitrite (0.48 mL, 4.04 mmol) were added, and the mixture was stirred at room temperature for two hours. The reaction solution was concentrated under reduced pressure, diluted with ethyl acetate, washed with 1 N hydrochloric acid and brine, and dried over anhydrous sodium sulfate. Following concentration under reduced pressure, the residue was purified by silica gel column chromatography (elution solvent: hexane/ethyl acetate=97/3, 95/5) to obtain 0.63 g of the title compound as a white solid (94%).

$^1$H NMR spectrum (400 MHz, CDCl$_3$) δ ppm: 1.28 (3H, t, J=7.53 Hz), 3.13 (2H, q, J=7.53 Hz), 3.87 (3H, s).

(22d) Methyl cis(±)-2-(4-{[(4-chloro-5-ethyl-1H-imidazol-2-yl)carbonyl]amino}-3-methoxypiperidin-1-yl)-4-ethyl-1,3-thiazole-5-carboxylate The same operation as in Example (1h) was performed using tert-butyl cis(±)-4-{[(4-chloro-5-ethyl-1H-imidazol-2-yl)carbonyl]amino}-3-methoxypiperidine-1-carboxylate obtained by the method described in Example (1g) (67 mg, 0.17 mmol), a 4 N hydrochloric acid/ethyl acetate solution (3 ml), diisopropylethylamine (0.12 mL, 0.69 mmol) and methyl 2-bromo-4-ethyl-1,3-thiazole-5-carboxylate obtained in Example (22c) (48 mg, 0.19 mmol), to obtain 49 mg of the title compound as a yellow solid (61%).

$^1$H NMR spectrum (400 MHz, CDCl$_3$) δ ppm: 1.19-1.34 (6H, m), 1.74-1.87 (1H, m), 1.98-2.10 (1H, m), 2.69 (2H, q, J=7.64 Hz), 3.40-3.57 (4H, m), 3.43 (3H, s), 3.78-3.86 (1H, m), 3.79 (3H, s), 3.93-4.02 (2H, m), 4.20-4.34 (1H, m), 4.55-4.69 (1H, m), 4.85 (1H, br s), 7.50-7.60 (1H, m), 11.43 (1H, br s).

(22e) cis(±)-2-(4-{[(4-Chloro-5-ethyl-1H-imidazol-2-yl)carbonyl]amino}-3-methoxypiperidin-1-yl)-4-ethyl-1,3-thiazole-5-carboxylic acid The same operation as in Example (1i) was performed using methyl cis(±)-2-(4-{[(4-chloro-5-ethyl-1H-imidazol-2-yl)carbonyl]amino}-3-methoxypiperidin-1-yl)-4-ethyl-1,3-thiazole-5-carboxylate obtained in Example (22d) (49 mg, 0.11 mmol) and a 2 N aqueous lithium hydroxide solution (1.5 mL), to obtain 31 mg of the title compound as a white solid (65%).

$^1$H NMR spectrum (400 MHz, DMSO-$d_6$) δ ppm: 1.10-1.17 (6H, m), 1.65-1.72 (1H, m), 1.79-1.92 (1H, m), 2.51-2.59 (2H, m), 2.74-2.96 (2H, m), 3.24-3.36 (2H, m), 3.34 (3H, s), 3.56 (1H, br s), 3.82-3.88 (1H, m), 4.16-4.25 (1H, m), 4.28-4.40 (1H, m), 7.64 (1H, d, J=8.54 Hz), 12.38 (1H, br s), 13.37 (1H, br s).

mass spectrum (ESI): m/z 442 (M+H)$^+$.

Example 23 cis(±)-2-(4-{[(4-Chloro-5-ethyl-1H-imidazol-2-yl)carbonyl]amino}-3-methoxypiperidin-1-yl)-4-isopropyl-1,3-thiazole-5-carboxylic acid (Exemplified Compound No. 23)

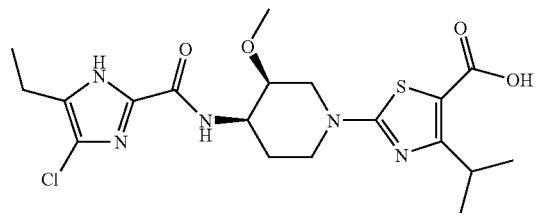

(23a) Ethyl 2-amino-4-isopropyl-1,3-thiazole-5-carboxylate

The compound was synthesized according to the method described in the following document.

J. Heterocycl. Chem., 1985, 1621-1630

(23b) Ethyl 2-bromo-4-isopropyl-1,3-thiazole-5-carboxylate

The same operation as in Example (22c) was performed using ethyl 2-amino-4-isopropyl-1,3-thiazole-5-carboxylate obtained in Example (23a) (0.5 g, 2.33 mmol), copper bromide (0.79 g, 3.53 mmol) and tert-butyl nitrite (0.42 mL, 3.53 mmol), to obtain 0.60 g of the title compound as a white solid (92%).

$^1$H NMR spectrum (400 MHz, CDCl$_3$) δ ppm: 1.28 (6H, d, J=6.84 Hz), 1.36 (3H, t, J=7.12 Hz), 3.89-3.99 (1H, m), 4.32 (2H, q, J=7.12 Hz).

(23c) Ethyl cis(±)-2-(4-{[(4-chloro-5-ethyl-1H-imidazol-2-yl)carbonyl]amino}-3-methoxypiperidin-1-yl)-4-isopropyl-1,3-thiazole-5-carboxylate The same operation as in Example (1h) was performed using tert-butyl cis(±)-4-{[(4-chloro-5-ethyl-1H-imidazol-2-yl)carbonyl]amino}-3-methoxypiperidine-1-carboxylate obtained by the method described in Example (1g) (67 mg, 0.17 mmol), a 4 N hydrochloric acid/ethyl acetate solution (3 ml), diisopropylethylamine (0.12 mL, 0.69 mmol) and ethyl 2-bromo-4-isopropyl-1,3-thiazole-5-carboxylate obtained in Example (23b) (55 mg, 0.19 mmol), to obtain 55 mg of the title compound as a yellow solid (65%).

$^1$H NMR spectrum (400 MHz, CDCl$_3$) δ ppm: 1.10-1.43 (9H, m), 1.76-1.97 (1H, m), 1.94-2.10 (1H, m), 2.69 (2H, q, J=7.64 Hz), 2.97-3.06 (1H, m), 3.10-3.29 (1H, m), 3.43 (3H, s), 3.49-3.52 (1H, m), 3.81-3.99 (2H, m), 4.21-4.30 (3H, m), 4.71-4.80 (1H, m), 7.47-7.53 (1H, m), 11.19 (1H, br s).

(23d) cis(±)-2-(4-{[(4-Chloro-5-ethyl-1H-imidazol-2-yl)carbonyl]amino}-3-methoxypiperidin-1-yl)-4-isopropyl-1,3-thiazole-5-carboxylic acid The same operation as in Example (1i) was performed using ethyl cis(±)-2-(4-{[(4-chloro-5-ethyl-1H-imidazol-2-yl)carbonyl]amino}-3-methoxypiperidin-1-yl)-4-isopropyl-1,3-thiazole-5-carboxylate obtained in Example (23c) (55 mg, 0.11 mmol) and a 2 N aqueous lithium hydroxide solution (2 mL), to obtain 32 mg of the title compound as a white solid (62%).

$^1$H NMR spectrum (400 MHz, DMSO-$d_6$) δ ppm: 1.11-1.18 (9H, m), 1.62-1.72 (1H, m), 1.79-1.92 (1H, m), 2.51-2.59 (2H, m), 3.21-3.37 (2H, m), 3.34 (3H, s), 3.55 (1H, br s), 3.76-3.87 (2H, m), 4.14-4.25 (1H, m), 4.36-4.51 (1H, m), 7.64 (1H, d, J=8.54 Hz), 12.40 (1H, br s), 13.37 (1H, br s).

mass spectrum (ESI): m/z 456 (M+H)$^+$.

Example 24 cis(±)-2-(4-{[(4-Chloro-5-ethyl-1H-imidazol-2-yl)carbonyl]amino}-3-methoxypiperidin-1-yl)-4-trifluoromethyl-1,3-thiazole-5-carboxylic acid (Exemplified Compound No. 24)

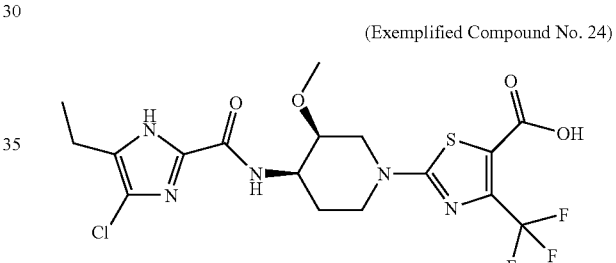

(24a) Ethyl cis(±)-2-(4-{[(4-chloro-5-ethyl-1H-imidazol-2-yl)carbonyl]amino}-3-methoxypiperidin-1-yl)-4-trifluoromethyl-1,3-thiazole-5-carboxylate The same operation as in Example (1h) was performed using tert-butyl cis(±)-4-{[(4-chloro-5-ethyl-1H-imidazol-2-yl)carbonyl]amino}-3-methoxypiperidine-1-carboxylate obtained in Example (1g) (77 mg, 0.20 mmol), a 4 N hydrochloric acid/ethyl acetate solution (3 ml), diisopropylethylamine (0.14 mL, 0.80 mmol) and ethyl 2-chloro-4-trifluoromethyl-1,3-thiazole-5-carboxylate (62 mg, 0.24 mmol), to obtain 88 mg of the title compound as a yellow solid (86%).

$^1$H NMR spectrum (400 MHz, CDCl$_3$) δ ppm: 1.23-1.37 (6H, m), 1.77-1.94 (1H, m), 1.96-2.06 (1H, m), 2.69 (2H, q, J=7.56 Hz), 3.06-3.15 (1H, m), 3.22-3.34 (1H, m), 3.42 (3H, s), 3.49-3.55 (1H, m), 3.88-4.00 (1H, m), 4.21-4.35 (3H, m), 4.57-4.67 (1H, m), 7.39-7.47 (1H, m), 10.58 (1H, br s).

(24b) cis(±)-2-(4-{[(4-Chloro-5-ethyl-1H-imidazol-2-yl)carbonyl]amino}-3-methoxypiperidin-1-yl)-4-trifluoromethyl-1,3-thiazole-5-carboxylic acid The same operation as in Example (1i) was performed using ethyl cis(±)-2-(4-{[(4-chloro-5-ethyl-1H-imidazol-2-yl)carbonyl]amino}-3-methoxypiperidin-1-yl)-4-trifluoromethyl-1,3-thiazole-5-carboxylate obtained in Example (24a) (85 mg, 0.17 mmol) and a 2 N aqueous lithium hydroxide solution (1.5 mL), to obtain 51 mg of the title compound as a white solid (63%).

¹H NMR spectrum (400 MHz, DMSO-d₆) δ ppm: 1.14 (3H, t, J=7.51 Hz), 1.65-1.74 (1H, m), 1.81-1.95 (1H, m), 2.55 (2H, q, J=7.51 Hz), 3.26-3.42 (5H, m), 3.59 (1H, br s), 3.82-3.99 (1H, m), 4.17-4.36 (2H, m), 7.69 (1H, d, J=8.30 Hz), 13.35-13.46 (2H, m).

mass spectrum (ESI): m/z 482 (M+H)⁺.

Example 25 cis(±)-2-(4-{[(4-Bromo-5-ethyl-1H-imidazol-2-yl)carbonyl]amino}-3-methoxypiperidin-1-yl)-4-methyl-1,3-thiazole-5-carboxylic acid (Exemplified Compound No. 25)

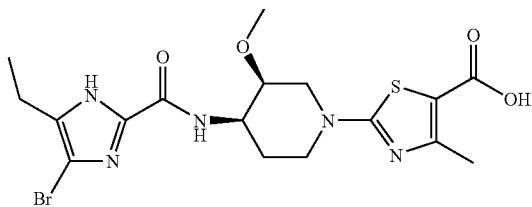

(25a) Ethyl 4-bromo-5-ethyl-1H-imidazole-2-carboxylate

The same operation as in Example (1c) was performed using ethyl 5-ethyl-1H-imidazole-2-carboxylate obtained by the method described in Example (1b) (0.29 g, 1.30 mmol) and NBS (0.28 g, 1.28 mmol), to obtain 0.22 g of the title compound as a white solid (69%).

¹H NMR spectrum (400 MHz, CDCl₃) δ ppm: 1.27 (3H, t, J=7.67 Hz), 1.41 (3H, t, J=7.12 Hz), 2.70 (2H, q, J=7.67 Hz), 4.42 (2H, q, J=7.12 Hz), 10.39 (1H, br s).

(25b) 4-Bromo-5-ethyl-1H-imidazole-2-carboxylic acid

The same operation as in Example (1d) was performed using ethyl 4-bromo-5-ethyl-1H-imidazole-2-carboxylate obtained in Example (25a) (0.22 g, 0.87 mmol) and a 3 N aqueous lithium hydroxide solution (3 mL), to obtain 0.18 g of the title compound as a white solid (95%).

¹H NMR spectrum (400 MHz, DMSO-d₆) δ ppm: 1.10 (3H, t, J=7.45 Hz), 2.30-2.56 (2H, m).

(25c) tert-Butyl cis(±)-4-{[(4-bromo-5-ethyl-1H-imidazol-2-yl)carbonyl]amino}-3-methoxypiperidine-1-carboxylate The same operation as in Example (1g) was performed using tert-butyl cis(±)-4-amino-3-methoxypiperidine-1-carboxylate obtained by the method described in Example (1e) (0.39 g, 1.67 mmol), 4-bromo-5-ethyl-1H-imidazole-2-carboxylic acid obtained in Example (25b) (0.18 g, 0.82 mmol), WSC hydrochloride (0.49 g, 2.53 mmol) and HOBT (0.11 g, 0.84 mmol), to obtain 0.33 g of the title compound as a white solid (92%).

¹H NMR spectrum (400 MHz, CDCl₃) δ ppm: 1.25 (3H, t, J=7.61 Hz), 1.47 (9H, s), 1.60-1.67 (1H, m), 1.79-1.92 (1H, m), 2.61-2.90 (2H, m), 2.67 (2H, q, J=7.61 Hz), 3.32-3.45 (2H, m), 3.41 (3H, s), 4.01-4.27 (1H, m), 4.34-4.57 (1H, m), 7.45-7.54 (1H, m), 11.22 (1H, br s).

(25d) Ethyl cis(±)-2-(4-{[(4-bromo-5-ethyl-1H-imidazol-2-yl)carbonyl]amino}-3-methoxypiperidin-1-yl)-4-methyl-1,3-thiazole-5-carboxylate The same operation as in Example (1h) was performed using tert-butyl cis(±)-4-{[(4-bromo-5-ethyl-1H-imidazol-2-yl)carbonyl]amino}-3-methoxypiperidine-1-carboxylate obtained in Example (25c) (74 mg, 0.17 mmol), a 4 N hydrochloric acid/ethyl acetate solution (3 ml), diisopropylethylamine (0.12 mL, 0.69 mmol) and ethyl 2-bromo-4-methyl-1,3-thiazole-5-carboxylate (56 mg, 0.22 mmol), to obtain 71 mg of the title compound as an orange solid substance (83%).

¹H NMR spectrum (400 MHz, CDCl₃) δ ppm: 1.26 (3H, t, J=7.61 Hz), 1.33 (3H, t, J=7.08 Hz), 1.75-1.83 (1H, m), 1.98-2.10 (1H, m), 2.54 (3H, s), 2.68 (2H, q, J=7.61 Hz), 3.07-3.13 (1H, m), 3.15-3.24 (1H, m), 3.42 (3H, s), 3.51 (1H, br s), 3.97-4.05 (1H, m), 4.21-4.30 (3H, m), 4.47-4.56 (1H, m), 7.48-7.53 (1H, m), 11.17 (1H, br s).

(25e) cis(±)-2-(4-{[(4-Bromo-5-ethyl-1H-imidazol-2-yl)carbonyl]amino}-3-methoxypiperidin-1-yl)-4-methyl-1,3-thiazole-5-carboxylic acid The same operation as in Example (1i) was performed using ethyl cis(±)-2-(4-{[(4-bromo-5-ethyl-1H-imidazol-2-yl)carbonyl]amino}-3-methoxypiperidin-1-yl)-4-methyl-1,3-thiazole-5-carboxylate obtained in Example (25d) (70 mg, 0.14 mmol) and a 2 N aqueous lithium hydroxide solution (2 mL), to obtain 36 mg of the title compound as a white solid (56%).

¹H NMR spectrum (400 MHz, DMSO-d₆) δ ppm: 1.13 (3H, t, J=7.44 Hz), 1.63-1.72 (1H, m), 1.79-1.92 (1H, m), 2.40 (3H, s), 2.50-2.57 (2H, m), 3.24-3.36 (2H, m), 3.34 (3H, s), 3.55 (1H, br s), 3.86-3.97 (1H, m), 4.14-4.29 (2H, m), 7.66 (1H, d, J=8.54 Hz), 13.41 (1H, br s).

mass spectrum (ESI): m/z 473 (M+H)⁺.

Example 26 cis(±)-2-(4-{[(4-Chloro-5-ethyl-1H-imidazol-2-yl)carbonyl]amino}-3-methoxypiperidin-1-yl)-1,3-thiazole-4-carboxylic acid (Exemplified Compound No. 26)

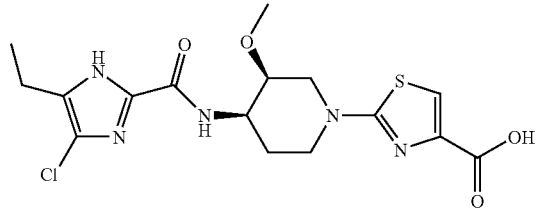

(26a) Ethyl cis(±)-2-(4-{[(4-chloro-5-ethyl-1H-imidazol-2-yl)carbonyl]amino}-3-methoxypiperidin-1-yl)-1,3-thiazole-4-carboxylate The same operation as in Example (1h) was performed using tert-butyl cis(±)-4-{[(4-chloro-5-ethyl-1H-imidazol-2-yl)carbonyl]amino}-3-methoxypiperidine-1-carboxylate obtained by the method described in Example (1g) (0.12 g, 0.30 mmol), a 4 N hydrochloric acid/ethyl acetate solution (3 ml), diisopropylethylamine (0.21 mL, 1.21 mmol), and ethyl 2-bromo-1,3-thiazole-4-carboxylate (75 mg, 0.32 mmol), to obtain 30 mg of the title compound as a yellow solid (22%).

¹H NMR spectrum (400 MHz, CDCl₃) δ ppm: 1.26 (3H, t, J=7.60 Hz), 1.37 (3H, t, J=7.19 Hz), 1.75-1.85 (1H, m), 2.01-2.15 (1H, m), 2.69 (2H, q, J=7.60 Hz), 3.11-3.25 (2H, m), 3.43 (3H, s), 3.50-3.54 (1H, m), 3.96-4.04 (1H, m), 4.20-4.29 (1H, m), 4.31-4.40 (2H, m), 4.45-4.52 (1H, m), 7.43 (1H, s), 7.46-7.54 (1H, m), 11.21 (1H, br s).

(26b) cis(±)-2-(4-{[(4-Chloro-5-ethyl-1H-imidazol-2-yl)carbonyl]amino}-3-methoxypiperidin-1-yl)-1,3-thiazole-4-carboxylic acid The same operation as in Example (1i) was performed using ethyl cis(±)-2-(4-{[(4-chloro-5-ethyl-1H-imidazol-2-yl)carbonyl]amino}-3-methoxypiperidin-1-yl)-1,3-thiazole- 4-carboxylate obtained in Example (26a) (30 mg, 0.068 mmol) and a 2 N aqueous lithium hydroxide solution (1 mL), to obtain 16 mg of the title compound as a white solid (58%).

$^1$H NMR spectrum (400 MHz, DMSO-$d_6$) δ ppm: 1.14 (3H, t, J=7.56 Hz), 1.61-1.73 (1H, m), 1.84-1.93 (1H, m), 2.55 (2H, q, J=7.56 Hz), 3.23-3.36 (2H, m), 3.33 (3H, s), 3.56 (1H, br s), 3.82-3.91 (1H, m), 4.14-4.25 (2H, m), 7.56 (1H, s), 7.65 (1H, d, J=8.29 Hz).

mass spectrum (ESI): m/z 414 (M+H)$^+$.

Example 27 cis(±)-2-(4-{[(4-Chloro-5-ethyl-1H-imidazol-2-yl)carbonyl]amino}-3-methoxypiperidin-1-yl)-4-(hydroxymethyl)-1,3-thiazole-5-carboxylic acid (Exemplified Compound No. 27)

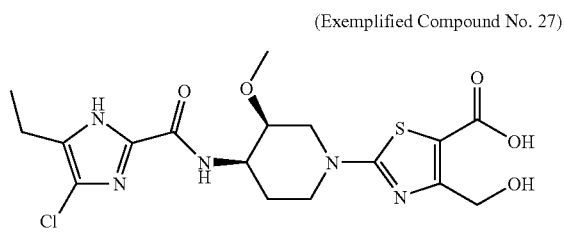 [SMILES: CCc1[nH]c(C(=O)N[C@@H]2CCN(c3nc(CO)c(C(=O)O)s3)C[C@@H]2OC)nc1Cl]

(27a) Ethyl 2-chloro-4-(hydroxymethyl)-1,3-thiazole-5-carboxylate

The compound was synthesized according to the method described in the following document.

WO 2006/087543 A1

(27b) Ethyl cis(±)-2-(4-{[(4-chloro-5-ethyl-1H-imidazol-2-yl)carbonyl]amino}-3-methoxypiperidin-1-yl)-4-(hydroxymethyl)-1,3-thiazole-5-carboxylate The same operation as in Example (1h) was performed using tert-butyl cis(±)-4-{[(4-chloro-5-ethyl-1H-imidazol-2-yl)carbonyl]amino}-3-methoxypiperidine-1-carboxylate obtained by the method described in Example (1g) (0.23 g, 0.60 mmol), a 4 N hydrochloric acid/ethyl acetate solution (9 ml), diisopropylethylamine (0.42 mL, 2.41 mmol) and ethyl 2-chloro-4-(hydroxymethyl)-1,3-thiazole-5-carboxylate obtained in Example (27a) (0.27 g, 1.01 mmol), to obtain 0.20 g of the title compound as a yellow solid (72%).

$^1$H NMR spectrum (400 MHz, CDCl$_3$) δ ppm: 1.27 (3H, t, J=7.56 Hz), 1.34 (3H, t, J=7.19 Hz), 1.76-1.85 (1H, m), 1.97-2.10 (1H, m), 2.69 (2H, q, J=7.56 Hz), 3.09-3.16 (1H, m), 3.19-3.28 (1H, m), 3.42 (3H, s), 3.52 (1H, br s), 3.96-4.02 (1H, m), 4.22-4.32 (3H, m), 4.50-4.61 (1H, m), 4.79 (2H, d, J=6.34 Hz), 7.44 (1H, d, J=8.78 Hz), 10.71 (1H, br s).

(27c) cis(±)-2-(4-{[(4-Chloro-5-ethyl-1H-imidazol-2-yl)carbonyl]amino}-3-methoxypiperidin-1-yl)-4-(hydroxymethyl)-1,3-thiazole-5-carboxylic acid The same operation as in Example (1i) was performed using ethyl cis(±)-2-(4-{[(4-chloro-5-ethyl-1H-imidazol-2-yl)carbonyl]amino}-3-methoxypiperidin-1-yl)-4-(hydroxymethyl)-1,3-thiazole-5-carboxylate obtained in Example (27b) (30 mg, 0.064 mmol) and a 2 N aqueous lithium hydroxide solution (0.8 mL), to obtain 16 mg of the title compound as a white solid (57%).

$^1$H NMR spectrum (400 MHz, DMSO-$d_6$) δ ppm: 1.14 (3H, t, J=7.56 Hz), 1.63-1.72 (1H, m), 1.80-1.93 (1H, m), 2.55 (2H, q, J=7.56 Hz), 3.23-3.37 (2H, m), 3.34 (3H, s), 3.57 (1H, br s), 3.91-4.04 (1H, m), 4.16-4.34 (2H, m), 4.55-4.62 (2H, m), 7.66 (1H, d, J=8.54 Hz), 13.37 (1H, br s).

mass spectrum (ESI): m/z 444 (M+H)$^+$.

Example 28 cis(±)-2-(4-{[(4-Chloro-5-ethyl-1H-imidazol-2-yl)carbonyl]amino}-3-methoxypiperidin-1-yl)-4-vinyl-1,3-thiazole-5-carboxylic acid (Exemplified Compound No. 28)

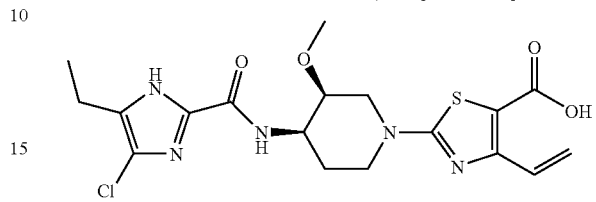

(28a) Ethyl cis(±)-2-(4-{[(4-chloro-5-ethyl-1H-imidazol-2-yl)carbonyl]amino}-3-methoxypiperidin-1-yl)-4-formyl-1,3-thiazole-5-carboxylate Ethyl cis(±)-2-(4-{[(4-chloro-5-ethyl-1H-imidazol-2-yl)carbonyl]amino}-3-methoxypiperidin-1-yl)-4-(hydroxymethyl)-1,3-thiazole-5-carboxylate obtained by the method described in Example (27b) (0.17 g, 0.36 mmol) was dissolved in dichloromethane (8 mL). The Dess-Martin reagent (0.2 g, 0.48 mmol) was added, and the mixture was stirred at room temperature for 45 minutes. Saturated aqueous sodium bicarbonate solution was added to the reaction solution, followed by extraction with dichloromethane. The organic layer was washed with saturated aqueous sodium thiosulfate solution, saturated aqueous sodium bicarbonate solution and brine, and dried over anhydrous sodium sulfate. Following concentration under reduced pressure, the residue was purified by silica gel column chromatography (elution solvent: hexane/ethyl acetate=5/1, 1/1, 1/3) to obtain 0.16 g of the title compound as a pale yellow solid (92%).

$^1$H NMR spectrum (400 MHz, CDCl$_3$) δ ppm: 1.26 (6H, t, J=7.67 Hz), 1.38 (3H, t, J=7.20 Hz), 1.77-1.86 (1H, m), 1.98-2.10 (1H, m), 2.69 (2H, q, J=7.67 Hz), 3.12-3.20 (1H, m), 3.23-3.33 (1H, m), 3.42 (3H, s), 3.53 (1H, br s), 4.02-4.10 (1H, m), 4.22-4.31 (1H, m), 4.33-4.41 (2H, m), 4.55-4.67 (1H, m), 7.46 (1H, d, J=8.54 Hz), 10.50 (1H, s), 11.04 (1H, br s).

(28b) Ethyl cis(±)-2-(4-{[(4-chloro-5-ethyl-1H-imidazol-2-yl)carbonyl]amino}-3-methoxypiperidin-1-yl)-4-vinyl-1,3-thiazole-5-carboxylate Methyltriphenylphosphonium bromide (0.19 g, 0.53 mmol) was suspended in THF (4 mL), followed by cooling to −78° C. An n-butyllithium/1.58 M hexane solution (0.34 mL, 0.54 mmol) was added dropwise, followed by stirring for 25 minutes. Ethyl cis(±)-2-(4-{[(4-chloro-5-ethyl-1H-imidazol-2-yl)carbonyl]amino}-3-methoxypiperidin-1-yl)-4-formyl-1,3-thiazole-5-carboxylate obtained in Example (28a) (74 mg, 0.16 mmol) was added, and the mixture was heated to room temperature and stirred for one hour. Brine was added to the reaction solution, followed by extraction with ethyl acetate. The organic layer was washed with brine and dried over anhydrous sodium sulfate. Following concentration under reduced pressure, the residue was purified by silica gel column chromatography (elution solvent: hexane/ethyl acetate=4/1, 3/1, 1/1) to obtain 15 mg of the title compound as a pale yellow solid (21%).

$^1$H NMR spectrum (400 MHz, CDCl$_3$) δ ppm: 1.27 (5H, t, J=7.64 Hz), 1.34 (3H, t, J=7.07 Hz), 1.75-1.84 (1H, m), 1.99-2.10 (1H, m), 2.70 (2H, q, J=7.64 Hz), 3.07-3.14 (1H, m), 3.18-3.29 (1H, m), 3.43 (3H, s), 3.51 (1H, br s), 3.96-4.07

(1H, m), 4.22-4.32 (3H, m), 4.58-4.68 (1H, m), 5.54 (1H, dd, J=10.73, 2.44 Hz), 6.24 (1H, dd, J=17.32, 2.44 Hz), 7.44-7.52 (2H, m), 11.15 (1H, br s).

(28c) cis(±)-2-(4-{[(4-Chloro-5-ethyl-1H-imidazol-2-yl)carbonyl]amino}-3-methoxypiperidin-1-yl)-4-vinyl-1,3-thiazole-5-carboxylic acid The same operation as in Example (1i) was performed using ethyl cis(±)-2-(4-{[(4-chloro-5-ethyl-1H-imidazol-2-yl)carbonyl]amino}-3-methoxypiperidin-1-yl)-4-vinyl-1,3-thiazole-5-carboxylate obtained in Example (28b) (15 mg, 0.033 mmol) and a 2 N aqueous lithium hydroxide solution (0.5 mL), to obtain 10 mg of the title compound as a white solid (72%).

$^1$H NMR spectrum (400 MHz, DMSO-$d_6$) δ ppm: 1.14 (3H, t, J=7.56 Hz), 1.64-1.74 (1H, m), 1.81-1.94 (1H, m), 2.55 (19H, q, J=7.56 Hz), 3.28-3.36 (3H, m), 3.35 (3H, s), 3.57 (1H, br s), 3.87-4.02 (1H, m), 4.17-4.26 (1H, m), 4.30-4.44 (1H, m), 5.52 (1H, dd, J=10.61, 2.68 Hz), 6.14 (1H, dd, J=17.32, 2.68 Hz), 7.38 (1H, dd, J=17.32, 10.61 Hz), 7.66 (1H, d, J=8.29 Hz), 12.74 (1H, br s), 13.37 (1H, br s).

mass spectrum (ESI): m/z 440 (M+H)$^+$.

Example 29 cis(±)-2-(4-{[(4-Chloro-5-ethyl-1H-imidazol-2-yl)carbonyl]amino}-3-methoxypiperidin-1-yl)-4-(fluoromethyl)-1,3-thiazole-5-carboxylic acid (Exemplified Compound No. 29)

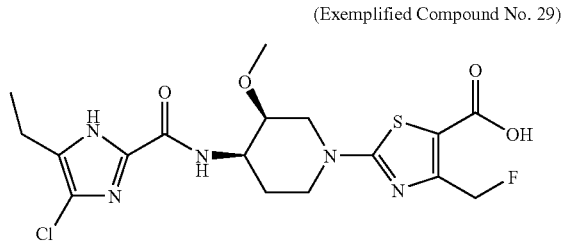 [SMILES: CCc1[nH]c(C(=O)N[C@@H]2CCN(c3nc(CF)c(C(=O)O)s3)C[C@@H]2OC)nc1Cl]

(29a) Ethyl cis(±)-2-(4-{[(4-chloro-5-ethyl-1H-imidazol-2-yl)carbonyl]amino}-3-methoxypiperidin-1-yl)-4-(fluoromethyl)-1,3-thiazole-5-carboxylate Ethyl cis(±)-2-(4-{[(4-chloro-5-ethyl-1H-imidazol-2-yl)carbonyl]amino}-3-methoxypiperidin-1-yl)-4-(hydroxymethyl)-1,3-thiazole-5-carboxylate obtained by the method described in Example (27b) (0.14 g, 0.30 mmol) was dissolved in dichloromethane (5 mL). A solution of DAST (0.05 mL, 0.38 mmol) in dichloromethane (2 mL) was added dropwise at −40° C. The mixture was stirred at that temperature for 30 minutes. Brine was added to the reaction solution, followed by extraction with dichloromethane. The organic layer was washed with brine and dried over anhydrous sodium sulfate. Following concentration under reduced pressure, the residue was purified by silica gel column chromatography (elution solvent: hexane/ethyl acetate=4/1, 3/1, 1/1) to obtain 83 mg of the title compound as a colorless oily substance (59%).

$^1$H NMR spectrum (400 MHz, CDCl$_3$) δ ppm: 1.27 (3H, t, J=7.62 Hz), 1.34 (3H, t, J=7.19 Hz), 1.72-1.85 (1H, m), 1.99-2.12 (1H, m), 2.70 (2H, q, J=7.62 Hz), 3.08-3.16 (1H, m), 3.19-3.29 (1H, m), 3.43 (3H, s), 3.52 (1H, br s), 3.97-4.07 (1H, m), 4.22-4.34 (3H, m), 4.55-4.65 (1H, m), 5.55 (1H, dd, J=13.66, 11.22 Hz), 5.67 (1H, dd, J=13.66, 11.22 Hz), 7.54 (1H, d, J=9.02 Hz), 11.72 (1H, br s).

(29b) cis(±)-2-(4-{[(4-Chloro-5-ethyl-1H-imidazol-2-yl)carbonyl]amino}-3-methoxypiperidin-1-yl)-4-(fluoromethyl)-1,3-thiazole-5-carboxylic acid The same operation as in Example (1i) was performed using ethyl cis(±)-2-(4-{[(4-chloro-5-ethyl-1H-imidazol-2-yl)carbonyl]amino}-3-methoxypiperidin-1-yl)-4-(fluoromethyl)-1,3-thiazole-5-carboxylate obtained in Example (29a) (80 mg, 0.17 mmol) and a 2 N aqueous lithium hydroxide solution (2 mL), to obtain 52 mg of the title compound as a pale red solid (69%).

$^1$H NMR spectrum (400 MHz, DMSO-$d_6$) δ ppm: 1.14 (3H, t, J=7.57 Hz), 1.65-1.73 (1H, m), 1.80-1.94 (1H, m), 2.55 (2H, q, J=7.57 Hz), 3.28-3.36 (2H, m), 3.34 (3H, s), 3.58 (1H, br s), 3.88-4.01 (1H, m), 4.17-4.34 (2H, m), 5.43-5.59 (2H, m), 7.67 (1H, d, J=8.30 Hz), 12.93-13.07 (1H, m), 13.37 (1H, br s).

mass spectrum (ESI): m/z 446 (M+H)$^+$.

Example 30 cis(±)-2-(4-{[(4-Chloro-5-methyl-1H-imidazol-2-yl)carbonyl]amino}-3-methoxypiperidin-1-yl)-4-ethyl-1,3-thiazole-5-carboxylic acid (Exemplified Compound No. 30)

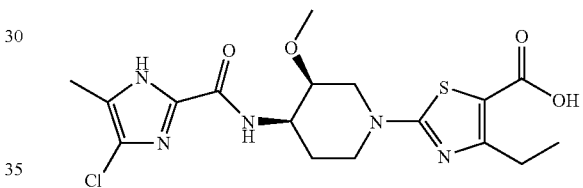

(30a) Methyl cis(±)-2-(4-{[(4-chloro-5-methyl-1H-imidazol-2-yl)carbonyl]amino}-3-methoxypiperidin-1-yl)-4-ethyl-1,3-thiazole-5-carboxylate The same operation as in Example (1h) was performed using tert-butyl cis(±)-4-{[(4-chloro-5-methyl-1H-imidazol-2-yl)carbonyl]amino}-3-methoxypiperidine-1-carboxylate obtained by the method described in Example (8a) (0.27 g, 0.72 mmol), a 4 N hydrochloric acid/ethyl acetate solution (5 ml), diisopropylethylamine (0.5 mL, 2.87 mmol) and methyl 2-bromo-4-ethyl-1,3-thiazole-5-carboxylate obtained by the method described in Example (22c) (0.24 g, 0.96 mmol), to obtain 0.22 g of the title compound as a yellow solid (68%).

$^1$H NMR spectrum (400 MHz, CDCl$_3$) δ ppm: 1.23 (3H, t, J=7.57 Hz), 1.76-1.85 (1H, m), 1.96-2.09 (1H, m), 2.30 (3H, s), 2.86-3.10 (3H, m), 3.17-3.27 (1H, m), 3.43 (3H, s), 3.51 (1H, br s), 3.79 (3H, s), 3.91-4.00 (1H, m), 4.20-4.30 (1H, m), 4.56-4.66 (1H, m), 7.41 (1H, d, J=8.71 Hz), 10.43 (1H, br s).

(30b) cis(±)-2-(4-{[(4-Chloro-5-methyl-1H-imidazol-2-yl)carbonyl]amino}-3-methoxypiperidin-1-yl)-4-ethyl-1,3-thiazole-5-carboxylic acid The same operation as in Example (1i) was performed using methyl cis(±)-2-(4-{[(4-chloro-5-methyl-1H-imidazol-2-yl)carbonyl]amino}-3-methoxypiperidin-1-yl)-4-ethyl-1,3-thiazole-5-carboxylate obtained in Example (30a) (0.22 g, 0.49 mmol) and a 2 N aqueous lithium hydroxide solution (3.5 mL), to obtain 0.20 g of the title compound as a white solid (94%).

$^1$H NMR spectrum (400 MHz, DMSO-$d_6$) δ ppm: 1.13 (3H, t, J=7.57 Hz), 1.63-1.72 (1H, m), 1.79-1.92 (1H, m), 2.16 (3H, s), 2.75-2.95 (2H, m), 3.24-3.32 (2H, m), 3.34 (3H, s), 3.56 (1H, br s), 3.81-3.96 (1H, m), 4.14-4.24 (1H, m), 4.27-4.40 (1H, m), 7.65 (1H, d, J=8.25 Hz), 12.40 (1H, br s).
mass spectrum (ESI): m/z 428 (M+H)$^+$.

Example 31 cis(±)-2-(4-{[(4-Bromo-5-methyl-1H-imidazol-2-yl)carbonyl]amino}-3-methoxypiperidin-1-yl)-4-methyl-1,3-thiazole-5-carboxylic acid (Exemplified Compound No. 31)

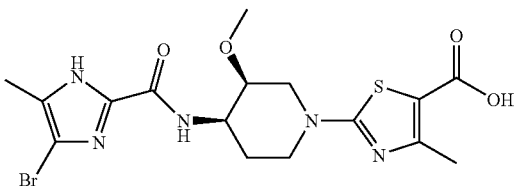

(31a) Ethyl 4-bromo-5-methyl-1H-imidazole-2-carboxylate

The same operation as in Example (1c) was performed using ethyl 5-methyl-1H-imidazole-2-carboxylate obtained by the method described in Example (5a) (0.30 g, 1.95 mmol) and NBS (0.35 g, 1.96 mmol), to obtain 0.43 g of the title compound as a white solid (94%).

$^1$H NMR spectrum (400 MHz, CDCl$_3$) δ ppm: 1.41 (3H, t, J=7.15 Hz), 2.32 (3H, s), 4.42 (2H, q, J=7.15 Hz), 10.53-11.21 (1H, m).

(31b) 4-Bromo-5-methyl-1H-imidazole-2-carboxylic acid

The same operation as in Example (1d) was performed using ethyl 4-bromo-5-methyl-1H-imidazole-2-carboxylate obtained in Example (31a) (0.43 g, 1.82 mmol) and a 3 N aqueous lithium hydroxide solution (3 mL), to obtain 0.37 g of the title compound as a white solid (99%).

$^1$H NMR spectrum (400 MHz, DMSO-d$_6$) δ ppm: 2.08 (3H, s).

(31c) tert-Butyl cis(±)-4-{[(4-bromo-5-methyl-1H-imidazol-2-yl)carbonyl]amino}-3-methoxypiperidine-1-carboxylate The same operation as in Example (1g) was performed using tert-butyl cis(±)-4-amino-3-methoxypiperidine-1-carboxylate obtained by the method described in Example (1e) (0.88 g, 3.82 mmol), 4-bromo-5-methyl-1H-imidazole-2-carboxylic acid obtained in Example (31b) (0.37 g, 1.80 mmol), WSC hydrochloride (1.03 g, 5.37 mmol) and HOBT (0.25 g, 1.81 mmol), to obtain 0.63 g of the title compound as a white solid (83%).

$^1$H NMR spectrum (400 MHz, CDCl$_3$) δ ppm: 1.47 (9H, s), 1.61-1.70 (1H, m), 1.77-1.92 (1H, m), 2.28 (3H, s), 2.67-2.92 (2H, m), 3.33-3.47 (1H, m), 3.41 (3H, s), 3.97-4.27 (2H, m), 4.35-4.58 (1H, m), 7.43-7.51 (1H, m), 11.17 (1H, brs).

(31d) Ethyl cis(±)-2-(4-{[(4-bromo-5-methyl-1H-imidazol-2-yl)carbonyl]amino}-3-methoxypiperidin-1-yl)-4-methyl-1,3-thiazole-5-carboxylate The same operation as in Example (1h) was performed using tert-butyl cis(±)-4-{[(4-bromo-5-methyl-1H-imidazol-2-yl)carbonyl]amino}-3-methoxypiperidine-1-carboxylate obtained in Example (31c) (0.2 g, 0.48 mmol), a 4 N hydrochloric acid/ethyl acetate solution (5 ml), diisopropylethylamine (0.34 mL, 1.95 mmol) and ethyl 2-bromo-4-methyl-1,3-thiazole-5-carboxylate (0.16 g, 0.62 mmol), to obtain 0.19 g of the title compound as an orange solid (82%).

$^1$H NMR spectrum (400 MHz, CDCl$_3$) δ ppm: 1.33 (3H, t, J=7.11 Hz), 1.75-1.84 (1H, m), 1.96-2.09 (1H, m), 2.29 (3H, s), 2.54 (3H, s), 3.07-3.13 (1H, m), 3.15-3.25 (1H, m), 3.42 (3H, s), 3.51 (1H, br s), 3.95-4.04 (1H, m), 4.20-4.30 (3H, m), 4.47-4.56 (1H, m), 7.45 (1H, d, J=8.71 Hz), 10.73 (1H, br s).

(31e) cis(±)-2-(4-{[(4-Bromo-5-methyl-1H-imidazol-2-yl)carbonyl]amino}-3-methoxypiperidin-1-yl)-4-methyl-1,3-thiazole-5-carboxylic acid The same operation as in Example (1i) was performed using ethyl cis(±)-2-(4-{[(4-bromo-5-methyl-1H-imidazol-2-yl)carbonyl]amino}-3-methoxypiperidin-1-yl)-4-methyl-1,3-thiazole-5-carboxylate obtained in Example (31d) (0.19 g, 0.39 mmol) and 2 N lithium hydroxide (4 mL), to obtain 0.11 g of the title compound as a white solid (61%).

$^1$H NMR spectrum (400 MHz, DMSO-d$_6$) δ ppm: 1.63-1.73 (1H, m), 1.82-1.90 (1H, m), 2.15 (3H, s), 2.41 (3H, s), 3.20-3.32 (2H, m), 3.33 (3H, s), 3.56 (1H, brs), 3.87-3.99 (1H, m), 4.14-4.32 (2H, m), 7.66 (1H, d, J=8.25 Hz), 12.41 (1H, br s).

mass spectrum (ESI): m/z 459 (M+H)$^+$.

Example 32 cis(±)-2-(4-{[(4-Bromo-5-methyl-1H-imidazol-2-yl)carbonyl]amino}-3-methoxypiperidin-1-yl)-4-ethyl-1,3-thiazole-5-carboxylic acid (Exemplified Compound No. 32)

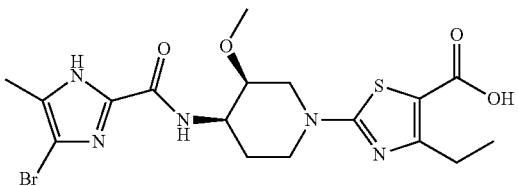

(32a) Methyl cis(±)-2-(4-{[(4-bromo-5-methyl-1H-imidazol-2-yl)carbonyl]amino}-3-methoxypiperidin-1-yl)-4-ethyl-1,3-thiazole-5-carboxylate The same operation as in Example (1h) was performed using tert-butyl cis(±)-4-{[(4-bromo-5-methyl-1H-imidazol-2-yl)carbonyl]amino}-3-methoxypiperidine-1-carboxylate obtained by the method described in Example (31c) (0.2 g, 0.48 mmol), a 4 N hydrochloric acid/ethyl acetate solution (5 ml), diisopropylethylamine (0.34 mL, 1.95 mmol) and methyl 2-bromo-4-ethyl-1,3-thiazole-5-carboxylate obtained by the method described in Example (22c) (0.16 g, 0.63 mmol), to obtain 0.17 g of the title compound as a yellow solid (71%).

$^1$H NMR spectrum (400 MHz, CDCl$_3$) δ ppm: 1.23 (3H, t, J=7.34 Hz), 1.75-1.85 (1H, m), 1.96-2.09 (1H, m), 2.30 (3H, s), 2.85-2.96 (1H, m), 2.99-3.10 (2H, m), 3.18-3.25 (1H, m), 3.42 (3H, s), 3.51 (1H, br s), 3.79 (3H, s), 3.91-4.00 (1H, m), 4.20-4.30 (1H, m), 4.56-4.66 (1H, m), 7.44 (1H, d, J=9.17 Hz), 10.54 (1H, br s).

(32b) cis(±)-2-(4-{[(4-Bromo-5-methyl-1H-imidazol-2-yl)carbonyl]amino}-3-methoxypiperidin-1-yl)-4-ethyl-1,3-thiazole-5-carboxylic acid The same operation as in Example (1i) was performed using methyl cis(±)-2-(4-{[(4-bromo-5-methyl-1H-imidazol-2-yl)carbonyl]amino}-3-methoxypiperidin-1-yl)-4-ethyl-1,3-thiazole-5-carboxylate obtained in Example (32a) (0.17 g, 0.34 mmol) and a 2 N aqueous lithium hydroxide solution (4 mL), to obtain 0.15 g of the title compound as a white solid (91%).

¹H NMR spectrum (400 MHz, DMSO-d₆) δ ppm: 1.13 (3H, t, J=7.57 Hz), 1.63-1.72 (1H, m), 1.80-1.92 (1H, m), 2.15 (3H, s), 2.74-2.96 (2H, m), 3.23-3.32 (2H, m), 3.34 (3H, s), 3.56 (1H, br s), 3.81-3.93 (1H, m), 4.14-4.24 (1H, m), 4.27-4.41 (1H, m), 7.65 (1H, d, J=8.25 Hz), 12.40 (1H, br s).
mass spectrum (ESI): m/z 473 (M+H)⁺.

Example 33 cis(±)-2-(4-{[(4-Trifluoromethyl-1H-imidazol-2-yl)carbonyl]amino}-3-methoxypiperidin-1-yl)-4-methyl-1,3-thiazole-5-carboxylic acid (Exemplified Compound No. 33)

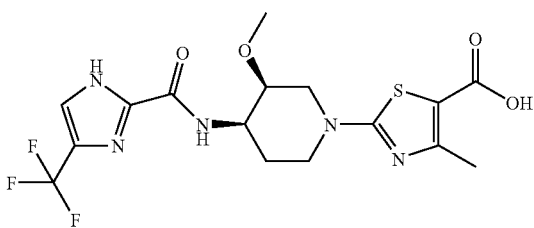

(33a) 2-(Dimethoxymethyl)-4-(trifluoromethyl)-1H-imidazole

Sodium acetate (1.33 g, 16.2 mmol) was added to a solution of 3,3-dibromo-1,1,1-trifluoropropan-2-one (2.0 g, 7.41 mmol) in water (10 ml), and the mixture was heated under reflux for 40 minutes. Following cooling to room temperature, dimethoxyacetaldehyde/60% aqueous solution (1.3 ml, 8.64 mmol), 28% aqueous ammonia solution (2 ml) and methanol (4 ml) were added, and the mixture was stirred for 19 hours. The reaction solution was extracted with ethyl acetate. Then, the organic layer was washed with brine, dried over anhydrous sodium sulfate and concentrated under reduced pressure, to obtain 1.41 g of the title compound as a pale yellow oily substance (90%).

¹H NMR spectrum (400 MHz, CDCl₃) δ ppm: 3.41 (6H, s), 5.49 (1H, s), 7.36 (1H, s), 9.60 (1H, br s).

(33b) 4-(Trifluoromethyl)-1H-imidazole-2-carbaldehyde

2 N sulfuric acid (20 ml) was added to 2-(dimethoxymethyl)-4-(trifluoromethyl)-1H-imidazole obtained in Example (33a) (720 mg, 3.43 mmol), and the mixture was stirred at 90° C. for one hour. The reaction solution was neutralized with a 1 N aqueous sodium hydroxide solution, followed by extraction with ethyl acetate. Then, the organic layer was washed with brine, dried over anhydrous sodium sulfate and concentrated under reduced pressure, to obtain 0.376 g of the title compound as a white solid (67%).

¹H NMR spectrum (400 MHz, DMSO-d₆) δ ppm: 8.02-8.08 (1H, m), 8.20 (1H, s), 9.71 (1H, s).

(33c) 4-(Trifluoromethyl)-1H-imidazole-2-carboxylic acid

Sodium dihydrogenphosphate dihydrate (720 mg, 4.62 mmol), 2-methyl-2-butene (1.2 ml, 11.4 mmol) and sodium chlorite (420 mg, 4.64 mmol) were added under ice-cooling to a solution of 4-(trifluoromethyl)-1H-imidazole-2-carbaldehyde obtained in Example (33b) (375 mg, 2.29 mmol) in t-butyl alcohol (12 ml)/distilled water (5 ml), followed by stirring for 1.5 hours. The reaction solution was concentrated under reduced pressure, and then the residue was purified by reverse phase silica gel column chromatography (elution solvent: distilled water) to obtain 0.402 g of the title compound as a white solid (98%).

¹H NMR spectrum (400 MHz, DMSO-d₆) δ ppm: 7.41 (1H, s).

(33d) tert-Butyl cis(±)-4-{[(4-trifluoromethyl-1H-imidazol-2-yl)carbonyl]amino}-3-methoxypiperidine-1-carboxylate The same operation as in Example (1g) was performed using tert-butyl cis(±)-4-amino-3-methoxypiperidine-1-carboxylate obtained by the method described in Example (1e) (0.90 g, 3.91 mmol), 4-(trifluoromethyl)-1H-imidazole-2-carboxylic acid obtained in Example (33c) (0.40 g, 2.22 mmol), WSC hydrochloride (1.25 g, 6.52 mmol) and HOBT (0.30 g, 2.22 mmol), to obtain 0.67 g of the title compound as a white foamy substance (77%).

¹H NMR spectrum (400 MHz, CDCl₃) δ ppm: 1.48 (9H, s), 1.66-1.73 (1H, m), 1.86-1.89 (1H, m), 2.83-2.90 (1H, m), 3.35-3.43 (2H, m), 3.44 (3H, s), 4.04-4.21 (2H, m), 4.43-4.50 (1H, m), 7.49 (1H, s), 7.63-7.65 (1H, m), 11.46 (1H, s).

(33e) Ethyl cis(±)-2-(4-{[(4-trifluoromethyl-1H-imidazol-2-yl)carbonyl]amino}-3-methoxypiperidin-1-yl)-4-methyl-1,3-thiazole-5-carboxylate The same operation as in Example (1h) was performed using tert-butyl cis(±)-4-{[(4-trifluoromethyl-1H-imidazol-2-yl)carbonyl]amino}-3-methoxypiperidine-1-carboxylate obtained in Example (33d) (0.2 g, 0.51 mmol), a 4 N hydrochloric acid/ethyl acetate solution (6 ml), diisopropylethylamine (0.35 mL, 2.01 mmol) and ethyl 2-bromo-4-methyl-1,3-thiazole-5-carboxylate (0.13 g, 0.52 mmol), to obtain 0.19 g of the title compound as a yellow solid (79%).

¹H NMR spectrum (400 MHz, CDCl₃) δ ppm: 1.33 (3H, t, J=7.11 Hz), 1.82-1.83 (1H, m), 2.01-2.13 (1H, m), 2.54 (3H, s), 3.10-3.14 (1H, m), 3.19-3.27 (1H, m), 3.45 (3H, s), 3.54 (1H, br s), 3.99-4.03 (1H, m), 4.21-4.32 (3H, m), 4.53-4.56 (1H, m), 7.50 (1H, s), 7.63 (1H, d, J=8.71 Hz), 11.10 (1H, s).

(33f) cis(±)-2-(4-{[(4-Trifluoromethyl-1H-imidazol-2-yl)carbonyl]amino}-3-methoxypiperidin-1-yl)-4-methyl-1,3-thiazole-5-carboxylic acid The same operation as in Example (1i) was performed using ethyl cis(±)-2-(4-{[(4-trifluoromethyl-1H-imidazol-2-yl)carbonyl]amino}-3-methoxypiperidin-1-yl)-4-methyl-1,3-thiazole-5-carboxylate obtained in Example (33e) (65.2 mg, 0.14 mmol) and a 2 N aqueous lithium hydroxide solution (2 mL), to obtain 41.6 mg of the title compound as a white solid (68%).

¹H NMR spectrum (400 MHz, DMSO-d₆) δ ppm: 1.68-1.71 (1H, m), 1.88-1.94 (1H, m), 2.41 (3H, s), 3.26-3.29 (2H, m), 3.34 (3H, s), 3.60 (1H, br s), 3.92-3.95 (1H, m), 4.21-4.29 (2H, m), 7.90 (1H, d, J=8.71 Hz), 7.97 (1H, s), 12.40 (1H, br s).
mass spectrum (ESI): m/z 434 (M+H)⁺.

Example 34 cis(±)-2-(4-{[(4-Chloro-5-ethyl-1H-imidazol-2-yl)carbonyl]amino}-3-ethoxypiperidin-1-yl)-4-methyl-1,3-thiazole-5-carboxylic acid (Exemplified Compound No. 34)

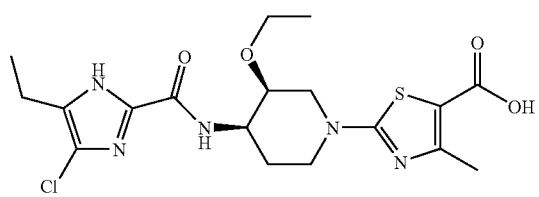

(34a) tert-Butyl cis(±)-4-{[(4-chloro-5-ethyl-1H-imidazol-2-yl)carbonyl]amino}-3-ethoxypiperidine-1-carboxylate The same operation as in Example (1g) was performed using tert-butyl cis(±)-4-amino-3-ethoxypiperidine-1-carboxylate obtained by the method described in Example (112d) (0.48 g, 1.96 mmol), 4-chloro-5-ethyl-1H-imidazole-2-carboxylic acid obtained by the method described in Example (1d) (0.31 g, 1.51 mmol), WSC hydrochloride (0.88 g, 4.59 mmol) and HOBT (0.21 g, 1.51 mmol), to obtain 0.59 g of the title compound as a white foamy substance (91%).

$^1$H NMR spectrum (400 MHz, CDCl$_3$) δ ppm: 1.14-1.26 (6H, m), 1.47 (9H, s), 1.62-1.67 (1H, m), 1.91-2.00 (1H, m), 2.68 (2H, q, J=7.64 Hz), 2.79-2.82 (2H, m), 3.36-3.43 (2H, m), 3.75 (1H, br s), 4.06-4.46 (3H, m), 7.50 (1H, br s), 11.14 (1H, br s).

(34b) Ethyl cis(±)-2-(4-{[(4-chloro-5-ethyl-1H-imidazol-2-yl)carbonyl]amino}-3-ethoxypiperidin-1-yl)-4-methyl-1,3-thiazole-5-carboxylate The same operation as in Example (1h) was performed using tert-butyl cis(±)-4-{[(4-chloro-5-ethyl-1H-imidazol-2-yl)carbonyl]amino}-3-ethoxypiperidine-1-carboxylate obtained in Example (34a) (0.29 g, 0.71 mmol), a 4 N hydrochloric acid/ethyl acetate solution (6 ml), diisopropylethylamine (0.5 mL, 2.87 mmol) and ethyl 2-bromo-4-methyl-1,3-thiazole-5-carboxylate (0.18 g, 0.71 mmol), to obtain 0.24 g of the title compound as a yellow foamy substance (71%).

$^1$H NMR spectrum (400 MHz, CDCl$_3$) δ ppm: 1.16 (3H, t, J=6.88 Hz), 1.25-1.27 (3H, m), 1.33 (3H, t, J=7.11 Hz), 1.75-1.80 (1H, m), 2.04-2.10 (1H, m), 2.54 (3H, s), 2.69 (2H, q, J=7.64 Hz), 3.15-3.19 (2H, m), 3.41-3.45 (1H, m), 3.60 (1H, br s), 3.72-3.76 (1H, m), 4.01-4.04 (1H, m), 4.20-4.30 (3H, m), 4.40-4.43 (1H, m), 7.45 (1H, d, J=8.71 Hz), 10.87 (1H, s).

(34c) cis(±)-2-(4-{[(4-Chloro-5-ethyl-1H-imidazol-2-yl)carbonyl]amino}-3-ethoxypiperidin-1-yl)-4-methyl-1,3-thiazole-5-carboxylic acid The same operation as in Example (1i) was performed using ethyl cis(±)-2-(4-{[(4-chloro-5-ethyl-1H-imidazol-2-yl)carbonyl]amino}-3-ethoxypiperidin-1-yl)-4-methyl-1,3-thiazole-5-carboxylate obtained in Example (34b) (0.23 g, 0.49 mmol) and a 2 N aqueous lithium hydroxide solution (3.5 mL), to obtain 0.20 g of the title compound as a white solid (91%).

$^1$H NMR spectrum (400 MHz, DMSO-d$_6$) δ ppm: 1.05 (3H, t, J=6.88 Hz), 1.14 (3H, t, J=7.57 Hz), 1.65-1.68 (1H, m), 1.83-1.89 (1H, m), 2.40 (3H, s), 2.55 (14H, q, J=7.64 Hz), 3.23-3.31 (2H, m), 3.41-3.45 (1H, m), 3.59-3.67 (2H, m), 3.93-3.96 (1H, m), 4.14-4.19 (2H, m), 7.63 (1H, d, J=8.25 Hz), 12.39 (1H, s).

mass spectrum (ESI): m/z 442 (M+H)$^+$.

Example 35 cis(±)-2-[4-({[4-Chloro-5-(propan-2-yl)-1H-imidazol-2-yl]carbonyl}amino)-3-methoxypiperidin-1-yl]-4-methyl-1,3-thiazole-5-carboxylic acid (Exemplified Compound No. 35)

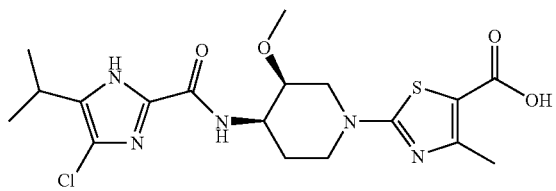

(35a) 1-Bromo-3-methylbutan-2-one

The compound was synthesized according to the method described in the following document.

Heterocycles, 57, 2002, 357-360

(35b) 2-(3-Methyl-2-oxobutyl)-1H-isoindole-1,3(2H)-dione

The same operation as in Example (15b) was performed using 1-bromo-3-methylbutan-2-one obtained in Example (35a) (3.94 g, 23.9 mmol) and potassium phthalimide (4.4 g, 23.8 mmol), to obtain 4.08 g of the title compound as a white solid (74%).

$^1$H NMR spectrum (400 MHz, CDCl$_3$) δ ppm: 1.09 (6H, d, J=6.88 Hz), 2.81-2.91 (1H, m), 4.64 (2H, s), 7.90-7.92 (4H, m), 11.35 (1H, br s).

(35c) 1-Amino-3-methylbutan-2-one hydrochloride

The same operation as in Example (15c) was performed using 2-(3-methyl-2-oxobutyl)-1H-isoindole-1,3(2H)-dione obtained in Example (35b) (4.08 g, 17.6 mmol) and 6 N hydrochloric acid (40 mL), to obtain the title compound as a white solid. The resulting compound was used for the next reaction without purification.

(35d) Ethyl 5-(propan-2-yl)-1H-imidazole-2-carboxylate

The same operation as in Example (1b) was performed using 1-amino-3-methylbutan-2-one hydrochloride obtained in Example (35c) (about 17.6 mmol) and ethyl imino(methylthio)acetate tetrafluoroborate obtained according to a method known in the literature (J. Med. Chem., 38, 1995, 2196-2201) (about 22 mmol), to obtain 1.83 g of the title compound as a yellow solid (57%).

$^1$H NMR spectrum (400 MHz, CDCl$_3$) δ ppm: 1.30 (6H, d, J=6.88 Hz), 1.41 (3H, t, J=7.14 Hz), 3.00-3.04 (1H, m), 4.43 (2H, q, J=7.14 Hz), 6.96 (1H, s), 10.27 (1H, br s).

(35e) Ethyl 4-chloro-5-(propan-2-yl)-1H-imidazole-2-carboxylate

The same operation as in Example (1c) was performed using ethyl 5-(propan-2-yl)-1H-imidazole-2-carboxylate obtained in Example (35d) (0.82 g, 4.50 mmol) and NCS (0.60 g, 4.51 mmol), to obtain 0.75 g of the title compound as a white solid (77%).

$^1$H NMR spectrum (400 MHz, CDCl$_3$) δ ppm: 1.31 (6H, d, J=7.34 Hz), 1.41 (3H, t, J=7.14 Hz), 3.11-3.21 (1H, m), 4.42 (2H, q, J=7.14 Hz), 10.15 (1H, br s).

(35f) 4-Chloro-5-(propan-2-yl)-1H-imidazole-2-carboxylic acid

The same operation as in Example (1d) was performed using ethyl 4-chloro-5-(propan-2-yl)-1H-imidazole-2-carboxylate obtained in Example (35e) (0.40 g, 1.85 mmol) and a 3 N aqueous lithium hydroxide solution (4 mL), to obtain 0.31 g of the title compound as a white solid (88%).

$^1$H NMR spectrum (400 MHz, DMSO-d$_6$) δ ppm: 1.19 (6H, d, J=6.88 Hz), 2.90-3.00 (1H, m).

(35g) tert-Butyl cis(±)-4-({[4-chloro-5-(propan-2-yl)-1H-imidazol-2-yl]carbonyl}amino)-3-methoxypiperidine-1-carboxylate The same operation as in Example (1g) was performed using tert-butyl cis(±)-4-amino-3-methoxypiperidine-1-carboxylate obtained by the method described in Example (1e) (0.50 g, 2.17 mmol), 4-chloro-5-(propan-2-yl)-1H-imidazole-2-carboxylic acid obtained in Example (35f) (0.30 g, 1.59 mmol), WSC hydrochloride (0.92 g, 4.80 mmol) and HOBT (0.22 g, 1.63 mmol), to obtain 0.60 g of the title compound as a white foamy substance (94%).

$^1$H NMR spectrum (400 MHz, CDCl$_3$) δ ppm: 1.30 (6H, d, J=6.88 Hz), 1.47 (9H, s), 1.61-1.64 (1H, m), 1.83-1.85 (1H, m), 2.76-2.79 (2H, m), 3.10-3.23 (1H, m), 3.32-3.35 (1H, m), 3.41 (3H, s), 4.03-4.20 (2H, m), 4.35-4.58 (1H, m), 7.49 (1H, br s), 10.91 (1H, brs).

(35h) Ethyl cis(±)-2-[4-({[4-chloro-5-(propan-2-yl)-1H-imidazol-2-yl]carbonyl}amino)-3-methoxypiperidin-1-yl]-4-methyl-1,3-thiazole-5-carboxylate The same operation as in Example (1h) was performed using tert-butyl cis(±)-4-({[4-chloro-5-(propan-2-yl)-1H-imidazol-2-yl]carbonyl}amino)-3-methoxypiperidine-1-carboxylate obtained in Example (35g) (0.31 g, 0.77 mmol), a 4 N hydrochloric acid/ethyl acetate solution (6 mL), diisopropylethylamine (0.54 mL, 3.10 mmol) and ethyl 2-bromo-4-methyl-1,3-thiazole-5-carboxylate (0.22 g, 0.88 mmol), to obtain 0.25 g of the title compound as a yellow foamy substance (67%).

$^1$H NMR spectrum (400 MHz, CDCl$_3$) δ ppm: 1.24-1.35 (9H, m), 1.77-1.81 (1H, m), 2.00-2.06 (1H, m), 2.54 (3H, s), 3.08-3.25 (3H, m), 3.43 (3H, s), 3.50 (1H, br s), 3.98-4.02 (1H, m), 4.24-4.29 (3H, m), 4.50-4.53 (1H, m), 7.45 (1H, d, J=8.71 Hz), 10.56 (1H, br s).

(35i) cis(±)-2-[4-({[4-Chloro-5-(propan-2-yl)-1H-imidazol-2-yl]carbonyl}amino)-3-methoxypiperidin-1-yl]-4-methyl-1,3-thiazole-5-carboxylic acid The same operation as in Example (1i) was performed using ethyl cis(±)-2-[4-({[4-chloro-5-(propan-2-yl)-1H-imidazol-2-yl]carbonyl}amino)-3-methoxypiperidin-1-yl]-4-methyl-1,3-thiazole-5-carboxylate obtained in Example (35h) (0.24 g, 0.51 mmol) and a 2 N aqueous lithium hydroxide solution (3 mL), to obtain 204 mg of the title compound as a white solid (91%).

$^1$H NMR spectrum (400 MHz, DMSO-d$_6$) δ ppm: 1.22 (6H, d, J=7.34 Hz), 1.65-1.69 (1H, m), 1.83-1.88 (1H, m), 2.41 (3H, s), 2.99-3.06 (1H, m), 3.23-3.30 (2H, m), 3.34 (3H, s), 3.55 (1H, br s), 3.91-3.93 (1H, m), 4.20-4.24 (2H, m), 7.65 (1H, d, J=8.25 Hz), 12.39 (1H, br s).

mass spectrum (ESI): m/z 442 (M+H)$^+$.

Example 36 cis(±)-2-(4-{[(5-Methyl-4-trifluoromethyl-1H-imidazol-2-yl)carbonyl]amino}-3-methoxypiperidin-1-yl)-1,3-thiazole-5-carboxylic acid (Exemplified Compound No. 36)

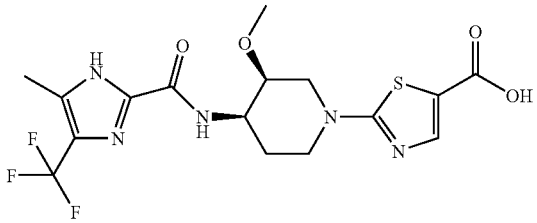

(36a) 2,2,2-Trifluoro-1-(2-methyl-1,3-dithian-2-yl)ethanone

2-Methyl-1,3-dithiane (1.50 g, 11.2 mmol) was dissolved in THF (50 mL), followed by cooling to −20° C. Then, n-butyllithium (1.58 M solution in hexane, 7 mL, 11.1 mmol) was added dropwise and the mixture was stirred for two hours. Ethyl trifluoroacetate (1.4 mL, 11.8 mmol) was added, and the mixture was heated to room temperature and stirred for 20 hours. Aqueous ammonium chloride solution was added to the reaction solution, followed by extraction with ethyl acetate. Then, the organic layer was washed with brine and dried over anhydrous sodium sulfate. Following concentration under reduced pressure, the residue was purified by silica gel column chromatography (elution solvent: hexane/ethyl acetate=100/0, 95/5, 85/15) to obtain 1.09 g of the title compound as a pale yellow solid (42%).

$^1$H NMR spectrum (400 MHz, CDCl$_3$) δ ppm: 1.58 (3H, s), 1.82-1.98 (1H, m), 2.05-2.16 (1H, m), 2.65-2.77 (2H, m), 2.91-3.09 (2H, m).

(36b) 2-(Dimethoxymethyl)-5-methyl-4-(trifluoromethyl)-1H-imidazole

NCS (870 mg, 6.51 mmol) and silver nitrate (1.48 g, 8.71 mmol) were dissolved in acetonitrile (40 mL) and distilled water (10 mL). 2,2,2-Trifluoro-1-(2-methyl-1,3-dithian-2-yl)ethanone obtained in Example (36a) (500 mg, 2.17 mmol) was added, and the mixture was stirred for 40 minutes. Thereafter, dimethoxyacetaldehyde (5.76 M aqueous solution, 0.4 mL, 23.0 mmol) and 28% aqueous ammonia (2 mL) were added, and the mixture was stirred at room temperature for 18 hours. The reaction solution was filtered through celite and then concentrated under reduced pressure. The resulting compound was used for the next reaction without purification.

(36c) 5-Methyl-4-(trifluoromethyl)-1H-imidazole-2-carbaldehyde

The same operation as in Example (33b) was performed using 2-(dimethoxymethyl)-5-methyl-4-(trifluoromethyl)-1H-imidazole obtained in Example (36b) (about 2.17 mmol) and 2 N sulfuric acid (15 mL), to obtain 30.5 mg of the title compound as a white solid (7.9%).

$^1$H NMR spectrum (400 MHz, CDCl$_3$) δ ppm: 2.52 (3H, s), 9.69 (1H, s), 10.47 (1H, br s).

(36d) 5-Methyl-4-(trifluoromethyl)-1H-imidazole-2-carboxylic acid

The same operation as in Example (33c) was performed using 5-methyl-4-(trifluoromethyl)-1H-imidazole-2-carbaldehyde obtained in Example (36c) (90 mg, 0.51 mmol), sodium chlorite (95 mg, 1.05 mmol), sodium dihydrogenphosphate (154 mg, 0.99 mmol) and 2-methyl-2-butene (0.3 mL, 2.84 mmol), to obtain 117 mg of the title compound as a white solid (100%).

mass spectrum (ESI): m/z 195 (M+H)$^+$.

(36e) tert-Butyl cis(±)-4-{[(5-methyl-4-trifluoromethyl-1H-imidazol-2-yl)carbonyl]amino}-3-methoxypiperidine-1-carboxylate The same operation as in Example (1g) was performed using tert-butyl cis(±)-4-amino-3-methoxypiperidine-1-carboxylate obtained by the method described in Example (1e) (0.22 g, 0.96 mmol), 5-methyl-4-(trifluoromethyl)-1H-imidazole-2-carboxylic acid obtained in Example (36d) (0.10 g, 0.51 mmol), WSC hydrochloride (0.30 g, 1.57 mmol) and HOBT (70 mg, 0.52 mmol), to obtain 0.17 g of the title compound as a white foamy substance (83%).

$^1$H NMR spectrum (400 MHz, CDCl$_3$) δ ppm: 1.48 (9H, s), 1.65-1.68 (1H, m), 1.89-1.99 (1H, m), 2.44 (3H, d, J=1.38 Hz), 2.79-2.83 (1H, m), 3.34-3.42 (2H, m), 3.43 (3H, s), 4.14-4.17 (2H, m), 4.42-4.51 (1H, m), 7.50-7.52 (1H, m), 10.61 (1H, br s).

(36f) Ethyl cis(±)-2-(4-{[(5-methyl-4-trifluoromethyl-1H-imidazol-2-yl)carbonyl]amino}-3-methoxypiperidin-1-yl)-1,3-thiazole-5-carboxylate The same operation as in Example (1h) was performed using tert-butyl cis(±)-4-{[(5-methyl-4-trifluoromethyl-1H-imidazol-2-yl)carbonyl]amino}-3-methoxypiperidine-1-carboxylate obtained in Example (36e) (53 mg, 0.13 mmol), a 4 N hydrochloric acid/ethyl acetate solution (3 mL), diisopropylethylamine (0.1 mL, 0.57 mmol) and ethyl 2-bromo-1,3-thiazole-5-carboxylate (50 μL, 0.40 mmol), to obtain 60 mg of the title compound as a colorless oily substance (100%).

$^1$H NMR spectrum (400 MHz, CDCl$_3$) δ ppm: 1.34 (3H, t, J=7.11 Hz), 1.82-1.84 (1H, m), 2.04-2.11 (1H, m), 2.45 (3H, s), 3.14 (1H, d, J=14.21 Hz), 3.23-3.28 (1H, m), 3.44 (3H, s), 3.54 (1H, br s), 3.98-4.02 (1H, m), 4.24-4.32 (3H, m), 4.57 (1H, d, J=14.21 Hz), 7.53 (1H, d, J=8.25 Hz), 7.84 (1H, s), 10.88 (1H, br s).

(36g) cis(±)-2-(4-{[(5-Methyl-4-trifluoromethyl-1H-imidazol-2-yl)carbonyl]amino}-3-methoxypiperidin-1-yl)-1,3-thiazole-5-carboxylic acid Ethyl cis(±)-2-(4-{[(5-methyl-4-trifluoromethyl-1H-imidazol-2-yl)carbonyl]amino}-3-methoxypiperidin-1-yl)-1,3-thiazole-5-carboxylate obtained in Example (36f) (30 mg, 0.065 mmol) was dissolved in methanol (1 mL). A 1 N aqueous sodium hydroxide solution (1 mL) was added, and the mixture was stirred at room temperature for 1.5 hours. The reaction solution was neutralized with 1 N hydrochloric acid, and the residue was purified by reverse phase silica gel column chromatography (elution solvent: distilled water, methanol/distilled water=20/80, 60/40) to obtain 9.1 mg of the title compound as a white solid (32%).

$^1$H NMR spectrum (400 MHz, DMSO-$d_6$) δ ppm: 1.70-1.71 (1H, m), 1.88-1.94 (1H, m), 2.33 (3H, s), 3.30-3.32 (2H, m), 3.33 (3H, s), 3.60 (1H, br s), 3.91-3.94 (1H, m), 4.22-4.24 (1H, m), 4.32-4.36 (1H, m), 7.74 (1H, s), 7.77 (1H, d, J=8.25 Hz).

mass spectrum (ESI): m/z 434 (M+H)$^+$.

Example 37 cis(±)-2-(4-{[(5-Methyl-4-trifluoromethyl-1H-imidazol-2-yl)carbonyl]amino}-3-methoxypiperidin-1-yl)-4-methyl-1,3-thiazole-5-carboxylic acid (Exemplified Compound No. 37)

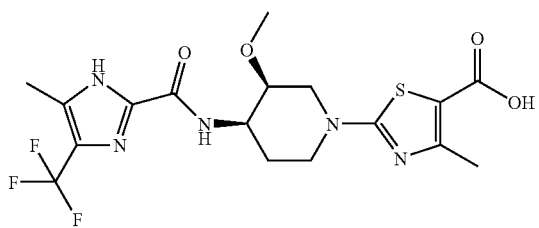

(37a) Ethyl cis(±)-2-(4-{[(5-methyl-4-trifluoromethyl-1H-imidazol-2-yl)carbonyl]amino}-3-methoxypiperidin-1-yl)-4-methyl-1,3-thiazole-5-carboxylate The same operation as in Example (1h) was performed using tert-butyl cis(±)-4-{[(5-methyl-4-trifluoromethyl-1H-imidazol-2-yl)carbonyl]amino}-3-methoxypiperidine-1-carboxylate obtained by the method described in Example (36e) (52 mg, 0.13 mmol), a 4 N hydrochloric acid/ethyl acetate solution (3 mL), diisopropylethylamine (0.11 mL, 0.63 mmol) and ethyl 2-bromo-4-methyl-1,3-thiazole-5-carboxylate (53 mg, 0.21 mmol), to obtain 48 mg of the title compound as a colorless oily substance (80%).

$^1$H NMR spectrum (400 MHz, CDCl$_3$) δ ppm: 1.33 (3H, t, J=7.11 Hz), 1.79-1.83 (1H, m), 2.05-2.09 (1H, m), 2.45 (3H, s), 2.54 (3H, s), 3.11 (1H, d, J=13.75 Hz), 3.17-3.26 (1H, m), 3.44 (3H, s), 3.51 (1H, br s), 3.99-4.02 (1H, m), 4.25-4.27 (3H, m), 4.51-4.55 (1H, m), 7.54 (1H, d, J=8.71 Hz), 10.92 (1H, br s).

(37b) cis(±)-2-(4-{[(5-Methyl-4-trifluoromethyl-1H-imidazol-2-yl)carbonyl]amino}-3-methoxypiperidin-1-yl)-4-methyl-1,3-thiazole-5-carboxylic acid The same operation as in Example (36g) was performed using ethyl cis(±)-2-(4-{[(5-methyl-4-trifluoromethyl-1H-imidazol-2-yl)carbonyl]amino}-3-methoxypiperidin-1-yl)-4-methyl-1,3-thiazole-5-carboxylate obtained in Example (37a) (48.3 mg, 0.10 mmol) and a 1 N aqueous sodium hydroxide solution (1 mL), to obtain 22.3 mg of the title compound as a white solid (49%).

$^1$H NMR spectrum (400 MHz, DMSO-$d_6$) δ ppm: 1.67-1.70 (1H, m), 1.88-1.90 (1H, m), 2.33 (3H, s), 2.41 (3H, s), 3.16-3.32 (2H, m), 3.34 (3H, s), 3.59 (1H, br s), 3.91 (1H, s), 4.23-4.27 (2H, m), 7.76 (1H, d, J=8.25 Hz), 12.39 (1H, br s).

mass spectrum (ESI): m/z 448 (M+H)$^+$.

Example 38 cis(±)-2-(4-{[(4-Chloro-5-ethyl-1H-imidazol-2-yl)carbonyl]amino}-3-methoxypiperidin-1-yl)-5-methyl-1,3-thiazole-4-carboxylic acid (Exemplified Compound No. 38)

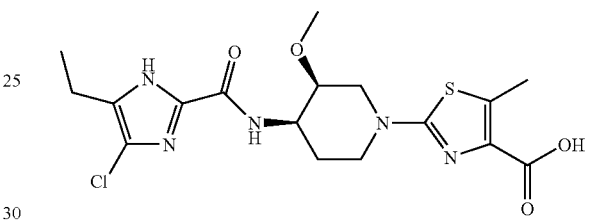

(38a) Ethyl 2-chloro-5-methyl-1,3-thiazole-4-carboxylate

The compound was synthesized according to the method described in the following document.

WO 2006/087543 A1

(38b) Ethyl cis(±)-2-(4-{[(4-chloro-5-ethyl-1H-imidazol-2-yl)carbonyl]amino}-3-methoxypiperidin-1-yl)-5-methyl-1,3-thiazole-4-carboxylate tert-Butyl cis(±)-4-{[(4-chloro-5-ethyl-1H-imidazol-2-yl)carbonyl]amino}-3-methoxypiperidine-1-carboxylate obtained by the method described in Example (1g) (80 mg, 0.21 mmol) was dissolved in methanol (1 mL). A 4 N hydrochloric acid/ethyl acetate solution (3 mL) was added, and the mixture was stirred at room temperature for one hour. Following concentration under reduced pressure, the residue was dissolved in DMF (2 mL).

Diisopropylethylamine (0.16 mL, 0.92 mmol) and ethyl 2-chloro-5-methyl-1,3-thiazole-4-carboxylate obtained in Example (38a) (70 mg, 0.34 mmol) were added, and the mixture was stirred using a microwave reactor at 160° C. for three hours. Dilute hydrochloric acid was added to the reaction solution, followed by extraction with ethyl acetate. The organic layer was washed with water, saturated aqueous sodium bicarbonate solution and brine, and dried over anhydrous sodium sulfate. Following concentration under reduced pressure, the residue was purified by silica gel column chromatography (elution solvent: hexane/ethyl acetate=4/1, 1/1, ethyl acetate) to obtain 15.3 mg of the title compound as a pale yellow solid (16%).

$^1$H NMR spectrum (400 MHz, CDCl$_3$) δ ppm: 1.26 (3H, t, J=7.60 Hz), 1.37 (3H, t, J=7.11 Hz), 1.76-1.78 (1H, m), 2.03-2.07 (1H, m), 2.59 (3H, s), 2.69 (2H, q, J=7.60 Hz), 3.06 (1H, dd, J=14.21, 1.38 Hz), 3.12-3.16 (1H, m), 3.43 (3H, s), 3.49 (1H, br s), 3.91-3.94 (1H, m), 4.19-4.28 (1H, m), 4.30-4.40 (3H, m), 7.49 (1H, d, J=8.71 Hz), 11.19 (1H, br s).

(38c) cis(±)-2-(4-{[(4-Chloro-5-ethyl-1H-imidazol-2-yl)carbonyl]amino}-3-methoxypiperidin-1-yl)-5-methyl-1,3-thiazole-4-carboxylic acid The same operation as in Example (1i) was performed using ethyl cis(±)-2-(4-{[(4-chloro-5-ethyl-1H-imidazol-2-yl)carbonyl]amino}-3-methoxypiperidin-1-yl)-5-methyl-1,3-thiazole-4-carboxylate obtained in Example (38b) (15.3 mg, 0.034 mmol) and a 2 N aqueous lithium hydroxide solution (1 mL), to obtain 5.7 mg of the title compound as a pale yellow solid (40%).

$^1$H NMR spectrum (400 MHz, DMSO-$d_6$) δ ppm: 1.14 (3H, t, J=7.34 Hz), 1.64-1.67 (1H, m), 1.83-1.89 (1H, m), 2.46-2.52 (3H, m), 2.53-2.59 (2H, m), 3.15-3.52 (3H, m), 3.79-3.82 (1H, m), 4.13-4.17 (2H, m), 7.62 (1H, d, J=8.25 Hz).

mass spectrum (ESI): m/z 428 (M+H)$^+$.

Example 39 cis(±)-2-(4-{[(5-Ethyl-4-trifluoromethyl-1H-imidazol-2-yl)carbonyl]amino}-3-methoxypiperidin-1-yl)-4-methyl-1,3-thiazole-5-carboxylic acid (Exemplified Compound No. 39)

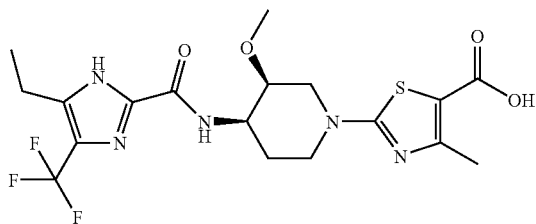

(39a) 2-Ethyl-1,3-dithiane

The compound was synthesized according to the method described in the following document.

Tetrahedron, 52, 6, 1996, 2125-2154.

(39b) 2,2,2-Trifluoro-1-(2-ethyl-1,3-dithian-2-yl)ethanone

The same operation as in Example (36a) was performed using 2-ethyl-1,3-dithiane obtained in Example (39a) (3.51 g, 23.7 mmol), n-butyllithium (1.58 M solution in hexane, 18 mL, 28.3 mmol) and ethyl trifluoroacetate (4 mL, 33.6 mmol), to obtain 2.02 g of the title compound as a pale yellow oily substance (35%).

$^1$H NMR spectrum (400 MHz, CDCl$_3$) δ ppm: 1.14 (3H, t, J=7.57 Hz), 1.76-1.95 (2H, m), 1.96-2.12 (2H, m), 2.69-2.74 (2H, m), 2.89-2.96 (1H, m), 2.99-3.07 (1H, m).

(39c) 2-(Dimethoxymethyl)-5-ethyl-4-(trifluoromethyl)-1H-imidazole

The same operation as in Example (36b) was performed using NCS (1.35 g, 10.1 mmol), silver nitrate (2.45 g, 14.4 mmol), 2,2,2-trifluoro-1-(2-ethyl-1,3-dithian-2-yl)ethanone obtained in Example (39b) (1.0 g, 4.09 mmol), dimethoxyacetaldehyde (5.76 M aqueous solution, 1.0 mL, 5.76 mmol) and 28% aqueous ammonia (4 mL). The resulting compound was used for the next reaction without purification.

(39d) 5-Ethyl-4-(trifluoromethyl)-1H-imidazole-2-carbaldehyde

The same operation as in Example (33b) was performed using 2-(dimethoxymethyl)-5-ethyl-4-(trifluoromethyl)-1H-imidazole obtained in Example (39c) (about 4.09 mmol) and 2 N sulfuric acid (30 mL), to obtain 228.3 mg of the title compound as a white solid (29%).

$^1$H NMR spectrum (400 MHz, CDCl$_3$) δ ppm: 1.33 (3H, t, J=7.79 Hz), 2.87-2.93 (2H, m), 9.69 (1H, s).

(39e) 5-Ethyl-4-(trifluoromethyl)-1H-imidazole-2-carboxylic acid

The same operation as in Example (33c) was performed using 5-ethyl-4-(trifluoromethyl)-1H-imidazole-2-carbaldehyde obtained in Example (39d) (110 mg, 0.57 mmol), sodium chlorite (108 mg, 1.19 mmol), sodium dihydrogenphosphate (178 mg, 1.14 mmol) and 2-methyl-2-butene (0.3 mL, 2.84 mmol), to obtain 117.5 mg of the title compound as a white solid (99%).

mass spectrum (ESI): m/z 209 (M+H)$^+$.

(39f) tert-Butyl cis(±)-4-{[(5-ethyl-4-trifluoromethyl-1H-imidazol-2-yl)carbonyl]amino}-3-methoxypiperidine-1-carboxylate The same operation as in Example (1g) was performed using tert-butyl cis(±)-4-amino-3-methoxypiperidine-1-carboxylate obtained by the method described in Example (1e) (0.26 g, 1.13 mmol), 5-ethyl-4-(trifluoromethyl)-1H-imidazole-2-carboxylic acid obtained in Example (39e) (117.5 mg, 0.56 mmol), WSC hydrochloride (0.38 g, 1.98 mmol) and HOBT (76 mg, 0.56 mmol), to obtain 0.19 g of the title compound as a white foamy substance (79%).

$^1$H NMR spectrum (400 MHz, CDCl$_3$) δ ppm: 1.29 (3H, t, J=7.79 Hz), 1.48 (9H, s), 1.64-1.68 (1H, m), 1.87-1.90 (1H, m), 2.81 (4H, m), 3.34-3.42 (1H, m), 3.43 (3H, s), 4.05-4.22 (2H, m), 4.42-4.49 (1H, m), 7.57 (1H, brs), 11.18 (1H, br s).

(39g) Ethyl cis(±)-2-(4-{[(5-ethyl-4-trifluoromethyl-1H-imidazol-2-yl)carbonyl]amino}-3-methoxypiperidin-1-yl)-4-methyl-1,3-thiazole-5-carboxylate The same operation as in Example (1h) was performed using tert-butyl cis(±)-4-{[(5-ethyl-4-trifluoromethyl-1H-imidazol-2-yl)carbonyl]amino}-3-methoxypiperidine-1-carboxylate obtained in Example (39f) (67.2 mg, 0.16 mmol), a 4 N hydrochloric acid/ethyl acetate solution (3 mL), diisopropylethylamine (0.1 mL, 0.57 mmol) and ethyl 2-bromo-4-methyl-1,3-thiazole-5-carboxylate (50 mg, 0.20 mmol), to obtain 65.3 mg of the title compound as a yellow oily substance (84%).

$^1$H NMR spectrum (400 MHz, CDCl$_3$) δ ppm: 1.24-1.35 (6H, m), 1.79-1.82 (1H, m), 2.03-2.09 (1H, m), 2.54 (3H, s), 2.84 (2H, q, J=7.64 Hz), 3.09-3.13 (1H, m), 3.19-3.22 (1H, m), 3.44 (3H, s), 3.53 (1H, br s), 3.99-4.02 (1H, m), 4.24-4.28 (3H, m), 4.53 (1H, d, J=14.21 Hz), 7.52 (1H, d, J=8.71 Hz), 10.62 (1H, br s).

(39h) cis(±)-2-(4-{[(5-Ethyl-4-trifluoromethyl-1H-imidazol-2-yl)carbonyl]amino}-3-methoxypiperidin-1-yl)-4-methyl-1,3-thiazole-5-carboxylic acid The same operation as in Example (36g) was performed using ethyl cis(±)-2-(4-{[(5-ethyl-4-trifluoromethyl-1H-imidazol-2-yl)carbonyl]amino}-3-methoxypiperidin-1-yl)-4-methyl-1,3-thiazole-5-carboxylate obtained in Example (39g) (65 mg, 0.13 mmol) and a 1 N aqueous sodium hydroxide solution (2 mL), to obtain 9.4 mg of the title compound as a white solid (15%).

$^1$H NMR spectrum (400 MHz, DMSO-$d_6$) δ ppm: 1.16 (3H, t, J=7.56 Hz), 1.66-1.69 (1H, m), 1.87-1.90 (1H, m), 2.39 (3H, s), 2.68-2.72 (3H, m), 3.34 (3H, s), 3.57 (1H, br s), 3.87-3.90 (1H, m), 4.20-4.23 (1H, m), 7.75 (1H, d, J=8.29 Hz).

mass spectrum (ESI): m/z 462 (M+H)$^+$.

Example 40 cis(±)-2-(4-{[(5-Ethyl-4-trifluoromethyl-1H-imidazol-2-yl)carbonyl]amino}-3-methoxypiperidin-1-yl)-5-methyl-1,3-thiazole-4-carboxylic acid (Exemplified Compound No. 40)

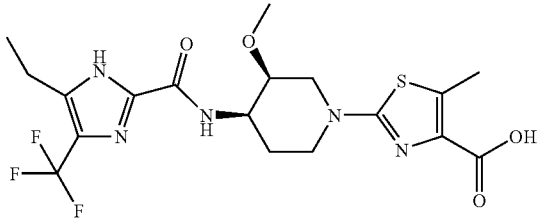

(40a) tert-Butyl cis(±)-4-{[(benzyloxy)carbonyl]amino}-3-methoxypiperidine-1-carboxylate tert-Butyl cis(±)-4-amino-3-methoxypiperidine-1-carboxylate obtained by the method described in Example (1e) (3.0 g, 13.0 mmol) was dissolved in THF (60 mL), followed by cooling to 0° C. Thereafter, aqueous sodium carbonate solution (30 mL) and benzyl chloroformate (2.8 mL, 19.6 mmol) were added, and the mixture was stirred for one hour. Ethyl acetate was added to the reaction solution, and the organic layer was washed with brine and dried over anhydrous sodium sulfate. Following concentration under reduced pressure, the residue was purified by silica gel column chromatography (elution solvent: hexane/ethyl acetate=90/10, 50/50) to obtain 4.29 g of the title compound as a pale yellow solid (90%).

(40b) Benzyl cis(±)-(3-methoxypiperidin-4-yl)-carbamate tert-Butyl cis(±)-4-{[(benzyloxy)carbonyl]amino}-3-methoxypiperidine-1-carboxylate obtained in Example (40a) (4.28 g, 11.7 mmol) was dissolved in methanol (20 mL). A 4 N hydrochloric acid/ethyl acetate solution (60 mL) was added, and the mixture was stirred at room temperature for 40 minutes. The reaction solution was concentrated under reduced pressure and then saturated aqueous sodium bicarbonate solution was added, followed by extraction with THF. The organic layer was dried over anhydrous sodium sulfate and concentrated under reduced pressure. The resulting compound was used for the next reaction without purification.

(40c) Ethyl 2-bromo-5-methyl-1,3-thiazole-4-carboxylate

The same operation as in Example (22c) was performed using ethyl 2-amino-5-methyl-1,3-thiazole-4-carboxylate (synthesized according to the method described in WO 2006/087543 A1, 0.5 g, 2.68 mmol), copper bromide (0.62 g, 2.70 mmol) and tert-butyl nitrite (0.35 mL, 2.94 mmol), to obtain 0.53 g of the title compound as a pale yellow oily substance (80%).

$^1$H NMR spectrum (400 MHz, CDCl$_3$) δ ppm: 1.41 (3H, t, J=7.14 Hz), 2.73 (3H, s), 4.41 (2H, q, J=7.14 Hz).

(40d) Ethyl cis(±)-2-(4-{[(benzyloxy)carbonyl]amino}-3-methoxypiperidin-1-yl)-5-methyl-1,3-thiazole-4-carboxylate The same operation as in Example (38b) was performed using benzyl cis(±)-(3-methoxypiperidin-4-yl)-carbamate obtained in Example (40b) (0.2 g, 0.76 mmol), diisopropylethylamine (0.25 mL, 1.44 mmol) and ethyl 2-bromo-5-methyl-1,3-thiazole-4-carboxylate obtained in Example (40c) (0.2 g, 0.80 mmol), to obtain 157.6 mg of the title compound as a yellow oily substance (48%).

$^1$H NMR spectrum (400 MHz, CDCl$_3$) δ ppm: 1.36 (3H, t, J=7.20 Hz), 1.74-1.83 (1H, m), 1.84-1.97 (1H, m), 2.58 (3H, s), 3.03-3.21 (2H, m), 3.39 (3H, s), 3.44 (1H, br s), 3.83-3.86 (2H, m), 4.26-4.39 (3H, m), 5.11 (2H, s), 7.32-7.36 (5H, m).

(40e) Ethyl cis(±)-2-(4-amino-3-methoxypiperidin-1-yl)-5-methyl-1,3-thiazole-4-carboxylate Ethyl cis(±)-2-(4-{[(benzyloxy)carbonyl]amino}-3-methoxypiperidin-1-yl)-5-methyl-1,3-thiazole-4-carboxylate obtained in Example (40d) (75 mg, 0.17 mmol) was dissolved in ethanol (3 mL). A 10% palladium-carbon catalyst (40 mg) was added, and the mixture was stirred in a hydrogen atmosphere for 21 hours. The reaction solution was filtered through celite and then concentrated under reduced pressure to obtain 44.9 mg of the title compound as a colorless oily substance. The resulting compound was used for the next reaction without purification.

(40f) Ethyl cis(±)-2-(4-{[(5-ethyl-4-trifluoromethyl-1H-imidazol-2-yl)carbonyl]amino}-3-methoxypiperidin-1-yl)-5-methyl-1,3-thiazole-4-carboxylate The same operation as in Example (1g) was performed using ethyl cis(±)-2-(4-amino-3-methoxypiperidin-1-yl)-5-methyl-1,3-thiazole-4-carboxylate obtained in Example (40e) (44.9 mg, 0.15 mmol), 5-ethyl-4-(trifluoromethyl)-1H-imidazole-2-carboxylic acid obtained by the method described in Example (39e) (29 mg, 0.14 mmol), WSC hydrochloride (80 mg, 0.42 mmol) and HOBT (20 mg, 0.15 mmol), to obtain 29.2 mg of the title compound as a colorless oily substance (43%).

$^1$H NMR spectrum (400 MHz, CDCl$_3$) δ ppm: 1.29 (3H, t, J=7.56 Hz), 1.38 (3H, t, J=7.19 Hz), 1.78-1.80 (1H, m), 2.07-2.11 (1H, m), 2.60 (3H, s), 2.84 (2H, q, J=7.56 Hz), 3.02-3.09 (1H, m), 3.12-3.17 (1H, m), 3.45 (3H, s), 3.52 (1H, br s), 3.92-3.96 (1H, m), 4.22-4.25 (1H, m), 4.30-4.41 (3H, m), 7.63 (1H, d, J=8.78 Hz), 11.69 (1H, br s).

(40g) cis(±)-2-(4-{[(5-Ethyl-4-trifluoromethyl-1H-imidazol-2-yl)carbonyl]amino}-3-methoxypiperidin-1-yl)-5-methyl-1,3-thiazole-4-carboxylic acid Ethyl cis(±)-2-(4-{[(5-ethyl-4-trifluoromethyl-1H-imidazol-2-yl)carbonyl]amino}-3-methoxypiperidin-1-yl)-5-methyl-1,3-thiazole-4-carboxylate obtained in Example (40f) (29.2 mg, 0.060 mmol) was dissolved in methanol (1 mL). The solution was subjected to the same operation as in Example (36g) using a 1 N aqueous sodium hydroxide solution (1.5 mL), to obtain 24.0 mg of the title compound as a white solid (87%).

$^1$H NMR spectrum (400 MHz, DMSO-d$_6$) δ ppm: 1.16 (3H, t, J=7.57 Hz), 1.65-1.68 (1H, m), 1.86-1.91 (1H, m), 2.50 (3H, s), 2.70 (2H, q, J=7.57 Hz), 3.16-3.21 (2H, m), 3.34 (3H, s), 3.56 (1H, br s), 3.79-3.83 (1H, m), 4.17-4.22 (2H, m), 7.74 (1H, d, J=8.25 Hz), 12.43 (1H, br s).

mass spectrum (ESI): m/z 462 (M+H)$^+$.

Example 41 cis(±)-2-(4-{[(4-Chloro-5-ethyl-1H-imidazol-2-yl)carbonyl]amino}-3-ethoxypiperidin-1-yl)-5-methyl-1,3-thiazole-4-carboxylic acid (Exemplified Compound No. 41)

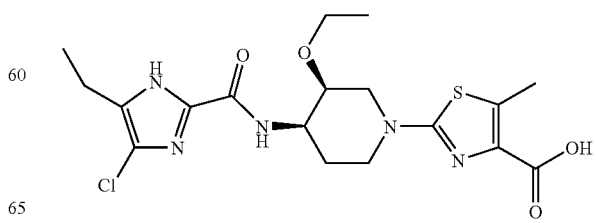

(41a) Ethyl cis(±)-2-(4-{[(4-chloro-5-ethyl-1H-imidazol-2-yl)carbonyl]amino}-3-ethoxypiperidin-1-yl)-5-methyl-1,3-thiazole-4-carboxylate The same operation as in Example (38b) was performed using tert-butyl cis(±)-4-{[(4-chloro-5-ethyl-1H-imidazol-2-yl)carbonyl]amino}-3-ethoxypiperidine-1-carboxylate obtained by the method described in Example (34a) (142 mg, 0.35 mmol), diisopropylethylamine (0.3 mL, 1.72 mmol), a 4 N hydrochloric acid/ethyl acetate solution (4 mL) and ethyl 2-bromo-5-methyl-1,3-thiazole-4-carboxylate obtained in Example (40c) (102 mg, 0.41 mmol), to obtain 59.3 mg of the title compound as a yellow oil substance (36%).

$^1$H NMR spectrum (400 MHz, CDCl$_3$) δ ppm: 1.17 (3H, t, J=7.11 Hz), 1.26 (3H, t, J=7.57 Hz), 1.38 (3H, t, J=7.11 Hz), 1.69-1.77 (1H, m), 2.05-2.17 (1H, m), 2.60 (3H, s), 2.69 (2H, q, J=7.57 Hz), 3.07-3.17 (2H, m), 3.42-3.45 (1H, m), 3.59 (1H, br s), 3.71-3.78 (1H, m), 3.95-3.98 (1H, m), 4.20-4.25 (2H, m), 4.30-4.40 (2H, m), 7.53 (1H, d, J=8.71 Hz), 11.66 (1H, br s).

(41b) cis(±)-2-(4-{[(4-Chloro-5-ethyl-1H-imidazol-2-yl)carbonyl]amino}-3-ethoxypiperidin-1-yl)-5-methyl-1,3-thiazole-4-carboxylic acid The same operation as in Example (1i) was performed using ethyl cis(±)-2-(4-{[(4-chloro-5-ethyl-1H-imidazol-2-yl)carbonyl]amino}-3-ethoxypiperidin-1-yl)-5-methyl-1,3-thiazole-4-carboxylate obtained in Example (41a) (59.3 mg, 0.13 mmol) and a 2 N aqueous lithium hydroxide solution (3 mL), to obtain 51.5 mg of the title compound as a pale yellow solid (92%).

$^1$H NMR spectrum (400 MHz, DMSO-d$_6$) δ ppm: 1.05 (3H, t, J=6.88 Hz), 1.14 (3H, t, J=7.34 Hz), 1.64-1.66 (1H, m), 1.85-1.88 (1H, m), 2.52-2.55 (5H, m), 3.19-3.40 (6H, m), 3.60-3.67 (2H, m), 3.82-3.85 (1H, m), 4.00-4.03 (1H, m), 4.14-4.16 (1H, m), 7.62 (1H, d, J=8.25 Hz).

mass spectrum (ESI): m/z 442 (M+H)$^+$.

Example 42 cis(±)-3-(4-{[(5-Ethyl-4-trifluoromethyl-1H-imidazol-2-yl)carbonyl]amino}-3-methoxypiperidin-1-yl)benzoic acid (Exemplified Compound No. 42)

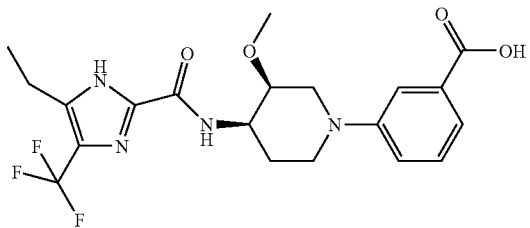

(42a) Methyl cis(±)-3-(4-{[(benzyloxy)carbonyl]amino}-3-methoxypiperidin-1-yl)benzoate Benzyl cis(±)-4-(3-methoxypiperidin-4-yl)-carbamate obtained by the method described in Example (40b) (0.5 g, 1.89 mmol) was dissolved in dioxane (20 ml) and DMF (6 mL). Methyl 3-bromobenzoate (0.35 g, 1.63 mmol), palladium acetate (39 mg, 0.17 mmol), BINAP (214 mg, 0.34 mmol) and cesium carbonate (1.35 g, 4.14 mmol) were added, and the mixture was stirred at 100° C. for 17 hours. Aqueous ammonium chloride solution was added to the reaction solution, followed by extraction with ethyl acetate. Then, the organic layer was washed with brine, dried over anhydrous sodium sulfate and concentrated under reduced pressure. Thereafter, the residue was purified by silica gel column chromatography (elution solvent: hexane/ethyl acetate=90/10, 80/20, 0/100) to obtain 250.9 mg of the title compound as a yellow oily substance (39%).

$^1$H NMR spectrum (400 MHz, CDCl$_3$) δ ppm: 1.85-1.89 (1H, m), 2.01-2.13 (1H, m), 2.88-2.92 (2H, m), 3.41 (3H, s), 3.51 (1H, br s), 3.60-3.71 (1H, m), 3.85-3.89 (2H, m), 3.90 (3H, s), 5.12 (2H, s), 5.26-5.30 (1H, m), 7.12 (1H, dd, J=8.02, 2.52 Hz), 7.25-7.40 (6H, m), 7.48-7.52 (1H, m), 7.59-7.63 (1H, m).

(42b) cis(±)-3-(4-{[(Benzyloxy)carbonyl]amino}-3-methoxypiperidin-1-yl)benzoic acid Methyl cis(±)-3-(4-{[(benzyloxy)carbonyl]amino}-3-methoxypiperidin-1-yl)benzoate obtained in Example (42a) (250 mg, 0.63 mmol) was dissolved in methanol (5 mL). A 1 N aqueous sodium hydroxide solution (4 mL) was added, and the mixture was stirred at 70° C. for one hour. The reaction solution was neutralized with 1 N hydrochloric acid, followed by extraction with ethyl acetate. Then, the organic layer was washed with brine, dried over anhydrous sodium sulfate and concentrated under reduced pressure. The resulting compound was used for the next reaction without purification.

(42c) tert-Butyl cis(±)-3-(4-{[(benzyloxy)carbonyl]amino}-3-methoxypiperidin-1-yl)benzoate cis(±)-3-(4-{[(Benzyloxy)carbonyl]amino}-3-methoxypiperidin-1-yl)benzoic acid obtained in Example (42b) (200 mg, about 0.52 mmol) was dissolved in THF (0.5 mL) and toluene (5 mL). N,N-Dimethylformamide di-tert-butylacetal (1 mL) was added, and the mixture was stirred at 90° C. for 50 minutes. Ethyl acetate was added to the reaction solution, which was then washed with a 1 N aqueous sodium hydroxide solution and brine, dried over anhydrous sodium sulfate and concentrated under reduced pressure. Thereafter, the residue was purified by silica gel column chromatography (elution solvent: hexane/ethyl acetate=75/25, 70/30) to obtain 117.7 mg of the title compound as a colorless oily substance (51%).

$^1$H NMR spectrum (400 MHz, CDCl$_3$) δ ppm: 1.58 (9H, s), 1.87-1.88 (1H, m), 1.94-2.05 (1H, m), 2.86-2.90 (2H, m), 3.42 (3H, s), 3.51 (1H, br s), 3.58-3.62 (1H, m), 3.84-3.88 (2H, m), 5.12 (2H, s), 5.28 (1H, d, J=8.25 Hz), 7.06-7.11 (1H, m), 7.25-7.40 (6H, m), 7.46 (1H, d, J=7.79 Hz), 7.56 (1H, s).

(42d) tert-Butyl cis(±)-3-(4-amino-3-methoxypiperidin-1-yl)benzoate

The same operation as in Example (40e) was performed using tert-butyl cis(±)-3-(4-{[(benzyloxy)carbonyl]amino}-3-methoxypiperidin-1-yl)benzoate obtained in Example (42c) (115 mg, 0.26 mmol) and a 10% palladium-carbon catalyst (40 mg), to obtain the title compound. The resulting compound was used for the next reaction without purification.

(42e) tert-Butyl cis(±)-3-(4-{[(5-ethyl-4-trifluoromethyl-1H-imidazol-2-yl)carbonyl]amino}-3-methoxypiperidin-1-yl)benzoate The same operation as in Example (1g) was performed using tert-butyl cis(±)-3-(4-amino-3-methoxypiperidin-1-yl)benzoate obtained in Example (42d) (about 0.26 mmol), 5-ethyl-4-(trifluoromethyl)-1H-imidazole-2-carboxylic acid obtained by the method described in Example (39e) (50 mg, 0.24 mmol), WSC hydrochloride (137 mg, 0.71 mmol) and HOBT (32 mg, 0.24 mmol), to obtain 79.7 mg of the title compound as a white solid (67%).

$^1$H NMR spectrum (400 MHz, CDCl$_3$) δ ppm: 1.30 (3H, t, J=7.57 Hz), 1.59 (9H, s), 1.86-1.89 (1H, m), 2.14-2.19 (1H, m), 2.86-2.92 (4H, m), 3.46 (3H, s), 3.57 (1H, br s), 3.65-3.74 (1H, m), 3.95-3.99 (1H, m), 4.20-4.27 (1H, m), 7.12 (1H, dd, J=8.25, 2.29 Hz), 7.26-7.32 (1H, m), 7.48 (1H, d, J=7.79 Hz), 7.59-7.62 (2H, m), 11.27 (1H, s).

(42f) cis(±)-3-(4-{[(5-Ethyl-4-trifluoromethyl-1H-imidazol-2-yl)carbonyl]amino}-3-methoxypiperidin-1-yl)benzoic acid tert-Butyl cis(±)-3-(4-{[(5-ethyl-4-trifluoromethyl-1H-imidazol-2-yl)carbonyl]amino}-3-methoxypiperidin-1-yl)benzoate obtained in Example (42e) (78 mg, 0.16 mmol) was dissolved in dichloromethane (3 ml). Trifluoroacetic acid (0.75 ml) was added, followed by stirring for five hours. The reaction solution was concentrated under reduced pressure, and the residue was purified by reverse phase silica gel column chromatography (elution solvent: distilled water, acetonitrile) to obtain 60.1 mg of the title compound as a white solid (87%).

$^1$H NMR spectrum (400 MHz, DMSO-$d_6$) δ ppm: 1.16 (3H, t, J=7.57 Hz), 1.71-1.75 (1H, m), 1.95-2.01 (1H, m), 2.70 (2H, q, J=7.57 Hz), 2.93-2.97 (2H, m), 3.33 (3H, s), 3.58 (1H, br s), 3.63-3.66 (1H, m), 3.96-3.99 (1H, m), 4.14-4.18 (1H, m), 7.23-7.24 (1H, m), 7.30-7.32 (2H, m), 7.46-7.46 (1H, m), 7.68 (1H, d, J=8.71 Hz).

mass spectrum (ESI): m/z 441 (M+H)$^+$.

Example 43 cis(±)-2-(4-{[(4,5-Diethyl-1H-imidazol-2-yl)carbonyl]amino}-3-methoxypiperidin-1-yl)-4-methyl-1,3-thiazole-5-carboxylic acid (Exemplified Compound No. 43)

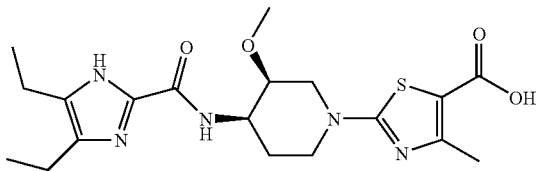

(43a) 4,5-Diethyl-2-(dimethoxymethyl)-1H-imidazole

The same operation as in Example (36b) was performed using hexane-3,4-dione (1.0 g, 8.76 mmol), dimethoxyacetaldehyde (5.76 M aqueous solution, 1.75 mL, 10.1 mmol) and 28% aqueous ammonia (2.5 mL). The resulting compound was used for the next reaction without purification.

(43b) 4,5-Diethyl-1H-imidazole-2-carbaldehyde

The same operation as in Example (33b) was performed using 4,5-diethyl-2-(dimethoxymethyl)-1H-imidazole obtained in Example (43a) (about 8.12 mmol) and 2 N sulfuric acid (40 mL), to obtain 352 mg of the title compound as a white solid (28%).

$^1$H NMR spectrum (400 MHz, CDCl$_3$) δ ppm: 1.26-1.28 (6H, m), 2.61 (2H, q, J=7.64 Hz), 2.69 (2H, q, J=7.64 Hz), 9.59 (1H, s), 10.05 (1H, br s).

(43c) 4,5-Diethyl-1H-imidazole-2-carboxylic acid

The same operation as in Example (33c) was performed using 4,5-diethyl-1H-imidazole-2-carbaldehyde obtained in Example (43b) (352 mg, 2.31 mmol), sodium chlorite (420 mg, 4.64 mmol), sodium dihydrogenphosphate (725 mg, 4.64 mmol) and 2-methyl-2-butene (1 mL, 9.45 mmol), to obtain 36.7 mg of the title compound as a white solid (9.4%).

mass spectrum (ESI): m/z 169 (M+H)$^+$.

(43d) tert-Butyl cis(±)-4-{[(4,5-diethyl-1H-imidazol-2-yl)carbonyl]amino}-3-methoxypiperidine-1-carboxylate The same operation as in Example (1g) was performed using tert-butyl cis(±)-4-amino-3-methoxypiperidine-1-carboxylate obtained by the method described in Example (1e) (120 mg, 0.52 mmol), 4,5-diethyl-1H-imidazole-2-carboxylic acid obtained in Example (43c) (36.7 mg, 0.22 mmol), WSC hydrochloride (145 mg, 0.76 mmol) and HOBT (35 mg, 0.26 mmol), to obtain 55.0 mg of the title compound as a white foamy substance (66%).

$^1$H NMR spectrum (400 MHz, CDCl$_3$) δ ppm: 1.20-1.32 (6H, m), 1.48 (9H, s), 1.60-1.65 (1H, m), 1.85-1.88 (1H, m), 2.54 (2H, q, J=7.64 Hz), 2.62 (2H, q, J=7.49 Hz), 2.79-2.81 (2H, m), 3.42 (3H, s), 3.90-4.19 (2H, m), 4.40-4.49 (1H, m), 7.49 (1H, br s), 10.71 (1H, br s).

(43e) Ethyl cis(±)-2-(4-{[(4,5-diethyl-1H-imidazol-2-yl)carbonyl]amino}-3-methoxypiperidin-1-yl)-4-methyl-1,3-thiazole-5-carboxylate The same operation as in Example (1h) was performed using tert-butyl cis(±)-4-{[(4,5-diethyl-1H-imidazol-2-yl)carbonyl]amino}-3-methoxypiperidine-1-carboxylate obtained in Example (43d) (55.0 mg, 0.14 mmol), a 4 N hydrochloric acid/ethyl acetate solution (3 mL), diisopropylethylamine (0.15 mL, 0.86 mmol) and ethyl 2-bromo-4-methyl-1,3-thiazole-5-carboxylate (43 mg, 0.17 mmol), to obtain 50.0 mg of the title compound as a yellow oily substance (77%).

$^1$H NMR spectrum (400 MHz, CDCl$_3$) δ ppm: 1.15-1.26 (6H, m), 1.33 (3H, t, J=7.11 Hz), 1.76-1.85 (1H, m), 2.03-2.09 (1H, m), 2.49-2.54 (4H, m), 2.63 (2H, q, J=7.64 Hz), 3.06-3.13 (1H, m), 3.19-3.23 (1H, m), 3.43 (3H, s), 3.53 (1H, br s), 3.96-4.05 (1H, m), 4.20-4.31 (3H, m), 4.48-4.52 (1H, m), 7.51 (1H, d, J=8.71 Hz), 10.70 (1H, br s).

(43f) cis(±)-2-(4-{[(4,5-Diethyl-1H-imidazol-2-yl)carbonyl]amino}-3-methoxypiperidin-1-yl)-4-methyl-1,3-thiazole-5-carboxylic acid The same operation as in Example (1i) was performed using ethyl cis(±)-2-(4-{[(4,5-diethyl-1H-imidazol-2-yl)carbonyl]amino}-3-methoxypiperidin-1-yl)-4-methyl-1,3-thiazole-5-carboxylate obtained in Example (43e) (50 mg, 0.11 mmol) and a 2 N aqueous lithium hydroxide solution (2 mL), to obtain 47 mg of the title compound as a white solid (100%).

$^1$H NMR spectrum (400 MHz, DMSO-$d_6$) δ ppm: 1.10-1.11 (6H, m), 1.64-1.66 (1H, m), 1.79-1.81 (1H, m), 2.35 (3H, s), 2.45-2.50 (4H, m), 3.11-3.15 (2H, m), 3.34 (3H, s), 3.51 (1H, br s), 3.82-3.85 (1H, m), 4.16-4.19 (2H, m), 7.43 (1H, d, J=8.71 Hz).

mass spectrum (ESI): m/z 422 (M+H)$^+$.

Example 44 cis(±)-2-(4-{[(4-Chloro-5-ethyl-1H-imidazol-2-yl)carbonyl]amino}-3-ethoxypiperidin-1-yl)-1,3-benzothiazole-7-carboxylic acid (Exemplified Compound No. 44)

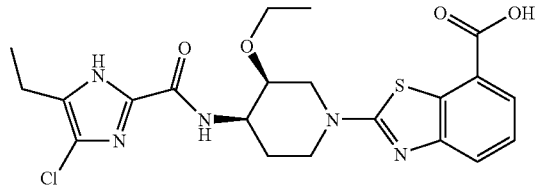

(44a) Ethyl cis(±)-2-(4-{[(4-chloro-5-ethyl-1H-imidazol-2-yl)carbonyl]amino}-3-ethoxypiperidin-1-yl)-1,3-benzothiazole-7-carboxylate The same operation as in Example (1h) was performed using tert-butyl cis(±)-4-{[(4-chloro-5-ethyl-1H-imidazol-2-yl)carbonyl]amino}-3-ethoxypiperidine-1-carboxylate obtained by the method described in Example (34a) (126.4 mg, 0.32 mmol), a 4 N hydrochloric acid/ethyl acetate solution (5 mL), diisopropylethylamine (0.22 mL, 1.26 mmol) and ethyl 2-bromo-1,3-benzothiazole-7-carboxylate obtained by the method described in Example (1f) (115 mg, 0.40 mmol), to obtain 127.4 mg of the title compound as a yellow oily substance (80%).

$^1$H NMR spectrum (400 MHz, CDCl$_3$) δ ppm: 1.14 (3H, t, J=7.48 Hz), 1.27 (3H, t, J=7.79 Hz), 1.44 (3H, t, J=7.15 Hz), 1.81-1.84 (1H, m), 2.10-2.16 (1H, m), 2.70 (2H, q, J=7.48 Hz), 3.26-3.31 (2H, m), 3.43-3.50 (1H, m), 3.65 (1H, brs), 3.76-3.84 (1H, m), 4.25-4.31 (2H, m), 4.45 (2H, q, J=7.15 Hz), 4.48-4.55 (1H, m), 7.35-7.37 (1H, m), 7.47 (1H, d, J=8.71 Hz), 7.69 (1H, d, J=7.34 Hz), 7.79 (1H, d, J=6.88 Hz), 10.79 (1H, brs).

(44b) cis(±)-2-(4-{[(4-Chloro-5-ethyl-1H-imidazol-2-yl)carbonyl]amino}-3-ethoxypiperidin-1-yl)-1,3-benzothiazole-7-carboxylic acid The same operation as in Example (1i) was performed using ethyl cis(±)-2-(4-{[(4-chloro-5-ethyl-1H-imidazol-2-yl)carbonyl]amino}-3-ethoxypiperidin-1-yl)-1,3-benzothiazole-7-carboxylate obtained in Example (44a) (125 mg, 0.25 mmol) and a 2 N aqueous lithium hydroxide solution (2 mL), to obtain 104.6 mg of the title compound as a pale yellow solid (90%).

$^1$H NMR spectrum (400 MHz, DMSO-d$_6$) δ ppm: 1.03 (3H, t, J=6.88 Hz), 1.14 (3H, t, J=7.53 Hz), 1.71-1.73 (1H, m), 1.89-1.95 (1H, m), 2.55 (2H, q, J=7.53 Hz), 3.25-3.51 (3H, m), 3.64-3.72 (3H, m), 4.16-4.28 (2H, m), 7.38-7.40 (1H, m), 7.64-7.66 (3H, m).

mass spectrum (ESI): m/z 478 (M+H)$^+$.

Example 45 cis(±)-2-(4-{[(5-Ethyl-4-trifluoromethyl-1H-imidazol-2-yl)carbonyl]amino}-3-ethoxypiperidin-1-yl)-4-methyl-1,3-thiazole-5-carboxylic acid (Exemplified Compound No. 45)

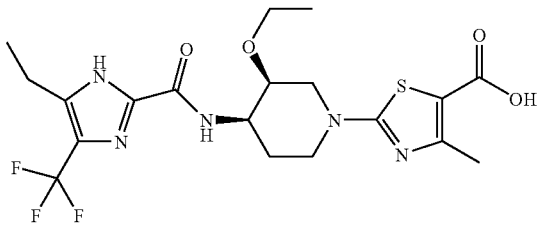

(45a) tert-Butyl cis(±)-4-{[(5-ethyl-4-trifluoromethyl-1H-imidazol-2-yl)carbonyl]amino}-3-ethoxypiperidine-1-carboxylate The same operation as in Example (1g) was performed using tert-butyl cis(±)-4-amino-3-ethoxypiperidine-1-carboxylate obtained in Example (112d) (178 mg, 0.73 mmol), 5-ethyl-4-(trifluoromethyl)-1H-imidazole-2-carboxylic acid obtained by the method described in Example (39e) (100 mg, 0.48 mmol), WSC hydrochloride (280 mg, 1.46 mmol) and HOBT (66 mg, 0.49 mmol), to obtain 173.5 mg of the title compound as a white foamy substance (91%).

$^1$H NMR spectrum (400 MHz, CDCl$_3$) δ ppm: 1.28 (3H, t, J=7.57 Hz), 1.47 (9H, s), 1.63-1.66 (1H, m), 1.88-1.91 (1H, m), 2.73-2.86 (4H, m), 3.39-3.44 (2H, m), 3.77 (1H, br s), 4.19-4.37 (3H, m), 7.59 (1H, br s), 11.07 (1H, br s).

(45b) Ethyl cis(±)-2-(4-{[(5-ethyl-4-trifluoromethyl-1H-imidazol-2-yl)carbonyl]amino}-3-ethoxypiperidin-1-yl)-4-methyl-1,3-thiazole-5-carboxylate The same operation as in Example (1h) was performed using tert-butyl cis(±)-4-{[(5-ethyl-4-trifluoromethyl-1H-imidazol-2-yl)carbonyl]amino}-3-ethoxypiperidine-1-carboxylate obtained in Example (45a) (170 mg, 0.39 mmol), a 4 N hydrochloric acid/ethyl acetate solution (6 ml), diisopropylethylamine (0.27 mL, 1.55 mmol) and ethyl 2-bromo-4-methyl-1,3-thiazole-5-carboxylate (0.13 g, 0.52 mmol), to obtain 179.5 mg of the title compound as a yellow foamy substance (91%).

$^1$H NMR spectrum (400 MHz, CDCl$_3$) δ ppm: 1.17 (3H, t, J=6.88 Hz), 1.24-1.35 (6H, m), 1.78-1.81 (1H, m), 2.05-2.15 (1H, m), 2.54 (3H, s), 2.84 (2H, q, J=7.49 Hz), 3.15-3.19 (2H, m), 3.42-3.46 (1H, m), 3.61 (1H, br s), 3.73-3.81 (1H, m), 4.02-4.05 (1H, m), 4.21-4.30 (3H, m), 4.42-4.45 (1H, m), 7.57 (1H, d, J=8.71 Hz), 10.83 (1H, br s).

(45c) cis(±)-2-(4-{[(5-Ethyl-4-trifluoromethyl-1H-imidazol-2-yl)carbonyl]amino}-3-ethoxypiperidin-1-yl)-4-methyl-1,3-thiazole-5-carboxylic acid The same operation as in Example (36g) was performed using ethyl cis(±)-2-(4-{[(5-ethyl-4-trifluoromethyl-1H-imidazol-2-yl)carbonyl]amino}-3-ethoxypiperidin-1-yl)-4-methyl-1,3-thiazole-5-carboxylate obtained in Example (45b) (178 mg, 0.35 mmol) and a 1 N aqueous sodium hydroxide solution (3 mL), to obtain 19.6 mg of the title compound as a white solid (12%).

$^1$H NMR spectrum (400 MHz, DMSO-d$_6$) δ ppm: 1.05 (3H, t, J=6.88 Hz), 1.16 (3H, t, J=7.53 Hz), 1.68-1.70 (1H, m), 1.85-1.89 (1H, m), 2.40 (3H, s), 2.70 (2H, q, J=7.53 Hz), 3.24-3.31 (2H, m), 3.41-3.45 (1H, m), 3.62-3.65 (2H, m), 3.96 (1H, br s), 4.19-4.21 (2H, m), 7.74 (1H, d, J=8.71 Hz), 12.40 (1H, br s).

mass spectrum (ESI): m/z 476 (M+H)$^+$.

Example 46 cis(±)-2-(4-{[(4-Chloro-5-propyl-1H-imidazol-2-yl)carbonyl]amino}-3-methoxypiperidin-1-yl)-4-methyl-1,3-thiazole-5-carboxylic acid (Exemplified Compound No. 46)

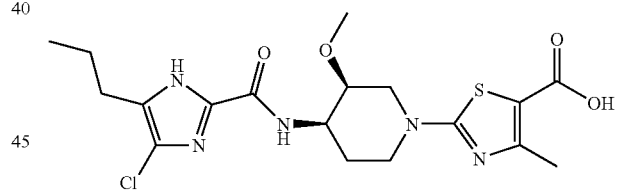

(46a) 1-Amino-pentan-2-one hydrochloride

The compound was synthesized according to the method described in the following document.

Eur. J. Med. Chem., 1987, 22, 283-292 (46b) Ethyl 5-propyl-1H-imidazole-2-carboxylate The same operation as in Example (lb) was performed using 1-amino-pentan-2-one hydrochloride obtained in Example (46a) (about 16.8 mmol) and ethyl imino(methylthio)acetate tetrafluoroborate obtained according to a method known in the literature (J. Med. Chem., 38, 1995, 2196-2201) (about 22.4 mmol), to obtain 2.61 g of the title compound as a brown foamy substance (86%).

$^1$H NMR spectrum (400 MHz, CDCl$_3$) δ ppm: 0.97 (3H, t, J=7.45 Hz), 1.42 (3H, t, J=7.14 Hz), 1.59-1.74 (2H, m), 2.64 (2H, t, J=7.45 Hz), 4.42 (2H, q, J=7.14 Hz), 6.96 (1H, s), 10.13 (1H, br s).

(46c) Ethyl 4-chloro-5-propyl-1H-imidazole-2-carboxylate

The same operation as in Example (1c) was performed using ethyl 5-propyl-1H-imidazole-2-carboxylate obtained in Example (46b) (1.01 g, 5.54 mmol) and NCS (0.74 g, 5.50 mmol), to obtain 876 mg of the title compound as a white solid (73%).

$^1$H NMR spectrum (400 MHz, CDCl$_3$) δ ppm: 0.97 (3H, t, J=7.34 Hz), 1.42 (3H, t, J=7.07 Hz), 1.66-1.70 (2H, m), 2.62-2.68 (2H, m), 4.42 (2H, q, J=7.07 Hz), 10.23 (1H, br s).

(46d) 4-Chloro-5-propyl-1H-imidazole-2-carboxylic acid

The same operation as in Example (1d) was performed using ethyl 4-chloro-5-propyl-1H-imidazole-2-carboxylate obtained in Example (46c) (0.40 g, 1.85 mmol) and a 3 N aqueous lithium hydroxide solution (8 mL), to obtain 0.32 g of the title compound as a white solid (100%).

(46e) tert-Butyl cis(±)-4-{[(4-chloro-5-propyl-1H-imidazol-2-yl)carbonyl]amino}-3-methoxypiperidine-1-carboxylate The same operation as in Example (1g) was performed using tert-butyl cis(±)-4-amino-3-methoxypiperidine-1-carboxylate obtained by the method described in Example (1e) (0.39 g, 1.69 mmol), 4-chloro-5-propyl-1H-imidazole-2-carboxylic acid obtained in Example (46d) (0.16 g, 0.85 mmol), WSC hydrochloride (0.50 g, 2.58 mmol) and HOBT (0.12 g, 0.87 mmol), to obtain 0.32 g of the title compound as a white foamy substance (94%).

$^1$H NMR spectrum (400 MHz, CDCl$_3$) δ ppm: 0.96 (3H, t, J=7.34 Hz), 1.47 (9H, s), 1.62-1.72 (3H, m), 1.83-1.85 (1H, m), 2.63 (2H, t, J=7.34 Hz), 2.73-2.78 (2H, m), 3.32-3.38 (1H, m), 3.41 (3H, s), 4.03-4.51 (3H, m), 7.41-7.50 (1H, m), 10.88 (1H, brs).

(46f) Ethyl cis(±)-2-(4-{[(4-chloro-5-propyl-1H-imidazol-2-yl)carbonyl]amino}-3-methoxypiperidin-1-yl)-4-methyl-1,3-thiazole-5-carboxylate The same operation as in Example (1h) was performed using tert-butyl cis(±)-4-{[(4-chloro-5-propyl-1H-imidazol-2-yl)carbonyl]amino}-3-methoxypiperidine-1-carboxylate obtained in Example (46e) (160 mg, 0.40 mmol), a 4 N hydrochloric acid/ethyl acetate solution (6 mL), diisopropylethylamine (0.28 mL, 1.61 mmol) and ethyl 2-bromo-4-methyl-1,3-thiazole-5-carboxylate (145 mg, 0.58 mmol), to obtain 118.9 mg of the title compound as a yellow solid (63%).

$^1$H NMR spectrum (400 MHz, CDCl$_3$) δ ppm: 0.96 (3H, t, J=7.34 Hz), 1.33 (3H, t, J=7.11 Hz), 1.65-1.69 (2H, m), 1.77-1.81 (1H, m), 2.00-2.06 (1H, m), 2.54 (3H, s), 2.64 (2H, t, J=7.34 Hz), 3.08-3.12 (1H, m), 3.16-3.25 (1H, m), 3.43 (3H, s), 3.50 (1H, br s), 3.98-4.02 (1H, m), 4.24-4.27 (3H, m), 4.50-4.53 (1H, m), 7.45 (1H, d, J=8.71 Hz), 10.71 (1H, br s).

(46g) cis(±)-2-(4-{[(4-Chloro-5-propyl-1H-imidazol-2-yl)carbonyl]amino}-3-methoxypiperidin-1-yl)-4-methyl-1,3-thiazole-5-carboxylic acid The same operation as in Example (1i) was performed using ethyl cis(±)-2-(4-{[(4-chloro-5-propyl-1H-imidazol-2-yl)carbonyl]amino}-3-methoxypiperidin-1-yl)-4-methyl-1,3-thiazole-5-carboxylate obtained in Example (46f) (115 mg, 0.24 mmol) and a 2 N aqueous lithium hydroxide solution (3 mL), to obtain 104.6 mg of the title compound as a white solid (97%).

$^1$H NMR spectrum (400 MHz, DMSO-d$_6$) δ ppm: 0.84 (3H, t, J=7.34 Hz), 1.56-1.60 (2H, m), 1.65-1.69 (1H, m), 1.80-1.99 (1H, m), 2.41 (3H, s), 2.50-2.53 (2H, m), 3.26-3.33 (2H, m), 3.34 (3H, s), 3.56 (1H, br s), 3.91-3.94 (1H, m), 4.20-4.23 (2H, m), 7.66 (1H, d, J=8.25 Hz), 12.40 (1H, br s).

mass spectrum (ESI): m/z 442 (M+H)$^+$.

Example 47 cis(±)-2-(4-{[(4-Chloro-5-ethyl-1H-imidazol-2-yl)carbonyl]amino}-3-propoxypiperidin-1-yl)-4-methyl-1,3-thiazole-5-carboxylic acid (Exemplified Compound No. 47)

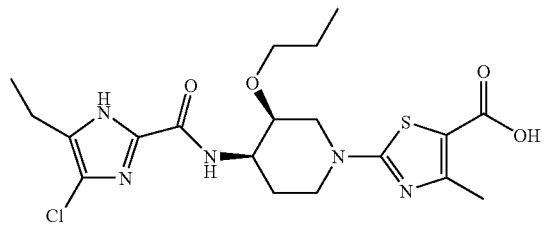

(47a) tert-Butyl cis(±)-4-{[(4-chloro-5-ethyl-1H-imidazol-2-yl)carbonyl]amino}-3-propoxypiperidine-1-carboxylate The same operation as in Example (1g) was performed using tert-butyl cis(±)-4-amino-3-propoxypiperidine-1-carboxylate obtained by the method described in Example (113d) (125.5 mg, 0.49 mmol), 4-chloro-5-ethyl-1H-imidazole-2-carboxylic acid obtained by the method described in Example (1d) (74 mg, 0.42 mmol), WSC hydrochloride (235 mg, 1.23 mmol) and HOBT (56 mg, 0.41 mmol), to obtain 145.6 mg of the title compound as a white foamy substance (83%).

$^1$H NMR spectrum (400 MHz, CDCl$_3$) δ ppm: 1.25-1.27 (6H, m), 1.47 (9H, s), 1.62-1.69 (1H, m), 1.86-1.88 (1H, m), 2.68 (3H, q, J=7.49 Hz), 2.77-2.81 (1H, m), 3.24-3.30 (1H, m), 3.40-3.49 (1H, m), 3.60-3.71 (1H, m), 4.08-4.51 (3H, m), 7.48 (1H, br s), 11.25 (1H, brs).

(47b) Ethyl cis(±)-2-(4-{[(4-chloro-5-ethyl-1H-imidazol-2-yl)carbonyl]amino}-3-propoxypiperidin-1-yl)-4-methyl-1,3-thiazole-5-carboxylate The same operation as in Example (1h) was performed using tert-butyl cis(±)-4-{[(4-chloro-5-ethyl-1H-imidazol-2-yl)carbonyl]amino}-3-propoxypiperidine-1-carboxylate obtained in Example (47a) (100 mg, 0.71 mmol), a 4 N hydrochloric acid/ethyl acetate solution (5 ml), diisopropylethylamine (0.2 mL, 1.15 mmol) and ethyl 2-bromo-4-methyl-1,3-thiazole-5-carboxylate (82 mg, 0.33 mmol), to obtain 92.0 mg of the title compound as a yellow foamy substance (79%).

$^1$H NMR spectrum (400 MHz, CDCl$_3$) δ ppm: 0.87 (3H, t, J=7.34 Hz), 1.27 (5H, t, J=7.60 Hz), 1.33 (3H, t, J=7.34 Hz), 1.49-1.61 (2H, m), 1.77-1.79 (1H, m), 2.01-2.13 (1H, m), 2.54 (3H, s), 2.69 (2H, q, J=7.60 Hz), 3.09-3.13 (1H, m), 3.19-3.22 (1H, m), 3.31-3.34 (1H, m), 3.62-3.67 (2H, m), 3.99-4.02 (1H, m), 4.20-4.30 (3H, m), 4.44-4.47 (1H, m), 7.49 (1H, d, J=8.71 Hz), 11.19 (1H, br s).

(47c) cis(±)-2-(4-{[(4-Chloro-5-ethyl-1H-imidazol-2-yl)carbonyl]amino}-3-propoxypiperidin-1-yl)-4-methyl-1,3-thiazole-5-carboxylic acid The same operation as in Example (1i) was performed using ethyl cis(±)-2-(4-{[(4-chloro-5-ethyl-1H-imidazol-2-yl)carbonyl]amino}-3-propoxypiperidin-1-yl)-4-methyl-1,3-thiazole-5-carboxylate obtained in Example (47b) (90 mg, 0.19 mmol) and a 2 N aqueous lithium hydroxide solution (3 mL), to obtain 28.2 mg of the title compound as a pale red solid (33%).

$^1$H NMR spectrum (400 MHz, DMSO-d$_6$) δ ppm: 0.81 (3H, t, J=7.57 Hz), 1.14 (3H, t, J=7.57 Hz), 1.42-1.46 (2H, m), 1.67-1.68 (1H, m), 1.83-1.89 (1H, m), 2.40 (3H, s), 2.51-2.59

(2H, m), 3.23-3.35 (3H, m), 3.54-3.57 (1H, m), 3.64 (1H, brs), 3.91-3.93 (1H, m), 4.17-4.19 (2H, m), 7.63 (1H, d, J=8.25 Hz), 12.39 (1H, br s).

mass spectrum (ESI): m/z 456 (M+H)+.

Example 48 cis(±)-3-(4-{[(5-Ethyl-4-trifluoromethyl-1H-imidazol-2-yl)carbonyl]amino}-3-ethoxypiperidin-1-yl)benzoic acid (Exemplified Compound No. 48)

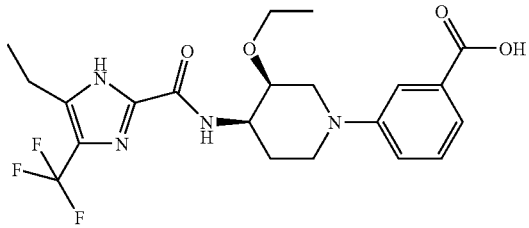

(48a) tert-Butyl cis(±)-4-{[(benzyloxy)carbonyl]amino}-3-ethoxypiperidine-1-carboxylate The same operation as in Example (40a) was performed using tert-butyl cis(±)-4-amino-3-ethoxypiperidine-1-carboxylate obtained by the method described in Example (112d) (0.5 g, 2.05 mmol) and benzyl chloroformate (0.5 mL, 3.50 mmol), to obtain 0.73 g of the title compound as a colorless oily substance (93%).

1H NMR spectrum (400 MHz, CDCl3) δ ppm: 1.15-1.16 (3H, m), 1.45 (9H, s), 1.61-1.77 (2H, m), 2.73-2.75 (2H, m), 3.32-3.45 (2H, m), 3.71-3.74 (2H, m), 4.09-4.28 (2H, m), 5.10 (2H, s), 5.23 (1H, br s), 7.32-7.38 (5H, m).

(48b) Benzyl cis(±)-3-ethoxypiperidin-4-yl)-carbamate

The same operation as in Example (40b) was performed using tert-butyl cis(±)-4-{[(benzyloxy)carbonyl]amino}-3-ethoxypiperidine-1-carboxylate obtained in Example (48a) (0.72 g, 1.90 mmol) and a 4 N hydrochloric acid/ethyl acetate solution (15 mL), to obtain the title compound. The resulting compound was used for the next reaction without purification.

(48c) Methyl cis(±)-3-(4-{[(benzyloxy)carbonyl]amino}-3-ethoxypiperidin-1-yl)benzoate The same operation as in Example (42a) was performed using benzyl cis(±)-(3-ethoxypiperidin-4-yl)-carbamate obtained in Example (48b) (about 1.90 mmol), palladium acetate (46 mg, 0.20 mmol), BINAP (240 mg, 0.39 mmol) and cesium carbonate (1.36 g, 4.17 mmol), to obtain 0.22 g of the title compound as a yellow oily substance (30%).

1H NMR spectrum (400 MHz, CDCl3) δ ppm: 1.15 (3H, t, J=7.11 Hz), 1.83-1.87 (1H, m), 2.00-2.03 (1H, m), 2.92-2.95 (2H, m), 3.43-3.46 (1H, m), 3.59-3.72 (3H, m), 3.82-3.84 (2H, m), 3.90 (3H, s), 5.12 (2H, s), 5.21-5.29 (1H, m), 7.10 (1H, dd, J=8.25, 1.83 Hz), 7.25-7.40 (6H, m), 7.46-7.51 (1H, m), 7.56-7.59 (1H, m).

(48d) tert-Butyl cis(±)-3-(4-{[(benzyloxy)carbonyl]amino}-3-ethoxypiperidin-1-yl)benzoate The same operation as in Example (42b) was performed using methyl cis(±)-3-(4-{[(benzyloxy)carbonyl]amino}-3-ethoxypiperidin-1-yl)benzoate obtained in Example (48c) (220 mg, 0.53 mmol) and a 1 N aqueous sodium hydroxide solution (4 mL). The resulting compound was used for the next reaction without purification.

The same operation as in Example (42c) was performed using cis(±)-3-(4-{[(benzyloxy)carbonyl]amino}-3-ethoxypiperidin-1-yl)benzoic acid obtained by the above operation and N,N-dimethylformamide di-tert-butylacetal (1 mL), to obtain 102.2 mg of the title compound as a yellow oily substance (42%).

1H NMR spectrum (400 MHz, CDCl3) δ ppm: 1.16 (3H, t, J=6.88 Hz), 1.58 (9H, s), 1.83-1.87 (1H, m), 1.99-2.03 (1H, m), 2.90-2.93 (2H, m), 3.43-3.47 (1H, m), 3.56-3.60 (2H, m), 3.67-3.71 (1H, m), 3.79-3.82 (2H, m), 5.12 (2H, s), 5.25 (1H, d, J=8.25 Hz), 7.04-7.10 (1H, m), 7.23-7.40 (6H, m), 7.43-7.45 (1H, m), 7.53-7.56 (1H, m).

(48e) tert-Butyl cis(±)-3-(4-amino-3-ethoxypiperidin-1-yl)benzoate

The same operation as in Example (40e) was performed using tert-butyl cis(±)-3-(4-{[(benzyloxy)carbonyl]amino}-3-ethoxypiperidin-1-yl)benzoate obtained in Example (48d) (100 mg, 0.22 mmol) and a 10% palladium-carbon catalyst (40 mg) to obtain the title compound. The resulting compound was used for the next reaction without purification.

(48f) tert-Butyl cis(±)-3-(4-{[(5-Ethyl-4-trifluoromethyl-1H-imidazol-2-yl)carbonyl]amino}-3-ethoxypiperidin-1-yl)benzoate The same operation as in Example (1g) was performed using tert-butyl cis(±)-3-(4-amino-3-ethoxypiperidin-1-yl)benzoate obtained in Example (48e) (about 0.22 mmol), 5-ethyl-4-(trifluoromethyl)-1H-imidazole-2-carboxylic acid obtained by the method described in Example (39e) (40 mg, 0.19 mmol), WSC hydrochloride (120 mg, 0.63 mmol) and HOBT (40 mg, 0.30 mmol), to obtain 81.0 mg of the title compound (83%).

1H NMR spectrum (400 MHz, CDCl3) δ ppm: 1.22 (3H, t, J=6.88 Hz), 1.30 (3H, t, J=7.53 Hz), 1.59 (9H, s), 1.85-1.89 (1H, m), 2.15-2.21 (1H, m), 2.85 (2H, q, J=7.53 Hz), 2.93-2.97 (2H, m), 3.45-3.53 (1H, m), 3.70-3.74 (3H, m), 3.91-3.94 (1H, m), 4.18-4.25 (1H, m), 7.10 (1H, dd, J=8.25, 2.75 Hz), 7.27-7.30 (1H, m), 7.46 (1H, d, J=7.34 Hz), 7.58 (1H, s), 7.66 (1H, d, J=8.71 Hz), 11.43 (1H, brs).

(48g) cis(±)-3-(4-{[(5-Ethyl-4-trifluoromethyl-1H-imidazol-2-yl)carbonyl]amino}-3-ethoxypiperidin-1-yl)benzoic acid The same operation as in Example (42f) was performed using tert-butyl cis(±)-3-(4-{[(5-ethyl-4-trifluoromethyl-1H-imidazol-2-yl)carbonyl]amino}-3-ethoxypiperidin-1-yl)benzoate obtained in Example (48f) (80 mg, 0.16 mmol) and trifluoroacetic acid (1 ml), to obtain 61.1 mg of the title compound (86%).

1H NMR spectrum (400 MHz, DMSO-d6) δ ppm: 1.04 (3H, t, J=7.11 Hz), 1.16 (3H, t, J=7.49 Hz), 1.72-1.74 (1H, m), 1.93-2.00 (1H, m), 2.70 (2H, q, J=7.49 Hz), 2.96-2.99 (2H, m), 3.41-3.48 (1H, m), 3.58-3.66 (3H, m), 3.92-3.95 (1H, m), 4.13-4.17 (1H, m), 7.19-7.24 (1H, m), 7.30-7.31 (2H, m), 7.45 (1H, s), 7.68 (1H, d, J=8.25 Hz).

mass spectrum (ESI): m/z 455 (M+H)+.

Example 49 cis(±)-2-(4-{[(4-Chloro-5-ethyl-1H-imidazol-2-yl)carbonyl]amino}-3-methoxypiperidin-1-yl)-4-(methoxyimino)methyl-1,3-thiazole-5-carboxylic acid (Exemplified Compound No. 49)

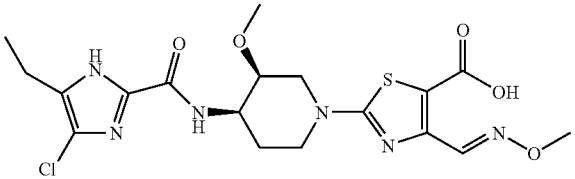

(49a) Ethyl cis(±)-2-(4-{[(4-chloro-5-ethyl-1H-imidazol-2-yl)carbonyl]amino}-3-methoxypiperidin-1-yl)-4-(methoxyimino)methyl-1,3-thiazole-5-carboxylate Ethyl cis(±)-2-(4-{[(4-chloro-5-ethyl-1H-imidazol-2-yl)carbonyl]amino}-3-methoxypiperidin-1-yl)-4-formyl-1,3-thiazole-5-carboxylate obtained by the method described in Example (28a) (100 mg, 0.21 mmol) was dissolved in pyridine (3 mL). Methoxyamine hydrochloride (28 mg, 0.34 mmol) was added, and the mixture was stirred at 60° C. for two hours. The reaction solution was concentrated under reduced pressure, diluted with ethyl acetate, washed with 1 N hydrochloric acid and brine, and dried over anhydrous sodium sulfate. Following concentration under reduced pressure, the residue was purified by silica gel column chromatography (elution solvent: hexane/ethyl acetate=4/1, ethyl acetate) to obtain 107 mg of the title compound (100%).

$^1$H NMR spectrum (400 MHz, CDCl$_3$) δ ppm: 1.27 (5H, t, J=7.60 Hz), 1.35 (3H, t, J=7.11 Hz), 1.76-1.83 (1H, m), 2.04-2.09 (3H, m), 2.69 (2H, q, J=7.60 Hz), 3.17-3.27 (2H, m), 3.43 (3H, s), 3.52 (1H, brs), 4.03 (3H, s), 4.10-4.19 (1H, m), 4.21-4.35 (3H, m), 4.44-4.48 (1H, m), 7.47 (1H, d, J=8.71 Hz), 8.82 (1H, s), 11.15 (1H, br s).

(49b) cis(±)-2-(4-{[(4-Chloro-5-ethyl-1H-imidazol-2-yl)carbonyl]amino}-3-methoxypiperidin-1-yl)-4-(methoxyimino)methyl-1,3-thiazole-5-carboxylic acid The same operation as in Example (1i) was performed using ethyl cis(±)-2-(4-{[(4-chloro-5-ethyl-1H-imidazol-2-yl)carbonyl]amino}-3-methoxypiperidin-1-yl)-4-(methoxyimino)methyl-1,3-thiazole-5-carboxylate obtained in Example (49a) (107 mg, 0.21 mmol) and a 2 N aqueous lithium hydroxide solution (2.5 mL), to obtain 82.3 mg of the title compound as a pale yellow solid (83%).

$^1$H NMR spectrum (400 MHz, DMSO-d$_6$) δ ppm: 1.14 (3H, t, J=7.60 Hz), 1.68-1.70 (1H, m), 1.83-1.93 (1H, m), 2.55 (2H, q, J=7.60 Hz), 3.29-3.31 (2H, m), 3.35 (3H, s), 3.58 (1H, br s), 3.91 (3H, s), 3.97-4.11 (1H, m), 4.21-4.23 (2H, m), 7.69 (1H, d, J=8.25 Hz), 8.68 (1H, s).

mass spectrum (ESI): m/z 471 (M+H)$^+$.

Example 50 cis(±)-2-(4-{[(4-Chloro-5-ethyl-1H-imidazol-2-yl)carbonyl]amino}-3-methoxypiperidin-1-yl)-5-(ethoxycarbonyl)-1,3-thiazole-4-carboxylic acid (Exemplified Compound No. 50)

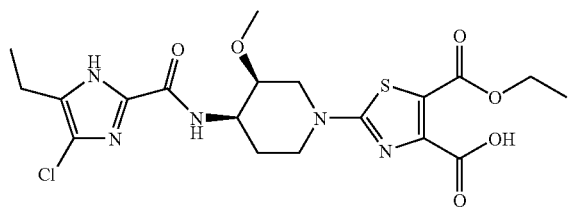

(50a) cis(±)-2-(4-{[(4-Chloro-5-ethyl-1H-imidazol-2-yl)carbonyl]amino}-3-methoxypiperidin-1-yl)-5-(ethoxycarbonyl)-1,3-thiazole-4-carboxylic acid The same operation as in Example (33c) was performed using ethyl cis(±)-2-(4-{[(4-chloro-5-ethyl-1H-imidazol-2-yl)carbonyl]amino}-3-methoxypiperidin-1-yl)-4-formyl-1,3-thiazole-5-carboxylate obtained by the method described in Example (28a) (400 mg, 0.85 mmol), sodium chlorite (158 mg, 1.75 mmol), sodium dihydrogenphosphate (410 mg, 2.63 mmol) and 2-methyl-2-butene (0.55 mL, 5.20 mmol), to obtain 439 mg of the title compound (100%).

$^1$H NMR spectrum (400 MHz, DMSO-d$_6$) δ ppm: 1.14 (3H, t, J=7.57 Hz), 1.22 (3H, t, J=7.11 Hz), 1.62-1.70 (1H, m), 1.84-1.90 (1H, m), 2.51-2.58 (2H, m), 3.33 (3H, s), 3.34-3.40 (2H, m), 3.57 (1H, br s), 3.96-4.03 (1H, m), 4.14-4.36 (4H, m), 7.69 (1H, d, J=8.71 Hz).

mass spectrum (ESI): m/z 486 (M+H)$^+$

Example 51 cis(±)-2-(4-{[(4-Methoxymethyl-5-methyl-1H-imidazol-2-yl)carbonyl]amino}-3-methoxypiperidin-1-yl)-4-methyl-1,3-thiazole-5-carboxylic acid and cis (±)-2-(4-{[(5-methoxymethyl-4-methyl-1H-imidazol-2-yl)carbonyl]amino}-3-methoxypiperidin-1-yl)-4-methyl-1,3-thiazole-5-carboxylic acid (Exemplified Compound No. 51)

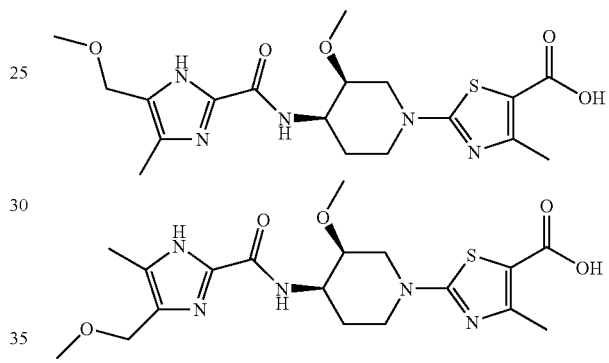

(51a) 4-({[tert-Butyl(dimethyl)silyl]oxy}methyl)-5-methyl-1H-imidazole 4-(Hydroxymethyl)-5-methyl-1H-imidazole (4 g, 26.9 mmol) was dissolved in DMF (80 mL). Triethylamine (13.5 mL, 96.9 mmol) and tert-butyl(dimethyl)silyl chloride (4.68 g, 31.0 mmol) were added, followed by stirring for three hours. Ethyl acetate was added to the reaction solution, and the organic layer was washed with brine and dried over anhydrous sodium sulfate. Following concentration under reduced pressure, the residue was purified by silica gel column chromatography (elution solvent: hexane/ethyl acetate=4/1, dichloromethane/methanol=92/8) to obtain 4.67 g of the title compound (77%).

$^1$H NMR spectrum (400 MHz, CDCl$_3$) δ ppm: 0.08 (6H, s), 0.91 (9H, s), 2.23 (3H, s), 4.67 (2H, s), 7.48 (1H, s).

(51b) 4-({[tert-Butyl(dimethyl)silyl]oxy}methyl)-5-methyl-1-{[2-(trimethylsilyl)ethoxy]methyl}-1H-imidazole and 5-({[tert-butyl(dimethyl)silyl]oxy}methyl)-4-methyl-1-{[2-(trimethylsilyl)ethoxy]methyl}-1H-imidazole 4-({[tert-Butyl(dimethyl)silyl]oxy}methyl)-5-methyl-1H-imidazole obtained in Example (51a) obtained in Example (51a) (4.67 g, 20.6 mmol) was dissolved in THF (120 mL), followed by cooling to 0° C. Then, sodium hydride (1.5 g, 34.4 mmol) and [2-(trimethylsilyl)ethoxy]methyl chloride (5 mL, 28.3 mmol) were added, and the mixture was heated to room temperature and stirred for four hours. Brine was added to the reaction solution, followed by extraction with ethyl acetate. The organic layer was washed with brine and dried over anhydrous sodium sulfate. Following concentration under reduced pressure, the residue was purified by silica gel column chromatography (elution solvent: hexane/ethyl acetate=9/1, 4/6) to obtain 2.57 g of the title compound as a yellow oily substance and as an about 3:2 mixture (35%).

$^1$H NMR spectrum (400 MHz, CDCl$_3$) δ ppm: −0.04 (9H, s), −0.02 (6×3/5H, s), 0.00-0.01 (2H, m), 0.07 (6×2/5H, s), 0.87 (9×3/5H, s), 0.89 (9×2/5H, s), 2.19 (3×3/5H, s), 2.26 (3×2/5H, s), 3.41-3.52 (2H, m), 4.63 (2×2/5H, s), 4.66 (2×3/5H, s), 5.15 (2×2/5H, s), 5.29 (2×3/5H, s), 7.40 (1×2/5H, s), 7.43 (1×3/5H, s).

(51c) Ethyl 4-({[tert-butyl(dimethyl)silyl]oxy}methyl)-5-methyl-1-{[2-(trimethylsilyl)ethoxy]methyl}-1H-imidazole-2-carboxylate and ethyl 5-({[tert-butyl(dimethyl)silyl]oxy}methyl)-4-methyl-1-{[2-(trimethylsilyl)ethoxy]methyl}-1H-imidazole-2-carboxylate The same operation as in Example (4b) was performed using the mixture of 4-({[tert-butyl(dimethyl)silyl]oxy}methyl)-5-methyl-1-{[2-(trimethylsilyl)ethoxy]methyl}-1H-imidazole and 5-({[tert-butyl(dimethyl)silyl]oxy}methyl)-4-methyl-1-{[2-(trimethylsilyl)ethoxy]methyl}-1H-imidazole obtained in Example (51b) (2.57 g, 7.21 mmol), n-butyllithium (1.57 M solution in hexane, 5.5 mL, 8.64 mmol) and ethyl chloroformate (0.8 mL, 8.37 mmol), to obtain 1.95 g of the title compound as a yellow oily substance and as an about 3:2 mixture (63%).

$^1$H NMR spectrum (400 MHz, CDCl$_3$) δ ppm: −0.03 (9H, s), 0.02-0.04 (2H, m), 0.08 (6×1/2H, s), 0.08 (6×1/2H, s), 0.89 (9×1/2H, s), 0.90 (9×1/2H, s), 1.36-1.44 (3H, m), 2.27 (3×1/2H, s), 2.38 (3×1/2H, s), 3.50-3.64 (2H, m), 4.34-4.48 (2H, m), 4.73 (2H, s), 5.80 (2×1/2H, s), 5.92 (2×1/2H, s).

(51d) Ethyl 4-(hydroxymethyl)-5-methyl-1-{[2-(trimethylsilyl)ethoxy]methyl}-1H-imidazole-2-carboxylate and ethyl 5-(hydroxymethyl)-4-methyl-1-{[2-(trimethylsilyl)ethoxy]methyl}-1H-imidazole-2-carboxylate The mixture of ethyl 4-({[tert-butyl(dimethyl)silyl]oxy}methyl)-5-methyl-1-{[2-(trimethylsilyl)ethoxy]methyl}-1H-imidazole-2-carboxylate and ethyl 5-({[tert-butyl(dimethyl)silyl]oxy}methyl)-4-methyl-1-{[2-(trimethylsilyl)ethoxy]methyl}-1H-imidazole-2-carboxylate obtained in Example (51c) (1.95 g, 4.54 mmol) was dissolved in THF (40 mL). Tetrabutylammonium fluoride (1.0 M solution in THF, 5 mL) was added, followed by stirring for one hour. Ethyl acetate was added to the reaction solution, and the organic layer was washed with brine and dried over anhydrous sodium sulfate. Following concentration under reduced pressure, the residue was purified by silica gel column chromatography (elution solvent: hexane/ethyl acetate=4/1, 4/6, ethyl acetate) to obtain 517.4 mg of the title compound (36%) and 421.9 mg of the title compound (30%).

$^1$H NMR spectrum (400 MHz, CDCl$_3$) δ ppm: −0.02 (9H, s), 0.89-0.94 (2H, m), 1.43 (3H, t, J=7.07 Hz), 2.32 (3H, s), 2.93 (1H, t, J=6.08 Hz), 3.59-3.62 (2H, m), 4.43 (2H, q, J=7.07 Hz), 4.64 (2H, d, J=6.08 Hz), 5.96 (2H, s).
−0.03 (9H, s), 0.85-0.97 (3H, m), 1.43 (3H, t, J=7.03 Hz), 2.36 (3H, s), 3.53-3.64 (2H, m), 4.43 (2H, q, J=7.03 Hz), 4.60-4.65 (2H, m), 5.81 (2H, s).

(51e) Ethyl 4 (or 5)-(methoxymethyl)-5 (or 4)-methyl-1-{[2-(trimethylsilyl)ethoxy]methyl}-1H-imidazole-2-carboxylate Ethyl 4 (or 5)-(hydroxymethyl)-5 (or 4)-methyl-1-{[2-(trimethylsilyl)ethoxy]methyl}-1H-imidazole-2-carboxylate obtained in Example (51d) (515 mg, 1.64 mmol) was dissolved in DMF (12 mL), followed by cooling to 0° C. Then, sodium hydride (1.5 g, 34.4 mmol) and iodomethane (0.3 mL, 4.82 mmol) were added, and the mixture was stirred for two hours. Brine was added to the reaction solution, followed by extraction with ethyl acetate. The organic layer was washed with brine and dried over anhydrous sodium sulfate. Following concentration under reduced pressure, the residue was purified by silica gel column chromatography (elution solvent: hexane/ethyl acetate=1/1, ethyl acetate) to obtain 285.3 mg of the title compound as a yellow oily substance (53%).

$^1$H NMR spectrum (400 MHz, CDCl$_3$) δ ppm: −0.03 (9H, s), 0.85-0.95 (2H, m), 1.42 (3H, t, J=7.14 Hz), 2.30 (3H, s), 3.33 (3H, s), 3.53-3.59 (2H, m), 4.42 (2H, q, J=7.14 Hz), 4.52 (2H, s), 5.88 (2H, s).

(51f) Ethyl 4-(methoxymethyl)-5-methyl-1H-imidazole-2-carboxylate

Ethyl 4 (or 5)-(methoxymethyl)-5 (or 4)-methyl-1-{[2-(trimethylsilyl)ethoxy]methyl}-1H-imidazole-2-carboxylate obtained in Example (51e) (285 mg, 0.87 mmol) was dissolved in methanol (2 mL). A 4 N hydrochloric acid/ethyl acetate solution (5 mL) was added, and the mixture was stirred at 50° C. for one hour. The reaction solution was concentrated under reduced pressure, and ethyl acetate was added, and the organic layer was washed with saturated aqueous sodium bicarbonate solution, and dried over anhydrous sodium sulfate. Following concentration under reduced pressure, the residue was purified by silica gel column chromatography (elution solvent: hexane/ethyl acetate=4/1, 1/1, ethyl acetate) to obtain 145.6 mg of the title compound (53%).

$^1$H NMR spectrum (400 MHz, CDCl$_3$) δ ppm: 1.40 (3H, t, J=7.11 Hz), 2.36 (3H, s), 3.37 (3H, s), 4.35-4.52 (4H, m), 10.64 (1H, br s).

(51g) 4-(Methoxymethyl)-5-methyl-1H-imidazole-2-carboxylic acid

The same operation as in Example (1d) was performed using ethyl 4-(methoxymethyl)-5-methyl-1H-imidazole-2-carboxylate obtained in Example (51f) (145.6 mg, 0.73 mmol) and a 2 N aqueous lithium hydroxide solution (2 mL), to obtain 109.9 mg of the title compound as a white solid (88%).

mass spectrum (ESI): m/z 171 (M+H)$^+$.

(51h) tert-Butyl cis(±)-3-methoxy-4-{[(4-methoxymethyl-5-methyl-1H-imidazol-2-yl)carbonyl]amino}piperidine-1-carboxylate and tert-butyl cis(±)-3-methoxy-4-{[(5-methoxymethyl-4-methyl-1H-imidazol-2-yl)carbonyl]amino}piperidine-1-carboxylate The same operation as in Example (1g) was performed using tert-butyl cis(±)-4-amino-3-methoxypiperidine-1-carboxylate obtained by the method described in Example (1e) (320 mg, 1.39 mmol), 4-(methoxymethyl)-5-methyl-1H-imidazole-2-carboxylic acid obtained in Example (51g) (109.9 mg, 0.65 mmol), WSC hydrochloride (0.38 g, 1.98 mmol) and HOBT (85 mg, 0.63 mmol), to obtain 283.1 mg of the title compound (100%).

mass spectrum (ESI): m/z 383 (M+H)$^+$.

(51i) Ethyl cis(±)-2-(4-{[(4-methoxymethyl-5-methyl-1H-imidazol-2-yl)carbonyl]amino}-3-methoxypiperidin-1-yl)-4-methyl-1,3-thiazole-5-carboxylate and ethyl cis(±)-2-(4-{[(5-methoxymethyl-4-methyl-1H-imidazol-2-yl)carbonyl]amino}-3-methoxypiperidin-1-yl)-4-methyl-1,3-thiazole-5-carboxylate The same operation as in Example (1h) was performed using the mixture of tert-butyl cis(±)-3-methoxy-4-{[(4-methoxymethyl-5-methyl-1H-imidazol-2-yl)carbonyl]amino}piperidine-1-carboxylate and tert-butyl cis(±)-3-methoxy-4-{[(5-methoxymethyl-4-methyl-1H-imidazol-2-yl)carbonyl]amino}piperidine-1-carboxylate obtained in Example (51h) (283 mg, 0.65 mmol), a 4 N hydrochloric acid/ethyl acetate solution (6 mL), diisopropylethylamine (0.8 mL, 4.60 mmol) and ethyl 2-bromo-4-methyl-1,3-thiazole-5-carboxylate (258 mg, 1.03 mmol), to obtain 278.9 mg of the title compound as a yellow foamy substance (96%).

¹H NMR spectrum (400 MHz, CDCl₃) δ ppm: 1.26-1.36 (3H, m), 1.78-1.81 (1H, m), 2.02-2.06 (1H, m), 2.33 (3H, s), 2.54 (3H, s), 3.33-3.36 (1H, m), 3.41-3.45 (6H, m), 3.52 (1H, br s), 3.96-4.04 (1H, m), 4.23-4.29 (3H, m), 4.36-4.39 (2H, m), 4.43-4.55 (2H, m), 7.45-7.56 (1H, m), 10.48-10.59 (1H, m).

(51j) cis(±)-2-(4-{[(4-Methoxymethyl-5-methyl-1H-imidazol-2-yl)carbonyl]amino}-3-methoxypiperidin-1-yl)-4-methyl-1,3-thiazole-5-carboxylic acid and cis(±)-2-(4-{[(5-methoxymethyl-4-methyl-1H-imidazol-2-yl)carbonyl]amino}-3-methoxypiperidin-1-yl)-4-methyl-1,3-thiazole-5-carboxylic acid The same operation as in Example (1i) was performed using the mixture of ethyl cis(±)-2-(4-{[(4-methoxymethyl-5-methyl-1H-imidazol-2-yl)carbonyl]amino}-3-methoxypiperidin-1-yl)-4-methyl-1,3-thiazole-5-carboxylate and ethyl cis(±)-2-(4-{[(5-methoxymethyl-4-methyl-1H-imidazol-2-yl)carbonyl]amino}-3-methoxypiperidin-1-yl)-4-methyl-1,3-thiazole-5-carboxylate obtained in Example (51i) (278 mg, 0.62 mmol) and a 2 N aqueous lithium hydroxide solution (4.5 mL), to obtain 191.4 mg of the title compound as a white solid and as an about 3:1 tautomer mixture (73%).

¹H NMR spectrum (400 MHz, DMSO-d₆) δ ppm: 1.62-1.67 (1H, m), 1.78-1.84 (1H, m), 2.13-2.22 (3H, m), 2.34 (3H, s), 3.06-3.11 (2H, m), 3.17-3.22 (3H, m), 3.34 (3H, s), 3.51 (1H, br s), 3.76-3.85 (1H, m), 4.13-4.16 (2H, m), 4.24 (2×3/4H, s), 4.32 (2×1/4H, s), 7.50-7.55 (1H, m).

mass spectrum (ESI): m/z 424 (M+H)⁺.

Example 52 cis(±)-2-(4-{[(4-Chloro-5-ethyl-1H-imidazol-2-yl)carbonyl]amino}-3-methoxypiperidin-1-yl)-4-(methylcarbamoyl)-1,3-thiazole-5-carboxylic acid (Exemplified Compound No. 52)

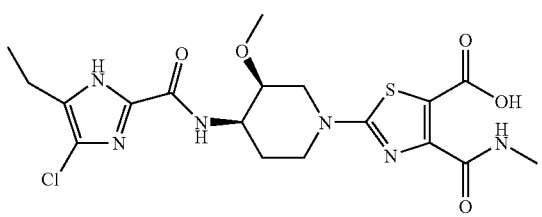

(52a) Ethyl cis(±)-2-(4-{[(4-chloro-5-ethyl-1H-imidazol-2-yl)carbonyl]amino}-3-methoxypiperidin-1-yl)-4-(methylcarbamoyl)-1,3-thiazole-5-carboxylate The same operation as in Example (1g) was performed using cis(±)-2-(4-{[(4-chloro-5-ethyl-1H-imidazol-2-yl)carbonyl]amino}-3-methoxypiperidin-1-yl)-5-(ethoxycarbonyl)-1,3-thiazole-4-carboxylic acid obtained by the method described in Example (50a) (100 mg, 0.21 mmol), methylamine hydrochloride (35 mg, 0.52 mmol), WSC hydrochloride (120 mg, 0.63 mmol) and HOBT (28 mg, 0.21 mmol), to obtain 84.2 mg of the title compound as a white solid (82%).

¹H NMR spectrum (400 MHz, DMSO-d₆) δ ppm: 1.14 (3H, t, J=7.60 Hz), 1.21 (3H, t, J=7.11 Hz), 1.67-1.69 (1H, m), 1.82-1.88 (1H, m), 2.55 (2H, q, J=7.60 Hz), 2.69 (3H, d, J=4.58 Hz), 3.32-3.33 (2H, m), 3.33 (3H, s), 3.57 (1H, br s), 3.97-4.24 (4H, m), 7.67 (1H, d, J=8.71 Hz), 8.32 (1H, q, J=4.58 Hz).

(52b) cis(±)-2-(4-{[(4-Chloro-5-ethyl-1H-imidazol-2-yl)carbonyl]amino}-3-methoxypiperidin-1-yl)-4-(methylcarbamoyl)-1,3-thiazole-5-carboxylic acid The same operation as in Example (1i) was performed using ethyl cis(±)-2-(4-{[(4-chloro-5-ethyl-1H-imidazol-2-yl)carbonyl]amino}-3-methoxypiperidin-1-yl)-4-(methylcarbamoyl)-1,3-thiazole-5-carboxylate obtained in Example (52a) (82 mg, 0.16 mmol) and a 2 N aqueous lithium hydroxide solution (3 mL), to obtain 66.7 mg of the title compound as a pale yellow solid (86%). This compound is estimated to be an about 6:1 rotamer mixture according to NMR and HPLC.

¹H NMR spectrum (400 MHz, DMSO-d₆) δ ppm: 1.14 (3H, t, J=7.11 Hz), 1.64-1.75 (1H, m), 1.83-1.96 (1H, m), 2.52-2.59 (2H, m), 2.75-2.91 (2H, m), 3.35 (3H, s), 3.36-3.42 (2H, m), 3.59 (1H, br s), 4.05-4.28 (3H, m), 7.65-7.73 (1H, m), 9.33-9.42 (1H, m).

mass spectrum (ESI): m/z 471 (M+H)⁺.

Example 53 cis(±)-2-(4-{[(4-Chloro-5-ethyl-1H-imidazol-2-yl)carbonyl]amino}-3-methoxypiperidin-1-yl)-4-[(methoxyethyl)carbamoyl]-1,3-thiazole-5-carboxylic acid (Exemplified Compound No. 53)

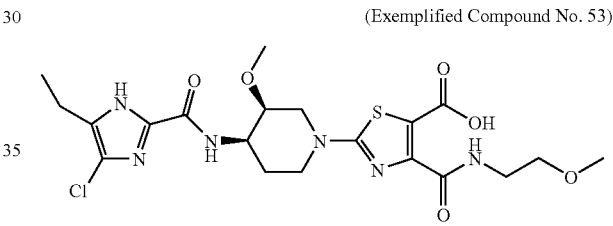

(53a) Ethyl cis(±)-2-(4-{[(4-chloro-5-ethyl-1H-imidazol-2-yl)carbonyl]amino}-3-methoxypiperidin-1-yl)-4-[(methoxyethyl)carbamoyl]-1,3-thiazole-5-carboxylate The same operation as in Example (1g) was performed using cis(±)-2-(4-{[(4-chloro-5-ethyl-1H-imidazol-2-yl)carbonyl]amino}-3-methoxypiperidin-1-yl)-5-(ethoxycarbonyl)-1,3-thiazole-4-carboxylic acid obtained by the method described in Example (50a) (120 mg, 0.25 mmol), methoxyethylamine (45 µL, 0.52 mmol), WSC hydrochloride (120 mg, 0.63 mmol) and HOBT (35 mg, 0.26 mmol), to obtain 117.9 mg of the title compound as a white solid (88%).

¹H NMR spectrum (400 MHz, CDCl₃) δ ppm: 1.26 (3H, t, J=7.53 Hz), 1.34 (3H, t, J=7.11 Hz), 1.79-1.81 (1H, m), 1.93-2.25 (1H, m), 2.69 (2H, q, J=7.53 Hz), 3.12-3.15 (1H, m), 3.22-3.25 (1H, m), 3.39 (3H, s), 3.43 (3H, s), 3.52 (1H, br s), 3.60-3.64 (4H, m), 4.02-4.05 (1H, m), 4.22-4.34 (3H, m), 4.54-4.57 (1H, m), 7.47 (1H, d, J=8.71 Hz), 8.46 (1H, br s), 11.30 (1H, br s).

(53b) cis(±)-2-(4-{[(4-Chloro-5-ethyl-1H-imidazol-2-yl)carbonyl]amino}-3-methoxypiperidin-1-yl)-4-[(methoxyethyl)carbamoyl]-1,3-thiazole-5-carboxylic acid The same operation as in Example (1i) was performed using ethyl cis(±)-2-(4-{[(4-chloro-5-ethyl-1H-imidazol-2-yl)carbonyl]amino}-3-methoxypiperidin-1-yl)-4-[(methoxyethyl)carbamoyl]-1,3-thiazole-5-carboxylate obtained in Example (53a) (115 mg, 0.21 mmol) and a 2 N aqueous lithium hydroxide solution (2.5 mL), to obtain 60.9 mg of the title compound as a pale yellow solid (56%).

¹H NMR spectrum (400 MHz, DMSO-d₆) δ ppm: 1.14 (3H, t, J=7.57 Hz), 1.66-1.75 (1H, m), 1.83-1.96 (1H, m), 2.52-2.60 (2H, m), 3.26 (3H, s), 3.30-3.40 (4H, m), 3.36 (3H, s), 3.49-3.51 (4H, m), 3.59 (1H, br s), 4.22-4.24 (1H, m), 7.70 (1H, d, J=8.25 Hz), 9.36 (1H, br s).

mass spectrum (ESI): m/z 516 (M+H)⁺.

Example 54 cis(±)-2-(4-{[(4-Chloro-5-ethyl-1H-imidazol-2-yl)carbonyl]amino}-3-propoxypiperidin-1-yl)-1,3-benzothiazole-7-carboxylic acid (Exemplified Compound No. 54)

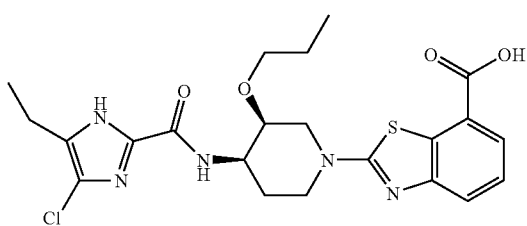

(54a) Ethyl cis(±)-2-(4-{[(4-chloro-5-ethyl-1H-imidazol-2-yl)carbonyl]amino}-3-propoxypiperidin-1-yl)-1,3-benzothiazole-7-carboxylate The same operation as in Example (1h) was performed using tert-butyl cis(±)-4-{[(4-chloro-5-ethyl-1H-imidazol-2-yl)carbonyl]amino}-3-propoxypiperidine-1-carboxylate obtained by the method described in Example (47a) (208.6 mg, 0.50 mmol), a 4 N hydrochloric acid/ethyl acetate solution (5 mL), diisopropylethylamine (0.35 mL, 2.01 mmol) and ethyl 2-bromo-1,3-benzothiazole-7-carboxylate obtained by the method described in Example (1f) (200 mg, 0.70 mmol), to obtain 199.6 mg of the title compound as a yellow oily substance (76%).

¹H NMR spectrum (400 MHz, CDCl₃) δ ppm: 0.82 (3H, t, J=7.34 Hz), 1.27 (3H, t, J=7.57 Hz), 1.44 (3H, t, J=7.11 Hz), 1.51-1.57 (2H, m), 1.82-1.85 (1H, m), 2.11-2.17 (1H, m), 2.70 (2H, q, J=7.64 Hz), 3.24-3.38 (3H, m), 3.64 (1H, br s), 3.67-3.75 (1H, m), 4.23-4.33 (2H, m), 4.45 (2H, q, J=7.18 Hz), 4.53-4.56 (1H, m), 7.35-7.37 (1H, m), 7.49 (1H, d, J=8.71 Hz), 7.69 (1H, d, J=7.79 Hz), 7.79 (1H, d, J=7.79 Hz), 10.83 (1H, br s).

(54b) cis(±)-2-(4-{[(4-Chloro-5-ethyl-1H-imidazol-2-yl)carbonyl]amino}-3-propoxypiperidin-1-yl)-1,3-benzothiazole-7-carboxylic acid The same operation as in Example (1i) was performed using ethyl cis(±)-2-(4-{[(4-chloro-5-ethyl-1H-imidazol-2-yl)carbonyl]amino}-3-propoxypiperidin-1-yl)-1,3-benzothiazole-7-carboxylate obtained in Example (54a) (198 mg, 0.38 mmol) and a 2 N aqueous lithium hydroxide solution (4 mL), to obtain 162.5 mg of the title compound as a pale yellow solid (87%).

¹H NMR spectrum (400 MHz, DMSO-d₆) δ ppm: 0.76 (3H, t, J=7.34 Hz), 1.14 (3H, t, J=7.57 Hz), 1.40-1.43 (2H, m), 1.71-1.73 (1H, m), 1.89-1.95 (1H, m), 2.52-2.59 (2H, m), 3.35-3.40 (3H, m), 3.58-3.68 (2H, m), 4.19-4.26 (3H, m), 7.35-7.37 (1H, m), 7.61-7.65 (3H, m).

mass spectrum (ESI): m/z 493 (M+H)⁺.

Example 55 cis(±)-2-(4-{[(4-Chloro-5-ethyl-1H-imidazol-2-yl)carbonyl]amino}-3-methoxypiperidin-1-yl)-4-acetyl-1,3-thiazole-5-carboxylic acid (Exemplified Compound No. 55)

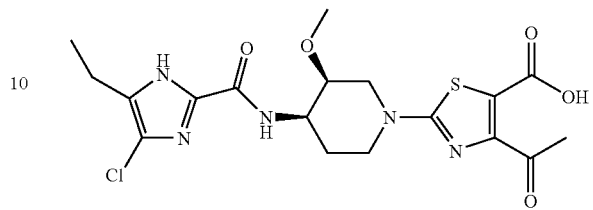

(55a) Methyl 4-acetyl-2-chloro-1,3-thiazole-5-carboxylate

The compound was synthesized according to the method described in the following document.

WO 2006/087543 A1

(55b) Methyl cis(±)-2-(4-{[(4-chloro-5-ethyl-1H-imidazol-2-yl)carbonyl]amino}-3-methoxypiperidin-1-yl)-4-acetyl-1,3-thiazole-5-carboxylate The same operation as in Example (1h) was performed using tert-butyl cis(±)-4-{[(4-chloro-5-ethyl-1H-imidazol-2-yl)carbonyl]amino}-3-methoxypiperidine-1-carboxylate obtained by the method described in Example (1g) (142 mg, 0.37 mmol), a 4 N hydrochloric acid/ethyl acetate solution (6 mL), diisopropylethylamine (0.25 mL, 1.44 mmol) and methyl 4-acetyl-2-chloro-1,3-thiazole-5-carboxylate obtained in Example (55a) (110 mg, 0.50 mmol), to obtain 165.5 mg of the title compound as a yellow foamy substance (96%).

¹H NMR spectrum (400 MHz, CDCl₃) δ ppm: 1.27 (3H, t, J=7.60 Hz), 1.80-1.82 (1H, m), 2.01-2.05 (1H, m), 2.55 (3H, s), 2.69 (2H, q, J=7.60 Hz), 3.11-3.14 (1H, m), 3.23-3.26 (1H, m), 3.43 (3H, s), 3.52 (1H, br s), 3.81 (3H, s), 3.96-3.99 (1H, m), 4.25-4.27 (1H, m), 4.53-4.57 (1H, m), 7.45 (1H, d, J=9.17 Hz), 10.82 (1H, br s).

(55c) cis(±)-2-(4-{[(4-Chloro-5-ethyl-1H-imidazol-2-yl)carbonyl]amino}-3-methoxypiperidin-1-yl)-4-acetyl-1,3-thiazole-5-carboxylic acid The same operation as in Example (1i) was performed using methyl cis(±)-2-(4-{[(4-chloro-5-ethyl-1H-imidazol-2-yl)carbonyl]amino}-3-methoxypiperidin-1-yl)-4-acetyl-1,3-thiazole-5-carboxylate obtained in Example (55b) (165 mg, 0.35 mmol) and a 2 N aqueous lithium hydroxide solution (3 mL), to obtain 141.9 mg of the title compound as a yellow solid (89%).

¹H NMR spectrum (400 MHz, DMSO-d₆) δ ppm: 1.14 (3H, t, J=7.53 Hz), 1.68-1.71 (1H, m), 1.85-1.89 (1H, m), 2.49 (3H, s), 2.55 (2H, q, J=7.53 Hz), 3.34 (3H, s), 3.36-3.39 (2H, m), 3.58 (1H, br s), 3.90-3.92 (1H, m), 4.22-4.25 (2H, m), 7.67 (1H, d, J=8.25 Hz).

mass spectrum (ESI): m/z 456 (M+H)⁺.

Example 56

2-[(3S,4R)-4-{[(4-Chloro-5-ethyl-1H-imidazol-2-yl)carbonyl]amino}-3-methoxypiperidin-1-yl]-4-methyl-1,3-thiazole-5-carboxylic acid (Exemplified Compound No. 56)

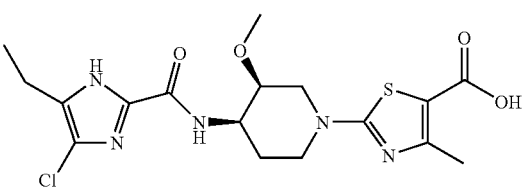

(56a) tert-Butyl (3S,4R)-4-amino-3-methoxypiperidine-1-carboxylate

The compound was synthesized according to the method described in the following document.

WO 2006/087543 A1

(56b) tert-Butyl (3S,4R)-4-{[(4-chloro-5-ethyl-1H-imidazol-2-yl)carbonyl]amino}-3-methoxypiperidine-1-carboxylate The same operation as in Example (1g) was performed using tert-butyl (3S,4R)-4-amino-3-methoxypiperidine-1-carboxylate obtained in Example (56a) (224.4 mg, 0.96 mmol), 4-chloro-5-ethyl-1H-imidazole-2-carboxylic acid synthesized by the method described in Example (1d) (140 mg, 0.80 mmol), WSC hydrochloride (440 mg, 2.29 mmol) and HOBT (110 mg, 0.81 mmol), to obtain 222.4 mg of the title compound as a white solid (72%).

$^1$H NMR spectrum (400 MHz, CDCl$_3$) δ ppm: 1.26 (3H, t, J=7.57 Hz), 1.47 (9H, s), 1.61-1.69 (1H, m), 1.79-1.91 (1H, m), 2.68 (2H, q, J=7.57 Hz), 2.72-2.89 (1H, m), 3.32-3.39 (2H, m), 3.41 (3H, s), 4.19-4.35 (3H, m), 7.45 (1H, br s), 10.90 (1H, br s).

(56c) Ethyl 2-[(3S,4R)-4-{[(4-chloro-5-ethyl-1H-imidazol-2-yl)carbonyl]amino}-3-methoxypiperidin-1-yl]-4-methyl-1,3-thiazole-5-carboxylate The same operation as in Example (1h) was performed using tert-butyl (3S,4R)-4-{[(4-chloro-5-ethyl-1H-imidazol-2-yl)carbonyl]amino}-3-methoxypiperidine-1-carboxylate obtained in Example (56b) (210 mg, 0.54 mmol), a 4 N hydrochloric acid/ethyl acetate solution (6 mL), diisopropylethylamine (0.4 mL, 2.87 mmol) and ethyl 2-bromo-4-methyl-1,3-thiazole-5-carboxylate (203 mg, 0.81 mmol), to obtain 228.4 mg of the title compound as a pale yellow foamy substance (92%).

$^1$H NMR spectrum (400 MHz, CDCl$_3$) δ ppm: 1.27 (5H, t, J=7.60 Hz), 1.33 (3H, t, J=7.11 Hz), 1.78-1.80 (1H, m), 2.01-2.07 (1H, m), 2.54 (3H, s), 2.70 (2H, q, J=7.60 Hz), 3.08-3.11 (1H, m), 3.15-3.24 (1H, m), 3.42 (3H, s), 3.51 (1H, br s), 4.00-4.03 (1H, m), 4.21-4.32 (3H, m), 4.50-4.53 (1H, m), 7.51 (1H, d, J=8.71 Hz), 11.39 (1H, br s).

(56d) 2-[(3S,4R)-4-{[(4-Chloro-5-ethyl-1H-imidazol-2-yl)carbonyl]amino}-3-methoxypiperidin-1-yl]-4-methyl-1,3-thiazole-5-carboxylic acid The same operation as in Example (1i) was performed using ethyl 2-[(3S,4R)-4-{[(4-chloro-5-ethyl-1H-imidazol-2-yl)carbonyl]amino}-3-methoxypiperidin-1-yl]-4-methyl-1,3-thiazole-5-carboxylate obtained in Example (56c) (225 mg, 0.49 mmol) and a 2 N aqueous lithium hydroxide solution (3.5 mL), to obtain 156.7 mg of the title compound as a pale red solid (74%).

$^1$H NMR spectrum (400 MHz, DMSO-d$_6$) δ ppm: 1.14 (3H, t, J=7.60 Hz), 1.65-1.69 (1H, m), 1.82-1.88 (1H, m), 2.41 (3H, s), 2.55 (2H, q, J=7.60 Hz), 3.23-3.33 (2H, m), 3.34 (3H, s), 3.56 (1H, br s), 3.91-3.94 (1H, m), 4.20-4.23 (2H, m), 7.66 (1H, d, J=8.25 Hz), 12.40 (1H, br s).

mass spectrum (FAB): m/z 428 (M+H)$^+$.

$[α]_D^{24}$: +38.1 (c=0.1185, THF/H$_2$O=5/1)

Example 57 cis(±)-2-(4-{[(4-Chloro-5-ethyl-1H-imidazol-2-yl)carbonyl]amino}-3-ethoxypiperidin-1-yl)-4-acetyl-1,3-thiazole-5-carboxylic acid (Exemplified Compound No. 57)

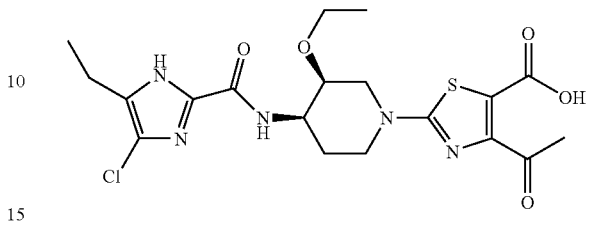

(57a) Methyl cis(±)-2-(4-{[(4-chloro-5-ethyl-1H-imidazol-2-yl)carbonyl]amino}-3-ethoxypiperidin-1-yl)-4-acetyl-1,3-thiazole-5-carboxylate The same operation as in Example (1h) was performed using tert-butyl cis(±)-4-{[(4-chloro-5-ethyl-1H-imidazol-2-yl)carbonyl]amino}-3-ethoxypiperidine-1-carboxylate obtained by the method described in Example (34a) (200 mg, 0.50 mmol), a 4 N hydrochloric acid/ethyl acetate solution (3 mL), diisopropylethylamine (0.35 mL, 2.01 mmol) and methyl 4-acetyl-2-chloro-1,3-thiazole-5-carboxylate obtained by the method described in Example (55a) (100 mg, 0.46 mmol), to obtain 192.5 mg of the title compound as a yellow foamy substance (87%).

$^1$H NMR spectrum (400 MHz, CDCl$_3$) δ ppm: 1.17 (3H, t, J=6.88 Hz), 1.27 (3H, t, J=7.57 Hz), 1.78-1.81 (1H, m), 2.05-2.09 (1H, m), 2.55 (3H, s), 2.69 (2H, q, J=7.64 Hz), 3.13-3.17 (1H, m), 3.21-3.28 (1H, m), 3.44 (1H, m), 3.62 (1H, br s), 3.72-3.76 (1H, m), 3.81 (3H, s), 3.99-4.02 (1H, m), 4.23-4.27 (1H, m), 4.43-4.47 (1H, m), 7.44 (1H, d, J=8.71 Hz), 10.74 (1H, br s).

(57b) cis(±)-2-(4-{[(4-Chloro-5-ethyl-1H-imidazol-2-yl)carbonyl]amino}-3-ethoxypiperidin-1-yl)-4-acetyl-1,3-thiazole-5-carboxylic acid The same operation as in Example (1i) was performed using methyl cis(±)-2-(4-{[(4-chloro-5-ethyl-1H-imidazol-2-yl)carbonyl]amino}-3-ethoxypiperidin-1-yl)-4-acetyl-1,3-thiazole-5-carboxylate obtained in Example (57a) (190 mg, 0.39 mmol) and a 2 N aqueous lithium hydroxide solution (3.5 mL), to obtain 154.3 mg of the title compound as a yellow solid (86%).

$^1$H NMR spectrum (400 MHz, DMSO-d$_6$) δ ppm: 1.05 (3H, t, J=6.88 Hz), 1.14 (3H, t, J=7.57 Hz), 1.67-1.70 (1H, m), 1.84-1.91 (1H, m), 2.48 (3H, s), 2.52-2.58 (2H, m), 3.30-3.48 (3H, m), 3.63-3.65 (2H, m), 3.96 (1H, br s), 4.18-4.22 (2H, m), 7.66 (1H, d, J=8.71 Hz).

mass spectrum (ESI): m/z 470 (M+H)$^+$.

Example 58 cis(±)-2-(4-{[(5-Ethyl-4-iodo-1H-imidazol-2-yl)carbonyl]amino}-3-methoxypiperidin-1-yl)-4-methyl-1,3-thiazole-5-carboxylic acid (Exemplified Compound No. 58)

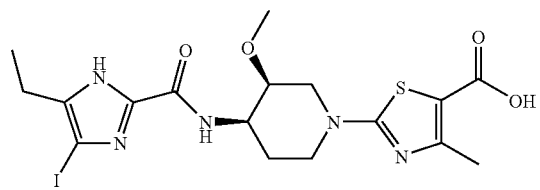

(58a) Ethyl 5-ethyl-4-iodo-1H-imidazole-2-carboxylate

The same operation as in Example (1c) was performed using ethyl 5-ethyl-1H-imidazole-2-carboxylate obtained by the method described in Example (1b) (0.20 g, 1.19 mmol) and NIS (0.29 g, 1.31 mmol), to obtain 0.35 g of the title compound as a pale yellow solid (100%).

$^1$H NMR spectrum (400 MHz, CDCl$_3$) δ ppm: 1.27 (3H, t, J=7.60 Hz), 1.41 (3H, t, J=7.14 Hz), 2.68 (2H, q, J=7.60 Hz), 4.43 (2H, q, J=7.14 Hz), 10.44 (1H, br s).

(58b) 5-Ethyl-4-iodo-1H-imidazole-2-carboxylic acid

The same operation as in Example (1d) was performed using ethyl 5-ethyl-4-iodo-1H-imidazole-2-carboxylate obtained in Example (58a) (230 mg, 0.78 mmol) and a 3 N aqueous lithium hydroxide solution (2.5 mL), to obtain 187.7 mg of the title compound as a white solid (90%).

mass spectrum (ESI): m/z 267 (M+H)$^+$.

(58c) tert-Butyl cis(±)-4-{[(5-ethyl-4-iodo-1H-imidazol-2-yl)carbonyl]amino}-3-methoxypiperidine-1-carboxylate The same operation as in Example (1g) was performed using tert-butyl cis(±)-4-amino-3-methoxypiperidine-1-carboxylate obtained by the method described in Example (1e) (130 mg, 0.56 mmol), 5-ethyl-4-iodo-1H-imidazole-2-carboxylic acid obtained in Example (58b) (95 mg, 0.36 mmol), WSC hydrochloride (220 mg, 1.15 mmol) and HOBT (46 mg, 0.34 mmol), to obtain 146.2 mg of the title compound as a white solid (86%).

$^1$H NMR spectrum (400 MHz, CDCl$_3$) δ ppm: 1.24 (5H, t, J=7.57 Hz), 1.48 (9H, s), 1.58-1.73 (1H, m), 1.86-1.87 (1H, m), 2.51-2.81 (4H, m), 3.39-3.42 (4H, m), 3.93-4.52 (3H, m), 7.51-7.61 (1H, m), 11.77 (1H, br s).

(58d) Ethyl cis(±)-2-(4-{[(5-ethyl-4-iodo-1H-imidazol-2-yl)carbonyl]amino}-3-methoxypiperidin-1-yl)-4-methyl-1,3-thiazole-5-carboxylate The same operation as in Example (1h) was performed using tert-butyl cis(±)-4-{[(5-ethyl-4-iodo-1H-imidazol-2-yl)carbonyl]amino}-3-methoxypiperidine-1-carboxylate obtained in Example (58c) (145 mg, 0.30 mmol), a 4 N hydrochloric acid/ethyl acetate solution (4 ml), diisopropylethylamine (0.21 mL, 1.21 mmol) and ethyl 2-bromo-4-methyl-1,3-thiazole-5-carboxylate (113 mg, 0.45 mmol), to obtain 133 mg of the title compound (80%).

$^1$H NMR spectrum (400 MHz, CDCl$_3$) δ ppm: 1.25 (3H, t, J=7.69 Hz), 1.33 (3H, t, J=7.16 Hz), 1.75-1.83 (1H, m), 2.03-2.08 (1H, m), 2.54 (3H, s), 2.67 (2H, q, J=7.69 Hz), 3.06-3.10 (1H, m), 3.17-3.20 (1H, m), 3.42 (3H, s), 3.51 (1H, br s), 4.00-4.03 (1H, m), 4.22-4.31 (3H, m), 4.50-4.53 (1H, m), 7.58 (1H, d, J=9.16 Hz), 11.69 (1H, br s).

(58e) cis(±)-2-(4-{[(5-Ethyl-4-iodo-1H-imidazol-2-yl)carbonyl]amino}-3-methoxypiperidin-1-yl)-4-methyl-1,3-thiazole-5-carboxylic acid The same operation as in Example (1i) was performed using ethyl cis(±)-2-(4-{[(5-ethyl-4-iodo-1H-imidazol-2-yl)carbonyl]amino}-3-methoxypiperidin-1-yl)-4-methyl-1,3-thiazole-5-carboxylate obtained in Example (58d) (130 mg, 0.24 mmol) and 2 N lithium hydroxide (3 mL), to obtain 40.7 mg of the title compound as a pale red solid (32%).

$^1$H NMR spectrum (400 MHz, DMSO-d$_6$) δ ppm: 1.11 (3H, t, J=7.45 Hz), 1.67-1.68 (1H, m), 1.84-1.88 (1H, m), 2.41 (3H, s), 2.43-2.53 (2H, m), 3.30-3.37 (5H, m), 3.56 (1H, s), 3.90-3.92 (1H, m), 4.21-4.24 (2H, m), 7.63 (1H, d, J=8.59 Hz), 12.40 (1H, br s).

mass spectrum (ESI): m/z 520 (M+H)$^+$.

Example 59 cis(±)-2-[(4-{[(5-Ethyl-4-(methylsulfanyl)-1H-imidazol-2-yl)carbonyl]amino}-3-methoxypiperidin-1-yl]-4-methyl-1,3-thiazole-5-carboxylic acid and cis (±)-2-[(4-{[(4-ethyl-5-(methylsulfanyl)-1H-imidazol-2-yl)carbonyl]amino}-3-methoxypiperidin-1-yl]-4-methyl-1,3-thiazole-5-carboxylic acid (Exemplified Compound No. 59)

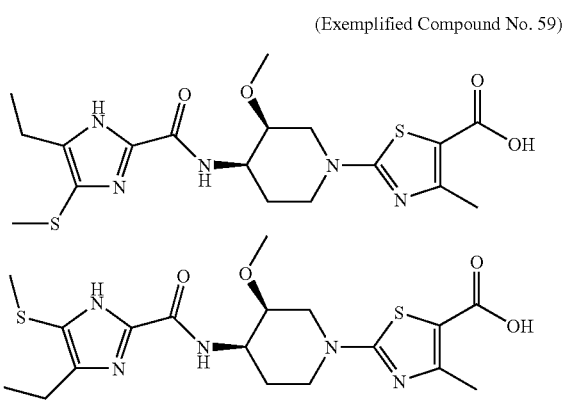

(59a) Ethyl 5-ethyl-4-(methylsulfanyl)-1H-imidazole-2-carboxylate and ethyl 4-ethyl-5-(methylsulfanyl)-1H-imidazole-2-carboxylate Ethyl 5-ethyl-4-iodo-1H-imidazole-2-carboxylate obtained by the method described in Example (58a) (171 mg, 0.58 mmol) was dissolved in N-methyl-pyrrolidone (2 mL). Copper chloride (84 mg, 0.81 mmol) and sodium methylmercaptan (131 mg, 1.78 mmol) were added, and the mixture was stirred at 140° C. for 1.5 hours. A 28% aqueous ammonia solution was added to the reaction solution, followed by extraction with ethyl acetate. Then, the organic layer was washed with brine and dried over anhydrous sodium sulfate. Following concentration under reduced pressure, the residue was purified by silica gel column chromatography (elution solvent: hexane/ethyl acetate=4/1, 1/1) to obtain 62.1 mg of the title compound as an about 2:1 mixture (50%).

$^1$H NMR spectrum (400 MHz, CDCl$_3$) δ ppm: 1.12-1.31 (3H, m), 1.36-1.43 (3H, m), 2.34 (3×1/3H, s), 2.43 (3×2/3H, s), 2.73-2.80 (2H, m), 4.38-4.46 (2H, m), 10.17-10.28 (1H, m).

(59b) 5-Ethyl-4-(methylsulfanyl)-1H-imidazole-2-carboxylic acid and 4-ethyl-5-(methylsulfanyl)-1H-imidazole-2-carboxylic acid The same operation as in Example (1d) was performed using the mixture of ethyl 5-ethyl-4-(methylsulfanyl)-1H-imidazole-2-carboxylate and ethyl 4-ethyl-5-(methylsulfanyl)-1H-imidazole-2-carboxylate obtained in Example (59a) (62.1 mg, 0.29 mmol) and a 3 N aqueous lithium hydroxide solution (3 mL), to obtain 43.9 mg of the title compound as a white solid (81%).

mass spectrum (ESI): m/z 187 (M+H)$^+$.

(59c) tert-Butyl cis(±)-4-({[(5-ethyl-4-(methylsulfanyl)-1H-imidazol-2-yl]carbonyl}amino)-3-methoxypiperidine-1-carboxylate and tert-butyl cis(±)-4-({[(4-ethyl-5-(methylsulfanyl)-1H-imidazol-2-yl]carbonyl}amino)-3-methoxypiperidine-1-carboxylate The same operation as in Example (1g) was performed using tert-butyl cis(±)-4-amino-3-methoxypiperidine-1-carboxylate obtained by the method described in Example (1e)

(120 mg, 0.52 mmol), the mixture of 5-ethyl-4-(methylsulfanyl)-1H-imidazole-2-carboxylic acid and 4-ethyl-5-(methylsulfanyl)-1H-imidazole-2-carboxylic acid obtained in Example (59b) (42 mg, 0.20 mmol), WSC hydrochloride (120 mg, 0.63 mmol) and HOBT (25 mg, 0.19 mmol), to obtain 81.7 mg of the title compound as a colorless oily substance and as an about 4:1 mixture.

$^1$H NMR spectrum (400 MHz, CDCl$_3$) δ ppm: 1.23-1.29 (3H, m), 1.48 (9H, s), 1.63-1.71 (1H, m), 1.80-1.93 (1H, m), 2.32 (3×⅕H, s), 2.38 (3×⅘H, s), 2.65-2.81 (2H, m), 3.27-3.46 (4H, m), 4.04-4.14 (2H, m), 4.42-4.48 (1H, m), 7.55-7.66 (1H, m), 11.47-11.69 (1H, m).

(59d) Ethyl cis(±)-2-[(4-{[(5-ethyl-4-(methylsulfanyl)-1H-imidazol-2-yl)carbonyl]amino}-3-methoxypiperidin-1-yl]-4-methyl-1,3-thiazole-5-carboxylate and ethyl cis(±)-2-[(4-{[(4-ethyl-5-(methylsulfanyl)-1H-imidazol-2-yl)carbonyl]amino}-3-methoxypiperidin-1-yl]-4-methyl-1,3-thiazole-5-carboxylate The same operation as in Example (1h) was performed using the mixture of tert-butyl cis(±)-4-({[(5-ethyl-4-(methylsulfanyl)-1H-imidazol-2-yl]carbonyl}amino)-3-methoxypiperidine-1-carboxylate and tert-butyl cis(±)-4-({[(4-ethyl-5-(methylsulfanyl)-1H-imidazol-2-yl]carbonyl}amino)-3-methoxypiperidine-1-carboxylate obtained in Example (59c) (about 0.20 mmol), a 4 N hydrochloric acid/ethyl acetate solution (2 ml), diisopropylethylamine (0.2 mL, 1.15 mmol) and ethyl 2-bromo-4-methyl-1,3-thiazole-5-carboxylate (60 mg, 0.24 mmol), to obtain 83.3 mg of the title compound as a yellow oily substance and as an about 4:1 mixture (91%).

$^1$H NMR spectrum (400 MHz, CDCl$_3$) δ ppm: 1.23-1.28 (3H, m), 1.31-1.36 (3H, m), 1.80-1.81 (1H, m), 2.01-2.10 (1H, m), 2.32 (3×⅕H, s), 2.38 (3×⅘H, s), 2.54 (3H, s), 2.68 (2×⅕H, q, J=7.64 Hz), 2.77 (2×⅘H, q, J=7.64 Hz), 3.10-3.13 (1H, m), 3.21-3.24 (1H, m), 3.42 (3×4/5H, s), 3.44 (3×⅕H, s), 3.50-3.55 (1H, m), 3.96-4.06 (1H, m), 4.22-4.30 (3H, m), 4.48-4.56 (1H, m), 7.56-7.63 (1H, m), 10.96 (1×⅕H, s), 11.14 (1×⅘H, s).

(59e) cis(±)-2-[(4-{[(5-Ethyl-4-(methylsulfanyl)-1H-imidazol-2-yl)carbonyl]amino}-3-methoxypiperidin-1-yl]-4-methyl-1,3-thiazole-5-carboxylic acid and cis(±)-2-[(4-{[(4-ethyl-5-(methylsulfanyl)-1H-imidazol-2-yl)carbonyl]amino}-3-methoxypiperidin-1-yl]-4-methyl-1,3-thiazole-5-carboxylic acid The same operation as in Example (1i) was performed using the mixture of ethyl cis(±)-2-[(4-{[(5-ethyl-4-(methylsulfanyl)-1H-imidazol-2-yl)carbonyl]amino}-3-methoxypiperidin-1-yl]-4-methyl-1,3-thiazole-5-carboxylate and ethyl cis(±)-2-[(4-{[(4-ethyl-5-(methylsulfanyl)-1H-imidazol-2-yl)carbonyl]amino}-3-methoxypiperidin-1-yl]-4-methyl-1,3-thiazole-5-carboxylate obtained in Example (59d) (83.3 mg, 0.18 mmol) and 2 N lithium hydroxide (2 mL), to obtain 40.6 mg of the title compound as an about 4:1 mixture (32%).

$^1$H NMR spectrum (400 MHz, DMSO-d$_6$) δ ppm: 1.13 (3H, m), 1.68-1.70 (1H, m), 1.83-1.84 (1H, m), 2.28 (3×⅘H, s), 2.31 (3×⅕H, s), 2.41 (3H, s), 2.59-2.63 (2H, m), 3.32-3.33 (2H, m), 3.35 (3H, s), 3.53-3.59 (1H, m), 3.87-3.99 (1H, m), 4.15-4.32 (2H, m), 7.56-7.64 (1H, m), 12.38-12.40 (1H, m).

mass spectrum (ESI): m/z 440 (M+H)$^+$.

Example 60 cis(±)-2-(4-{[(4-Chloro-5-ethyl-1H-imidazol-2-yl)carbonyl]amino}-3-methoxypiperidin-1-yl)-4-[(4-methylpiperazin-1-yl)carbonyl]-1,3-thiazole-5-carboxylic acid

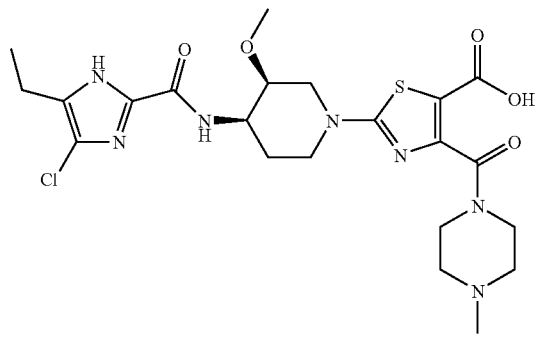

(Exemplified Compound No. 60)

(60a) Ethyl cis(±)-2-(4-{[(4-chloro-5-ethyl-1H-imidazol-2-yl)carbonyl]amino}-3-methoxypiperidin-1-yl)-4-[(4-methylpiperazin-1-yl)carbonyl]-1,3-thiazole-5-carboxylate The same operation as in Example (1g) was performed using cis(±)-2-(4-{[(4-chloro-5-ethyl-1H-imidazol-2-yl)carbonyl]amino}-3-methoxypiperidin-1-yl)-5-(ethoxycarbonyl)-1,3-thiazole-4-carboxylic acid obtained by the method described in Example (50a) (65 mg, 0.13 mmol), 4-methylpiperazine (35 µL, 0.27 mmol), WSC hydrochloride (80 mg, 0.42 mmol) and HOBT (18 mg, 0.13 mmol), to obtain 52.1 mg of the title compound as a white solid (69%).

$^1$H NMR spectrum (400 MHz, CDCl$_3$) δ ppm: 1.26 (3H, t, J=7.68 Hz), 1.31 (3H, t, J=7.16 Hz), 1.67-1.82 (1H, m), 2.02-2.06 (1H, m), 2.33 (3H, s), 2.33-2.42 (2H, m), 2.46-2.55 (2H, m), 2.69 (2H, q, J=7.68 Hz), 3.10-3.13 (1H, m), 3.23-3.25 (1H, m), 3.29-3.34 (2H, m), 3.42 (3H, s), 3.52 (1H, br s), 3.78-3.84 (2H, m), 3.95-3.97 (1H, m), 4.23-4.27 (3H, m), 4.56-4.58 (1H, m), 7.47 (1H, d, J=9.16 Hz), 11.21 (1H, br s).

(60b) cis(±)-2-(4-{[(4-Chloro-5-ethyl-1H-imidazol-2-yl)carbonyl]amino}-3-methoxypiperidin-1-yl)-4-[(4-methylpiperazin-1-yl)carbonyl]-1,3-thiazole-5-carboxylic acid The same operation as in Example (1i) was performed using ethyl cis(±)-2-(4-{[(4-chloro-5-ethyl-1H-imidazol-2-yl)carbonyl]amino}-3-methoxypiperidin-1-yl)-4-[(4-methylpiperazin-1-yl)carbonyl]-1,3-thiazole-5-carboxylate obtained in Example (60a) (52.1 mg, 0.092 mmol) and a 2 N aqueous lithium hydroxide solution (1 mL), to obtain 42.3 mg of the title compound as a pale yellow solid (85%).

$^1$H NMR spectrum (400 MHz, DMSO-d$_6$) δ ppm: 1.14 (3H, t, J=7.55 Hz), 1.67-1.69 (1H, m), 1.83-1.90 (1H, m), 2.23 (3H, s), 2.38-2.49 (4H, m), 2.55 (2H, q, J=7.55 Hz), 3.15-3.23 (2H, m), 3.28-3.33 (5H, m), 3.48-3.64 (3H, m), 3.83-3.85 (1H, m), 4.19-4.30 (2H, m), 7.67 (1H, d, J=8.59 Hz).

mass spectrum (ESI): m/z 541 (M+H)$^+$.

Example 61 cis(±)-2-(4-{[(4-Chloro-5-ethyl-1H-imidazol-2-yl)carbonyl]amino}-3-methoxypiperidin-1-yl)-4-{[2-(dimethylamino)ethyl]carbamoyl}-1,3-thiazole-5-carboxylic acid (Exemplified Compound No. 61)

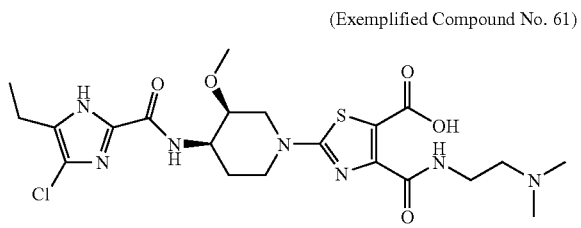 [SMILES: CCc1[nH]c(C(=O)N[C@@H]2CCN(c3nc(C(=O)NCCN(C)C)c(C(=O)O)s3)C[C@@H]2OC)nc1Cl]

(61a) Ethyl cis(±)-2-(4-{[(4-chloro-5-ethyl-1H-imidazol-2-yl)carbonyl]amino}-3-methoxypiperidin-1-yl)-4-{[2-(dimethylamino)ethyl]carbamoyl}-1,3-thiazole-5-carboxylate The same operation as in Example (1g) was performed using cis(±)-2-(4-{[(4-chloro-5-ethyl-1H-imidazol-2-yl)carbonyl]amino}-3-methoxypiperidin-1-yl)-5-(ethoxycarbonyl)-1,3-thiazole-4-carboxylic acid obtained by the method described in Example (50a) (65 mg, 0.13 mmol), N,N-dimethylethylenediamine (35 µL, 0.27 mmol), WSC hydrochloride (80 mg, 0.42 mmol) and HOBT (18 mg, 0.13 mmol), to obtain 61.5 mg of the title compound as a white solid (83%).

$^1$H NMR spectrum (400 MHz, CDCl$_3$) δ ppm: 1.26 (3H, t, J=7.68 Hz), 1.33 (3H, t, J=7.16 Hz), 1.78-1.81 (1H, m), 1.98-2.09 (1H, m), 2.27 (6H, s), 2.53 (2H, t, J=6.30 Hz), 2.69 (2H, q, J=7.68 Hz), 3.11-3.14 (1H, m), 3.22-3.24 (1H, m), 3.43 (3H, s), 3.48-3.55 (3H, m), 3.96-4.06 (1H, m), 4.26-4.30 (3H, m), 4.51-4.62 (1H, m), 7.48 (1H, d, J=9.16 Hz), 8.11-8.16 (1H, m).

(61b) cis(±)-2-(4-{[(4-Chloro-5-ethyl-1H-imidazol-2-yl)carbonyl]amino}-3-methoxypiperidin-1-yl)-4-{[2-(dimethylamino)ethyl]carbamoyl}-1,3-thiazole-5-carboxylic acid The same operation as in Example (1i) was performed using ethyl cis(±)-2-(4-{[(4-chloro-5-ethyl-1H-imidazol-2-yl)carbonyl]amino}-3-methoxypiperidin-1-yl)-4-{[2-(dimethylamino)ethyl]carbamoyl}-1,3-thiazole-5-carboxylate obtained in Example (61a) (61.5 mg, 0.11 mmol) and a 2 N aqueous lithium hydroxide solution (1 mL), to obtain 51.4 mg of the title compound as a pale yellow solid (88%).

$^1$H NMR spectrum (400 MHz, DMSO-d$_6$) δ ppm: 1.14 (3H, t, J=7.68 Hz), 1.67-1.69 (1H, m), 1.84-1.89 (1H, m), 2.34 (6H, s), 2.55 (3H, q, J=7.68 Hz), 2.61-2.67 (2H, m), 3.24-3.34 (2H, m), 3.35 (3H, s), 3.37-3.43 (1H, m), 3.56 (1H, br s), 3.97-3.99 (1H, m), 4.18-4.22 (2H, m), 4.28-4.30 (1H, m), 7.66 (1H, d, J=8.59 Hz).

mass spectrum (ESI): m/z 529 (M+H)$^+$.

Example 62 cis(±)-2-(4-{[(4-Chloro-5-ethyl-1H-imidazol-2-yl)carbonyl]amino}-3-methoxypiperidin-1-yl)-4-propanoyl-1,3-thiazole-5-carboxylic acid (Exemplified Compound No. 62)

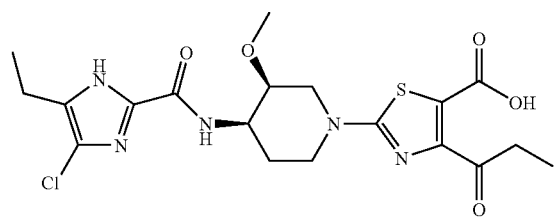

(62a) Ethyl 2-amino-4-({[tert-butyl(dimethyl)silyl]oxy}methyl)-1,3-thiazole-5-carboxylate The compound was synthesized according to the method described in the following document.

WO 2006/087543 A1

(62b) Ethyl 2-[bis(tert-butoxycarbonyl)amino]-4-({[tert-butyl(dimethyl)silyl]oxy}methyl)-1,3-thiazole-5-carboxylate Ethyl 2-amino-4-({[tert-butyl(dimethyl)silyl]oxy}methyl)-1,3-thiazole-5-carboxylate obtained in Example (62a) (2.0 g, 6.32 mmol) was dissolved in THF (50 mL). Di-tert-butyl dicarboxylate (4.1 g, 18.8 mmol), triethylamine (2 mL, 14.3 mmol) and DMAP (150 mg, 1.23 mmol) were added, followed by stirring for 4.5 hours. Ethyl acetate was added to the reaction solution, and the organic layer was washed with 1 N hydrochloric acid and brine, and dried over anhydrous sodium sulfate. Following concentration under reduced pressure, the residue was purified by silica gel column chromatography (elution solvent: hexane/ethyl acetate=97/3, 95/5) to obtain 2.87 g of the title compound as a white solid (88%).

$^1$H NMR spectrum (400 MHz, CDCl$_3$) δ ppm: 0.08 (6H, s), 0.89 (9H, s), 1.34 (3H, t, J=7.19 Hz), 1.57 (18H, s), 4.30 (2H, q, J=7.19 Hz), 5.01 (2H, s).

(62c) Ethyl 2-[bis(tert-butoxycarbonyl)amino]-4-(hydroxymethyl)-1,3-thiazole-5-carboxylate Ethyl 2-[bis(tert-butyl(dimethyl)silyl]oxy}methyl)-1,3-thiazole-5-carboxylate obtained in Example (62b) (2.87 g, 5.55 mmol) was dissolved in THF (60 mL). TBAF (1 M solution in THF, 9.3 mL) and acetic acid (0.48 mL, 8.39 mmol) were added, followed by stirring for 15 hours. Ethyl acetate was added to the reaction solution, and the organic layer was washed with saturated aqueous sodium bicarbonate solution and brine, and dried over anhydrous sodium sulfate. Following concentration under reduced pressure, the residue was purified by silica gel column chromatography (elution solvent: hexane/ethyl acetate=90/10, 70/30) to obtain 1.83 g of the title compound as a white solid (82%).

$^1$H NMR spectrum (400 MHz, CDCl$_3$) δ ppm: 1.35 (3H, t, J=7.15 Hz), 1.58 (18H, s), 3.84 (1H, t, J=6.54 Hz), 4.33 (2H, q, J=7.15 Hz), 4.86 (2H, d, J=6.54 Hz). (62d) Ethyl 2-[bis(tert-butoxycarbonyl)amino]-4-formyl-1,3-thiazole-5-carboxylate The same operation as in Example (28a) was performed using ethyl 2-[bis(tert-butoxycarbonyl)amino]-4-(hydroxymethyl)-1,3-thiazole-5-carboxylate obtained in Example (62c) (1 g, 2.48 mmol) and the Dess-Martin reagent (1.28 g, 3.02 mmol), to obtain 915.5 mg of the title compound as a yellow solid (92%).

$^1$H NMR spectrum (400 MHz, CDCl$_3$) δ ppm: 1.39 (3H, t, J=7.14 Hz), 1.59 (18H, s), 4.40 (2H, q, J=7.14 Hz), 10.54 (1H, s).

(62e) Ethyl 2-[bis(tert-butoxycarbonyl)amino]-4-(1-hydroxypropyl)-1,3-thiazole-5-carboxylate Ethyl 2-[bis(tert-butoxycarbonyl)amino]-4-formyl-1,3-thiazole-5-carboxylate obtained in Example (62d) (915.5 mg, 2.29 mmol) was dissolved in diethyl ether (30 mL), followed by cooling to −78° C. Then, tetrabutylammonium bromide (890 mg, 2.76 mmol) and ethylmagnesium bromide (1 M solution in THF, 2.8 mL) were added, and the mixture was stirred for one hour. Diethyl ether was added to the reaction solution, and the organic layer was washed with brine and dried over anhydrous sodium sulfate. Following concentration under reduced pressure, the residue was purified by silica gel column chromatography (elution solvent: hexane/ethyl acetate=91/9, 85/15) to obtain 327.2 mg of the title compound (33%).

$^1$H NMR spectrum (400 MHz, CDCl$_3$) δ ppm: 0.96 (3H, t, J=7.35 Hz), 1.35 (3H, t, J=7.16 Hz), 1.57 (18H, s), 1.75-1.89 (2H, m), 3.86 (1H, d, J=9.16 Hz), 4.32 (2H, q, J=7.35 Hz), 5.00-5.08 (1H, m).

(62f) Ethyl 2-[bis(tert-butoxycarbonyl)amino]-4-propanoyl-1,3-thiazole-5-carboxylate The same operation as in Example (28a) was performed using ethyl 2-[bis(tert-butoxycarbonyl)amino]-4-(1-hydroxypropyl)-1,3-thiazole-5-carboxylate obtained in Example (62e) (327.2 mg, 0.76 mmol) and the Dess-Martin reagent (420 mg, 0.99 mmol), to obtain 270.5 mg of the title compound as a white solid (83%).

$^1$H NMR spectrum (400 MHz, CDCl$_3$) δ ppm: 1.18 (3H, t, J=7.26 Hz), 1.33 (3H, t, J=7.14 Hz), 1.57 (18H, s), 2.91 (2H, q, J=7.26 Hz), 4.32 (2H, q, J=7.14 Hz). (62g) Ethyl 2-chloro-4-propanoyl-1,3-thiazole-5-carboxylate Ethyl 2-[bis(tert-butoxycarbonyl)amino]-4-propanoyl-1,3-thiazole-5-carboxylate obtained in Example (62f) (270.5 mg, 0.63 mmol) was dissolved in methanol (2 mL). A 4 N hydrochloric acid/ethyl acetate solution (6 mL) was added, and the mixture was stirred at 50° C. for 50 minutes. The reaction solution was washed with saturated aqueous sodium bicarbonate solution, dried over anhydrous sodium sulfate, and then concentrated under reduced pressure. The same operation as in Example (22c) was performed using the resulting crude product, copper chloride (96 mg, 0.71 mmol) and tert-butyl nitrite (86 μL, 0.72 mmol), to obtain 49.0 mg of the title compound as a colorless oily substance (31%).

$^1$H NMR spectrum (400 MHz, CDCl$_3$) δ ppm: 1.21 (3H, t, J=7.11 Hz), 1.35 (3H, t, J=7.21 Hz), 2.98 (2H, q, J=7.11 Hz), 4.36 (2H, q, J=7.21 Hz).

(62h) Ethyl cis(±)-2-(4-{[(4-chloro-5-ethyl-1H-imidazol-2-yl)carbonyl]amino}-3-methoxypiperidin-1-yl)-4-propanoyl-1,3-thiazole-5-carboxylate The same operation as in Example (1h) was performed using tert-butyl cis(±)-4-{[(4-chloro-5-ethyl-1H-imidazol-2-yl)carbonyl]amino}-3-methoxypiperidine-1-carboxylate obtained by the method described in Example (1g) (62 mg, 0.16 mmol), ethyl 2-chloro-4-propanoyl-1,3-thiazole-5-carboxylate obtained in Example (62g) (24 mg, 0.097 mmol), a 4 N hydrochloric acid/ethyl acetate solution (2 mL) and diisopropylethylamine (0.11 mL, 0.6 mmol), to obtain 20.2 mg of the title compound (42%).

$^1$H NMR spectrum (400 MHz, CDCl$_3$) δ ppm: 1.19 (3H, t, J=7.16 Hz), 1.25-1.34 (6H, m), 1.79-1.82 (1H, m), 2.02-2.05 (1H, m), 2.69 (2H, q, J=7.64 Hz), 2.85-2.91 (2H, m), 3.11-3.12 (1H, m), 3.22-3.26 (1H, m), 3.42 (3H, s), 3.52 (1H, br s), 3.95-3.98 (1H, m), 4.22-4.28 (3H, m), 4.55-4.58 (1H, m), 7.48 (1H, d, J=8.59 Hz), 11.17 (1H, br s).

(62i) cis(±)-2-(4-{[(4-Chloro-5-ethyl-1H-imidazol-2-yl)carbonyl]amino}-3-methoxypiperidin-1-yl)-4-propanoyl-1,3-thiazole-5-carboxylic acid The same operation as in Example (1i) was performed using ethyl cis(±)-2-(4-{[(4-chloro-5-ethyl-1H-imidazol-2-yl)carbonyl]amino}-3-methoxypiperidin-1-yl)-4-propanoyl-1,3-thiazole-5-carboxylate obtained in Example (62h) (20.2 mg, 0.041 mmol) and a 2 N aqueous lithium hydroxide solution (0.7 mL), to obtain 22.2 mg of the title compound as a yellow solid (100%).

$^1$H NMR spectrum (400 MHz, DMSO-d$_6$) δ ppm: 1.04 (3H, t, J=7.11 Hz), 1.14 (3H, t, J=7.26 Hz), 1.65-1.74 (1H, m), 1.83-1.92 (1H, m), 2.52-2.59 (2H, m), 2.84 (2H, q, J=7.26 Hz), 3.33 (5H, m), 3.58 (1H, br s), 3.89-3.91 (1H, m), 4.19-4.28 (2H, m), 7.68 (1H, d, J=8.71 Hz).

mass spectrum (ESI): m/z 470 (M+H)$^+$.

Example 63 cis(±)-2-(4-{[(4-Chloro-5-ethyl-1H-imidazol-2-yl)carbonyl]amino}-3-ethoxypiperidin-1-yl)-4-propanoyl-1,3-thiazole-5-carboxylic acid (Exemplified Compound No. 63)

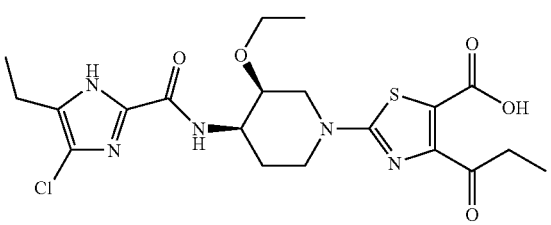

(63a) Ethyl cis(±)-2-(4-{[(4-chloro-5-ethyl-1H-imidazol-2-yl)carbonyl]amino}-3-ethoxypiperidin-1-yl)-4-propanoyl-1,3-thiazole-5-carboxylate The same operation as in Example (1h) was performed using tert-butyl cis(±)-4-{[(4-chloro-5-ethyl-1H-imidazol-2-yl)carbonyl]amino}-3-ethoxypiperidine-1-carboxylate obtained by the method described in Example (34a) (66 mg, 0.16 mmol), ethyl 2-chloro-4-propanoyl-1,3-thiazole-5-carboxylate obtained in Example (62g) (24 mg, 0.097 mmol), a 4 N hydrochloric acid/ethyl acetate solution (2 mL) and diisopropylethylamine (0.11 mL, 0.6 mmol), to obtain 33.1 mg of the title compound (67%).

$^1$H NMR spectrum (400 MHz, CDCl$_3$) δ ppm: 1.14-1.22 (6H, m), 1.23-1.39 (6H, m), 1.74-1.81 (1H, m), 2.06-2.10 (1H, m), 2.70 (2H, q, J=7.49 Hz), 2.86-2.88 (2H, m), 3.12-3.15 (1H, m), 3.19-3.27 (1H, m), 3.42-3.45 (1H, m), 3.62 (1H, br s), 3.70-3.82 (1H, m), 3.93-4.06 (1H, m), 4.22-4.27 (3H, m), 4.44-4.47 (1H, m), 7.50 (1H, d, J=8.71 Hz), 11.37 (1H, br s).

(63b) cis(±)-2-(4-{[(4-Chloro-5-ethyl-1H-imidazol-2-yl)carbonyl]amino}-3-ethoxypiperidin-1-yl)-4-propanoyl-1,3-thiazole-5-carboxylic acid The same operation as in Example (1i) was performed using ethyl cis(±)-2-(4-{[(4-chloro-5-ethyl-1H-imidazol-2-yl)carbonyl]amino}-3-ethoxypiperidin-1-yl)-4-propanoyl-1,3-thiazole-5-carboxylate obtained in Example (63a) (33.1 mg, 0.065 mmol) and a 2 N aqueous lithium hydroxide solution (0.8 mL), to obtain 26.4 mg of the title compound as a yellow solid (84%).

$^1$H NMR spectrum (400 MHz, DMSO-d$_6$) δ ppm: 1.04-1.06 (6H, m), 1.14 (3H, t, J=7.45 Hz), 1.67-1.69 (1H, m), 1.86-1.88 (1H, m), 2.52-2.58 (2H, m), 2.83 (2H, q, J=7.06 Hz), 3.29-3.47 (1H, m), 3.62-3.65 (2H, m), 3.94-3.96 (1H, m), 4.18-4.21 (2H, m), 7.65 (1H, d, J=8.59 Hz).

mass spectrum (ESI): m/z 484 (M+H)$^+$.

Example 64 cis(±)-[2-(4-{[(4-Chloro-5-ethyl-1H-imidazol-2-yl)carbonyl]amino}-3-methoxypiperidin-1-yl)-1,3-thiazol-4-yl]acetic acid (Exemplified Compound No. 64)

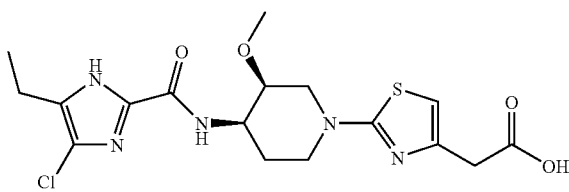

(64a) Benzyl cis(±)-[1-(1H-imidazol-1-ylthiocarbonyl)-3-methoxypiperidin-4-yl]-carbamate Benzyl cis(±)-4-(3-methoxypiperidin-4-yl)-carbamate obtained by the method described in Example (40b) (735 mg, 1.37 mmol) was dissolved in THF (8 mL). 1,1'-Thiocarbonyldiimidazole (270 mg, 1.36 mmol) was added, and the mixture was stirred for 1.5 hours. 0.5 M hydrochloric acid was added to the reaction solution, followed by extraction with ethyl acetate and dichloromethane. The organic layer was dried over anhydrous sodium sulfate and then concentrated under reduced pressure. The resulting compound was used for the next reaction without purification.

(64b) Benzyl cis(±)-(1-carbamothioyl-3-methoxypiperidin-4-yl)-carbamate

Benzyl cis(±)-[1-(1H-imidazol-1-ylthiocarbonyl)-3-methoxypiperidin-4-yl]-carbamate obtained in Example (64a) (about 1.36 mmol) was dissolved in THF (2 mL). A 2 N ammonia/methanol solution (10 mL) was added, and the mixture was stirred for 42 hours. Brine was added to the reaction solution, followed by extraction with ethyl acetate. The organic layer was dried over anhydrous sodium sulfate and then concentrated under reduced pressure. The precipitated solid was collected by filtration to obtain 296.5 mg of the title compound as a white solid (67%).

mass spectrum (ESI): m/z 324 (M+H)$^+$.

(64c) Ethyl cis(±)-[2-(4-{[(benzyloxy)carbonyl]amino}-3-methoxypiperidin-1-yl)-1,3-thiazol-4-yl]acetate The same operation as in Example (22b) was performed using benzyl cis(±)-(1-carbamothioyl-3-methoxypiperidin-4-yl)-carbamate obtained in Example (64b) (97 mg, 0.30 mmol) and ethyl 4-chloro-acetoacetate (60 μL, 0.44 mmol), to obtain 125.4 mg of the title compound as a colorless oily substance (96%).

$^1$H NMR spectrum (400 MHz, CDCl$_3$) δ ppm: 1.26 (3H, t, J=7.11 Hz), 1.78-1.80 (1H, m), 1.88-1.93 (1H, m), 3.01-3.04 (1H, m), 3.10-3.12 (1H, m), 3.38 (3H, s), 3.45 (1H, br s), 3.56 (2H, s), 3.81-3.84 (2H, m), 4.17 (2H, q, J=7.11 Hz), 4.34-4.38 (1H, m), 5.11 (2H, s), 5.27 (1H, d, J=9.16 Hz), 6.34 (1H, s), 7.32-7.36 (5H, m).

(64d) Ethyl cis(±)-[2-(4-amino-3-methoxypiperidin-1-yl)-1,3-thiazol-4-yl]acetate Ethyl cis(±)-[2-(4-{[(benzyloxy)carbonyl]amino}-3-methoxypiperidin-1-yl)-1,3-thiazol-4-yl]acetate obtained in Example (64c) (124 mg, 0.29 mmol) was dissolved in ethanol (5 mL). A 10% palladium-carbon catalyst (75 mg) and ammonium formate (90 mg, 1.43 mmol) were added, and the mixture was heated under reflux for 15 hours. The reaction solution was filtered through celite. The filtrate was washed with saturated sodium bicarbonate, dried over anhydrous sodium sulfate and then concentrated under reduced pressure. The resulting compound was used for the next reaction without purification.

(64e) Ethyl cis(±)-[2-(4-{[(4-chloro-5-ethyl-1H-imidazol-2-yl)carbonyl]amino}-3-methoxypiperidin-1-yl)-1,3-thiazol-4-yl]acetate The same operation as in Example (1g) was performed using ethyl cis(±)-[2-(4-amino-3-methoxypiperidin-1-yl)-1,3-thiazol-4-yl]acetate obtained in Example (64d) (about 0.29 mmol), 4-chloro-5-ethyl-1H-imidazole-2-carboxylic acid obtained by the method described in Example (1d) (45 mg, 0.26 mmol), WSC hydrochloride (150 mg, 0.78 mmol) and HOBT (35 mg, 0.26 mmol), to obtain 42.6 mg of the title compound (36%).

$^1$H NMR spectrum (400 MHz, CDCl$_3$) δ ppm: 1.25-1.30 (6H, m), 1.86-1.88 (1H, m), 2.03-2.12 (1H, m), 2.69 (2H, q, J=7.64 Hz), 3.03-3.06 (1H, m), 3.12-3.14 (1H, m), 3.41 (3H, s), 3.50 (1H, br s), 3.58 (2H, s), 3.89-3.92 (1H, m), 4.13-4.26 (3H, m), 4.43-4.45 (1H, m), 6.38 (1H, s), 7.56 (1H, d, J=9.16 Hz), 11.81 (1H, br s).

(64f) cis(±)-[2-(4-{[(4-Chloro-5-ethyl-1H-imidazol-2-yl)carbonyl]amino}-3-methoxypiperidin-1-yl)-1,3-thiazol-4-yl]acetic acid The same operation as in Example (1i) was performed using ethyl cis(±)-[2-(4-{[(4-chloro-5-ethyl-1H-imidazol-2-yl)carbonyl]amino}-3-methoxypiperidin-1-yl)-1,3-thiazol-4-yl]acetate obtained in Example (64e) (42.6 mg, 0.093 mmol) and a 2 N aqueous lithium hydroxide solution, (0.8 mL) to obtain 22.0 mg of the title compound as a red solid (55%).

$^1$H NMR spectrum (400 MHz, DMSO-d$_6$) δ ppm: 1.14 (3H, t, J=7.55 Hz), 1.67-1.68 (1H, m), 1.87-1.89 (1H, m), 2.55 (2H, q, J=7.55 Hz), 3.23-3.26 (2H, m), 3.33 (3H, s), 3.47-3.55 (4H, m), 3.79-3.82 (1H, m), 4.18-4.20 (2H, m), 6.55 (1H, s), 7.65 (1H, d, J=8.59 Hz).

mass spectrum (ESI): m/z 428 (M+H)$^+$.

Example 65 cis(±)-[2-(4-{[(4-Chloro-5-ethyl-1H-imidazol-2-yl)carbonyl]amino}-3-methoxypiperidin-1-yl)-5-methyl-1,3-thiazol-4-yl]acetic acid (Exemplified Compound No. 65)

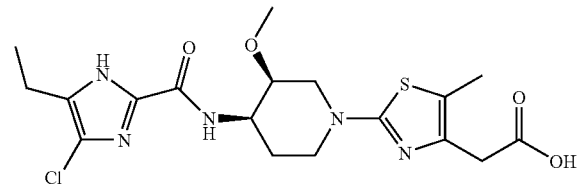

(65a) Methyl 4-bromo-3-oxopentanoate

Methyl 3-oxopentanoate (1 g, 7.68 mmol) was dissolved in chloroform (30 mL). Bromine (0.4 mL, 7.80 mmol) was added under ice-cooling and the mixture was stirred for 40 minutes. The reaction solution was washed with saturated aqueous sodium bicarbonate solution, dried over anhydrous sodium sulfate and then concentrated under reduced pressure. The resulting compound was used for the next reaction without purification.

(65b) cis(±)-4-Chloro-5-ethyl-N-[1-(1H-imidazol-1-ylthiocarbonyl)-3-methoxypiperidin-4-yl]-1H-imidazole-2-carboxamide tert-Butyl cis(±)-4-{[(4-chloro-5-ethyl-1H-imidazol-2-yl)carbonyl]amino}-3-methoxypiperidine-1-carboxylate obtained by the method described in Example (1g) (130 mg, 0.34 mmol) was dissolved in methanol (1 mL). A 4 N hydrochloric acid/ethyl acetate solution (3 mL) was added, and the mixture was stirred for 15 minutes. The reaction solution was concentrated under reduced pressure, and then the same operation as in Example (64a) was performed using 1,1'-thiocarbonyldiimidazole (81 mg, 0.45 mmol), to obtain the title compound. The resulting compound was used for the next reaction without purification.

(65c) cis(±)-N-(1-Carbamothioyl-3-methoxypiperidin-4-yl)-4-chloro-5-ethyl-1H-imidazole-2-carboxamide The same operation as in Example (64b) was performed using cis(±)-4-chloro-5-ethyl-N-[1-(1H-imidazol-1-ylthiocarbonyl)-3-methoxypiperidin-4-yl]-1H-imidazole-2-carboxamide obtained in Example (65b) (about 0.34 mmol) and a 2 N ammonia/methanol solution (5 mL), to obtain 80.4 mg of the title compound as a white solid (69%).

mass spectrum (ESI): m/z 346 (M+H)$^+$.

(65d) Methyl cis(±)-[2-(4-{[(4-chloro-5-ethyl-1H-imidazol-2-yl)carbonyl]amino}-3-methoxypiperidin-1-yl)-5-methyl-1,3-thiazol-4-yl]acetate The same operation as in Example (22b) was performed using cis(±)-N-(1-carbamothioyl-3-methoxypiperidin-4-yl)-4-chloro-5-ethyl-1H-imidazole-2-carboxamide (40 mg, 0.12 mmol) obtained in Example (65c) and methyl 4-bromo-3-oxopentanoate obtained in Example (65a) (45 mg, 0.22 mmol), to obtain 44.5 mg of the title compound (84%).

$^1$H NMR spectrum (400 MHz, CDCl$_3$) δ ppm: 1.26 (3H, t, J=7.68 Hz), 1.73-1.77 (1H, m), 2.03-2.06 (1H, m), 2.23 (3H, s), 2.69 (2H, q, J=7.68 Hz), 2.97-3.00 (1H, m), 3.07-3.09 (1H, m), 3.41 (3H, s), 3.48 (1H, br s), 3.52 (2H, s), 3.69 (3H, s), 3.82-3.83 (1H, m), 4.19-4.21 (1H, m), 4.35-4.38 (1H, m), 7.54 (1H, d, J=8.59 Hz), 11.75 (1H, br s).

(65e) cis(±)-[2-(4-{[(4-Chloro-5-ethyl-1H-imidazol-2-yl)carbonyl]amino}-3-methoxypiperidin-1-yl)-5-methyl-1,3-thiazol-4-yl]acetic acid The same operation as in Example (1i) was performed using methyl cis(±)-[2-(4-{[(4-chloro-5-ethyl-1H-imidazol-2-yl)carbonyl]amino}-3-methoxypiperidin-1-yl)-5-methyl-1,3-thiazol-4-yl]acetate obtained in Example (65d) (44.5 mg, 0.098 mmol) and a 2 N aqueous lithium hydroxide solution (0.8 mL), to obtain 35.6 mg of the title compound as a pale yellow solid (83%).

$^1$H NMR spectrum (400 MHz, DMSO-d$_6$) δ ppm: 1.14 (3H, t, J=7.45 Hz), 1.63-1.65 (1H, m), 1.83-1.86 (1H, m), 2.17 (3H, s), 2.55 (2H, q, J=7.45 Hz), 3.11-3.14 (2H, m), 3.30-3.35 (2H, m), 3.37 (3H, s), 3.51 (1H, br s), 3.71-3.74 (1H, m), 4.11-4.15 (2H, m), 7.60 (1H, d, J=8.59 Hz).

mass spectrum (ESI): m/z 442 (M+H)$^+$.

Example 66

4-Chloro-5-ethyl-N-[(3S,4R)-3-methoxy-1-(5-methyl-1,3-thiazol-2-yl)piperidin-4-yl]-1H-imidazole-2-carboxamide (Exemplified Compound No. 66)

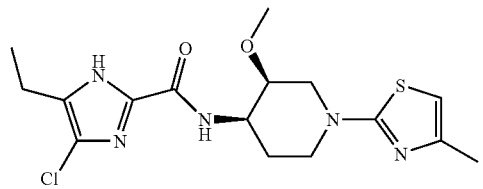

(66a) 4-Chloro-5-ethyl-N-[(3S,4R)-3-methoxy-1-(5-methyl-1,3-thiazol-2-yl)piperidin-4-yl]-1H-imidazole-2-carboxamide 2-[(3S,4R)-4-{[(4-Chloro-5-ethyl-1H-imidazol-2-yl)carbonyl]amino}-3-methoxypiperidin-1-yl]-4-methyl-1,3-thiazole-5-carboxylic acid obtained by the method described in Example (56d) (15 mg, 0.035 mmol) was dissolved in THF (3 mL). 1 N hydrochloric acid (1 mL) was added, and the mixture was stirred at 60° C. for 40 minutes. A 1 N aqueous sodium hydroxide solution was added to the reaction solution, followed by extraction with ethyl acetate. Then, the organic layer was washed with brine and dried over anhydrous sodium sulfate. Following concentration under reduced pressure, the residue was purified by silica gel column chromatography (elution solvent: hexane/ethyl acetate=1/1, ethyl acetate) to obtain 13.5 mg of the title compound as a white solid (100%).

$^1$H NMR spectrum (400 MHz, CDCl$_3$) δ ppm: 1.27 (3H, t, J=7.55 Hz), 1.77-1.80 (1H, m), 2.06-2.11 (1H, m), 2.24 (3H, s), 2.69 (2H, q, J=7.55 Hz), 3.04-3.15 (2H, m), 3.42 (3H, s), 3.51 (1H, br s), 3.92-3.95 (1H, m), 4.22-4.25 (1H, m), 4.39-4.40 (1H, m), 6.11 (1H, s), 7.56 (1H, d, J=8.59 Hz), 11.70 (1H, br s).

Example 67 cis(±)-[2-(4-{[(4-Chloro-5-ethyl-1H-imidazol-2-yl)carbonyl]amino}-3-methoxypiperidin-1-yl)-1,3-thiazol-4-yl]cyclopropanecarboxylic acid (Exemplified Compound No. 67)

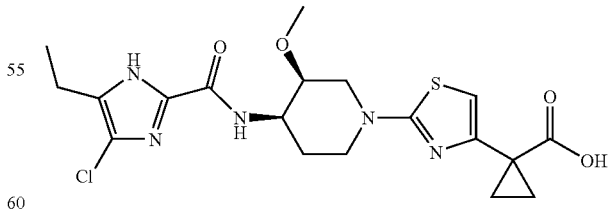

(67a) Ethyl cis(±)-[2-(4-{[(4-chloro-5-ethyl-1H-imidazol-2-yl)carbonyl]amino}-3-methoxypiperidin-1-yl)-1,3-thiazol-4-yl]cyclopropanecarboxylate The same operation as in Example (22b) was performed using cis(±)-N-(1-carbamothioyl-3-methoxypiperidin-4-yl)-4-chloro-5-ethyl-1H-imidazole-2-carboxamide obtained by the method described in Example (65c) (40 mg, 0.12 mmol) and ethyl 1-(bromoacetyl)cyclopropanecarboxylate obtained according to a method known in the literature (Heterocycles, 63, 3, 2004, 699-706) (60 mg, 0.26 mmol), to obtain 23.5 mg of the title compound as a colorless oily substance (42%).

$^1$H NMR spectrum (400 MHz, CDCl$_3$) δ ppm: 1.12-1.31 (6H, m), 1.37-1.48 (2H, m), 1.53-1.63 (2H, m), 1.77-1.78 (1H, m), 2.05-2.09 (1H, m), 2.69 (2H, q, J=7.64 Hz), 3.00-3.02 (1H, m), 3.10-3.12 (1H, m), 3.41 (3H, s), 3.50 (1H, br s), 3.85-3.87 (1H, m), 4.10-4.25 (3H, m), 4.42-4.46 (1H, m), 6.68 (1H, s), 7.54 (1H, d, J=8.59 Hz), 11.67 (1H, br s).

(67b) cis(±)-[2-(4-{[(4-Chloro-5-ethyl-1H-imidazol-2-yl)carbonyl]amino}-3-methoxypiperidin-1-yl)-1,3-thiazol-4-yl]cyclopropanecarboxylic acid The same operation as in Example (1i) was performed using ethyl cis(±)-[2-(4-{[(4-chloro-5-ethyl-1H-imidazol-2-yl)carbonyl]amino}-3-methoxypiperidin-1-yl)-1,3-thiazol-4-yl]cyclopropanecarboxylate obtained in Example (67a) (23.5 mg, 0.049 mmol) and a 2 N aqueous lithium hydroxide solution (0.8 mL), to obtain 14.3 mg of the title compound as a pale yellow solid (65%).

$^1$H NMR spectrum (400 MHz, DMSO-d$_6$) δ ppm: 1.14 (3H, t, J=7.53 Hz), 1.25-1.30 (2H, m), 1.37-1.40 (2H, m), 1.64-1.67 (1H, m), 1.82-1.88 (1H, m), 2.55 (2H, q, J=7.53 Hz), 3.14-3.21 (2H, m), 3.32 (3H, s), 3.52 (1H, br s), 3.72-3.76 (1H, m), 4.15-4.19 (2H, m), 6.73 (1H, s), 7.60 (1H, d, J=8.71 Hz), 12.39 (1H, br s).

mass spectrum (ESI): m/z 454 (M+H)$^+$.

Example 68 cis(±)-2-(4-{[(4-Chloro-5-ethyl-1H-imidazol-2-yl)carbonyl]amino}-3-ethoxypiperidin-1-yl)-4-[(methoxyethyl)carbamoyl]-1,3-thiazole-5-carboxylic acid (Exemplified Compound No. 68)

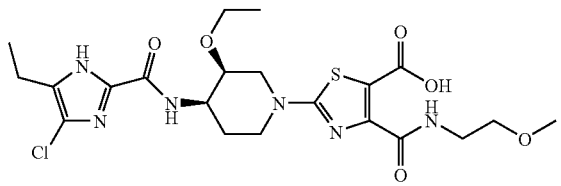

(68a) Ethyl cis(±)-2-(4-{[(4-chloro-5-ethyl-1H-imidazol-2-yl)carbonyl]amino}-3-ethoxypiperidin-1-yl)-4-(hydroxymethyl)-1,3-thiazole-5-carboxylate The same operation as in Example (1h) was performed using tert-butyl cis(±)-4-{[(4-chloro-5-ethyl-1H-imidazol-2-yl)carbonyl]amino}-3-ethoxypiperidine-1-carboxylate obtained by the method described in Example (34a) (600 mg, 1.50 mmol), a 4 N hydrochloric acid/ethyl acetate solution (15 mL), diisopropylethylamine (1.2 mL, 6.89 mmol) and ethyl 2-chloro-4-(hydroxymethyl)-1,3-thiazole-5-carboxylate obtained by the method described in Example (27a) (700 mg, 2.63 mmol), to obtain 607.2 mg of the title compound (83%).

(68b) Ethyl cis(±)-2-(4-{[(4-chloro-5-ethyl-1H-imidazol-2-yl)carbonyl]amino}-3-ethoxypiperidin-1-yl)-4-formyl-1,3-thiazole-5-carboxylate The same operation as in Example (28a) was performed using ethyl cis(±)-2-(4-{[(4-chloro-5-ethyl-1H-imidazol-2-yl)carbonyl]amino}-3-ethoxypiperidin-1-yl)-4-(hydroxymethyl)-1,3-thiazole-5-carboxylate obtained in Example (68a) (305 mg, 0.63 mmol) and the Dess-Martin reagent (365 mg, 0.86 mmol), to obtain 319.4 mg of the title compound (100%).

(68c) cis(±)-2-(4-{[(4-Chloro-5-ethyl-1H-imidazol-2-yl)carbonyl]amino}-3-ethoxypiperidin-1-yl)-5-(ethoxycarbonyl)-1,3-thiazole-4-carboxylic acid The same operation as in Example (33c) was performed using ethyl cis(±)-2-(4-{[(4-chloro-5-ethyl-1H-imidazol-2-yl)carbonyl]amino}-3-ethoxypiperidin-1-yl)-4-formyl-1,3-thiazole-5-carboxylate obtained in Example (68b) (about 0.63 mmol), sodium chlorite (113 mg, 1.25 mmol), sodium dihydrogenphosphate (320 mg, 2.05 mmol) and 2-methyl-2-butene (0.33 mL, 3.12 mmol), to obtain 312.7 mg of the title compound as a white solid (99%).

$^1$H NMR spectrum (400 MHz, DMSO-d$_6$) δ ppm: 1.08 (3H, t, J=6.87 Hz), 1.15-1.17 (6H, m), 1.65-1.67 (1H, m), 1.85-1.86 (1H, m), 2.52-2.57 (2H, m), 3.20-3.23 (1H, m), 3.31-3.33 (2H, m), 3.40-3.46 (1H, m), 3.63-3.65 (2H, m), 3.98-4.10 (3H, m), 4.17-4.19 (1H, m), 7.66 (1H, d, J=8.59 Hz).

(68d) Ethyl cis(±)-2-(4-{[(4-chloro-5-ethyl-1H-imidazol-2-yl)carbonyl]amino}-3-ethoxypiperidin-1-yl)-4-[(methoxyethyl)carbamoyl]-1,3-thiazole-5-carboxylate The same operation as in Example (1g) was performed using cis(±)-2-(4-{[(4-chloro-5-ethyl-1H-imidazol-2-yl)carbonyl]amino}-3-ethoxypiperidin-1-yl)-5-(ethoxycarbonyl)-1,3-thiazole-4-carboxylic acid obtained in Example (68c) (112 mg, 0.22 mmol), methoxyethylamine (40 μL, 0.46 mmol), WSC hydrochloride (130 mg, 0.68 mmol) and HOBT (30 mg, 0.22 mmol), to obtain 88.8 mg of the title compound as a white solid (71%).

$^1$H NMR spectrum (400 MHz, CDCl$_3$) δ ppm: 1.16 (3H, t, J=7.11 Hz), 1.26 (3H, t, J=7.53 Hz), 1.34 (3H, t, J=7.11 Hz), 1.77-1.80 (1H, m), 2.04-2.10 (1H, m), 2.69 (2H, q, J=7.53 Hz), 3.15-3.27 (2H, m), 3.39 (3H, s), 3.42-3.46 (1H, m), 3.57-3.65 (5H, m), 3.73-3.77 (1H, m), 4.06-4.10 (1H, m), 4.21-4.34 (3H, m), 4.41-4.45 (1H, m), 7.43 (1H, d, J=9.17 Hz), 8.42-8.44 (1H, m), 10.73 (1H, br s).

(68e) cis(±)-2-(4-{[(4-Chloro-5-ethyl-1H-imidazol-2-yl)carbonyl]amino}-3-ethoxypiperidin-1-yl)-4-[(methoxyethyl)carbamoyl]-1,3-thiazole-5-carboxylic acid The same operation as in Example (1i) was performed using ethyl cis(±)-2-(4-{[(4-chloro-5-ethyl-1H-imidazol-2-yl)carbonyl]amino}-3-ethoxypiperidin-1-yl)-4-[(methoxyethyl)carbamoyl]-1,3-thiazole-5-carboxylate obtained in Example (68d) (85 mg, 0.15 mmol) and a 2 N aqueous lithium hydroxide solution (1.2 mL), to obtain 65.1 mg of the title compound as a pale yellow solid (81%).

$^1$H NMR spectrum (400 MHz, DMSO-d$_6$) δ ppm: 1.03 (3H, t, J=6.87 Hz), 1.14 (3H, t, J=7.55 Hz), 1.68-1.71 (1H, m), 1.86-1.91 (1H, m), 2.55 (2H, q, J=7.55 Hz), 3.27 (3H, s), 3.32-3.34 (2H, m), 3.40-3.54 (7H, m), 3.65-3.69 (2H, m), 4.20-4.23 (1H, m), 7.65 (1H, d, J=8.59 Hz), 9.32-9.33 (1H, m).

mass spectrum (ESI): m/z 530 (M+H)$^+$.

Example 69 cis(±)-2-(4-{[(4-Chloro-5-ethyl-1H-imidazol-2-yl)carbonyl]amino}-3-methoxypiperidin-1-yl)-4-(dimethylcarbamoyl)-1,3-thiazole-5-carboxylic acid (Exemplified Compound No. 69)

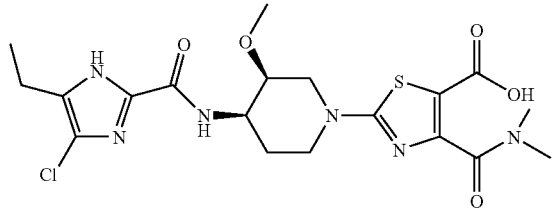

(69a) Ethyl cis(±)-2-(4-{[(4-chloro-5-ethyl-1H-imidazol-2-yl)carbonyl]amino}-3-methoxypiperidin-1-yl)-4-(dimethylcarbamoyl)-1,3-thiazole-5-carboxylate The same operation as in Example (1g) was performed using cis(±)-2-(4-{[(4-chloro-5-ethyl-1H-imidazol-2-yl)carbonyl]amino}-3-methoxypiperidin-1-yl)-5-(ethoxycarbonyl)-1,3-thiazole-4-carboxylic acid obtained by the method described in Example (50a) (65 mg, 0.13 mmol), dimethylamine hydrochloride (29 mg, 0.36 mmol), WSC hydrochloride (78 mg, 0.41 mmol) and HOBT (20 mg, 0.15 mmol), to obtain 52.9 mg of the title compound (77%).

$^1$H NMR spectrum (400 MHz, CDCl$_3$) δ ppm: 1.21-1.35 (6H, m), 1.77-1.81 (1H, m), 2.00-2.03 (1H, m), 2.69 (2H, q, J=7.64 Hz), 2.91 (3H, s), 3.11 (3H, s), 3.15 (1H, br s), 3.19-3.29 (1H, m), 3.42 (3H, s), 3.51 (1H, br s), 3.98-4.01 (1H, m), 4.23-4.27 (3H, m), 4.53-4.56 (1H, m), 7.46 (1H, d, J=8.71 Hz), 11.07 (1H, br s).

(69b) cis(±)-2-(4-{[(4-Chloro-5-ethyl-1H-imidazol-2-yl)carbonyl]amino}-3-methoxypiperidin-1-yl)-4-(dimethylcarbamoyl)-1,3-thiazole-5-carboxylic acid The same operation as in Example (1i) was performed using ethyl cis(±)-2-(4-{[(4-chloro-5-ethyl-1H-imidazol-2-yl)carbonyl]amino}-3-methoxypiperidin-1-yl)-4-(dimethylcarbamoyl)-1,3-thiazole-5-carboxylate obtained in Example (69a) (52.9 mg, 0.10 mmol) and a 2 N aqueous lithium hydroxide solution (0.8 mL), to obtain 39.2 mg of the title compound as a pale yellow solid (78%).

$^1$H NMR spectrum (400 MHz, DMSO-d$_6$) δ ppm: 1.14 (3H, t, J=7.57 Hz), 1.67-1.69 (1H, m), 1.86-1.88 (1H, m), 2.55-2.57 (2H, m), 2.78 (3H, s), 2.91 (3H, s), 3.30-3.33 (2H, m), 3.33 (3H, s), 3.56 (1H, br s), 3.83-3.94 (1H, m), 4.20-4.22 (2H, m), 7.67 (1H, d, J=8.71 Hz).

mass spectrum (ESI): m/z 485 (M+H)$^+$.

Example 70 cis(±)-2-(4-{[(4-Chloro-5-ethyl-1H-imidazol-2-yl)carbonyl]amino}-3-methoxypiperidin-1-yl)-5-ethyl-1,3-thiazole-4-carboxylic acid (Exemplified Compound No. 70)

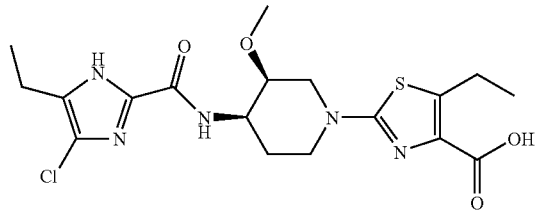

(70a) Butyl cis(±)-2-(4-{[(4-chloro-5-ethyl-1H-imidazol-2-yl)carbonyl]amino}-3-methoxypiperidin-1-yl)-5-ethyl-1,3-thiazole-4-carboxylate The same operation as in Example (22b) was performed using cis(±)-N-(1-carbamothioyl-3-methoxypiperidin-4-yl)-4-chloro-5-ethyl-1H-imidazole-2-carboxamide obtained by the method described in Example (65c) (78.5 mg, 0.23 mmol) and butyl 3-bromo-2-oxopentanoate obtained in Example (110a) (95 mg, 0.38 mmol), to obtain 87.8 mg of the title compound (78%).

$^1$H NMR spectrum (400 MHz, CDCl$_3$) δ ppm: 0.96 (3H, t, J=7.45 Hz), 1.21-1.34 (6H, m), 1.40-1.49 (2H, m), 1.70-1.80 (3H, m), 2.02-2.12 (1H, m), 2.69 (2H, q, J=7.64 Hz), 3.04-3.20 (4H, m), 3.43 (3H, s), 3.51 (1H, br s), 3.90-3.97 (1H, m), 4.19-4.34 (3H, m), 4.37-4.44 (1H, m), 7.57 (1H, d, J=8.59 Hz), 12.10 (1H, br s).

(70b) cis(±)-2-(4-{[(4-Chloro-5-ethyl-1H-imidazol-2-yl)carbonyl]amino}-3-methoxypiperidin-1-yl)-5-ethyl-1,3-thiazole-4-carboxylic acid The same operation as in Example (1i) was performed using butyl cis(±)-2-(4-{[(4-chloro-5-ethyl-1H-imidazol-2-yl)carbonyl]amino}-3-methoxypiperidin-1-yl)-5-ethyl-1,3-thiazole-4-carboxylate obtained in Example (70a) (80 mg, 0.16 mmol) and a 2 N aqueous lithium hydroxide solution (2 mL), to obtain 49.2 mg of the title compound as a pale yellow solid (69%).

$^1$H NMR spectrum (400 MHz, DMSO-d$_6$) δ ppm: 1.12-1.19 (6H, m), 1.64-1.67 (1H, m), 1.84-1.91 (1H, m), 2.55 (2H, q, J=7.64 Hz), 3.02 (2H, q, J=7.45 Hz), 3.14-3.21 (2H, m), 3.33 (3H, s), 3.53 (1H, br s), 3.77-3.85 (1H, m), 4.14-4.17 (2H, m), 7.63 (1H, d, J=8.59 Hz).

mass spectrum (ESI): m/z 442 (M+H)$^+$.

Example 71 cis(±)-2-(4-{[(4,5-Diiodo-1H-imidazol-2-yl)carbonyl]amino}-3-methoxypiperidin-1-yl)-4-methyl-1,3-thiazole-5-carboxylic acid (Exemplified Compound No. 71)

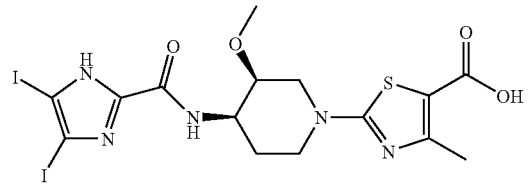

(71a) Ethyl 4,5-diiodoimidazole-2-carboxylate

The same operation as in Example (1c) was performed using ethyl 1H-imidazole-2-carboxylate (200 mg, 1.43 mmol) and NIS (970 mg, 4.31 mmol), to obtain 439.8 mg of the title compound (79%).

mass spectrum (ESI): m/z 560 (M+H)$^+$.

(71b) 4,5-Diiodoimidazole-2-carboxylic acid

The same operation as in Example (1d) was performed using ethyl 4,5-diiodoimidazole-2-carboxylate obtained in Example (71a) (132 mg, 0.34 mmol) and a 3 N aqueous lithium hydroxide solution (3 mL), to obtain 127.7 mg of the title compound as a white solid (100%).

mass spectrum (ESI): m/z 364 (M+H)$^+$.

(71c) tert-Butyl cis(±)-4-{[(4,5-diiodo-1H-imidazol-2-yl)carbonyl]amino}-3-methoxypiperidine-1-carboxylate The same operation as in Example (1g) was performed using tert-butyl cis(±)-4-amino-3-methoxypiperidine-1-carboxylate obtained by the method described in Example (1e) (170 mg, 0.74 mmol), 4,5-diiodoimidazole-2-carboxylic acid obtained in Example (71b) (about 0.34 mmol), WSC hydrochloride (195 mg, 1.02 mmol) and HOBT (46 mg, 0.34 mmol), to obtain 83.1 mg of the title compound as a white solid (43%).

$^1$H NMR spectrum (400 MHz, CDCl$_3$) δ ppm: 1.47 (9H, s), 1.68-1.70 (1H, m), 1.84-1.86 (1H, m), 2.79-2.82 (2H, m), 3.27-3.43 (4H, m), 4.03-4.05 (1H, m), 4.20-4.22 (1H, m), 4.41-4.51 (1H, m), 7.52 (1H, br s), 11.74 (1H, br s).

(71d) Ethyl cis(±)-2-(4-{[(4,5-diiodo-1H-imidazol-2-yl)carbonyl]amino}-3-methoxypiperidin-1-yl)-4-methyl-1,3-thiazole-5-carboxylate The same operation as in Example (1h) was performed using tert-butyl cis(±)-4-{[(4,5-diiodo-1H-imidazol-2-yl)carbonyl]amino}-3-methoxypiperidine-1-carboxylate obtained in Example (71c) (85 mg, 0.14 mmol), a 4 N hydrochloric acid/ethyl acetate solution (4 ml), sodium carbonate (101 mg, 0.95 mmol) and ethyl 2-bromo-4-methyl-1,3-thiazole-5-carboxylate (58 mg, 0.23 mmol), to obtain 83.4 mg of the title compound (89%).

$^1$H NMR spectrum (400 MHz, CDCl$_3$) δ ppm: 1.33 (3H, t, J=7.16 Hz), 1.82-1.84 (1H, m), 2.03-2.09 (1H, m), 2.54 (3H, s), 3.09-3.12 (1H, m), 3.19-3.21 (1H, m), 3.43 (3H, s), 3.54 (1H, br s), 3.99-4.02 (1H, m), 4.24-4.29 (3H, m), 4.51-4.54 (1H, m), 7.54 (1H, brs).

(71e) cis(±)-2-(4-{[(4,5-Diiodo-1H-imidazol-2-yl)carbonyl]amino}-3-methoxypiperidin-1-yl)-4-methyl-1,3-thiazole-5-carboxylic acid The same operation as in Example (1i) was performed using ethyl cis(±)-2-(4-{[(4,5-diiodo-1H-imidazol-2-yl)carbonyl]amino}-3-methoxypiperidin-1-yl)-4-methyl-1,3-thiazole-5-carboxylate obtained in Example (71d) (83 mg, 0.13 mmol) and 2 N lithium hydroxide (2 mL), to obtain 66.9 mg of the title compound as a white solid (84%).

$^1$H NMR spectrum (400 MHz, DMSO-d$_6$) δ ppm: 1.65-1.68 (1H, m), 1.84-1.89 (1H, m), 2.40 (3H, s), 3.23-3.27 (2H, m), 3.33 (3H, s), 3.56 (1H, br s), 3.90-3.92 (1H, m), 4.16-4.26 (2H, m), 7.74 (1H, d, J=8.59 Hz), 12.39 (1H, br s).

mass spectrum (ESI): m/z 618 (M+H)$^+$.

Example 72 cis(±)-2-(4-{[(4-Chloro-5-ethyl-1H-imidazol-2-yl)carbonyl]amino}-3-methoxypiperidin-1-yl)-4-(dimethylcarbamoyl)-1,3-thiazole-5-carboxylic acid (Exemplified Compound No. 72)

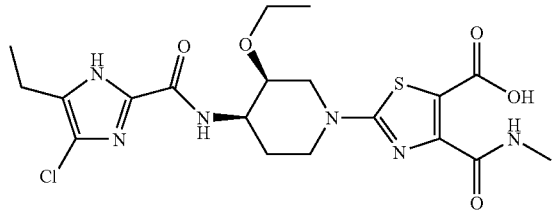

(72a) Ethyl cis(±)-2-(4-{[(4-chloro-5-ethyl-1H-imidazol-2-yl)carbonyl]amino}-3-ethoxypiperidin-1-yl)-4-(methylcarbamoyl)-1,3-thiazole-5-carboxylate The same operation as in Example (1g) was performed using cis(±)-2-(4-{[(4-chloro-5-ethyl-1H-imidazol-2-yl)carbonyl]amino}-3-ethoxypiperidin-1-yl)-5-(ethoxycarbonyl)-1,3-thiazole-4-carboxylic acid obtained by the method described in Example (68c) (100 mg, 0.20 mmol), methylamine hydrochloride (45 mg, 0.67 mmol), WSC hydrochloride (117 mg, 0.61 mmol) and HOBT (23 mg, 0.17 mmol), to obtain 78.6 mg of the title compound as a white solid (77%).

$^1$H NMR spectrum (400 MHz, CDCl$_3$) δ ppm: 1.16 (3H, t, J=6.87 Hz), 1.26 (3H, t, J=7.68 Hz), 1.35 (3H, t, J=7.16 Hz), 1.78-1.79 (1H, m), 2.04-2.12 (1H, m), 2.69 (2H, q, J=7.68 Hz), 2.98 (3H, d, J=5.15 Hz), 3.11-3.26 (2H, m), 3.44-3.46 (1H, m), 3.62 (1H, br s), 3.73-3.76 (1H, m), 4.04-4.14 (1H, m), 4.21-4.35 (3H, m), 4.42-4.45 (1H, m), 7.48 (1H, d, J=9.16 Hz), 8.45-8.52 (1H, m), 11.34 (1H, br s).

(72b) cis(±)-2-(4-{[(4-Chloro-5-ethyl-1H-imidazol-2-yl)carbonyl]amino}-3-ethoxypiperidin-1-yl)-4-(methylcarbamoyl)-1,3-thiazole-5-carboxylic acid The same operation as in Example (1i) was performed using ethyl cis(±)-2-(4-{[(4-chloro-5-ethyl-1H-imidazol-2-yl)carbonyl]amino}-3-ethoxypiperidin-1-yl)-4-(methylcarbamoyl)-1,3-thiazole-5-carboxylate obtained in Example (72a) (78.6 mg, 0.15 mmol) and a 2 N aqueous lithium hydroxide solution (2 mL), to obtain 55.8 mg of the title compound as a pale yellow solid (75%).

$^1$H NMR spectrum (400 MHz, DMSO-d$_6$) δ ppm: 1.03 (3H, t, J=7.16 Hz), 1.14 (3H, t, J=7.55 Hz), 1.68-1.70 (1H, m), 1.88-1.90 (1H, m), 2.55 (2H, q, J=7.55 Hz), 2.86 (3H, d, J=5.15 Hz), 3.31-3.33 (3H, m), 3.42-3.46 (2H, m), 3.64-3.67 (2H, m), 4.20-4.22 (1H, m), 7.66 (1H, d, J=8.59 Hz), 9.32-9.38 (1H, m).

mass spectrum (ESI): m/z 485 (M+H)$^+$.

Example 73 cis(±)-2-(4-{[(4-Chloro-5-ethyl-1H-imidazol-2-yl)carbonyl]amino}-3-propoxypiperidin-1-yl)-4-acetyl-1,3-thiazole-5-carboxylic acid (Exemplified Compound No. 73)

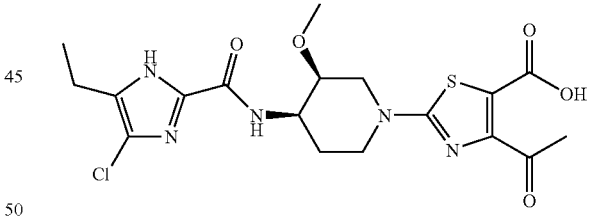

(73a) Methyl cis(±)-2-(4-{[(4-chloro-5-ethyl-1H-imidazol-2-yl)carbonyl]amino}-3-propoxypiperidin-1-yl)-4-acetyl-1,3-thiazole-5-carboxylate The same operation as in Example (1h) was performed using tert-butyl cis(±)-4-{[(4-chloro-5-ethyl-1H-imidazol-2-yl)carbonyl]amino}-3-propoxypiperidine-1-carboxylate obtained by the method described in Example (47a) (180 mg, 0.43 mmol), a 4 N hydrochloric acid/ethyl acetate solution (4 mL), sodium carbonate (300 mg, 2.83 mmol) and methyl 4-acetyl-2-chloro-1,3-thiazole-5-carboxylate obtained by the method described in Example (55a) (100 mg, 0.46 mmol), to obtain 215.5 mg of the title compound as a yellow foamy substance (99%).

$^1$H NMR spectrum (400 MHz, CDCl$_3$) δ ppm: 0.88 (3H, t, J=7.45 Hz), 1.27 (3H, t, J=7.55 Hz), 1.54-1.58 (2H, m), 1.80-1.81 (1H, m), 2.04-2.13 (1H, m), 2.55 (3H, s), 2.69 (2H, q, J=7.55 Hz), 3.14-3.15 (1H, m), 3.23-3.26 (1H, m), 3.32-3.34 (1H, m), 3.62-3.65 (2H, m), 3.81 (3H, s), 3.95-4.03 (1H, m), 4.23-4.26 (1H, m), 4.46-4.49 (1H, m), 7.48 (1H, d, J=9.16 Hz), 10.99 (1H, br s).

(73b) cis(±)-2-(4-{[(4-Chloro-5-ethyl-1H-imidazol-2-yl)carbonyl]amino}-3-propoxypiperidin-1-yl)-4-acetyl-1,3-thiazole-5-carboxylic acid The same operation as in Example (1i) was performed using methyl cis(±)-2-(4-{[(4-chloro-5-ethyl-1H-imidazol-2-yl)carbonyl]amino}-3-propoxypiperidin-1-yl)-4-acetyl-1,3-thiazole-5-carboxylate obtained in Example (73a) (212 mg, 0.43 mmol) and a 2 N aqueous lithium hydroxide solution (2.5 mL), to obtain 183.4 mg of the title compound as a yellow solid (89%).

$^1$H NMR spectrum (400 MHz, DMSO-$d_6$) δ ppm: 0.82 (3H, t, J=7.45 Hz), 1.14 (3H, t, J=7.55 Hz), 1.43-1.46 (2H, m), 1.68-1.71 (1H, m), 1.86-1.91 (1H, m), 2.48 (3H, s), 2.55 (2H, q, J=7.55 Hz), 3.32-3.38 (3H, m), 3.54-3.57 (1H, m), 3.66 (1H, br s), 3.93-3.95 (1H, m), 4.19-4.22 (1H, m), 7.65 (1H, d, J=8.59 Hz).

mass spectrum (ESI): m/z 484 (M+H)$^+$.

Example 74 cis(±)-2-(4-{[(4-Chloro-5-ethyl-1H-imidazol-2-yl)carbonyl]amino}-3-propoxypiperidin-1-yl)-4-[(methoxyethyl)carbamoyl]-1,3-thiazole-5-carboxylic acid (Exemplified Compound No. 74)

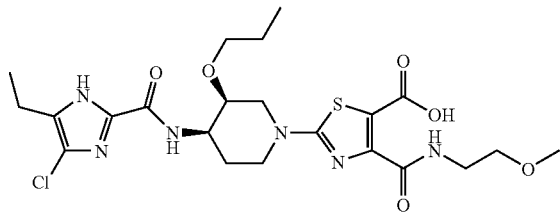

(74a) Ethyl cis(±)-2-(4-{[(4-chloro-5-ethyl-1H-imidazol-2-yl)carbonyl]amino}-3-propoxypiperidin-1-yl)-4-(hydroxymethyl)-1,3-thiazole-5-carboxylate The same operation as in Example (1h) was performed using tert-butyl cis(±)-4-{[(4-chloro-5-ethyl-1H-imidazol-2-yl)carbonyl]amino}-3-propoxypiperidine-1-carboxylate obtained by the method described in Example (47a) (440 mg, 1.50 mmol), a 4 N hydrochloric acid/ethyl acetate solution (6 mL), sodium carbonate (600 mg, 5.66 mmol) and ethyl 2-chloro-4-(hydroxymethyl)-1,3-thiazole-5-carboxylate obtained by the method described in Example (27a) (423 mg, 1.59 mmol), to obtain 493.6 mg of the title compound (93%).

$^1$H NMR spectrum (400 MHz, CDCl$_3$) δ ppm: 0.87 (3H, t, J=7.45 Hz), 1.26 (3H, t, J=7.80 Hz), 1.34 (3H, t, J=7.16 Hz), 1.51-1.62 (2H, m), 1.78-1.81 (1H, m), 2.03-2.12 (1H, m), 2.69 (2H, q, J=7.80 Hz), 3.13-3.15 (1H, m), 3.23-3.25 (1H, m), 3.32-3.34 (1H, m), 3.61-3.64 (2H, m), 3.97-3.98 (2H, m), 4.25-4.28 (3H, m), 4.45-4.47 (1H, m), 4.76-4.80 (2H, m), 7.45 (1H, d, J=9.16 Hz), 10.65 (1H, br s).

(74b) Ethyl cis(±)-2-(4-{[(4-chloro-5-ethyl-1H-imidazol-2-yl)carbonyl]amino}-3-propoxypiperidin-1-yl)-4-formyl-1,3-thiazole-5-carboxylate The same operation as in Example (28a) was performed using ethyl cis(±)-2-(4-{[(4-chloro-5-ethyl-1H-imidazol-2-yl)carbonyl]amino}-3-propoxypiperidin-1-yl)-4-(hydroxymethyl)-1,3-thiazole-5-carboxylate obtained in Example (74a) (490 mg, 0.98 mmol) and the Dess-Martin reagent (500 mg, 1.18 mmol), to obtain 448.1 mg of the title compound as a yellow solid (92%).

$^1$H NMR spectrum (400 MHz, CDCl$_3$) δ ppm: 0.84 (3H, t, J=7.45 Hz), 1.26 (3H, t, J=7.55 Hz), 1.38 (3H, t, J=7.21 Hz), 1.48-1.59 (2H, m), 1.80-1.81 (1H, m), 2.09-2.13 (1H, m), 2.69 (2H, q, J=7.55 Hz), 3.17-3.19 (1H, m), 3.27-3.33 (2H, m), 3.62-3.67 (2H, m), 4.03-4.15 (1H, m), 4.22-4.30 (1H, m), 4.37 (2H, q, J=7.21 Hz), 4.50-4.52 (1H, m), 7.46 (1H, d, J=9.16 Hz), 10.50 (1H, s), 10.98 (1H, br s).

(74c) cis(±)-2-(4-{[(4-Chloro-5-ethyl-1H-imidazol-2-yl)carbonyl]amino}-3-propoxypiperidin-1-yl)-5-(ethoxycarbonyl)-1,3-thiazole-4-carboxylic acid The same operation as in Example (33c) was performed using ethyl cis(±)-2-(4-{[(4-chloro-5-ethyl-1H-imidazol-2-yl)carbonyl]amino}-3-propoxypiperidin-1-yl)-4-formyl-1,3-thiazole-5-carboxylate obtained in Example (74b) (445 mg, 0.89 mmol), sodium chlorite (180 mg, 1.99 mmol), sodium dihydrogenphosphate (557.6 mg, 3.57 mmol) and 2-methyl-2-butene (0.57 mL, 5.36 mmol), to obtain 445.4 mg of the title compound as a white solid (97%).

$^1$H NMR spectrum (400 MHz, DMSO-$d_6$) δ ppm: 0.84 (3H, t, J=7.34 Hz), 1.12-1.24 (6H, m), 1.45-1.48 (2H, m), 1.65-1.68 (1H, m), 1.83-1.89 (1H, m), 2.51-2.59 (2H, m), 3.15-3.28 (2H, m), 3.54-3.57 (1H, m), 3.63 (1H, br s), 3.95-3.98 (1H, m), 4.07-4.09 (3H, m), 4.13-4.16 (2H, m), 7.63-7.70 (1H, m).

(74d) Ethyl cis(±)-2-(4-{[(4-chloro-5-ethyl-1H-imidazol-2-yl)carbonyl]amino}-3-propoxypiperidin-1-yl)-4-[(methoxyethyl)carbamoyl]-1,3-thiazole-5-carboxylate The same operation as in Example (1g) was performed using cis(±)-2-(4-{[(4-chloro-5-ethyl-1H-imidazol-2-yl)carbonyl]amino}-3-propoxypiperidin-1-yl)-5-(ethoxycarbonyl)-1,3-thiazole-4-carboxylic acid obtained in Example (74c) (222 mg, 0.43 mmol), methoxyethylamine (0.1 mL, 1.15 mmol), WSC hydrochloride (260 mg, 1.36 mmol) and HOBT (55 mg, 0.41 mmol), to obtain 154.6 mg of the title compound as a white solid (63%).

$^1$H NMR spectrum (400 MHz, CDCl$_3$) δ ppm: 0.87 (3H, t, J=7.34 Hz), 1.26 (3H, t, J=7.60 Hz), 1.34 (3H, t, J=7.11 Hz), 1.50-1.62 (2H, m), 1.80-1.85 (1H, m), 2.05-2.15 (1H, m), 2.69 (2H, q, J=7.60 Hz), 3.12-3.28 (2H, m), 3.30-3.36 (1H, m), 3.39 (3H, s), 3.55-3.69 (6H, m), 4.07-4.15 (1H, m), 4.20-4.36 (3H, m), 4.39-4.51 (1H, m), 7.53 (1H, d, J=8.71 Hz), 8.45-8.52 (1H, m), 11.80 (1H, br s).

(74e) cis(±)-2-(4-{[(4-Chloro-5-ethyl-1H-imidazol-2-yl)carbonyl]amino}-3-propoxypiperidin-1-yl)-4-[(methoxyethyl)carbamoyl]-1,3-thiazole-5-carboxylic acid The same operation as in Example (1i) was performed using ethyl cis(±)-2-(4-{[(4-chloro-5-ethyl-1H-imidazol-2-yl)carbonyl]amino}-3-propoxypiperidin-1-yl)-4-[(methoxyethyl)carbamoyl]-1,3-thiazole-5-carboxylate obtained in Example (74d) (154.6 mg, 0.27 mmol) and a 2 N aqueous lithium hydroxide solution (2.5 mL), to obtain 117.6 mg of the title compound as a white solid (80%).

$^1$H NMR spectrum (400 MHz, DMSO-$d_6$) δ ppm: 0.79 (3H, t, J=7.45 Hz), 1.14 (3H, t, J=7.55 Hz), 1.37-1.47 (2H, m), 1.70-1.71 (1H, m), 1.83-1.95 (1H, m), 2.55 (2H, q, J=7.55 Hz), 3.34-3.38 (7H, m), 3.45-3.52 (5H, m), 3.58-3.60 (1H, m), 3.67 (1H, br s), 4.20-4.23 (1H, m), 7.65 (1H, d, J=8.59 Hz), 9.35 (1H, br s).

mass spectrum (ESI): m/z 544 (M+H)$^+$.

Example 75 cis(±)-2-(4-{[(4-Chloro-5-ethyl-1H-imidazol-2-yl)carbonyl]amino}-3-propoxypiperidin-1-yl)-4-(methylcarbamoyl)-1,3-thiazole-5-carboxylic acid (Exemplified Compound No. 75)

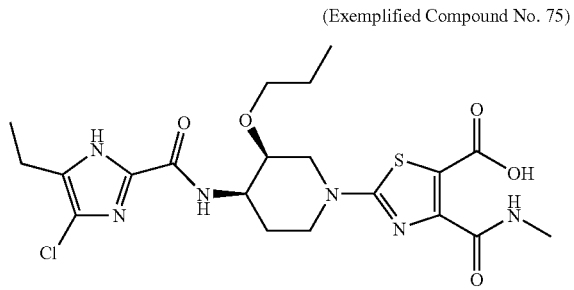 [SMILES: CCCO[C@H]1CN(c2nc(C(=O)NC)c(C(=O)O)s2)CC[C@H]1NC(=O)c1nc(Cl)c(CC)[nH]1]

(75a) Ethyl cis(±)-2-(4-{[(4-chloro-5-ethyl-1H-imidazol-2-yl)carbonyl]amino}-3-propoxypiperidin-1-yl)-4-(methylcarbamoyl)-1,3-thiazole-5-carboxylate The same operation as in Example (1g) was performed using cis(±)-2-(4-{[(4-chloro-5-ethyl-1H-imidazol-2-yl)carbonyl]amino}-3-propoxypiperidin-1-yl)-5-(ethoxycarbonyl)-1,3-thiazole-4-carboxylic acid obtained by the method described in Example (74c) (223 mg, 0.43 mmol), methylamine hydrochloride (60 mg, 0.89 mmol), WSC hydrochloride (260 mg, 1.36 mmol) and HOBT (60 mg, 0.44 mmol), to obtain 142.5 mg of the title compound as a white solid (77%).

$^1$H NMR spectrum (400 MHz, CDCl$_3$) δ ppm: 0.86 (3H, t, J=7.45 Hz), 1.26 (3H, t, J=7.68 Hz), 1.35 (3H, t, J=7.16 Hz), 1.53-1.56 (2H, m), 1.77-1.81 (1H, m), 2.05-2.10 (1H, m), 2.68 (2H, q, J=7.68 Hz), 2.98 (3H, d, J=5.15 Hz), 3.14-3.19 (1H, m), 3.23-3.26 (1H, m), 3.32-3.34 (1H, m), 3.61-3.67 (2H, m), 4.03-4.12 (1H, m), 4.21-4.33 (3H, m), 4.44-4.47 (1H, m), 7.45 (1H, d, J=9.16 Hz), 8.41-8.48 (1H, m), 10.80 (1H, br s).

(75b) cis(±)-2-(4-{[(4-Chloro-5-ethyl-1H-imidazol-2-yl)carbonyl]amino}-3-propoxypiperidin-1-yl)-4-(methylcarbamoyl)-1,3-thiazole-5-carboxylic acid The same operation as in Example (1i) was performed using ethyl cis(±)-2-(4-{[(4-chloro-5-ethyl-1H-imidazol-2-yl)carbonyl]amino}-3-propoxypiperidin-1-yl)-4-(methylcarbamoyl)-1,3-thiazole-5-carboxylate obtained in Example (75a) (140 mg, 0.27 mmol) and a 2 N aqueous lithium hydroxide solution (2 mL), to obtain 121.5 mg of the title compound as a white solid (92%).

$^1$H NMR spectrum (400 MHz, DMSO-d$_6$) δ ppm: 0.79 (3H, t, J=7.45 Hz), 1.14 (3H, t, J=7.68 Hz), 1.40-1.44 (2H, m), 1.69-1.71 (1H, m), 1.86-1.93 (1H, m), 2.55 (2H, q, J=7.68 Hz), 2.86 (3H, d, J=5.15 Hz), 3.30-3.36 (5H, m), 3.56-3.62 (1H, m), 3.64-3.69 (1H, m), 4.20-4.23 (1H, m), 7.65 (1H, d, J=8.59 Hz), 9.31-9.39 (1H, m).

mass spectrum (ESI): m/z 499 (M+H)$^+$.

Example 76 cis(±)-2-(4-{[(4-Chloro-5-ethyl-1H-imidazol-2-yl)carbonyl]amino}-3-ethoxypiperidin-1-yl)-5-ethyl-1,3-thiazole-4-carboxylic acid (Exemplified Compound No. 76)

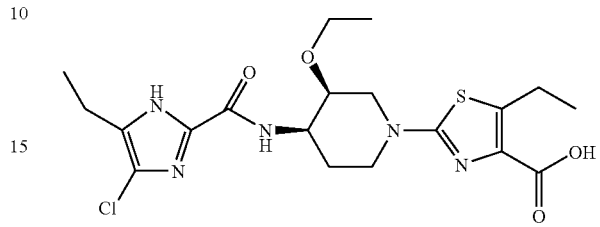

(76a) cis(±)-4-Chloro-5-ethyl-N-[1-(1H-imidazol-1-ylthiocarbonyl)-3-ethoxypiperidin-4-yl]-1H-imidazole-2-carboxamide The same operation as in Example (64a) was performed using tert-butyl cis(±)-4-{[(4-chloro-5-ethyl-1H-imidazol-2-yl)carbonyl]amino}-3-ethoxypiperidine-1-carboxylate obtained by the method described in Example (34a) (300 mg, 0.75 mmol), a 4 N hydrochloric acid/ethyl acetate solution (5 mL) and 1,1'-thiocarbonyldiimidazole (180 mg, 0.91 mmol), to obtain the title compound. The resulting compound was used for the next reaction without purification.

(76b) cis(±)-N-(1-Carbamothioyl-3-ethoxypiperidin-4-yl)-4-chloro-5-ethyl-1H-imidazole-2-carboxamide The same operation as in Example (64b) was performed using cis(±)-4-chloro-5-ethyl-N-[1-(1H-imidazol-1-ylthiocarbonyl)-3-ethoxypiperidin-4-yl]-1H-imidazole-2-carboxamide obtained in Example (76a) (about 0.75 mmol) and a 2 N ammonia/methanol solution (8 mL), to obtain 104.0 mg of the title compound as a white solid (39%).

mass spectrum (ESI): m/z 360 (M+H)$^+$.

(76c) Butyl cis(±)-2-(4-{[(4-chloro-5-ethyl-1H-imidazol-2-yl)carbonyl]amino}-3-ethoxypiperidin-1-yl)-5-ethyl-1,3-thiazole-4-carboxylate The same operation as in Example (22b) was performed using cis(±)-N-(1-carbamothioyl-3-ethoxypiperidin-4-yl)-4-chloro-5-ethyl-1H-imidazole-2-carboxamide obtained in Example (76b) (104 mg, 0.29 mmol) and butyl 3-bromo-2-oxopentanoate obtained by the method described in Example (110a) (113 mg, 0.45 mmol), to obtain 132.1 mg of the title compound (89%).

$^1$H NMR spectrum (400 MHz, CDCl$_3$) δ ppm: 0.96 (3H, t, J=7.45 Hz), 1.17 (3H, t, J=7.16 Hz), 1.23-1.38 (6H, m), 1.41-1.46 (2H, m), 1.72-1.76 (3H, m), 2.05-2.17 (1H, m), 2.69 (2H, q, J=7.64 Hz), 3.06-3.20 (4H, m), 3.38-3.53 (1H, m), 3.60 (1H, br s), 3.73-3.76 (1H, m), 3.95-3.97 (1H, m), 4.18-4.33 (4H, m), 7.54 (1H, d, J=8.59 Hz), 11.73 (1H, br s).

(76d) cis(±)-2-(4-{[(4-Chloro-5-ethyl-1H-imidazol-2-yl)carbonyl]amino}-3-ethoxypiperidin-1-yl)-5-ethyl-1,3-thiazole-4-carboxylic acid The same operation as in Example (1i) was performed using butyl cis(±)-2-(4-{[(4-chloro-5-ethyl-1H-imidazol-2-yl)carbonyl]amino}-3-ethoxypiperidin-1-yl)-5-ethyl-1,3-thiazole-4-carboxylate obtained in Example (76c) (130 mg, 0.25 mmol) and a 2 N aqueous lithium hydroxide solution (2 mL), to obtain 110.3 mg of the title compound as a white solid (95%).

$^1$H NMR spectrum (400 MHz, DMSO-d$_6$) δ ppm: 1.05 (3H, t, J=6.87 Hz), 1.11-1.18 (6H, m), 1.62-1.68 (1H, m), 1.82-1.93 (1H, m), 2.55 (2H, q, J=7.64 Hz), 2.99-3.04 (2H, m), 3.13-3.26 (2H, m), 3.41-3.44 (1H, m), 3.62-3.66 (2H, m), 3.84-3.87 (1H, m), 4.03-4.04 (1H, m), 4.14-4.16 (1H, m), 7.61 (1H, d, J=8.59 Hz), 12.38 (1H, br s).

mass spectrum (ESI): m/z 456 (M+H)$^+$.

Example 77 trans(±)-2-[3-(Butylamino)-4-{[(4-chloro-5-ethyl-1H-imidazol-2-yl)carbonyl]amino}piperidin-1-yl]-1,3-benzothiazole-7-carboxylic acid (Exemplified Compound No. 77)

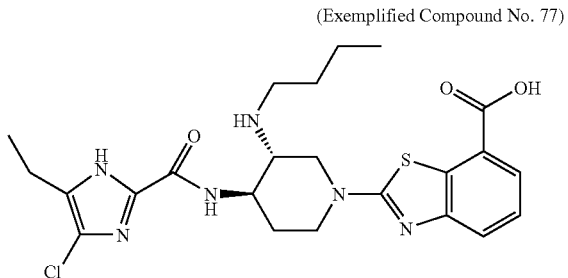 [SMILES: CCCCN[C@@H]1CN(c2nc3cccc(C(=O)O)c3s2)CC[C@H]1NC(=O)c1nc(Cl)c(CC)[nH]1]

(77a) tert-Butyl trans(±)-4-amino-3-hydroxypiperidine-1-carboxylate

The compound was synthesized according to the method described in the following document.

J. Med. Chem., 41, 19, 1998, 3563-3567

(77b) tert-Butyl trans(±)-4-{[(4-chloro-5-ethyl-1H-imidazol-2-yl)carbonyl]amino}-3-hydroxypiperidine-1-carboxylate The same operation as in Example (1g) was performed using tert-butyl trans(±)-4-amino-3-hydroxypiperidine-1-carboxylate obtained in Example (77a) (510 mg, 2.36 mmol), 4-chloro-5-ethyl-1H-imidazole-2-carboxylic acid obtained by the method described in Example (1d) (440 mg, 2.14 mmol), WSC hydrochloride (1.2 g, 6.26 mmol) and HOBT (284 mg, 2.10 mmol), to obtain 604.1 mg of the title compound as a white solid (76%).

$^1$H NMR spectrum (400 MHz, DMSO-d$_6$) δ ppm: 1.14 (3H, t, J=7.45 Hz), 1.40 (9H, s), 1.44-1.51 (1H, m), 1.67-1.74 (1H, m), 2.55 (2H, q, J=7.45 Hz), 3.29-3.32 (4H, m), 3.42-3.48 (1H, m), 3.70-3.74 (1H, m), 3.86-3.99 (2H, m), 5.02 (1H, d, J=5.15 Hz), 8.22 (1H, d, J=9.16 Hz).

(77c) tert-Butyl 4-{[(4-chloro-5-ethyl-1H-imidazol-2-yl)carbonyl]amino}-3-oxopiperidine-1-carboxylate tert-Butyl trans(±)-4-{[(4-chloro-5-ethyl-1H-imidazol-2-yl)carbonyl]amino}-3-hydroxypiperidine-1-carboxylate obtained in Example (77b) (300 mg, 0.80 mmol) was dissolved in DMSO (3 mL). Triethylamine (1.2 mL, 8.61 mmol) and sulfur trioxide-pyridine complex (737 mg, 4.63 mmol) were added, and the mixture was stirred for 15 hours. Ethyl acetate was added, to the reaction solution. This was washed with 5% saline, dried over anhydrous sodium sulfate, and then concentrated under reduced pressure. The resulting compound was used for the next reaction without purification.

(77d) tert-Butyl trans(±)-3-(butylamino)-4-{[(4-chloro-5-ethyl-1H-imidazol-2-yl)carbonyl]amino}piperidine-1-carboxylate and tert-butyl cis(±)-3-(butylamino)-4-{[(4-chloro-5-ethyl-1H-imidazol-2-yl)carbonyl]amino}piperidine-1-carboxylate tert-Butyl 4-{[(4-chloro-5-ethyl-1H-imidazol-2-yl)carbonyl]amino}-3-oxopiperidine-1-carboxylate obtained in Example (77c) (about 0.80 mmol) was dissolved in THF (5 mL). Butylamine (0.24 mL, 2.43 mmol) was added, followed by stirring for two hours. Thereafter, methanol (4 mL), acetic acid (0.2 mL) and sodium cyanoborohydride (171 mg, 2.72 mmol) were added to the reaction solution, followed by stirring for one hour. Saturated aqueous sodium bicarbonate solution was added to the reaction solution, followed by extraction with ethyl acetate. The organic layer was washed with brine, dried over anhydrous sodium sulfate, and then concentrated under reduced pressure. The residue was purified by silica gel column chromatography (elution solvent: hexane/ethyl acetate=85/15, 75/25, 70/30, 1/1, ethyl acetate) to obtain 16.3 mg of the trans isomer of the title compound (4.73%) and 12.3 mg of the cis isomer of the title compound (3.57%).

$^1$H NMR spectrum (400 MHz, CDCl$_3$) δ ppm: 0.89-0.96 (3H, m), 1.25 (3H, t, J=7.55 Hz), 1.34-1.44 (2H, m), 1.47 (9H, s), 1.50-1.58 (1H, m), 1.75-1.86 (1H, m), 2.45-2.49 (2H, m), 2.68 (2H, q, J=7.55 Hz), 2.78-2.96 (3H, m), 3.21-3.25 (1H, m), 3.87-3.93 (1H, m), 4.00-4.08 (2H, m), 4.22-4.25 (1H, m), 7.88 (1H, d, J=8.02 Hz), 11.51 (1H, br s).: trans $^1$H NMR spectrum (400 MHz, CDCl$_3$) δ ppm: 0.86 (3H, t, J=7.16 Hz), 1.26 (3H, t, J=7.45 Hz), 1.38-1.44 (2H, m), 1.48 (9H, s), 1.65-1.83 (1H, m), 1.97-2.06 (1H, m), 2.34-2.59 (4H, m), 2.67-2.70 (3H, m), 2.82-2.84 (1H, m), 3.78-3.88 (1H, m), 4.00-4.11 (1H, m), 7.01-7.07 (1H, m).: cis (77e) Ethyl trans(±)-2-[3-(butylamino)-4-{[(4-chloro-5-ethyl-1H-imidazol-2-yl)carbonyl]amino}piperidin-1-yl]-1,3-benzothiazole-7-carboxylate The same operation as in Example (1h) was performed using tert-butyl trans(±)-3-(butylamino)-4-{[(4-chloro-5-ethyl-1H-imidazol-2-yl)carbonyl]amino}piperidine-1-carboxylate obtained in Example (77d) (16.3 mg, 0.038 mmol), sodium carbonate (40 mg, 0.38 mmol) and ethyl 2-bromo-1,3-benzothiazole-7-carboxylate obtained by the method described in Example (1f) (13.2 mg, 0.046 mmol), to obtain 15.5 mg of the title compound (76%).

$^1$H NMR spectrum (400 MHz, CDCl$_3$) δ ppm: 0.89 (3H, t, J=7.16 Hz), 1.27 (3H, t, J=7.55 Hz), 1.34-1.42 (4H, m), 1.44 (3H, t, J=7.11 Hz), 1.79-1.84 (1H, m), 1.97-2.00 (1H, m), 2.55-2.57 (1H, m), 2.70 (2H, q, J=7.55 Hz), 2.87-2.90 (2H, m), 3.23-3.36 (2H, m), 4.21-4.27 (3H, m), 4.46 (2H, q, J=7.11 Hz), 7.37-7.39 (1H, m), 7.71 (1H, d, J=8.02 Hz), 7.81 (1H, d, J=6.87 Hz), 7.93 (1H, d, J=8.02 Hz), 11.55 (1H, br s).

(77f) trans(±)-2-[3-(Butylamino)-4-{[(4-chloro-5-ethyl-1H-imidazol-2-yl)carbonyl]amino}piperidin-1-yl]-1,3-benzothiazole-7-carboxylic acid The same operation as in Example (1i) was performed using ethyl trans(±)-2-[3-(butylamino)-4-{[(4-chloro-5-ethyl-1H-imidazol-2-yl)carbonyl]amino}piperidin-1-yl]-1,3-benzothiazole-7-carboxylate obtained in Example (77e) (15.5 mg, 0.029 mmol) and a 2 N aqueous lithium hydroxide solution (0.3 mL), to obtain 10.8 mg of the title compound as a pale yellow solid (73%).

$^1$H NMR spectrum (400 MHz, DMSO-d$_6$) δ ppm: 0.81 (3H, t, J=7.16 Hz), 1.14 (3H, t, J=7.73 Hz), 1.27-1.35 (4H, m), 1.74-1.76 (1H, m), 1.90-1.92 (1H, m), 2.53-2.59 (2H, m), 2.73-2.75 (1H, m), 2.91 (1H, br s), 3.31-3.33 (3H, m), 3.37-3.39 (1H, m), 3.46-3.48 (1H, m), 4.01-4.03 (2H, m), 4.17-4.19 (1H, m), 7.37-7.38 (1H, m), 7.59-7.68 (2H, m), 8.05 (1H, d, J=8.02 Hz).

$^1$H NMR spectrum (400 MHz, DMSO-d$_6$) δ ppm: 0.81 (3H, t, J=7.16 Hz), 1.14 (3H, t, J=7.73 Hz), 1.27-1.35 (4H, m), 1.74-1.76 (1H, m), 1.90-1.92 (1H, m), 2.53-2.59 (2H, m), 2.73-2.75 (1H, m), 2.91 (1H, br s), 3.31-3.33 (3H, m), 3.37-3.39 (1H, m), 3.46-3.48 (1H, m), 4.01-4.03 (2H, m), 4.17-4.19 (1H, m), 7.37-7.38 (1H, m), 7.59-7.68 (2H, m), 8.05 (1H, d, J=8.02 Hz).

mass spectrum (ESI): m/z 506 (M+H)$^+$.

Example 78 cis(±)-2-[3-(Butylamino)-4-{[(4-chloro-5-ethyl-1H-imidazol-2-yl)carbonyl]amino}piperidin-1-yl]-1,3-benzothiazole-7-carboxylic acid (Exemplified Compound No. 78)

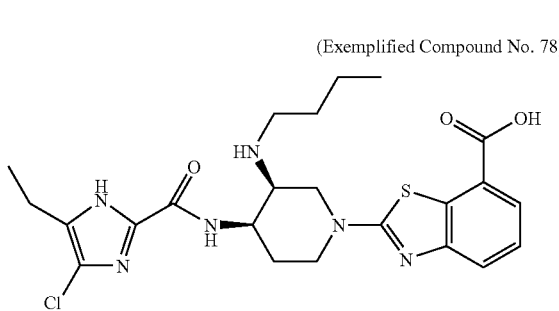

(78a) Ethyl cis(±)-2-[3-(butylamino)-4-{[(4-chloro-5-ethyl-1H-imidazol-2-yl)carbonyl]amino}piperidin-1-yl]-1,3-benzothiazole-7-carboxylate The same operation as in Example (1h) was performed using tert-butyl cis(±)-3-(butylamino)-4-{[(4-chloro-5-ethyl-1H-imidazol-2-yl)carbonyl]amino}piperidine-1-carboxylate obtained by the method described in Example (77d) (12.3 mg, 0.029 mmol), sodium carbonate (45 mg, 0.42 mmol) and ethyl 2-bromo-1,3-benzothiazole-7-carboxylate obtained in Example (1f) (10.4 mg, 0.036 mmol), to obtain 10.0 mg of the title compound (65%).

$^1$H NMR spectrum (400 MHz, CDCl$_3$) δ ppm: 0.89 (3H, t, J=7.16 Hz), 1.27 (3H, t, J=7.45 Hz), 1.31-1.37 (4H, m), 1.44 (3H, t, J=7.16 Hz), 1.69-1.77 (1H, m), 2.20-2.22 (1H, m), 2.60-2.63 (1H, m), 2.69-2.72 (3H, m), 2.80-2.82 (1H, m), 2.95-2.99 (1H, m), 3.22-3.28 (1H, m), 3.94-4.01 (1H, m), 4.27-4.30 (1H, m), 4.45-4.46 (3H, m), 7.12 (1H, d, J=8.59 Hz), 7.37-7.39 (1H, m), 7.72 (1H, d, J=8.02 Hz), 7.81 (1H, d, J=8.02 Hz).

(78b) cis(±)-2-[3-(Butylamino)-4-{[(4-chloro-5-ethyl-1H-imidazol-2-yl)carbonyl]amino}piperidin-1-yl]-1,3-benzothiazole-7-carboxylic acid The same operation as in Example (1i) was performed using ethyl cis(±)-2-[3-(butylamino)-4-{[(4-chloro-5-ethyl-1H-imidazol-2-yl)carbonyl]amino}piperidin-1-yl]-1,3-benzothiazole-7-carboxylate obtained in Example (78a) (10.0 mg, 0.019 mmol) and a 2 N aqueous lithium hydroxide solution (0.3 mL), to obtain 6.9 mg of the title compound as a pale yellow solid (73%).

$^1$H NMR spectrum (400 MHz, DMSO-d$_6$) δ ppm: 0.82 (3H, t, J=7.45 Hz), 1.14 (3H, t, J=7.45 Hz), 1.24-1.30 (4H, m), 1.78-1.80 (1H, m), 1.87-1.89 (1H, m), 2.53-2.61 (2H, m), 2.98-3.00 (1H, m), 3.26-3.30 (3H, m), 3.92-3.94 (1H, m), 4.08-4.10 (2H, m), 4.24-4.26 (1H, m), 7.36 (1H, t, J=7.73 Hz), 7.61-7.65 (2H, m), 8.46 (1H, d, J=8.02 Hz).

mass spectrum (ESI): m/z 506 (M+H)$^+$.

Example 79 trans(±)-2-(3-{[(Benzyloxy)carbonyl]amino}-4-{[(4-chloro-5-ethyl-1H-imidazol-2-yl)carbonyl]amino}piperidin-1-yl)-4-methyl-1,3-thiazole-5-carboxylic acid (Exemplified Compound No. 79)

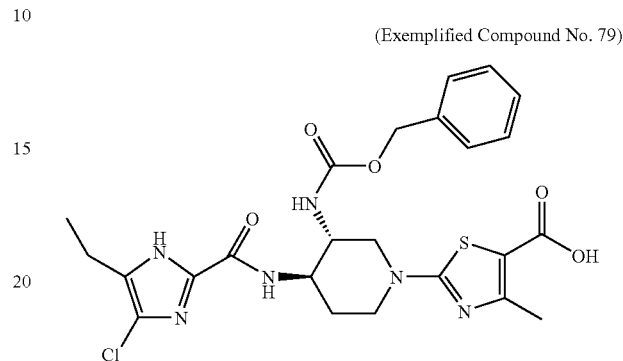

(79a) tert-Butyl trans(±)-4-{[(benzyloxy)carbonyl]amino}-3-[(methylsulfonyl)oxy]piperidine-1-carboxylate The compound was synthesized according to the method described in the following document.

WO 2005/66176 A1

(79b) tert-Butyl trans(±)-4-azido-3-{[(benzyloxy)carbonyl]amino}piperidine-1-carboxylate tert-Butyl trans(±)-4-{[(benzyloxy)carbonyl]amino}-3-[(methylsulfonyl)oxy]piperidine-1-carboxylate obtained in Example (79a) (538.1 mg, 1.26 mmol) was dissolved in DMF (12 mL). Trimethylsilyl azide (0.72 mL, 5.42 mmol) and TBAF (1 M solution in THF, 5.3 mL) were added, and the mixture was stirred at 80° C. for 3.5 hours. Ethyl acetate was added to the reaction solution, and the organic layer was washed with a 1 N aqueous sodium hydroxide solution and 5% saline, and dried over anhydrous sodium sulfate. The residue obtained by concentration under reduced pressure was purified by silica gel column chromatography (elution solvent: hexane/ethyl acetate=95/5, 85/15, 65/35) to obtain 265.6 mg of the title compound as a colorless oily substance (56%).

$^1$H NMR spectrum (400 MHz, CDCl$_3$) δ ppm: 1.45 (9H, s), 1.63-1.68 (1H, m), 1.88-2.05 (1H, m), 3.21-3.33 (1H, m), 3.54-3.60 (2H, m), 3.76-3.87 (1H, m), 4.98-5.01 (1H, m), 5.09-5.16 (3H, m), 7.30-7.39 (5H, m).

(79c) tert-Butyl trans(±)-4-amino-3-{[(benzyloxy)carbonyl]amino}piperidine-1-carboxylate tert-Butyl trans(±)-4-azido-3-{[(benzyloxy)carbonyl]amino}piperidine-1-carboxylate obtained in Example (79b) (265.6 mg, 0.71 mmol) was dissolved in THF (6 mL) and methanol (3 mL). Nickel chloride dihydrate (345 mg, 1.42 mmol) and sodium borohydride (117 mg, 2.85 mmol) were added under ice-cooling, and the mixture was heated to room temperature and stirred for 30 minutes. Saturated aqueous sodium bicarbonate solution was added to the reaction solution, followed by filtration through celite and extraction with ethyl acetate. The organic layer was dried over anhydrous sodium sulfate and then concentrated under reduced pressure. The resulting compound was used for the next reaction without purification.

125

(79d) tert-Butyl trans(±)-3-{[(benzyloxy)carbonyl]amino}-4-{[(4-chloro-5-ethyl-1H-imidazol-2-yl)carbonyl]amino}piperidine-1-carboxylate The same operation as in Example (1g) was performed using tert-butyl trans(±)-4-amino-3-{[(benzyloxy)carbonyl]amino}piperidine-1-carboxylate obtained in Example (79c) (98 mg, 0.28 mmol), 4-chloro-5-ethyl-1H-imidazole-2-carboxylic acid obtained by the method described in Example (1d) (48 mg, 0.25 mmol), WSC hydrochloride (150 mg, 0.78 mmol) and HOBT (35 mg, 0.26 mmol), to obtain 88.2 mg of the title compound as a white solid (69%).

$^1$H NMR spectrum (400 MHz, CDCl$_3$) δ ppm: 1.20-1.27 (3H, m), 1.48 (9H, s), 1.66-1.69 (1H, m), 1.94-1.96 (1H, m), 2.64-2.73 (3H, m), 3.46-3.51 (1H, m), 3.91-4.09 (2H, m), 4.42-4.44 (1H, m), 5.09-5.17 (3H, m), 7.01 (1H, d, J=9.17 Hz), 7.30-7.37 (5H, m).

(79e) Ethyl trans(±)-2-(3-{[(benzyloxy)carbonyl]amino}-4-{[(4-chloro-5-ethyl-1H-imidazol-2-yl)carbonyl]amino}piperidin-1-yl)-4-methyl-1,3-thiazole-5-carboxylate The same operation as in Example (1h) was performed using tert-butyl trans(±)-3-{[(benzyloxy)carbonyl]amino}-4-{[(4-chloro-5-ethyl-1H-imidazol-2-yl)carbonyl]amino}piperidine-1-carboxylate obtained in Example (79d) (85 mg, 0.17 mmol), sodium carbonate (160 mg, 1.51 mmol) and ethyl 2-bromo-4-methyl-1,3-thiazole-5-carboxylate (55 mg, 0.22 mmol), to obtain 82.3 mg of the title compound as a yellow solid (85%).

$^1$H NMR spectrum (400 MHz, DMSO-d$_6$) δ ppm: 1.15 (3H, t, J=7.45 Hz), 1.24 (3H, t, J=7.11 Hz), 1.79-1.88 (2H, m), 2.45 (3H, s), 2.56 (2H, q, J=7.45 Hz), 2.99-3.02 (1H, m), 3.15-3.17 (1H, m), 3.71-3.78 (1H, m), 3.94-4.04 (3H, m), 4.18 (2H, q, J=7.11 Hz), 4.95 (1H, d, J=12.60 Hz), 5.07 (1H, d, J=12.60 Hz), 7.24-7.28 (6H, m), 8.43 (1H, d, J=9.16 Hz).

(79f) trans(±)-2-(3-{[(Benzyloxy)carbonyl]amino}-4-{[(4-chloro-5-ethyl-1H-imidazol-2-yl)carbonyl]amino}piperidin-1-yl)-4-methyl-1,3-thiazole-5-carboxylic acid The same operation as in Example (1i) was performed using ethyl trans(±)-2-(3-{[(benzyloxy)carbonyl]amino}-4-{[(4-chloro-5-ethyl-1H-imidazol-2-yl)carbonyl]amino}piperidin-1-yl)-4-methyl-1,3-thiazole-5-carboxylate obtained in Example (79e) (20 mg, 0.035 mmol) and a 2 N aqueous lithium hydroxide solution (0.6 mL), to obtain 16.1 mg of the title compound as a yellow solid (85%).

$^1$H NMR spectrum (400 MHz, DMSO-d$_6$) δ ppm: 1.15 (3H, t, J=7.45 Hz), 1.77-1.87 (2H, m), 2.42 (3H, s), 2.56 (2H, q, J=7.45 Hz), 2.96-2.99 (1H, m), 3.13-3.15 (1H, m), 3.76-3.85 (2H, m), 4.02-4.05 (2H, m), 4.95 (1H, d, J=12.60 Hz), 5.06 (1H, d, J=12.60 Hz), 7.07-7.40 (6H, m), 8.43 (1H, d, J=8.59 Hz).

mass spectrum (ESI): m/z 548 (M+H)$^+$.

126

Example 80 trans(±)-2-[4-{[(4-Chloro-5-ethyl-1H-imidazol-2-yl)carbonyl]amino}-3-(dimethylamino)piperidin-1-yl]-4-methyl-1,3-thiazole-5-carboxylic acid (Exemplified Compound No. 80)

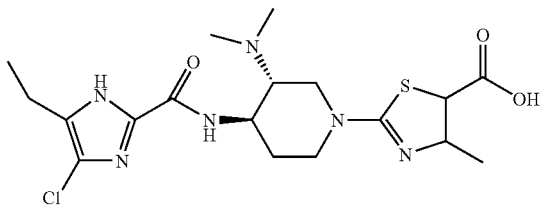

(80a) Ethyl trans(±)-2-(3-amino-4-{[(4-chloro-5-ethyl-1H-imidazol-2-yl)carbonyl]amino}piperidin-1-yl)-4-methyl-1,3-thiazole-5-carboxylate Hydrobromic acid/acetic acid solution (1 mL) was added to ethyl trans(±)-2-(3-{[(benzyloxy)carbonyl]amino}-4-{[(4-chloro-5-ethyl-1H-imidazol-2-yl)carbonyl]amino}piperidin-1-yl)-4-methyl-1,3-thiazole-5-carboxylate obtained by the method described in Example (79e) (62 mg, 0.11 mmol), and the mixture was stirred for 25 minutes. Saturated aqueous sodium bicarbonate solution was added to the reaction solution. Purification by reverse phase silica gel chromatography (elution solvent: distilled water, distilled water/THF=70/30, 60/40) gave 51.3 mg of the title compound (100%).

(80b) Ethyl trans(±)-2-[4-{[(4-chloro-5-ethyl-1H-imidazol-2-yl)carbonyl]amino}-3-(dimethylamino)piperidin-1-yl]-4-methyl-1,3-thiazole-5-carboxylate The same operation as in Example (77d) was performed using ethyl trans(±)-2-(3-amino-4-{[(4-chloro-5-ethyl-1H-imidazol-2-yl)carbonyl]amino}piperidin-1-yl)-4-methyl-1,3-thiazole-5-carboxylate obtained in Example (80a) (25.2 mg, 0.053 mmol), aqueous formalin solution (30 μL) and sodium (triacetoxy)borohydride (111 mg, 0.52 mmol), to obtain 13.4 mg of the title compound (54%).

$^1$H NMR spectrum (400 MHz, CDCl$_3$) δ ppm: 1.26 (3H, t, J=7.73 Hz), 1.33 (3H, t, J=7.16 Hz), 1.53-1.65 (1H, m), 2.39 (6H, s), 2.45-2.51 (1H, m), 2.55 (3H, s), 2.65-2.73 (3H, m), 2.97-3.13 (2H, m), 3.95-4.08 (2H, m), 4.24-4.27 (3H, m), 7.43-7.48 (1H, m), 11.51 (1H, br s).

(80c) trans(±)-2-[4-{[(4-Chloro-5-ethyl-1H-imidazol-2-yl)carbonyl]amino}-3-(dimethylamino)piperidin-1-yl]-4-methyl-1,3-thiazole-5-carboxylic acid The same operation as in Example (1i) was performed using ethyl trans(±)-2-[4-{[(4-chloro-5-ethyl-1H-imidazol-2-yl)carbonyl]amino}-3-(dimethylamino)piperidin-1-yl]-4-methyl-1,3-thiazole-5-carboxylate obtained in Example (80b) (13.4 mg, 0.035 mmol) and a 2 N aqueous lithium hydroxide solution (0.6 mL), to obtain 13 mg of the title compound as a white solid (100%).

$^1$H NMR spectrum (400 MHz, CDCl$_3$) δ ppm: 1.26 (3H, t, J=7.73 Hz), 1.52-1.67 (2H, m), 2.56 (6H, s), 2.65-2.71 (2H, m), 3.02-3.14 (2H, m), 4.04-4.25 (4H, m), 7.16-7.29 (1H, m).

mass spectrum (ESI): m/z 441 (M+H)$^+$.

Example 81 cis(±)-2-[4-{[(4-Chloro-5-ethyl-1H-imidazol-2-yl)carbonyl]amino}-3-(propylamino)piperidin-1-yl]-1,3-benzothiazole-7-carboxylic acid (Exemplified Compound No. 81)

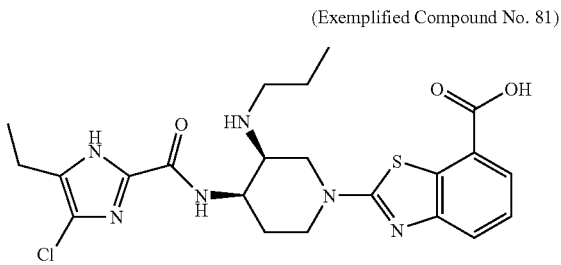 [SMILES: CCCN[C@H]1CN(c2nc3cccc(C(=O)O)c3s2)CC[C@H]1NC(=O)c1nc(Cl)c(CC)[nH]1]

(81a) tert-Butyl cis(±)-4-amino-3-azidopiperidine-1-carboxylate

The compound was synthesized according to the method described in the following document.
WO 2006/087543 A1

(81b) 4-Chloro-5-ethyl-1H-imidazole-2-carbonyl chloride

4-Chloro-5-ethyl-1H-imidazole-2-carboxylic acid obtained by the method described in Example (1d) (55 mg, 0.29 mmol) was dissolved in thionyl chloride (1.5 mL), and the mixture was stirred at 75° C. for 50 minutes. The reaction solution was concentrated under reduced pressure. The resulting compound was used for the next reaction without purification.

(81c) tert-Butyl cis(±)-3-azido-4-{[(4-chloro-5-ethyl-1H-imidazol-2-yl)carbonyl]amino}piperidine-1-carboxylate tert-Butyl cis(±)-4-amino-3-azidopiperidine-1-carboxylate obtained in Example (81a) (about 0.29 mmol) was dissolved in dichloromethane (4 mL).

Diisopropylethylamine (0.2 mL, 1.15 mmol) and 4-chloro-5-ethyl-1H-imidazole-2-carbonyl chloride obtained in Example (81b) (about 0.29 mmol) were added, followed by stirring for 2.5 hours. Dichloromethane was added to the reaction solution, and the organic layer was washed with 1 N hydrochloric acid, a 1 N aqueous sodium hydroxide solution and brine, and dried over anhydrous sodium sulfate. The residue obtained by concentration under reduced pressure was purified by silica gel column chromatography (elution solvent: hexane/ethyl acetate=90/10, 70/30, 55/45) to obtain 90.4 mg of the title compound (78%).

$^1$H NMR spectrum (400 MHz, CDCl$_3$) δ ppm: 1.26 (3H, t, J=7.68 Hz), 1.49 (9H, s), 1.62-1.71 (1H, m), 1.77-1.86 (1H, m), 2.69 (3H, q, J=7.68 Hz), 2.73-2.83 (1H, m), 3.01-3.14 (1H, m), 3.89 (1H, br s), 4.13-4.20 (1H, m), 4.26-4.51 (2H, m), 7.25-7.27 (1H, m), 11.24 (1H, br s).

(81d) Ethyl cis(±)-2-(3-azido-4-{[(4-chloro-5-ethyl-1H-imidazol-2-yl)carbonyl]amino}piperidin-1-yl)-1,3-benzothiazole-7-carboxylate The same operation as in Example (1h) was performed using tert-butyl cis(±)-3-azido-4-{[(4-chloro-5-ethyl-1H-imidazol-2-yl)carbonyl]amino}piperidine-1-carboxylate obtained in Example (81c) (90 mg, 0.23 mmol), a 4 N hydrochloric acid/ethyl acetate solution (4 mL), sodium carbonate (216 mg, 2.04 mmol) and ethyl 2-bromo-1,3-benzothiazole-7-carboxylate obtained in Example (1f) (83 mg, 0.29 mmol), to obtain 84.2 mg of the title compound (74%).

$^1$H NMR spectrum (400 MHz, CDCl$_3$) δ ppm: 1.28 (3H, t, J=7.45 Hz), 1.44 (3H, t, J=7.11 Hz), 1.83-1.90 (1H, m), 2.01-2.11 (1H, m), 2.70 (2H, q, J=7.45 Hz), 3.27-3.35 (1H, m), 3.48-3.52 (1H, m), 4.08-4.10 (1H, m), 4.25-4.36 (2H, m), 4.46 (2H, q, J=7.11 Hz), 4.61-4.63 (1H, m), 7.23-7.25 (1H, m), 7.38-7.39 (1H, m), 7.73 (1H, t, J=4.01 Hz), 7.82 (1H, dd, J=7.45, 1.15 Hz), 10.49 (1H, br s).

(81e) Ethyl cis(±)-2-(3-amino-4-{[(4-chloro-5-ethyl-1H-imidazol-2-yl)carbonyl]amino}piperidin-1-yl)-1,3-benzothiazole-7-carboxylate Ethyl cis(±)-2-(3-azido-4-{[(4-chloro-5-ethyl-1H-imidazol-2-yl)carbonyl]amino}piperidin-1-yl)-1,3-benzothiazole-7-carboxylate obtained in Example (81d) (84 mg, 0.17 mmol) was dissolved in THF (3 mL). Triphenylphosphine (63 mg, 0.24 mmol) and distilled water (0.2 mL) were added, and the mixture was heated under reflux for 15 hours. The reaction solution was concentrated under reduced pressure and the precipitated solid was collected by filtration, to obtain 59.6 mg of the title compound as a white solid (75%).

$^1$H NMR spectrum (400 MHz, DMSO-d$_6$) δ ppm: 1.14 (3H, t, J=7.68 Hz), 1.37 (3H, t, J=7.11 Hz), 1.76-1.78 (1H, m), 1.86-1.92 (1H, m), 2.56 (2H, q, J=7.68 Hz), 3.31-3.34 (2H, m), 3.54-3.62 (1H, m), 3.95-3.97 (1H, m), 4.07-4.19 (2H, m), 4.39 (2H, q, J=7.11 Hz), 7.42-7.43 (1H, m), 7.67-7.71 (2H, m), 8.06-8.10 (1H, m).

(81f) Ethyl cis(±)-2-[4-{[(4-chloro-5-ethyl-1H-imidazol-2-yl)carbonyl]amino}-3-(propylamino)piperidin-1-yl]-1,3-benzothiazole-7-carboxylate The same operation as in Example (77d) was performed using ethyl cis(±)-2-(3-amino-4-{[(4-chloro-5-ethyl-1H-imidazol-2-yl)carbonyl]amino}piperidin-1-yl)-1,3-benzothiazole-7-carboxylate obtained in Example (81e) (38 mg, 0.080 mmol), 1-propanal (7 μL, 0.097 mmol) and sodium (triacetoxy)borohydride (80 mg, 0.38 mmol), to obtain 31.9 mg of the title compound as a white solid (77%).

$^1$H NMR spectrum (400 MHz, CDCl$_3$) δ ppm: 0.92 (3H, t, J=7.45 Hz), 1.27 (3H, t, J=7.55 Hz), 1.45 (3H, t, J=7.11 Hz), 1.47-1.58 (2H, m), 1.77-1.87 (1H, m), 1.98-2.00 (1H, m), 2.50-2.57 (1H, m), 2.70 (2H, q, J=7.55 Hz), 2.83-2.86 (1H, m), 2.91-2.92 (1H, m), 3.24-3.39 (2H, m), 4.17-4.30 (3H, m), 4.46 (2H, q, J=7.11 Hz), 7.36-7.40 (1H, m), 7.70-7.73 (1H, m), 7.80-7.83 (1H, m), 7.92 (1H, d, J=8.59 Hz), 11.54 (1H, br s).

(81g) cis(±)-2-[4-{[(4-Chloro-5-ethyl-1H-imidazol-2-yl)carbonyl]amino}-3-(propylamino)piperidin-1-yl]-1,3-benzothiazole-7-carboxylic acid The same operation as in Example (1i) was performed using ethyl cis(±)-2-[4-{[(4-chloro-5-ethyl-1H-imidazol-2-yl)carbonyl]amino}-3-(propylamino)piperidin-1-yl]-1,3-benzothiazole-7-carboxylate obtained in Example (81f) (31.9 mg, 0.061 mmol) and a 2 N aqueous lithium hydroxide solution (2 mL), to obtain 20.7 mg of the title compound as a white solid (69%).

$^1$H NMR spectrum (400 MHz, DMSO-d$_6$) δ ppm: 0.86 (3H, t, J=7.45 Hz), 1.15 (3H, t, J=7.68 Hz), 1.39-1.51 (2H, m), 1.76-1.85 (1H, m), 1.89-2.00 (1H, m), 2.56 (2H, q, J=7.68 Hz), 2.72-2.87 (1H, m), 3.31-3.33 (3H, m), 3.43-3.68 (1H, m), 3.98-4.04 (2H, m), 4.24-4.38 (1H, m), 7.39-7.41 (1H, m), 7.63-7.71 (2H, m).

mass spectrum (ESI): m/z 492 (M+H)$^+$.

Example 82 cis(±)-2-(4-{[(4-Chloro-5-ethyl-1H-imidazol-2-yl)carbonyl]amino}-3-[(cyclopropylmethyl)amino]piperidin-1-yl)-1,3-benzothiazole-7-carboxylic acid (Exemplified Compound No. 82)

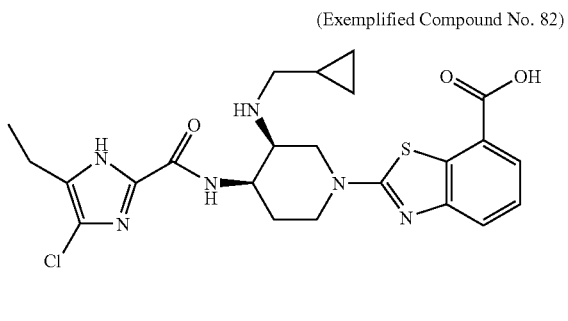 [SMILES: CCc1[nH]c(C(=O)N[C@@H]2CCN(c3nc4cccc(C(=O)O)c4s3)C[C@@H]2NCC2CC2)nc1Cl]

(82a) Ethyl cis(±)-2-(4-{[(4-chloro-5-ethyl-1H-imidazol-2-yl)carbonyl]amino}-3-[(cyclopropylmethyl)amino]piperidin-1-yl)-1,3-benzothiazole-7-carboxylate The same operation as in Example (77d) was performed using ethyl cis(±)-2-(3-amino-4-{[(4-chloro-5-ethyl-1H-imidazol-2-yl)carbonyl]amino}piperidin-1-yl)-1,3-benzothiazole-7-carboxylate obtained by the method described in Example (81e) (37 mg, 0.071 mmol), cyclopropanecarbaldehyde (6.5 μL, 0.087 mmol) and sodium (triacetoxy)borohydride (44 mg, 0.21 mmol), to obtain 35.3 mg of the title compound as a white solid (93%).

$^1$H NMR spectrum (400 MHz, CDCl$_3$) δ ppm: 0.01-0.07 (1H, m), 0.16-0.18 (1H, m), 0.35-0.42 (1H, m), 0.44-0.51 (1H, m), 0.96-1.00 (1H, m), 1.28 (3H, t, J=7.57 Hz), 1.44 (3H, t, J=7.15 Hz), 1.81-1.87 (1H, m), 1.97-2.01 (1H, m), 2.44-2.52 (1H, m), 2.68-2.72 (3H, m), 2.97-2.97 (1H, m), 3.28-3.35 (2H, m), 4.17-4.32 (3H, m), 4.45 (2H, q, J=7.15 Hz), 7.37-7.39 (1H, m), 7.69-7.72 (1H, m), 7.81 (1H, d, J=7.79 Hz), 7.94 (1H, d, J=8.25 Hz), 11.31 (1H, br s).

(82b) cis(±)-2-(4-{[(4-Chloro-5-ethyl-1H-imidazol-2-yl)carbonyl]amino}-3-[(cyclopropylmethyl)amino]piperidin-1-yl)-1,3-benzothiazole-7-carboxylic acid The same operation as in Example (1i) was performed using ethyl cis(±)-2-(4-{[(4-chloro-5-ethyl-1H-imidazol-2-yl)carbonyl]amino}-3-[(cyclopropylmethyl)amino]piperidin-1-yl)-1,3-benzothiazole-7-carboxylate obtained in Example (82a) (35.3 mg, 0.066 mmol) and a 2 N aqueous lithium hydroxide solution (2 mL), to obtain 30.4 mg of the title compound as a white solid (91%).

$^1$H NMR spectrum (400 MHz, DMSO-d$_6$) δ ppm: 0.04-0.05 (1H, m), 0.12-0.14 (1H, m), 0.31-0.40 (2H, m), 0.85-0.86 (1H, m), 1.14 (3H, t, J=7.57 Hz), 1.72-1.81 (1H, m), 1.86-1.98 (1H, m), 2.52-2.60 (2H, m), 3.00-3.02 (1H, m), 3.28-3.32 (2H, m), 3.39-3.53 (2H, m), 4.01-4.05 (2H, m), 4.19-4.22 (1H, m), 7.37-7.39 (1H, m), 7.60-7.67 (2H, m), 8.05-8.12 (1H, m).

mass spectrum (ESI): m/z 504 (M+H)$^+$.

Example 83 cis(±)-2-[4-{[(4-Chloro-5-ethyl-1H-imidazol-2-yl)carbonyl]amino}-3-(pentylamino)piperidin-1-yl]-1,3-benzothiazole-7-carboxylic acid (Exemplified Compound No. 83)

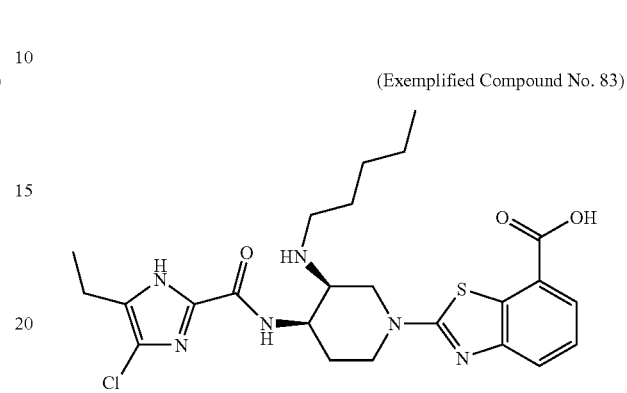

(83a) Ethyl cis(±)-2-[4-{[(4-chloro-5-ethyl-1H-imidazol-2-yl)carbonyl]amino}-3-(pentylamino)piperidin-1-yl]-1,3-benzothiazole-7-carboxylate The same operation as in Example (77d) was performed using ethyl cis(±)-2-(3-amino-4-{[(4-chloro-5-ethyl-1H-imidazol-2-yl)carbonyl]amino}piperidin-1-yl)-1,3-benzothiazole-7-carboxylate obtained by the method described in Example (81e) (30 mg, 0.063 mmol), 1-pentanal (14 μL, 0.13 mmol) and sodium (triacetoxy)borohydride (120 mg, 0.57 mmol), to obtain 30.8 mg of the title compound as a colorless oily substance (90%).

$^1$H NMR spectrum (400 MHz, CDCl$_3$) δ ppm: 0.84 (3H, t, J=7.16 Hz), 1.25-1.34 (7H, m), 1.44-1.45 (6H, m), 1.47-1.58 (2H, m), 1.79-1.84 (1H, m), 1.97-2.00 (1H, m), 2.54-2.56 (1H, m), 2.70 (2H, q, J=7.64 Hz), 2.85-2.91 (2H, m), 3.27-3.32 (2H, m), 4.17-4.38 (3H, m), 4.45 (2H, q, J=7.06 Hz), 7.36-7.39 (1H, m), 7.71 (1H, d, J=8.02 Hz), 7.81 (1H, t, J=4.30 Hz), 7.92 (1H, d, J=8.02 Hz), 11.40 (1H, br s).

(83b) cis(±)-2-[4-{[(4-Chloro-5-ethyl-1H-imidazol-2-yl)carbonyl]amino}-3-(pentylamino)piperidin-1-yl]-1,3-benzothiazole-7-carboxylic acid The same operation as in Example (1i) was performed using ethyl cis(±)-2-[4-{[(4-chloro-5-ethyl-1H-imidazol-2-yl)carbonyl]amino}-3-(pentylamino)piperidin-1-yl]-1,3-benzothiazole-7-carboxylate obtained in Example (83a) (30.8 mg, 0.056 mmol) and a 2 N aqueous lithium hydroxide solution (2 mL), to obtain 26.2 mg of the title compound as a white solid (90%).

$^1$H NMR spectrum (400 MHz, DMSO-d$_6$) δ ppm: 0.78 (3H, t, J=6.87 Hz), 1.14 (3H, t, J=7.55 Hz), 1.20-1.28 (4H, m), 1.37-1.49 (4H, m), 1.74-1.84 (1H, m), 1.88-2.01 (1H, m), 2.56 (2H, q, J=7.55 Hz), 3.31-3.34 (3H, m), 3.94-4.12 (3H, m), 7.39-7.41 (1H, m), 7.65-7.68 (2H, m).

mass spectrum (ESI): m/z 520 (M+H)$^+$.

Example 84 cis(±)-2-[4-{[(4-Chloro-5-ethyl-1H-imidazol-2-yl)carbonyl]amino}-3-(hexylamino)piperidin-1-yl]-1,3-benzothiazole-7-carboxylic acid (Exemplified Compound No. 84)

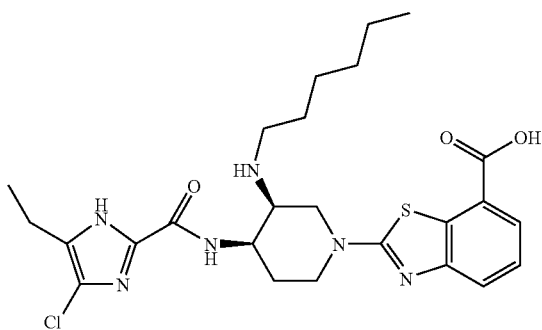

(84a) Ethyl cis(±)-2-[4-{[(4-chloro-5-ethyl-1H-imidazol-2-yl)carbonyl]amino}-3-(hexylamino)piperidin-1-yl]-1,3-benzothiazole-7-carboxylate The same operation as in Example (77d) was performed using ethyl cis(±)-2-(3-amino-4-{[(4-chloro-5-ethyl-1H-imidazol-2-yl)carbonyl]amino}piperidin-1-yl)-1,3-benzothiazole-7-carboxylate obtained by the method described in Example (81e) (30 mg, 0.063 mmol), 1-hexanal (22 μL, 0.18 mmol) and sodium (triacetoxy)borohydride (175 mg, 0.83 mmol), to obtain 28.4 mg of the title compound as a colorless oily substance (80%).

$^1$H NMR spectrum (400 MHz, CDCl$_3$) δ ppm: 0.83 (3H, t, J=6.87 Hz), 1.20-1.35 (9H, m), 1.48 (5H, m), 1.79-1.84 (1H, m), 1.96-2.00 (1H, m), 2.53-2.58 (1H, m), 2.70 (2H, q, J=7.64 Hz), 2.87-2.90 (2H, m), 3.27-3.32 (2H, m), 4.19-4.34 (3H, m), 4.45 (2H, q, J=7.26 Hz), 7.36-7.39 (1H, m), 7.69-7.72 (1H, m), 7.81 (1H, d, J=7.45 Hz), 7.91 (1H, d, J=8.02 Hz), 11.42 (1H, br s).

(84b) cis(±)-2-[4-{[(4-Chloro-5-ethyl-1H-imidazol-2-yl)carbonyl]amino}-3-(hexylamino)piperidin-1-yl]-1,3-benzothiazole-7-carboxylic acid The same operation as in Example (1i) was performed using ethyl cis(±)-2-[4-{[(4-chloro-5-ethyl-1H-imidazol-2-yl)carbonyl]amino}-3-(hexylamino)piperidin-1-yl]-1,3-benzothiazole-7-carboxylate obtained in Example (84a) (28.4 mg, 0.051 mmol) and a 2 N aqueous lithium hydroxide solution (2 mL), to obtain 25.0 mg of the title compound as a white solid (93%).

$^1$H NMR spectrum (400 MHz, DMSO-d$_6$) δ ppm: 0.78-0.84 (3H, m), 1.15 (3H, t, J=7.45 Hz), 1.20-1.27 (8H, m), 1.51-1.53 (2H, m), 1.85-1.94 (1H, m), 1.96-2.07 (1H, m), 2.57 (2H, q, J=7.45 Hz), 3.31-3.33 (3H, m), 3.94-3.96 (2H, m), 4.11-4.13 (1H, m), 7.42-7.44 (1H, m), 7.68-7.71 (3H, m).

mass spectrum (ESI): m/z 534 (M+H)$^+$.

Example 85 cis(±)-2-(4-{[(4-Chloro-5-ethyl-1H-imidazol-2-yl)carbonyl]amino}-3-[(2-methylpropyl)amino]piperidin-1-yl)-1,3-benzothiazole-7-carboxylic acid (Exemplified Compound No. 85)

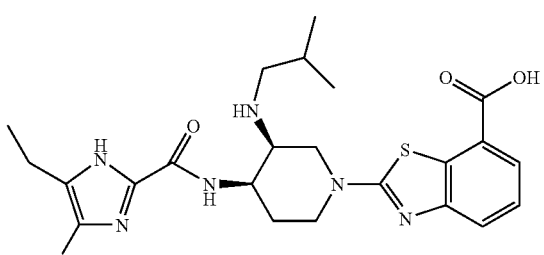

(85a) Ethyl cis(±)-2-(4-{[(4-chloro-5-ethyl-1H-imidazol-2-yl)carbonyl]amino}-3-[(2-methylpropyl)amino]piperidin-1-yl)-1,3-benzothiazole-7-carboxylate The same operation as in Example (77d) was performed using ethyl cis(±)-2-(3-amino-4-{[(4-chloro-5-ethyl-1H-imidazol-2-yl)carbonyl]amino}piperidin-1-yl)-1,3-benzothiazole-7-carboxylate obtained by the method described in Example (81e) (30 mg, 0.063 mmol), 2-methylpropanal (7 μL, 0.077 mmol) and sodium (triacetoxy)borohydride (60 mg, 0.28 mmol), to obtain 29.6 mg of the title compound as a white solid (88%).

$^1$H NMR spectrum (400 MHz, CDCl$_3$) δ ppm: 0.88 (3H, d, J=6.87 Hz), 0.94 (3H, d, J=6.87 Hz), 1.26 (3H, t, J=7.73 Hz), 1.44 (3H, t, J=7.11 Hz), 1.65-1.71 (1H, m), 1.79-1.84 (1H, m), 1.94-2.02 (1H, m), 2.33-2.39 (1H, m), 2.68-2.71 (3H, m), 2.87-2.89 (1H, m), 3.26-3.35 (2H, m), 4.20-4.28 (3H, m), 4.45 (2H, q, J=7.11 Hz), 7.37-7.38 (1H, m), 7.71 (1H, d, J=8.02 Hz), 7.79-7.83 (1H, m), 7.89 (1H, d, J=8.59 Hz), 10.55 (1H, br s).

(85b) cis(±)-2-(4-{[(4-Chloro-5-ethyl-1H-imidazol-2-yl)carbonyl]amino}-3-[(2-methylpropyl)amino]piperidin-1-yl)-1,3-benzothiazole-7-carboxylic acid The same operation as in Example (1i) was performed using ethyl cis(±)-2-(4-{[(4-chloro-5-ethyl-1H-imidazol-2-yl)carbonyl]amino}-3-[(2-methylpropyl)amino]piperidin-1-yl)-1,3-benzothiazole-7-carboxylate obtained in Example (85a) (29.6 mg, 0.051 mmol) and a 2 N aqueous lithium hydroxide solution (2 mL), to obtain 25.1 mg of the title compound as a white solid (90%).

$^1$H NMR spectrum (400 MHz, DMSO-d$_6$) δ ppm: 0.81-0.92 (6H, m), 1.14 (3H, t, J=7.55 Hz), 1.60-1.85 (2H, m), 1.90-2.01 (2H, m), 2.56 (2H, q, J=7.55 Hz), 3.16-3.17 (1H, m), 3.30-3.34 (3H, m), 3.92-4.11 (3H, m), 7.39-7.41 (1H, m), 7.65-7.68 (2H, m).

mass spectrum (ESI): m/z 506 (M+H)$^+$.

Example 86 cis(±)-2-[4-{[(4-Chloro-5-ethyl-1H-imidazol-2-yl)carbonyl]amino}-3-(cyclopentylamino)piperidin-1-yl]-1,3-benzothiazole-7-carboxylic acid (Exemplified Compound No. 86)

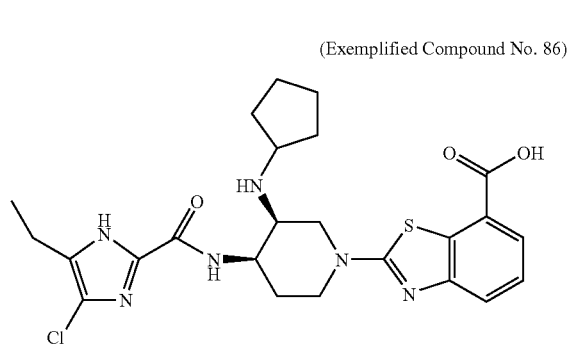 [SMILES: CCc1[nH]c(C(=O)N[C@@H]2CCN(c3nc4cccc(C(=O)O)c4s3)C[C@@H]2NC2CCCC2)nc1Cl]

(86a) Ethyl cis(±)-2-[4-{[(4-chloro-5-ethyl-1H-imidazol-2-yl)carbonyl]amino}-3-(cyclopentylamino)piperidin-1-yl]-1,3-benzothiazole-7-carboxylate The same operation as in Example (77d) was performed using ethyl cis(±)-2-(3-amino-4-{[(4-chloro-5-ethyl-1H-imidazol-2-yl)carbonyl]amino}piperidin-1-yl)-1,3-benzothiazole-7-carboxylate obtained by the method described in Example (81e) (30 mg, 0.063 mmol), cyclopentanone (33.5 μL, 0.038 mmol) and sodium (triacetoxy)borohydride (175 mg, 0.83 mmol), to obtain 25.6 mg of the title compound as a white solid (75%).

$^1$H NMR spectrum (400 MHz, CDCl$_3$) δ ppm: 1.27 (5H, m), 1.34-1.41 (1H, m), 1.44 (3H, t, J=7.11 Hz), 1.50-1.60 (1H, m), 1.67-1.86 (5H, m), 1.94-1.97 (1H, m), 2.69 (2H, q, J=7.68 Hz), 2.93-2.93 (1H, m), 3.20-3.34 (3H, m), 4.16-4.19 (1H, m), 4.28-4.30 (2H, m), 4.46 (2H, q, J=7.11 Hz), 7.37-7.39 (1H, m), 7.71 (1H, dd, J=8.02, 1.15 Hz), 7.81 (1H, dd, J=8.02, 1.15 Hz), 7.89 (1H, d, J=8.59 Hz), 11.01 (1H, br s).

(86b) cis(±)-2-[4-{[(4-Chloro-5-ethyl-1H-imidazol-2-yl)carbonyl]amino}-3-(cyclopentylamino)piperidin-1-yl]-1,3-benzothiazole-7-carboxylic acid The same operation as in Example (1i) was performed using ethyl cis(±)-2-[4-{[(4-chloro-5-ethyl-1H-imidazol-2-yl)carbonyl]amino}-3-(cyclopentylamino)piperidin-1-yl]-1,3-benzothiazole-7-carboxylate obtained in Example (86a) (25.6 mg, 0.047 mmol) and a 2 N aqueous lithium hydroxide solution (2 mL), to obtain 21.8 mg of the title compound as a white solid (90%).

$^1$H NMR spectrum (400 MHz, DMSO-d$_6$) δ ppm: 1.15 (3H, t, J=7.53 Hz), 1.23-1.52 (4H, m), 1.72-1.87 (5H, m), 2.56 (2H, q, J=7.53 Hz), 3.30-3.35 (3H, m), 3.97-4.09 (3H, m), 4.25-4.27 (2H, m), 7.40-7.41 (1H, m), 7.66-7.68 (2H, m), 8.12 (1H, br s).

mass spectrum (ESI): m/z 518 (M+H)$^+$.

Example 87 cis(±)-2-(4-{[(4-Chloro-5-ethyl-1H-imidazol-2-yl)carbonyl]amino}-3-[(3-methylbutyl)amino]piperidin-1-yl)-1,3-benzothiazole-7-carboxylic acid (Exemplified Compound No. 87)

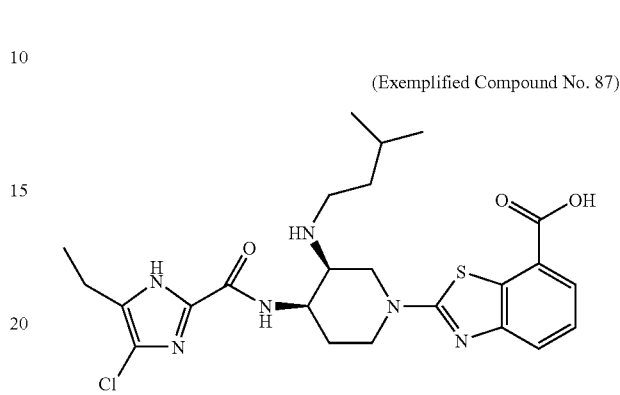

(87a) Ethyl cis(±)-2-(4-{[(4-chloro-5-ethyl-1H-imidazol-2-yl)carbonyl]amino}-3-[(3-methylbutyl)amino]piperidin-1-yl)-1,3-benzothiazole-7-carboxylate The same operation as in Example (77d) was performed using ethyl cis(±)-2-(3-amino-4-{[(4-chloro-5-ethyl-1H-imidazol-2-yl)carbonyl]amino}piperidin-1-yl)-1,3-benzothiazole-7-carboxylate obtained by the method described in Example (81e) (30 mg, 0.063 mmol), 3-methylbutanal (10.8 μL, 0.010 mmol) and sodium (triacetoxy)borohydride (87 mg, 0.41 mmol), to obtain 34.2 mg of the title compound as a colorless oily substance (99%).

$^1$H NMR spectrum (400 MHz, CDCl$_3$) δ ppm: 0.86-0.89 (6H, m), 1.27 (3H, t, J=7.55 Hz), 1.36-1.42 (2H, m), 1.44 (3H, t, J=7.11 Hz), 1.65-1.73 (1H, m), 1.78-1.83 (1H, m), 1.97-2.00 (1H, m), 2.55-2.58 (1H, m), 2.70 (2H, q, J=7.55 Hz), 2.90-2.92 (2H, m), 3.27-3.32 (2H, m), 4.16-4.28 (2H, m), 4.30-4.36 (1H, m), 4.45 (2H, q, J=7.11 Hz), 7.37-7.39 (1H, m), 7.69-7.72 (1H, m), 7.80-7.83 (1H, m), 7.93 (1H, d, J=8.02 Hz), 11.56 (1H, br s).

(87b) cis(±)-2-(4-{[(4-Chloro-5-ethyl-1H-imidazol-2-yl)carbonyl]amino}-3-[(3-methylbutyl)amino]piperidin-1-yl)-1,3-benzothiazole-7-carboxylic acid The same operation as in Example (1i) was performed using ethyl cis(±)-2-(4-{[(4-chloro-5-ethyl-1H-imidazol-2-yl)carbonyl]amino}-3-[(3-methylbutyl)amino]piperidin-1-yl)-1,3-benzothiazole-7-carboxylate obtained in Example (87a) (34.2 mg, 0.063 mmol) and a 2 N aqueous lithium hydroxide solution (2 mL), to obtain 30.3 mg of the title compound as a white solid (94%).

$^1$H NMR spectrum (400 MHz, DMSO-d$_6$) δ ppm: 0.79-0.85 (6H, m), 1.14 (3H, t, J=7.55 Hz), 1.23-1.38 (2H, m), 1.62-1.67 (1H, m), 1.73-1.84 (1H, m), 1.88-2.00 (1H, m), 2.56 (2H, q, J=7.55 Hz), 2.79-2.90 (1H, m), 3.29-3.34 (3H, m), 3.41-3.50 (1H, m), 3.96-4.14 (2H, m), 4.23-4.35 (1H, m), 7.39-7.41 (1H, m), 7.64-7.67 (2H, m).

mass spectrum (ESI): m/z 520 (M+H)$^+$.

Example 88 cis(±)-2-[4-{[(4-Chloro-5-ethyl-1H-imidazol-2-yl)carbonyl]amino}-3-(cyclobutylamino)piperidin-1-yl]-1,3-benzothiazole-7-carboxylic acid

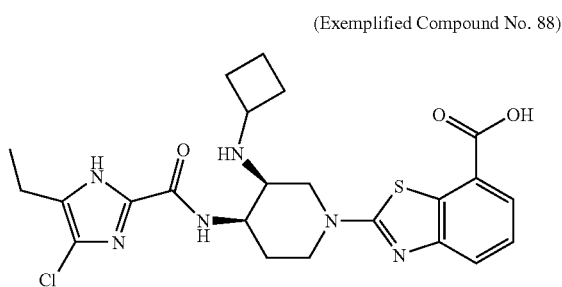 [SMILES: CCc1[nH]c(C(=O)N[C@@H]2CCN(c3nc4cccc(C(=O)O)c4s3)C[C@@H]2NC2CCC2)nc1Cl]

(Exemplified Compound No. 88)

(88a) Ethyl cis(±)-2-[4-{[(4-chloro-5-ethyl-1H-imidazol-2-yl)carbonyl]amino}-3-(cyclobutylamino)piperidin-1-yl]-1,3-benzothiazole-7-carboxylate The same operation as in Example (77d) was performed using ethyl cis(±)-2-(3-amino-4-{[(4-chloro-5-ethyl-1H-imidazol-2-yl)carbonyl]amino}piperidin-1-yl)-1,3-benzothiazole-7-carboxylate obtained by the method described in Example (81e) (30 mg, 0.063 mmol), cyclobutanone (95 μL, 1.27 mmol) and sodium (triacetoxy)borohydride (245 mg, 1.16 mmol), to obtain 17.6 mg of the title compound as a white solid (53%).

$^1$H NMR spectrum (400 MHz, CDCl$_3$) δ ppm: 1.28 (3H, t, J=7.68 Hz), 1.45 (3H, t, J=7.11 Hz), 1.54-1.88 (5H, m), 1.97-2.02 (1H, m), 2.11-2.29 (2H, m), 2.70 (2H, q, J=7.68 Hz), 2.91-2.91 (1H, m), 3.23-3.29 (1H, m), 3.35-3.40 (2H, m), 4.15-4.18 (2H, m), 4.22-4.25 (1H, m), 4.46 (2H, q, J=7.11 Hz), 7.37-7.40 (1H, m), 7.72 (1H, d, J=8.02 Hz), 7.82-7.83 (2H, m), 11.42 (1H, br s).

(88b) cis(±)-2-[4-{[(4-Chloro-5-ethyl-1H-imidazol-2-yl)carbonyl]amino}-3-(cyclobutylamino)piperidin-1-yl]-1,3-benzothiazole-7-carboxylic acid The same operation as in Example (1i) was performed using ethyl cis(±)-2-[4-{[(4-chloro-5-ethyl-1H-imidazol-2-yl)carbonyl]amino}-3-(cyclobutylamino)piperidin-1-yl]-1,3-benzothiazole-7-carboxylate obtained in Example (88a) (17.6 mg, 0.033 mmol) and a 2 N aqueous lithium hydroxide solution (1 mL), to obtain 10.3 mg of the title compound as a pale yellow solid (63%).

$^1$H NMR spectrum (400 MHz, DMSO-d$_6$) δ ppm: 1.15 (3H, t, J=7.45 Hz), 1.61-1.76 (5H, m), 1.92-1.97 (2H, m), 2.13-2.15 (2H, m), 2.56 (2H, q, J=7.45 Hz), 3.31-3.33 (3H, m), 3.95-3.97 (3H, m), 7.40-7.41 (1H, m), 7.67-7.68 (2H, m).

mass spectrum (ESI): m/z 504 (M+H)$^+$.

Example 89 cis(±)-2-[4-{[(4-Chloro-5-ethyl-1H-imidazol-2-yl)carbonyl]amino}-3-(tetrahydro-2H-pyran-4-ylamino)piperidin-1-yl]-1,3-benzothiazole-7-carboxylic acid

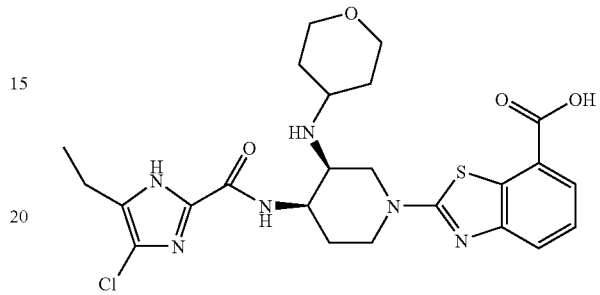

(Exemplified Compound No. 89)

(89a) Ethyl cis(±)-2-[4-{[(4-chloro-5-ethyl-1H-imidazol-2-yl)carbonyl]amino}-3-(tetrahydro-2H-pyran-4-ylamino)piperidin-1-yl]-1,3-benzothiazole-7-carboxylate The same operation as in Example (77d) was performed using ethyl cis(±)-2-(3-amino-4-{[(4-chloro-5-ethyl-1H-imidazol-2-yl)carbonyl]amino}piperidin-1-yl)-1,3-benzothiazole-7-carboxylate obtained by the method described in Example (81e) (30 mg, 0.063 mmol), tetrahydro-4H-pyran-4-one (0.11 mL, 1.19 mmol) and sodium (triacetoxy)borohydride (238 mg, 1.12 mmol), to obtain 19.1 mg of the title compound as a white solid (54%).

$^1$H NMR spectrum (400 MHz, CDCl$_3$) δ ppm: 1.27 (3H, t, J=7.55 Hz), 1.45 (3H, t, J=7.11 Hz), 1.65-1.67 (3H, m), 1.76-1.86 (2H, m), 1.94-2.01 (1H, m), 2.70 (2H, q, J=7.55 Hz), 2.84-2.90 (1H, m), 3.04-3.04 (1H, m), 3.24-3.27 (1H, m), 3.32-3.48 (3H, m), 3.91-4.03 (2H, m), 4.15-4.23 (1H, m), 4.28-4.37 (2H, m), 4.46 (2H, q, J=7.11 Hz), 7.37-7.40 (1H, m), 7.69-7.72 (1H, m), 7.81-7.83 (2H, m), 11.33 (1H, br s).

(89b) cis(±)-2-[4-{[(4-Chloro-5-ethyl-1H-imidazol-2-yl)carbonyl]amino}-3-(tetrahydro-2H-pyran-4-ylamino)piperidin-1-yl]-1,3-benzothiazole-7-carboxylic acid The same operation as in Example (1i) was performed using ethyl cis(±)-2-[4-{[(4-chloro-5-ethyl-1H-imidazol-2-yl)carbonyl]amino}-3-(tetrahydro-2H-pyran-4-ylamino)piperidin-1-yl]-1,3-benzothiazole-7-carboxylate obtained in Example (89a) (19.1 mg, 0.034 mmol) and a 2 N aqueous lithium hydroxide solution (1 mL), to obtain 10.5 mg of the title compound as a pale yellow solid (58%).

$^1$H NMR spectrum (400 MHz, DMSO-d$_6$) δ ppm: 1.14 (3H, t, J=7.45 Hz), 1.22-1.32 (3H, m), 1.61-1.63 (1H, m), 1.73-1.75 (2H, m), 1.89-1.91 (1H, m), 2.55 (2H, q, J=7.45 Hz), 2.80-2.82 (1H, m), 3.06-3.08 (1H, m), 3.24-3.31 (3H, m), 3.35-3.52 (1H, m), 3.77-3.85 (2H, m), 4.02-4.17 (2H, m), 7.38-7.40 (1H, m), 7.63-7.67 (2H, m), 7.99-8.06 (1H, m).

mass spectrum (ESI): m/z 534 (M+H)$^+$.

Example 90 cis(±)-2-{3-(Benzyloxy)-4-[(1H-imidazol-2-ylcarbonyl)amino]piperidin-1-yl}-1,3-thiazole-5-carboxylic acid (Exemplified Compound No. 90)

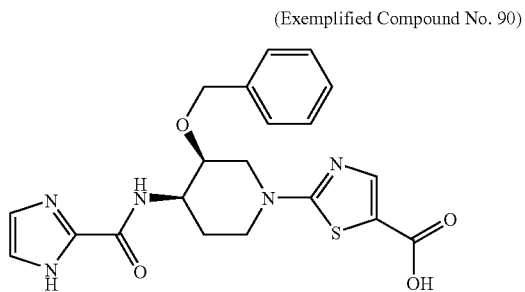 [SMILES: O=C(N[C@@H]1CCN(c2ncc(C(=O)O)s2)C[C@@H]1OCc1ccccc1)c1ncc[nH]1]

(90a) tert-Butyl 3-(benzyloxy)-4,4-dimethoxypiperidine-1-carboxylate

Sodium hydride (55% content, 0.79 g, 18 mmol) was added to a solution of tert-butyl 3-hydroxy-4,4-dimethoxypiperidine-1-carboxylate (described in Tetrahedron Lett.; [[EN;]] 46; 3; 2005; 447-450, 3.9 g, 15 mmol) in DMF (50 mL). Following stirring at room temperature for 30 minutes, benzyl bromide (2.82 g, 16.5 mmol) was added, and the mixture was stirred at room temperature for two hours. A 0.5 N aqueous hydrochloric acid solution was added to the reaction solution, followed by extraction with ethyl acetate. Then, the organic layer was washed with water (three times) and brine, and dried over anhydrous magnesium sulfate. Following concentration under reduced pressure, the residue was purified by silica gel column chromatography (elution solvent: hexane/ethyl acetate=10/1, 4/1, 2/1) to obtain 4.99 g of the title compound as a colorless solid (95%).

mass spectrum (APCI): m/z 352 (M+H)$^+$ (90b) tert-Butyl 3-(benzyloxy)-4-oxopiperidine-1-carboxylate A water/TFA mixed solution (1/1, 35 mL) was added to tert-butyl 3-(benzyloxy)-4,4-dimethoxypiperidine-1-carboxylate obtained in Example (90a) (4.99 g, 14.2 mmol), and the mixture was stirred at 60° C. for one hour. The reaction solution was concentrated to obtain crude 3-(benzyloxy)piperidin-4-one TFA salt as a brown oily substance. A 2 N aqueous sodium hydroxide solution (20 mL) was added to the crude 3-(benzyloxy)piperidin-4-one TFA salt, and a solution of di-tert-butyl dicarbonate (4.36 g, 20 mmol) in THF (10 mL) was added at room temperature. Following stirring for one hour, the reaction solution was diluted with water, followed by extraction with ethyl acetate. Then, the organic layer was washed with brine and dried over anhydrous magnesium sulfate. Following concentration under reduced pressure, the residue was purified by silica gel column chromatography (elution solvent: hexane/ethyl acetate=10/1, 5/1, 2/1) to obtain 3.81 g of the title compound as a light brown oily substance (88%).

mass spectrum (APCI): m/z 306 (M+H)$^+$ (90c) tert-Butyl cis(±)-4-(benzylamino)-3-(benzyloxy)piperidine-1-carboxylate Benzylamine (1.47 g, 13.7 mmol) and sodium (triacetoxy)borohydride (5.30 g, 25 mmol) were added to a solution of tert-butyl 3-(benzyloxy)-4-oxopiperidine-1-carboxylate obtained in Example (90b) (3.81 g, 12.5 mmol) in 1,2-dichloroethane (40 mL), and the mixture was stirred at room temperature for 40 minutes. The reaction solution was diluted with dichloromethane, washed with a 1 N aqueous sodium hydroxide solution and brine, and dried over magnesium sulfate. Following concentration under reduced pressure, the residue was purified by silica gel column chromatography (elution solvent: hexane/ethyl acetate=4/1, 1/1, 1/3, 0/1) to obtain 4.34 g of the title compound as a colorless solid (91%).

$^1$H NMR spectrum (400 MHz, CDCl$_3$) δ ppm: 1.44 (9.0H, s), 1.61-1.64 (2.0H, m), 2.74 (1.0H, dt, J=9.60, 3.54 Hz), 2.95 (1.0H, dd, J=13.92, 2.20 Hz), 2.96-2.90 (1.0H, m), 3.70-3.64 (3.0H, m), 3.97-3.87 (1.0H, m), 4.22-4.16 (1.0H, m), 4.41 (1.0H, d, J=11.47 Hz), 4.73 (1.0H, d, J=11.47 Hz), 7.22-7.37 (10.0H, m).

(90d) tert-Butyl cis(±)-4-amino-3-(benzyloxy)piperidine-1-carboxylate

10% Pd/C (wet, 1.1 g) and ammonium formate (2.87 g, 46 mmol) were added to a solution of tert-butyl cis(±)-4-(benzylamino)-3-(benzyloxy)piperidine-1-carboxylate obtained in Example (90c) (4.84 g, 11.4 mmol) in methanol (30 mL) in a nitrogen atmosphere, and the mixture was stirred at 70° C. for 40 minutes. The reaction solution was filtered to remove the Pd/C. Following concentration under reduced pressure, a 1 N aqueous sodium hydroxide solution was added to the residue, followed by extraction with dichloromethane three times. The organic layer was dried over anhydrous magnesium sulfate and then concentrated under reduced pressure, to obtain 3.15 g of the crude title compound as a colorless oily substance (94%).

$^1$H NMR spectrum (400 MHz, CDCl$_3$) δ ppm: 1.44 (9.0H, s), 1.68-1.71 (2.0H, m), 2.87-2.97 (3.0H, m), 3.47 (1.0H, brs), 3.86-3.98 (1.0H, m), 4.16-4.26 (1.0H, m), 4.41-4.44 (1.0H, br m), 4.77 (1.0H, d, J=11.46 Hz), 7.34-7.29 (5.0H, m).

(90e) tert-Butyl cis(±)-3-(benzyloxy)-4-[(1H-imidazol-2-ylcarbonyl)amino]piperidine-1-carboxylate tert-Butyl cis(±)-4-amino-3-(benzyloxy)piperidine-1-carboxylate obtained in Example (90d) (0.92 g, 3.0 mmol) was dissolved in DMA (10 mL). 1H-Imidazol-2-ylcarboxylic acid (0.19 g, 1.70 mmol), WSC (0.82 g, 0.43 mmol) and DMAP (60 mg, 0.49 mmol) were added, and the mixture was stirred at room temperature for one hour. The reaction solution was diluted with dichloromethane, washed with water and brine, and dried over anhydrous magnesium sulfate. Following concentration under reduced pressure, the residue was purified by silica gel column chromatography (elution solvent: hexane/ethyl acetate=2/1, 1/1, 1/3) to obtain 0.31 g of the title compound as a colorless solid (46%).

$^1$H NMR spectrum (400 MHz, DMSO-d$_6$) δ ppm: 1.37 (9.0H, s), 1.57-1.60 (1.0H, m), 1.68-1.80 (1.0H, m), 2.84-2.98 (2.0H, m), 3.61 (1.0H, brs), 3.93-4.10 (2.0H, m), 4.28-4.46 (2.0H, m), 4.70-4.73 (1.0H, m), 7.13-7.37 (6.0H, m), 7.71-7.73 (1.0H, m).

(90f) Ethyl cis(±)-2-{3-(benzyloxy)-4-[(1H-imidazol-2-ylcarbonyl)amino]piperidin-1-yl}-1,3-thiazole-5-carboxylate A 4 N hydrochloric acid/ethyl acetate solution (10 mL, 40 mmol) was added to tert-butyl cis(±)-3-(benzyloxy)-4-[(1H-imidazol-2-ylcarbonyl)amino]piperidine-1-carboxylate obtained in Example (90e) (0.3 g, 0.75 mmol), and the mixture was stirred at room temperature for 20 minutes. Following concentration under reduced pressure, the residue was dissolved in DMF (8 mL). Diisopropylethylamine (0.45 g, 3.5 mmol) and ethyl 2-bromo-1,3-thiazole-5-carboxylate (0.21 g, 0.9 mmol) were added, and the mixture was stirred at 70° C. for 1.5 hours. Dilute hydrochloric acid was added to the reaction solution, followed by extraction with ethyl acetate. The organic layer was washed with water, saturated aqueous sodium bicarbonate solution and brine, and dried over anhydrous sodium magnesium sulfate. Following concentration under reduced pressure, the residue was purified by silica gel column chromatography (elution solvent: hexane/ethyl acetate=5/1, ethyl acetate) to obtain 0.26 g of the title compound as a light brown solid (76%).

$^1$H NMR spectrum (400 MHz, DMSO-d$_6$) δ ppm: 1.25 (3.0H, t, J=7.19 Hz), 1.73-1.76 (1.0H, m), 1.95 (1.0H, dq, J=4.05, 12.20 Hz), 3.39-3.42 (2.0H, m), 3.77 (1.0H, br s), 3.97-4.02 (1.0H, m), 4.21 (2.0H, q, J=7.19 Hz), 4.24-4.28 (1.0H, m), 4.40-4.44 (1.0H, m), 4.48 (1.0H, d, J=11.95 Hz), 4.69 (1.0H, d, J=11.95 Hz), 7.06-7.07 (1.0H, m), 7.18-7.21 (3.0H, m), 7.26-7.30 (3.0H, m), 7.79-7.81 (2.0H, m), 13.08 (1.0H, s).

mass spectrum (FAB): m/z 456 (M+H)$^+$.

(90g) cis(±)-2-{3-(Benzyloxy)-4-[(1H-imidazol-2-ylcarbonyl)amino]piperidin-1-yl}-1,3-thiazole-5-carboxylic acid Ethyl cis(±)-2-{3-(benzyloxy)-4-[(1H-imidazol-2-ylcarbonyl)amino]piperidin-1-yl}-1,3-thiazole-5-carboxylate obtained in Example (90f) (0.25 g, 0.55 mmol) was dissolved in methanol (5 mL) and dichloromethane (1 mL). A 2 N aqueous lithium hydroxide solution (5 mL, 10 mmol) was added, and the mixture was stirred at 70° C. for 20 minutes. The organic solvent was evaporated under reduced pressure, and 1 N hydrochloric acid was added until the pH of the solution was about 4. Purification by reverse phase chromatography (elution solvent: acetonitrile/water=1/1, 4/1) gave 0.15 g of the title compound as a white solid (66%).

$^1$H NMR spectrum (400 MHz, DMSO-d$_6$) δ ppm: 1.73-1.75 (1.0H, m), 1.94 (1.0H, dq, J=4.88, 11.95 Hz), 3.37-3.40 (2.0H, m), 3.76 (1.0H, br s), 3.98 (1.0H, d, J=12.93 Hz), 4.23-4.27 (1.0H, m), 4.39-4.42 (1.0H, m), 4.48 (1.0H, d, J=12.19 Hz), 4.69 (1.0H, d, J=12.19 Hz), 7.07 (1.0H, s), 7.18-7.21 (3.0H, m), 7.27-7.28 (3.0H, m), 7.73 (1.0H, s), 7.80 (1.0H, d, J=8.54 Hz), 13.08 (1.0H, br s).

mass spectrum (FAB): m/z 428 (M+H)$^+$.

Example 91

2-(4-{[(4-Chloro-5-ethyl-1H-imidazol-2-yl)carbonyl]amino}phenyl)-1,3-thiazole-5-carboxylic acid (Exemplified Compound No. 91)

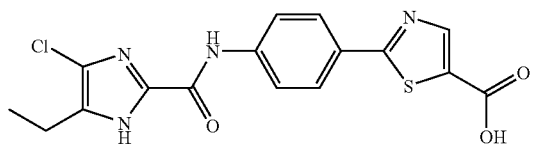

(91a) Ethyl 2-(4-nitrophenyl)-1,3-thiazole-5-carboxylate

Water (5 mL) and 1,4-dioxane (5 mL) were added to 4-nitrophenylboronic acid (667 mg, 4 mmol), ethyl 2-bromo-1,3-thiazole-5-carboxylate (448 μL, 4 mmol), sodium bicarbonate (1.01 g, 12 mmol) and tetrakis(triphenylphosphine)palladium (462 mg, 0.4 mmol), and the mixture was stirred in a nitrogen atmosphere at 100° C. for 1.5 hours. Ethyl acetate was added to the reaction solution, and the organic layer was washed with water and brine, and dried over anhydrous magnesium sulfate. Following concentration under reduced pressure, the residue was purified by silica gel column chromatography (elution solvent: hexane/ethyl acetate=10/1, 4/1, 2/1) to obtain 0.6 g of the title compound as a colorless solid (54%).

$^1$H NMR spectrum (400 MHz, CDCl$_3$) δ ppm: 1.42 (3.0H, t, J=7.19 Hz), 4.42 (2.0H, q, J=7.19 Hz), 8.17 (2.0H, d, J=8.12 Hz), 8.34 (2.0H, d, J=8.12 Hz), 8.49 (1.0H, s).

(91b) Ethyl 2-(4-aminophenyl)-1,3-thiazole-5-carboxylate

The same operation as in Example (90d) was performed using ethyl 2-(4-nitrophenyl)-1,3-thiazole-5-carboxylate obtained in Example (91a) (0.18 g, 0.65 mmol), 10% Pd/C (wet, 0.1 g), ammonium formate (0.2 g, 3.24 mmol) and methanol (5 mL), to obtain 0.12 g of the crude title compound as a yellow solid (75%).

$^1$H NMR spectrum (400 MHz, CDCl$_3$) δ ppm: 1.39 (3.0H, t, J=7.19 Hz), 4.01 (2.0H, s), 4.37 (2.0H, q, J=7.19 Hz), 6.71 (2.0H, d, J=8.54 Hz), 7.80 (2.0H, d, J=8.54 Hz), 8.32 (1.0H, s).

(91c) Ethyl 2-(4-{[(4-chloro-5-ethyl-1H-imidazol-2-yl)carbonyl]amino}phenyl)-1,3-thiazole-5-carboxylate Thionyl chloride (4 mL) was added to 4-chloro-5-ethyl-1H-imidazole-2-carboxylic acid (described in Example 1c, 200 mg, 0.8 mmol), and the mixture was stirred at 85° C. for 40 minutes. Following concentration under reduced pressure, the residue was azeotropically distilled with toluene twice to obtain crude 4-chloro-5-ethyl-1H-imidazole-2-carboxylic acid chloride. 5 mL pyridine was added and then ethyl 2-(4-aminophenyl)-1,3-thiazole-5-carboxylate obtained in Example (91b) was added. The mixture was stirred at room temperature for one hour. The reaction solution was diluted with ethyl acetate. The precipitated solid was collected by filtration and washed with ethyl acetate, to obtain 214 mg of the title compound as a white solid (73%).

$^1$H NMR spectrum (400 MHz, DMSO-d$_6$) δ ppm: 1.17 (3.0H, t, J=7.49 Hz), 1.32 (3.0H, t, J=7.11 Hz), 2.58 (2.0H, q, J=7.49 Hz), 4.34 (2.0H, q, J=7.11 Hz), 8.00 (2.0H, d, J=9.17 Hz), 8.03 (2.0H, d, J=9.17 Hz), 8.46 (1.0H, s), 10.54 (1.0H, br s).

(91d) 2-(4-{[(4-Chloro-5-ethyl-1H-imidazol-2-yl)carbonyl]amino}phenyl)-1,3-thiazole-5-carboxylic acid Ethyl 2-(4-{[(4-chloro-5-ethyl-1H-imidazol-2-yl)carbonyl]amino}phenyl)-1,3-thiazole-5-carboxylate obtained in Example (91c) (89 mg, 0.22 mmol) was dissolved in methanol (15 mL) and dichloromethane (10 mL). A 2 N aqueous lithium hydroxide solution (3 mL, 6 mmol) was added, and the mixture was stirred at 70° C. for 30 minutes. The organic solvent was evaporated under reduced pressure and 1 N hydrochloric acid was added until the pH of the solution was about 4. The resulting solid was collected by filtration and washed with distilled water to obtain 67 mg of the title compound as a light brown solid (80%).

$^1$H NMR spectrum (400 MHz, DMSO-d$_6$) δ ppm: 1.18 (3.0H, t, J=7.49 Hz), 2.61 (2.0H, q, J=7.49 Hz), 8.00 (2.0H, d, J=9.17 Hz), 8.04 (2.0H, d, J=9.17 Hz), 8.39 (1.0H, s), 10.75 (1.0H, s).

mass spectrum (FAB): m/z 377 (M+H)$^+$.

Example 92

2-(5-{[(4-Chloro-5-ethyl-1H-imidazol-2-yl)carbonyl]amino}-1,3-dihydro-2H-isoindol-2-yl)-1,3-thiazole-5-carboxylic acid (Exemplified Compound No. 92)

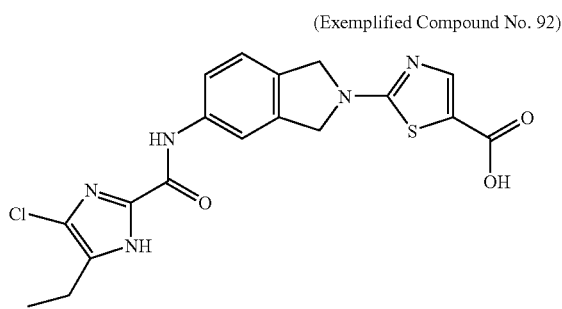 [SMILES: CCc1[nH]c(C(=O)Nc2ccc3c(c2)CN(c2ncc(C(=O)O)s2)C3)nc1Cl]

(92a) tert-Butyl 5-{[(4-chloro-5-ethyl-1H-imidazol-2-yl)carbonyl]amino}-1,3-dihydro-2H-isoindole-2-carboxylate The same operation as in Example (91c) was performed using 4-chloro-5-ethyl-1H-imidazole-2-carboxylic acid (410 mg, 2.36 mmol), thionyl chloride (5 mL), tert-butyl 5-amino-1,3-dihydro-2H-isoindole-2-carboxylate (described in Andronati, S. A.; Krys'ko, A. A.; Chugunov, B. M.; Kabanova, T. A.; Artemenko, A. G.; Russ. J. Org. Chem., 42, 8, 2006, 1174-1182, 0.94 g, 4 mmol) and pyridine (5 mL), to obtain 619 mg of the title compound as a white solid (64%).

$^1$H NMR spectrum (400 MHz, DMSO-$d_6$) δ ppm: 1.17 (3.0H, t, J=7.45 Hz), 1.46 (9.0H, s), 2.60 (2.0H, q, J=7.45 Hz), 4.56 (4.0H, t, J=15.18 Hz), 7.25-7.29 (1.0H, m), 7.70 (1.0H, t, J=8.88 Hz), 7.83 (1.0H, d, J=17.18 Hz), 10.40 (1.0H, s).

(92b) Ethyl 2-(5-{[(4-chloro-5-ethyl-1H-imidazol-2-yl)carbonyl]amino}-1,3-dihydro-2H-isoindol-2-yl)-1,3-thiazole-5-carboxylate The same operation as in Example (90f) was performed using tert-butyl 5-{[(4-chloro-5-ethyl-1H-imidazol-2-yl)carbonyl]amino}-1,3-dihydro-2H-isoindole-2-carboxylate obtained in Example (92a) (0.28 g, 0.69 mmol), a 4 N hydrochloric acid/ethyl acetate solution (15 ml, 60 mmol), diisopropylethylamine (0.45 g, 3.5 mmol), ethyl 2-bromo-1,3-thiazole-5-carboxylate (0.18 mL, 1.2 mmol) and DMF (10 mL), to obtain 0.28 g of the title compound as a light brown solid (90%).

$^1$H NMR spectrum (400 MHz, DMSO-$d_6$) δ ppm: 1.18 (3.0H, t, J=7.57 Hz), 1.29 (3.0H, t, J=7.03 Hz), 2.61 (2.0H, q, J=7.57 Hz), 4.24 (2.0H, q, J=7.03 Hz), 4.80 (4.0H, d, J=15.59 Hz), 7.38 (1.0H, d, J=8.25 Hz), 7.77 (1.0H, d, J=8.25 Hz), 7.95 (1.0H, s), 7.96 (1.0H, s), 10.50 (1.0H, s).

(92c) 2-(5-{[(4-Chloro-5-ethyl-1H-imidazol-2-yl)carbonyl]amino}-1,3-dihydro-2H-isoindol-2-yl)-1,3-thiazole-5-carboxylic acid The same operation as in Example (90g) was performed using ethyl 2-(5-{[(4-chloro-5-ethyl-1H-imidazol-2-yl)carbonyl]amino}-1,3-dihydro-2H-isoindol-2-yl)-1,3-thiazole-5-carboxylate obtained in Example (92b) (92 mg, 0.21 mmol), 2 N lithium hydroxide (3 mL, 6 mmol), methanol (5 mL) and dichloromethane (5 mL). Purification by reverse phase chromatography (elution solvent: acetonitrile/water=0/1, 1/1, 4/1) gave 49 mg of the title compound as a light brown solid (57%).

$^1$H NMR spectrum (400 MHz, DMSO-$d_6$) δ ppm: 1.18 (3.0H, t, J=7.57 Hz), 2.60 (2.0H, q, J=7.57 Hz), 4.78 (4.0H, d, J=15.13 Hz), 6.87 (1.0H, s), 7.38 (1.0H, d, J=8.25 Hz), 7.76 (1.0H, d, J=8.25 Hz), 7.83 (1.0H, s), 7.94 (1.0H, s), 10.49 (1.0H, s).

mass spectrum (FAB): m/z 418 (M+H)$^+$.

Example 93 trans(±)-2-[(5-{[(4-Chloro-5-ethyl-1H-imidazol-2-yl)carbonyl]amino}-1,3-dihydro-2H-isoindol-2-yl)carbonyl]cyclopropanecarboxylic acid (Exemplified Compound No. 93)

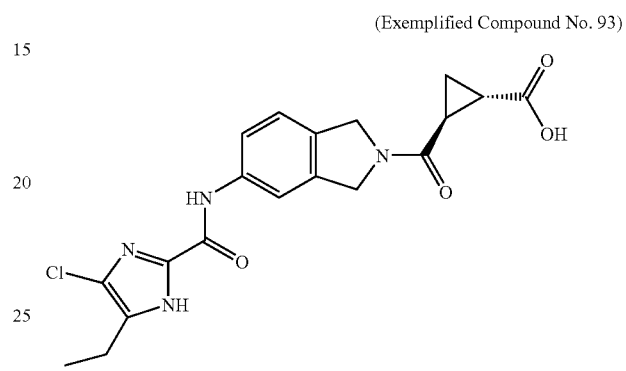

(93a) Ethyl trans(±)-2-[(5-{[(4-chloro-5-ethyl-1H-imidazol-2-yl)carbonyl]amino}-1,3-dihydro-2H-isoindol-2-yl)carbonyl]cyclopropanecarboxylate tert-Butyl 5-{[(4-chloro-5-ethyl-1H-imidazol-2-yl)carbonyl]amino}-1,3-dihydro-2H-isoindole-2-carboxylate (described in Example (92a), 0.17 g, 0.42 mmol) was dissolved in dichloromethane (3 mL) and methanol (1 mL). A 4 N hydrochloric acid/ethyl acetate solution (15 ml, 60 mmol) was added, followed by stirring for 20 minutes. The solvent was evaporated under reduced pressure. The resulting residue was dissolved in dichloromethane (5 mL) and DMA (5 mL). trans-2-(Ethoxycarbonyl)cyclopropanecarboxylic acid (described in Wessjohann, Ludger A.; Fulhorst, Michael; Zakharova, Svetlana, Pol. J. Chem., 80, 4, 2006, 673-678, 87 mg, 0.55 mmol), WSC (191 mg, 1 mmol) and DMAP (10 mg) were added, and the mixture was stirred at room temperature for one hour. The reaction solution was concentrated, diluted with ethyl acetate, washed with water and brine, and dried over anhydrous magnesium sulfate. Following concentration under reduced pressure, the residue was purified by silica gel column chromatography (elution solvent: chloroform/methanol=95/5, 90/10) to obtain 117 mg of the title compound as a light brown solid (65%).

$^1$H NMR spectrum (400 MHz, DMSO-$d_6$) δ ppm: 1.17 (3.0H, t, J=7.34 Hz), 1.21 (3.0H, t, J=7.18 Hz), 1.31-1.33 (2.0H, m), 1.97-2.02 (1.0H, m), 2.32-2.37 (1.0H, m), 2.60 (2.0H, q, J=7.34 Hz), 4.11 (2.0H, q, J=7.18 Hz), 4.63 (2.0H, d, J=15.13 Hz), 4.98-5.06 (2.0H, m), 7.31 (1.0H, d, J=8.25 Hz), 7.73 (1.0H, d, J=8.25 Hz), 7.88 (1.0H, s), 10.45 (1.0H, d, J=6.88 Hz).

(93b) trans(±)-2-[(5-{[(4-Chloro-5-ethyl-1H-imidazol-2-yl)carbonyl]amino}-1,3-dihydro-2H-isoindol-2-yl) carbonyl]cyclopropanecarboxylic acid Ethyl trans(±)-2-[(5-{[(4-chloro-5-ethyl-1H-imidazol-2-yl)carbonyl]amino}-1,3-dihydro-2H-isoindol-2-yl)carbonyl]cyclopropanecarboxylate obtained in Example (93a) (0.11 g, 0.26 mmol) was dissolved in methanol (5 mL) and dichloromethane (2 mL). The solution was subjected to the same operation as in Example (91d) using a 2 N aqueous lithium hydroxide solution (2 mL, 4 mmol), to obtain 71 mg of the title compound as a light brown solid (69%).

$^1$H NMR spectrum (400 MHz, DMSO-$d_6$) δ ppm: 1.18 (3.0H, t, J=7.57 Hz), 1.26-1.32 (2.0H, m), 1.90-1.92 (1.0H, m), 2.27-2.34 (1.0H, m), 2.60 (2.0H, q, J=7.57 Hz), 4.63 (2.0H, d, J=15.13 Hz), 4.95-5.09 (2.0H, m), 7.31 (1.0H, d, J=8.25 Hz), 7.73 (1.0H, d, J=8.25 Hz), 7.87 (1.0H, s), 10.45 (1.0H, d, J=6.88 Hz).

mass spectrum (FAB): m/z 403 (M+H)$^+$.

Example 94

2-(4-{[(4-Chloro-5-ethyl-1H-imidazol-2-yl)carbonyl]amino}phenyl)-4-methyl-1,3-thiazole-5-carboxylic acid (Exemplified Compound No. 94)

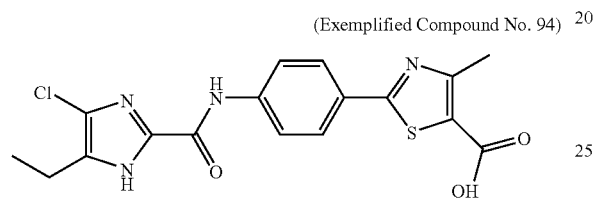

(94a) Ethyl 4-methyl-2-(4-nitrophenyl)-1,3-thiazole-5-carboxylate

The same operation as in Example (91a) was performed using 4-nitrophenylboronic acid (1 g, 6 mmol), ethyl 2-bromo-4-methyl-1,3-thiazole-5-carboxylate (1 g, 4 mmol), sodium bicarbonate (1.34 g, 16 mmol), tetrakis(triphenylphosphine)palladium (460 mg, 0.4 mmol), water (5 mL) and 1,4-dioxane (10 mL), to obtain 0.97 g of the title compound as a light yellow solid (83%).

$^1$H NMR spectrum (400 MHz, CDCl$_3$) δ ppm: 1.41 (3.0H, t, J=7.06 Hz), 2.81 (3.0H, s), 4.38 (2.0H, q, J=7.06 Hz), 8.14 (2.0H, d, J=8.59 Hz), 8.31 (2.0H, d, J=8.59 Hz).

(94b) Ethyl 2-(4-aminophenyl)-4-methyl-1,3-thiazole-5-carboxylate

The same operation as in Example (90d) was performed using ethyl 4-methyl-2-(4-nitrophenyl)-1,3-thiazole-5-carboxylate obtained in Example (94a) (0.40 g, 1.36 mmol), 10% Pd/C (wet, 1.2 g), ammonium formate (0.52 g, 8.22 mmol) and methanol (10 mL), to obtain 0.27 g of the crude title compound as a light yellow solid (75%).

$^1$H NMR spectrum (400 MHz, CDCl$_3$) δ ppm: 1.38 (3.0H, t, J=7.18 Hz), 2.75 (3.0H, s), 4.34 (2.0H, q, J=7.18 Hz), 6.69 (2.0H, d, J=8.51 Hz), 7.78 (2.0H, d, J=8.51 Hz). (94c) Ethyl 2-(4-{[(4-chloro-5-ethyl-1H-imidazol-2-yl)carbonyl]amino}phenyl)-4-methyl-1,3-thiazole-5-carboxylate The same operation as in Example (91c) was performed using 4-chloro-5-ethyl-1H-imidazole-2-carboxylic acid (50 mg, 0.29 mmol), thionyl chloride (3 mL), pyridine (5 mL) and ethyl 2-(4-aminophenyl)-4-methyl-1,3-thiazole-5-carboxylate obtained in Example (94b) (113 mg, 0.43 mmol), to obtain 96 mg of the title compound as a pale yellow solid (80%).

$^1$H NMR spectrum (400 MHz, DMSO-$d_6$) δ ppm: 1.18 (3.0H, t, J=7.57 Hz), 1.31 (3.0H, t, J=7.03 Hz), 2.61 (2.0H, q, J=7.57 Hz), 2.69 (3.0H, s), 4.30 (2.0H, q, J=7.03 Hz), 7.97 (2.0H, d, J=9.17 Hz), 8.02 (2.0H, d, J=9.17 Hz), 10.74 (1.0H, s).

(94d) 2-(4-{[(4-Chloro-5-ethyl-1H-imidazol-2-yl)carbonyl]amino}phenyl)-4-methyl-1,3-thiazole-5-carboxylic acid The same operation as in Example (90g) was performed using ethyl 2-(4-{[(4-chloro-5-ethyl-1H-imidazol-2-yl)carbonyl]amino}phenyl)-4-methyl-1,3-thiazole-5-carboxylate obtained in Example (94c) (96 mg, 0.23 mmol), 2 N lithium hydroxide (2 mL, 4 mmol), methanol (5 mL) and dichloromethane (3 mL). Purification by reverse phase chromatography (elution solvent: THF/water=0/1, 1/1, 4/1) gave 69 mg of the title compound as a light brown solid (77%).

$^1$H NMR spectrum (400 MHz, DMSO-$d_6$) δ ppm: 1.18 (3.0H, t, J=7.57 Hz), 2.61 (2.0H, q, J=7.57 Hz), 2.62 (3.0H, s), 7.87 (2.0H, d, J=8.71 Hz), 7.97 (2.0H, d, J=9.17 Hz), 10.66 (1.0H, s).

mass spectrum (FAB): m/z 391 (M+H)$^+$.

(Exemplified Compound No. 95)

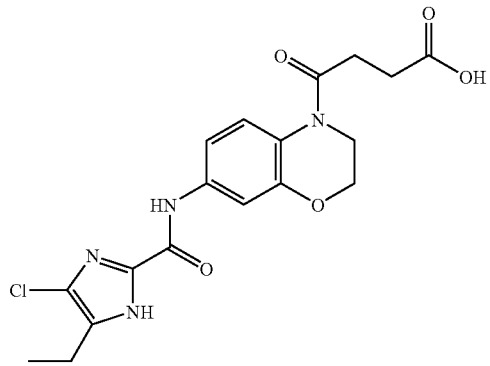

Example 95

4-(7-{[(4-Chloro-5-ethyl-1H-imidazol-2-yl)carbonyl]amino}-2,3-dihydro-4H-1,4-benzoxazin-4-yl)-4-oxobutanoic acid (95a) tert-Butyl 7-nitro-2,3-dihydro-4H-1,4-benzoxazine-4-carboxylate Di-tert-butyl dicarbonate (0.76 g, 3.48 mmol) and DMAP (10 mg) were added to a solution of 7-nitro-2,3-dihydro-4H-1,4-benzoxazine (described in Higuchi, Robert I.; Arienti, Kristen L.; Lopez, Francisco J.; Mani, Neelakhanda S.; Mais, Dale E.; Caferro, Thomas R.; Long, Yun Oliver; Jones, Todd K.; Edwards, James P.; Zhi, Lin; Schrader, William T.; et al., J. Med. Chem., 50, 10, 2007, 2486-2496, 0.47 g, 2.61 mmol) in THF (15 mL), and the mixture was stirred at 70° C. for one hour. The reaction solution was concentrated under reduced pressure, and the resulting residue was purified by silica gel column chromatography (elution solvent: hexane/ethyl acetate=10/1, 4/1) to obtain 0.81 g of the title compound as a light yellow solid (100%).

mass spectrum (APCI): m/z 281 (M+H)$^+$.
(95b) tert-Butyl 7-amino-2,3-dihydro-4H-1,4-benzoxazine-4-carboxylate 10% Pd/C (0.24 g) was added to a solution of tert-butyl 7-nitro-2,3-dihydro-4H-1,4-benzoxazine-2-carboxylate obtained in Example (95a) (0.81 g, 2.89 mmol) in methanol (10 mL) in a nitrogen atmosphere. The atmosphere was replaced with hydrogen and the mixture was stirred at room temperature for 30 minutes. 10% Pd/C was filtered off and the mother liquor was concentrated under reduced pressure. The residue was purified by silica gel column chromatography (elution solvent: hexane/ethyl acetate=3/1, 2/1, 2/3) to obtain 0.66 g of the title compound as a light brown amorphous solid (100%).

mass spectrum (APCI): m/z 251 (M+H)$^+$.

(95c) tert-Butyl 7-{[(4-chloro-5-ethyl-1H-imidazol-2-yl) carbonyl]amino}-2,3-dihydro-4H-1,4-benzoxazine-4-carboxylate The same operation as in Example (91c) was performed using 4-chloro-5-ethyl-1H-imidazole-2-carboxylic acid (100 mg, 0.59 mmol), thionyl chloride (5 mL), pyridine (10 mL) and tert-butyl 7-amino-2,3-dihydro-4H-1,4-benzoxazine-4-carboxylate obtained in Example (95b) (0.3 g, 1.20 mmol), to obtain 0.13 g of the title compound as a pale yellow solid (56%).

mass spectrum (APCI): m/z 407 (M+H)$^+$.

(95d) Ethyl 4-(7-{[(4-chloro-5-ethyl-1H-imidazol-2-yl)carbonyl]amino}-2,3-dihydro-4H-1,4-benzoxazin-4-yl)-4-oxobutanoate The same operation as in Example (93a) was performed using tert-butyl 7-{[(4-chloro-5-ethyl-1H-imidazol-2-yl)carbonyl]amino}-2,3-dihydro-4H-1,4-benzoxazine-4-carboxylate obtained in Example (95c) (0.11 g, 0.27 mmol), a 4 N hydrochloric acid/ethyl acetate solution (8 ml, 32 mmol), monoethyl succinate (150 mg, 1 mmol), WSC hydrochloride (288 mg, 1.5 mmol), N,N-diisopropylethylamine (0.52 g, 4 mmol) and DMAP (10 mg). Purification by silica gel column chromatography (elution solvent: hexane/ethyl acetate=3/1, 2/1, 2/3, 0/1) gave 45 mg of the title compound as a light yellow solid (38%).

mass spectrum (APCI): m/z 435 (M+H)$^+$.

(95e) 4-(7-{[(4-Chloro-5-ethyl-1H-imidazol-2-yl)carbonyl] amino}-2,3-dihydro-4H-1,4-benzoxazin-4-yl)-4-oxobutanoic acid The same operation as in Example (91d) was performed using ethyl 4-(7-{[(4-chloro-5-ethyl-1H-imidazol-2-yl)carbonyl]amino}-2,3-dihydro-4H-1,4-benzoxazin-4-yl)-4-oxobutanoate obtained in Example (95d) (45 mg, 0.10 mmol), 2 N lithium hydroxide (3 mL, 6 mmol) and methanol (5 mL), to obtain 10.4 mg of the title compound as a colorless solid (25%).

$^1$H NMR spectrum (400 MHz, DMSO-d$_6$) δ ppm: 1.17 (3.0H, t, J=7.57 Hz), 2.59 (2.0H, q, J=7.57 Hz), 2.77 (2.0H, t, J=6.42 Hz), 3.16-3.17 (2.0H, m), 3.86 (2.0H, t, J=4.12 Hz), 4.23 (2.0H, t, J=4.12 Hz), 7.36 (1.0H, d, J=7.79 Hz), 7.51 (1.0H, s), 10.40 (1H, s), 12.13 (1H, br s).

mass spectrum (FAB): m/z 406 (M+H)$^+$.

(Exemplified Compound No. 96)

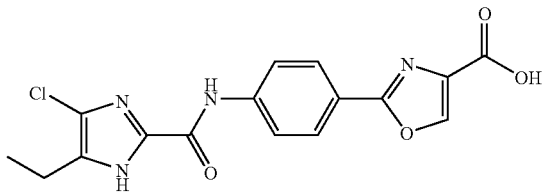

Example 96

2-(4-{[(4-Chloro-5-ethyl-1H-imidazol-2-yl)carbonyl]amino}phenyl)-1,3-oxazole-4-carboxylic acid (96a) Methyl 2-(4-nitrophenyl)-1,3-oxazole-4-carboxylate α,α-Bisisobutyronitrile (66 mg, 0.4 mmol) was added to a solution of methyl 2-(4-nitrophenyl)-4,5-dihydro-1,3-oxazole-4-carboxylate (described in Kline, Toni; Andersen, Niels H.; Harwood, Eric A.; Bowman, Jason; Malanda, Andre; Endsley, Stephanie; Erwin, Alice L.; Doyle, Michael; Fong, Susan; Harris, Alex L.; Mendelsohn, Brian; et al., J. Med. Chem., 45, 14, 2002, 3112-3129, 1.95 g, 7.8 mmol) in benzene (30 mL). The mixture was heated to 80° C. and N-bromosuccinimide (1.53 g, 8.58 mmol) was added. The mixture was stirred at the same temperature for 1.5 hours and then ethyl acetate and dichloromethane were added, followed by sequentially washing with water and brine. This was dried over anhydrous magnesium sulfate and then concentrated under reduced pressure. The residue was purified by silica gel column chromatography (elution solvent: chloroform/methanol=100/0, 20/1, 10/1) to obtain 1.29 g of the title compound as a colorless solid (67%).

$^1$H NMR spectrum (400 MHz, DMSO-d$_6$) δ ppm: 3.87 (3.0H, s), 8.28 (2.0H, d, J=9.17 Hz), 8.40 (2.0H, d, J=9.17 Hz). (96b) Methyl 2-(4-aminophenyl)-1,3-oxazole-4-carboxylate The same operation as in Example (95b) was performed using methyl 2-(4-nitrophenyl)-1,3-oxazole-4-carboxylate obtained in (96a) (1.29 g, 5.20 mmol), 10% Pd/C (0.55 g) and methanol (20 mL), to obtain 0.99 g of the title compound as a colorless solid (83%).

$^1$H NMR spectrum (400 MHz, CDCl$_3$) δ ppm: 3.82 (3.0H, s), 5.87 (2.0H, br s), 6.65 (2.0H, d, J=8.71 Hz), 7.67 (2.0H, d, J=8.71 Hz), 8.76 (1.0H, s).

(96c) Methyl 2-(4-{[(4-chloro-5-ethyl-1H-imidazol-2-yl) carbonyl]amino}phenyl)-1,3-oxazole-4-carboxylate The same operation as in Example (91c) was performed using 4-chloro-5-ethyl-1H-imidazole-2-carboxylic acid (0.13 g, 0.75 mmol), thionyl chloride (5 mL), methyl 2-(4-aminophenyl)-1,3-oxazole-4-carboxylate obtained in Example (96b) (0.15 g, 0.69 mmol) and pyridine (5 mL), to obtain 0.12 g of the title compound as a light purple solid (47%).

$^1$H NMR spectrum (400 MHz, DMSO-d$_6$) δ ppm: 1.19 (3.0H, t, J=7.49 Hz), 2.61 (2.0H, q, J=7.49 Hz), 3.85 (3.0H, s), 7.98 (2.0H, d, J=8.71 Hz), 8.06 (2.0H, d, J=8.71 Hz), 8.94 (1.0H, s), 10.74 (1.0H, s).

(96d) 2-(4-{[(4-Chloro-5-ethyl-1H-imidazol-2-yl)carbonyl] amino}phenyl)-1,3-oxazole-4-carboxylic acid The same operation as in Example (91d) was performed using methyl 2-(4-{[(4-chloro-5-ethyl-1H-imidazol-2-yl) carbonyl]amino}phenyl)-1,3-oxazole-4-carboxylate obtained in Example (96c) (0.12 g, 0.32 mmol), 2 N lithium hydroxide (2 mL, 4 mmol), methanol (3 mL) and tetrahydrofuran (5 mL), to obtain 56 mg of the title compound as a light brown solid (48%).

$^1$H NMR spectrum (400 MHz, DMSO-d$_6$) δ ppm: 1.19 (3.0H, t, J=7.57 Hz), 2.61 (2.0H, q, J=7.57 Hz), 7.97 (2.0H, d, J=8.71 Hz), 8.06 (2.0H, d, J=8.71 Hz), 8.79 (1.0H, s), 10.72 (1.0H, s).

mass spectrum (FAB): m/z 361 (M+H)$^+$.

Example 97

2-(4-{[(4-Chloro-5-ethyl-1H-imidazol-2-yl)carbonyl]amino}phenyl)-5-methyl-1,3-oxazole-4-carboxylic acid (Exemplified Compound No. 97)

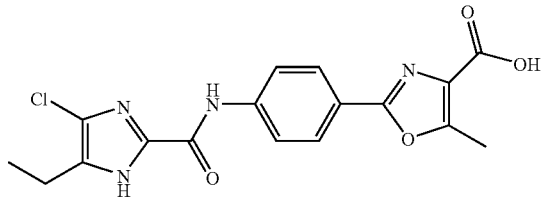

(97a) N-(4-Nitrobenzoyl)threonine methyl ester

Dichloromethane (80 mL) was added to threonine methyl ester hydrochloride (3.39 g, 20 mmol), 4-nitrobenzoic acid (3.34 g, 20 mmol), WSC hydrochloride (3.83 g, 20 mmol), HOBt (2.87 g, 20 mmol) and N,N-diisopropylethylamine (2.58 g, 20 mmol), and the mixture was stirred at room temperature for three days. The reaction solution was washed with water and brine, dried over anhydrous magnesium sulfate, and concentrated under reduced pressure. The residue was purified by silica gel column chromatography (elution solvent: ethyl acetate/hexane=1/2, 1/1, 1/2) to obtain 5.31 g of the title compound as a colorless solid (94%).

$^1$H NMR spectrum (400 MHz, CDCl$_3$) δ ppm: 1.32 (3.0H, d, J=6.78 Hz), 3.83 (3.0H, s), 4.51 (1.0H, dq, J=3.67, 6.78 Hz), 4.82-4.84 (1.0H, m), 7.02 (1.0H, d, J=8.25 Hz), 8.03 (2.0H, d, J=8.14 Hz), 8.32 (2.0H, d, J=8.14 Hz).

(97b) Methyl 5-methyl-2-(4-nitrophenyl)-4,5-dihydro-1,3-oxazole-4-carboxylate

The Burgess reagent (0.60 g, 2.5 mmol) was added to a solution of N-(4-nitrobenzoyl)threonine methyl ester obtained in Example (97a) (0.57 g, 3 mmol) in THF (20 mL), and the mixture was stirred at 60° C. for two hours. The reaction solution was concentrated under reduced pressure, and the residue was purified by silica gel column chromatography (elution solvent: ethyl acetate/hexane=1/4, 1/2, 1/1, 1/2) to obtain 1.06 g of the title compound as a colorless solid (100%).

$^1$H NMR spectrum (400 MHz, CDCl$_3$) δ ppm: 1.42 (3.0H, d, J=6.42 Hz), 3.81 (3.0H, s), 5.05 (1.0H, d, J=10.09 Hz), 5.13-5.18 (1.0H, m), 8.17 (2.0H, d, J=8.25 Hz), 8.28 (2.0H, d, J=8.25 Hz).

(97c) Methyl 5-methyl-2-(4-nitrophenyl)-1,3-oxazole-4-carboxylate

The same operation as in Example (96a) was performed using methyl 5-methyl-2-(4-nitrophenyl)-4,5-dihydro-1,3-oxazole-4-carboxylate obtained in Example (97b) (1.1 g, 4.16 mmol), α,α-bisisobutyronitrile (33 mg, 0.2 mmol), N-bromosuccinimide (0.78 g, 4.37 mmol) and benzene (20 mL). Purification by silica gel column chromatography (elution solvent: ethyl acetate/hexane=1/4, 1/2, 1/1, 2/1) gave 0.75 g of the title compound as a light yellow solid (69%).

$^1$H NMR spectrum (400 MHz, CDCl$_3$) δ ppm: 2.76 (3.0H, s), 3.98 (3.0H, s), 8.25 (2.0H, d, J=8.71 Hz), 8.33 (2.0H, d, J=8.71 Hz).

(97d) Methyl 2-(4-aminophenyl)-5-methyl-1,3-oxazole-4-carboxylate

The same operation as in Example (95b) was performed using methyl 5-methyl-2-(4-nitrophenyl)-1,3-oxazole-4-carboxylate obtained in Example (97c) (0.75 g, 2.86 mmol), 10% Pd/C (0.3 g) and methanol (10 mL). Purification by silica gel column chromatography (elution solvent: ethyl acetate/hexane=1/2, 1/1, 1/2, 1/4) gave 0.44 g of the title compound as a colorless solid (66%).

$^1$H NMR spectrum (400 MHz, CDCl$_3$) δ ppm: 7.62 (2.0H, d, J=8.71 Hz), 6.63 (2.0H, d, J=8.71 Hz), 3.80 (3.0H, s), 2.61 (3.0H, s).

(97e) Methyl 2-(4-{[(4-chloro-5-ethyl-1H-imidazol-2-yl)carbonyl]amino}phenyl)-5-methyl-1,3-oxazole-4-carboxylate The same operation as in Example (91c) was performed using 4-chloro-5-ethyl-1H-imidazole-2-carboxylic acid (0.17 g, 1 mmol), thionyl chloride (5 mL), methyl 2-(4-aminophenyl)-5-methyl-1,3-oxazole-4-carboxylate obtained in Example (97d) (0.15 g, 0.65 mmol) and pyridine (5 mL), to obtain 0.14 g of the title compound as a light pink solid (56%).

$^1$H NMR spectrum (400 MHz, DMSO-d$_6$) δ ppm: 1.19 (3.0H, t, J=7.57 Hz), 2.61 (2.0H, q, J=7.57 Hz), 2.66 (3.0H, s), 3.84 (3.0H, s), 7.93 (2.0H, d, J=8.71 Hz), 8.04 (2.0H, d, J=8.71 Hz), 10.70 (1.0H, s).

(97f) 2-(4-{[(4-Chloro-5-ethyl-1H-imidazol-2-yl)carbonyl]amino}phenyl)-5-methyl-1,3-oxazole-4-carboxylic acid The same operation as in Example (91d) was performed using methyl 2-(4-{[(4-chloro-5-ethyl-1H-imidazol-2-yl)carbonyl]amino}phenyl)-5-methyl-1,3-oxazole-4-carboxylate obtained in Example (97e) (0.14 g, 0.36 mmol), 2 N lithium hydroxide (2 mL, 4 mmol), methanol (3 mL) and tetrahydrofuran (5 mL), to obtain 107 mg of the title compound as a light pink solid (79%).

$^1$H NMR spectrum (400 MHz, DMSO-d$_6$) δ ppm: 1.19 (3.0H, t, J=7.57 Hz), 2.62 (2.0H, q, J=7.57 Hz), 2.65 (3.0H, s), 7.92 (2.0H, d, J=8.71 Hz), 8.03 (2.0H, d, J=8.71 Hz), 10.69 (1.0H, s).

mass spectrum (FAB): m/z 375 (M+H)$^+$.

Example 98 trans(±)-2-[(2-{[(4-Chloro-5-ethyl-1H-imidazol-2-yl)carbonyl]amino}-2,3-dihydro-1H-inden-5-yl)carbamoyl]cyclopropanecarboxylic acid (Exemplified Compound No. 98)

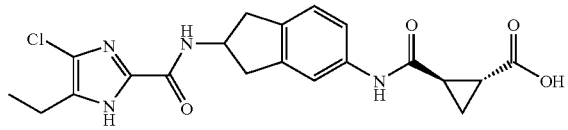

(98a) Ethyl trans(±)-2-[(2-amino-2,3-dihydro-1H-inden-5-yl)carbamoyl]cyclopropanecarboxylate The same operation as in Example (93a) was performed using tert-butyl 5-amino-1,3-dihydro-2H-inden-2-carboxylate (described in Andronati, S. A.; Krys'ko, A. A.; Chugunov, B. M.; Kabanova, T. A.; Artemenko, A. G.; Russ. J. Org. Chem.; 42; 8; 2006; 1174-1182, 0.19 g, 0.77 mmol), trans-2-(ethoxycarbonyl)cyclopropanecarboxylic acid (described in Wessjohann, Ludger A.; Fulhorst, Michael; Zakharova, Svetlana; Pol. J. Chem.; 80; 4; 2006; 673-678, 182 mg, 1.15 mmol), WSC hydrochloride (0.29 g, 1.5 mmol), DMAP (10 mg) and dichloromethane (20 mL). Purification by silica gel column chromatography (elution solvent: hexane/ethyl acetate=4/1, 2/1, 1/1, 1/2) gave 0.24 g of the title compound as a colorless solid (81%).

mass spectrum (APCI): m/z 389 (M+H)+

(98b) Ethyl trans(±)-2-[(2-{[(4-chloro-5-ethyl-1H-imidazol-2-yl)carbonyl]amino}-2,3-dihydro-1H-inden-5-yl)carbamoyl]cyclopropanecarboxylate The same operation as in Example (91c) was performed using 4-chloro-5-ethyl-1H-imidazole-2-carboxylic acid (0.23 g, 1.32 mmol), thionyl chloride (4 mL), ethyl trans(±)-2-[(2-amino-2,3-dihydro-1H-inden-5-yl)carbamoyl]cyclopropanecarboxylate obtained in Example (98a) (95 mg, 0.24 mmol) and pyridine (5 mL). Purification by silica gel column chromatography (elution solvent: hexane/ethyl acetate=1/2, 3/2, 1/0) gave 0.10 g of the title compound as a light yellow solid (92%).

$^1$H NMR spectrum (400 MHz, DMSO-$d_6$) δ ppm: 1.23-1.31 (8.5H, m), 1.41-1.43 (0.5H, m), 2.11-2.15 (1.0H, m), 2.25-2.27 (1.0H, m), 2.68 (2.0H, q, J=7.64 Hz), 2.88 (2.0H, dd, J=15.98, 4.02 Hz), 3.29 (2.0H, dd, J=16.71, 6.95 Hz), 4.18 (2.0H, q, J=7.32 Hz), 4.83-4.85 (1.0H, br m), 7.14-7.61 (3.0H, m), 11.16 (1.0H, br s).

(98c) trans(±)-2-[(2-{[(4-Chloro-5-ethyl-1H-imidazol-2-yl)carbonyl]amino}-2,3-dihydro-1H-inden-5-yl)carbamoyl]cyclopropanecarboxylic acid The same operation as in Example (91d) was performed using ethyl trans(±)-2-[(2-{[(4-chloro-5-ethyl-1H-imidazol-2-yl)carbonyl]amino}-2,3-dihydro-1H-inden-5-yl)carbamoyl]cyclopropanecarboxylate obtained in Example (98b) (100 mg, 0.23 mmol), 2 N lithium hydroxide (3 mL, 6 mmol) and methanol (3 mL), to obtain 71 mg of the title compound as a colorless solid (76%).

$^1$H NMR spectrum (400 MHz, DMSO-$d_6$) δ ppm: 1.08-1.09 (3.0H, m), 1.14 (3.0H, t, J=7.57 Hz), 1.73 (1.0H, t, J=8.67 Hz), 2.13 (1.0H, d, J=3.42 Hz), 2.55 (2.0H, q, J=7.57 Hz), 2.91-2.97 (2.0H, m), 4.60-4.68 (1.0H, m), 7.09 (1.0H, d, J=8.30 Hz), 7.32 (1.0H, d, J=8.30 Hz), 7.50 (1.0H, s), 8.64 (1.0H, d, J=7.81 Hz), 10.23 (1.0H, s).

mass spectrum (FAB): m/z 417 (M+H)$^+$.

Example 99

2-(4-{[(4-Chloro-5-ethyl-1H-imidazol-2-yl)carbonyl]amino}phenyl)-5-ethyl-1,3-oxazole-4-carboxylic acid (Exemplified Compound No. 99)

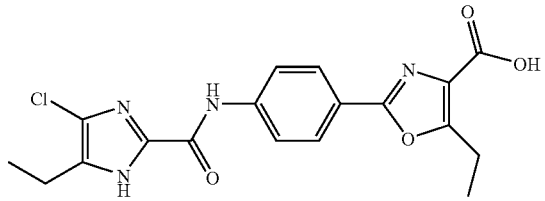

(99a) Ethyl 5-ethyl-2-(4-nitrophenyl)-1,3-oxazole-4-carboxylate

Dioxane (30 mL) was added to ethyl 5-ethyl-1,3-oxazole-4-carboxylate (described in Armarego, Wilfred L. F.; Taguchi, Hiroyasu; Cotton, Richard G. H.; Battiston, Sandra; Leong, Lillian; Eur. J. Med. Chem. Chim. Ther.; 22; 1987; 283-292, 1.69 g, 10 mmol), 1-iodo-4-nitrobenzene (2.74 g, 11 mmol), palladium acetate (179.6 mg, 0.8 mmol), tris(2-methylphenyl)phosphine (0.49 g, 1.6 mmol) and cesium carbonate (3.25 g, 10 mmol), and the mixture was stirred at 100° C. for 13 hours. Water was added, followed by extraction with ethyl acetate and washing with brine. This was dried over anhydrous magnesium sulfate and then concentrated under reduced pressure. The residue was purified by silica gel column chromatography (elution solvent: hexane/ethyl acetate=5/1, 3/1, 2/1) to obtain 1.08 g of the title compound as a colorless solid (37%).

$^1$H NMR spectrum (400 MHz, CDCl$_3$) δ ppm: 1.38 (3.0H, t, J=7.64 Hz), 1.43 (3.0H, t, J=7.07 Hz), 3.17 (2.0H, q, J=7.64 Hz), 4.45 (2.0H, q, J=7.07 Hz), 8.26 (2.0H, d, J=9.02 Hz), 8.33 (2.0H, d, J=9.02 Hz). (99b) Ethyl 2-(4-aminophenyl)-5-ethyl-1,3-oxazole-4-carboxylate The same operation as in Example (95b) was performed using ethyl 5-ethyl-2-(4-nitrophenyl)-1,3-oxazole-4-carboxylate obtained in Example (99a) (0.57 g, 2 mmol), 10% Pd/C (0.2 g) and methanol (10 mL), to obtain 0.45 g of the title compound as a yellow solid (88%).

$^1$H NMR spectrum (400 MHz, CDCl$_3$) δ ppm: 1.32 (3.0H, t, J=7.57 Hz), 1.41 (3.0H, t, J=7.08 Hz), 3.10 (2.0H, q, J=7.57 Hz), 4.41 (2.0H, q, J=7.08 Hz), 6.70 (2.0H, d, J=8.44 Hz), 7.87 (2.0H, d, J=8.44 Hz).

(99c) Ethyl 2-(4-{[(4-chloro-5-ethyl-1H-imidazol-2-yl)carbonyl]amino}phenyl)-5-ethyl-1,3-oxazole-4-carboxylate The same operation as in Example (91c) was performed using 4-chloro-5-ethyl-1H-imidazole-2-carboxylic acid (0.21 g, 1.2 mmol), thionyl chloride (5 mL), ethyl 2-(4-aminophenyl)-5-ethyl-1,3-oxazole-4-carboxylate obtained in Example (99b) (0.2 g, 0.77 mmol) and pyridine (5 mL), to obtain 0.23 g of the title compound as a light pink solid (72%).

$^1$H NMR spectrum (400 MHz, DMSO-$d_6$) δ ppm: 1.18 (3.0H, t, J=7.56 Hz), 1.28 (3.0H, t, J=7.56 Hz), 1.32 (3.0H, t, J=7.07 Hz), 2.61 (2.0H, q, J=7.56 Hz), 3.08 (2.0H, q, J=7.56 Hz), 4.31 (2.0H, q, J=7.07 Hz), 7.94 (2.0H, d, J=8.78 Hz), 8.04 (2.0H, d, J=8.78 Hz), 10.68 (1.0H, s), 13.53 (1.0H, br s).

(99d) 2-(4-{[(4-Chloro-5-ethyl-1H-imidazol-2-yl)carbonyl]amino}phenyl)-5-ethyl-1,3-oxazole-4-carboxylic acid The same operation as in Example (91d) was performed using ethyl 2-(4-{[(4-chloro-5-ethyl-1H-imidazol-2-yl)carbonyl]amino}phenyl)-5-ethyl-1,3-oxazole-4-carboxylate obtained in Example (99c) (0.12 g, 2.88 mmol), 2 N lithium hydroxide (2 mL, 4 mmol), methanol (2 mL) and tetrahydrofuran (5 mL), to obtain 97 mg of the title compound as a light pink solid (87%).

$^1$H NMR spectrum (400 MHz, DMSO-$d_6$) δ ppm: 1.19 (3.0H, t, J=7.56 Hz), 1.27 (3.0H, t, J=7.56 Hz), 2.61 (2.0H, q, J=7.56 Hz), 3.07 (2.0H, q, J=7.56 Hz), 7.93 (2.0H, d, J=8.78 Hz), 8.04 (2.0H, d, J=8.78 Hz), 10.68 (1.0H, s), 13.54 (1.0H, br s).

mass spectrum (ESI): m/z 389 (M+H)$^+$.

Example 100

3-[(7-{[(4-Chloro-5-ethyl-1H-imidazol-2-yl)carbonyl]amino}-2,3-dihydro-4H-1,4-benzoxazin-4-yl)methyl]benzoic acid (Exemplified Compound No. 100)

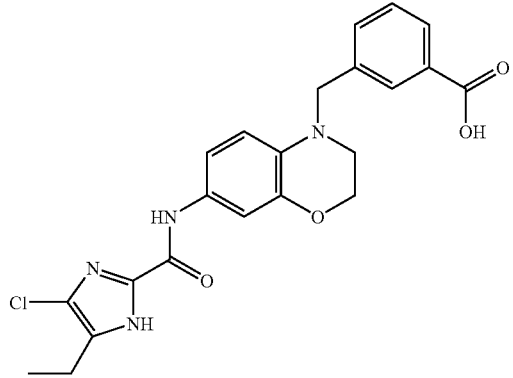

(100a) Methyl 3-[(7-nitro-2,3-dihydro-4H-1,4-benzoxazin-4-yl)methyl]benzoate

The same operation as in Example (90a) was performed using 7-nitro-2,3-dihydro-4H-1,4-benzoxazine (described in Higuchi, Robert I.; Arienti, Kristen L.; Lopez, Francisco J.; Mani, Neelakhanda S.; Mais, Dale E.; Caferro, Thomas R.; Long, Yun Oliver; Jones, Todd K.; Edwards, James P.; Zhi, Lin; Schrader, William T.; et al.; J. Med. Chem.; 50; 10; 2007; 2486-2496, 0.6 g, 3.3 mmol), sodium hydride (55% content, 145 mg, 3.3 mmol), methyl 3-bromomethylbenzoate (0.76 g, 3.3 mmol) and DMF (50 mL). Purification by silica gel column chromatography (elution solvent: hexane/ethyl acetate=1/1) gave 1.11 g of the title compound as a deep yellow solid (100%).

$^1$H NMR spectrum (400 MHz, DMSO-$d_6$) δ ppm: 3.62 (2.0H, t, J=4.36 Hz), 3.84 (3.0H, s), 4.29 (2.0H, t, J=4.36 Hz), 4.81 (2.0H, s), 6.78 (1.0H, d, J=9.17 Hz), 7.51-7.56 (3.0H, m), 7.70 (1.0H, dd, J=8.94, 2.52 Hz), 7.86-7.89 (2.0H, m).

(100b) Methyl 3-[(7-amino-2,3-dihydro-4H-1,4-benzoxazin-4-yl)methyl]benzoate

DMF (5 mL), water (5 mL), zinc (0.7 g, 10.7 mmol) and iron trichloride hexahydrate (0.12 g, 0.4 mmol) were added to methyl 3-[(7-nitro-2,3-dihydro-4H-1,4-benzoxazin-4-yl)methyl]benzoate obtained in Example (100a) (0.35 g, 1.07 mmol), and the mixture was stirred at 100° C. for 50 minutes. The insoluble matter was filtered off and ethyl acetate was added to the mother liquor, and the organic layer was washed with water and brine, and dried over anhydrous magnesium sulfate. Concentration under reduced pressure gave 0.28 g of the crude title compound as a brown oily substance (88%).

mass spectrum (APCI): m/z 299 (M+H)$^+$ (100c) Methyl 3-[(7-{[(4-chloro-5-ethyl-1H-imidazol-2-yl)carbonyl]amino}-2,3-dihydro-4H-1,4-benzoxazin-4-yl)methyl]benzoate The same operation as in Example (91c) was performed using 4-chloro-5-ethyl-1H-imidazole-2-carboxylic acid (0.21 g, 1.2 mmol), thionyl chloride (4 mL), methyl 3-[(7-amino-2,3-dihydro-4H-1,4-benzoxazin-4-yl)methyl]benzoate obtained in Example (100b) (0.28 g, 0.97 mmol) and pyridine (5 mL). The resulting solid was washed with dichloromethane/hexane=1/1 to obtain 0.29 g of the title compound as a colorless solid (66%).

$^1$H NMR spectrum (400 MHz, DMSO-$d_6$) δ ppm: 1.16 (3.0H, t, J=7.49 Hz), 2.57 (2.0H, q, J=7.49 Hz), 3.35 (2.0H, t, J=4.36 Hz), 3.84 (3.0H, s), 4.23 (2.0H, t, J=4.36 Hz), 4.52 (2.0H, s), 6.61 (1.0H, d, J=8.91 Hz), 7.16 (1.0H, dd, J=8.91, 2.29 Hz), 7.31 (1.0H, d, J=2.29 Hz), 7.50 (1.0H, t, J=7.79 Hz), 7.59 (1.0H, d, J=7.79 Hz), 7.86 (1.0H, d, J=7.79 Hz), 7.92 (1.0H, s), 10.07 (1.0H, s).

(100d) 3-[(7-{[(4-Chloro-5-ethyl-1H-imidazol-2-yl)carbonyl]amino}-2,3-dihydro-4H-1,4-benzoxazin-4-yl)methyl]benzoic acid The same operation as in Example (91d) was performed using methyl 3-[(7-{[(4-chloro-5-ethyl-1H-imidazol-2-yl)carbonyl]amino}-2,3-dihydro-4H-1,4-benzoxazin-4-yl)methyl]benzoate obtained in Example (100c) (0.16 g, 0.35 mmol), 2 N lithium hydroxide (3 mL, 6 mmol), methanol (3 mL) and tetrahydrofuran (8 mL), to obtain 0.11 g of the title compound as a light pink solid (71%).

$^1$H NMR spectrum (400 MHz, DMSO-$d_6$) δ ppm: 1.16 (3.0H, t, J=7.57 Hz), 2.57 (2.0H, q, J=7.57 Hz), 3.33 (2.0H, t, J=4.36 Hz), 4.21 (2.0H, t, J=4.36 Hz), 4.45 (2.0H, s), 6.63 (1.0H, d, J=8.71 Hz), 7.16 (1.0H, dd, J=8.71, 2.75 Hz), 7.27-7.29 (2.0H, m), 7.30 (1.0H, d, J=2.75 Hz), 7.76-7.77 (1.0H, m), 7.84 (1.0H, s), 10.07 (1.0H, s).

mass spectrum (ESI): m/z 441 (M+H)$^+$.

Example 101

4-[(7-{[(4-Chloro-5-ethyl-1H-imidazol-2-yl)carbonyl]amino}-2,3-dihydro-4H-1,4-benzoxazin-4-yl)methyl]benzoic acid (Exemplified Compound No. 101)

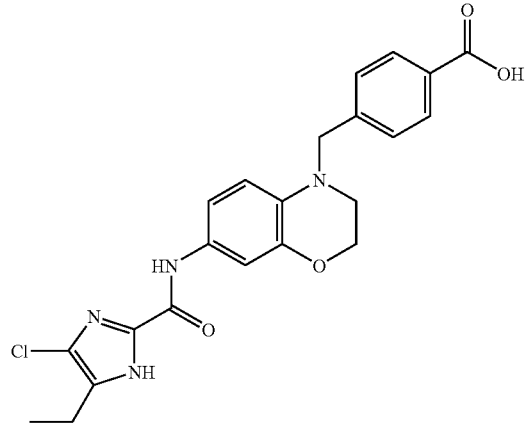

(101a) Methyl 4-[(7-nitro-2,3-dihydro-4H-1,4-benzoxazin-4-yl)methyl]benzoate

The same operation as in Example (90a) was performed using 7-nitro-2,3-dihydro-4H-1,4-benzoxazine (described in Higuchi, Robert I.; Arienti, Kristen L.; Lopez, Francisco J.; Mani, Neelakhanda S.; Mais, Dale E.; Caferro, Thomas R.; Long, Yun Oliver; Jones, Todd K.; Edwards, James P.; Zhi, Lin; Schrader, William T.; et al.; J. Med. Chem.; 50; 10; 2007; 2486-2496, 0.6 g, 3.3 mmol), sodium hydride (55% content, 145 mg, 3.3 mmol), methyl 4-bromomethylbenzoate (0.76 g, 3.3 mmol) and DMF (20 mL). The resulting solid was washed with ethyl acetate/hexane=1/1 to obtain 0.98 g of the title compound as a yellow solid (90%).

$^1$H NMR spectrum (400 MHz, DMSO-$d_6$) δ ppm: 3.64 (2.0H, t, J=4.39 Hz), 3.84 (3.0H, s), 4.30 (2.0H, t, J=4.39 Hz), 4.81 (2.0H, s), 6.71 (1.0H, d, J=9.09 Hz), 7.42 (2.0H, d, J=8.18 Hz), 7.54 (1.0H, d, J=2.62 Hz), 7.69 (1.0H, dd, J=9.09, 2.62 Hz), 7.94 (2.0H, d, J=8.18 Hz).

(101b) Methyl 4-[(7-amino-2,3-dihydro-4H-1,4-benzoxazin-4-yl)methyl]benzoate

The same operation as in Example (100b) was performed using methyl 4-[(7-nitro-2,3-dihydro-4H-1,4-benzoxazin-4-yl)methyl]benzoate obtained in Example (101a) (0.35 g, 1.07 mmol), zinc (0.7 g, 10.7 mmol), iron trichloride hexahydrate (0.12 g, 0.4 mmol), DMF (5 mL) and water (5 mL), to obtain 0.28 g of the crude title compound as a brown oily substance (88%).

mass spectrum (APCI): m/z 299 (M+H)$^+$ (101c) Methyl 4-[(7-{[(4-chloro-5-ethyl-1H-imidazol-2-yl)carbonyl]amino}-2,3-dihydro-4H-1,4-benzoxazin-4-yl)methyl]benzoate The same operation as in Example (91c) was performed using 4-chloro-5-ethyl-1H-imidazole-2-carboxylic acid (0.21 g, 1.2 mmol), thionyl chloride (2 mL), methyl 4-[(7-amino-2,3-dihydro-4H-1,4-benzoxazin-4-yl)methyl]benzoate obtained in Example (101b) (0.28 g, 0.97 mmol) and pyridine (5 mL). The resulting solid was washed with dichloromethane/hexane=1/1 to obtain 0.31 g of the title compound as a light yellow solid (70%).

¹H NMR spectrum (400 MHz, DMSO-d₆) δ ppm: 1.16 (3.0H, t, J=7.57 Hz), 2.57 (2.0H, q, J=7.57 Hz), 3.38 (2.0H, t, J=4.13 Hz), 3.84 (3.0H, s), 4.24 (2.0H, t, J=4.13 Hz), 4.53 (2.0H, s), 6.54 (1.0H, d, J=9.17 Hz), 7.15 (1.0H, dd, J=9.17, 2.29 Hz), 7.30 (1.0H, d, J=2.29 Hz), 7.45 (2.0H, d, J=8.01 Hz), 7.94 (2.0H, d, J=8.01 Hz), 10.06 (1.0H, s).

(101d) 4-[(7-{[(4-Chloro-5-ethyl-1H-imidazol-2-yl)carbonyl]amino}-2,3-dihydro-4H-1,4-benzoxazin-4-yl)methyl]benzoic acid The same operation as in Example (91d) was performed using methyl 4-[(7-{[(4-chloro-5-ethyl-1H-imidazol-2-yl)carbonyl]amino}-2,3-dihydro-4H-1,4-benzoxazin-4-yl)methyl]benzoate obtained in Example (101c) (0.13 g, 0.29 mmol), 2 N lithium hydroxide (3 mL, 6 mmol), methanol (3 mL) and tetrahydrofuran (8 mL), to obtain 0.13 g of the title compound as a light brown solid (100%).

¹H NMR spectrum (400 MHz, DMSO-d₆) δ ppm: 1.15 (3.0H, t, J=7.57 Hz), 2.56 (2.0H, q, J=7.57 Hz), 3.38 (2.0H, t, J=4.13 Hz), 4.20 (2.0H, t, J=4.13 Hz), 4.41 (2.0H, s), 6.62 (1.0H, d, J=9.17 Hz), 7.14-7.17 (3.0H, m), 7.28 (1.0H, d, J=2.29 Hz), 7.77 (2.0H, d, J=7.79 Hz).

mass spectrum (ESI): m/z 441 (M+H)⁺.

Example 102

2-(4-{[(4-Chloro-5-ethyl-1H-imidazol-2-yl)carbonyl]amino}-3-methoxyphenyl)-1,3-oxazole-4-carboxylic acid (Exemplified Compound No. 102)

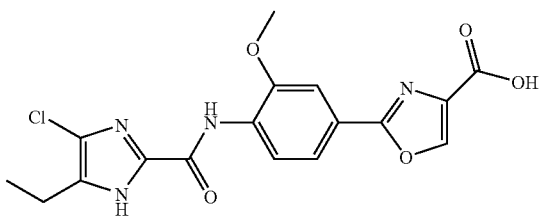

(102a) N-(3-Methoxy-4-nitrobenzoyl)serine methyl ester

Dichloromethane (80 mL) was added to serine methyl ester hydrochloride (2.64 g, 17 mmol), 3-methoxy-4-nitrobenzoic acid (3 g, 15.2 mmol), WSC hydrochloride (3.83 g, 20 mmol), DMAP (0.18 g, 1.5 mmol) and N,N-diisopropylethylamine (2.58 g, 20 mmol), and the mixture was stirred at room temperature for one day. The reaction solution was washed with water and brine, dried over anhydrous magnesium sulfate, and concentrated under reduced pressure. The residue was purified by silica gel column chromatography (elution solvent: ethyl acetate/hexane=1/2, 1/1, 2/1, 1/0) to obtain 3.11 g of the title compound as a colorless solid (69%).

¹H NMR spectrum (400 MHz, CDCl₃) δ ppm: 3.85 (3.0H, s), 4.02 (3.0H, s), 4.04-4.08 (1.0H, m), 4.13-4.17 (1.0H, m), 4.86-4.89 (1.0H, m), 7.15 (1.0H, d, J=6.88 Hz), 7.26 (1.0H, s), 7.39 (1.0H, dd, J=8.25, 1.83 Hz), 7.64 (1.0H, d, J=1.83 Hz), 7.87 (1.0H, d, J=8.25 Hz).

(102b) Methyl 2-(3-methoxy-4-nitrophenyl)-4,5-dihydro-1,3-oxazole-4-carboxylate

The same operation as in Example (97b) was performed using N-(3-methoxy-4-nitrobenzoyl)serine methyl ester obtained in Example (102a) (2.46 g, 8.26 mmol), the Burgess reagent (2.56 g, 10.7 mmol) and THF (50 mL). Purification by silica gel column chromatography (elution solvent: ethyl acetate/hexane=1/4, 1/2, 1/1, 1/2) gave 1.72 g of the title compound as a light yellow solid (74%).

mass spectrum (APCI): m/z 281 (M+H)⁺.

(102c) Methyl 2-(3-methoxy-4-nitrophenyl)-1,3-oxazole-4-carboxylate

The same operation as in Example (96a) was performed using methyl 2-(3-methoxy-4-nitrophenyl)-4,5-dihydro-1,3-oxazole-4-carboxylate obtained in Example (102b) (1.72 g, 6.14 mmol), α,α-bisisobutyronitrile (50 mg, 0.3 mmol), N-bromosuccinimide (1.20 g, 6.75 mmol) and benzene (30 mL). Purification by silica gel column chromatography (elution solvent: chloroform/methanol=99/1, 98/2, 95/5) gave 1.46 g of the title compound as a light yellow solid (85%).

¹H NMR spectrum (400 MHz, CDCl₃) δ ppm: 3.98 (3.0H, s), 4.07 (3.0H, s), 7.75 (1.0H, dd, J=8.25, 1.38 Hz), 7.87 (1.0H, d, J=1.38 Hz), 7.94 (1.0H, d, J=8.25 Hz), 8.36 (1.0H, s).

(102d) Methyl 2-(4-amino-3-methoxyphenyl)-1,3-oxazole-4-carboxylate

The same operation as in Example (95b) was performed using methyl 2-(3-methoxy-4-nitrophenyl)-1,3-oxazole-4-carboxylate obtained in Example (102c) (1.46 g, 5.25 mmol), 10% Pd/C (0.3 g) and ethanol (20 mL). The resulting solid was washed with dichloromethane/hexane to obtain 0.88 g of the title compound as a colorless solid (67%).

¹H NMR spectrum (400 MHz, CDCl₃) δ ppm: 3.94 (3.0H, s), 3.95 (3.0H, s), 6.75 (1.0H, d, J=8.51 Hz), 7.54-7.56 (2.0H, m), 8.21 (1.0H, s).

(102e) Methyl 2-(4-{[(4-chloro-5-ethyl-1H-imidazol-2-yl)carbonyl]amino}-3-methoxyphenyl)-1,3-oxazole-4-carboxylate The same operation as in Example (91c) was performed using 4-chloro-5-ethyl-1H-imidazole-2-carboxylic acid (0.13 g, 0.75 mmol), thionyl chloride (2 mL), methyl 2-(4-amino-3-methoxyphenyl)-1,3-oxazole-4-carboxylate obtained in Example (102d) (0.25 g, 1.01 mmol) and pyridine (5 mL), to obtain 0.26 g of the title compound as a colorless solid (86%).

¹H NMR spectrum (400 MHz, DMSO-d₆) δ ppm: 1.18 (3.0H, t, J=7.57 Hz), 2.60 (2.0H, q, J=7.57 Hz), 3.85 (3.0H, s), 4.06 (3.0H, s), 7.64 (1.0H, d, J=1.83 Hz), 7.70 (1.0H, dd, J=8.45, 1.83 Hz), 8.47 (1.0H, d, J=8.45 Hz), 8.97 (1.0H, s), 9.48 (1.0H, s).

(102f) 2-(4-{[(4-Chloro-5-ethyl-1H-imidazol-2-yl)carbonyl]amino}-3-methoxyphenyl)-1,3-oxazole-4-carboxylic acid The same operation as in Example (91d) was performed using methyl 2-(4-{[(4-chloro-5-ethyl-1H-imidazol-2-yl)carbonyl]amino}-3-methoxyphenyl)-1,3-oxazole-4-carboxylate obtained in Example (102e) (0.26 g, 0.64 mmol), 2 N lithium hydroxide (3 mL, 6 mmol), methanol (3 mL) and tetrahydrofuran (5 mL), to obtain 156 mg of the title compound as a colorless solid (62%).

¹H NMR spectrum (400 MHz, DMSO-d₆) δ ppm: 1.18 (3.0H, t, J=7.57 Hz), 2.60 (2.0H, q, J=7.57 Hz), 4.04 (3.0H, s), 7.62-7.64 (2.0H, m), 8.43 (1.0H, d, J=9.03 Hz), 9.45 (1.0H, s).

mass spectrum (ESI): m/z 391 (M+H)⁺.

Example 103 cis(±)-2-(4-{[(4-Chloro-5-ethyl-1H-imidazol-2-yl)carbonyl]amino}-3-methoxypiperidin-1-yl)-1,3-oxazole-4-carboxylic acid (Exemplified Compound No. 103)

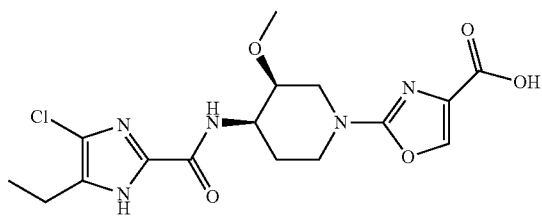

(103a) tert-Butyl cis(±)-4-{[(benzyloxy)carbonyl]amino}-3-methoxypiperidine-1-carboxylate THF (20 mL) and water (15 mL) were added to tert-butyl cis(±)-4-amino-3-methoxypiperidine-1-carboxylate (described in Example (1e), 4.6 g, 20 mmol). The mixture was stirred, during which sodium bicarbonate (3.44 g, 40 mmol) and benzyl chloroformate (3.95 g, 22 mmol) were added at room temperature, followed by stirring for one hour. The reaction solution was diluted with water, followed by extraction with ethyl acetate. The organic layer was washed with brine, dried over anhydrous magnesium sulfate, and then concentrated under reduced pressure. The residue was purified by silica gel column chromatography (elution solvent: ethyl acetate/hexane=1/4, 1/2, 1/1) to obtain 6.89 g of the title compound as a colorless solid (95%).

mass spectrum (APCI): m/z 365 (M+H)$^+$.

(103b) cis(±)-Benzyl (1-carbamoyl-3-methoxypiperidin-4-yl)carbamate

A 4 N hydrochloric acid/ethyl acetate solution (30 ml, 120 mmol) was added to a solution of tert-butyl cis(±)-4-{[(benzyloxy)carbonyl]amino}-3-methoxypiperidine-1-carboxylate obtained in Example (103a) in ethyl acetate (10 mL). The mixture was stirred for 45 minutes and the solvent was evaporated under reduced pressure. The residue was diluted with dichloromethane, washed with a 1 N aqueous sodium hydroxide solution and brine, dried over anhydrous magnesium sulfate, and then concentrated under reduced pressure. Trimethylsilyl isocyanate (0.86 g, 7.5 mmol) was added to the resulting residue, and the mixture was stirred at room temperature for 15 hours. Methanol (1 mL) was added, followed by stirring for 30 minutes. The precipitated solid was filtered off and washed with dichloromethane to obtain 1.44 g of the title compound as a colorless solid (81%).

$^1$H NMR spectrum (400 MHz, DMSO-d$_6$) δ ppm: 1.40-1.44 (1.0H, m), 1.54-1.62 (1.0H, m), 2.49-2.51 (2.0H, m), 3.25 (3.0H, s), 3.64-3.70 (2.0H, m), 3.95 (1.0H, dd, J=13.90, 4.39 Hz), 5.03 (2.0H, s), 5.85 (2.0H, br s), 7.12 (1.0H, d, J=8.05 Hz), 7.28-7.39 (5.0H, m).

(103c) Ethyl cis(±)-2-(4-{[(benzyloxy)carbonyl]amino}-3-methoxypiperidin-1-yl)-1,3-oxazole-4-carboxylate Ethyl bromopyruvate (2.93 g, 15 mmol) and sodium bicarbonate (2.10 g, 25 mmol) were added to a solution of cis(±)-benzyl (1-carbamoyl-3-methoxypiperidin-4-yl)carbamate obtained in Example (103b) (1.4 g, 4.56 mmol) in THF (30 mL), and the mixture was stirred at 70° C. for three hours. The insoluble matter was filtered off, followed by dilution with ethyl acetate. This was washed with water and brine, dried over anhydrous magnesium sulfate, and then concentrated under reduced pressure. The resulting residue was purified by silica gel column chromatography (elution solvent: ethyl acetate/hexane=1/4, 1/2, 1/1, 2/1, 4/1) to obtain 1.46 g of the title compound as a colorless solid (79%).

$^1$H NMR spectrum (400 MHz, CDCl$_3$) δ ppm: 1.34 (3.0H, t, J=7.56 Hz), 1.59-1.62 (1.0H, m), 1.73-1.79 (1.0H, m), 1.87 (1.0H, ddd, J=24.45, 12.26, 4.57 Hz), 3.36 (3.0H, s), 3.43-3.43 (1.0H, m), 3.79-3.85 (1.0H, br m), 4.09-4.17 (1.0H, m), 4.30-4.40 (3.0H, m), 5.11 (2.0H, s), 5.23 (1.0H, d, J=8.29 Hz), 7.32-7.37 (5.0H, m), 7.74 (1.0H, s).

(103d) Ethyl cis(±)-2-(4-amino-3-methoxypiperidin-1-yl)-1,3-oxazole-4-carboxylate The same operation as in Example (95b) was performed using ethyl cis(±)-2-(4-{[(benzyloxy)carbonyl]amino}-3-methoxypiperidin-1-yl)-1,3-oxazole-4-carboxylate obtained in Example (103c) (0.7 g, 1.74 mmol), 10% Pd/C (0.25 g) and ethanol (10 mL), to obtain 0.48 g of the title compound as a yellow amorphous solid (100%).

$^1$H NMR spectrum (400 MHz, CDCl$_3$) δ ppm: 1.35 (3.0H, t, J=7.18 Hz), 1.73-1.79 (1.0H, m), 1.82-1.91 (1.0H, m), 3.14-3.21 (3.0H, m), 3.41 (3.0H, s), 3.48-3.49 (1.0H, m), 4.02-4.05 (1.0H, m), 4.19 (1.0H, dq, J=4.15, 12.21 Hz), 4.34 (2.0H, q, J=7.18 Hz), 7.74 (1.0H, s).

(103e) Ethyl cis(±)-2-(4-{[(4-chloro-5-ethyl-1H-imidazol-2-yl)carbonyl]amino}-3-methoxypiperidin-1-yl)-1,3-oxazole-4-carboxylate The same operation as in Example (91c) was performed using 4-chloro-5-ethyl-1H-imidazole-2-carboxylic acid (0.13 g, 0.75 mmol), thionyl chloride (2 mL) and ethyl cis(±)-2-(4-amino-3-methoxypiperidin-1-yl)-1,3-oxazole-4-carboxylate obtained in Example (103d) (0.3 g, 1.12 mmol). Purification by silica gel column chromatography (elution solvent: ethyl acetate/hexane=4/1, 1/0) gave 0.19 g of the title compound as a brown oily substance (60%).

$^1$H NMR spectrum (400 MHz, CDCl$_3$) δ ppm: 1.26 (3.0H, t, J=7.49 Hz), 1.36 (3.0H, t, J=7.18 Hz), 1.74-1.79 (2.0H, m), 2.69 (2.0H, q, J=7.49 Hz), 3.03-3.13 (2.0H, m), 3.40 (3.0H, s), 3.48 (1.0H, br s), 4.19-4.38 (2.0H, m), 4.36 (2.0H, q, J=7.18 Hz), 4.46 (1.0H, d, J=14.21 Hz), 7.52 (1.0H, d, J=9.17 Hz), 11.72 (1.0H, s).

(103f) cis(±)-2-(4-{[(4-Chloro-5-ethyl-1H-imidazol-2-yl)carbonyl]amino}-3-methoxypiperidin-1-yl)-1,3-oxazole-4-carboxylic acid The same operation as in Example (91d) was performed using ethyl cis(±)-2-(4-{[(4-chloro-5-ethyl-1H-imidazol-2-yl)carbonyl]amino}-3-methoxypiperidin-1-yl)-1,3-oxazole-4-carboxylate obtained in Example (103e) (0.19 g, 0.45 mmol), 2 N lithium hydroxide (2 mL, 4 mmol) and methanol (3 mL), to obtain 76 mg of the title compound as a colorless solid (43%).

$^1$H NMR spectrum (400 MHz, DMSO-d$_6$) δ ppm: 1.14 (3.0H, t, J=7.57 Hz), 1.62-1.64 (1.0H, m), 1.86 (1.0H, dq, J=4.15, 12.21 Hz), 2.56 (2.0H, q, J=7.57 Hz), 3.13-3.19 (2.0H, m), 3.51 (1.0H, br s), 3.92 (1.0H, d, J=13.43 Hz), 4.13-4.20 (2.0H, m), 7.60 (1.0H, d, J=8.54 Hz), 8.01 (1.0H, s), 13.37 (1.0H, s).

mass spectrum (FAB): m/z 398 (M+H)$^+$.

Example 104

2-[(7-{[(4-Chloro-5-ethyl-1H-imidazol-2-yl)carbonyl]amino}-2,3-dihydro-4H-1,4-benzoxazin-4-yl)methyl]benzoic acid (Exemplified Compound No. 104)

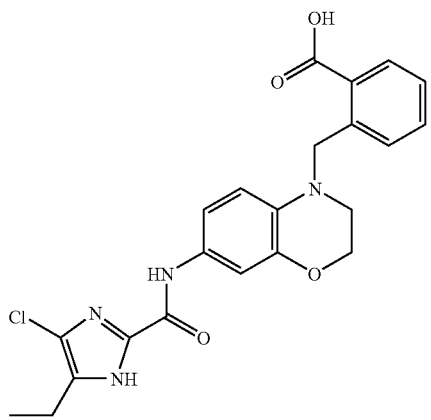

(104a) Ethyl 2-[(7-nitro-2,3-dihydro-4H-1,4-benzoxazin-4-yl)methyl]benzoate

The same operation as in Example (90a) was performed using 7-nitro-2,3-dihydro-4H-1,4-benzoxazine (described in Higuchi, Robert I.; Arienti, Kristen L.; Lopez, Francisco J.; Mani, Neelakhanda S.; Mais, Dale E.; Caferro, Thomas R.; Long, Yun Oliver; Jones, Todd K.; Edwards, James P.; Zhi, Lin; Schrader, William T.; et al.; J. Med. Chem.; 50; 10; 2007; 2486-2496, 0.6 g, 3.3 mmol), sodium hydride (55% content, 145 mg, 3.3 mmol), ethyl 2-chloromethyl-benzoate (1.95 g, 10.8 mmol) and DMF (30 mL). The resulting residue was purified by silica gel column chromatography (elution solvent: ethyl acetate/hexane=1/3, 2/3, 3/2, 3/1) to obtain 2.68 g of the title compound as a yellow solid (72%).

$^1$H NMR spectrum (400 MHz, CDCl$_3$) δ ppm: 1.42 (3.0H, t, J=7.07 Hz), 3.57 (2.0H, t, J=4.58 Hz), 4.32 (2.0H, t, J=4.58 Hz), 4.38 (2.0H, q, J=7.07 Hz), 5.02 (2.0H, s), 6.41 (1.0H, d, J=8.25 Hz), 7.21 (1.0H, d, J=7.79 Hz), 7.26 (1.0H, s), 7.38 (1.0H, t, J=7.57 Hz), 7.48 (1.0H, t, J=7.57 Hz), 7.70-7.73 (1.0H, m), 8.08 (1.0H, d, J=7.79 Hz).

(104b) Ethyl 2-[(7-amino-2,3-dihydro-4H-1,4-benzoxazin-4-yl)methyl]benzoate

The same operation as in Example (100b) was performed using methyl 4-[(7-nitro-2,3-dihydro-4H-1,4-benzoxazin-4-yl)methyl]benzoate obtained in Example (101a) (0.75 g, 2 mmol), zinc (1.4 g, 20 mmol), iron trichloride hexahydrate (0.26 g, 0.8 mmol), DMF (5 mL) and water (5 mL), to obtain 0.51 g of the crude title compound as a brown oily substance (75%).

$^1$H NMR spectrum (400 MHz, CDCl$_3$) δ ppm: 1.37 (3.0H, t, J=7.14 Hz), 3.25 (2.0H, t, J=4.13 Hz), 3.30 (2.0H, br s), 4.26 (2.0H, t, J=4.13 Hz), 4.33 (2.0H, q, J=7.14 Hz), 4.66 (2.0H, s), 6.15 (1.0H, dd, J=8.25, 2.75 Hz), 6.26 (1.0H, d, J=2.75 Hz), 6.38 (1.0H, d, J=8.25 Hz), 7.32 (1.0H, t, J=7.57 Hz), 7.45 (1.0H, t, J=7.57 Hz), 7.51 (1.0H, d, J=7.57 Hz), 7.92 (1.0H, d, J=7.57 Hz).

(104c) Ethyl 2-[(7-{[(4-chloro-5-ethyl-1H-imidazol-2-yl)carbonyl]amino}-2,3-dihydro-4H-1,4-benzoxazin-4-yl)methyl]benzoate The same operation as in Example (91c) was performed using 4-chloro-5-ethyl-1H-imidazole-2-carboxylic acid (0.14 g, 0.8 mmol), thionyl chloride (3 mL), ethyl 2-[(7-amino-2,3-dihydro-4H-1,4-benzoxazin-4-yl)methyl]benzoate obtained in Example (104b) (0.35 g, 1.12 mmol) and pyridine (5 mL). The resulting residue was purified by silica gel column chromatography (elution solvent: ethyl acetate/hexane=1/3, 2/3, 3/2, 3/1) to obtain 0.29 g of the title compound as a yellow solid (77%).

$^1$H NMR spectrum (400 MHz, CDCl$_3$) δ ppm: 1.21 (3.0H, t, J=7.49 Hz), 1.40 (3.0H, t, J=7.18 Hz), 2.70 (2.0H, q, J=7.49 Hz), 3.41 (2.0H, t, J=4.25 Hz), 4.31 (2.0H, t, J=4.25 Hz), 4.36 (2.0H, q, J=7.18 Hz), 4.82 (2.0H, s), 6.44 (1.0H, d, J=8.71 Hz), 6.91 (1.0H, dd, J=8.71, 2.29 Hz), 7.28 (1.0H, d, J=2.29 Hz), 7.35 (1.0H, t, J=7.57 Hz), 7.41-7.49 (2.0H, m), 8.00 (1.0H, d, J=7.79 Hz), 8.70 (1.0H, s), 12.01 (1.0H, s).

(104d) 2-[(7-{[(4-Chloro-5-ethyl-1H-imidazol-2-yl)carbonyl]amino}-2,3-dihydro-4H-1,4-benzoxazin-4-yl)methyl]benzoic acid The same operation as in Example (91d) was performed using methyl 2-[(7-{[(4-chloro-5-ethyl-1H-imidazol-2-yl)carbonyl]amino}-2,3-dihydro-4H-1,4-benzoxazin-4-yl)methyl]benzoate obtained in Example (104c) (0.13 g, 0.29 mmol), 2 N lithium hydroxide (3 mL, 6 mmol), methanol (3 mL) and tetrahydrofuran (3 mL), to obtain 0.13 g of the title compound as a light brown solid (92%).

$^1$H NMR spectrum (400 MHz, DMSO-d$_6$) δ ppm: 1.16 (3.0H, t, J=7.56 Hz), 2.57 (2.0H, q, J=7.56 Hz), 3.36 (2.0H, t, J=4.27 Hz), 4.25 (2.0H, t, J=4.27 Hz), 4.74 (2.0H, s), 6.36 (1.0H, d, J=8.78 Hz), 7.11 (1.0H, dd, J=8.78, 2.44 Hz), 7.30 (1.0H, d, J=2.44 Hz), 7.35-7.37 (1.0H, m), 7.39-7.39 (1.0H, m), 7.50-7.52 (1.0H, m), 7.87 (1.0H, dd, J=7.44, 1.10 Hz), 10.04 (1.0H, s), 13.34 (1.0H, s).

mass spectrum (ESI): m/z 463 (M+Na)$^+$.

Example 105

2-(4-{[(4-Chloro-5-ethyl-1H-imidazol-2-yl)carbonyl]amino}-3-methoxyphenyl)-5-methyl-1,3-oxazole-4-carboxylic acid (Exemplified Compound No. 105)

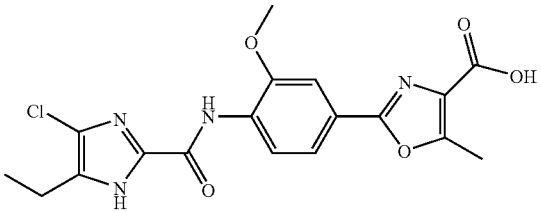

(105a) N-(3-Methoxy-4-nitrobenzoyl)threonine methyl ester

The same operation as in Example (102a) was performed using threonine methyl ester hydrochloride (2.88 g, 17 mmol), 3-methoxy-4-nitrobenzoic acid (3 g, 15.2 mmol), WSC hydrochloride (3.83 g, 20 mmol), DMAP (0.18 g, 1.5 mmol), N,N-diisopropylethylamine (2.58 g, 20 mmol) and dichloromethane (40 mL). The resulting residue was purified by silica gel column chromatography (elution solvent: ethyl acetate/hexane=1/2, 1/1, 2/1, 1/0) to obtain 4.49 g of the title compound as a light yellow amorphous solid (95%).

mass spectrum (APCI): m/z 313 (M+H)$^+$ (105b) Methyl 2-(3-methoxy-4-nitrophenyl)-5-methyl-4,5-dihydro-1,3-oxazole-4-carboxylate The same operation as in Example (97b) was performed using N-(3-methoxy-4-nitrobenzoyl)threonine methyl ester obtained in Example (105a) (4.49 g, 14.4 mmol), the Burgess reagent (3.94 g, 16.5 mmol) and THF (50 mL). Purification by silica gel column chromatography (elution solvent: ethyl acetate/hexane=1/4, 1/2, 1/1, 1/2) gave 3.6 g of the title compound as a light yellow solid (85%).

mass spectrum (APCI): m/z 295 (M+H)$^+$.

(105c) Methyl 2-(3-methoxy-4-nitrophenyl)-5-methyl-1,3-oxazole-4-carboxylate

The same operation as in Example (96a) was performed using methyl 2-(3-methoxy-4-nitrophenyl)-5-methyl-4,5-dihydro-1,3-oxazole-4-carboxylate obtained in Example (105b) (3.6 g, 12.2 mmol), α,α-bisisobutyronitrile (99 mg, 0.6 mmol), N-bromosuccinimide (2.40 g, 13.5 mmol) and benzene (50 mL). Purification by silica gel column chromatography (elution solvent: chloroform/methanol=99/1, 98/2, 96/4, 94/6) gave 1.84 g of the title compound as a light yellow solid (51%).

$^1$H NMR spectrum (400 MHz, CDCl$_3$) δ ppm: 2.75 (3.0H, s), 3.98 (3.0H, s), 4.06 (3.0H, s), 7.70 (1.0H, dd, J=8.25, 1.38 Hz), 7.80 (1.0H, d, J=1.38 Hz), 7.93 (1.0H, d, J=8.25 Hz).

(105d) Methyl 2-(4-amino-3-methoxyphenyl)-5-methyl-1,3-oxazole-4-carboxylate

The same operation as in Example (95b) was performed using methyl 2-(3-methoxy-4-nitrophenyl)-5-methyl-1,3-oxazole-4-carboxylate obtained in Example (105c) (0.75 g, 2.57 mmol), 10% Pd/C (0.2 g) and methanol (20 mL), to obtain 0.68 g of the title compound as a yellow solid (100%).

$^1$H NMR spectrum (400 MHz, CDCl$_3$) δ ppm: 2.67 (3.0H, s), 3.93 (3.0H, s), 6.68-6.73 (1.0H, m), 7.49-7.51 (2.0H, m).

(105e) Methyl 2-(4-{[(4-chloro-5-ethyl-1H-imidazol-2-yl)carbonyl]amino}-3-methoxyphenyl)-5-methyl-1,3-oxazole-4-carboxylate The same operation as in Example (91c) was performed using 4-chloro-5-ethyl-1H-imidazole-2-carboxylic acid (0.135 g, 0.78 mmol), thionyl chloride (4 mL), methyl 2-(4-amino-3-methoxyphenyl)-5-methyl-1,3-oxazole-4-carboxylate obtained in Example (105d) (0.3 g, 1.03 mmol) and pyridine (5 mL), to obtain 0.23 g of the title compound as a colorless solid (71%).

$^1$H NMR spectrum (400 MHz, DMSO-d$_6$) δ ppm: 1.17 (3.0H, t, J=7.57 Hz), 2.59 (2.0H, q, J=7.57 Hz), 2.68 (3.0H, s), 3.84 (3.0H, s), 4.04 (3.0H, s), 7.58 (1.0H, d, J=1.83 Hz), 7.63 (1.0H, dd, J=8.25, 1.83 Hz), 8.46 (1.0H, d, J=8.25 Hz).

(105f) 2-(4-{[(4-Chloro-5-ethyl-1H-imidazol-2-yl)carbonyl]amino}-3-methoxyphenyl)-5-methyl-1,3-oxazole-4-carboxylic acid The same operation as in Example (91d) was performed using methyl 2-(4-{[(4-chloro-5-ethyl-1H-imidazol-2-yl)carbonyl]amino}-3-methoxyphenyl)-5-methyl-1,3-oxazole-4-carboxylate obtained in Example (102e) (90 mg, 0.21 mmol), 2 N lithium hydroxide (3 mL, 6 mmol), methanol (3 mL) and tetrahydrofuran (3 mL), to obtain 74 mg of the title compound as a light pink solid (85%).

$^1$H NMR spectrum (400 MHz, DMSO-d$_6$) δ ppm: 1.18 (3.0H, t, J=7.57 Hz), 2.60 (2.0H, q, J=7.57 Hz), 2.61 (3.0H, s), 4.03 (3.0H, s), 7.57 (1.0H, dd, J=8.25, 1.38 Hz), 7.60 (1.0H, d, J=1.38 Hz), 8.41 (1.0H, d, J=8.25 Hz), 9.45 (1.0H, s).

mass spectrum (ESI): m/z 427 (M+Na)$^+$.

Example 106 cis(±)-2-(4-{[(4-Chloro-5-ethyl-1H-imidazol-2-yl)carbonyl]amino}-3-methoxypiperidin-1-yl)-5-methyl-1,3-oxazole-4-carboxylic acid (Exemplified Compound No. 106)

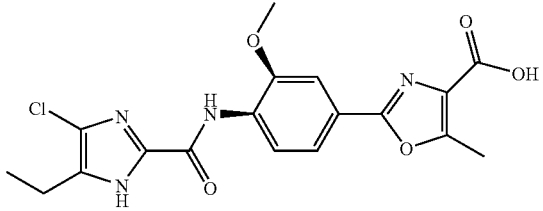

(106a) Butyl 3-bromo-2-oxobutanoate

A solution of butyl 2-oxobutanoate (described in Patent; IMPERIAL CHEMICAL INDUSTRIES PLC; Publ.: EP 375457 B1 (1994/03/16), Appl.: EP 1989-313521 (1989/12/22), 14g, 88.6 mmol) in dichloromethane (100 mL) was cooled to 0° C., and bromine (4 mL, 80 mmol) was added over 15 minutes. Following stirring at room temperature for 30 minutes, the reaction solution was washed with aqueous sodium bicarbonate solution, washed with brine, dried over anhydrous magnesium sulfate, and then concentrated under reduced pressure to obtain 21.8 g of the title compound as a colorless liquid (100%).

$^1$H NMR spectrum (400 MHz, CDCl$_3$) δ ppm: 0.97 (3.0H, t, J=7.37 Hz), 1.49-1.40 (2.0H, m), 1.77-1.72 (2.0H, m), 1.82 (3.0H, d, J=6.88 Hz), 4.35-4.32 (2.0H, m), 5.16 (1.0H, q, J=6.88 Hz).

(106b) Ethyl cis(±)-2-(4-{[(benzyloxy)carbonyl]amino}-3-methoxypiperidin-1-yl)-5-methyl-1,3-oxazole-4-carboxylate The same operation as in Example (103c) was performed using cis(±)-benzyl (1-carbamoyl-3-methoxypiperidin-4-yl)carbamate obtained in Example (103b) (1.97 g, 6.4 mmol), butyl 3-bromo-2-oxobutanoate obtained in Example (106a) (10 g, 42.3 mmol), sodium bicarbonate (1.26 g, 15 mmol) and THF (40 mL). The resulting residue was purified by silica gel column chromatography (elution solvent: ethyl acetate/hexane=1/10, 1/2, 1/1, 2/1, 4/1) to obtain 2.09 g of the title compound as a yellow oily substance (73%).

$^1$H NMR spectrum (400 MHz, CDCl$_3$) δ ppm: 0.95 (3.0H, t, J=7.57 Hz), 1.42 (2.0H, tq, J=7.34, 7.57 Hz), 1.68-1.76 (3.0H, m), 1.86 (1.0H, tdd, J=12.04, 12.04, 4.24 Hz), 2.48 (3.0H, s), 2.97-3.06 (2.0H, m), 3.37 (3.0H, s), 3.41-3.43 (1.0H, br m), 3.80-3.82 (1.0H, br m), 4.08-4.10 (1.0H, m), 4.28 (1.0H, q, J=6.88 Hz), 4.28-4.34 (1.0H, m), 4.29 (1.0H, q, J=6.88 Hz), 5.11 (2.0H, s), 5.24 (1.0H, d, J=8.71 Hz), 7.33-7.38 (5.0H, m).

(106c) Butyl cis(±)-2-(4-amino-3-methoxypiperidin-1-yl)-5-methyl-1,3-oxazole-4-carboxylate The same operation as in Example (95b) was performed using butyl cis(±)-2-(4-{[(benzyloxy)carbonyl]amino}-3-methoxypiperidin-1-yl)-5-methyl-1,3-oxazole-4-carboxylate obtained in Example (106b) (0.82 g, 1.84 mmol), 10% Pd/C (0.25 g) and ethyl acetate (15 mL), to obtain 0.65 g of the title compound as a yellow amorphous solid (100%).

$^1$H NMR spectrum (400 MHz, CDCl$_3$) δ ppm: 0.95 (3.0H, t, J=7.34 Hz), 1.42 (2.0H, tq, J=7.23, 7.34 Hz), 1.64-1.85

(3.0H, m), 2.49 (3.0H, s), 3.04 (1.0H, dt, J=9.63, 3.67 Hz), 3.13-3.17 (2.0H, m), 3.36-3.37 (1.0H, m), 3.42 (3.0H, s), 3.92 (1.0H, dt, J=13.30, 4.13 Hz), 4.04-4.10 (1.0H, m), 4.28 (1.0H, t, J=7.32 Hz), 4.28 (1.0H, t, J=7.32 Hz).

(106d) Butyl cis(±)-2-(4-{[(4-chloro-5-ethyl-1H-imidazol-2-yl)carbonyl]amino}-methoxypiperidin-1-yl)-5-methyl-3-1,3-oxazole-4-carboxylate Butyl cis(±)-2-(4-amino-3-methoxypiperidin-1-yl)-5-methyl-1,3-oxazole-4-carboxylate obtained in Example (106c) (0.45 g, 1.45 mmol) was added to a solution of 4-chloro-5-ethyl-1H-imidazole-2-carboxylic acid (0.18 g, 1 mmol) in DMA (3 mL). WSC hydrochloride (0.58 g, 3 mmol), HOBt (0.2 g, 1.5 mmol) and dichloromethane (5 mL) were added, and the mixture was stirred at room temperature for 12 hours. Ethyl acetate was added to the reaction solution, and the organic layer was washed with water and brine, and dried over anhydrous magnesium sulfate. The resulting residue was purified by silica gel column chromatography (elution solvent: ethyl acetate/hexane=1/2, 1/1, 2/1, 1/0) to obtain 0.32 g of the title compound as a light brown solid (69%).

$^1$H NMR spectrum (400 MHz, CDCl$_3$) δ ppm: 0.95 (3.0H, t, J=7.44 Hz), 1.26 (3.0H, t, J=7.56 Hz), 1.42 (2.0H, tq, J=7.34, 7.44 Hz), 1.70-1.75 (3.0H, m), 2.00-2.05 (2.0H, m), 2.50 (3.0H, s), 2.69 (2.0H, q, J=7.56 Hz), 2.99-3.09 (2.0H, m), 3.41 (3.0H, s), 3.47 (1.0H, s), 4.15-4.24 (2.0H, m), 4.28 (1.0H, t, J=7.11 Hz), 4.29 (1.0H, t, J=7.11 Hz), 4.38-4.42 (1.0H, m), 7.49 (1.0H, d, J=9.41 Hz), 11.48 (1.0H, s).

(106e) cis(±)-2-(4-{[(4-Chloro-5-ethyl-1H-imidazol-2-yl)carbonyl]amino}-3-methoxypiperidin-1-yl)-5-methyl-1,3-oxazole-4-carboxylic acid The same operation as in Example (91d) was performed using butyl cis(±)-2-(4-{[(4-chloro-5-ethyl-1H-imidazol-2-yl)carbonyl]amino}-3-methoxypiperidin-1-yl)-5-methyl-1,3-oxazole-4-carboxylate obtained in Example (106d) (0.32 g, 0.69 mmol), 2 N lithium hydroxide (3 mL, 6 mmol), methanol (2 mL) and THF (5 mL), to obtain 0.28 g of the title compound as a colorless solid (99%).

$^1$H NMR spectrum (400 MHz, DMSO-d$_6$) δ ppm: 1.14 (3.0H, t, J=7.56 Hz), 1.57-1.60 (1.0H, m), 1.85 (1.0H, dq, J=4.05, 12.20 Hz), 2.40 (3.0H, s), 2.55 (2.0H, q, J=7.56 Hz), 3.09-3.12 (2.0H, m), 3.30 (3.0H, s), 3.47-3.50 (1.0H, m), 3.85 (1.0H, d, J=12.93 Hz), 4.10-4.13 (2.0H, m), 7.59 (1.0H, d, J=8.29 Hz).

mass spectrum (FAB): m/z 412 (M+H)$^+$.

Example 107 cis(±)-2-(4-{[(4-Chloro-5-ethyl-1H-imidazol-2-yl)carbonyl]amino}-3-methoxypiperidin-1-yl)-4-methyl-1,3-oxazole-5-carboxylic acid (Exemplified Compound No. 107)

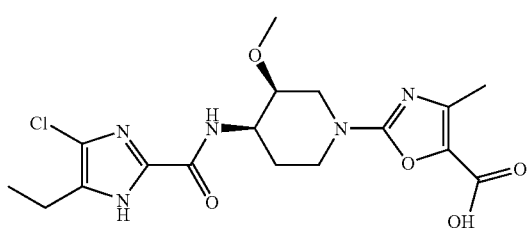

(107a) Ethyl cis(±)-2-(4-{[(benzyloxy)carbonyl]amino}-3-methoxypiperidin-1-yl)-4-methyl-1,3-oxazole-5-carboxylate cis(±)-Benzyl (1-carbamoyl-3-methoxypiperidin-4-yl) carbamate obtained in Example (103b) (0.92 g, 3 mmol), ethyl α-chloroacetoacetate (3.29 g, 20 mmol) and sodium bicarbonate (0.84 g, 10 mmol) were stirred at 120° C. for three hours. The reaction solution was diluted with ethyl acetate, washed with water and brine, and dried over anhydrous magnesium sulfate. Following concentration under reduced pressure, the residue was purified by silica gel column chromatography (elution solvent: ethyl acetate/hexane=1/4, 1/2, 2/1, 4/1) to obtain 0.39 g of the title compound as a light brown solid (27%).

$^1$H NMR spectrum (400 MHz, CDCl$_3$) δ ppm: 1.34 (3.0H, t, J=7.45 Hz), 1.54-1.55 (1.0H, m), 1.79-1.86 (2.0H, m), 2.35 (3.0H, s), 3.03-3.10 (2.0H, m), 3.33-3.44 (1.0H, m), 3.37 (1.0H, s), 4.19-4.33 (3.0H, m), 4.45-4.49 (1.0H, m), 5.11 (2.0H, s), 5.21-5.25 (1.0H, m), 7.33-7.38 (5.0H, m).

(107b) Ethyl cis(±)-2-(4-amino-3-methoxypiperidin-1-yl)-4-methyl-1,3-oxazole-5-carboxylate The same operation as in Example (95b) was performed using ethyl cis(±)-2-(4-{[(benzyloxy)carbonyl]amino}-3-methoxypiperidin-1-yl)-4-methyl-1,3-oxazole-5-carboxylate obtained in Example (107a) (0.32 g, 0.77 mmol), 10% Pd/C (0.3 g), ethyl acetate (3 mL) and methanol (3 mL), to obtain 0.22 g of the title compound as a brown oily substance (100%).

mass spectrum (APCI): m/z 284 (M+H)$^+$.

(107c) Ethyl cis(±)-2-(4-{[(4-chloro-5-ethyl-1H-imidazol-2-yl)carbonyl]amino}-3-methoxypiperidin-1-yl)-4-methyl-1,3-oxazole-5-carboxylate The same operation as in Example (106d) was performed using ethyl cis(±)-2-(4-amino-3-methoxypiperidin-1-yl)-4-methyl-1,3-oxazole-5-carboxylate obtained in Example (107b) (0.22 g, 0.78 mmol), 4-chloro-5-ethyl-1H-imidazole-2-carboxylic acid (0.16 g, 0.92 mmol), WSC hydrochloride (0.46 g, 2.4 mmol), HOBt (0.2 g, 1.2 mmol), DMA (3 mL) and dichloromethane (3 mL). The resulting residue was purified by silica gel column chromatography (elution solvent: ethyl acetate/hexane=1/2, 1/1, 2/1, 1/0, ethyl acetate/methanol=97/3, 93/7) to obtain 0.24 g of the title compound as a light yellow solid (70%).

$^1$H NMR spectrum (400 MHz, DMSO-d$_6$) δ ppm: 1.14 (3.0H, t, J=7.64 Hz), 1.26 (3.0H, t, J=7.11 Hz), 1.61-1.68 (1.0H, m), 1.82 (1.0H, dq, J=4.59, 12.49 Hz), 2.27 (3.0H, s), 2.55 (2.0H, q, J=7.64 Hz), 3.19-3.27 (2.0H, m), 3.31 (3.0H, s), 3.54 (1.0H, s), 3.98-4.03 (1.0H, m), 4.16-4.29 (2.0H, m), 4.22 (2.0H, q, J=7.11 Hz), 7.63 (1.0H, d, J=8.25 Hz).

(107d) cis(±)-2-(4-{[(4-Chloro-5-ethyl-1H-imidazol-2-yl)carbonyl]amino}-3-methoxypiperidin-1-yl)-4-methyl-1,3-oxazole-5-carboxylic acid The same operation as in Example (91d) was performed using ethyl cis(±)-2-(4-{[(4-chloro-5-ethyl-1H-imidazol-2-yl)carbonyl]amino}-3-methoxypiperidin-1-yl)-4-methyl-1,3-oxazole-5-carboxylate obtained in Example (107c) (0.12 g, 0.27 mmol), 2 N lithium hydroxide (3 mL, 6 mmol), methanol (5 mL) and THF (3 mL), to obtain 0.10 g of the title compound as a colorless solid (89%).

$^1$H NMR spectrum (400 MHz, DMSO-d$_6$) δ ppm: 1.13 (3.0H, t, J=7.56 Hz), 1.59-1.61 (1.0H, m), 1.78-1.82 (1.0H, m), 2.18 (3.0H, s), 2.54 (2.0H, q, J=7.56 Hz), 3.07-3.11 (2.0H, m), 3.31 (3.0H, s), 3.46-3.49 (1.0H, m), 3.89 (1.0H, d, J=13.66 Hz), 4.13-4.18 (2.0H, m), 7.61 (1.0H, d, J=8.29 Hz), 13.55 (1.0H, br s).

mass spectrum (FAB): m/z 412 (M+H)$^+$.

Example 108

2-(4-{[(4-Chloro-5-ethyl-1H-imidazol-2-yl)carbonyl]amino}-3-methylphenyl)-5-methyl-1,3-oxazole-4-carboxylic acid (Exemplified Compound No. 108)

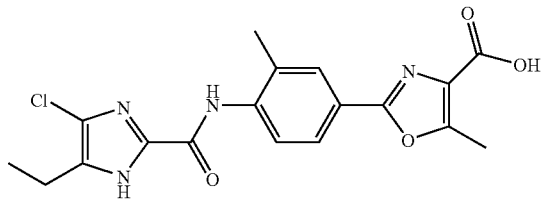

(108a) N-(3-Methyl-4-nitrobenzoyl)threonine methyl ester

The same operation as in Example (102a) was performed using threonine methyl ester hydrochloride (6.73 g, 39.6 mmol), 3-methyl-4-nitrobenzoic acid (7.18 g, 3.96 mmol), WSC hydrochloride (8.05 g, 42 mmol), DMAP (0.18 g, 1.5 mmol), N,N-diisopropylethylamine (5.42 g, 42 mmol) and dichloromethane (100 mL). The resulting residue was purified by silica gel column chromatography (elution solvent: ethyl acetate/hexane=1/3, 2/3, 3/2, 3/1) to obtain 10.56 g of the title compound as a light yellow amorphous solid (90%).

mass spectrum (APCI): m/z 297 (M+H)$^+$ (108b) N-(4-{[(Benzyloxy)carbonyl]amino}-3-methylbenzoyl)threonine methyl ester 10% Pd/C (1.2 g) was added to a solution of N-(3-methyl-4-nitrobenzoyl)threonine methyl ester obtained in Example (108a) (7.2 g, 24.3 mmol) in ethanol (40 mL), and the mixture was stirred in a hydrogen atmosphere at room temperature for one hour and 20 minutes. Pd/C was filtered off, and the filtrate was concentrated under reduced pressure. Water (20 mL), THF (20 mL), sodium bicarbonate (2.52 g, 30 mmol) and benzyl chloroformate (5.37 g, 30 mmol) were added to the resulting residue, and the mixture was stirred at room temperature for one hour. Following extraction with dichloromethane, the organic layer was washed with water, a 1 N aqueous hydrochloric acid solution and brine, dried over magnesium sulfate, and concentrated. Thereafter, the resulting residue was purified by silica gel column chromatography (elution solvent: chloroform/methanol=1/0, 95/5, 90/10, 85/15) to obtain 7.4 g of the title compound as a colorless solid (76%).

mass spectrum (APCI): m/z 401 (M+H)$^+$ (108c) Methyl 2-(4-{[(benzyloxy)carbonyl]amino}-3-methylphenyl)-5-methyl-4,5-dihydro-1,3-oxazole-4-carboxylate The same operation as in Example (97b) was performed using N-(4-{[(benzyloxy)carbonyl]amino}-3-methylbenzoyl)threonine methyl ester obtained in Example (108b) (5.37 g, 13.4 mmol), the Burgess reagent (4.0 g, 16.8 mmol) and THF (50 mL). Purification by silica gel column chromatography (elution solvent: ethyl acetate/hexane=1/3, 2/3, 3/2, 3/1) gave 4.42 g of the title compound as a colorless solid (86%).

mass spectrum (APCI): m/z 383 (M+H)$^+$.

(108d) Methyl 2-(4-{[(benzyloxy)carbonyl]amino}-3-methylphenyl)-5-methyl-1,3-oxazole-4-carboxylate A solution of methyl 2-(4-{[(benzyloxy)carbonyl]amino}-3-methylphenyl)-5-methyl-4,5-dihydro-1,3-oxazole-4-carboxylate obtained in Example (108c) (4.4 g, 11.5 mmol) in dichloromethane (50 mL) was cooled to 0° C., and bromotrichloroethane (3.20 g, 16.1 mmol) and DBU (2.45 g, 16.1 mmol) were added. The mixture was stirred at the same temperature for three hours, washed with a 1 N aqueous hydrochloric acid solution and brine, and dried over magnesium sulfate. Following concentration, the resulting residue was purified by silica gel column chromatography (elution solvent: ethyl acetate/hexane=1/4, 1/2, 2/2, 2/1) to obtain 1.75 g of the title compound as a colorless solid (40%).

mass spectrum (APCI): m/z 381 (M+H)$^+$.

(108e) Methyl 2-(4-amino-3-methylphenyl)-5-methyl-1,3-oxazole-4-carboxylate

The same operation as in Example (95b) was performed using methyl 2-(4-{[(benzyloxy)carbonyl]amino}-3-methylphenyl)-5-methyl-1,3-oxazole-4-carboxylate obtained in Example (108d) (0.7 g, 1.7 mmol), 10% Pd/C (0.3 g) and methanol (20 mL), to obtain 0.44 g of the title compound as a yellow solid (97%).

mass spectrum (APCI): m/z 247 (M+H)$^+$.

(108f) Methyl 2-(4-{[(4-Chloro-5-ethyl-1H-imidazol-2-yl)carbonyl]amino}-3-methylphenyl)-5-methyl-1,3-oxazole-4-carboxylic acid The same operation as in Example (91c) was performed using 4-chloro-5-ethyl-1H-imidazole-2-carboxylic acid (0.18 g, 1.03 mmol), thionyl chloride (4 mL), methyl 4-amino-3-methylphenyl)-5-methyl-1,3-oxazole-4-carboxylate obtained in Example (108e) (0.28 g, 1.14 mmol) and pyridine (5 mL), to obtain 0.32 g of the title compound as a colorless solid (77%).

$^1$H NMR spectrum (400 MHz, DMSO-d$_6$) δ ppm: 1.18 (3.0H, t, J=7.49 Hz), 2.35 (3.0H, s), 2.60 (2.0H, q, J=7.49 Hz), 2.67 (3.0H, s), 3.84 (3.0H, s), 7.77 (1.0H, d, J=8.25 Hz), 7.82 (1.0H, dd, J=8.25, 1.83 Hz), 7.89 (1.0H, s).

(108g) 2-(4-{[(4-Chloro-5-ethyl-1H-imidazol-2-yl)carbonyl]amino}-3-methylphenyl)-5-methyl-1,3-oxazole-4-carboxylic acid The same operation as in Example (91d) was performed using methyl 2-(4-{[(4-chloro-5-ethyl-1H-imidazol-2-yl)carbonyl]amino}-3-methylphenyl)-5-methyl-1,3-oxazole-4-carboxylate obtained in Example (108f) (0.12 g, 0.30 mmol), 2 N lithium hydroxide (3 mL, 6 mmol), methanol (5 mL) and tetrahydrofuran (5 mL), to obtain 0.10 g of the title compound as a colorless solid (86%).

$^1$H NMR spectrum (400 MHz, DMSO-d$_6$) δ ppm: 1.18 (3.0H, t, J=7.57 Hz), 2.33 (3.0H, s), 2.60 (2.0H, q, J=7.57 Hz), 2.61 (3.0H, s), 7.73 (1.0H, d, J=8.25 Hz), 7.77 (1.0H, dd, J=8.25, 1.60 Hz), 7.83 (1.0H, d, J=1.60 Hz), 9.89 (1.0H, br s).

mass spectrum (FAB): m/z 389 (M+H)$^+$.

Example 109

2-(4-{[(4-Chloro-5-ethyl-1H-imidazol-2-yl)carbonyl]amino}-3-methylphenyl)-1,3-oxazole-4-carboxylic acid (Exemplified Compound No. 109)

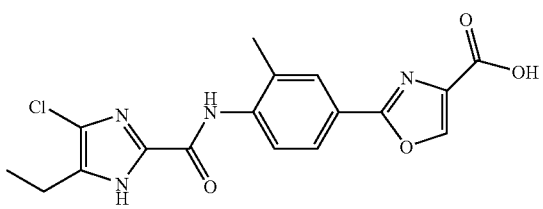

(109a) N-(3-Methyl-4-nitrobenzoyl)serine methyl ester

The same operation as in Example (102a) was performed using serine methyl ester hydrochloride (5.24 g, 33.7 mmol), 3-methyl-4-nitrobenzoic acid (6.1 g, 33.7 mmol), WSC hydrochloride (6.71 g, 35 mmol), DMAP (0.18 g, 1.5 mmol), N,N-diisopropylethylamine (4.52 g, 35 mmol) and dichloromethane (100 mL). The resulting residue was purified by silica gel column chromatography (elution solvent: ethyl acetate/hexane=1/4, 1/2, 2/1, 1/0) to obtain 8.35 g of the title compound as a light yellow solid (88%).

mass spectrum (APCI): m/z 283 (M+H)$^+$ (109b) N-(4-{[(Benzyloxy)carbonyl]amino}-3-methylbenzoyl)serine methyl ester 10% Pd/C (1.2 g) was added to N-(3-methyl-4-nitrobenzoyl)serine methyl ester obtained in Example (109a) (2.39 g, 8.47 mmol) in ethanol (20 mL), and the mixture was stirred in a hydrogen atmosphere at room temperature for one hour. Pd/C was filtered off, and the filtrate was concentrated under reduced pressure. Water (10 mL), THF (10 mL), sodium bicarbonate (0.84 g, 10 mmol) and benzyl chloroformate (1.62 g, 9 mmol) were added to the resulting residue, and the mixture was stirred at room temperature for one hour. Following extraction with ethyl acetate, the organic layer was washed with water, a 1 N aqueous hydrochloric acid solution and brine, dried over magnesium sulfate, and concentrated. Thereafter, the resulting residue was purified by silica gel column chromatography (elution solvent: chloroform/methanol=1/0, 98/2, 96/4, 94/6, 92/8) to obtain 1.8 g of the title compound as a colorless solid (55%).

$^1$H NMR spectrum (400 MHz, DMSO-$d_6$) δ ppm: 2.27 (3.0H, s), 3.64 (3.0H, s), 3.78 (2.0H, t, J=5.73 Hz), 4.52 (1.0H, dd, J=12.56, 5.49 Hz), 5.00-5.05 (1.0H, m), 5.17 (2.0H, s), 7.33-7.45 (5.0H, m), 7.58 (1.0H, d, J=8.29 Hz), 7.69-7.73 (2.0H, m), 8.43 (1.0H, d, J=7.32 Hz), 9.14 (1.0H, s).

(109c) Methyl 2-(4-{[(benzyloxy)carbonyl]amino}-3-methylphenyl)-4,5-dihydro-1,3-oxazole-4-carboxylate The same operation as in Example (97b) was performed using N-(4-{[(benzyloxy)carbonyl]amino}-3-methylbenzoyl)serine methyl ester obtained in Example (109b) (1.8 g, 4.66 mmol), the Burgess reagent (1.44 g, 6.06 mmol) and THF (15 mL). Purification by silica gel column chromatography (elution solvent: ethyl acetate/hexane=1/4, 1/2, 1/1, 2/1) gave 1.43 g of the title compound as a colorless solid (83%).

$^1$H NMR spectrum (400 MHz, DMSO-$d_6$) δ ppm: 2.25 (3.0H, s), 3.81 (3.0H, s), 4.58 (1.0H, dd, J=10.09, 8.71 Hz), 4.67 (1.0H, dd, J=8.71, 7.79 Hz), 4.93 (1.0H, dd, J=10.09, 7.79 Hz), 5.22 (2.2H, s), 6.63 (1.0H, s), 7.36-7.43 (5.2H, m), 7.81 (1.0H, d, J=7.79 Hz), 7.82 (1.0H, s), 8.06 (1.0H, d, J=7.79 Hz).

(109d) Methyl 2-(4-{[(benzyloxy)carbonyl]amino}-3-methylphenyl)-1,3-oxazole-4-carboxylate The same operation as in Example (108d) was performed using methyl 2-(4-{[(benzyloxy)carbonyl]amino}-3-methylphenyl)-4,5-dihydro-1,3-oxazole-4-carboxylate obtained in Example (109c) (1.43 g, 3.88 mmol), bromotrichloroethane (414 μL, 4.1 mmol), DBU (628 μL, 4.1 mmol) and dichloromethane (10 mL). The resulting residue was purified by silica gel column chromatography (elution solvent: ethyl acetate/hexane=1/4, 1/2, 1/1, 2/1) to obtain 0.7 g of the title compound as a colorless solid (49%).

mass spectrum (APCI): m/z 367 (M+H)$^+$.

(109e) Methyl 2-(4-amino-3-methylphenyl)-1,3-oxazole-4-carboxylate

The same operation as in Example (95b) was performed using methyl 2-(4-{[(benzyloxy)carbonyl]amino}-3-methylphenyl)-1,3-oxazole-4-carboxylate obtained in Example (109d) (0.4 g, 1.09 mmol), 10% Pd/C (0.2 g) and methanol (10 mL), to obtain 0.26 g of the title compound as a colorless oily substance (100%).

mass spectrum (APCI): m/z 243 (M+H)$^+$.

(109f) Methyl 2-(4-{[(4-Chloro-5-ethyl-1H-imidazol-2-yl)carbonyl]amino}-3-methylphenyl)-1,3-oxazole-4-carboxylate The same operation as in Example (91c) was performed using 4-chloro-5-ethyl-1H-imidazole-2-carboxylic acid (0.12 g, 0.69 mmol), thionyl chloride (4 mL), methyl 4-amino-3-methylphenyl)-1,3-oxazole-4-carboxylate obtained in Example (109e) (0.23 g, 0.95 mmol) and pyridine (5 mL), to obtain 135 mg of the title compound as a light brown solid (50%).

$^1$H NMR spectrum (400 MHz, DMSO-$d_6$) δ ppm: 1.18 (3.0H, t, J=7.64 Hz), 2.36 (3.0H, s), 2.61 (2.0H, q, J=7.64 Hz), 3.85 (3.0H, s), 7.79 (1.0H, d, J=8.71 Hz), 7.87 (1.0H, d, J=8.71 Hz), 7.94 (1.0H, s), 8.97 (1.0H, d, J=1.38 Hz), 9.92 (1.0H, s).

(109g) 2-(4-{[(4-Chloro-5-ethyl-1H-imidazol-2-yl)carbonyl]amino}-3-methylphenyl)-5-methyl-1,3-oxazole-4-carboxylic acid The same operation as in Example (91d) was performed using methyl 2-(4-{[(4-chloro-5-ethyl-1H-imidazol-2-yl)carbonyl]amino}-3-methylphenyl)-1,3-oxazole-4-carboxylate obtained in Example (109f) (0.13 g, 0.33 mmol), 2 N lithium hydroxide (3 mL, 6 mmol), methanol (3 mL) and tetrahydrofuran (5 mL), to obtain 0.10 g of the title compound as a colorless solid (80%).

$^1$H NMR spectrum (400 MHz, DMSO-$d_6$) δ ppm: 1.18 (3.0H, t, J=7.49 Hz), 2.60 (2.0H, q, J=7.49 Hz), 7.76 (1.0H, d, J=8.71 Hz), 7.82 (1.0H, dd, J=8.71, 1.38 Hz), 7.88 (1.0H, d, J=1.38 Hz), 8.24 (1.0H, s), 9.90 (1.0H, s).

mass spectrum (FAB): m/z 375 (M+H)$^+$.

Example 110 cis(±)-2-(4-{[(4-Chloro-5-ethyl-1H-imidazol-2-yl)carbonyl]amino}-3-methoxypiperidin-1-yl)-5-ethyl-1,3-oxazole-4-carboxylic acid (Exemplified Compound No. 110)

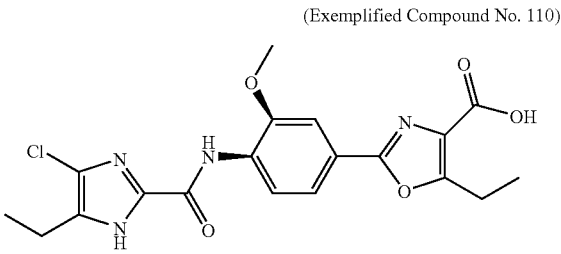

(110a) Butyl 3-bromo-2-oxopentanoate

The same operation as in Example (106a) was performed using butyl 2-oxopentanoate (described in Cuvigny; C. R. Hebd. Seances Acad. Sci.; 240; 1955; 206, 12g, 69.8 mmol), bromine (3.33 mL, 65 mmol) and chloroform (80 mL), to obtain 16.15 g of the title compound as a colorless liquid (99%).

$^1$H NMR spectrum (400 MHz, CDCl$_3$) δ ppm: 0.96 (3.0H, t, J=7.34 Hz), 1.08 (3.0H, t, J=7.11 Hz), 1.42-1.46 (2.0H, m), 1.72-1.76 (2.0H, m), 1.96-2.09 (1.0H, m), 2.10-2.20 (1.0H, m), 4.33 (2.0H, td, J=6.65, 3.52 Hz), 4.96 (1.0H, dd, J=8.02, 6.19 Hz).

(110b) Ethyl cis(±)-2-(4-{[(benzyloxy)carbonyl]amino}-3-methoxypiperidin-1-yl)-5-ethyl-1,3-oxazole-4-carboxylate The same operation as in Example (103c) was performed using cis(±)-benzyl (1-carbamoyl-3-methoxypiperidin-4-yl)carbamate obtained in Example (103b) (0.98 g, 3.2 mmol), butyl 3-bromo-2-oxopentanoate obtained in Example (110a) (5 g, 19.9 mmol), sodium bicarbonate (0.63 g, 7.5 mmol) and THF (20 mL). The resulting residue was purified by silica gel column chromatography (elution solvent: ethyl acetate/hexane=1/4, 1/2, 1/1, 2/1, 4/1) to obtain 1.5 g of the title compound as a yellow solid (100%).

$^1$H NMR spectrum (400 MHz, CDCl$_3$) δ ppm: 0.95 (3.0H, t, J=7.57 Hz), 1.22 (3.0H, d, J=7.39 Hz), 1.41 (2.0H, tq, J=7.45, 7.57 Hz), 1.72 (2.0H, tt, J=7.45, 7.34 Hz), 1.71-1.78 (1.0H, m), 1.88 (1.0H, tdd, J=12.11, 12.11, 4.24 Hz), 2.75 (2.0H, q, J=7.39 Hz), 2.99-3.04 (2.0H, m), 3.37 (3.0H, s), 3.63-3.69 (1.0H, m), 3.80-3.83 (1.0H, br m), 4.11-4.13 (1.0H, m), 4.27 (1.0H, t, J=7.11 Hz), 4.28 (1.0H, t, J=7.11 Hz), 4.29-4.35 (1.0H, m), 5.11 (2.0H, s), 5.23 (1.0H, d, J=8.71 Hz), 7.30-7.38 (5.0H, m).

(110c) Butyl cis(±)-2-(4-amino-3-methoxypiperidin-1-yl)-5-ethyl-1,3-oxazole-4-carboxylate The same operation as in Example (95b) was performed using butyl cis(±)-2-(4-{[(benzyloxy)carbonyl]amino}-3-methoxypiperidin-1-yl)-5-ethyl-1,3-oxazole-4-carboxylate obtained in Example (110b) (0.5 g, 1.09 mmol), 10% Pd/C (0.2 g), ethyl acetate (3 mL) and methanol (3 mL), to obtain 0.38 g of the title compound as a yellow oily substance (100%).

mass spectrum (APCI): m/z 325 (M+H)$^+$.

(110d) Butyl cis(±)-2-(4-{[(4-chloro-5-ethyl-1H-imidazol-2-yl)carbonyl]amino}-3-methoxypiperidin-1-yl)-5-ethyl-1,3-oxazole-4-carboxylate The same operation as in Example (106d) was performed using butyl cis(±)-2-(4-amino-3-methoxypiperidin-1-yl)-5-ethyl-1,3-oxazole-4-carboxylate obtained in Example (110c) (0.35 g, 1.45 mmol), 4-chloro-5-ethyl-1H-imidazole-2-carboxylic acid (0.11 g, 0.6 mmol), WSC hydrochloride (0.38 g, 2 mmol), HOBt (0.13 g, 1 mmol), DMA (3 mL) and dichloromethane (3 mL). The resulting residue was purified by silica gel column chromatography (elution solvent: ethyl acetate/hexane=1/4, 1/2, 3/2, 2/1) to obtain 0.23 g of the title compound as a colorless solid (80%).

$^1$H NMR spectrum (400 MHz, CDCl$_3$) δ ppm: 0.92 (3.0H, t, J=7.39 Hz), 1.14 (3.0H, t, J=7.45 Hz), 1.15 (3.0H, d, J=7.11 Hz), 1.37 (2.0H, tq, J=7.45, 7.39 Hz), 1.63 (2.0H, tt, J=7.45, 7.45 Hz), 1.61-1.66 (1.0H, m), 1.81-1.88 (1.0H, m), 2.55 (2.0H, q, J=7.45 Hz), 2.87 (2.0H, q, J=7.39 Hz), 3.11-3.17 (2.0H, m), 3.32 (3.0H, s), 3.49-3.51 (1.0H, br m), 3.55-3.62 (1.0H, m), 3.92 (1.0H, d, J=11.96 Hz), 4.18 (2.0H, t, J=7.34 Hz), 4.14-4.20 (2.0H, m), 7.59 (1.0H, d, J=8.54 Hz).

(110e) cis(±)-2-(4-{[(4-Chloro-5-ethyl-1H-imidazol-2-yl)carbonyl]amino}-3-methoxypiperidin-1-yl)-5-ethyl-1,3-oxazole-4-carboxylic acid The same operation as in Example (91d) was performed using butyl cis(±)-2-(4-{[(4-chloro-5-ethyl-1H-imidazol-2-yl)carbonyl]amino}-3-methoxypiperidin-1-yl)-5-ethyl-1,3-oxazole-4-carboxylate obtained in Example (110d) (0.14 g, 0.29 mmol), 2 N lithium hydroxide (3 mL, 6 mmol), methanol (5 mL) and THF (5 mL), to obtain 78 mg of the title compound as a colorless solid (63%).

$^1$H NMR spectrum (400 MHz, DMSO-d$_6$) δ ppm: 1.09 (3.0H, t, J=7.57 Hz), 1.13 (3.0H, t, J=7.57 Hz), 1.53-1.55 (1.0H, m), 1.84 (1.0H, tdd, J=12.04, 12.04, 3.55 Hz), 2.54 (2.0H, q, J=7.57 Hz), 2.79-2.83 (1.0H, m), 2.89-2.96 (1.0H, m), 3.05-3.13 (2.0H, m), 3.29 (3.0H, s), 3.45-3.48 (1.0H, m), 3.85 (1.0H, d, J=13.30 Hz), 4.12-4.14 (2.0H, m), 7.57 (1.0H, d, J=8.71 Hz).

mass spectrum (ESI): m/z 426 (M+H)$^+$.

Example 111 cis(±)-2-(4-{[(4-Chloro-5-ethyl-1H-imidazol-2-yl)carbonyl]amino}-3-methoxypiperidin-1-yl)-5-isopropyl-1,3-oxazole-4-carboxylic acid (Exemplified Compound No. 111)

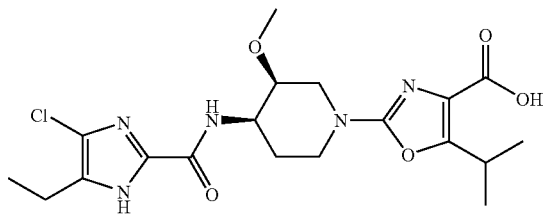

(111a) Butyl 3-bromo-4-methyl-2-oxobutanoate

The same operation as in Example (106a) was performed using butyl 2-oxopentanoate (described in Akimova, L. N.; Bel'di, E. S.; J. Org. Chem. USSR (Engl. Transl.); 5; 9; 1969; 1530-1531; Zh. Org. Khim.; 5; 9; 1969; 1569-1571, 13.2 g, 76.7 mmol), bromine (3.59 mL, 70 mmol) and chloroform (80 mL), to obtain 18.5 g of the title compound as a colorless liquid (99%).

$^1$H NMR spectrum (400 MHz, CDCl$_3$) δ ppm: 0.96 (3.0H, t, J=7.34 Hz), 1.06 (3.0H, d, J=6.88 Hz), 1.14 (3.0H, d, J=6.42 Hz), 1.46-1.42 (2.0H, m), 1.74 (2.0H, tt, J=7.34, 6.56 Hz), 2.40-2.30 (1.0H, m), 4.32 (2.0H, td, J=6.65, 2.75 Hz), 4.84 (1.0H, d, J=7.79 Hz).

(111b) Ethyl cis(±)-2-(4-{[(benzyloxy)carbonyl]amino}-3-methoxypiperidin-1-yl)-5-isopropyl-1,3-oxazole-4-carboxylate The same operation as in Example (103c) was performed using cis(±)-benzyl (1-carbamoyl-3-methoxypiperidin-4-yl)carbamate obtained in Example (103b) (0.97 g, 3.16 mmol), butyl 3-bromo-4-methyl-2-oxobutanoate obtained in Example (111a) (7.6 g, 30.2 mmol), sodium bicarbonate (0.7 g, 8.3 mmol) and THF (20 mL). The resulting residue was purified by silica gel column chromatography (elution solvent: ethyl acetate/hexane=1/4, 2/3, 1/1, 3/2, 2/1) to obtain 0.43 g of the title compound as a colorless solid (100%).

$^1$H NMR spectrum (400 MHz, CDCl$_3$) δ ppm: 0.95 (3.0H, t, J=7.57 Hz), 1.22 (3.0H, d, J=6.88 Hz), 1.23 (3.0H, d, J=6.88 Hz), 1.41 (2.0H, tq, J=7.45, 7.57 Hz), 1.71-1.78 (1.0H, m), 1.72 (2.0H, tt, J=7.45, 7.34 Hz), 1.88 (1.0H, tdd, J=12.11, 12.11, 4.24 Hz), 2.99-3.04 (2.0H, m), 3.37 (3.0H, s), 3.42-3.44 (1.0H, br m), 3.63-3.69 (1.0H, m), 3.80-3.83 (1.0H, br m), 4.11-4.13 (1.0H, m), 4.27 (1.0H, t, J=7.11 Hz), 4.28 (1.0H, t, J=7.11 Hz), 4.29-4.35 (1.0H, m), 5.11 (2.0H, s), 5.23 (1.0H, d, J=8.71 Hz), 7.30-7.38 (5.0H, m).

(111c) Butyl cis(±)-2-(4-amino-3-methoxypiperidin-1-yl)-5-isopropyl-1,3-oxazole-4-carboxylate The same operation as in Example (95b) was performed using butyl cis(±)-2-(4-{[(benzyloxy)carbonyl]amino}-3-methoxypiperidin-1-yl)-5-isopropyl-1,3-oxazole-4-carboxylate obtained in Example (111b) (0.45 g, 0.95 mmol), 10% Pd/C (0.2 g) and methanol (3 mL), to obtain 0.31 g of the title compound as a yellow oily substance (96%).

mass spectrum (APCI): m/z 340 (M+H)$^+$.

(111d) Butyl cis(±)-2-(4-{[(4-chloro-5-ethyl-1H-imidazol-2-yl)carbonyl]amino}-3-methoxypiperidin-1-yl)-5-isopropyl-1,3-oxazole-4-carboxylate The same operation as in Example (106d) was performed using butyl cis(±)-2-(4-amino-3-methoxypiperidin-1-yl)-5-isopropyl-1,3-oxazole-4-carboxylate obtained in Example (111c) (0.31 g, 0.91 mmol), 4-chloro-5-ethyl-1H-imidazole-2-carboxylic acid (0.11 g, 0.6 mmol), WSC hydrochloride (0.39 g, 2 mmol), HOBt (0.13 g, 1 mmol), DMA (3 mL) and dichloromethane (3 mL). The resulting residue was purified by silica gel column chromatography (elution solvent: ethyl acetate/hexane=1/4, 2/3, 3/2, 4/1) to obtain 0.24 g of the title compound as a colorless solid (77%).

$^1$H NMR spectrum (400 MHz, DMSO-d$_6$) δ ppm: 0.92 (3.0H, t, J=7.39 Hz), 1.14 (3.0H, t, J=7.45 Hz), 1.21 (6.0H, d, J=7.11 Hz), 1.37 (2.0H, tq, J=7.45, 7.39 Hz), 1.61-1.66 (1.0H, m), 1.63 (2.0H, tt, J=7.45, 7.45 Hz), 1.81-1.88 (1.0H, m), 2.55 (2.0H, q, J=7.45 Hz), 3.11-3.17 (2.0H, m), 3.32 (3.0H, s), 3.49-3.51 (1.0H, br m), 3.55-3.62 (1.0H, m), 3.92 (1.0H, d, J=11.96 Hz), 4.14-4.20 (2.0H, m), 4.18 (2.0H, t, J=7.34 Hz), 7.59 (1.0H, d, J=8.54 Hz).

(111e) cis(±)-2-(4-{[(4-Chloro-5-ethyl-1H-imidazol-2-yl)carbonyl]amino}-3-methoxypiperidin-1-yl)-5-isopropyl-1,3-oxazole-4-carboxylic acid The same operation as in Example (91d) was performed using butyl cis(±)-2-(4-{[(4-chloro-5-ethyl-1H-imidazol-2-yl)carbonyl]amino}-3-methoxypiperidin-1-yl)-5-isopropyl-1,3-oxazole-4-carboxylate obtained in Example (111d) (0.15 g, 0.30 mmol), 2 N lithium hydroxide (3 mL, 6 mmol), methanol (3 mL) and THF (5 mL), to obtain 0.12 g of the title compound as a colorless solid (90%).

$^1$H NMR spectrum (400 MHz, DMSO-d$_6$) δ ppm: 1.11-1.16 (9.0H, m), 1.53-1.55 (1.0H, m), 1.79-1.86 (1.0H, m), 2.55 (2.0H, q, J=7.45 Hz), 3.06-3.12 (2.0H, m), 3.29 (3.0H, s), 3.47 (1.0H, s), 3.69-3.75 (1.0H, m), 3.88 (1.0H, d, J=12.45 Hz), 4.14-4.17 (2.0H, m), 7.57 (1.0H, d, J=8.54 Hz), 13.36 (1.0H, br s).

mass spectrum (FAB): m/z 439 (M+H)$^+$.

Example 112 cis(±)-2-(4-{[(4-Chloro-5-ethyl-1H-imidazol-2-yl)carbonyl]amino}-3-ethoxypiperidin-1-yl)-5-methyl-1,3-oxazole-4-carboxylic acid (Exemplified Compound No. 112)

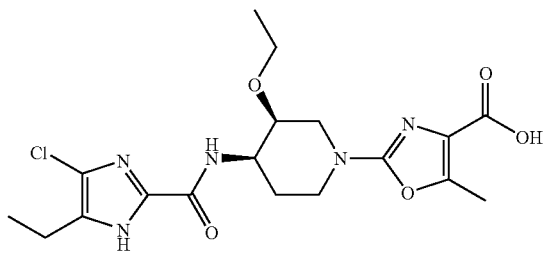

(112a) tert-Butyl 3-ethoxy-4,4-dimethoxypiperidine-1-carboxylate

The same operation as in Example (90a) was performed using tert-butyl 3-hydroxy-4,4-dimethoxypiperidine-1-carboxylate (5.2 g, 20 mmol), sodium hydride (55% content, 1.31 g, 30 mmol), 1-iodoethane (6.24 g, 40 mmol) and DMF (50 mL). The residue was purified by silica gel column chromatography (elution solvent: hexane/ethyl acetate=10/1, 4/1, 2/1) to obtain 4.90 g of the title compound as a colorless oily substance (85%).

$^1$H NMR spectrum (400 MHz, CDCl$_3$) δ ppm: 1.21-1.24 (3.0H, br m), 1.46 (9.0H, s), 1.73-1.79 (2.0H, m), 2.76-2.82 (1.0H, m), 2.93-3.04 (1.0H, m), 3.22 (3.0H, s), 3.23 (3.0H, s), 3.32-3.40 (1.0H, m), 3.43 (1.0H, dq, J=8.71, 7.34 Hz), 3.75-3.80 (1.0H, br m), 4.00-4.27 (1.0H, m).

mass spectrum (APCI): m/z 290 (M+H)$^+$ (112b) tert-Butyl 3-ethoxy-4-oxopiperidine-1-carboxylate The same operation as in Example (90b) was performed using tert-butyl 3-ethoxy-4,4-dimethoxypiperidine-1-carboxylate obtained in Example (112a) (4.99 g, 14.2 mmol), a water/TFA mixed solution (1/1, 35 mL) and di-tert-butyl dicarbonate (4.37 g, 20 mol). The resulting residue was purified by silica gel column chromatography (elution solvent: hexane/ethyl acetate=10/1, 5/1, 2/1, 1/1) to obtain 3.3 g of the title compound as a light brown oily substance (77%).

mass spectrum (APCI): m/z 244 (M+H)$^+$ (112c) tert-Butyl cis(±)-4-(benzylamino)-3-ethoxypiperidine-1-carboxylate The same operation as in Example (90c) was performed using tert-butyl 3-ethoxy-4-oxopiperidine-1-carboxylate obtained in Example (90b) (3.4 g, 14 mmol), benzylamine (1.65 g, 15.4 mmol), sodium (triacetoxy)borohydride (5.93 g, 28 mmol) and 1,2-dichloroethane (40 mL). The resulting residue was purified by silica gel column chromatography (elution solvent: hexane/ethyl acetate=4/1, 1/1, 1/3, 0/1) to obtain 4.06 g of the title compound as a colorless oily substance (87%).

$^1$H NMR spectrum (400 MHz, CDCl$_3$) δ ppm: 1.16-1.20 (3.0H, m), 1.46 (9.0H, s), 1.61-1.72 (3.0H, m), 2.71-2.75 (1.0H, m), 2.92-2.95 (2.0H, m), 3.37 (1.0H, dq, J=8.71, 7.34 Hz), 3.47-3.51 (1.0H, m), 3.66-4.05 (2.0H, m), 3.77 (1.0H, d, J=12.84 Hz), 3.83 (1.0H, d, J=12.84 Hz), 7.22-7.36 (5.0H, m).

(112d) tert-Butyl cis(±)-4-amino-3-ethoxypiperidine-1-carboxylate

The same operation as in Example (90d) was performed using tert-butyl cis(±)-4-(benzylamino)-3-ethoxypiperidine-1-carboxylate obtained in Example (112c) (4.06 g, 12.1 mmol), 10% Pd/C (wet, 1.1 g), ammonium formate (2.87 g, 46 mmol) and methanol (30 mL), to obtain 2.28 g of the title compound as a colorless oily substance (94%).

mass spectrum (APCI): m/z 201 (M+H)$^+$ (112e) tert-Butyl cis(±)-4-{[(benzyloxy)carbonyl]amino}-3-ethoxypiperidine-1-carboxylate The same operation as in Example (103a) was performed using tert-butyl cis(±)-4-amino-3-ethoxypiperidine-1-carboxylate obtained in Example (112d) (2.28 g, 11.4 mmol), sodium bicarbonate (1.26 g, 15 mmol), benzyl chloroformate (2.69 g, 15 mmol), THF (15 mL) and water (15 mL). The residue was purified by silica gel column chromatography (elution solvent: ethyl acetate/hexane=1/4, 1/2, 1/1) to obtain 4.34 g of the title compound as a colorless solid (100%).

$^1$H NMR spectrum (400 MHz, CDCl$_3$) δ ppm: 1.14-1.18 (3.0H, br m), 1.45 (9.0H, s), 1.62-1.78 (2.0H, m), 2.71-2.77 (2.0H, m), 3.32 (1.0H, dq, J=8.71, 7.34 Hz), 3.39-3.42 (1.0H, br m), 3.68-3.76 (2.0H, br m), 4.00-4.18 (1.0H, m), 4.28-4.40 (1.0H, m), 5.10 (2.0H, s), 5.17-5.24 (1.0H, m), 7.33-7.38 (5.0H, m).

(112f) cis(±)-Benzyl (1-carbamoyl-3-ethoxypiperidin-4-yl)carbamate

The same operation as in Example (103b) was performed using tert-butyl cis(±)-4-{[(benzyloxy)carbonyl]amino}-3-ethoxypiperidine-1-carboxylate obtained in Example (112e) (3.6 g, 9.52 mmol), a 4 N hydrochloric acid/ethyl acetate solution (30 ml, 120 mmol) and trimethylsilyl isocyanate (1.37 g, 11.9 mmol), to obtain 2.5 g of the title compound as a colorless solid (82%).

$^1$H NMR spectrum (400 MHz, DMSO-$d_6$) δ ppm: 1.05 (3.0H, t, J=7.34 Hz), 1.40-1.44 (1.0H, m), 1.55-1.64 (1.0H, m), 2.92-2.94 (2.0H, m), 3.34-3.37 (2.0H, m), 3.52 (1.0H, tq, J=7.34, 8.17 Hz), 3.61-3.71 (2.0H, m), 3.83 (1.0H, dd, J=13.75, 5.04 Hz), 5.01 (1.0H, d, J=12.38 Hz), 5.06 (1.0H, d, J=12.38 Hz), 5.85 (2.0H, s), 7.08 (1.0H, d, J=8.25 Hz), 7.31-7.37 (5.0H, m).

(112g) Ethyl cis(±)-2-(4-{[(benzyloxy)carbonyl]amino}-3-ethoxypiperidin-1-yl)-5-methyl-1,3-oxazole-4-carboxylate The same operation as in Example (103c) was performed using cis(±)-benzyl (1-carbamoyl-3-ethoxypiperidin-4-yl)carbamate obtained in Example (112f) (0.88 g, 2.74 mmol), butyl 3-bromo-2-oxobutanoate obtained in Example (106a) (4 g, 15.8 mmol), sodium bicarbonate (0.7 g, 8.33 mmol) and THF (15 mL). The resulting residue was purified by silica gel column chromatography (elution solvent: ethyl acetate/hexane=1/10, 1/2, 1/1, 2/1, 4/1) to obtain 1.05 g of the title compound as a light brown oily substance (83%).

$^1$H NMR spectrum (400 MHz, CDCl$_3$) δ ppm: 0.95 (3.0H, t, J=7.34 Hz), 1.09 (3.0H, t, J=7.11 Hz), 1.37-1.47 (2.0H, m), 1.64 (1.8H, d, J=9.63 Hz), 1.68-1.75 (3.0H, m), 1.91 (1.0H, dq, J=4.58, 12.15 Hz), 2.48 (3.0H, s), 2.98-3.06 (2.0H, m), 3.36 (1.0H, dq, J=9.17, 7.34 Hz), 3.51 (1.0H, br s), 3.69 (1.0H, dq, J=9.17, 7.34 Hz), 3.78-3.81 (1.0H, m), 4.06-4.13 (1.0H, m), 4.19-4.35 (3.0H, m), 5.11 (2.0H, s), 5.21 (1.0H, d, J=8.71 Hz), 7.32-7.38 (5.0H, m).

(112h) Butyl cis(±)-2-(4-amino-3-ethoxypiperidin-1-yl)-5-methyl-1,3-oxazole-4-carboxylate The same operation as in Example (95b) was performed using butyl cis(±)-2-(4-{[(benzyloxy)carbonyl]amino}-3-ethoxypiperidin-1-yl)-5-methyl-1,3-oxazole-4-carboxylate obtained in Example (112g) (1.05 g, 2.1 mmol), 10% Pd/C (0.25 g) and methanol (15 mL), to obtain 0.66 g of the title compound as a light brown oily substance (88%).

$^1$H NMR spectrum (400 MHz, CDCl$_3$) δ ppm: 0.95 (3.0H, t, J=7.44 Hz), 1.15 (3.0H, t, J=6.95 Hz), 1.42 (2.0H, tq, J=7.44, 7.40 Hz), 1.65-1.85 (5.0H, m), 2.49 (3.0H, s), 3.00 (1.0H, dt, J=9.35, 3.60 Hz), 3.13-3.21 (2.0H, m), 3.42-3.46 (1.0H, m), 3.69 (1.0H, dq, J=9.76, 6.95 Hz), 3.86-3.92 (1.0H, m), 3.99 (1.0H, ddd, J=13.66, 5.12, 1.22 Hz), 4.28 (2.0H, td, J=6.83, 2.93 Hz).

(112i) Butyl cis(±)-2-(4-{[(4-chloro-5-ethyl-1H-imidazol-2-yl)carbonyl]amino}-3-ethoxypiperidin-1-yl)-5-methyl-1,3-oxazole-4-carboxylate The same operation as in Example (106d) was performed using butyl cis(±)-2-(4-amino-3-ethoxypiperidin-1-yl)-5-methyl-1,3-oxazole-4-carboxylate obtained in Example (112h) (0.66 g, 2.03 mmol), 4-chloro-5-ethyl-1H-imidazole-2-carboxylic acid (85% content, 0.2 g, 1 mmol), WSC hydrochloride (0.5 g, 2.5 mmol), HOBt (0.2 g, 1.5 mmol), dichloromethane (5 mL) and DMA (3 mL), to obtain 0.21 g of the title compound as a yellow amorphous solid (44%).

$^1$H NMR spectrum (400 MHz, CDCl$_3$) δ ppm: 0.91 (3.0H, t, J=7.57 Hz), 1.02 (3.0H, t, J=6.88 Hz), 1.14 (3.0H, t, J=7.49 Hz), 1.37 (2.0H, tq, J=7.57, 7.57 Hz), 1.58-1.66 (3.0H, m), 1.86 (1.0H, tdd, J=12.38, 12.38, 4.36 Hz), 2.45 (3.0H, s), 2.55 (2.0H, q, J=7.49 Hz), 3.09-3.18 (2.0H, m), 3.39 (1.0H, dq, J=9.63, 6.88 Hz), 3.56-3.64 (2.0H, m), 3.90 (1.0H, br d), 4.08-4.19 (4.0H, m), 7.56 (1.0H, d, J=8.71 Hz).

(112j) cis(±)-2-(4-{[(4-Chloro-5-ethyl-1H-imidazol-2-yl)carbonyl]amino}-3-ethoxypiperidin-1-yl)-5-methyl-1,3-oxazole-4-carboxylic acid The same operation as in Example (91d) was performed using butyl cis(±)-2-(4-{[(4-chloro-5-ethyl-1H-imidazol-2-yl)carbonyl]amino}-3-ethoxypiperidin-1-yl)-5-methyl-1,3-oxazole-4-carboxylate obtained in Example (112i) (0.2 g, 0.42 mmol), 2 N lithium hydroxide (3 mL, 6 mmol), methanol (2 mL) and THF (3 mL), to obtain 90 mg of the title compound as a colorless solid (51%).

$^1$H NMR spectrum (400 MHz, DMSO-$d_6$) δ ppm: 1.02 (3.0H, t, J=6.88 Hz), 1.14 (3.0H, t, J=7.57 Hz), 1.58-1.60 (1.0H, m), 1.86 (1.0H, dq, J=4.13, 12.38 Hz), 2.42 (3.0H, s), 2.55 (2.0H, q, J=7.57 Hz), 3.08-3.15 (2.0H, m), 3.29-3.43 (2.0H, m), 3.58-3.61 (2.0H, m), 3.86 (1.0H, d, J=12.84 Hz), 4.05-4.14 (2.0H, m), 7.56 (1.0H, d, J=8.71 Hz).

mass spectrum (FAB): m/z 426 (M+H)$^+$.

Example 113 cis(±)-2-(4-{[(4-Chloro-5-ethyl-1H-imidazol-2-yl)carbonyl]amino}-3-propoxypiperidin-1-yl)-5-ethyl-1,3-oxazole-4-carboxylic acid

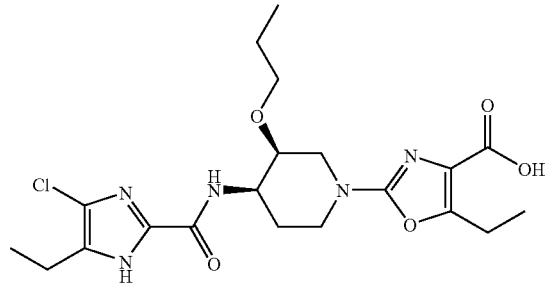

(Exemplified Compound No. 113)

(113a) tert-Butyl 3-allyloxy-4,4-dimethoxypiperidine-1-carboxylate

The same operation as in Example (90a) was performed using tert-butyl 3-hydroxy-4,4-dimethoxypiperidine-1-carboxylate (5.2 g, 20 mmol), sodium hydride (55% content, 1.31 g, 30 mmol), allyl iodide (5.03 g, 30 mmol) and DMF (50 mL). The residue was purified by column chromatography (elution solvent: hexane/ethyl acetate=10/1, 4/1, 2/1) to obtain 5.64 g of the title compound as a colorless oily substance (93%).

$^1$H NMR spectrum (400 MHz, CDCl$_3$) δ ppm: 1.46 (9.0H, s), 1.73-1.86 (2.0H, m), 2.73-2.85 (1.0H, m), 2.92-3.02 (1.0H, m), 3.40-3.45 (1.0H, m), 3.82-4.04 (2.0H, m), 4.14-4.25 (2.0H, m), 5.16-5.21 (1.0H, m), 5.30 (1.0H, dd, J=16.96, 1.38 Hz), 5.91-5.97 (1.0H, m).

(113b) tert-Butyl 3-allyloxy-4-oxopiperidine-1-carboxylate

The same operation as in Example (90b) was performed using tert-butyl 3-allyloxy-4,4-dimethoxypiperidine-1-carboxylate obtained in Example (113a) (5.64 g, 18.7 mmol), a water/TFA mixed solution (1/1, 35 mL) and di-tert-butyl dicarbonate (4.8 g, 22 mol). The resulting residue was purified by silica gel column chromatography (elution solvent: hexane/ethyl acetate=10/1, 5/1, 2/1, 1/1) to obtain 4.37 g of the title compound as a light brown oily substance (91%).

$^1$H NMR spectrum (400 MHz, CDCl$_3$) δ ppm: 1.50 (9.0H, s), 2.41-2.58 (2.0H, m), 3.31-3.33 (2.0H, br m), 3.86-3.88 (1.0H, br m), 4.02-4.08 (2.0H, m), 4.21-4.26 (1.0H, m), 5.22 (1.0H, d, J=10.54 Hz), 5.31 (1.0H, d, J=17.00 Hz), 5.91 (1.0H, ddt, J=17.00, 10.54, 5.50 Hz). (113c) tert-Butyl cis(±)-4-(benzylamino)-3-allyloxypiperidine-1-carboxylate The same operation as in Example (90c) was performed using tert-butyl 3-allyloxy-4-oxopiperidine-1-carboxylate obtained in Example (113b) (4.37 g, 17.1 mmol), benzylamine (2.02 g, 18.9 mmol), sodium (triacetoxy)borohydride (6.36 g, 30 mmol) and 1,2-dichloroethane (40 mL). The resulting residue was purified by silica gel column chromatography (elution solvent: hexane/ethyl acetate=4/1, 1/1, 1/3, 0/1) to obtain 4.96 g of the title compound as a colorless oily substance (84%).

$^1$H NMR spectrum (400 MHz, CDCl$_3$) δ ppm: 1.45 (9.0H, s), 1.61-1.71 (4.0H, m), 2.72-2.76 (1.0H, m), 2.92-2.96 (2.0H, m), 3.53-3.58 (0.0H, br m), 3.80 (2.0H, d, J=3.67 Hz), 3.88-3.93 (2.0H, m), 4.03-4.18 (2.0H, m), 5.17 (1.0H, d, J=10.54 Hz), 5.27 (1.0H, dd, J=16.55, 1.60 Hz), 5.91 (1.0H, ddt, J=16.55, 10.54, 5.50 Hz), 7.24-7.26 (1.0H, m), 7.30-7.35 (4.0H, m).

(113d) tert-Butyl cis(±)-4-amino-3-propoxypiperidine-1-carboxylate

The same operation as in Example (90d) was performed using tert-butyl cis(±)-4-(benzylamino)-3-allyloxypiperidine-1-carboxylate obtained in Example (113c) (4.96 g, 14.3 mmol), 10% Pd/C (wet, 1.5 g), ammonium formate (5.42 g, 86 mmol) and methanol (30 mL), to obtain 3.41 g of the title compound as a colorless oily substance (93%).

mass spectrum (APCI): m/z 259 (M+H)$^+$ (113e) tert-Butyl cis(±)-4-{[(benzyloxy)carbonyl]amino}-3-propoxypiperidine-1-carboxylate The same operation as in Example (103a) was performed using tert-butyl cis(±)-4-amino-3-propoxypiperidine-1-carboxylate obtained in Example (113d) (3.41 g, 13.2 mmol), sodium bicarbonate (1.26 g, 15 mmol), benzyl chloroformate (2.81 g, 16 mmol), THF (15 mL) and water (15 mL). The residue was purified by silica gel column chromatography (elution solvent: ethyl acetate/hexane=1/4, 1/2, 1/1) to obtain 5.14 g of the title compound as a colorless oily substance (99%).

$^1$H NMR spectrum (400 MHz, CDCl$_3$) δ ppm: 0.88-0.92 (3.0H, m), 1.45 (9.0H, s), 1.50-1.77 (4.0H, m), 2.65-2.85 (2.0H, m), 3.22 (1.0H, dt, J=9.17, 6.88 Hz), 3.36-3.43 (1.0H, m), 3.58-3.63 (1.0H, brm), 3.70-3.76 (1.0H, m), 3.95-4.18 (1.0H, m), 4.29-4.41 (1.0H, m), 5.10 (2.0H, s), 5.18-5.26 (1.0H, m), 7.30-7.38 (5.0H, m).

(113f) cis(±)-Benzyl (1-carbamoyl-3-propoxypiperidin-4-yl)carbamate

The same operation as in Example (103b) was performed using tert-butyl cis(±)-4-{[(benzyloxy)carbonyl]amino}-3-propoxypiperidine-1-carboxylate obtained in Example (112e) (3.9 g, 10 mmol), a 4 N hydrochloric acid/ethyl acetate solution (30 ml, 120 mmol) and trimethylsilyl isocyanate (1.49 g, 13 mmol), to obtain 2.66 g of the title compound as a colorless solid (80%).

$^1$H NMR spectrum (400 MHz, DMSO-d$_6$) δ ppm: 0.82 (3.0H, t, J=7.34 Hz), 1.42-1.47 (3.0H, m), 1.57-1.64 (1.0H, m), 2.91-2.97 (2.0H, m), 3.25 (1.0H, dt, J=8.71, 6.88 Hz), 3.36 (1.0H, br s), 3.44 (1.0H, dt, J=8.71, 6.88 Hz), 3.60-3.64 (1.0H, m), 3.68-3.71 (1.0H, m), 3.83 (1.0H, dd, J=13.75, 4.58 Hz), 5.03 (2.0H, q, J=12.69 Hz), 5.85 (2.0H, br s), 7.06 (1.0H, d, J=8.25 Hz), 7.29-7.39 (4.0H, m).

(113g) Butyl cis(±)-2-(4-{[(benzyloxy)carbonyl]amino}-3-propoxypiperidin-1-yl)-5-ethyl-1,3-oxazole-4-carboxylate The same operation as in Example (103c) was performed using cis(±)-benzyl (1-carbamoyl-3-propoxypiperidin-4-yl) carbamate obtained in Example (113f) (0.80 g, 2.39 mmol), butyl 3-bromo-2-oxopentanoate obtained in Example (110a) (4 g, 15.9 mmol), sodium bicarbonate (0.7 g, 8.33 mmol) and THF (15 mL). The resulting residue was purified by silica gel column chromatography (elution solvent: ethyl acetate/hexane=1/10, 1/2, 1/1, 2/1, 4/1) to obtain 1.01 g of the title compound as a light brown oily substance (87%).

$^1$H NMR spectrum (400 MHz, CDCl$_3$) δ ppm: 0.83 (3.0H, t, J=7.34 Hz), 0.95 (3.0H, t, J=7.34 Hz), 1.21 (3.0H, t, J=7.49 Hz), 1.41 (2.0H, tq, J=7.34, 7.34 Hz), 1.44-1.53 (2.0H, m), 1.70-1.75 (1.0H, m), 1.72 (2.0H, tt, J=7.34, 7.34 Hz), 1.92 (1.0H, tdd, J=12.15, 12.15, 4.36 Hz), 2.91 (2.0H, q, J=7.49 Hz), 3.01-3.05 (2.0H, m), 3.26 (1.0H, dt, J=9.17, 7.34 Hz), 3.51 (1.0H, br s), 3.58 (1.0H, dt, J=9.17, 7.34 Hz), 3.77-3.83 (1.0H, br m), 4.08-4.13 (1.0H, m), 4.22-4.31 (3.0H, m), 5.11 (2.0H, s), 5.19 (1.0H, d, J=8.71 Hz), 5.30 (1.0H, s), 7.32-7.38 (5.0H, m).

(113h) Butyl cis(±)-2-(4-amino-3-propoxypiperidin-1-yl)-5-ethyl-1,3-oxazole-4-carboxylate The same operation as in Example (95b) was performed using butyl cis(±)-2-(4-{[(benzyloxy)carbonyl]amino}-3-propoxypiperidin-1-yl)-5-ethyl-1,3-oxazole-4-carboxylate obtained in Example (113g) (1.01 g, 2.1 mmol), 10% Pd/C (0.25 g) and methanol (15 mL), to obtain 0.70 g of the title compound as a light yellow oily substance (95%).

$^1$H NMR spectrum (400 MHz, CDCl$_3$) δ ppm: 0.88 (3.0H, t, J=6.87 Hz), 0.95 (3.0H, t, J=7.44 Hz), 1.42 (2.0H, tq, J=7.31, 7.44 Hz), 1.52-1.55 (2.0H, m), 1.61-1.81 (5.0H, m), 2.48 (3.0H, s), 3.00 (1.0H, dt, J=9.35, 3.54 Hz), 3.14-3.19 (1.0H, m), 3.34 (1.0H, dt, J=9.02, 6.34 Hz), 3.41-3.45 (1.0H, m), 3.59 (1.0H, dt, J=9.02, 6.34 Hz), 3.88-3.94 (1.0H, m), 4.01 (1.0H, ddd, J=13.78, 5.00, 1.34 Hz), 4.28 (2.0H, td, J=6.93, 2.93 Hz).

(113i) Butyl cis(±)-2-(4-{[(4-chloro-5-ethyl-1H-imidazol-2-yl)carbonyl]amino}-3-propoxypiperidin-1-yl)-5-ethyl-1,3-oxazole-4-carboxylate The same operation as in Example (106d) was performed using butyl cis(±)-2-(4-amino-3-propoxypiperidin-1-yl)-5-ethyl-1,3-oxazole-4-carboxylate obtained in Example (113h) (0.70 g, 2.0 mmol), 4-chloro-5-ethyl-1H-imidazole-2-carboxylic acid (85% content, 0.2 g, 1 mmol), WSC hydrochloride (0.5 g, 2.5 mmol), HOBt (0.2 g, 1.5 mmol), dichloromethane (5 mL) and DMA (3 mL), to obtain 0.21 g of the title compound as a colorless amorphous solid (41%).

$^1$H NMR spectrum (400 MHz, DMSO-d$_6$) δ ppm: 0.80 (3.0H, t, J=7.57 Hz), 0.91 (3.0H, t, J=7.57 Hz), 1.13 (3.0H, t, J=7.49 Hz), 1.15 (3.0H, t, J=7.64 Hz), 1.32-1.45 (4.0H, m), 1.58-1.66 (3.0H, m), 1.86 (1.0H, ddd, J=24.76, 12.38, 4.13 Hz), 2.54 (2.0H, q, J=7.64 Hz), 2.87 (2.0H, q, J=7.49 Hz), 3.09-3.18 (2.0H, m), 3.29 (1.0H, dt, J=9.17, 7.34 Hz), 3.52 (1.0H, dt, J=9.17, 7.34 Hz), 3.58 (1.0H, s), 3.91 (1.0H, d, J=13.75 Hz), 4.12-4.22 (4.0H, m), 7.58 (1.0H, d, J=8.71 Hz).

(113j) cis(±)-2-(4-{[(4-Chloro-5-ethyl-1H-imidazol-2-yl) carbonyl]amino}-3-propoxypiperidin-1-yl)-5-ethyl-1,3-oxazole-4-carboxylic acid The same operation as in Example (91d) was performed using butyl cis(±)-2-(4-{[(4-chloro-5-ethyl-1H-imidazol-2-yl)carbonyl]amino}-3-propoxypiperidin-1-yl)-5-ethyl-1,3-oxazole-4-carboxylate obtained in Example (113i) (0.2 g, 0.39 mmol), 2 N lithium hydroxide (3 mL, 6 mmol), methanol (3 mL) and THF (5 mL), to obtain 119 mg of the title compound as a colorless solid (67%).

$^1$H NMR spectrum (400 MHz, DMSO-d$_6$) δ ppm: 0.81 (3.0H, t, J=7.45 Hz), 1.13 (3.0H, t, J=7.45 Hz), 1.13 (3.0H, t, J=7.37 Hz), 1.41 (2.0H, tq, J=7.45, 7.37 Hz), 1.57-1.63 (1.0H, m), 1.87 (1.0H, dq, J=4.24, 12.04 Hz), 2.55 (2.0H, q, J=7.45 Hz), 2.86 (1.0H, dq, J=2.05, 7.34 Hz), 2.88 (1.0H, dq, J=2.05, 7.34 Hz), 3.09-3.17 (2.0H, m), 3.28 (1.0H, dt, J=9.17, 6.53 Hz), 3.52 (1.0H, dt, J=9.17, 6.53 Hz), 3.57 (1.0H, br s), 3.89 (1.0H, d, J=13.30 Hz), 4.09-4.15 (2.0H, m), 7.57 (1.0H, d, J=8.25 Hz).

mass spectrum (FAB): m/z 454 (M+H)$^+$.

Example 114 cis(±)-2-(4-{[(4-Chloro-5-ethyl-1H-imidazol-2-yl)carbonyl]amino}-3-propoxypiperidin-1-yl)-5-methyl-1,3-oxazole-4-carboxylic acid (Exemplified Compound No. 114)

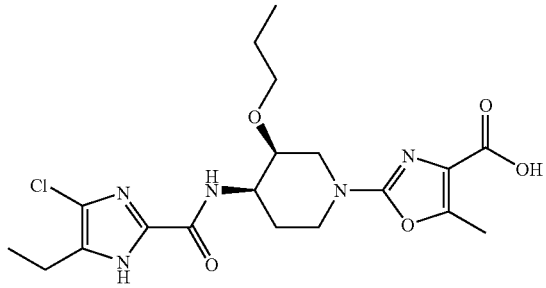

(114a) Butyl cis(±)-2-(4-{[(benzyloxy)carbonyl]amino}-3-propoxypiperidin-1-yl)-5-methyl-1,3-oxazole-4-carboxylate The same operation as in Example (103c) was performed using cis(±)-benzyl (1-carbamoyl-3-propoxypiperidin-4-yl)carbamate obtained in Example (113f) (0.80 g, 2.39 mmol), butyl 3-bromo-2-oxobutanoate obtained in Example (106a) (4 g, 16.9 mmol), sodium bicarbonate (0.7 g, 8.33 mmol) and THF (15 mL). The resulting residue was purified by silica gel column chromatography (elution solvent: ethyl acetate/hexane=1/10, 1/2, 1/1, 2/1, 4/1) to obtain 0.98 g of the title compound as a light brown oily substance (98%).

$^1$H NMR spectrum (400 MHz, CDCl$_3$) δ ppm: 0.83 (3.0H, t, J=7.34 Hz), 0.95 (3.0H, t, J=7.34 Hz), 1.37-1.51 (4.0H, m), 1.68-1.75 (3.0H, m), 1.91 (1.0H, tdd, J=12.38, 12.26, 4.47 Hz), 2.48 (3.0H, s), 3.00-3.04 (2.0H, m), 3.26 (1.0H, dt, J=9.17, 6.88 Hz), 3.49-3.52 (1.0H, br m), 3.58 (1.0H, dt, J=9.17, 6.88 Hz), 3.77-3.83 (0.9H, br m), 4.08-4.15 (1.0H, m), 4.23-4.33 (3.0H, m), 5.11 (2.0H, s), 5.19 (1.0H, d, J=8.71 Hz), 5.30 (1.0H, s), 7.32-7.38 (5.0H, m).

(114b) Butyl cis(±)-2-(4-amino-3-propoxypiperidin-1-yl)-5-methyl-1,3-oxazole-4-carboxylate The same operation as in Example (95b) was performed using butyl cis(±)-2-(4-{[(benzyloxy)carbonyl]amino}-3-propoxypiperidin-1-yl)-5-methyl-1,3-oxazole-4-carboxylate obtained in Example (114a) (0.98 g, 2.1 mmol), 10% Pd/C (0.25 g) and methanol (15 mL), to obtain 0.67 g of the title compound as a light yellow oily substance (95%).

$^1$H NMR spectrum (400 MHz, CDCl$_3$) δ ppm: 0.88 (3.0H, t, J=6.87 Hz), 0.95 (3.0H, t, J=7.44 Hz), 1.42 (2.0H, tq, J=7.31, 7.44 Hz), 1.52-1.55 (2.0H, m), 1.61-1.81 (5.0H, m), 2.48 (3.0H, s), 3.00 (1.0H, dt, J=9.35, 3.54 Hz), 3.14-3.19 (1.0H, m), 3.34 (1.0H, dt, J=9.02, 6.34 Hz), 3.41-3.45 (1.0H, m), 3.59 (1.0H, dt, J=9.02, 6.34 Hz), 3.88-3.94 (1.0H, m), 4.01 (1.0H, ddd, J=13.78, 5.00, 1.34 Hz), 4.28 (2.0H, td, J=6.93, 2.93 Hz).

(114c) Butyl cis(±)-2-(4-{[(4-chloro-5-ethyl-1H-imidazol-2-yl)carbonyl]amino}-3-propoxypiperidin-1-yl)-5-methyl-1,3-oxazole-4-carboxylate The same operation as in Example (106d) was performed using butyl cis(±)-2-(4-amino-3-propoxypiperidin-1-yl)-5-methyl-1,3-oxazole-4-carboxylate obtained in Example (114b) (0.67 g, 1.98 mmol), 4-chloro-5-ethyl-1H-imidazole-2-carboxylic acid (85% content, 0.2 g, 1 mmol), WSC hydrochloride (0.5 g, 2.5 mmol), HOBt (0.2 g, 1.5 mmol), dichloromethane (5 mL) and DMA (3 mL), to obtain 0.22 g of the title compound as a colorless amorphous solid (44%).

$^1$H NMR spectrum (400 MHz, DMSO-d$_6$) δ ppm: 0.80 (3.0H, t, J=7.34 Hz), 0.91 (3.0H, t, J=7.57 Hz), 1.13 (3.0H, t, J=7.57 Hz), 1.38 (2.0H, tq, J=7.34, 7.34 Hz), 1.59-1.65 (3.0H, m), 1.85 (1.0H, dq, J=4.24, 12.04 Hz), 2.45 (3.0H, s), 2.54 (2.0H, q, J=7.57 Hz), 3.09-3.28 (3.0H, m), 3.29 (1.0H, dt, J=9.17, 6.88 Hz), 3.52 (1.0H, dt, J=9.17, 6.88 Hz), 3.58 (1.0H, br s), 3.91 (1.0H, br d), 4.08-4.20 (4.0H, m), 7.57 (1.0H, d, J=8.25 Hz).

(114d) cis(±)-2-(4-{[(4-Chloro-5-ethyl-1H-imidazol-2-yl)carbonyl]amino}-3-propoxypiperidin-1-yl)-5-methyl-1,3-oxazole-4-carboxylic acid The same operation as in Example (91d) was performed using butyl cis(±)-2-(4-{[(4-chloro-5-ethyl-1H-imidazol-2-yl)carbonyl]amino}-3-propoxypiperidin-1-yl)-5-methyl-1,3-oxazole-4-carboxylate obtained in Example (113i) (0.21 g, 0.42 mmol), 2 N lithium hydroxide (3 mL, 6 mmol), methanol (3 mL) and THF (5 mL), to obtain 153 mg of the title compound as a colorless solid (82%).

$^1$H NMR spectrum (400 MHz, DMSO-d$_6$) δ ppm: 0.81 (3.0H, t, J=7.57 Hz), 1.14 (3.0H, t, J=7.57 Hz), 1.36-1.47 (2.0H, m), 1.60-1.61 (1.0H, m), 1.87 (1.0H, dq, J=4.24, 12.04 Hz), 2.42 (3.0H, s), 2.55 (2.0H, q, J=7.57 Hz), 3.08-3.18 (2.0H, m), 3.28 (1.0H, dt, J=9.17, 6.88 Hz), 3.52 (1.0H, dt, J=9.17, 6.88 Hz), 3.57 (1.0H, s), 3.88 (1.0H, d, J=13.75 Hz), 4.09-4.15 (2.0H, m), 7.57 (1.0H, d, J=8.25 Hz).

mass spectrum (FAB): m/z 440 (M+H)$^+$.

Example 115 cis(±)-2-(4-{[(4-Chloro-5-ethyl-1H-imidazol-2-yl)carbonyl]amino}-3-ethoxypiperidin-1-yl)-5-ethyl-1,3-oxazole-4-carboxylic acid (Exemplified Compound No. 115)

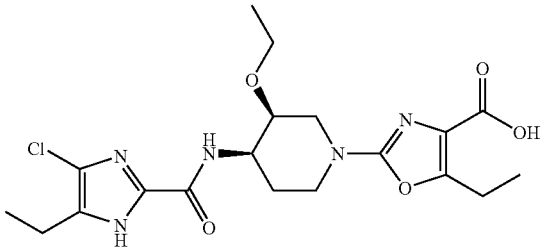

(115a) Ethyl cis(±)-2-(4-{[(benzyloxy)carbonyl]amino}-3-ethoxypiperidin-1-yl)-5-ethyl-1,3-oxazole-4-carboxylate The same operation as in Example (103c) was performed using cis(±)-benzyl (1-carbamoyl-3-ethoxypiperidin-4-yl)carbamate obtained in Example (112f) (0.95 g, 3 mmol), butyl 3-bromo-2-oxopentanoate obtained in Example (106a) (5 g, 19.9 mmol), sodium bicarbonate (0.72 g, 9 mmol) and THF (15 mL). The resulting residue was purified by silica gel column chromatography (elution solvent: ethyl acetate/hexane=1/10, 1/2, 1/1, 2/1, 4/1) to obtain 1.21 g of the title compound as a light yellow oily substance (86%).

$^1$H NMR spectrum (400 MHz, CDCl$_3$) δ ppm: 0.95 (3.0H, t, J=7.34 Hz), 1.10 (3.0H, t, J=7.11 Hz), 1.21 (3.0H, t, J=7.64 Hz), 1.42 (2.0H, tq, J=7.94, 7.34 Hz), 1.70-1.76 (1.0H, m), 1.71 (2.0H, tt, J=7.94, 7.74 Hz), 1.91 (1.0H, tdd, J=12.48, 12.48, 5.47 Hz), 2.91 (2.0H, q, J=7.64 Hz), 2.98-3.07 (2.0H, m), 3.36 (1.0H, dq, J=9.17, 7.11 Hz), 3.52 (1.0H, br s), 3.69 (1.0H, dq, J=9.17, 7.11 Hz), 3.79-3.81 (1.0H, br m), 4.09-4.13 (2.0H, m), 4.22-4.33 (3.0H, m), 5.11 (2.0H, s), 5.21 (1.0H, d, J=8.71 Hz), 7.30-7.38 (5.0H, m).

(115b) Butyl cis(±)-2-(4-amino-3-ethoxypiperidin-1-yl)-5-ethyl-1,3-oxazole-4-carboxylate The same operation as in Example (95b) was performed using butyl cis(±)-2-(4-{[(benzyloxy)carbonyl]amino}-3-ethoxypiperidin-1-yl)-5-ethyl-1,3-oxazole-4-carboxylate obtained in Example (115a) (1.21 g, 2.5 mmol), 10% Pd/C (0.25 g) and methanol (15 mL), to obtain 0.89 g of the title compound as a light brown oily substance (97%).

$^1$H NMR spectrum (400 MHz, CDCl$_3$) δ ppm: 0.95 (3.0H, t, J=7.32 Hz), 1.16 (3.0H, t, J=6.95 Hz), 1.21 (3.0H, t, J=7.44 Hz), 1.42 (2.0H, tq, J=7.32, 7.32 Hz), 1.62-1.83 (5.0H, m), 2.92 (2.0H, q, J=7.44 Hz), 2.99-3.01 (1.0H, m), 3.13-3.23 (1.5H, m), 3.44-3.50 (2.5H, m), 3.66-3.73 (1.0H, m), 3.89-4.02 (1.5H, m), 4.26-4.29 (1.5H, m).

(115c) Butyl cis(±)-2-(4-{[(4-chloro-5-ethyl-1H-imidazol-2-yl)carbonyl]amino}-3-ethoxypiperidin-1-yl)-5-ethyl-1,3-oxazole-4-carboxylate The same operation as in Example (106d) was performed using butyl cis(±)-2-(4-amino-3-ethoxypiperidin-1-yl)-5-ethyl-1,3-oxazole-4-carboxylate obtained in Example (115b) (0.89 g, 2.63 mmol), 4-chloro-5-ethyl-1H-imidazole-2-carboxylic acid (85% content, 0.2 g, 1 mmol), WSC hydrochloride (0.5 g, 2.5 mmol), HOBt (0.2 g, 1.5 mmol), dichloromethane (5 mL) and DMA (3 mL), to obtain 0.25 g of the title compound as a colorless amorphous solid (49%).

$^1$H NMR spectrum (400 MHz, DMSO-d$_6$) δ ppm: 0.91 (3.0H, t, J=7.34 Hz), 1.02 (3.0H, t, J=6.88 Hz), 1.14 (3.0H, t, J=6.88 Hz), 1.16 (3.0H, t, J=7.79 Hz), 1.37 (2.0H, tq, J=7.34, 7.34 Hz), 1.59-1.66 (3.0H, m), 1.86 (1.0H, dq, J=4.13, 12.15, Hz), 2.55 (2.0H, q, J=7.79 Hz), 2.88 (2.0H, ddd, J=15.02, 7.68, 1.95 Hz), 3.09-3.18 (2.0H, m), 3.40 (1.0H, dq, J=9.17, 7.34 Hz), 3.57-3.64 (2.0H, m), 3.92 (1.0H, br d), 4.09-4.20 (4.0H, m), 7.57 (1.0H, d, J=8.25 Hz).

(115d) cis(±)-2-(4-{[(4-Chloro-5-ethyl-1H-imidazol-2-yl)carbonyl]amino}-3-ethoxypiperidin-1-yl)-5-ethyl-1,3-oxazole-4-carboxylic acid The same operation as in Example (91d) was performed using butyl cis(±)-2-(4-{[(4-chloro-5-ethyl-1H-imidazol-2-yl)carbonyl]amino}-3-ethoxypiperidin-1-yl)-5-ethyl-1,3-oxazole-4-carboxylate obtained in Example (115c) (0.24 g, 0.48 mmol), 2 N lithium hydroxide (3 mL, 6 mmol), methanol (4 mL) and THF (6 mL), to obtain 160 mg of the title compound as a colorless solid (75%).

$^1$H NMR spectrum (400 MHz, DMSO-d$_6$) δ ppm: 1.02 (3.0H, t, J=7.11 Hz), 1.13 (3.0H, t, J=7.45 Hz), 1.14 (3.0H, t, J=7.34 Hz), 1.59-1.61 (1.0H, m), 1.86 (1.0H, dq, J=4.05, 12.20 Hz), 2.55 (2.0H, q, J=7.45 Hz), 2.85-2.91 (2.0H, m), 3.10-3.16 (2.0H, m), 3.39-3.42 (1.0H, m), 3.58-3.63 (2.0H, m), 3.89 (1.0H, d, J=13.30 Hz), 4.10-4.13 (2.0H, m), 7.57 (1.0H, d, J=8.71 Hz).

mass spectrum (FAB): m/z 440 (M+H)$^+$.

Example 116 cis(±)-2-(4-{[(4-Chloro-5-ethyl-1H-imidazol-2-yl)carbonyl]amino}-3-methoxypiperidin-1-yl)-5-propyl-1,3-oxazole-4-carboxylic acid (Exemplified Compound No. 116)

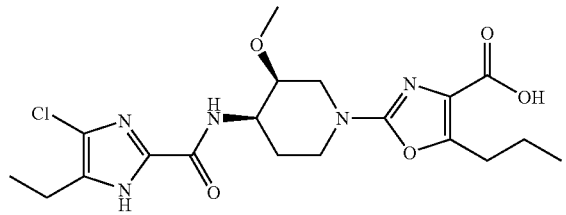

(116a) Butyl 3-bromo-2-oxohexanoate

The same operation as in Example (106a) was performed using butyl 2-oxohexanoate (Lapkin, I. I.; Dvinskikh, V. V.; J. Gen. Chem. USSR (Engl. Transl.); 48; 1978; 2278-2280; Zh. Obshch. Khim.; 48; 1978; 2509-2511, 3.41 g, 18.3 mmol), bromine (2.55 g, 16 mmol) and chloroform (30 mL), to obtain 5.14 g of the title compound as a colorless liquid (100%).

$^1$H NMR spectrum (400 MHz, CDCl$_3$) δ ppm: 0.96 (3.0H, t, J=7.45 Hz), 0.98 (3.0H, t, J=7.45 Hz), 1.39-1.49 (4.0H, m), 1.72-1.76 (2.0H, m), 1.94-2.12 (2.0H, m), 4.33 (1.0H, t, J=7.45 Hz), 4.33 (1.0H, t, J=7.45 Hz), 5.03 (1.0H, dd, J=8.48, 6.19 Hz).

(116b) Ethyl cis(±)-2-(4-{[(benzyloxy)carbonyl]amino}-3-methoxypiperidin-1-yl)-5-propyl-1,3-oxazole-4-carboxylate The same operation as in Example (103c) was performed using cis(±)-benzyl (1-carbamoyl-3-methoxypiperidin-4-yl)carbamate obtained in Example (103b) (0.95 g, 3.09 mmol), butyl 3-bromo-2-oxohexanoate obtained in Example (116a) (5.1 g, 19.2 mmol), sodium bicarbonate (0.64 g, 7.6 mmol) and THF (20 mL). The resulting residue was purified by silica gel column chromatography (elution solvent: ethyl acetate/hexane=1/4, 2/3, 1/1, 3/2, 2/1) to obtain 1.02 g of the title compound as a light yellow solid (70%).

$^1$H NMR spectrum (400 MHz, CDCl$_3$) δ ppm: 0.95 (3.0H, t, J=7.34 Hz), 0.96 (3.0H, t, J=7.34 Hz), 1.42 (2.0H, tq, J=7.56, 7.34 Hz), 1.64 (2.0H, tt, J=7.56, 7.56 Hz), 1.65-1.77 (1.0H, m), 1.71 (2.0H, tq, J=7.45, 7.34 Hz), 1.87 (1.0H, tdd, J=12.35, 12.34, 4.47 Hz), 2.87 (2.0H, td, J=7.45, 2.60 Hz), 2.97-3.05 (2.0H, m), 3.37 (3.0H, s), 3.42 (1.0H, brs), 3.78-3.84 (1.0H, br m), 4.09-4.13 (1.0H, m), 4.22-4.35 (3.0H, m), 5.11 (2.0H, s), 5.24 (1.0H, d, J=8.71 Hz), 7.34-7.38 (5.0H, m).

(116c) Butyl cis(±)-2-(4-amino-3-methoxypiperidin-1-yl)-5-propyl-1,3-oxazole-4-carboxylate The same operation as in Example (95b) was performed using butyl cis(±)-2-(4-{[(benzyloxy)carbonyl]amino}-3-methoxypiperidin-1-yl)-5-propyl-1,3-oxazole-4-carboxylate obtained in Example (116b) (1.0 g, 2.1 mmol), 10% Pd/C (0.25 g) and methanol (10 mL), to obtain 0.69 g of the title compound as a yellow oily substance (96%).

mass spectrum (APCI): m/z 340 (M+H)$^+$.

(116d) Butyl cis(±)-2-(4-{[(4-chloro-5-ethyl-1H-imidazol-2-yl)carbonyl]amino}-3-methoxypiperidin-1-yl)-5-propyl-1,3-oxazole-4-carboxylate The same operation as in Example (106d) was performed using butyl cis(±)-2-(4-amino-3-methoxypiperidin-1-yl)-5-propyl-1,3-oxazole-4-carboxylate obtained in Example (116c) (0.69 g, 2.0 mmol), 4-chloro-5-ethyl-1H-imidazole-2-carboxylic acid (85% content, 0.2 g, 1 mmol), WSC hydrochloride (0.5 g, 2.5 mmol), HOBt (0.2 g, 1.5 mmol), DMA (3 mL) and dichloromethane (3 mL). The resulting residue was purified by silica gel column chromatography (elution solvent: ethyl acetate/hexane=1/4, 2/3, 3/2, 4/1) to obtain 0.22 g of the title compound as a colorless solid (44%).

$^1$H NMR spectrum (400 MHz, DMSO-$d_6$) δ ppm: 0.90 (3.0H, t, J=7.34 Hz), 0.91 (3.0H, t, J=7.34 Hz), 1.14 (3.0H, t, J=7.57 Hz), 1.33-1.42 (2.0H, m), 1.56-1.66 (5.0H, m), 1.85 (1.0H, ddd, J=24.53, 12.38, 4.36 Hz), 2.49-2.51 (2.0H, m), 2.54 (2.0H, q, J=7.79 Hz), 2.78-2.91 (2.0H, m), 3.10-3.18 (2.0H, m), 3.30 (3.0H, s), 3.50 (1.0H, s), 3.91 (1.0H, d, J=13.30 Hz), 4.14-4.20 (4.0H, m), 7.60 (1.0H, d, J=8.25 Hz).

(116e) cis(±)-2-(4-{[(4-Chloro-5-ethyl-1H-imidazol-2-yl)carbonyl]amino}-3-methoxypiperidin-1-yl)-5-propyl-1,3-oxazole-4-carboxylic acid The same operation as in Example (91d) was performed using butyl cis(±)-2-(4-{[(4-chloro-5-ethyl-1H-imidazol-2-yl)carbonyl]amino}-5-propyl-3-methoxypiperidin-1-yl)-1,3-oxazole-4-carboxylate obtained in Example (116d) (0.22 g, 0.44 mmol), 2 N lithium hydroxide (3 mL, 6 mmol), methanol (2 mL) and THF (3 mL), to obtain 176 mg of the title compound as a colorless solid (91%).

$^1$H NMR spectrum (400 MHz, DMSO-$d_6$) δ ppm: 0.91 (3.0H, q, J=7.03 Hz), 1.14 (3.0H, t, J=7.57 Hz), 1.55-1.62 (3.0H, m), 1.85 (1.0H, dq, J=4.01, 12.26 Hz), 2.55 (2.0H, q, J=7.57 Hz), 2.82-2.87 (2.0H, m), 3.09-3.18 (2.0H, m), 3.30 (3.0H, s), 3.50 (1.0H, br s), 3.90 (1.0H, d, J=13.30 Hz), 4.13-4.20 (2.0H, m), 7.60 (1.0H, d, J=8.71 Hz).

mass spectrum (FAB): m/z 440 (M+H)$^+$.

Example 117 cis(±)-2-(4-{[(4-Chloro-5-ethyl-1H-imidazol-2-yl)carbonyl]amino}-3-isobutoxypiperidin-1-yl)-1,3-thiazole-5-carboxylic acid (Exemplified Compound No. 117)

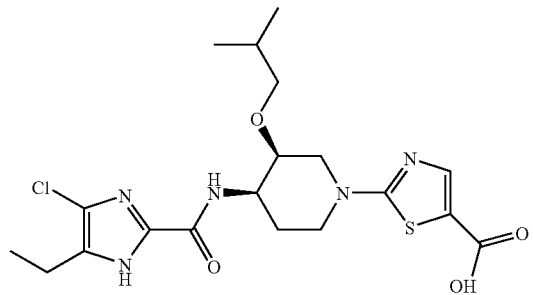

(117a) tert-Butyl 4,4-dimethoxy-3-[(2-methyl-2-propen-1-yl)oxy]piperidine-1-carboxylate The same operation as in Example (90a) was performed using tert-butyl 3-hydroxy-4,4-dimethoxypiperidine-1-carboxylate (5.2 g, 20 mmol), sodium hydride (55% content, 1.31 g, 30 mmol), 3-chloro-2-methyl-1-propene (3.63 g, 40 mmol) and DMF (50 mL). The residue was purified by column chromatography (elution solvent: hexane/ethyl acetate=10/1, 4/1, 2/1) to obtain 4.85 g of the title compound as a colorless oily substance (77%).

$^1$H NMR spectrum (400 MHz, CDCl$_3$) δ ppm: 1.45 (9.0H, s), 1.70-1.74 (1.0H, m), 1.76 (3.0H, s), 1.83-1.89 (1.0H, m), 2.73-2.85 (1.0H, m), 2.95-3.02 (1.0H, m), 3.21 (3.0H, s), 3.22 (3.0H, s), 3.38-3.44 (1.0H, m), 3.86 (1.0H, d, J=12.38 Hz), 4.02-4.29 (3.0H, m), 4.88 (1.0H, br s), 5.00 (1.0H, s).

(117b) tert-Butyl 3-[(2-methyl-2-propen-1-yl)oxy]-4-oxopiperidine-1-carboxylate

The same operation as in Example (90b) was performed using tert-butyl 4,4-dimethoxy-3-[(2-methyl-2-propen-1-yl)oxy]piperidine-1-carboxylate obtained in Example (117a) (4.8 g, 18.7 mmol), a water/TFA mixed solution (1/1, 20 mL) and di-tert-butyl dicarbonate (4.8 g, 22 mol). The resulting residue was purified by silica gel column chromatography (elution solvent: hexane/ethyl acetate=10/1, 5/1, 2/1, 1/1) to obtain 3.43 g of the title compound as a light brown oily substance (84%).

$^1$H NMR spectrum (400 MHz, CDCl$_3$) δ ppm: 1.49 (9.0H, s), 1.75 (3.0H, s), 2.40-2.47 (1.0H, m), 2.55-2.59 (1.0H, br m), 3.26-3.39 (2.0H, br m), 3.81-3.84 (1.0H, br m), 3.93-4.29 (2.0H, m), 3.94 (4.0H, d, J=12.84 Hz), 4.13 (4.0H, d, J=12.84 Hz), 4.93 (1.0H, s), 4.99 (1.0H, s).

(117c) tert-Butyl cis(±)-4-(benzylamino)-3-[(2-methyl-2-propen-1-yl)oxy]piperidine-1-carboxylate The same operation as in Example (90c) was performed using tert-butyl 3-[(2-methyl-2-propen-1-yl)oxy]-4-oxopiperidine-1-carboxylate obtained in Example (117b) (3.43 g, 17.1 mmol), benzylamine (1.5 g, 14 mmol), sodium (triacetoxy)borohydride (4 g, 18.9 mmol) and 1,2-dichloroethane (30 mL). The resulting residue was purified by silica gel column chromatography (elution solvent: hexane/ethyl acetate=4/1, 1/1, 1/3, 0/1) to obtain 3.97 g of the title compound as a colorless oily substance (86%).

$^1$H NMR spectrum (400 MHz, CDCl$_3$) δ ppm: 1.45 (9.0H, s), 1.60-1.74 (5.0H, m), 2.75-2.77 (1.0H, m), 2.96 (2.0H, d, J=12.84 Hz), 3.54-3.58 (1.0H, m), 3.76-3.84 (3.0H, m), 4.04 (2.0H, d, J=11.92 Hz), 4.87 (1.0H, br s), 4.97 (1.0H, br s), 7.23-7.25 (1.0H, m), 7.30-7.34 (4.0H, m).

(117d) tert-Butyl cis(±)-4-amino-3-isobutoxypiperidine-1-carboxylate

The same operation as in Example (90d) was performed using tert-butyl cis(±)-4-(benzylamino)-3-[(2-methyl-2-propen-1-yl)oxy]piperidine-1-carboxylate obtained in Example (117c) (1.8 g, 5 mmol), 10% Pd/C (wet, 0.5 g), ammonium formate (2.52 g, 40 mmol) and methanol (20 mL), to obtain 1.26 g of the title compound as a colorless oily substance (93%).

$^1$H NMR spectrum (400 MHz, CDCl$_3$) δ ppm: 0.91 (6.0H, d, J=6.42 Hz), 1.45 (9.0H, s), 1.46-1.55 (1.0H, m), 1.61-1.69 (1.0H, m), 1.81-1.88 (1.0H, m), 2.83-2.96 (3.0H, br m), 3.06-3.11 (1.0H, br m), 3.27-3.32 (1.0H, br m), 3.44 (1.0H, dd, J=8.71, 6.42 Hz), 3.77-4.04 (1.0H, m), 4.10 (1.0H, ddd, J=14.21, 4.59, 1.83 Hz).

(117e) tert-Butyl cis(±)-4-{[(4-chloro-5-ethyl-1H-imidazol-2-yl)carbonyl]amino}-3-isobutoxypiperidine-1-carboxylate The same operation as in Example (106d) was performed using tert-butyl cis(±)-4-amino-3-isobutoxypiperidine-1-carboxylate obtained in Example (117d) (1.26 g, 4.6 mmol), 4-chloro-5-ethyl-1H-imidazole-2-carboxylic acid (85% content, 1.02 g, 5 mmol), WSC hydrochloride (2.88 g, 15 mmol), HOBt (1.01 g, 7.5 mmol), DMA (15 mL) and dichloromethane (15 mL). The resulting residue was purified by silica gel column chromatography (elution solvent: ethyl acetate/hexane=1/4, 2/3, 3/2, 4/1) to obtain 1.71 g of the title compound as a colorless solid (87%).

$^1$H NMR spectrum (400 MHz, CDCl$_3$) δ ppm: 0.94 (6.0H, d, J=5.50 Hz), 1.26 (3.0H, t, J=7.64 Hz), 1.47 (9.0H, s), 1.63-1.69 (1.0H, br m), 1.87-1.92 (2.0H, br m), 2.68 (2.0H, q, J=7.64 Hz), 2.70-2.87 (2.0H, m), 3.08 (1.0H, t, J=7.11 Hz), 3.44-3.47 (2.0H, br m), 4.08-4.27 (2.0H, m), 4.37-4.51 (1.0H, m), 7.55 (1.0H, br s), 11.84 (1.0H, br s).

(117f) Ethyl cis(±)-2-(4-{[(4-chloro-5-ethyl-1H-imidazol-2-yl)carbonyl]amino}-3-isobutoxypiperidin-1-yl)-1,3-thiazole-5-carboxylate The same operation as in Example (90f) was performed using tert-butyl cis(±)-4-{[(4-chloro-5-ethyl-1H-imidazol-2-yl)carbonyl]amino}-3-isobutoxypiperidine-1-carboxylate obtained in Example (117e) (0.21 g, 0.5 mmol), a 4 N hydrochloric acid/ethyl acetate solution (5 ml, 20 mmol), diisopropylethylamine (260 µL, 1.5 mmol), ethyl 2-bromo-1,3-thiazole-5-carboxylate (104 µL, 0.7 mmol) and DMA (8 mL), to obtain 0.17 g of the title compound as a light brown amorphous solid (70%).

$^1$H NMR spectrum (400 MHz, DMSO-$d_6$) δ ppm: 0.83 (3.0H, d, J=6.88 Hz), 0.88 (3.0H, d, J=6.88 Hz), 1.27 (3.0H, t, J=7.64 Hz), 1.34 (3.0H, t, J=7.34 Hz), 1.78-1.87 (2.0H, m), 2.10 (1.0H, dq, J=4.47, 12.26 Hz), 2.69 (2.0H, q, J=7.64 Hz), 3.11-3.17 (2.0H, m), 3.25 (1.0H, td, J=12.95, 2.75 Hz), 3.45 (1.0H, dd, J=8.48, 7.11 Hz), 3.60 (1.0H, br s), 4.00 (0.9H, d, J=13.75 Hz), 4.21-4.29 (1.0H, m), 4.30 (3.0H, q, J=7.34 Hz), 4.51 (1.0H, d, J=14.21 Hz), 7.49 (1.0H, d, J=8.71 Hz), 7.84 (1.0H, s), 11.03 (1.0H, s).

(117g) cis(±)-2-(4-{[(4-Chloro-5-ethyl-1H-imidazol-2-yl)carbonyl]amino}-3-isobutoxypiperidin-1-yl)-1,3-thiazole-5-carboxylic acid The same operation as in Example (91d) was performed using ethyl cis(±)-2-(4-{[(4-chloro-5-ethyl-1H-imidazol-2-yl)carbonyl]amino}-3-isobutoxypiperidin-1-yl)-1,3-oxazole-4-carboxylate obtained in Example (117f) (0.17 g, 0.21 mmol), 2 N lithium hydroxide (3 mL, 6 mmol), methanol (3 mL) and THF (5 mL), to obtain 135 mg of the title compound as a colorless solid (84%).

$^1$H NMR spectrum (400 MHz, DMSO-$d_6$) δ ppm: 0.78 (3.0H, d, J=6.65 Hz), 0.81 (3.0H, d, J=6.65 Hz), 1.14 (3.0H, t, J=7.57 Hz), 1.68-1.73 (2.0H, m), 1.89 (1.0H, dq, J=3.90, 12.38 Hz), 2.56 (2.0H, q, J=7.57 Hz), 3.13 (1.0H, dd, J=8.94, 6.19 Hz), 3.28-3.39 (3.0H, m), 3.64 (1.0H, s), 3.93 (1.0H, d, J=13.30 Hz), 4.16-4.28 (2.0H, m), 7.65 (1.0H, d, J=8.71 Hz), 7.67 (1.0H, s).

mass spectrum (FAB): m/z 456 (M+H)$^+$.

Example 118 cis(±)-2-(4-{[(4-Chloro-5-ethyl-1H-imidazol-2-yl)carbonyl]amino}-3-isobutoxypiperidin-1-yl)-4-methyl-1,3-thiazole-5-carboxylic acid (Exemplified Compound No. 118)

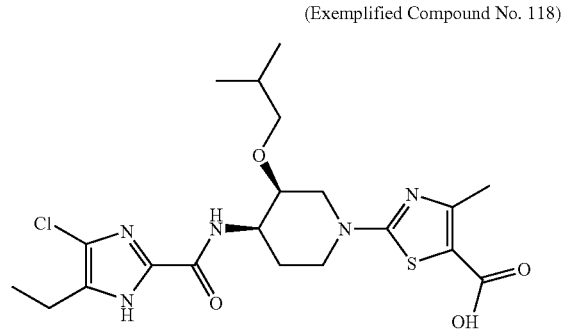 [SMILES: CCc1[nH]c(C(=O)N[C@@H]2CCN(c3nc(C)c(C(=O)O)s3)C[C@@H]2OCC(C)C)nc1Cl]

(118a) Ethyl cis(±)-2-(4-{[(4-chloro-5-ethyl-1H-imidazol-2-yl)carbonyl]amino}-3-isobutoxypiperidin-1-yl)-4-methyl-1,3-thiazole-5-carboxylate The same operation as in Example (90f) was performed using tert-butyl cis(±)-4-{[(4-chloro-5-ethyl-1H-imidazol-2-yl)carbonyl]amino}-3-isobutoxypiperidine-1-carboxylate obtained in Example (117e) (0.21 g, 0.5 mmol), a 4 N hydrochloric acid/ethyl acetate solution (5 ml, 20 mmol), diisopropylethylamine (260 µL, 1.5 mmol), ethyl 2-bromo-4-methyl-1,3-thiazole-5-carboxylate (175 mg, 0.7 mmol) and DMA (8 mL), to obtain 0.21 g of the title compound as a light brown amorphous solid (84%).

$^1$H NMR spectrum (400 MHz, DMSO-$d_6$) δ ppm: 0.83 (3.0H, d, J=6.42 Hz), 0.89 (3.0H, d, J=6.88 Hz), 1.26 (3.0H, t, J=7.64 Hz), 1.33 (3.0H, t, J=7.04 Hz), 1.77-1.86 (2.0H, m), 2.09 (1.0H, dq, J=4.96, 11.92 Hz), 2.54 (3.0H, s), 2.69 (2.0H, q, J=7.64 Hz), 3.08-3.14 (3.0H, m), 3.21 (1.0H, td, J=12.95, 2.60 Hz), 3.47 (1.0H, dd, J=8.71, 6.88 Hz), 3.58 (1.0H, br s), 3.98 (1.0H, d, J=12.84 Hz), 4.20-4.26 (1.0H, m), 4.26 (2.0H, q, J=7.04 Hz), 4.49 (1.0H, d, J=13.75 Hz), 7.51 (1.0H, d, J=8.71 Hz), 11.24 (1.0H, s).

(118b) cis(±)-2-(4-{[(4-Chloro-5-ethyl-1H-imidazol-2-yl)carbonyl]amino}-3-isobutoxypiperidin-1-yl)-4-methyl-1,3-thiazole-5-carboxylic acid The same operation as in Example (91d) was performed using ethyl cis(±)-2-(4-{[(4-chloro-5-ethyl-1H-imidazol-2-yl)carbonyl]amino}-3-isobutoxypiperidin-1-yl)-4-methyl-1,3-oxazole-4-carboxylate obtained in Example (118a) (0.16 g, 0.32 mmol), 2 N lithium hydroxide (3 mL, 6 mmol), methanol (3 mL) and THF (5 mL), to obtain 143 mg of the title compound as a colorless solid (95%).

$^1$H NMR spectrum (400 MHz, DMSO-$d_6$) δ ppm: 0.79 (3.0H, d, J=6.88 Hz), 0.82 (3.0H, d, J=6.88 Hz), 1.14 (3.0H, t, J=7.11 Hz), 1.67-1.73 (2.0H, m), 1.88 (1.0H, dq, J=4.30, 12.21 Hz), 2.40 (3.0H, s), 2.55 (2.0H, q, J=7.11 Hz), 3.11-3.13 (1.0H, m), 3.27-3.39 (3.0H, m), 3.62 (1.0H, s), 3.88-3.93 (1.0H, m), 4.18-4.22 (2.0H, m), 7.64 (1.0H, d, J=8.71 Hz).

mass spectrum (FAB): m/z 470 (M+H)$^+$.

Example 119 cis(±)-2-(3-Butoxy-4-{[(4-chloro-5-ethyl-1H-imidazol-2-yl)carbonyl]amino}piperidin-1-yl)-1,3-thiazole-5-carboxylic acid (Exemplified Compound No. 119)

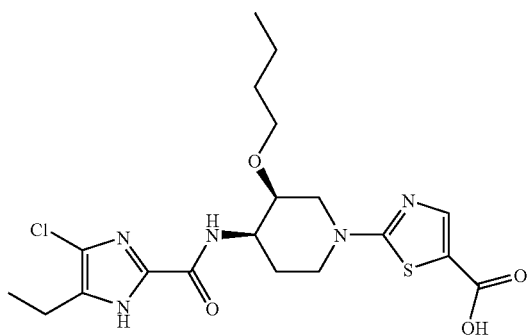

(119a) tert-Butyl 3-[(2E)-2-buten-1-yloxy]-4,4-dimethoxypiperidine-1-carboxylate The same operation as in Example (90a) was performed using tert-butyl 3-hydroxy-4,4-dimethoxypiperidine-1-carboxylate (5.2 g, 20 mmol), sodium hydride (55% content, 1.31 g, 30 mmol), crotyl chloride (3.63 g, 40 mmol) and DMF (50 mL). The residue was purified by column chromatography (elution solvent: hexane/ethyl acetate=10/1, 4/1, 2/1) to obtain 5.05 g of the title compound as a colorless oily substance (80%).

¹H NMR spectrum (400 MHz, CDCl₃) δ ppm: 1.46 (9.0H, s), 1.71-1.81 (5.0H, m), 2.70-2.85 (1.0H, m), 2.90-3.03 (1.0H, m), 3.21 (6.0H, s), 3.39-3.45 (1.0H, m), 3.87-3.98 (2.0H, m), 4.15-4.24 (2.0H, m), 5.55-5.61 (1.0H, m), 5.65-5.77 (1.0H, m).

(119b) tert-Butyl 3-[(2E)-2-buten-1-yloxy]-4-oxopiperidine-1-carboxylate

The same operation as in Example (90b) was performed using tert-butyl 3-[(2E)-2-buten-1-yloxy]-4,4-dimethoxypiperidine-1-carboxylate obtained in Example (119a) (5.05 g, 16.0 mmol), a water/TFA mixed solution (1/1, 20 mL) and di-tert-butyl dicarbonate (5.2 g, 23.8 mol). The resulting residue was purified by silica gel column chromatography (elution solvent: hexane/ethyl acetate=10/1, 5/1, 2/1, 1/1) to obtain 4.31 g of the title compound as a light brown oily substance (100%).

mass spectrum (APCI): m/z 270 (M+H)⁺.

(119c) tert-Butyl cis(±)-4-(benzylamino)-[(2E)-2-buten-1-yloxy]piperidine-1-carboxylate The same operation as in Example (90c) was performed using tert-butyl 3-[(2E)-2-buten-1-yloxy]-4-oxopiperidine-1-carboxylate obtained in Example (119b) (5 g, 16 mmol), benzylamine (2.04 g, 19 mmol), sodium (triacetoxy)borohydride (7.41 g, 35 mmol) and 1,2-dichloroethane (50 mL). The resulting residue was purified by silica gel column chromatography (elution solvent: hexane/ethyl acetate=4/1, 1/1, 1/3, 0/1) to obtain 5.74 g of the title compound as a colorless solid (99%).

¹H NMR spectrum (400 MHz, CDCl₃) δ ppm: 1.45 (9.0H, s), 1.61-1.74 (5.0H, m), 2.73-2.76 (1.0H, br m), 2.95 (2.0H, d, J=13.30 Hz), 3.52-3.57 (1.0H, br m), 3.75-3.86 (3.0H, m), 3.93-4.19 (3.0H, m), 5.52-5.58 (1.0H, m), 5.63-5.73 (1.0H, m), 7.23-7.27 (1.0H, m), 7.31-7.35 (4.0H, m).

(119d) tert-Butyl cis(±)-4-amino-3-butoxypiperidine-1-carboxylate

The same operation as in Example (90d) was performed using tert-butyl cis(±)-4-(benzylamino)-[(2E)-2-buten-1-yloxy]piperidine-1-carboxylate obtained in Example (119c) (1.8 g, 5 mmol), 10% Pd/C (wet, 0.5 g), ammonium formate (2.52 g, 40 mmol) and methanol (20 mL), to obtain 1.24 g of the title compound as a colorless oily substance (93%).

¹H NMR spectrum (400 MHz, CDCl₃) δ ppm: 0.92 (3.0H, t, J=7.34 Hz), 1.38 (2.0H, q, J=7.34 Hz), 1.45-1.55 (3.0H, m), 1.46 (9.0H, s), 1.60-1.70 (1.0H, m), 2.83-2.96 (2.8H, br m), 3.28-3.33 (1.0H, m), 3.33 (1.0H, dt, J=9.17, 6.42 Hz), 3.63-3.69 (1.0H, m), 3.79-3.96 (1.0H, m), 4.07 (1.0H, ddd, J=14.21, 4.59, 1.83 Hz).

(119e) tert-Butyl cis(±)-3-butoxy-4-{[(4-chloro-5-ethyl-1H-imidazol-2-yl)carbonyl]amino}piperidine-1-carboxylate The same operation as in Example (106d) was performed using tert-butyl cis(±)-4-amino-3-butoxypiperidine-1-carboxylate obtained in Example (119d) (1.26 g, 4.6 mmol), 4-chloro-5-ethyl-1H-imidazole-2-carboxylic acid (85% content, 1.03 g, 5 mmol), WSC hydrochloride (2.88 g, 15 mmol), HOBt (1.01 g, 7.5 mmol), DMA (15 mL) and dichloromethane (15 mL). The resulting residue was purified by silica gel column chromatography (elution solvent: ethyl acetate/hexane=1/4, 2/3, 3/2, 4/1) to obtain 2.31 g of the title compound as a colorless solid (100%).

¹H NMR spectrum (400 MHz, CDCl₃) δ ppm: 0.90-0.97 (3.0H, br m), 1.26 (3.0H, t, J=7.57 Hz), 1.40-1.46 (2.0H, m), 1.47 (9.0H, s), 1.56-1.67 (3.0H, m), 1.83-1.94 (1.0H, m), 2.68-2.87 (2.0H, m), 2.69 (2.0H, q, J=7.57 Hz), 3.29-3.32 (1.0H, m), 3.42-3.47 (1.0H, br m), 3.66-3.73 (1.0H, br m), 4.02-4.15 (2.0H, m), 4.36-4.50 (1.0H, m), 7.53 (1.0H, s), 11.74 (1.0H, s).

(119f) Ethyl cis(±)-2-(3-butoxy-4-{[(4-chloro-5-ethyl-1H-imidazol-2-yl)carbonyl]amino}piperidin-1-yl)-1,3-thiazole-5-carboxylate The same operation as in Example (90f) was performed using tert-butyl cis(±)-3-butoxy-4-{[(4-chloro-5-ethyl-1H-imidazol-2-yl)carbonyl]amino}piperidine-1-carboxylate obtained in Example (119e) (0.34 g, 0.8 mmol), a 4 N hydrochloric acid/ethyl acetate solution (10 ml, 40 mmol), diisopropylethylamine (1.5 g, 11.6 mmol), ethyl 2-bromo-1,3-thiazole-5-carboxylate (240 μL, 1.3 mmol) and DMA (8 mL), to obtain 0.39 g of the title compound as a light brown amorphous solid (100%).

¹H NMR spectrum (400 MHz, CDCl₃) δ ppm: 0.88 (3.0H, t, J=7.11 Hz), 1.27 (3.0H, t, J=7.49 Hz), 1.30-1.36 (2.0H, m), 1.35 (3.0H, t, J=7.18 Hz), 1.48-1.56 (2.0H, m), 1.78-1.83 (1.0H, m), 2.09 (1.0H, tt, J=17.19, 5.43 Hz), 2.70 (2.0H, q, J=7.49 Hz), 3.15 (1.0H, dd, J=14.21, 1.38 Hz), 3.23 (1.0H, td, J=12.95, 2.75 Hz), 3.36 (1.0H, dt, J=9.17, 6.42 Hz), 3.61 (1.0H, br s), 3.69 (1.0H, dt, J=9.17, 6.42 Hz), 4.02 (1.0H, d, J=13.75 Hz), 4.22-4.27 (1.0H, m), 4.30 (2.0H, q, J=7.18 Hz), 4.49 (1.0H, d, J=13.75 Hz), 7.52 (1.0H, d, J=9.34 Hz), 7.84 (1.0H, s), 11.49 (1.0H, s).

(119g) cis(±)-2-(3-Butoxy-4-{[(4-chloro-5-ethyl-1H-imidazol-2-yl)carbonyl]amino}piperidin-1-yl)-1,3-thiazole-5-carboxylic acid The same operation as in Example (91d) was performed using ethyl cis(±)-2-(3-butoxy-4-{[(4-chloro-5-ethyl-1H-imidazol-2-yl)carbonyl]amino}piperidin-1-yl)-1,3-thiazole-5-carboxylate obtained in Example (119f) (0.39 g, 0.8 mmol), 2 N lithium hydroxide (5 mL, 10 mmol), methanol (3 mL) and THF (3 mL), to obtain 0.30 g of the title compound as a colorless solid (82%).

¹H NMR spectrum (400 MHz, DMSO-d₆) δ ppm: 0.79 (3.0H, t, J=7.19 Hz), 1.14 (3.0H, t, J=7.44 Hz), 1.28 (2.0H, tq, J=7.19, 7.32 Hz), 1.38-1.40 (2.0H, m), 1.68-1.70 (1.0H, m), 1.86-1.88 (1.0H, m), 2.55 (2.0H, q, J=7.44 Hz), 3.27-3.37 (3.0H, m), 3.58-3.65 (2.0H, m), 3.95 (1.0H, d, J=11.22 Hz), 4.15-4.24 (2.0H, m), 7.63 (1.0H, d, J=8.29 Hz), 7.70 (1.0H, s), 13.36 (1.0H, s).

mass spectrum (FAB): m/z 456 (M+H)⁺.

Example 120 cis(±)-2-(3-Butoxy-4-{[(4-chloro-5-ethyl-1H-imidazol-2-yl)carbonyl]amino}piperidin-1-yl)-4-methyl-1,3-thiazole-5-carboxylic acid (Exemplified Compound No. 120)

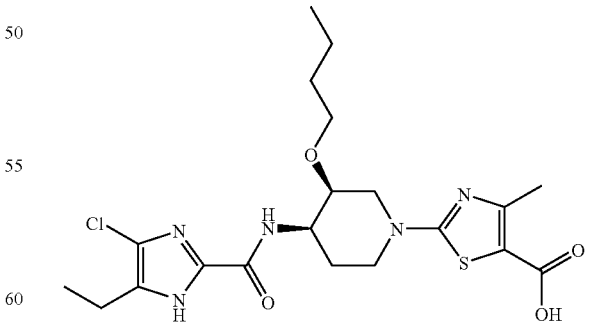

(120a) Ethyl cis(±)-2-(3-butoxy-4-{[(4-chloro-5-ethyl-1H-imidazol-2-yl)carbonyl]amino}piperidin-1-yl)-4-methyl-1,3-thiazole-5-carboxylate The same operation as in Example (90f) was performed using tert-butyl cis(±)-3-butoxy-4-{[(4-chloro-5-ethyl-1H- imidazol-2-yl)carbonyl]amino}piperidine-1-carboxylate obtained in Example (119e) (0.34 g, 0.8 mmol), a 4 N hydrochloric acid/ethyl acetate solution (10 ml, 40 mmol), diisopropylethylamine (1.5 g, 11.6 mmol), ethyl 2-bromo-4-methyl-1,3-thiazole-5-carboxylate (350 mg, 1.3 mmol) and DMA (10 mL), to obtain 0.34 g of the title compound as a light brown amorphous solid (86%).

$^1$H NMR spectrum (400 MHz, CDCl$_3$) δ ppm: 0.88 (3.0H, t, J=7.34 Hz), 1.27 (3.0H, t, J=7.79 Hz), 1.31-1.36 (5.0H, m), 1.51 (2.0H, tt, J=6.42, 12.38 Hz), 1.78 (1.0H, dq, J=12.84, 3.67 Hz), 2.08 (1.0H, dq, J=4.13, 12.26 Hz), 2.54 (3.0H, s), 2.70 (2.0H, q, J=7.73 Hz), 3.10 (1.0H, d, J=13.30 Hz), 3.19 (1.0H, td, J=12.95, 2.75 Hz), 3.35 (1.0H, dt, J=8.71, 6.88 Hz), 3.59 (1.0H, s), 3.70 (1.0H, dt, J=8.71, 6.88 Hz), 4.02 (1.0H, d, J=13.30 Hz), 4.19-4.27 (1.0H, br m), 4.27 (2.0H, q, J=7.34 Hz), 4.46 (1.0H, d, J=14.21 Hz), 7.55 (1.0H, d, J=8.71 Hz), 11.72 (1.0H, br s).

(120b) cis(±)-2-(3-Butoxy-4-{[(4-chloro-5-ethyl-1H-imidazol-2-yl)carbonyl]amino}piperidin-1-yl)-4-methyl-1,3-thiazole-5-carboxylic acid The same operation as in Example (91d) was performed using ethyl cis(±)-2-(3-butoxy-4-{[(4-chloro-5-ethyl-1H-imidazol-2-yl)carbonyl]amino}piperidin-1-yl)-4-methyl-1,3-thiazole-5-carboxylate obtained in Example (120a) (0.34 g, 0.68 mmol), 2 N lithium hydroxide (5 mL, 10 mmol), methanol (3 mL) and THF (5 mL), to obtain 0.28 g of the title compound as a colorless solid (88%).

$^1$H NMR spectrum (400 MHz, DMSO-d$_6$) δ ppm: 0.80 (3.0H, t, J=7.19 Hz), 1.14 (3.0H, t, J=7.56 Hz), 1.30 (2.0H, tt, J=7.19, 7.19 Hz), 1.39-1.43 (2.0H, m), 1.67-1.69 (1.0H, m), 1.80-1.89 (1.0H, m), 2.40 (3.0H, s), 2.55 (2.0H, q, J=7.56 Hz), 3.28-3.33 (3.0H, m), 3.60 (2.0H, dt, J=11.54, 4.94 Hz), 3.91-3.96 (1.0H, m), 4.14-4.20 (2.0H, m), 7.62 (1.0H, d, J=8.54 Hz), 13.36 (1.0H, brs).

mass spectrum (FAB): m/z 470 (M+H)$^+$.

Example 121 cis(±)-2-(4-{[(4-Chloro-5-ethyl-1H-imidazol-2-yl)carbonyl]amino}-3-(2,2-difluoroethoxy)piperidin-1-yl)-1,3-thiazole-5-carboxylic acid (Exemplified Compound No. 121)

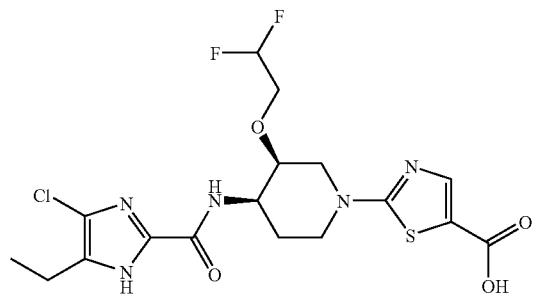

(121a) tert-Butyl 3-(2,2-difluoroethoxy)-4,4-dimethoxypiperidine-1-carboxylate

The same operation as in Example (90a) was performed using tert-butyl 3-hydroxy-4,4-dimethoxypiperidine-1-carboxylate (4.6 g, 17.6 mmol), sodium hydride (55% content, 1g, 22.9 mmol), 2,2-difluoroethyl p-toluenesulfonate (5 g, 21.6 mmol) and DMF (50 mL). The residue was purified by column chromatography (elution solvent: hexane/ethyl acetate=10/1, 4/1, 2/1) to obtain 4.85 g of the title compound as a colorless oily substance (85%).

$^1$H NMR spectrum (400 MHz, CDCl$_3$) δ ppm: 1.45 (9.0H, s), 1.71-1.83 (2.0H, m), 2.69-2.86 (1.0H, m), 2.98-3.09 (1.0H, m), 3.21 (3.0H, s), 3.23 (3.0H, s), 3.39-4.37 (4.0H, m), 5.73-6.03 (1.0H, m).

(121b) 3-(2,2-Difluoroethoxy)-4,4-dimethoxy-1-(trifluoroacetyl)piperidine

A 4 N hydrochloric acid/ethyl acetate solution (20 mL, 80 mmol) was added to a solution of tert-butyl 3-(2,2-difluoroethoxy)-4,4-dimethoxypiperidine-1-carboxylate obtained in Example (121a) (5.1 g, 15.6 mmol) in dichloromethane (10 mL), and the mixture was stirred at room temperature for 40 minutes. The solvent was evaporated under reduced pressure, and the resulting residue was dissolved in dichloromethane (20 mL), followed by cooling to 0° C. N,N-Diisopropylamine (7.68 g, 60 mmol) and trifluoroacetic anhydride (4.20 g, 20 mmol) were added, and the mixture was stirred for 40 minutes. Washing with a 1 N aqueous hydrochloric acid solution and brine, drying with anhydrous magnesium sulfate, and concentration under reduced pressure gave a solid, which was purified by silica gel column chromatography (elution solvent: hexane/ethyl acetate=10/1, 5/1, 2/1, 1/1) to obtain 1.5 g of the title compound as a light brown oily substance (30%).

$^1$H NMR spectrum (400 MHz, CDCl$_3$) δ ppm: 1.20-1.38 (2.0H, m), 3.24 (3.0H, s), 3.26 (3.0H, s), 2.69-4.37 (7.0H, m), 5.70-6.04 (1.0H, m).

(121c) 3-(2,2-Difluoroethoxy)-1-(trifluoroacetyl)piperidin-4-one

Water (5 mL) and TFA (2 mL) were added to a solution of tert-butyl 3-(2,2-difluoroethoxy)-4,4-dimethoxypiperidine-1-carboxylate obtained in Example (121b) (1.5 g, 4.67 mmol) in THF (30 mL), and the mixture was stirred at 70° C. for one hour. Sodium bicarbonate was added to a pH of about 8, followed by extraction with ethyl acetate. The organic layer was washed with brine, dried over anhydrous magnesium sulfate, and concentrated under reduced pressure. The resulting residue was purified by silica gel column chromatography (elution solvent: hexane/ethyl acetate=10/1, 5/1, 2/1, 1/1) to obtain 1.1 g of the title compound as a light brown oily substance (86%).

$^1$H NMR spectrum (400 MHz, CDCl$_3$) δ ppm: 2.51-2.60 (1.0H, m) 2.67-2.75 (1.0H, m), 3.46-3.81 (3.0H, m), 3.90-4.51 (4.0H, m), 5.77-6.07 (1.0H, m).

(121d) cis(±)-N-benzyl-3-(2,2-difluoroethoxy)-1-(trifluoroacetyl)piperidin-4-amine The same operation as in Example (90c) was performed using 3-(2,2-difluoroethoxy)-1-(trifluoroacetyl)piperidin-4-one obtained in Example (121c) (1.1 g, 4 mmol), benzylamine (0.54 g, 5 mmol), sodium (triacetoxy)borohydride (0.85 g, 6 mmol) and 1,2-dichloroethane (15 mL). The resulting residue was purified by silica gel column chromatography (elution solvent: hexane/ethyl acetate=4/1, 1/1, 1/3, 0/1) to obtain 1.16 g of the title compound as a yellow oily substance (79%).

$^1$H NMR spectrum (400 MHz, CDCl$_3$) δ ppm: 1.75-1.80 (2.0H, m), 2.85-4.45 (8.0H, m), 5.68-5.98 (1.0H, m), 7.24-7.35 (4.0H, m).

(121e) cis(±)-3-(2,2-Difluoroethoxy)-1-(trifluoroacetyl)piperidin-4-amine

The same operation as in Example (95b) was performed using cis(±)-N-benzyl-3-(2,2-difluoroethoxy)-1-(trifluoroacetyl)piperidin-4-amine obtained in Example (121d) (1.1 g, 3 mmol), 10% Pd/C (wet, 0.35 g) and methanol (10 mL), to obtain 0.79 g of the title compound as a colorless oily substance (95%).

¹H NMR spectrum (400 MHz, CDCl₃) δ ppm: 1.70-1.81 (2.0H, m), 3.04-3.78 (6.0H, m), 3.81-3.97 (2.0H, m), 4.11-4.54 (1.0H, m), 5.70-6.01 (1.0H, m).

(121f) cis(±)-4-Chloro-N-{3-(2,2-difluoroethoxy)-1-(trifluoroacetyl)piperidin-4-yl}-5-ethyl-1H-imidazole-2-carboxamide The same operation as in Example (106d) was performed using cis(±)-3-(2,2-difluoroethoxy)-1-(trifluoroacetyl)piperidin-4-amine obtained in Example (121e) (0.79 g, 2.86 mmol), 4-chloro-5-ethyl-1H-imidazole 2-carboxylic acid (85% content, 0.62 g, 3 mmol), WSC hydrochloride (1.15 g, 6 mmol), HOBt (0.61 g, 4.5 mmol), DMA (15 mL) and dichloromethane (15 mL). The resulting residue was purified by silica gel column chromatography (elution solvent: ethyl acetate/hexane=1/4, 2/3, 3/2, 4/1) to obtain 0.82 g of the title compound as a colorless amorphous solid (63%).

¹H NMR spectrum (400 MHz, CDCl₃) δ ppm: 1.26 (3.0H, t, J=7.79 Hz), 1.80-1.87 (1.0H, m), 1.98 (1.0H, dq, J=4.13, 12.34 Hz), 2.69 (2.0H, dq, J=2.29, 7.34 Hz), 2.88 (1.0H, d, J=14.67 Hz), 3.21-3.31 (1.0H, m), 3.79-3.94 (2.0H, m), 4.06-4.19 (1.0H, m), 4.22-4.33 (1.0H, m), 4.58-4.63 (1/3H, m), 4.85 (2/3H, dt, J=14.52, 2.98 Hz), 5.71-6.03 (1.0H, m), 7.37 (1/3H, d, J=9.17 Hz), 7.42 (2/3H, d, J=9.17 Hz), 10.88 (1.0H, br s).

(121g) Ethyl cis(±)-2-(4-{[(4-chloro-5-ethyl-1H-imidazol-2-yl)carbonyl]amino}-3-(2,2-difluoroethoxy)piperidin-1-yl)-1,3-thiazole-5-carboxylate cis(±)-4-Chloro-N-{3-(2,2-difluoroethoxy)-1-(trifluoroacetyl)piperidin-4-yl}-5-ethyl-1H-imidazole-2-carboxamide obtained in Example (121f) (144 mg, 0.33 mmol) was dissolved in methanol (4 mL). A 2 N aqueous lithium hydroxide solution (0.4 mL) was added, and the mixture was stirred at 40° C. for 40 minutes. The pH was adjusted to 4 by adding a 1 N aqueous hydrochloric acid solution, and the solvent was evaporated under reduced pressure. The residue was dissolved in DMA (5 mL). Diisopropylethylamine (130 mg, 1 mmol) and ethyl 2-bromo-1,3-thiazole-5-carboxylate (155 mg, 0.66 mmol) were added, and the mixture was stirred at 75° C. for one hour. Dilution with ethyl acetate, washing with water and brine, drying over anhydrous magnesium sulfate, and concentration under reduced pressure gave a residue, which was purified by silica gel column chromatography (elution solvent: ethyl acetate/hexane=1/4, 2/3, 3/2, 4/1) to obtain 0.12 g of the title compound as a colorless amorphous solid (74%).

¹H NMR spectrum (400 MHz, CDCl₃) δ ppm: 1.27 (3.0H, t, J=7.64 Hz), 1.35 (3.0H, t, J=7.18 Hz), 1.81 (1.0H, dq, J=12.84, 3.36 Hz), 2.07 (1.0H, dq, J=4.58, 12.38 Hz), 2.69 (2.0H, q, J=7.64 Hz), 3.19 (1.0H, dd, J=13.30, 1.38 Hz), 3.29 (1.0H, td, J=13.07, 2.75 Hz), 3.66 (1.0H, ddd, J=24.07, 12.38, 4.81 Hz), 3.79-3.96 (3.0H, m), 4.26-4.32 (1.0H, m), 4.30 (2.0H, q, J=7.18 Hz), 4.59 (1.0H, dt, J=14.62, 2.75 Hz), 5.81 (1.0H, tt, J=55.02, 4.13 Hz), 7.37 (1.0H, d, J=9.17 Hz), 7.84 (1.0H, s), 10.54 (1.0H, br s).

(121h) cis(±)-2-(4-{[(4-Chloro-5-ethyl-1H-imidazol-2-yl)carbonyl]amino}-3-(2,2-difluoroethoxy)piperidin-1-yl)-1,3-thiazole-5-carboxylic acid The same operation as in Example (91d) was performed using ethyl cis(±)-2-(4-{[(4-chloro-5-ethyl-1H-imidazol-2-yl)carbonyl]amino}-3-(2,2-difluoroethoxy)piperidin-1-yl)-1,3-thiazole-5-carboxylate obtained in Example (121g) (0.12 g, 0.24 mmol), 2 N lithium hydroxide (3 mL, 6 mmol), methanol (4 mL) and THF (4 mL), to obtain 90 mg of the title compound as a colorless solid (80%).

¹H NMR spectrum (400 MHz, DMSO-d₆) δ ppm: 1.14 (3.0H, t, J=7.57 Hz), 1.68-1.71 (1.0H, m), 1.92 (1.0H, dq, J=4.05, 12.04 Hz), 2.55 (2.0H, q, J=7.57 Hz), 3.28-3.39 (2.0H, m), 3.74-3.84 (3.0H, m), 3.92 (1.0H, d, J=12.84 Hz), 4.24-4.27 (2.0H, m), 6.04 (1.0H, tt, J=55.02, 3.44 Hz), 7.67 (1.0H, s), 7.82 (1.0H, d, J=8.25 Hz).

mass spectrum (FAB): m/z 464 (M+H)⁺.

Example 122 cis(±)-2-(4-{[(4-Chloro-5-ethyl-1H-imidazol-2-yl)carbonyl]amino}-3-(2,2-difluoroethoxy)piperidin-1-yl)-4-methyl-1,3-thiazole-5-carboxylic acid (Exemplified Compound No. 122)

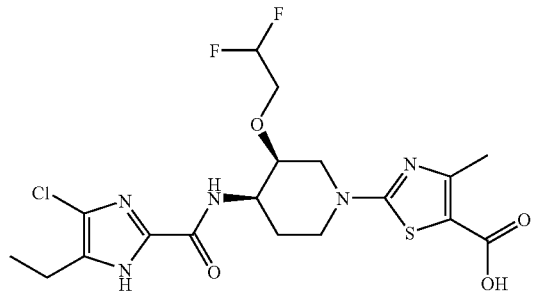

(122a) Ethyl cis(±)-2-(4-{[(4-chloro-5-ethyl-1H-imidazol-2-yl)carbonyl]amino}-3-(2,2-difluoroethoxy)piperidin-1-yl)-4-methyl-1,3-oxazole-5-carboxylate The same operation as in Example (121g) was performed using cis(±)-4-chloro-N-{3-(2,2-difluoroethoxy)-1-(trifluoroacetyl)piperidin-4-yl}-5-ethyl-1H-imidazole-2-carboxamide obtained in Example (121f) (0.24 g, 0.55 mmol), a 2 N aqueous lithium hydroxide solution (0.6 mL), ethyl 2-bromo-4-methyl-1,3-thiazole-5-carboxylate (250 mg, 1 mmol) and N,N-diisopropylethylamine (0.19 g, 1.5 mmol), to obtain 0.24 g of the title compound as a light brown amorphous solid (86%).

¹H NMR spectrum (400 MHz, DMSO-d₆) δ ppm: 1.14 (3.0H, t, J=7.34 Hz), 1.24 (3.0H, t, J=7.11 Hz), 1.69 (1.0H, dd, J=12.84, 3.67 Hz), 1.90 (1.0H, dq, J=4.59, 11.92 Hz), 2.43 (3.0H, s), 2.55 (2.0H, q, J=7.34 Hz), 3.24-3.39 (2.0H, m), 3.75-3.84 (3.0H, m), 3.89-3.97 (1.0H, br m), 4.17 (2.0H, qd, J=7.11, 1.83 Hz), 4.21-4.27 (2.0H, m), 6.04 (1.0H, tt, J=54.56, 3.67 Hz), 7.81 (1.0H, d, J=8.25 Hz).

(122b) cis(±)-2-(4-{[(4-Chloro-5-ethyl-1H-imidazol-2-yl)carbonyl]amino}-3-(2,2-difluoroethoxy)piperidin-1-yl)-4-methyl-1,3-thiazole-5-carboxylic acid The same operation as in Example (91d) was performed using ethyl cis(±)-2-(4-{[(4-chloro-5-ethyl-1H-imidazol-2-yl)carbonyl]amino}-3-(2,2-difluoroethoxy)piperidin-1-yl)-4-methyl-1,3-thiazole-5-carboxylate obtained in Example (122a) (0.24 g, 0.48 mmol), 2 N lithium hydroxide (3 mL, 6 mmol), methanol (3 mL) and THF (8 mL) to obtain 0.16 g of the title compound as a colorless solid (71%).

¹H NMR spectrum (400 MHz, DMSO-d₆) δ ppm: 1.14 (3.0H, t, J=7.57 Hz), 1.68 (1.0H, dd, J=12.84, 3.67 Hz), 1.90 (1.0H, ddd, J=24.41, 12.04, 4.01 Hz), 2.41 (3.0H, s), 2.55 (2.0H, q, J=7.64 Hz), 3.24-3.37 (2.0H, m), 3.75-3.83 (3.0H, m), 3.92 (1.0H, d, J=10.55 Hz), 4.18-4.27 (2.0H, m), 6.05 (1.0H, tt, J=55.02, 3.67 Hz), 7.81 (1.0H, d, J=8.25 Hz).

mass spectrum (ESI): m/z 478 (M+H)⁺.

Example 123 cis(±)-2-(4-{[(4-Chloro-5-ethyl-1H-imidazol-2-yl)carbonyl]amino}-3-(2-fluoroethoxy)piperidin-1-yl)-1,3-thiazole-5-carboxylic acid (Exemplified Compound No. 123)

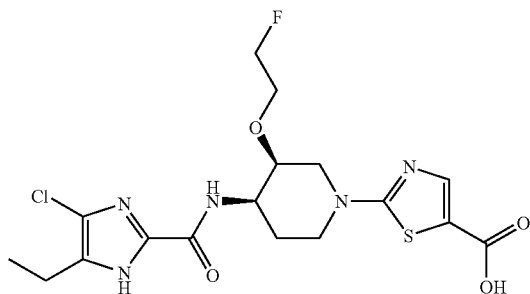

(123a) tert-Butyl 3-(2-fluoroethoxy)-4,4-dimethoxypiperidine-1-carboxylate

The same operation as in Example (90a) was performed using tert-butyl 3-hydroxy-4,4-dimethoxypiperidine-1-carboxylate (6.2 g, 23.7 mmol), sodium hydride (55% content, 1.57 g, 36 mmol), 2-fluoroethyl p-toluenesulfonate (7.85 g, 46 mmol) and DMF (50 mL). The residue was purified by column chromatography (elution solvent: hexane/ethyl acetate=10/1, 4/1, 2/1) to obtain 7.12 g of the title compound as a colorless oily substance (98%).

$^1$H NMR spectrum (400 MHz, CDCl$_3$) δ ppm: 1.45 (9.0H, s), 1.71-1.82 (2.0H, m), 2.73-2.86 (1.0H, m), 3.01 (1.0H, dd, J=34.39, 13.30 Hz), 3.22 (3.0H, s), 3.24 (3.0H, s), 3.42-3.50 (1.0H, m), 3.63-3.76 (1.0H, br m), 3.81-4.02 (2.0H, br m), 4.10-4.31 (1.0H, br m), 4.47-4.53 (1.0H, br m), 4.58-4.65 (1.0H, br m).

(123b) tert-Butyl 3-(2-fluoroethoxy)-4-oxopiperidine-1-carboxylate

The same operation as in Example (90b) was performed using tert-butyl 3-(2-fluoroethoxy)-4,4-dimethoxypiperidine-1-carboxylate obtained in Example (123a) (6.5 g, 21.2 mmol), a water/TFA mixed solution (1/1, 20 mL) and di-tert-butyl dicarbonate (6.54 g, 30 mol). The resulting residue was purified by silica gel column chromatography (elution solvent: hexane/ethyl acetate=10/1, 5/1, 2/1, 1/1) to obtain 5.4 g of the title compound as a light brown oily substance (98%).

$^1$H NMR spectrum (400 MHz, CDCl$_3$) δ ppm: 1.45-1.46 (1.0H, brm), 1.50 (9.0H, s), 2.42-2.50 (1.0H, m), 2.56 (1.0H, dt, J=13.91, 3.90 Hz), 3.18-3.32 (2.0H, m), 3.71-3.83 (1.0H, m), 3.89-4.04 (2.0H, m), 4.07-4.12 (1.0H, m), 4.22-4.33 (1.0H, br m), 4.48-4.57 (1.0H, m), 4.60-4.70 (1.0H, m).

(123c) tert-Butyl cis(±)-4-(benzylamino)-3-(2-fluoroethoxy)piperidine-1-carboxylate The same operation as in Example (90c) was performed using tert-butyl 3-(2-fluoroethoxy)-4-oxopiperidine-1-carboxylate obtained in Example (123b) (5.4 g, 20.6 mmol), benzylamine (2.68 g, 25 mmol), sodium (triacetoxy)borohydride (7.41 g, 35 mmol) and 1,2-dichloroethane (50 mL). The resulting residue was purified by silica gel column chromatography (elution solvent: hexane/ethyl acetate=4/1, 1/1, 1/3, 0/1) to obtain 5.6 g of the title compound as a colorless solid (77%).

$^1$H NMR spectrum (400 MHz, CDCl$_3$) δ ppm: 1.46 (9.0H, s), 1.62-1.73 (4.0H, m), 2.72-2.77 (1.0H, m), 2.86-2.95 (2.0H, br m), 3.56-3.69 (2.0H, m), 3.75-3.98 (4.0H, m), 4.06-4.17 (1.0H, br m), 4.48 (1.0H, br s), 4.60 (1.0H, br s), 7.23-7.26 (1.0H, m), 7.30-7.36 (4.0H, m).

(123d) tert-Butyl cis(±)-4-amino-3-(2-fluoroethoxy)piperidine-1-carboxylate

The same operation as in Example (95b) was performed using tert-butyl cis(±)-4-(benzylamino)-3-(2-fluoroethoxy)piperidine-1-carboxylate obtained in Example (123c) (1.5 g, 4 mmol), 10% Pd/C (wet, 0.5 g) and methanol (20 mL), in a hydrogen atmosphere, to obtain 1.06 g of the title compound as a colorless oily substance (95%).

mass spectrum (APCI): m/z 293 (M+H)$^+$ (123e) tert-Butyl cis(±)-4-{[(4-chloro-5-ethyl-1H-imidazol-2-yl)carbonyl]amino}-3-(2-fluoroethoxy)piperidine-1-carboxylate The same operation as in Example (106d) was performed using tert-butyl cis(±)-4-amino-3-butoxypiperidine-1-carboxylate obtained in Example (123d) (1.06 g, 3.6 mmol), 4-chloro-5-ethyl-1H-imidazole-2-carboxylic acid (85% content, 0.82 g, 4 mmol), WSC hydrochloride (1.53 g, 8 mmol), HOBt (0.81 g, 6 mmol), DMA (15 mL) and dichloromethane (15 mL). The resulting residue was purified by silica gel column chromatography (elution solvent: ethyl acetate/hexane=1/4, 2/3, 3/2, 4/1) to obtain 1.43 g of the title compound as a colorless solid (86%).

$^1$H NMR spectrum (400 MHz, CDCl$_3$) δ ppm: 1.26 (3.0H, t, J=7.79 Hz), 1.47 (9.0H, s), 1.63-1.95 (4.0H, m), 2.68 (2.0H, q, J=7.79 Hz), 2.69-2.90 (2.0H, m), 3.60 (1.0H, s), 3.61-3.71 (1.0H, m), 3.84-4.49 (4.0H, m), 4.52 (1.0H, br s), 4.64 (1.0H, br s), 7.47-7.55 (1.0H, br m), 11.38 (1.0H, s).

(123f) Ethyl cis(±)-2-(4-{[(4-chloro-5-ethyl-1H-imidazol-2-yl)carbonyl]amino}-3-(2-fluoroethoxy)piperidin-1-yl)-1,3-thiazole-5-carboxylate The same operation as in Example (90f) was performed using tert-butyl cis(±)-4-{[(4-chloro-5-ethyl-1H-imidazol-2-yl)carbonyl]amino}-3-(2-fluoroethoxy)piperidine-1-carboxylate obtained in Example (123e) (0.3 g, 0.74 mmol), a 4 N hydrochloric acid/ethyl acetate solution (10 ml, 40 mmol), diisopropylethylamine (0.42 g, 3.24 mmol), ethyl 2-bromo-1,3-thiazole-5-carboxylate (255 mg, 1.1 mmol) and DMA (8 mL), to obtain 0.25 g of the title compound as a light brown solid (74%).

$^1$H NMR spectrum (400 MHz, CDCl$_3$) δ ppm: 1.26 (3.0H, t, J=7.57 Hz), 1.34 (3.0H, t, J=7.11 Hz), 1.81-1.82 (1.0H, m), 2.11 (1.0H, dq, J=4.58, 12.38 Hz), 2.69 (2.0H, q, J=7.57 Hz), 3.19 (1.0H, dd, J=14.67, 1.38 Hz), 3.26 (1.0H, td, J=12.95, 2.60 Hz), 3.68-3.79 (2.0H, m), 3.83-3.95 (1.0H, m), 4.00 (1.0H, d, J=13.75 Hz), 4.25-4.33 (1.0H, m), 4.30 (2.0H, q, J=7.11 Hz), 4.46-4.48 (1.0H, m), 4.52-4.62 (2.0H, m), 7.51 (1.0H, d, J=8.71 Hz), 7.83 (1.0H, s), 11.16 (1.0H, s).

(123g) cis(±)-2-(4-{[(4-Chloro-5-ethyl-1H-imidazol-2-yl)carbonyl]amino}-3-(2-fluoroethoxy)piperidin-1-yl)-1,3-thiazole-5-carboxylic acid The same operation as in Example (91d) was performed using ethyl cis(±)-2-(4-{[(4-chloro-5-ethyl-1H-imidazol-2-yl)carbonyl]amino}-3-(2-fluoroethoxy)piperidin-1-yl)-1,3-thiazole-5-carboxylate obtained in Example (123f) (0.25 g, 0.8 mmol), 2 N lithium hydroxide (3 mL, 6 mmol), methanol (8 mL) and THF (8 mL), to obtain 0.17 g of the title compound as a light brown solid (72%).

$^1$H NMR spectrum (400 MHz, DMSO-d$_6$) δ ppm: 1.14 (3.0H, t, J=7.49 Hz), 1.70 (1.0H, d, J=9.63 Hz), 1.92 (1.0H, ddd, J=24.19, 12.04, 4.47 Hz), 2.55 (2.0H, q, J=7.49 Hz), 3.33 (2.0H, dd, J=27.51, 12.84 Hz), 3.65-3.85 (3.0H, m), 3.94 (1.0H, d, J=12.84 Hz), 4.24 (2.0H, d, J=11.92 Hz), 4.35-4.59 (2.0H, m), 7.68 (1.0H, s), 7.72 (1.0H, d, J=8.25 Hz).

mass spectrum (ESI): m/z 446 (M+H)$^+$.

Example 124 cis(±)-2-(4-{[(4-Chloro-5-ethyl-1H-imidazol-2-yl)carbonyl]amino}-3-(2-fluoroethoxy)piperidin-1-yl)-4-methyl-1,3-thiazole-5-carboxylic acid (Exemplified Compound No. 124)

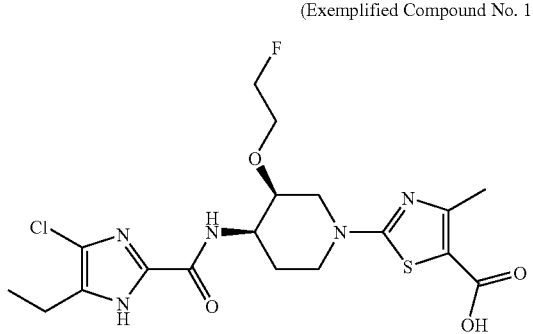

(124a) Ethyl cis(±)-2-(4-{[(4-chloro-5-ethyl-1H-imidazol-2-yl)carbonyl]amino}-3-(2-fluoroethoxy)piperidin-1-yl)-4-methyl-1,3-thiazole-5-carboxylate The same operation as in Example (90f) was performed using tert-butyl cis(±)-4-{[(4-chloro-5-ethyl-1H-imidazol-2-yl)carbonyl]amino}-3-(2-fluoroethoxy)piperidine-1-carboxylate obtained in Example (123e) (0.32 g, 0.77 mmol), a 4 N hydrochloric acid/ethyl acetate solution (10 ml, 40 mmol), diisopropylethylamine (0.42 g, 3.25 mmol), ethyl 2-bromo-4-methyl-1,3-thiazole-5-carboxylate (270 mg, 1.08 mmol) and DMA (10 mL), to obtain 0.25 g of the title compound as a light brown amorphous solid (67%).

$^1$H NMR spectrum (400 MHz, CDCl$_3$) δ ppm: 1.26 (3.0H, t, J=7.57 Hz), 1.33 (3.0H, t, J=7.11 Hz), 1.79-1.80 (1.0H, m), 2.09 (1.0H, dq, J=4.13, 12.61 Hz), 2.53 (3.0H, s), 2.69 (2.0H, q, J=7.57 Hz), 3.15 (1.0H, dd, J=14.21, 1.38 Hz), 3.22 (1.0H, td, J=12.95, 2.60 Hz), 3.68-3.79 (2.0H, m), 3.84-3.97 (1.0H, m), 3.99 (1.0H, d, J=13.95 Hz), 4.23-4.31 (1.0H, m), 4.26 (2.0H, dq, J=1.49, 7.11 Hz), 4.48 (2.0H, dt, J=9.32, 3.90 Hz), 4.57-4.60 (1.0H, m), 7.50 (1.0H, d, J=8.71 Hz), 11.04 (1.0H, s).

(124b) cis(±)-2-(4-{[(4-Chloro-5-ethyl-1H-imidazol-2-yl)carbonyl]amino}-3-(2-fluoroethoxy)piperidin-1-yl)-4-methyl-1,3-thiazole-5-carboxylic acid The same operation as in Example (91d) was performed using ethyl cis(±)-2-(4-{[(4-chloro-5-ethyl-1H-imidazol-2-yl)carbonyl]amino}-3-(2-fluoroethoxy)piperidin-1-yl)-4-methyl-1,3-thiazole-5-carboxylate obtained in Example (124a) (0.24 g, 0.49 mmol), 2 N lithium hydroxide (4 mL, 8 mmol), methanol (6 mL) and THF (6 mL), to obtain 0.21 g of the title compound as a light brown solid (93%).

$^1$H NMR spectrum (400 MHz, DMSO-d$_6$) δ ppm: 1.14 (3.0H, t, J=7.57 Hz), 1.67-1.70 (1.0H, m), 1.88-1.91 (1.0H, m), 2.40 (3.0H, s), 2.55 (2.0H, q, J=7.57 Hz), 3.20-3.39 (2.0H, m), 3.65-3.86 (3.0H, m), 3.91-3.96 (1.0H, m), 4.17-4.23 (2.0H, m), 4.36-4.58 (2.0H, m), 7.71 (1.0H, d, J=8.25 Hz).

mass spectrum (ESI): m/z 460 (M+H)$^+$.

Example 125 cis(±)-2-(4-{[(4-Chloro-5-ethyl-1H-imidazol-2-yl)carbonyl]amino}-3-ethoxypiperidin-1-yl)-1,3-thiazole-5-carboxylic acid (Exemplified Compound No. 125)

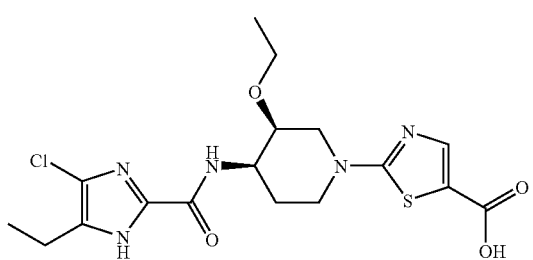

(125a) tert-Butyl cis(±)-4-{[(4-chloro-5-ethyl-1H-imidazol-2-yl)carbonyl]amino}-3-ethoxypiperidine-1-carboxylate The same operation as in Example (106d) was performed using tert-butyl cis(±)-4-amino-3-ethoxypiperidine-1-carboxylate obtained in Example (112d) (0.74 g, 2.9 mmol), 4-chloro-5-ethyl-1H-imidazole-2-carboxylic acid (85% content, 0.61 g, 2.98 mmol), WSC hydrochloride (1.15 g, 6 mmol), HOBt (0.61 g, 4.5 mmol), DMA (15 mL) and dichloromethane (15 mL). The resulting residue was purified by silica gel column chromatography (elution solvent: ethyl acetate/hexane=1/4, 2/3, 3/2, 4/1) to obtain 0.96 g of the title compound as a colorless solid (82%).

$^1$H NMR spectrum (400 MHz, CDCl$_3$) δ ppm: 0.92-0.99 (3.0H, br m), 1.26 (3.0H, t, J=7.79 Hz), 1.47 (9.0H, s), 1.57-1.67 (1.0H, br m), 1.85-1.94 (1.0H, br m), 2.69 (2.0H, q, J=7.79 Hz), 2.71-2.86 (2.0H, m), 3.27 (1.0H, dt, J=8.71, 6.42 Hz), 3.41-3.49 (1.0H, br m), 3.60-3.70 (1.0H, br m), 4.05-4.52 (3.0H, m), 7.55 (1.0H, s), 11.92 (1.0H, s).

(125b) Ethyl cis(±)-2-(4-{[(4-chloro-5-ethyl-1H-imidazol-2-yl)carbonyl]amino}-3-ethoxypiperidin-1-yl)-1,3-thiazole-5-carboxylate The same operation as in Example (90f) was performed using tert-butyl cis(±)-4-{[(4-chloro-5-ethyl-1H-imidazol-2-yl)carbonyl]amino}-3-ethoxypiperidine-1-carboxylate obtained in Example (125a) (0.20 g, 0.5 mmol), a 4 N hydrochloric acid/ethyl acetate solution (10 ml, 40 mmol), diisopropylethylamine (1.03 g, 8 mmol), ethyl 2-bromo-1,3-thiazole-5-carboxylate (0.24 g, 1 mmol) and DMA (8 mL), to obtain 0.27 g of the title compound as a light brown solid (100%).

$^1$H NMR spectrum (400 MHz, CDCl$_3$) δ ppm: 1.16 (3.0H, t, J=7.34 Hz), 1.27 (3.0H, t, J=7.64 Hz), 1.35 (3.0H, t, J=7.60 Hz), 1.77-1.83 (1.0H, m), 2.10 (1.0H, dq, J=4.17, 12.38 Hz), 2.70 (2.0H, q, J=7.64 Hz), 3.15 (1.0H, dd, J=14.21, 1.38 Hz), 3.23 (1.0H, td, J=12.84, 2.75 Hz), 3.44 (1.0H, dq, J=9.17, 7.34 Hz), 3.63 (1.0H, br s), 3.74 (1.0H, dq, J=9.17, 7.34 Hz), 4.03 (1.0H, d, J=13.75 Hz), 4.21-4.28 (1.0H, m), 4.30 (2.0H, q, J=7.60 Hz), 4.47 (1.0H, d, J=14.21 Hz), 7.52 (1.0H, d, J=9.17 Hz), 7.84 (1.0H, s), 11.54 (1.0H, s).

(125c) cis(±)-2-(4-{[(4-Chloro-5-ethyl-1H-imidazol-2-yl)carbonyl]amino}-3-ethoxypiperidin-1-yl)-1,3-thiazole-5-carboxylic acid The same operation as in Example (91d) was performed using ethyl cis(±)-2-(4-{[(4-chloro-5-ethyl-1H-imidazol-2-yl)carbonyl]amino}-3-ethoxypiperidin-1-yl)-1,3-thiazole-5-carboxylate obtained in Example (125b) (0.27 g, 0.59 mmol), 2 N lithium hydroxide (5 mL, 10 mmol), methanol (5 mL) and THF (5 mL), to obtain 0.21 g of the title compound as a colorless solid (83%).

$^1$H NMR spectrum (400 MHz, DMSO-$d_6$) δ ppm: 1.04 (3.0H, t, J=6.88 Hz), 1.14 (3.0H, t, J=7.57 Hz), 1.68 (1.0H, dd, J=12.26, 4.24 Hz), 1.88 (1.0H, dq, J=4.24, 12.26 Hz), 2.55 (2.0H, q, J=7.57 Hz), 3.29-3.35 (2.0H, m), 3.43 (1.0H, dq, J=10.76, 6.88 Hz), 3.62 (1.0H, dq, J=10.76, 6.88 Hz), 3.67 (1.0H, br s), 3.96 (1.0H, d, J=12.84 Hz), 4.16-4.24 (2.0H, m), 7.65 (1.0H, d, J=8.71 Hz), 7.72 (1.0H, s).

mass spectrum (ESI): m/z 428 (M+H)$^+$.

Example 126 cis(±)-2-(4-{[(4-Chloro-5-ethyl-1H-imidazol-2-yl)carbonyl]amino}-3-propoxypiperidin-1-yl)-1,3-thiazole-5-carboxylic acid

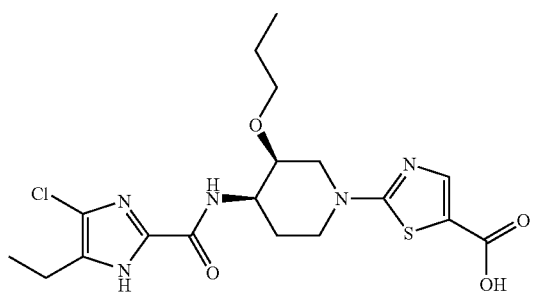

(Exemplified Compound No. 126)

(126a) tert-Butyl cis(±)-4-{[(4-chloro-5-ethyl-1H-imidazol-2-yl)carbonyl]amino}-3-propoxypiperidine-1-carboxylate The same operation as in Example (106d) was performed using tert-butyl cis(±)-4-amino-3-propoxypiperidine-1-carboxylate obtained in Example (113d) (0.73 g, 2.8 mmol), 4-chloro-5-ethyl-1H-imidazole-2-carboxylic acid (85% content, 0.61 g, 2.98 mmol), WSC hydrochloride (1.15 g, 6 mmol), HOBt (0.61 g, 4.5 mmol), DMA (15 mL) and dichloromethane (15 mL). The resulting residue was purified by silica gel column chromatography (elution solvent: ethyl acetate/hexane=1/4, 2/3, 3/2, 4/1) to obtain 0.89 g of the title compound as a colorless solid (77%).

$^1$H NMR spectrum (400 MHz, CDCl$_3$) δ ppm: 1.18-1.27 (1.0H, br m), 1.26 (3.0H, t, J=7.88 Hz), 1.47 (9.0H, s), 1.61-1.66 (1.0H, br m), 1.86-1.93 (1.0H, br m), 2.66-2.85 (2.0H, m), 2.69 (2.0H, q, J=7.79 Hz), 3.36 (2.0H, t, J=6.88 Hz), 3.40 (2.0H, t, J=6.88 Hz), 3.44-3.48 (1.0H, br m), 3.75 (1.0H, br s), 4.02-4.50 (3.0H, m), 7.53 (1.0H, s), 11.86 (1.0H, s).

(126b) Ethyl cis(±)-2-(4-{[(4-chloro-5-ethyl-1H-imidazol-2-yl)carbonyl]amino}-3-propoxypiperidin-1-yl)-1,3-thiazole-5-carboxylate The same operation as in Example (90f) was performed using tert-butyl cis(±)-4-{[(4-chloro-5-ethyl-1H-imidazol-2-yl)carbonyl]amino}-3-propoxypiperidine-1-carboxylate obtained in Example (126a) (0.21 g, 0.5 mmol), a 4 N hydrochloric acid/ethyl acetate solution (10 ml, 40 mmol), diisopropylethylamine (1.03 g, 8 mmol), ethyl 2-bromo-1,3-thiazole-5-carboxylate (0.24 g, 1 mmol) and DMA (8 mL), to obtain 0.27 g of the title compound as a light brown solid (100%).

$^1$H NMR spectrum (400 MHz, CDCl$_3$) δ ppm: 0.86 (3.0H, t, J=7.34 Hz), 1.27 (3.0H, t, J=7.64 Hz), 1.34 (3.0H, t, J=7.03 Hz), 1.56 (2.0H, td, J=14.21, 7.18 Hz), 1.79-1.82 (1.0H, br m), 2.10 (1.0H, dq, J=4.97, 12.95 Hz), 2.69 (2.0H, q, J=7.64 Hz), 3.15 (1.0H, d, J=14.21 Hz), 3.24 (1.0H, td, J=12.95, 2.90 Hz), 3.33 (1.0H, dt, J=8.71, 7.34 Hz), 3.61-3.66 (2.0H, m), 4.02 (1.0H, d, J=14.21 Hz), 4.22-4.28 (1.0H, m), 4.30 (2.0H, q, J=7.03 Hz), 4.49 (1.0H, d, J=14.21 Hz), 7.51 (1.0H, d, J=9.17 Hz), 7.84 (1.0H, s), 11.30 (1.0H, s).

(126c) cis(±)-2-(4-{[(4-Chloro-5-ethyl-1H-imidazol-2-yl)carbonyl]amino}-3-propoxypiperidin-1-yl)-1,3-thiazole-5-carboxylic acid The same operation as in Example (91d) was performed using ethyl cis(±)-2-(4-{[(4-chloro-5-ethyl-1H-imidazol-2-yl)carbonyl]amino}-3-propoxypiperidin-1-yl)-1,3-thiazole-5-carboxylate obtained in Example (126b) (0.27 g, 0.59 mmol), 2 N lithium hydroxide (5 mL, 10 mmol), methanol (5 mL) and THF (5 mL), to obtain 0.22 g of the title compound as a colorless solid (87%).

$^1$H NMR spectrum (400 MHz, DMSO-$d_6$) δ ppm: 0.81 (3.0H, t, J=7.34 Hz), 1.14 (3.0H, t, J=7.57 Hz), 1.44 (2.0H, td, J=13.64, 7.34 Hz), 1.66-1.72 (1.0H, m), 1.84-1.92 (1.0H, m), 2.55 (2.0H, q, J=7.57 Hz), 3.29-3.37 (3.0H, m), 3.54 (1.0H, dd, J=13.64, 8.42 Hz), 3.65 (1.0H, br s), 3.94 (1.0H, d, J=12.38 Hz), 4.18-4.26 (2.0H, m), 7.65 (1.0H, d, J=8.25 Hz), 7.68 (1.0H, s).

mass spectrum (FAB): m/z 442 (M+H)$^+$.

Example 127 cis(±)-2-(4-{[(4-Chloro-5-ethyl-1H-imidazol-2-yl)carbonyl]amino}-3-(3-fluoropropoxy)piperidin-1-yl)-1,3-thiazole-5-carboxylic acid

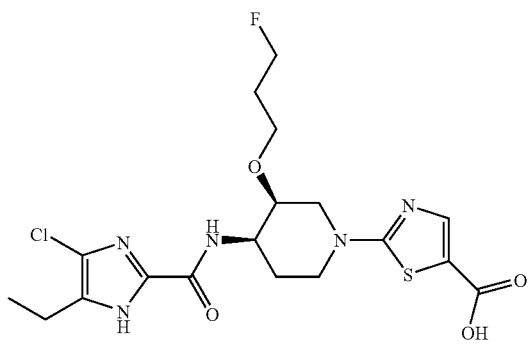

(Exemplified Compound No. 127)

(127a) tert-Butyl 3-(3-fluoropropoxy)-4,4-dimethoxypiperidine-1-carboxylate

The same operation as in Example (90a) was performed using tert-butyl 3-hydroxy-4,4-dimethoxypiperidine-1-carboxylate (6.4 g, 24.5 mmol), sodium hydride (55% content, 1.33 g, 30.6 mmol), 2-fluoropropyl p-toluenesulfonate (described in Costa, Brian de; Radesca, Lilian; Dominguez, Celia; Paolo, Lisa Di; Bowen, Wayne D.; J. Med. Chem.; 35; 12; 1992; 2221-2230, 7.1 g, 30.6 mmol) and DMF (50 mL). The residue was purified by column chromatography (elution solvent: hexane/ethyl acetate=10/1, 4/1, 2/1) to obtain 1.39 g of the title compound as a colorless oily substance (18%).

$^1$H NMR spectrum (400 MHz, CDCl$_3$) δ ppm: 1.46 (9.0H, s), 1.72-1.79 (2.0H, m), 1.92-1.99 (2.0H, m), 2.72-2.82 (1.0H, m), 2.92-3.03 (1.0H, m), 3.21 (3.0H, s), 3.21 (3.0H, s), 3.33-3.38 (1.0H, m), 3.45-3.49 (1.0H, m), 3.80-3.86 (1.0H, br m), 3.85-4.06 (1.0H, m), 4.14-4.29 (1.0H, m), 4.44-4.52 (1.0H, m), 4.58-4.66 (1.0H, m).

(127b) tert-Butyl 3-(3-fluoropropoxy)-4-oxopiperidine-1-carboxylate

The same operation as in Example (90b) was performed using tert-butyl 3-(3-fluoropropoxy)-4,4-dimethoxypiperidine-1-carboxylate obtained in Example (127a) (2.27 g, 21.2 mmol), a water/TFA mixed solution (3/1, 12 mL) and di-tert-butyl dicarbonate (2.18 g, 10 mol). The resulting residue was purified by silica gel column chromatography (elution solvent: hexane/ethyl acetate=10/1, 5/1, 2/1, 1/1) to obtain 1.71 of the title compound as a colorless oily substance (88%).

$^1$H NMR spectrum (400 MHz, CDCl$_3$) δ ppm: 1.50 (9.0H, s), 1.96 (1.0H, tt, J=5.96, 5.96 Hz), 2.02 (1.0H, tt, J=5.96, 5.96 Hz), 2.41-2.45 (1.0H, m), 2.54-2.58 (1.0H, m), 3.24-3.42 (1.0H, m), 3.62 (1.0H, dt, J=9.17, 5.96 Hz), 3.76-3.83 (1.0H, m), 3.78 (1.0H, dt, J=9.17, 5.96 Hz), 3.99-4.31 (2.0H, m), 4.51 (1.0H, t, J=5.96 Hz), 4.63 (1.0H, t, J=5.96 Hz).

(127c) tert-Butyl cis(±)-4-(benzylamino)-3-(3-fluoropropoxy)piperidine-1-carboxylate The same operation as in Example (90c) was performed using tert-butyl 3-(3-fluoropropoxy)-4-oxopiperidine-1-carboxylate obtained in Example (127b) (1.71 g, 6.21 mmol), benzylamine (0.75 g, 7 mmol), sodium (triacetoxy)borohydride (2.54 g, 12 mmol) and 1,2-dichloroethane (20 mL). The resulting residue was purified by silica gel column chromatography (elution solvent: hexane/ethyl acetate=4/1, 1/1, 1/3, 0/1) to obtain 1.97 g of the title compound as a colorless oily substance (87%).

$^1$H NMR spectrum (400 MHz, CDCl$_3$) δ ppm: 1.45 (9.0H, s), 1.61-1.66 (2.0H, m), 1.91-2.00 (2.0H, m), 2.72-2.75 (1.0H, br m), 2.87-2.94 (1.0H, br m), 2.90 (1.0H, dd, J=13.98, 2.06 Hz), 3.45-3.56 (1.0H, m), 3.45 (1.0H, dt, J=9.17, 5.04 Hz), 3.74-4.15 (4.0H, m), 3.76 (1.0H, dt, J=9.17, 5.04 Hz), 3.80 (2.0H, d, J=4.59 Hz), 4.47 (1.0H, t, J=5.96 Hz), 4.59 (1.0H, t, J=5.96 Hz), 7.25-7.26 (1.0H, m), 7.30-7.35 (4.0H, m).

(127d) tert-Butyl cis(±)-4-amino-3-(3-fluoropropoxy)piperidine-1-carboxylate

The same operation as in Example (95d) was performed using tert-butyl cis(±)-4-(benzylamino)-3-(3-fluoropropoxy)piperidine-1-carboxylate obtained in Example (127c) (1.06 g, 2.89 mmol), 10% Pd/C (wet, 0.4 g), ammonium formate (1.09 g, 17.4 mmol) and methanol (15 mL), to obtain 0.84 g of the title compound as a colorless oily substance (100%).

mass spectrum (APCI): m/z 277 (M+H)+

(127e) tert-Butyl cis(±)-4-{[(4-chloro-5-ethyl-1H-imidazol-2-yl)carbonyl]amino}-3-(3-fluoropropoxy)piperidine-1-carboxylate The same operation as in Example (106d) was performed using tert-butyl cis(±)-4-amino-3-butoxypiperidine-1-carboxylate obtained in Example (127d) (0.84 g, 3.0 mmol), 4-chloro-5-ethyl-1H-imidazole-2-carboxylic acid (85% content, 0.41 g, 2 mmol), WSC hydrochloride (0.77 g, 4 mmol), HOBt (0.41 g, 3 mmol), DMA (15 mL) and dichloromethane (15 mL). The resulting residue was purified by silica gel column chromatography (elution solvent: ethyl acetate/hexane=1/4, 2/3, 3/2, 4/1) to obtain 1.01 g of the title compound as a colorless solid (100%).

$^1$H NMR spectrum (400 MHz, CDCl$_3$) δ ppm: 1.26 (3.0H, t, J=7.64 Hz), 1.47 (9.0H, s), 1.78-2.10 (3.0H, m), 2.69 (2.0H, q, J=7.64 Hz), 2.76-2.83 (2.0H, m), 3.45-3.51 (1.0H, m), 3.45 (1.0H, dt, J=9.17, 6.42 Hz), 3.83-3.86 (1.0H, m), 4.09-4.53 (3.0H, m), 4.63 (1.0H, t, J=5.73 Hz), 7.46 (1.0H, br s), 11.49 (1.0H, br s).

(127f) Ethyl cis(±)-2-(4-{[(4-chloro-5-ethyl-1H-imidazol-2-yl)carbonyl]amino}-3-(3-fluoropropoxy)piperidin-1-yl)-1,3-thiazole-5-carboxylate The same operation as in Example (90f) was performed using tert-butyl cis(±)-4-{[(4-chloro-5-ethyl-1H-imidazol-2-yl)carbonyl]amino}-3-(3-fluoropropoxy)piperidine-1-carboxylate obtained in Example (127e) (0.2 g, 0.46 mmol), a 4 N hydrochloric acid/ethyl acetate solution (5 ml, 20 mmol), diisopropylethylamine (0.6 g, 4.6 mmol), ethyl 2-bromo-1,3-thiazole-5-carboxylate (0.19 g, 0.8 mmol) and DMA (8 mL), to obtain 0.16 g of the title compound as a light brown amorphous solid (72%).

$^1$H NMR spectrum (400 MHz, CDCl$_3$) δ ppm: 1.27 (3.0H, t, J=7.64 Hz), 1.35 (3.0H, t, J=7.26 Hz), 1.78-1.84 (1.0H, m), 1.91 (1.0H, tt, J=5.92, 5.92 Hz), 1.95 (1.0H, tt, J=5.92, 5.92 Hz), 2.07 (1.0H, dq, J=4.60, 12.46 Hz), 2.69 (2.0H, q, J=7.64 Hz), 3.17 (1.0H, dd, J=14.32, 1.72 Hz), 3.26 (1.0H, td, J=12.89, 2.48 Hz), 3.51 (1.0H, dt, J=8.59, 5.96 Hz), 3.64-3.66 (1.0H, br m), 3.83 (1.0H, dt, J=8.59, 5.96 Hz), 3.99 (1.0H, d, J=13.17 Hz), 4.24-4.30 (1.0H, m), 4.30 (2.0H, q, J=7.26 Hz), 4.37-4.57 (3.0H, m), 7.45 (1.0H, d, J=8.59 Hz), 7.84 (1.0H, s), 11.11 (1.0H, s).

(127g) cis(±)-2-(4-{[(4-Chloro-5-ethyl-1H-imidazol-2-yl)carbonyl]amino}-3-(3-fluoropropoxy)piperidin-1-yl)-1,3-thiazole-5-carboxylic acid The same operation as in Example (91d) was performed using ethyl cis(±)-2-(4-{[(4-chloro-5-ethyl-1H-imidazol-2-yl)carbonyl]amino}-3-(3-fluoropropoxy)piperidin-1-yl)-1,3-thiazole-5-carboxylate obtained in Example (127f) (0.16 g, 0.8 mmol), 2 N lithium hydroxide (6 mL, 12 mmol) and methanol (5 mL), to obtain 0.13 g of the title compound as a light brown solid (88%).

$^1$H NMR spectrum (400 MHz, DMSO-d$_6$) δ ppm: 1.14 (3.0H, t, J=7.45 Hz), 1.66-1.68 (1.0H, m), 1.75-1.85 (2.0H, m), 1.92 (1.0H, dq, J=4.01, 12.60 Hz), 2.55 (2.0H, q, J=7.45 Hz), 3.21-3.39 (2H, m), 3.46 (1.0H, dt, J=9.74, 6.30 Hz), 3.65-3.69 (2.0H, m), 3.95 (1.0H, br d), 4.18-4.27 (2.0H, m), 4.38-4.40 (1.0H, m), 4.47-4.49 (1.0H, m), 7.73 (1.0H, s), 7.77 (1.0H, d, J=8.59 Hz).

mass spectrum (ESI): m/z 460 (M+H)+.

Example 128 cis(±)-2-(4-{[(4-Chloro-5-ethyl-1H-imidazol-2-yl)carbonyl]amino}-3-(2,2-difluoropropoxy)piperidin-1-yl)-1,3-thiazole-5-carboxylic acid (Exemplified Compound No. 128)

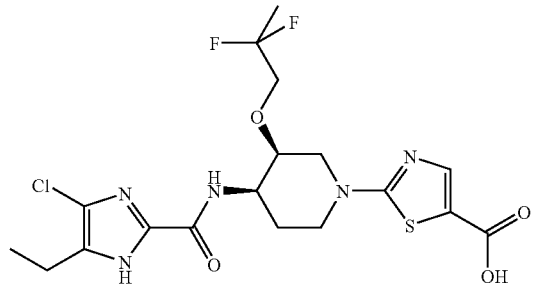

(128a) tert-Butyl cis(±)-4-{benzyl[(benzyloxy)carbonyl]amino}-3-[{2-methyl-2-propen-1-yl}oxy]piperidine-1-carboxylate The same operation as in Example (103a) was performed using tert-butyl cis(±)-4-(benzylamino)-3-[(2-methyl-2-propen-1-yl)oxy]piperidine-1-carboxylate obtained in Example (117c) (4.4 g, 12.2 mmol), sodium bicarbonate, benzyl chloroformate (2.81 g, 16 mmol), THF (15 mL) and water (15 mL). The residue was purified by silica gel column chromatography (elution solvent: ethyl acetate/hexane=1/4, 1/2, 1/1) to obtain 5.46 g of the title compound as a colorless oily substance (99%).

mass spectrum (APCI): m/z 495 (M+H)$^+$ (128b) tert-Butyl cis(±)-4-{benzyl[(benzyloxy)carbonyl]amino}-3-(2-oxypropoxy)piperidine-1-carboxylate Microcapsulated osmium tetroxide (about 10% content, 245 mg, 0.1 mmol) and sodium periodate (5.34 g, 25 mmol) were added to a mixed solution of tert-butyl cis(±)-4-{benzyl[(benzyloxy)carbonyl]amino}-3-[{2-methyl-2-propen-1-yl}oxy]piperidine-1-carboxylate obtained in Example (128a) (5.46 g, 11 mmol) in THF/water (30 mL/10 mL), and the mixture was stirred at room temperature for two days. The insoluble matter was filtered off, and the mother liquor was washed with sodium sulfite and brine, dried over magnesium sulfate, and concentrated under reduced pressure. Thereafter, the resulting residue was purified by silica gel column chromatography (elution solvent: ethyl acetate/hexane=1/4, 1/2, 1/1, 2/1) to obtain 4.09 g of the title compound as a colorless oily substance (75%).

$^1$H NMR spectrum (400 MHz, CDCl$_3$) δ ppm: 1.41 (9.0H, s), 2.02-2.09 (4.0H, m), 2.65-2.80 (2.0H, m), 3.69 (2.0H, t, J=16.51 Hz), 4.06-4.44 (4.0H, m), 4.59-4.71 (1.0H, m), 4.86-4.92 (1.0H, m), 5.12-5.25 (2.0H, m), 7.10-7.37 (10.0H, m).

mass spectrum (APCI): m/z 495 (M+H)+

(128c) tert-Butyl cis(±)-4-{benzyl[(benzyloxy)carbonyl]amino}-3-(2,2-difluoropropoxy)piperidine-1-carboxylate A solution of tert-butyl cis(±)-4-{benzyl[(benzyloxy)carbonyl]amino}-3-(2-oxopropoxy)piperidine-1-carboxylate obtained in Example (128b) (2.9 g, 5.85 mmol) in dichloromethane (30 mL) was cooled to 0° C. DAST (N,N-diethylammonium trifluorosulfide) (843 µL, 6.43 mmol) was added, and the mixture was stirred at room temperature overnight. The reaction solution was diluted with dichloromethane, washed with sodium bicarbonate and brine, dried over magnesium sulfate, and concentrated under reduced pressure. Thereafter, the resulting residue was purified by silica gel column chromatography (elution solvent: ethyl acetate/hexane=1/4, 1/2, 1/1, 2/1) to obtain 1.31 g of the title compound as a colorless oily substance (33%).

$^1$H NMR spectrum (400 MHz, CDCl$_3$) δ ppm: 1.33-1.35 (1.0H, br m), 1.43 (4.5H, s), 1.44 (4.5H, s), 1.58 (3.0H, t, J=18.57 Hz), 1.96-2.02 (1.0H, br m), 2.75 (2.0H, dt, J=50.13, 16.39 Hz), 3.39-3.43 (1.0H, m), 3.67-3.82 (2.0H, m), 4.05-4.58 (4.0H, m), 4.86 (1.0H, d, J=17.42 Hz), 5.03-5.18 (2.0H, m), 7.09-7.39 (10.0H, m).

(128d) tert-Butyl cis(±)-4-amino-3-(2,2-difluoropropoxy)piperidine-1-carboxylate The same operation as in Example (90d) was performed using tert-butyl cis(±)-4-{benzyl[(benzyloxy)carbonyl]amino}-3-(2,2-difluoropropoxy)piperidine-1-carboxylate obtained in Example (128c) (1.31 g, 2.5 mmol), 10% Pd/C (wet, 0.4 g), ammonium formate (0.95 g, 15 mmol) and methanol (20 mL), to obtain 0.69 g of the title compound as a colorless oily substance (64%).

mass spectrum (APCI): m/z 295 (M+H)$^+$ (128e) tert-Butyl cis(±)-4-{[(4-chloro-5-ethyl-1H-imidazol-2-yl)carbonyl]amino}-3-(2,2-difluoropropoxy)piperidine-1-carboxylate The same operation as in Example (106d) was performed using tert-butyl cis(±)-4-amino-3-(2,2-difluoropropoxy)piperidine-1-carboxylate obtained in Example (128d) (0.68 g, 2.3 mmol), 4-chloro-5-ethyl-1H-imidazole-2-carboxylic acid (85% content, 0.41 g, 2 mmol), WSC hydrochloride (0.77 g, 4 mmol), HOBt (0.41 g, 3 mmol), DMA (15 mL) and dichloromethane (15 mL). The resulting residue was purified by silica gel column chromatography (elution solvent: ethyl acetate/hexane=1/4, 2/3, 3/2, 4/1) to obtain 0.85 g of the title compound as a colorless solid (94%).

$^1$H NMR spectrum (400 MHz, CDCl$_3$) δ ppm: 1.26 (3.0H, t, J=7.64 Hz), 1.47 (9.0H, s), 1.63-1.69 (2.0H, m), 1.88 (1.0H, br s), 2.68 (2.0H, q, J=7.64 Hz), 2.73-2.89 (2.0H, m), 3.53-3.57 (1.0H, m), 3.66 (1.0H, br s), 3.77-3.90 (1.0H, m), 4.05-4.51 (3.0H, m).

(128f) Ethyl cis(±)-2-(4-{[(4-chloro-5-ethyl-1H-imidazol-2-yl)carbonyl]amino}-3-(2,2-difluoropropoxy)piperidin-1-yl)-1,3-thiazole-5-carboxylate The same operation as in Example (90f) was performed using tert-butyl cis(±)-4-{[(4-chloro-5-ethyl-1H-imidazol-2-yl)carbonyl]amino}-3-(2,2-difluoropropoxy)piperidine-1-carboxylate obtained in Example (128e), a 4 N hydrochloric acid/ethyl acetate solution (5 ml, 20 mmol), diisopropylethylamine (0.6 g, 4.6 mmol), ethyl 2-bromo-1,3-thiazole-5-carboxylate (0.19 g, 0.8 mmol) and DMA (8 mL), to obtain 0.20 g of the title compound as a light brown amorphous solid (85%).

$^1$H NMR spectrum (400 MHz, CDCl$_3$) δ ppm: 1.27 (3.0H, t, J=7.64 Hz), 1.35 (3.0H, t, J=6.87 Hz), 1.56 (3.0H, t, J=18.90 Hz), 1.81-1.84 (1.0H, m), 2.09 (1.0H, dq, J=4.58, 12.60 Hz), 2.69 (2.0H, q, J=7.64 Hz), 3.19 (1.0H, dd, J=14.32, 1.72 Hz), 3.29 (1.0H, td, J=13.03, 2.67 Hz), 3.62 (1.0H, q, J=10.69 Hz), 3.73-3.83 (2.0H, m), 3.95-3.98 (1.0H, m), 4.27-4.31 (1.0H, m), 4.30 (2.0H, q, J=6.87 Hz), 4.58 (1.0H, d, J=14.89 Hz), 7.44 (1.0H, d, J=9.16 Hz), 7.84 (1.0H, s), 10.94 (1.0H, s).

(128g) cis(±)-2-(4-{[(4-Chloro-5-ethyl-1H-imidazol-2-yl)carbonyl]amino}-3-(2,2-difluoropropoxy)piperidin-1-yl)-1,3-thiazole-5-carboxylic acid The same operation as in Example (91d) was performed using ethyl cis(±)-2-(4-{[(4-chloro-5-ethyl-1H-imidazol-2-yl)carbonyl]amino}-3-(2,2-difluoropropoxy)piperidin-1-yl)-1,3-thiazole-5-carboxylate obtained in Example (128f) (0.2 g, 0.8 mmol), 2 N lithium hydroxide (6 mL, 12 mmol) and methanol (5 mL), to obtain 145 mg of the title compound as a light brown solid (77%).

$^1$H NMR spectrum (400 MHz, DMSO-d$_6$) δ ppm: 1.14 (3.0H, t, J=7.45 Hz), 1.52 (3.0H, t, J=19.47 Hz), 1.67-1.70 (1.0H, m), 1.95 (1.0H, dq, J=4.58, 12.60 Hz), 2.55 (2.0H, q, J=7.45 Hz), 3.32-3.37 (2.0H, m), 3.71-3.74 (2.0H, m), 3.84 (1.0H, br s), 3.91-3.93 (1.0H, m), 4.22-4.25 (1.0H, m), 4.30 (1.0H, d, J=13.17 Hz), 7.68 (1.0H, s), 7.85 (1.0H, d, J=8.59 Hz).

mass spectrum (ESI): m/z 478 (M+H)$^+$.

Example 129 cis(±)-2-(4-{[(4-Chloro-5-ethyl-1H-imidazol-2-yl)carbonyl]amino}-3-(3-fluoropropoxy)piperidin-1-yl)-4-methyl-1,3-thiazole-5-carboxylic acid (Exemplified Compound No. 129)

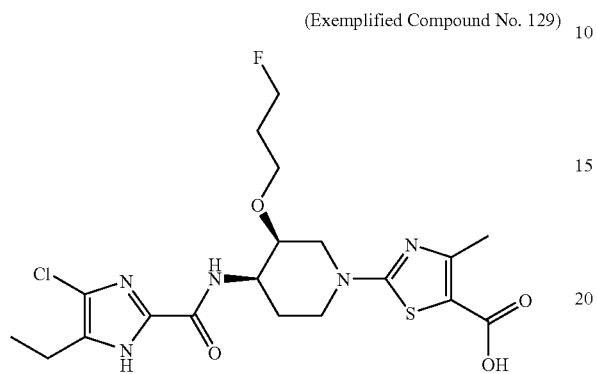

(129a) Ethyl cis(±)-2-(4-{[(4-chloro-5-ethyl-1H-imidazol-2-yl)carbonyl]amino}-3-(3-fluoropropoxy)piperidin-1-yl)-4-methyl-1,3-thiazole-5-carboxylate The same operation as in Example (90f) was performed using tert-butyl cis(±)-4-{[(4-chloro-5-ethyl-1H-imidazol-2-yl)carbonyl]amino}-3-(3-fluoropropoxy)piperidine-1-carboxylate obtained in Example (127e) (0.2 g, 0.46 mmol), a 4 N hydrochloric acid/ethyl acetate solution (10 ml, 40 mmol), N,N-diisopropylethylamine (0.6 g, 4.6 mmol), ethyl 2-bromo-4-methyl-1,3-thiazole-5-carboxylate (200 mg, 0.8 mmol) and DMA (10 mL), to obtain 0.20 g of the title compound as a light brown amorphous solid (91%).

$^1$H NMR spectrum (400 MHz, CDCl$_3$) δ ppm: 1.27 (3.0H, t, J=7.45 Hz), 1.33 (3.0H, t, J=7.14 Hz), 1.77-1.80 (1.0H, m), 1.91 (1.0H, tt, J=5.73, 5.73 Hz), 1.96 (1.0H, tt, J=5.73, 5.73 Hz), 2.05 (1.0H, dq, J=4.58, 12.03 Hz), 2.54 (3.0H, s), 2.69 (2.0H, q, J=7.45 Hz), 3.13 (1.0H, dd, J=14.32, 1.15 Hz), 3.22 (1.0H, td, J=12.89, 2.48 Hz), 3.51 (1.0H, dt, J=8.59, 6.30 Hz), 3.63-3.65 (1.0H, br m), 3.84 (1.0H, dt, J=8.59, 6.30 Hz), 3.98 (1.0H, d, J=13.17 Hz), 4.22-4.29 (1.0H, m), 4.26 (2.0H, q, J=7.14 Hz), 4.38-4.57 (3.0H, m), 7.45 (1.0H, d, J=8.59 Hz), 11.11 (1.0H, s).

(129b) cis(±)-2-(4-{[(4-Chloro-5-ethyl-1H-imidazol-2-yl)carbonyl]amino}-3-(3-fluoropropoxy)piperidin-1-yl)-4-methyl-1,3-thiazole-5-carboxylic acid The same operation as in Example (91d) was performed using ethyl cis(±)-2-(4-{[(4-chloro-5-ethyl-1H-imidazol-2-yl)carbonyl]amino}-3-(3-fluoropropoxy)piperidin-1-yl)-4-methyl-1,3-thiazole-5-carboxylate obtained in Example (129a) (0.20 g, 0.49 mmol), 2 N lithium hydroxide (6 mL, 12 mmol) and methanol (5 mL), to obtain 0.15 g of the title compound as a light brown solid (79%).

$^1$H NMR spectrum (400 MHz, DMSO-d$_6$) δ ppm: 1.14 (3.0H, t, J=7.45 Hz), 1.64-1.67 (1.0H, m), 1.78 (1.0H, tt, J=5.73, 5.73 Hz), 1.83 (1.0H, tt, J=5.73, 5.73 Hz), 1.90 (1.0H, dq, J=4.01, 12.60 Hz), 2.40 (3.0H, s), 2.55 (2.0H, q, J=7.45 Hz), 3.26-3.31 (2.0H, m), 3.46 (1.0H, dt, J=9.74, 5.73 Hz), 3.65-3.70 (2.0H, m), 3.90-3.93 (1.0H, br m), 4.17-4.20 (2.0H, m), 4.40 (1.0H, td, J=6.30, 2.29 Hz), 4.49 (1.0H, td, J=6.30, 2.29 Hz), 7.75 (1.0H, d, J=8.02 Hz), 12.39 (1.0H, s).

mass spectrum (ESI): m/z 474 (M+H)$^+$.

Example 130 cis(±)-2-(4-{[(4-Chloro-5-ethyl-1H-imidazol-2-yl)carbonyl]amino}-3-(2,2-difluoropropoxy)piperidin-1-yl)-4-methyl-1,3-thiazole-5-carboxylic acid (Exemplified Compound No. 130)

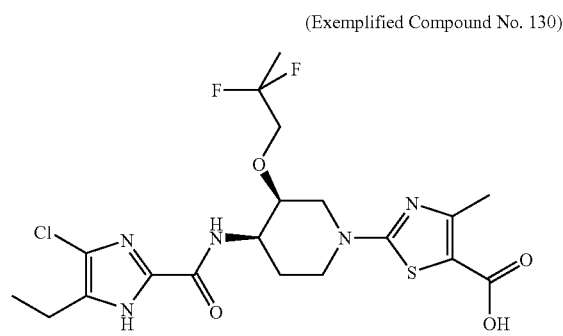 [SMILES: CCc1[nH]c(C(=O)N[C@@H]2CCN(c3nc(C)c(C(=O)O)s3)C[C@@H]2OCC(C)(F)F)nc1Cl]

(130a) Ethyl cis(±)-2-(4-{[(4-chloro-5-ethyl-1H-imidazol-2-yl)carbonyl]amino}-3-(2,2-difluoropropoxy)piperidin-1-yl)-4-methyl-1,3-thiazole-5-carboxylate The same operation as in Example (90f) was performed using tert-butyl cis(±)-4-{[(4-chloro-5-ethyl-1H-imidazol-2-yl)carbonyl]amino}-3-(2,2-difluoropropoxy)piperidine-1-carboxylate obtained in Example (128e) (0.21 g, 0.46 mmol), a 4 N hydrochloric acid/ethyl acetate solution (10 ml, 40 mmol), N,N-diisopropylethylamine (0.6 g, 4.6 mmol), ethyl 2-bromo-4-methyl-1,3-thiazole-5-carboxylate (200 mg, 0.8 mmol) and DMA (10 mL), to obtain 0.24 g of the title compound as a light brown amorphous solid (99%).

$^1$H NMR spectrum (400 MHz, CDCl$_3$) δ ppm: 1.26 (3.0H, t, J=7.64 Hz), 1.33 (3.0H, t, J=7.16 Hz), 1.56 (3.0H, t, J=18.90 Hz), 1.80 (1.0H, dq, J=12.74, 3.34 Hz), 2.08 (1.0H, dq, J=4.87, 12.03 Hz), 2.53 (3.0H, s), 2.69 (2.0H, q, J=7.64 Hz), 3.15 (1.0H, dd, J=14.32, 1.15 Hz), 3.22-3.28 (1.0H, m), 3.61 (1.0H, q, J=10.50 Hz), 3.79-3.83 (2.0H, m), 3.95 (1.0H, d, J=14.32 Hz), 4.25-4.29 (1.0H, m), 4.27 (2.0H, q, J=7.16 Hz), 4.55 (1.0H, d, J=14.32 Hz), 7.46 (1.0H, d, J=9.16 Hz), 11.25 (1.0H, s).

(130b) cis(±)-2-(4-{[(4-Chloro-5-ethyl-1H-imidazol-2-yl)carbonyl]amino}-3-(2,2-difluoropropoxy)piperidin-1-yl)-4-methyl-1,3-thiazole-5-carboxylic acid The same operation as in Example (91d) was performed using ethyl cis(±)-2-(4-{[(4-chloro-5-ethyl-1H-imidazol-2-yl)carbonyl]amino}-3-(2,2-difluoropropoxy)piperidin-1-yl)-4-methyl-1,3-thiazole-5-carboxylate obtained in Example (130a) (0.20 g, 0.49 mmol), 2 N lithium hydroxide (6 mL, 12 mmol) and methanol (5 mL), to obtain 0.16 g of the title compound as a light brown solid (74%).

$^1$H NMR spectrum (400 MHz, DMSO-d$_6$) δ ppm: 1.14 (3.0H, t, J=7.64 Hz), 1.52 (3.0H, t, J=19.47 Hz), 1.66-1.68 (1.0H, m), 1.93 (1.0H, dq, J=4.30, 12.60 Hz), 2.40 (3.0H, s), 2.55 (2.0H, q, J=7.64 Hz), 3.29-3.34 (2.0H, m), 3.67-3.79 (2.0H, m), 3.82 (1.0H, br s), 3.90-3.92 (1.0H, br m), 4.21-4.25 (2.0H, m), 7.84 (1.0H, d, J=8.59 Hz), 12.41 (1.0H, s).

mass spectrum (ESI): m/z 492 (M+H)$^+$.

Example 131 cis(±)-4-Chloro-N-(3-ethoxy-1-pyridin-2-ylpiperidin-4-yl)-5-ethyl-1H-imidazole-2-carboxamide (Exemplified Compound No. 131)

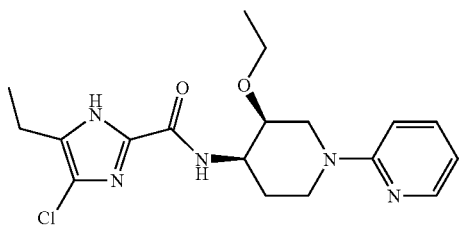

(131a) cis(±)-4-Chloro-N-(3-ethoxypiperidin-4-yl)-5-ethyl-1H-imidazole-2-carboxamide hydrochloride tert-Butyl cis(±)-4-{[(4-chloro-5-ethyl-1H-imidazol-2-yl)carbonyl]amino}-3-ethoxypiperidine-1-carboxylate obtained in Example (125a) (4.31 g, 10.8 mmol) was dissolved in ethanol (25 mL). A 4 N hydrochloric acid/dioxane solution (25 mL, 100 mmol) was added, and the mixture was stirred at room temperature for 1.5 hours. The reaction solution was concentrated under reduced pressure to obtain 4.22 g of the title compound as a pale pink amorphous solid (quant.).

$^1$H NMR spectrum (400 MHz, DMSO-$d_6$) δ ppm: 1.02-1.17 (6H, m), 1.69-1.78 (1H, m), 1.92-2.04 (1H, m), 2.54 (2H, q, J=7.57 Hz), 2.93-3.22 (3H, m), 3.38-3.81 (5H, m), 4.12-4.22 (1H, m), 7.85 (1H, d, J=8.30 Hz), 8.18-8.33 (1H, m), 9.32 (1H, br s).

Example 131b cis(±)-4-Chloro-N-(3-ethoxy-1-pyridin-2-ylpiperidin-4-yl)-5-ethyl-1H-imidazole-2-carboxamide cis(±)-4-Chloro-N-(3-ethoxypiperidin-4-yl)-5-ethyl-1H-imidazole-2-carboxamide hydrochloride obtained in Example (131a) (100 mg, 0.297 mmol), 2-chloropyridine (0.035 mL, 0.37 mmol) and sodium carbonate (157 mg, 1.48 mmol) were suspended in DMF (1 mL), and the suspension was heated using a microwave reactor at 180° C. for 30 minutes. The reaction solution was diluted with ethyl acetate, washed with water and brine, and dried over anhydrous sodium sulfate. Following concentration under reduced pressure, the residue was purified by silica gel column chromatography (elution solvent: hexane/ethyl acetate=7/3→1/0) to obtain 3.9 mg of the title compound as a white amorphous solid (3%).

$^1$H NMR spectrum (400 MHz, CDCl$_3$) δ ppm: 1.10 (3H, t, J=7.08 Hz), 1.27 (3H, t, J=7.81 Hz), 1.75-1.83 (1H, m), 1.99-2.12 (1H, m), 2.70 (2H, q, J=7.81 Hz), 2.95-3.10 (2H, m), 3.38-3.74 (3H, m), 4.09-4.31 (2H, m), 4.66-4.73 (1H, m), 6.57-6.70 (2H, m), 7.43-7.56 (2H, m), 8.15-8.19 (1H, m), 11.38 (1H, br s).

mass spectrum (ESI): m/z 378 (M+H)$^+$.

Example 132

Methyl cis(±)-(4-{[(4-chloro-5-ethyl-1H-imidazol-2-yl)carbonyl]amino}-3-ethoxypiperidin-1-yl)(oxo)acetate (Exemplified Compound No. 132)

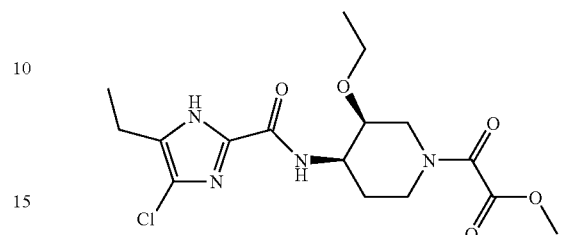

Example 132a

Methyl cis(±)-(4-{[(4-chloro-5-ethyl-1H-imidazol-2-yl)carbonyl]amino}-3-ethoxypiperidin-1-yl)(oxo)acetate cis(±)-4-Chloro-N-(3-ethoxypiperidin-4-yl)-5-ethyl-1H-imidazole-2-carboxamide hydrochloride obtained in Example (131a) (200 mg, 0.593 mmol) was suspended in dichloromethane (5 mL). Methyl chloroglyoxylate (0.070 mL, 0.76 mmol), triethylamine (0.250 mL, 1.80 mmol) and DMAP (catalytic amount) were added under ice-cooling, and the mixture was stirred at room temperature for one hour. The reaction solution was diluted with ethyl acetate, washed with water and brine, and dried over anhydrous sodium sulfate. Following concentration under reduced pressure, the residue was purified by silica gel column chromatography (elution solvent: hexane/ethyl acetate=7/3→1/0) to obtain 208.1 mg of the title compound as a colorless oily substance (91%).

$^1$H NMR spectrum (400 MHz, CDCl$_3$) δ ppm: 1.18-1.30 (6H, m), 1.69-1.80 (1H, m), 1.88-2.08 (1H, m), 2.65-2.85 (3H, m), 3.14-3.24 (1H, m), 3.35-4.27 (8H, m), 4.52-4.58 (1H×⅖, m), 4.77-4.84 (1H×⅗, m), 7.42-7.58 (1H, m), 11.49 (1H, br s).

mass spectrum (ESI): m/z 387 (M+H)$^+$.

Example 133 cis(±)-4-Chloro-N-[3-ethoxy-1-(1,3-thiazol-2-yl)piperidin-4-yl]-5-ethyl-1H-imidazole-2-carboxamide (Exemplified Compound No. 133)

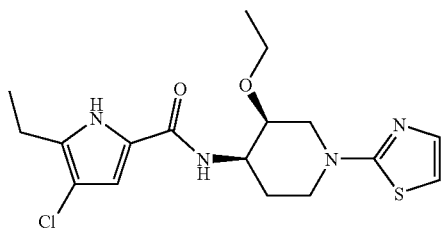

(133a) cis(±)-4-Chloro-N-[3-ethoxy-1-(1,3-thiazol-2-yl)piperidin-4-yl]-5-ethyl-1H-imidazole-2-carboxamide cis(±)-4-Chloro-N-(3-ethoxypiperidin-4-yl)-5-ethyl-1H-imidazole-2-carboxamide hydrochloride obtained in Example (131a) (100 mg, 0.297 mmol), 2-bromothiazole (0.040 mL, 0.44 mmol) and sodium carbonate (157 mg, 1.48 mmol) were suspended in DMF (3 mL). The suspension was subjected to the same operation as in Example (131b) to obtain 45.8 mg of the title compound as a colorless oily substance (40%).

$^1$H NMR spectrum (400 MHz, CDCl$_3$) δ ppm: 1.14-1.32 (6H, m), 1.74-1.82 (1H, m), 2.08-2.21 (1H, m), 2.70 (2H, q, J=7.56 Hz), 3.09-3.22 (2H, m), 3.40-3.50 (1H, m), 3.59-3.78 (2H, m), 3.91-3.99 (1H, m), 4.19-4.41 (2H, m), 6.55 (1H, d, J=3.66 Hz), 7.17 (1H, d, J=3.66 Hz), 7.54 (1H, d, J=9.02 Hz), 11.60 (1H, br s).

mass spectrum (ESI): m/z 384 (M+H)$^+$.

Example 134 cis(±)-N-[1-(1,3-Benzothiazol-2-yl)-3-ethoxypiperidin-4-yl]-4-chloro-5-ethyl-1H-imidazole-2-carboxamide (Exemplified Compound No. 134)

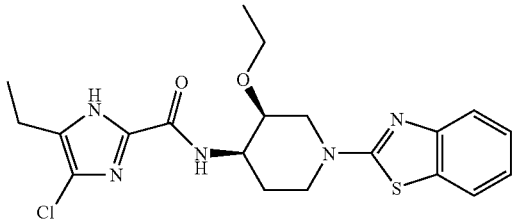

(134a) cis(±)-N-[1-(1,3-Benzothiazol-2-yl)-3-ethoxypiperidin-4-yl]-4-chloro-5-ethyl-1H-imidazole-2-carboxamide cis(±)-4-Chloro-N-(3-ethoxypiperidin-4-yl)-5-ethyl-1H-imidazole-2-carboxamide hydrochloride obtained in Example (131a) (100 mg, 0.297 mmol), 2-bromobenzothiazole (95 mg, 0.44 mmol) and sodium carbonate (157 mg, 1.48 mmol) were suspended in DMF (3 mL). The suspension was subjected to the same operation as in Example (131b) to obtain 83.4 mg of the title compound as a colorless oily substance (65%).

$^1$H NMR spectrum (400 MHz, CDCl$_3$) δ ppm: 1.15 (3H, t, J=7.07 Hz), 1.27 (3H, t, J=7.56 Hz), 1.78-1.85 (1H, m), 2.07-2.19 (1H, m), 2.70 (2H, q, J=7.56 Hz), 3.19-3.31 (2H, m), 3.42-3.52 (1H, m), 3.62-3.67 (1H, m), 3.74-3.83 (1H, m), 4.14-4.32 (2H, m), 4.42-4.48 (1H, m), 7.05-7.11 (1H, m), 7.26-7.32 (1H, m), 7.49-7.62 (3H, m), 11.29 (1H, br s).

mass spectrum (ESI): m/z 434 (M+H)$^+$.

Example 135 cis(±)-(4-{[(4-Chloro-5-ethyl-1H-imidazol-2-yl)carbonyl]amino}-3-ethoxypiperidin-1-yl)(oxo)acetic acid (Exemplified Compound No. 135)

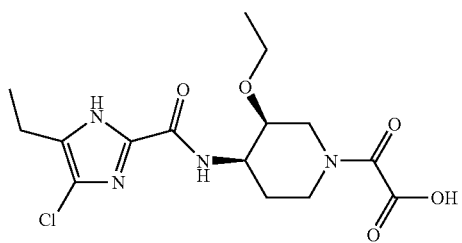

Example 135a cis(±)-(4-{[(4-Chloro-5-ethyl-1H-imidazol-2-yl)carbonyl]amino}-3-ethoxypiperidin-1-yl)(oxo)acetic acid Ethyl cis(±)-(4-{[(4-chloro-5-ethyl-1H-imidazol-2-yl)carbonyl]amino}-3-ethoxypiperidin-1-yl)(oxo)acetate obtained in Example (132a) (122 mg, 0.316 mmol) was dissolved in THF (3 mL). A 1 N aqueous sodium hydroxide solution (0.95 ml, 0.95 mmol) was added, and the mixture was stirred at room temperature for 1.5 hours. The reaction solution was neutralized with 1 N hydrochloric acid and concentrated under reduced pressure. Then, the residue was purified by preparative HPLC (TSK-gel, Toso, elution solvent: water/acetonitrile=17/3→1/1) to obtain 79.8 mg of the title compound as a colorless amorphous solid (68%).

$^1$H NMR spectrum (400 MHz, DMSO-d$_6$) δ ppm: 1.03-1.18 (6H, m), 1.58-1.82 (2H, m), 2.47-2.59 (1H, m), 2.80-2.94 (1H, m), 3.14-3.82 (5H, m), 4.07-4.46 (2H, m), 7.57-7.63 (1H, m), 13.34 (1H, br s).

mass spectrum (ESI): m/z 373 (M+H)$^+$.

Example 136 cis(±)-4-Chloro-N-(3-ethoxy-1-pyrimidin-2-ylpiperidin-4-yl)-5-ethyl-1H-imidazole-2-carboxamide (Exemplified Compound No. 136)

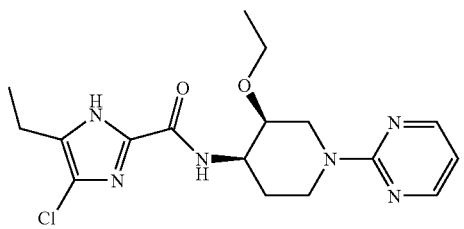

(136a) cis(±)-4-Chloro-N-(3-ethoxy-1-pyrimidin-2-ylpiperidin-4-yl)-5-ethyl-1H-imidazole-2-carboxamide cis(±)-4-Chloro-N-(3-ethoxypiperidin-4-yl)-5-ethyl-1H-imidazole-2-carboxamide hydrochloride obtained in Example (131a) (100 mg, 0.297 mmol), 2-chloropyrimidine (51 mg, 0.45 mmol) and sodium carbonate (157 mg, 1.48 mmol) were suspended in DMF (1 mL). The suspension was subjected to the same operation as in Example (131b) to obtain 25.1 mg of the title compound as a white solid (22%).

$^1$H NMR spectrum (400 MHz, CDCl$_3$) δ ppm: 1.08 (3H, t, J=7.08 Hz), 1.29 (3H, t, J=7.56 Hz), 1.73-1.80 (1H, m), 1.91-2.04 (1H, m), 2.70 (2H, q, J=7.56 Hz), 2.95-3.07 (2H, m), 3.35-3.44 (1H, m), 3.56-3.62 (1H, m), 3.69-3.79 (1H, m), 4.21-4.30 (1H, m), 4.72-4.82 (1H, m), 5.08-5.15 (1H, m), 6.47 (1H, t, J=4.88 Hz), 7.56 (1H, d, J=8.79 Hz), 8.30 (2H, d, J=4.88 Hz), 11.87 (1H, brs).

mass spectrum (ESI): m/z 379 (M+H)$^+$.

Example 137 cis(±)-4-Chloro-N-[3-ethoxy-1-(1-methyl-2-oxo-1,2-dihydropyridin-4-yl)piperidin-4-yl]-5-ethyl-1H-imidazole-2-carboxamide (Exemplified Compound No. 137)

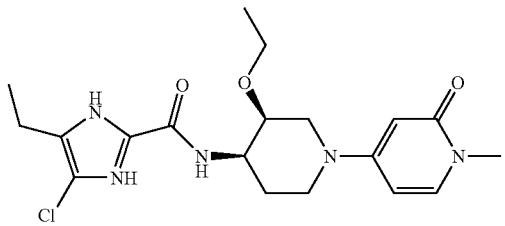

(137a) 4-Chloro-1-methylpyridin-2(1H)-one

The compound was synthesized according to the method described in the following document.

Heterocycles, 52, 2000, 253-260

(137b) cis(±)-4-Chloro-N-[3-ethoxy-1-(1-methyl-2-oxo-1,2-dihydropyridin-4-yl)piperidin-4-yl]-5-ethyl-1H-imidazole-2-carboxamide cis(±)-4-Chloro-N-(3-ethoxypiperidin-4-yl)-5-ethyl-1H-imidazole-2-carboxamide hydrochloride obtained in Example (131a) (50 mg, 0.15 mmol), 4-chloro-1-methylpyridin-2(1H)-one obtained in Example (137a) (25 mg, 0.17 mmol) and sodium carbonate (78 mg, 0.74 mmol) were suspended in DMSO (1 mL). The suspension was subjected to the same operation as in Example (131b) to obtain 9.8 mg of the title compound as a pale brown amorphous solid (16%).

$^1$H NMR spectrum (400 MHz, CDCl$_3$) δ ppm: 1.17 (3H, t, J=7.08 Hz), 1.26 (3H, t, J=7.57 Hz), 1.73-1.81 (1H, m), 1.97-2.09 (1H, m), 2.69 (2H, q, J=7.57 Hz), 2.92-3.02 (2H, m), 3.40-3.49 (4H, m), 3.57-3.68 (2H, m), 3.71-3.80 (1H, m), 3.92-4.00 (1H, m), 4.18-4.25 (1H, m), 5.85-5.92 (2H, m), 7.08 (1H, d, J=7.57 Hz), 7.43 (1H, d, J=8.55 Hz).

mass spectrum (ESI): m/z 408 (M+H)$^+$.

Example 138 cis(±)-N-{1-[Amino(oxo)acetyl]-3-ethoxypiperidin-4-yl}-4-chloro-5-ethyl-1H-imidazole-2-carboxamide (Exemplified Compound No. 138)

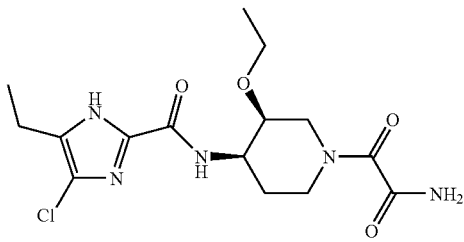

Example 138a cis(±)-N-{1-[Amino(oxo)acetyl]-3-ethoxypiperidin-4-yl}-4-chloro-5-ethyl-1H-imidazole-2-carboxamide cis(±)-4-Chloro-N-(3-ethoxypiperidin-4-yl)-5-ethyl-1H-imidazole-2-carboxamide hydrochloride obtained in Example (131a) (100 mg, 0.297 mmol), oxamic acid (26 mg, 0.29 mmol) and WSC hydrochloride (120 mg, 0.626 mmol) were suspended in DMF (3 mL). Triethylamine (0.040 mL, 0.29 mmol) and HOBT (40 mg, 0.30 mmol) were added, and the mixture was stirred at room temperature overnight. The reaction solution was diluted with ethyl acetate, washed with saturated aqueous sodium bicarbonate solution, water and brine, and dried over anhydrous sodium sulfate. Following concentration under reduced pressure, the residue was purified by silica gel column chromatography (elution solvent: dichloromethane/methanol=1/0→9/1) to obtain 64.7 mg of the title compound as a colorless solid (59%).

$^1$H NMR spectrum (400 MHz, CDCl$_3$) δ ppm: 1.16-1.29 (6H, m), 1.73-2.06 (2H, m), 2.64-2.83 (3H, m), 3.13-3.79 (3H, m), 4.15-4.28 (1H, m), 4.52-4.59 (1H, m), 4.80-4.99 (1H, m), 5.29-5.38 (1H, m), 5.58-5.75 (1H, m), 6.98-7.50 (2H, m), 10.94 (1H, br s).

mass spectrum (ESI): m/z 372 (M+H)$^+$.

Example 139 cis(±)-4-Chloro-N-[3-ethoxy-1-(2-oxo-1,2-dihydropyridin-4-yl)piperidin-4-yl]-5-ethyl-1H-imidazole-2-carboxamide (Exemplified Compound No. 139)

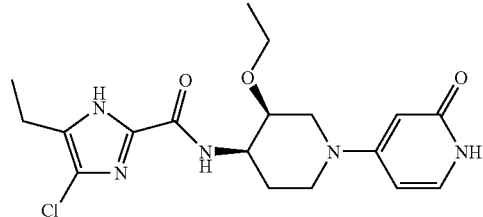

(139a) cis(±)-4-Chloro-N-[3-ethoxy-1-(2-oxo-1,2-dihydropyridin-4-yl)piperidin-4-yl]-5-ethyl-1H-imidazole-2-carboxamide cis(±)-4-Chloro-N-(3-ethoxypiperidin-4-yl)-5-ethyl-1H-imidazole-2-carboxamide hydrochloride obtained in Example (131a) (100 mg, 0.297 mmol), 4-chloro-2-hydroxypyridine (46 mg, 0.36 mmol) and sodium carbonate (157 mg, 1.48 mmol) were suspended in DMSO (1 mL). The suspension was subjected to the same operation as in Example (131b) to obtain 6.3 mg of the title compound as a pale yellow amorphous solid (5%).

$^1$H NMR spectrum (400 MHz, CDCl$_3$) δ ppm: 1.17 (3H, t, J=7.08 Hz), 1.26 (3H, t, J=7.56 Hz), 1.73-1.82 (1H, m), 1.95-2.07 (1H, m), 2.69 (2H, q, J=7.56 Hz), 2.97-3.07 (2H, m), 3.38-3.68 (3H, m), 3.75-3.86 (1H, m), 3.98-4.07 (1H, m), 4.18-4.29 (1H, m), 5.73 (1H, d, J=2.44 Hz), 5.92-5.98 (1H, m), 7.12 (1H, d, J=7.81 Hz), 7.43 (1H, d, J=8.78 Hz), 10.50 (1H, br s), 11.07 (1H, brs).

mass spectrum (ESI): m/z 394 (M+H)$^+$.

Example 140 cis(±)-2-[4-(4-{[(4-Chloro-5-ethyl-1H-imidazol-2-yl)carbonyl]amino}-3-ethoxypiperidin-1-yl)-2-oxopyridin-1(2H)-yl]-4-methyl-1,3-thiazole-5-carboxylic acid (Exemplified Compound No. 140)

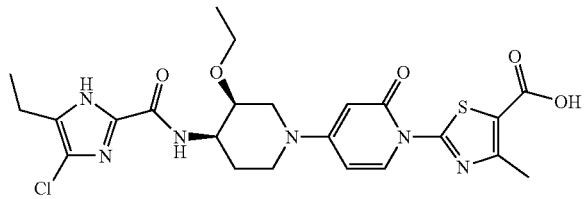

Example 140a

Ethyl 2-(4-chloro-2-oxopyridin-1(2H)-yl)-4-methyl-1,3-thiazole-5-carboxylate

4-Chloro-2-hydroxypyridine (500 mg, 3.86 mmol), ethyl 2-bromo-4-methyl-1,3-thiazole-5-carboxylate (1.06 g, 4.24 mmol), potassium carbonate (1.06 g, 7.67 mmol) and copper (I) iodide (73 mg, 0.38 mmol) were suspended in DMF (4 mL). trans(±)-N,N'-Dimethylcyclohexane-1,2-diamine (82 mg, 0.58 mmol) was added, and the mixture was stirred at 100° C. for five hours. The reaction solution was diluted with ethyl acetate, washed with water, and dried over anhydrous sodium sulfate. Following concentration under reduced pressure, the residue was purified by silica gel column chromatography (elution solvent: hexane/ethyl acetate=5/1→2/1) to obtain 3.2 mg of the title compound as a white solid (0.3%).

$^1$H NMR spectrum (400 MHz, CDCl$_3$) δ ppm: 1.38 (3H, t, J=7.08 Hz), 2.72 (3H, s), 4.35 (2H, q, J=7.08 Hz), 6.47 (1H, dd, J=8.05, 2.44 Hz), 6.84 (1H, d, J=2.44 Hz), 8.80 (1H, d, J=8.05 Hz).

(140b) Ethyl cis(±)-2-[4-(4-{[(4-chloro-5-ethyl-1H-imidazol-2-yl)carbonyl]amino}-3-ethoxypiperidin-1-yl)-2-oxopyridin-1(2H)-yl]-4-methyl-1,3-thiazole-5-carboxylate cis(±)-4-Chloro-N-(3-ethoxypiperidin-4-yl)-5-ethyl-1H-imidazole-2-carboxamide hydrochloride obtained in Example (131a) (100 mg, 0.297 mmol), ethyl 2-(4-chloro-2-oxopyridin-1(2H)-yl)-4-methyl-1,3-thiazole-5-carboxylate obtained in Example (140a) (106 mg, 0.355 mmol) and sodium carbonate (157 mg, 1.48 mmol) were suspended in DMSO (1 mL). The suspension was subjected to same operation as in Example (131b) to obtain 10.8 mg of the title compound as a pale yellow solid (6%).

$^1$H NMR spectrum (400 MHz, CD$_3$OD) δ ppm: 1.11-1.45 (9H, m), 1.79-2.08 (2H, m), 2.60-2.74 (5H, m), 3.12-3.75 (5H, m), 3.97-4.41 (5H, m), 5.75-5.85 (1H, m), 6.50-6.58 (1H, m), 7.70-7.81 (2H, m), 8.60-8.71 (1H, m).

(140c) cis(±)-2-[4-(4-{[(4-Chloro-5-ethyl-1H-imidazol-2-yl)carbonyl]amino}-3-ethoxypiperidin-1-yl)-2-oxopyridin-1(2H)-yl]-4-methyl-1,3-thiazole-5-carboxylic acid Ethyl cis(±)-2-[4-(4-{[(4-chloro-5-ethyl-1H-imidazol-2-yl)carbonyl]amino}-3-ethoxypiperidin-1-yl)-2-oxopyridin-1(2H)-yl]-4-methyl-1,3-thiazole-5-carboxylate obtained in Example (140b) (10.8 mg, 0.0192 mmol) was dissolved in dioxane (0.5 mL). A 1 N aqueous sodium hydroxide solution (0.5 ml, 0.5 mmol) was added, and the mixture was stirred at room temperature overnight. The reaction solution was neutralized with 1 N hydrochloric acid and brine was added, followed by extraction with chloroform three times. The organic layer was dried over anhydrous sodium sulfate and concentrated under reduced pressure. Thereafter, the residue was purified by silica gel column chromatography (elution solvent: dichloromethane/methanol=9/1) to obtain 4.5 mg of the title compound as a colorless solid (44%).

$^1$H NMR spectrum (400 MHz, CDCl$_3$) δ ppm: 1.10-1.39 (6H, m), 1.78-2.09 (2H, m), 2.58-2.77 (5H, m), 3.09-3.72 (5H, m), 3.91-4.36 (3H, m), 5.73-5.82 (1H, m), 6.27-6.38 (1H, m), 7.32-7.52 (2H, m), 8.56-8.65 (1H, m).

mass spectrum (ESI): m/z 535 (M+H)$^+$.

Example 141 cis(±)-4-Chloro-N-{3-ethoxy-1-[oxo(phenyl)acetyl]piperidin-4-yl}-5-ethyl-1H-imidazole-2-carboxamide (Exemplified Compound No. 141)

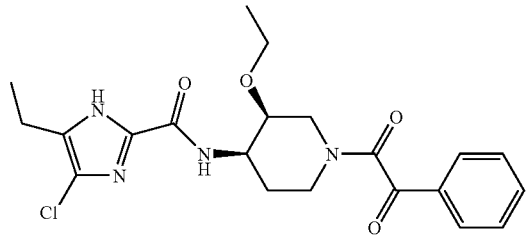

(141a) cis(±)-4-Chloro-N-{3-ethoxy-1-[oxo(phenyl)acetyl]piperidin-4-yl}-5-ethyl-1H-imidazole-2-carboxamide cis(±)-4-Chloro-N-(3-ethoxypiperidin-4-yl)-5-ethyl-1H-imidazole-2-carboxamide hydrochloride obtained in Example (131a) (100 mg, 0.297 mmol) and benzoylformic acid (45 mg, 0.30 mmol) were suspended in DMF (3 mL). The suspension was subjected to the same operation as in Example (138a) to obtain 86.2 mg of the title compound as a colorless amorphous solid (67%).

$^1$H NMR spectrum (400 MHz, CDCl$_3$) δ ppm: 1.25 (3H, t, J=7.55 Hz), 1.35 (3H, J=7.07 Hz), 1.74-2.07 (2H, m), 2.62-2.93 (3H, m), 3.04-4.00 (5H, m), 4.19-4.30 (1H, m), 4.70-4.78 (1H×⅓, m), 4.98-5.07 (1H×⅔, m), 7.38-7.72 (4H, m), 7.97-8.05 (2H, m), 11.10 (1H, br s).

mass spectrum (ESI): m/z 433 (M+H)$^+$.

Example 142 cis(±)-4-Chloro-N-[3-ethoxy-1-(1,3-thiazol-2-ylmethyl)piperidin-4-yl]-5-ethyl-1H-imidazole-2-carboxamide (Exemplified Compound No. 142)

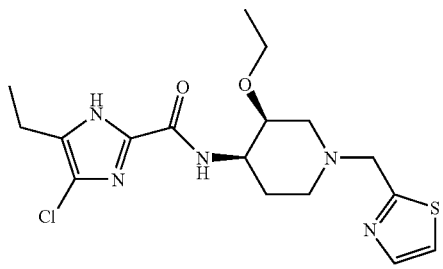

Example 142a cis(±)-4-Chloro-N-[3-ethoxy-1-(1,3-thiazol-2-ylmethyl)piperidin-4-yl]-5-ethyl-1H-imidazole-2-carboxamide cis(±)-4-Chloro-N-(3-ethoxypiperidin-4-yl)-5-ethyl-1H-imidazole-2-carboxamide hydrochloride obtained in Example (131a) (100 mg, 0.297 mmol) and 2-thiazolecarboxyaldehyde (40 mg, 0.35 mmol) were suspended in 1,2-dichloroethane (3 mL). Sodium triacetoxyborohydride (94 mg, 0.44 mmol) was added under ice-cooling, and the mixture was stirred at room temperature overnight. The reaction solution was diluted with ethyl acetate, washed with water and brine, and dried over anhydrous sodium sulfate. Following concentration under reduced pressure, the residue was purified by silica gel column chromatography (elution solvent: dichloromethane/methanol=19/1→9/1) to obtain 20.1 mg of the title compound as a pale yellow amorphous solid (17%).

$^1$H NMR spectrum (400 MHz, CDCl$_3$) δ ppm: 1.21-1.28 (6H, m), 1.67-1.78 (1H, m), 2.03-2.16 (1H, m), 2.32-2.49 (2H, m), 2.68 (2H, q, J=7.56 Hz), 2.89-2.97 (1H, m), 3.08-3.17 (1H, m), 3.33-3.69 (3H, m), 3.89-4.15 (3H, m), 7.31 (1H, d, J=3.41 Hz), 7.50 (1H, d, J=8.30 Hz), 7.73 (1H, d, J=3.41 Hz), 11.62 (1H, br s).

mass spectrum (ESI): m/z 398 (M+H)$^+$.

Example 143 cis(±)-4-Chloro-N-[3-ethoxy-1-(1,3-thiazol-4-ylcarbonyl)piperidin-4-yl]-5-ethyl-1H-imidazole-2-carboxamide

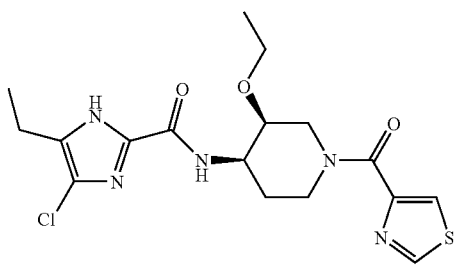

(Exemplified Compound No. 143)

Example 143a cis(±)-4-Chloro-N-[3-ethoxy-1-(1,3-thiazol-4-ylcarbonyl)piperidin-4-yl]-5-ethyl-1H-imidazole-2-carboxamide cis(±)-4-Chloro-N-(3-ethoxypiperidin-4-yl)-5-ethyl-1H-imidazole-2-carboxamide hydrochloride obtained in Example (131a) (100 mg, 0.297 mmol) and 4-thiazolecarboxylic acid (39 mg, 0.30 mmol) were suspended in DMF (3 mL). The suspension was subjected to the same operation as in Example (138a) to obtain 51.6 mg of the title compound as a colorless solid (42%).

$^1$H NMR spectrum (400 MHz, CDCl$_3$) δ ppm: 0.93-1.30 (6H, m), 1.70-1.83 (1H, m), 1.97-2.09 (1H, m), 2.69 (2H, q, J=7.57 Hz), 2.83-2.96 (1H, m), 3.07-3.32 (2H, m), 3.40-3.49 (1H, m), 3.62-3.90 (1H, m), 4.19-4.30 (1H, m), 4.55-4.76 (1H, m), 5.01-5.09 (1H, m), 7.40-7.57 (1H, m), 7.97-8.14 (1H, m), 8.80 (1H, d, J=1.95 Hz), 11.41 (1H, br s).

mass spectrum (ESI): m/z 412 (M+H)$^+$.

Example 144 cis(±)-N-{1-[Anilino(oxo)acetyl]-3-ethoxypiperidin-4-yl}-4-chloro-5-ethyl-1H-imidazole-2-carboxamide

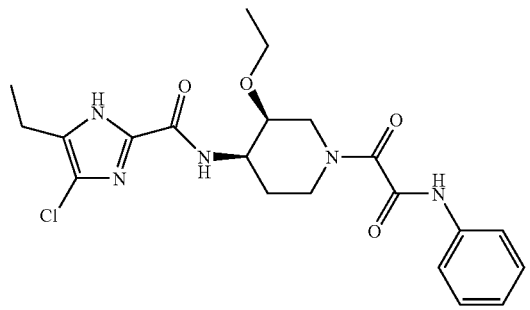

(Exemplified Compound No. 144)

Example 144a cis(±)-N-{1-[Anilino(oxo)acetyl]-3-ethoxypiperidin-4-yl}-4-chloro-5-ethyl-1H-imidazole-2-carboxamide cis(±)-4-Chloro-N-(3-ethoxypiperidin-4-yl)-5-ethyl-1H-imidazole-2-carboxamide hydrochloride obtained in Example (131a) (100 mg, 0.297 mmol) and anilino(oxo)acetic acid (49 mg, 0.30 mmol) were suspended in DMF (3 mL). The suspension was subjected to the same operation as in Example (138a) to obtain 64.3 mg of the title compound as a colorless solid (48%).

$^1$H NMR spectrum (400 MHz, CDCl$_3$) δ ppm: 1.08-1.28 (6H, m), 1.73-2.10 (2H, m), 2.55-3.00 (3H, m), 3.22-5.05 (7H, m), 7.11-7.72 (6H, m), 9.79 (1H×⅓, s), 9.92 (1H×⅔, s), 12.82 (1H, br s).

mass spectrum (ESI): m/z 448 (M+H)$^+$.

Example 145 cis(±)-4-Chloro-N-[3-ethoxy-1-(1,3-thiazol-5-ylmethyl)piperidin-4-yl]-5-ethyl-1H-imidazole-2-carboxamide

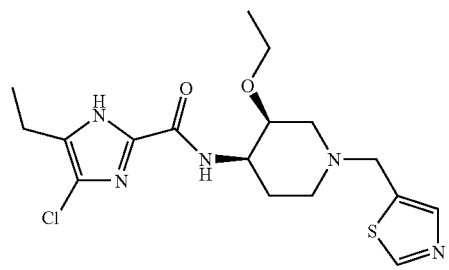

(Exemplified Compound No. 145)

Example 145a cis(±)-4-Chloro-N-[3-ethoxy-1-(1,3-thiazol-5-ylmethyl)piperidin-4-yl]-5-ethyl-1H-imidazole-2-carboxamide cis(±)-4-Chloro-N-(3-ethoxypiperidin-4-yl)-5-ethyl-1H-imidazole-2-carboxamide hydrochloride obtained in Example (131a) (100 mg, 0.297 mmol) and 5-thiazolecarboxyaldehyde (40 mg, 0.35 mmol) were suspended in 1,2-dichloroethane (3 mL). The suspension was subjected to the same operation as in Example (142a) to obtain 47.4 mg of the title compound as a colorless solid (40%).

$^1$H NMR spectrum (400 MHz, CDCl$_3$) δ ppm: 1.18-1.29 (6H, m), 1.66-1.77 (1H, m), 2.01-2.37 (3H, m), 2.68 (2H, q, J=7.57 Hz), 2.81-3.06 (2H, m), 3.32-3.64 (3H, m), 3.78 (1H, d, J=13.98 Hz), 3.91 (1H, d, J=13.98 Hz), 4.02-4.11 (1H, m), 7.47 (1H, d, J=8.54 Hz), 7.72 (1H, s), 8.78 (1H, s), 11.58 (1H, br s).

mass spectrum (ESI): m/z 398 (M+H)$^+$.

Example 146 cis(±)-7-(4-{[(4-Chloro-5-ethyl-1H-imidazol-2-yl)carbonyl]amino}-3-ethoxypiperidin-1-yl)-1-cyclopropyl-8-methoxy-4-oxo-1,4-dihydroquinoline-3-carboxylic acid (Exemplified Compound No. 146)

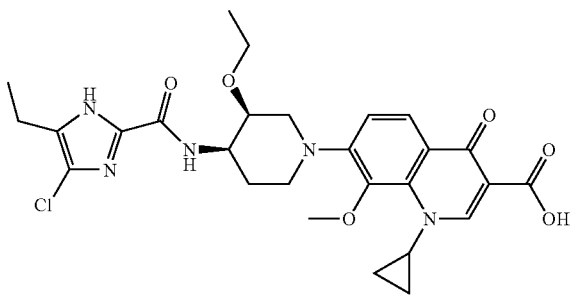

(146a) (1-Cyclopropyl-7-fluoro-8-methoxy-4-oxo-1,4-dihydroquinolin-3-yl)carbonyl difluoroborate The compound was synthesized according to the method described in the following document.
WO 2005/049602 A1

(146b) cis(±)-7-(4-{[(4-Chloro-5-ethyl-1H-imidazol-2-yl)carbonyl]amino}-3-ethoxypiperidin-1-yl)-1-cyclopropyl-8-methoxy-4-oxo-1,4-dihydroquinoline-3-carboxylic acid Ethyl acetate was added to cis(±)-4-chloro-N-(3-ethoxypiperidin-4-yl)-5-ethyl-1H-imidazole-2-carboxamide hydrochloride obtained in Example (131a) (100 mg, 0.297 mmol), and the organic layer was washed with saturated aqueous sodium bicarbonate solution and dried over anhydrous sodium sulfate. Following concentration under reduced pressure, the residue and (1-cyclopropyl-7-fluoro-8-methoxy-4-oxo-1,4-dihydroquinolin-3-yl)carbonyl difluoroborate obtained in Example (146a) (82 mg, 0.30 mmol) were dissolved in DMSO (0.6 mL). Triethylamine (0.100 mL, 0.721 mmol) was added, and the mixture was stirred at 40° C. overnight. Ethanol (3 mL), water (0.3 mL) and triethylamine (0.3 mL) were added to the reaction solution, and the mixture was stirred at 80° C. for six hours. The reaction solution was cooled to room temperature. The resulting solid was collected by filtration and washed with ethanol to obtain 102.5 mg of the title compound as a pale yellow solid (62%).

$^1$H NMR spectrum (400 MHz, DMSO-d$_6$) δ ppm: 0.82-1.22 (10H, m), 1.70-1.80 (1H, m), 2.01-2.14 (1H, m), 2.43-3.80 (11H, m), 4.02-4.25 (3H, m), 7.34 (1H, d, J=9.02 Hz), 7.56 (1H, d, J=8.29 Hz), 8.00 (1H, d, J=9.02 Hz), 8.67 (1H, s), 13.35 (1H, br s).

mass spectrum (ESI): m/z 558 (M+H)$^+$.

Example 147 cis(±)-2-(4-{[(4-Chloro-5-ethyl-1H-imidazol-2-yl)carbonyl]amino}-3-isopropoxypiperidin-1-yl)-4-methyl-1,3-thiazole-5-carboxylic acid (Exemplified Compound No. 147)

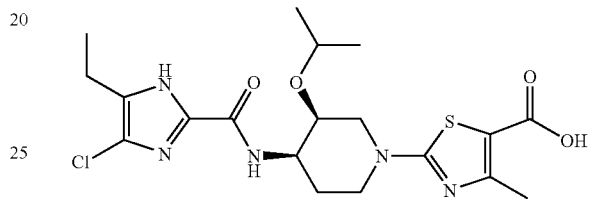

(147a) tert-Butyl 3-acetoxy-4,4-dimethoxypiperidine-1-carboxylate

A mixture of tert-butyl 3-hydroxy-4,4-dimethoxypiperidine-1-carboxylate [synthesized by the method described in Tetrahedron Lett., 46(3), 447-450 (2005)] (10 g, 38.3 mmol), pyridine (100 mL) and acetic anhydride (18.1 mL, 192 mmol) was stirred at 70° C. overnight. The reaction solution was cooled to room temperature, diluted with ethyl acetate, washed with 1 N hydrochloric acid and brine, and dried over magnesium sulfate. Thereafter, the solvent was evaporated under reduced pressure. The resulting residue was purified by silica gel column chromatography (Elution solvent: hexane/ethyl acetate=4/1) to obtain 9.65 g of the title compound as a colorless oil (83%).

$^1$H NMR spectrum (400 MHz, CDCl$_3$) δ ppm: 1.44 (9H, s), 1.82 (2H, br s), 2.09 (3H, br s), 2.68-2.89 (1H, m), 2.94-3.14 (1H, m), 3.16 (3H, s), 3.23 (3H, s), 3.88-4.30 (2H, m), 4.79-4.97 (1H, m).

(147b) tert-Butyl 3-isopropoxy-4,4-dimethoxypiperidine-1-carboxylate tert-Butyl 3-acetoxy-4,4-dimethoxypiperidine-1-carboxylate obtained in Example (147a) (1.58 g, 4.94 mmol) was dissolved in toluene (22.5 mL), tetrahydrofuran (7.5 mL) and pyridine (0.75 mL), followed by cooling to −40° C. Tebbe's reagent (0.5 M solution in toluene, 25 mL, 12.5 mmol) was added at the same temperature, and the mixture was stirred at −10 to −40° C. for 1.5 hours. A 1 N aqueous sodium hydroxide solution and dichloromethane were added, and the precipitate was filtered off. The organic layer was dried over magnesium sulfate, and then the solvent was evaporated under reduced pressure. Methanol was added to the resulting residue, and the precipitate was filtered off again. 10% palladium-carbon (wet, 3.0 g) was added to the resulting solution, which was catalytically hydrogenated at room temperature for three hours. The catalyst was filtered off, and then the solution was concentrated under reduced pressure. The resulting residue was purified by silica gel column chromatography (elution solvent: hexane/ethyl acetate) to obtain 701 mg of the title compound as a colorless solid (47%).

¹H NMR spectrum (400 MHz, CDCl₃) δ ppm: 1.16 (6H, s), 1.46 (9H, s), 1.63-1.73 (1H, m), 1.77-1.91 (1H, m), 2.82-3.05 (2H, m), 3.22 (3H, s), 3.23 (3H, s), 3.46 (1H, d, J=21.55 Hz), 3.75-3.89 (2H, m), 3.97-4.23 (1H, m).

mass spectrum (ESI): m/z 326 (M+Na)⁺.

(147c) tert-Butyl 3-isopropoxy-4-oxopiperidine-1-carboxylate

Methanesulfonic acid (0.8 mL) was added to a solution of tert-butyl 3-isopropoxy-4,4-dimethoxypiperidine-1-carboxylate obtained in Example (147b) (248 mg, 0.817 mmol) in acetone (3 mL). The mixture was stirred at room temperature overnight and further stirred at 50° C. for 35 minutes. Following cooling, saturated aqueous sodium bicarbonate solution was added to the reaction solution, and the organic substance was extracted with ethyl acetate. The organic layer was dried over magnesium sulfate, and then the solvent was evaporated under reduced pressure. The resulting residue was purified by silica gel column chromatography (elution solvent: hexane/ethyl acetate) to obtain 111 mg of the title compound as a colorless oily substance (53%).

¹H NMR spectrum (400 MHz, CDCl₃) δ ppm: 1.18 (3H, d, J=6.42 Hz), 1.22 (3H, d, J=5.96 Hz), 1.51 (9H, s), 2.39-2.46 (1H, m), 2.51-2.64 (1H, m), 3.23 (1H, d, J=5.96 Hz), 3.27-3.46 (1H, m), 3.72-3.78 (1H, m), 3.88 (1H, br s), 3.94-4.33 (2H, m).

(147d) tert-Butyl cis(±)-4-(benzylamino)-3-isopropoxypiperidine-1-carboxylate

A solution of tert-butyl 3-isopropoxy-4-oxopiperidine-1-carboxylate obtained in Example (147c) (105 mg, 0.408 mmol) in 1,2-dichloroethane (2 mL) was cooled in an ice water bath. Benzylamine (87.6 µL) and sodium (triacetoxy) borohydride (212 mg, 1.0 mmol) were added, and the mixture was stirred at room temperature overnight. The reaction solution was concentrated under reduced pressure, diluted with ethyl acetate, washed with saturated aqueous sodium bicarbonate solution and brine, and dried over magnesium sulfate. Following concentration under reduced pressure, the residue was purified by silica gel column chromatography (elution solvent: hexane/ethyl acetate) to obtain 120 mg of the title compound as a colorless oily substance (85%).

¹H NMR spectrum (400 MHz, CDCl₃) δ ppm: 1.11-1.19 (6H, m), 1.46 (9H, s), 1.53-1.77 (3H, m), 2.69-2.75 (1H, m), 2.98 (2H, dd, J=13.53, 2.52 Hz), 3.59 (1H, br s), 3.69-3.99 (5H, m), 7.21-7.25 (1H, m), 7.29-7.36 (4H, m).

mass spectrum (ESI): m/z 349 (M+1)⁺.

(147e) tert-Butyl cis(±)-4-{[(4-chloro-5-ethyl-1H-imidazol-2-yl)carbonyl]amino}-3-isopropoxypiperidine-1-carboxylate 20% palladium hydroxide (wet, 60 mg) was added to a solution of tert-butyl cis(±)-4-(benzylamino)-3-isopropoxypiperidine-1-carboxylate obtained in Example (147d) (120 mg, 0.345 mmol) in methanol (1.2 mL), and the mixture was catalytically hydrogenated at room temperature for three hours. The catalyst was filtered off, and then the filtrate was concentrated under reduced pressure. A 1 N aqueous sodium hydroxide solution was added to the resulting residue, and the organic substance was extracted with ethyl acetate. The organic layer was dried over magnesium sulfate, and the solvent was evaporated under reduced pressure to obtain 74 mg of tert-butyl cis(±)-4-amino-3-isopropoxypiperidine-1-carboxylate as a colorless oily substance (83%). The resulting amine was dissolved in DMF (1 mL). 4-Chloro-5-ethyl-1H-imidazole-2-carboxylic acid (described in Example 1d, 54 mg, 0.29 mmol) was added, and the mixture was cooled in an ice water bath. 1-Hydroxybenzotriazole (44 mg, 0.31 mmol) and 1-ethyl-3-(3-dimethylaminopropyl)-carbodiimide hydrochloride (60 mg, 0.31 mmol) were added thereto, and the mixture was stirred at room temperature overnight. The reaction solution was diluted with ethyl acetate, sequentially washed with brine, water and brine, and dried over magnesium sulfate. The solvent was evaporated under reduced pressure. The resulting residue was purified by silica gel column chromatography (elution solvent: chloroform/methanol) to obtain 60.6 mg of the title compound as a colorless solid (50%).

¹H NMR spectrum (400 MHz, CDCl₃) δ ppm: 1.09-1.32 (9H, m), 1.48 (9H, s), 1.89 (1H, br s), 2.66-2.90 (4H, m), 3.55 (1H, br s), 3.73 (1H, br s), 4.03-4.15 (2H, m), 4.20-4.46 (2H, m), 7.45 (1H, s), 11.31 (1H, s).

mass spectrum (ESI): m/z 415 (M+1)⁺, 437 (M+Na).

(147f) cis(±)-2-(4-{[(4-Chloro-5-ethyl-1H-imidazol-2-yl)carbonyl]amino}-3-isopropoxypiperidin-1-yl)-4-methyl-1,3-thiazole-5-carboxylic acid The operation as in Example (1h) was performed using tert-butyl cis(±)-4-{[(4-chloro-5-ethyl-1H-imidazol-2-yl)carbonyl]amino}-3-isopropoxypiperidine-1-carboxylate obtained in Example (147e) (60.6 mg, 0.146 mmol), a 4 N hydrochloric acid/1,4-dioxane solution (2 mL, 8 mmol), diisopropylethylamine (63.6 µL, 0.365 mmol) and ethyl 2-bromo-4-methyl-1,3-thiazole-5-carboxylate (40.2 mg, 0.161 mmol), to obtain 67 mg of ethyl cis(±)-2-(4-{[(4-chloro-5-ethyl-1H-imidazol-2-yl)carbonyl]amino}-3-isopropoxypiperidin-1-yl)-4-methyl-1,3-thiazole-5-carboxylate as a pale brown oily substance (95%). The same operation as in Example (1i) was performed using the resulting compound and 2 N lithium hydroxide (0.207 mL, 0.414 mL), to obtain 40 mg of the title compound as a pale red solid (64%).

¹H NMR spectrum (400 MHz, CDCl₃) δ ppm: 1.05-1.09 (6H, m), 1.22 (3H, td, J=7.57, 1.53 Hz), 1.71 (1H, d, J=12.38 Hz), 1.97-2.10 (1H, m), 2.50 (3H, d, J=1.83 Hz), 2.63 (1H, m), 2.75 (3H, br s), 3.17 (2H, dd, J=22.47, 13.75 Hz), 3.66-3.72 (2H, m), 4.00 (1H, d, J=12.84 Hz), 4.18 (2H, dd, J=25.45, 12.61 Hz), 7.54 (1H, d, J=8.71 Hz).

mass spectrum (ESI): m/z 456 (M+1)⁺.

Example 148 cis(±)-2-(4-{[(4-Chloro-5-ethyl-1H-imidazol-2-yl)carbonyl]amino}-3-isopropoxypiperidin-1-yl)-1,3-benzothiazole-7-carboxylic acid (Exemplified Compound No. 148)

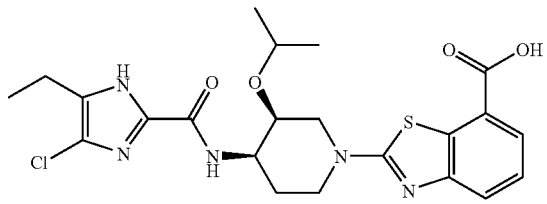

(148a) cis(±)-4-Chloro-N-(3-isopropoxypiperidin-4-yl)-5-ethyl-1H-imidazole-2-carboxamide hydrochloride The same operation as in Example (131a) was performed using tert-butyl cis(±)-4-{[(4-chloro-5-ethyl-1H-imidazol-2-yl)carbonyl]amino}-3-isopropoxypiperidine-1-carboxylate obtained by the method of Example (147e) (0.520 g, 1.25 mmol), dichloromethane (5 mL) and a 4 N hydrochloric acid/dioxane solution (3.12 mL, 12.5 mmol), to obtain 0.395 g of the title compound as a colorless foamy solid (quant.).

(148b) Ethyl cis(±)-2-(4-{[(4-chloro-5-ethyl-1H-imidazol-2-yl)carbonyl]amino}-3-isopropoxypiperidin-1-yl)-1,3-benzothiazole-7-carboxylate The same operation as in Example (1h) was performed using cis(±)-4-chloro-N-(3-isopropoxypiperidin-4-yl)-5-ethyl-1H-imidazole-2-carboxamide hydrochloride obtained in Example (148a) (0.150 g, 0.427 mmol), diisopropylethylamine (0.186 mL, 1.07 mmol) and ethyl 2-bromo-1,3-benzothiazole-7-carboxylate obtained in Example (1f) (0.147 g, 0.514 mmol), to obtain 0.140g of the title compound as a yellow foamy solid (63%).

$^1$H NMR spectrum (400 MHz, CDCl$_3$) δ ppm: 1.08 (3H, d, J=6.1 Hz), 1.14 (3H, d, J=6.1 Hz), 1.28 (3H, t, J=7.6 Hz), 1.44 (3H, t, J=7.1 Hz), 1.78-1.83 (1H, m), 2.08-2.21 (1H, m), 2.70 (2H, q, J=7.6 Hz), 3.22-3.32 (2H, m), 3.73 (1H, s), 3.76-3.83 (1H, m), 4.21-4.36 (3H, m), 4.43-4.48 (2H, m), 7.36 (1H, t, J=7.8 Hz), 7.49-7.57 (1H, m), 7.69 (1H, dd, J=8.1, 1.0 Hz), 7.79 (1H, dd, J=7.8, 1.0 Hz), 11.77 (1H, br s).

(148c) cis(±)-2-(4-{[(4-Chloro-5-ethyl-1H-imidazol-2-yl)carbonyl]amino}-3-isopropoxypiperidin-1-yl)-1,3-benzothiazole-7-carboxylic acid Ethyl cis(±)-2-(4-{[(4-chloro-5-ethyl-1H-imidazol-2-yl)carbonyl]amino}-3-isopropoxypiperidin-1-yl)-1,3-benzothiazole-7-carboxylate obtained in Example (148b) (0.140 g, 0.269 mmol) was dissolved in tetrahydrofuran (5 mL). The solution was subjected to the same operation as in Example (1i) using lithium hydroxide monohydrate (0.135 g, 3.23 mmol) and water (5 mL), to obtain 0.129 g of the title compound as a white solid (98%).

$^1$H NMR spectrum (400 MHz, DMSO-d$_6$) δ ppm: 0.99 (3H, d, J=6.0 Hz), 1.04 (3H, d, J=6.0 Hz), 1.14 (3H, t, J=7.6 Hz), 1.65-1.74 (1H, m), 1.84-1.96 (1H, m), 2.55 (2H, q, J=7.6 Hz), 3.33-3.43 (3H, m), 3.73-3.79 (2H, m), 4.11-4.28 (2H, m), 7.33 (1H, t, J=7.8 Hz), 7.53-7.64 (3H, m), 13.36 (1H, s).

mass spectrum (ESI): m/z 492 (M+H)$^+$.

Example 149 cis(±)-2-(4-{[(4-Chloro-5-ethyl-1H-imidazol-2-yl)carbonyl]amino}-3-isopropoxypiperidin-1-yl)-4-(2-methoxyethylcarbamoyl)-1,3-thiazole-5-carboxylic acid (Exemplified Compound No. 149)

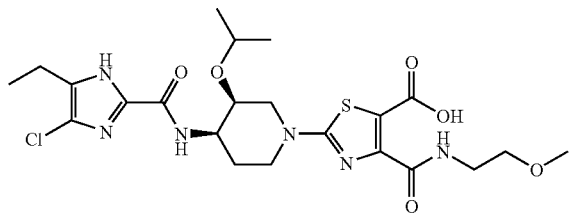

(149a) Ethyl 2-chloro-4-[(2-methoxyethyl)carbamoyl]-1,3-thiazole-5-carboxylate

The compound was synthesized according to the method described in the following document.
WO 2008/20222 A1

(149b) Ethyl cis(±)-2-(4-{[(4-chloro-5-ethyl-1H-imidazol-2-yl)carbonyl]amino}-3-isopropoxypiperidin-1-yl)-4-(2-methoxyethylcarbamoyl)-1,3-thiazole-5-carboxylate The same operation as in Example (1h) was performed using cis(±)-4-chloro-N-(3-isopropoxypiperidin-4-yl)-5-ethyl-1H-imidazole-2-carboxamide hydrochloride obtained in Example (148a) (0.150 g, 0.427 mmol), diisopropylethylamine (0.186 mL, 1.07 mmol) and ethyl 2-chloro-4-[(2-methoxyethyl)carbamoyl]-1,3-thiazole-5-carboxylate obtained in Example (149a) (0.167 g, 0.572 mmol), to obtain 0.180g of the title compound as a yellow solid (74%).

$^1$H NMR spectrum (400 MHz, CDCl$_3$) δ ppm: 1.10 (3H, d, J=6.1 Hz), 1.13 (3H, d, J=6.1 Hz), 1.26 (3H, t, J=7.6 Hz), 1.34 (3H, t, J=7.6 Hz), 1.72-1.79 (1H, m), 2.00-2.12 (1H, m), 2.68 (2H, q, J=7.6 Hz), 3.15-3.27 (2H, m), 3.38 (3H, br s), 3.56-3.60 (2H, m), 3.60-3.66 (2H, m), 3.67-3.78 (2H, m), 4.08-4.25 (3H, m), 4.27-4.34 (2H, m), 7.36 (1H, d, J=8.8 Hz), 8.39 (1H, br s), 10.35 (1H, br s).

(149c) cis(±)-2-(4-{[(4-Chloro-5-ethyl-1H-imidazol-2-yl)carbonyl]amino}-3-isopropoxypiperidin-1-yl)-4-(2-methoxyethylcarbamoyl)-1,3-thiazole-5-carboxylic acid Ethyl cis(±)-2-(4-{[(4-chloro-5-ethyl-1H-imidazol-2-yl)carbonyl]amino}-3-isopropoxypiperidin-1-yl)-4-(2-methoxyethylcarbamoyl)-1,3-thiazole-5-carboxylate obtained in Example (149b) (0.180 g, 0.315 mmol) was dissolved in tetrahydrofuran (5 mL). The solution was subjected to the same operation as in Example (1i) using lithium hydroxide monohydrate (52.9 g, 1.26 mmol) and water (5 mL), to obtain 0.167 g of the title compound as a white solid (98%).

$^1$H NMR spectrum (400 MHz, DMSO-d$_6$) δ ppm: 0.99 (3H, d, J=6.0 Hz), 1.03 (3H, d, J=6.0 Hz), 1.14 (3H, t, J=7.6 Hz), 1.62-1.72 (1H, m), 1.81-1.91 (1H, m), 2.55 (2H, q, J=7.6 Hz), 3.21-3.31 (1H, m), 3.24 (3H, s), 3.30 (2H, s), 3.34-3.58 (5H, m), 3.72-3.80 (2H, m), 4.16 (1H, s), 7.59 (1H, d, J=8.7 Hz), 9.33 (1H, br s).

mass spectrum (ESI): m/z 543 (M+H)$^+$.

Example 150 cis(±)-4-Chloro-N-[3-ethoxy-1-(1,3,4-thiadiazol-2-yl)piperidin-4-yl]-5-ethyl-1H-imidazole-2-carboxamide (Exemplified Compound No. 150)

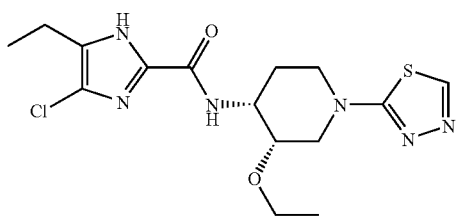

cis(±)-4-Chloro-N-(3-ethoxypiperidin-4-yl)-5-ethyl-1H-imidazole-2-carboxamide hydrochloride obtained in Example (131a) (0.100 g, 0.296 mmol), diisopropylethylamine (0.0568 mL, 0.326 mmol), 2-bromo-1,3,4-thiadiazole (0.0587 g, 0.356 mmol) and cesium carbonate (0.106 g, 0.326 mmol) were suspended in N-methylpyrrolidone (2 mL). The suspension was heated using a microwave reactor at 180° C. for 30 minutes. Ethyl acetate and water were added to the reaction solution, and the aqueous layer was extracted with ethyl acetate. The organic layer was washed with water and brine, and then dried over anhydrous sodium sulfate. Following concentration under reduced pressure, the residue was purified by silica gel chromatography (elution solvent: hexane/ethyl acetate=1/1, then methanol/ethyl acetate=0/1, 1/9) to obtain 80 mg of the crude title compound. This was further purified by thin layer silica gel chromatography (developing solvent: methanol/dichloromethane=5/95) to obtain 43 mg of the title compound as a pale brown solid (36%).

¹H NMR spectrum (400 MHz, CDCl₃) δ ppm: 1.16 (3H, t, J=7.3 Hz), 1.27 (3H, t, J=7.3 Hz), 1.76-1.84 (1H, m), 2.09-2.21 (1H, m), 2.70 (2H, q, J=7.3 Hz), 3.24 (1H, d, J=14.1 Hz), 3.27-3.36 (1H, m), 3.41-3.50 (1H, m), 3.64 (1H, s), 3.70-3.78 (1H, m), 3.90-3.97 (1H, m), 4.20-4.29 (1H, m), 4.37-4.45 (1H, m), 7.48 (1H, d, J=8.8 Hz), 8.43-8.45 (1H, m), 11.11 (1H, s).

mass spectrum (ESI): m/z 385 (M+H)⁺.

Example 151 cis(±)-1-[(4-{[(4-Chloro-5-ethyl-1H-imidazol-2-yl)carbonyl]amino}-3-ethoxypiperidin-1-yl)carbonyl]-L-proline (Exemplified Compound No. 151)

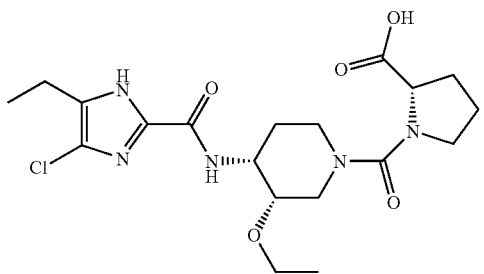

(151a) 1-(1H-Imidazol-1-ylcarbonyl)-L-proline methyl ester

L-proline methyl ester hydrochloride (0.300 g, 1.81 mmol) was dissolved in dichloromethane (5 ml). Triethylamine (0.202 g, 1.99 mmol) and 1,1'-carbonylbis-1H-imidazole (0.352 g, 2.17 mmol) were added, and the mixture was stirred at room temperature for five days. Water was added to the reaction solution, followed by extraction with dichloromethane. Then, the organic layer was washed with brine and dried over anhydrous sodium sulfate. Following concentration under reduced pressure, 0.404g of the title compound was obtained as a colorless oily substance (100%).

¹H NMR spectrum (400 MHz, CDCl₃) δ ppm: 1.98-2.17 (3H, m), 2.32-2.42 (1H, m), 3.72-3.85 (2H, m), 3.78 (3H, s), 4.64 (1H, dd, J=7.9, 5.5 Hz), 7.09-7.10 (1H, m), 7.37 (1H, s), 8.04 (1H, s).

(151b) 3-{(S)-2-Methoxycarbonylpyrrolidine-1-carbonyl}-3-methyl-1H-imidazol-3-ium iodide 1-(1H-Imidazol-1-ylcarbonyl)-L-proline methyl ester obtained in Example (151a) (0.200 g, 0.896 mmol) was dissolved in acetonitrile (2 ml). Methyl iodide (0.508 g, 3.58 mmol) was added, and the mixture was stirred at room temperature for 24 hours. The reaction solution was concentrated under reduced pressure to obtain 0.327 g of the title compound as a pale yellow foamy substance (100%).

(151c) cis(±)-1-[(4-{[(4-Chloro-5-ethyl-1H-imidazol-2-yl)carbonyl]amino}-3-ethoxypiperidin-1-yl)carbonyl]-L-proline methyl ester Ethyl acetate and saturated sodium bicarbonate solution were added to cis(±)-4-chloro-N-(3-ethoxypiperidin-4-yl)-5-ethyl-1H-imidazole-2-carboxamide hydrochloride obtained in Example (131a) (0.100 g, 0.296 mmol), and the aqueous layer was extracted with ethyl acetate. Thereafter, drying over anhydrous sodium sulfate gave cis(±)-4-{[(5-chloro-4-ethyl-1H-imidazol-2-yl)carbonyl]amino}-3-ethoxypiperidine. This and 3-{(S)-2-methoxycarbonylpyrrolidine-1-carbonyl}-3-methyl-1H-imidazol-3-ium iodide obtained in Example (151b) (0.162 g, 0.444 mmol) were dissolved in dichloromethane (5 ml), and the solution was stirred at room temperature for 24 hours. Water and ethyl acetate were added to the reaction solution, followed by extraction with ethyl acetate and further extraction with dichloromethane. The organic layers were combined and dried over anhydrous sodium sulfate. Following concentration under reduced pressure, the residue was purified by silica gel chromatography (elution solvent: hexane/ethyl acetate=1/1, then methanol/ethyl acetate=0/100, 5/95, 10/90) to obtain 38 mg of the crude title compound. This was further purified by thin layer silica gel chromatography (developing solvent: methanol/dichloromethane=5/95) to obtain 24 mg of the title compound as a colorless oily substance (18%).

¹H NMR spectrum (400 MHz, CDCl₃) δ ppm: 1.18-1.29 (6H, m), 1.67-1.75 (1H, m), 1.81-1.93 (2H, m), 1.94-2.09 (2H, m), 2.19-2.32 (1H, m), 2.69 (2H, q, J=7.6 Hz), 2.87-2.97 (2H, m), 3.37-3.58 (4H, m), 3.66-3.78 (2H, m), 3.72 (3H, s), 3.99-4.03 (1H, m), 4.12-4.20 (1H, m), 4.48-4.66 (1H, m), 7.49-7.58 (1H, m), 12.06 (1H, br s).

(151d) cis(±)-1-[(4-{[(4-Chloro-5-ethyl-1H-imidazol-2-yl)carbonyl]amino}-3-ethoxypiperidin-1-yl)carbonyl]-L-proline The same operation as in Example (1i) was performed using cis(±)-1-[(4-{[(4-chloro-5-ethyl-1H-imidazol-2-yl)carbonyl]amino}-3-ethoxypiperidin-1-yl)carbonyl]-L-proline obtained in Example (151c) (24.0 mg, 0.0526 mmol) and lithium hydroxide hydrate (2.43 mg, 0.0579 mmol), to obtain 20.0 mg of the title compound as a white solid (86%).

¹H NMR spectrum (400 MHz, CD₃OD) δ ppm: 1.16-1.29 (6H, m), 1.38-1.41 (1H, m), 1.66-1.89 (3H, m), 1.90-2.36 (2H, m), 2.64 (2H, q, J=7.6 Hz), 2.93-3.15 (2H, m), 3.38-3.64 (3H, m), 3.67-3.75 (3H, m), 3.81-4.47 (3H, m).

mass spectrum (ESI): m/z 442 (M+H)⁺

Example 152 cis(±)-(2E)-4-(4-{[(4-Chloro-5-ethyl-1H-imidazol-2-yl)carbonyl]amino}-3-methoxypiperidin-1-yl)-4-oxo-2-butenoic acid (Exemplified Compound No. 152)

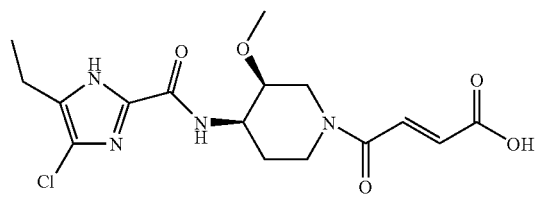

(152a) Ethyl cis(±)-(2E)-4-(4-{[(4-chloro-5-ethyl-1H-imidazol-2-yl)carbonyl]amino}-3-methoxypiperidin-1-yl)-4-oxo-2-butenoate tert-Butyl cis(±)-4-{[(4-chloro-5-ethyl-1H-imidazol-2-yl)carbonyl]amino}-3-methoxypiperidine-1-carboxylate obtained by the method described in Example (1g) (133 mg, 0.34 mmol) was dissolved in methanol (2 mL). A 4 N hydrochloric acid/ethyl acetate solution (4 mL) was added, and the mixture was stirred at 70° C. for 30 minutes. Following concentration under reduced pressure, the residue was dissolved in DMA (5 mL). Fumaric acid monoethyl ester (54.42 mg, 0.38 mmol), WSC hydrochloride (197.41 mg, 1.03 mmol) and DMAP (41.94 mg, 0.34 mmol) were added, and the mixture was stirred at room temperature overnight. Dilute hydrochloric acid was added to the reaction solution, followed by extraction with ethyl acetate. Then, the organic layer was washed with brine and dried over anhydrous sodium sulfate.

Following concentration under reduced pressure, the residue was purified by silica gel column chromatography (elution solvent: dichloromethane/methanol=40/1, 20/1, 10/1) to obtain 147.3 mg of the title compound as a solid (100%).

$^1$H NMR spectrum (400 MHz, CDCl$_3$) δ ppm: 1.26 (3H, t, J=7.57 Hz), 1.32 (3H, t, J=7.20 Hz), 1.80-1.86 (2H, m), 2.69 (2H, q, J=7.57 Hz), 3.18-3.22 (1H, m), 3.41 (3H, s), 3.47-3.53 (1H, m), 3.96-4.05 (1H, m), 4.20-4.30 (3H, m), 4.61-4.72 (1H, m), 5.02-5.06 (1H, m), 6.76 (1H, d, J=15.38 Hz), 7.40-7.49 (2H, m), 11.00 (1H, br s).

(152b) cis(±)-(2E)-4-(4-{[(4-Chloro-5-ethyl-1H-imidazol-2-yl)carbonyl]amino}-3-methoxypiperidin-1-yl)-4-oxo-2-butenoic acid The same operation as in Example (1i) was performed using ethyl cis(±)-(2E)-4-(4-{[(4-chloro-5-ethyl-1H-imidazol-2-yl)carbonyl]amino}-3-methoxypiperidin-1-yl)-4-oxo-2-butenoate obtained in Example (152a) (140.6 mg, 0.34 mmol) and a 2 N aqueous lithium hydroxide solution (6 mL), to obtain 72.2 mg of the title compound as a white solid (55%). This compound is estimated to be an about 1:1 rotamer mixture according to NMR. $^1$H NMR spectrum (400 MHz, DMSO-d$_6$) δ ppm: 1.11-1.18 (3H, m), 1.65-1.72 (2H, m), 2.52-2.59 (2H, m), 2.79-2.95 (1H, m), 3.47-3.52 (2H, m), 3.57 (3H, s), 3.93-4.24 (2H, m), 4.34-4.37 (1×1/2H, m), 4.70-4.73 (1×1/2H, m), 6.46-6.55 (1H, m), 7.33-7.44 (1H, m), 7.54-7.66 (1H, m), 13.36-13.38 (1H, m).

mass spectrum (ESI): m/z 385 (M+H)$^+$.

Example 153 cis(±)-4-Chloro-5-ethyl-N-{3-methoxy-1-[(2E)-4-(methoxyamino)-4-oxobuten-2-oyl]piperidin-4-yl}-1H-imidazole-2-carboxamide (Exemplified Compound No. 153)

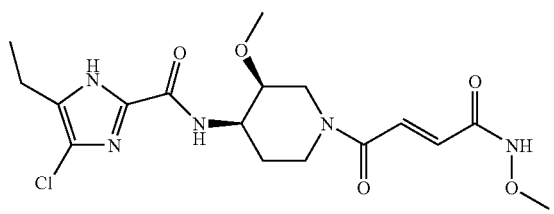

(153a) cis(±)-4-Chloro-5-ethyl-N-{3-methoxy-1-[(2E)-4-(methoxyamino)-4-oxobuten-2-oyl]piperidin-4-yl}-1H-imidazole-2-carboxamide The same operation as in Example (1g) was performed using cis(±)-(2E)-4-(4-{[(4-chloro-5-ethyl-1H-imidazol-2-yl)carbonyl]amino}-3-methoxypiperidin-1-yl)-4-oxo-2-butenoic acid obtained in Example (153b) (55 mg, 0.14 mmol), O-methylhydroxylamine hydrochloride (23.87 mg, 0.29 mmol), WSC hydrochloride (82.2 mg, 0.43 mmol) and DMAP (17.46 mg, 0.14 mmol), to obtain 25.4 mg of the title compound as a white solid (43%). This compound is estimated to be an about 1:1 rotamer mixture according to NMR.

$^1$H NMR spectrum (400 MHz, DMSO-d$_6$) δ ppm: 1.11-1.17 (3H, m), 1.64-1.71 (2H, m), 2.52-2.59 (2H, m), 2.77-2.96 (1H, m), 3.26-3.31 (1H, m), 3.33 (3H, s), 3.47-3.52 (1H, m), 3.66 (3H, s), 3.98-4.24 (2H, m), 4.34-4.38 (1×½H, m), 4.70-4.74 (1×½H, m), 6.59-6.63 (1H, m), 7.32-7.36 (1H, m), 7.56-7.61 (1H, m).

Example 154 cis(±)-4-[(1E)-3-(4-{[(4-Chloro-5-ethyl-1H-imidazol-2-yl)carbonyl]amino}-3-methoxypiperidin-1-yl)-3-oxo-1-propen-1-yl]benzoic acid (Exemplified Compound No. 154)

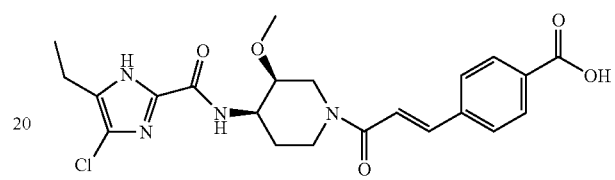

(154a) Methyl cis(±)-4-[(1E)-3-(4-{[(4-chloro-5-ethyl-1H-imidazol-2-yl)carbonyl]amino}-3-methoxypiperidin-1-yl)-3-oxo-1-propen-1-yl]benzoate The same operation as in Example (152a) was performed using tert-butyl cis(±)-4-{[(4-chloro-5-ethyl-1H-imidazol-2-yl)carbonyl]amino}-3-methoxypiperidine-1-carboxylate obtained by the method described in Example (1g) (86.7 mg, 0.22 mmol), a 4 N hydrochloric acid/ethyl acetate solution (4 mL), (2E)-3-[4-(methoxycarbonyl)phenyl]-2-propenoic acid (63.53 mg, 0.27 mmol) (reference: Journal of Organometallic Chemistry; 682; 1-2; 2003; 20-25), WSC hydrochloride (128.88 mg, 0.67 mmol), HOBt (30.3 mg, 0.22 mmol) and diisopropylethylamine (173.79 mg, 1.34 mmol), to obtain 135.2 mg of the title compound as a pale yellow oily substance.

$^1$H NMR spectrum (400 MHz, CDCl$_3$) δ ppm: 1.24-1.30 (3H, m), 1.66-2.01 (2H, m), 2.64-2.74 (2H, m), 2.96 (3H, s), 3.20-3.52 (3H, m), 3.93 (3H, s), 4.10-4.37 (2H, m), 4.66-5.19 (1H, m), 6.92-7.05 (1H, m), 7.52-7.69 (3H, m), 8.03-8.04 (3H, m), 11.31 (1H, brs).

(154b) cis(±)-4-[(1E)-3-(4-{[(4-Chloro-5-ethyl-1H-imidazol-2-yl)carbonyl]amino}-3-methoxypiperidin-1-yl)-3-oxo-1-propen-1-yl]benzoic acid The same operation as in Example (1i) was performed using methyl cis(±)-4-[(1E)-3-(4-{[(4-chloro-5-ethyl-1H-imidazol-2-yl)carbonyl]amino}-3-methoxypiperidin-1-yl)-3-oxo-1-propen-1-yl]benzoate obtained in Example (154a) (135.2 mg, 0.28 mmol) and a 2 N aqueous lithium hydroxide solution (6 mL), to obtain 87.7 mg of the title compound as a white solid (66%). This compound is estimated to be an about 1:1 rotamer mixture according to NMR.

$^1$H NMR spectrum (400 MHz, DMSO-d$_6$) δ ppm: 1.10-1.18 (3H, m), 1.59-1.85 (2H, m), 2.52-2.60 (2H, m), 2.81-2.94 (1H, m), 3.28-3.31 (1H, m), 3.33 (3H, s), 3.48-3.53 (1H, m), 4.17-4.20 (1H, m), 4.29-4.32 (1×½H, m), 4.42-4.45 (1×½H, m), 4.56-4.60 (1×½H, m), 4.80-4.83 (1×1/2H, m), 7.35-7.60 (3H, m), 7.80-7.95 (4H, m), 13.37 (1H, brs).

mass spectrum (ESI): m/z 461 (M+H)$^+$.

Example 155 cis(±)-4-[(1E)-3-(4-{[(4-Chloro-5-ethyl-1H-imidazol-2-yl)carbonyl]amino}-3-methoxypiperidin-1-yl)-3-oxo-1-propen-1-yl]-3-methoxybenzoic acid

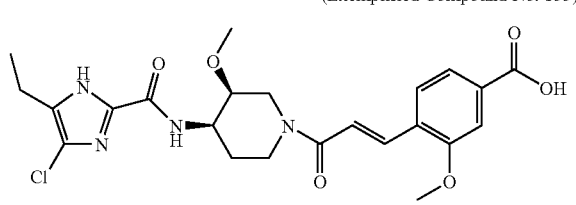

(Exemplified Compound No. 155)

(155a) Methyl cis(±)-4-[(1E)-3-(4-{[(4-chloro-5-ethyl-1H-imidazol-2-yl)carbonyl]amino}-3-methoxypiperidin-1-yl)-3-oxo-1-propen-1-yl]-3-methoxybenzoate The same operation as in Example (152a) was performed using tert-butyl cis(±)-4-{[(4-chloro-5-ethyl-1H-imidazol-2-yl)carbonyl]amino}-3-methoxypiperidine-1-carboxylate obtained by the method described in Example (1g) (86.7 mg, 0.22 mmol), a 4 N hydrochloric acid/ethyl acetate solution (4 mL), (2E)-3-[2-methoxy-4-(methoxycarbonyl)phenyl]-2-propenoic acid (63.53 mg, 0.27 mmol) (reference: Journal of Organometallic Chemistry; 682; 1-2; 2003; 20-25), WSC hydrochloride (128.88 mg, 0.67 mmol), HOBt (30.3 mg, 0.22 mmol) and diisopropylethylamine (173.79 mg, 1.34 mmol), to obtain 127.4 mg of the title compound as a pale yellow oily substance.

$^1$H NMR spectrum (400 MHz, CDCl$_3$) δ ppm: 1.27 (3H, t, J=7.56 Hz), 1.72-1.92 (2H, m), 2.69 (2H, q, J=7.56 Hz), 2.89 (3H, s), 2.96 (3H, s), 3.41-3.48 (2H, m), 3.92-3.95 (3H, m), 4.11-4.34 (3H, m), 4.82-5.04 (1H, m), 7.05-7.12 (1H, m), 7.45-7.64 (3H, m), 7.84-8.02 (2H, m), 11.19 (1H, br s).

(155b) cis(±)-4-[(1E)-3-(4-{[(4-Chloro-5-ethyl-1H-imidazol-2-yl)carbonyl]amino}-3-methoxypiperidin-1-yl)-3-oxo-1-propen-1-yl]-3-methoxybenzoic acid The same operation as in Example (1i) was performed using methyl cis(±)-4-[(1E)-3-(4-{[(4-chloro-5-ethyl-1H-imidazol-2-yl)carbonyl]amino}-3-methoxypiperidin-1-yl)-3-oxo-1-propen-1-yl]-3-methoxybenzoate obtained in Example (155a) (127.4 mg, 0.25 mmol) and a 2 N aqueous lithium hydroxide solution (6 mL), to obtain 87.1 mg of the title compound as a white solid (70%). This compound is estimated to be an about 1:1 rotamer mixture according to NMR.

$^1$H NMR spectrum (400 MHz, DMSO-d$_6$) δ ppm: 1.10-1.18 (3H, m), 1.63-1.78 (2H, m), 2.51-2.59 (2H, m), 2.79-2.93 (1H, m), 3.28-3.37 (7H, m), 3.47-3.52 (1H, m), 3.92 (3H, s), 4.12-4.22 (1H, m), 4.25-4.28 (1×½H, m), 4.42-4.45 (1×½H, m), 4.51-4.54 (1×½H, m), 4.79-4.83 (1×½H, m), 7.35 (1H, d, J=15.62 Hz), 7.51-7.62 (3H, m), 7.75-7.84 (1H, m), 7.90-7.97 (1H, m), 13.37 (1H, br s).

mass spectrum (ESI): m/z 491 (M+H)$^+$.

Example 156 cis(±)-4-Chloro-N-{1-[(2Z)-2-(2,4-dioxo-1,3-thiazolidin-5-ylidene)acetyl]-3-methoxypiperidin-4-yl}-5-ethyl-1H-imidazole-2-carboxamide

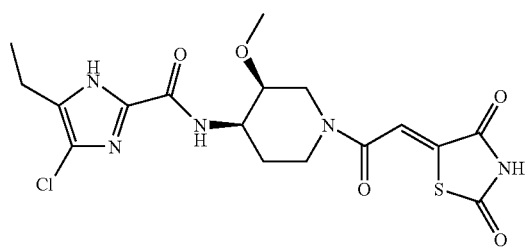

(Exemplified Compound No. 156)

(156a) cis(±)-4-Chloro-N-{1-[(2Z)-2-(2,4-dioxo-1,3-thiazolidin-5-ylidene)acetyl]-3-methoxypiperidin-4-yl}-5-ethyl-1H-imidazole-2-carboxamide The same operation as in Example (152a) was performed using tert-butyl cis(±)-4-{[(4-chloro-5-ethyl-1H-imidazol-2-yl)carbonyl]amino}-3-methoxypiperidine-1-carboxylate obtained by the method described in Example (1g) (73.65 mg, 0.19 mmol), a 4 N hydrochloric acid/ethyl acetate solution (4 mL), (2Z)-(2,4-dioxo-1,3-thiazolidin-5-ylidene)acetic acid (39.55 mg, 0.23 mmol) (reference: Journal of the Indian Chemical Society; 42; 1965; 825-830), WSC hydrochloride (109.48 mg, 0.57 mmol), HOBt (25.74 mg, 0.19 mmol) and diisopropylethylamine (147.63 mg, 1.14 mmol), to obtain 38.6 mg of the title compound as a pale yellow solid (46%). This compound is estimated to be an about 1:1 rotamer mixture according to NMR.

$^1$H NMR spectrum (400 MHz, DMSO-d$_6$) δ ppm: 1.12-1.15 (3H, m), 1.63-1.76 (2H, m), 2.52-2.59 (2H, m), 2.84-2.99 (1H, m), 3.28-3.31 (1H, m), 3.50-3.60 (4H, m), 4.20-4.36 (2H, m), 4.43-4.46 (1×½H, m), 4.71-4.75 (1×½H, m), 7.49 (1H, s), 7.55-7.68 (1H, m), 12.58 (1H, br s), 13.36 (1H, d, J=7.32 Hz).

mass spectrum (ESI): m/z 442 (M+H)$^+$.

Example 157 cis(±)-4-[(1E)-3-(4-{[(4-Chloro-5-ethyl-1H-imidazol-2-yl)carbonyl]amino}-3-methoxypiperidin-1-yl)-3-oxo-1-propen-1-yl]-3-fluorobenzoic acid

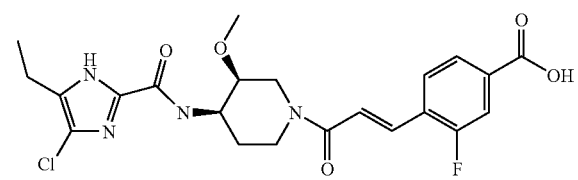

(Exemplified Compound No. 157)

(157a) Methyl cis(±)-4-[(1E)-3-(4-{[(4-chloro-5-ethyl-1H-imidazol-2-yl)carbonyl]amino}-3-methoxypiperidin-1-yl)-3-oxo-1-propen-1-yl]-3-fluorobenzoate The same operation as in Example (152a) was performed using tert-butyl cis(±)-4-{[(4-chloro-5-ethyl-1H-imidazol-2- yl)carbonyl]amino}-3-methoxypiperidine-1-carboxylate obtained by the method described in Example (1g) (73.65 mg, 0.19 mmol), a 4 N hydrochloric acid/ethyl acetate solution (4 mL), (2E)-3-[2-fluoro-4-(methoxycarbonyl)phenyl]-2-propenoic acid (51.21 mg, 0.23 mmol) (reference: Journal of Organometallic Chemistry; 682; 1-2; 2003; 20-25), WSC hydrochloride (109.48 mg, 0.57 mmol), HOBt (25.74 mg, 0.19 mmol) and diisopropylethylamine (147.63 mg, 1.14 mmol), to obtain 89.3 mg of the title compound as a pale yellow oily substance (95%). This compound is estimated to be an about 2:1 rotamer mixture according to NMR. $^1$H NMR spectrum (400 MHz, CDCl$_3$) δ ppm: 1.27 (3H, t, J=7.56 Hz), 1.80-1.94 (2H, m), 2.69 (2H, q, J=7.56 Hz), 3.20-3.26 (1H, m), 3.41-3.50 (5H, m), 3.94 (3H, s), 4.16-4.26 (2H, m), 4.71-4.74 (1×1/3H, m), 5.13 (1×2/3H, m), 7.11-7.15 (1H, m), 7.39-7.92 (4H, m), 8.02 (1H, s), 10.79 (1H, br s).

(157b) cis(±)-4-[(1E)-3-(4-{[(4-Chloro-5-ethyl-1H-imidazol-2-yl)carbonyl]amino}-3-methoxypiperidin-1-yl)-3-oxo-1-propen-1-yl]-3-fluorobenzoic acid The same operation as in Example (1i) was performed using methyl cis(±)-4-[(1E)-3-(4-{[(4-chloro-5-ethyl-1H-imidazol-2-yl)carbonyl]amino}-3-methoxypiperidin-1-yl)-3-oxo-1-propen-1-yl]-3-fluorobenzoate obtained in Example (157a) (89.3 mg, 0.18 mmol) and a 2 N aqueous lithium hydroxide solution (3 mL), to obtain 32.4 mg of the title compound as a white solid (37%). This compound is estimated to be an about 1:1 rotamer mixture according to NMR.

$^1$H NMR spectrum (400 MHz, DMSO-d$_6$) δ ppm: 1.10-1.18 (3H, m), 1.64-1.79 (2H, m), 2.52-2.59 (2H, m), 2.87-2.90 (1H, m), 3.29-3.33 (1H, m), 3.50-3.55 (4H, m), 4.18-4.20 (1H, m), 4.25-4.29 (1×½H, m), 4.42-4.45 (1×½H, m), 4.51-4.55 (1×½H, m), 4.79-4.83 (1×½H, m), 7.43-7.79 (5H, m), 8.06-8.16 (1H, m), 13.37 (1H, br s).

mass spectrum (ESI): m/z 479 (M+H)$^+$.

Example 158 cis(±)-6-(4-{[(4-Chloro-5-ethyl-1H-imidazol-2-yl)carbonyl]amino}-3-methoxypiperidin-1-yl)pyridine-2-carboxylic acid (Exemplified Compound No. 158)

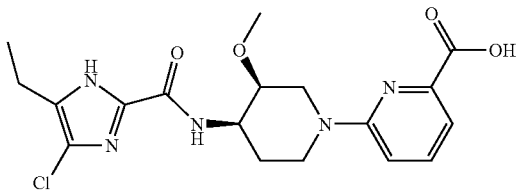

(158a) Methyl cis(±)-6-(4-{[(4-chloro-5-ethyl-1H-imidazol-2-yl)carbonyl]amino}-3-methoxypiperidin-1-yl)pyridine-2-carboxylate tert-Butyl cis(±)-4-{[(4-chloro-5-ethyl-1H-imidazol-2-yl)carbonyl]amino}-3-methoxypiperidine-1-carboxylate obtained by the method described in Example (1g) (25 mg, 0.06 mmol) was dissolved in methanol (3 mL). A 4 N hydrochloric acid/ethyl acetate solution (2 mL) was added, and the mixture was stirred at room temperature for one hour. Following concentration under reduced pressure, the residue was dissolved in NMP (0.5 mL). Triethylamine (9.81 mg, 0.1 mmol) and methyl 6-bromo-pyridine-2-carboxylate (13.96 mg, 0.06 mmol) were added, and the mixture was stirred using a microwave irradiation reactor at 150° C. for 10 minutes. Water was added to the reaction solution, followed by extraction with ethyl acetate. Sodium chloride was added to the aqueous layer, followed by reextraction with ethyl acetate four times. The organic layers were combined and dried over anhydrous sodium sulfate. Following concentration under reduced pressure, the residue was purified by silica gel column chromatography (elution solvent: dichloromethane/methanol=40/1, 20/1, 10/1) to obtain 30.6 mg of the title compound.

(158b) cis(±)-6-(4-{[(4-Chloro-5-ethyl-1H-imidazol-2-yl)carbonyl]amino}-3-methoxypiperidin-1-yl)pyridine-2-carboxylic acid The same operation as in Example (1i) was performed using methyl cis(±)-6-(4-{[(4-chloro-5-ethyl-1H-imidazol-2-yl)carbonyl]amino}-3-methoxypiperidin-1-yl)pyridine-2-carboxylate obtained in Example (158a) (66.6 mg, 0.16 mmol) and a 2 N aqueous lithium hydroxide solution (3 mL), to obtain 21.8 mg of the title compound as a white solid (34%).

$^1$H NMR spectrum (400 MHz, DMSO-d$_6$) δ ppm: 1.14 (3H, t, J=7.57 Hz), 1.61-1.82 (2H, m), 2.52-2.56 (2H, m), 3.02-3.06 (1H, m), 3.29-3.50 (5H, m), 4.11-4.37 (2H, m), 4.72-4.84 (1H, m), 6.95-7.04 (1H, m), 7.16-7.19 (1H, m), 7.54-7.56 (2H, m).

mass spectrum (ESI): m/z 408 (M+H)$^+$.

Example 159 cis(±)-2-(4-{[(4-Chloro-5-ethyl-1H-imidazol-2-yl)carbonyl]amino}-3-methoxypiperidin-1-yl)pyridine-4-carboxylic acid (Exemplified Compound No. 159)

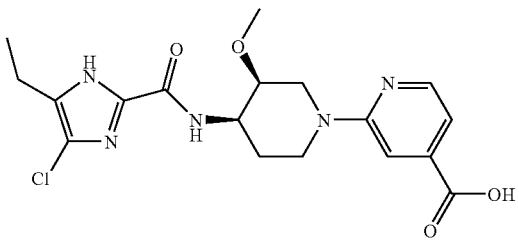

(159a) cis(±)-4-Chloro-5-ethyl-N-(3-methoxypiperidin-4-yl)-1H-imidazole-2-carboxamide hydrochloride tert-Butyl cis(±)-4-{[(4-chloro-5-ethyl-1H-imidazol-2-yl)carbonyl]amino}-3-methoxypiperidine-1-carboxylate obtained by the method described in Example (1g) (500 mg, 1.29 mmol) was dissolved in methanol (30 mL). A 4 N hydrochloric acid/ethyl acetate solution (20 mL) was added, and the mixture was stirred at room temperature for one hour. Concentration under reduced pressure gave 419 mg of the title compound as a white solid (100%). (159b) Ethyl cis(±)-2-(4-{[(4-chloro-5-ethyl-1H-imidazol-2-yl)carbonyl]amino}-3-methoxypiperidin-1-yl)pyridine-4-carboxylate The same operation as in Example (158a) was performed using cis(±)-4-chloro-5-ethyl-N-(3-methoxypiperidin-4-yl)-1H-imidazole-2-carboxamide hydrochloride obtained in Example (159a) (38.22 mg, 0.12 mmol), ethyl 2-fluoropyridine-4-carboxylate (20 mg, 0.12 mmol) (reference: Journal of Medicinal Chemistry; English; 33; 6; 1990; 1667-1675) and diisopropylethylamine (45.85 mg, 0.35 mmol), to obtain 15.3 mg of the title compound as a yellow oily substance (30%).

$^1$H NMR spectrum (400 MHz, CDCl$_3$) δ ppm: 1.22-1.30 (3H, m), 1.40-1.44 (3H, m), 1.99-2.06 (2H, m), 2.37-2.39 (2H, m), 3.02-3.15 (2H, m), 3.37-3.40 (3H, m), 3.49-3.58 (1H, m), 4.27-4.29 (2H, m), 4.35-4.45 (2H, m), 4.87-5.01 (1H, m), 7.12-7.14 (1H, m), 7.24-7.26 (1H, m), 7.45-7.47 (1H, m), 8.25-8.28 (1H, m), 10.70 (1H, br s).

(159c) cis(±)-2-(4-{[(4-Chloro-5-ethyl-1H-imidazol-2-yl)carbonyl]amino}-3-methoxypiperidin-1-yl)pyridine-4-carboxylic acid The same operation as in Example (1i) was performed using ethyl cis(±)-2-(4-{[(4-chloro-5-ethyl-1H-imidazol-2-yl)carbonyl]amino}-3-methoxypiperidin-1-yl)pyridine-4-carboxylate obtained in Example (159b) (15.2 mg, 0.03 mmol) and a 2 N aqueous lithium hydroxide solution (1 mL), to obtain 3.2 mg of the title compound as a white solid (23%).

$^1$H NMR spectrum (400 MHz, DMSO-d$_6$) δ ppm: 1.11-1.18 (3H, m), 1.71-1.78 (2H, m), 2.52-2.60 (2H, m), 3.29-3.39 (5H, m), 4.09-4.12 (2H, m), 4.68-4.71 (2H, m), 6.97 (1H, d, J=4.88 Hz), 7.22 (1H, s), 7.56 (1H, d, J=8.30 Hz), 8.21 (1H, d, J=4.88 Hz), 13.37 (1H, br s).

mass spectrum (ESI): m/z 408 (M+H)$^+$.

Example 160 cis(±)-2-(4-{[(4-Chloro-5-ethyl-1H-imidazol-2-yl)carbonyl]amino}-3-methoxypiperidin-1-yl)pyridine-4-carboxylic acid

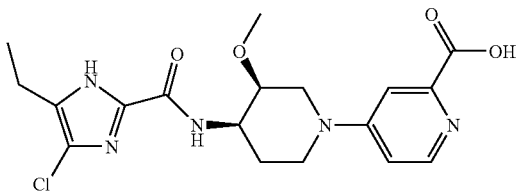

(Exemplified Compound No. 160)

(160a) Benzyl cis(±)-[3-methoxypiperidin-4-yl]carbamate hydrochloride tert-Butyl cis(±)-4-{[(benzyloxy)carbonyl]amino}-3-methoxypiperidine-1-carboxylate obtained in Example (40a) (800 mg, 2.2 mmol) was dissolved in methanol (40 mL). A 4 N hydrochloric acid/ethyl acetate solution (30 mL) was added, and the mixture was stirred at room temperature for one hour. Concentration under reduced pressure gave 691 mg of the title compound as a colorless oily substance (100%).

(160b) Methyl cis(±)-4-(4-{[(benzyloxy)carbonyl]amino}-3-methoxypiperidin-1-yl)pyridine-2-carboxylate Benzyl cis(±)-[3-methoxypiperidin-4-yl]carbamate hydrochloride obtained in Example (160a) (192.83 mg, 0.64 mmol) and methyl 4-chloropyridine-2-carboxylate (100 mg, 0.58 mmol) were dissolved in dioxane (3 ml) and DMF (1 mL). Palladium acetate (26.17 mg, 0.12 mmol), BINAP (145.16 mg, 0.23 mmol) and cesium carbonate (569.68 mg, 1.75 mmol) were added, and the mixture was stirred using a microwave irradiation reactor at 160° C. for 40 minutes. Water was added to the reaction solution, followed by extraction with ethyl acetate. Then, the organic layer was dried over anhydrous sodium sulfate and concentrated under reduced pressure. Thereafter, the residue was purified by silica gel column chromatography (elution solvent: dichloromethane/methanol=40/1, 20/1, 10/1) to obtain 74.8 mg of the title compound as a yellow oily substance.

mass spectrum (ESI): m/z 400 (M+H)$^+$.

(160c) Methyl cis(±)-4-(4-amino-3-methoxypiperidin-1-yl)pyridine-2-carboxylate

Methyl cis(±)-4-(4-{[(benzyloxy)carbonyl]amino}-3-methoxypiperidin-1-yl)pyridine-2-carboxylate obtained in Example (160b) (74.8 mg) was dissolved in ethanol (10 mL). A 10% palladium-carbon catalyst (100 mg) was added, and the mixture was stirred in a hydrogen atmosphere overnight. The reaction solution was filtered through celite and then concentrated under reduced pressure, to obtain 21.2 mg of the title compound as a colorless oily substance. The resulting compound was used for the next reaction without purification.

mass spectrum (ESI): m/z 266 (M+H)$^+$.

(160d) Methyl cis(±)-4-(4-{[(4-chloro-5-ethyl-1H-imidazol-2-yl)carbonyl]amino}-3-methoxypiperidin-1-yl)pyridine-2-carboxylate The same operation as in Example (1g) was performed using methyl cis(±)-4-(4-amino-3-methoxypiperidin-1-yl)pyridine-2-carboxylate obtained in Example (160c) (21.2 mg, 0.08 mmol), 4-chloro-5-ethyl-1H-imidazole-2-carboxylic acid obtained by the method described in Example (1d) (14 mg, 0.08 mmol), WSC hydrochloride (45.98 mg, 0.24 mmol) and HOBt (10.81 mg, 0.08 mmol), to obtain 13.8 mg of the title compound as a white solid.

(160e) cis(±)-2-(4-{[(4-Chloro-5-ethyl-1H-imidazol-2-yl)carbonyl]amino}-3-methoxypiperidin-1-yl)pyridine-4-carboxylic acid The same operation as in Example (1i) was performed using methyl cis(±)-4-(4-{[(4-chloro-5-ethyl-1H-imidazol-2-yl)carbonyl]amino}-3-methoxypiperidin-1-yl)pyridine-2-carboxylate obtained in Example (160d) (13.8 mg, 0.03 mmol) and a 2 N aqueous lithium hydroxide solution (1 mL), to obtain 1.7 mg of the title compound as a pale yellow solid (13%).

$^1$H NMR spectrum (400 MHz, DMSO-d$_6$) δ ppm: 1.14 (3H, t, J=7.57 Hz), 1.61-1.90 (2H, m), 2.52-2.58 (2H, m), 3.01-3.63 (6H, m), 4.13-4.17 (1H, m), 4.22-4.31 (1H, m), 4.43-4.52 (1H, m), 7.14 (1H, dd, J=7.08, 2.81 Hz), 7.43 (1H, d, J=2.81 Hz), 7.70 (1H, d, J=8.30 Hz), 7.97 (1H, d, J=7.08 Hz).

Example 161 cis(±)-2-(4-{[(4-Chloro-5-ethyl-1H-imidazol-2-yl)carbonyl]amino}-3-methoxypiperidin-1-yl)pyrimidine-4-carboxylic acid

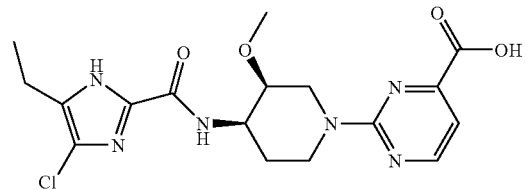

(Exemplified Compound No. 161)

(161a) Methyl cis(±)-2-(4-{[(4-chloro-5-ethyl-1H-imidazol-2-yl)carbonyl]amino}-3-methoxypiperidin-1-yl)pyrimidine-4-carboxylate The same operation as in Example (158a) was performed using cis(±)-4-chloro-5-ethyl-N-(3-methoxypiperidin-4-yl)-1H-imidazole-2-carboxamide hydrochloride obtained in Example (159a) (127.36 mg, 0.39 mmol), methyl 2-chloropyrimidine-4-carboxylate (68 mg, 0.39 mmol) (reference:

U.S. Pat. No. 5,591,853 A1) and diisopropylethylamine (152.79 mg, 1.18 mmol), to obtain 95.8 mg of the title compound as a yellow oily substance (58%).

$^1$H NMR spectrum (400 MHz, CDCl$_3$) δ ppm: 1.24-1.31 (3H, m), 1.78-2.05 (2H, m), 2.70 (2H, q, J=7.49 Hz), 3.00-3.03 (2H, m), 3.39 (3H, s), 3.49-3.53 (1H, m), 3.95 (3H, s), 4.23-4.33 (1H, m), 4.86-4.96 (1H, m), 5.25-5.35 (1H, m), 7.09-7.13 (1H, m), 7.46-7.52 (1H, m), 8.48-8.49 (1H, m), 11.14 (1H, brs).

(161b) cis(±)-2-(4-{[(4-Chloro-5-ethyl-1H-imidazol-2-yl)carbonyl]amino}-3-methoxypiperidin-1-yl)pyrimidine-4-carboxylic acid The same operation as in Example (1i) was performed using methyl cis(±)-2-(4-{[(4-chloro-5-ethyl-1H-imidazol-2-yl)carbonyl]amino}-3-methoxypiperidin-1-yl)pyrimidine-4-carboxylate obtained in Example (161a) (95.8 mg, 0.23 mmol), and a 2 N aqueous lithium hydroxide solution (3 mL), to obtain 58.4 mg of the title compound as a pale yellow solid (58%).

$^1$H NMR spectrum (400 MHz, DMSO-d$_6$) δ ppm: 1.14 (3H, t, J=7.45 Hz), 1.64-1.77 (2H, m), 2.51-2.59 (2H, m), 3.07-3.10 (2H, m), 3.30 (3H, s), 3.51-3.53 (1H, m), 4.19-4.21 (1H, m), 4.67-4.70 (1H, m), 5.03-5.07 (1H, m), 6.92-6.97 (1H, m), 7.54 (1H, d, J=8.54 Hz), 8.43-8.50 (1H, m), 13.38 (1H, br s).

mass spectrum (ESI): m/z 409 (M+H)$^+$.

Example 162 cis(±)-5-(4-{[(4-Chloro-5-ethyl-1H-imidazol-2-yl)carbonyl]amino}-3-methoxypiperidin-1-yl)pyridine-3-carboxylic acid (Exemplified Compound No. 162)

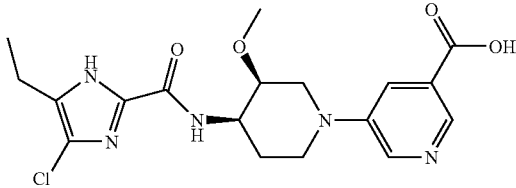

(162a) Ethyl cis(±)-5-(4-{[(benzyloxy)carbonyl]amino}-3-methoxypiperidin-1-yl)pyridine-3-carboxylate The same operation as in Example (160b) was performed using benzyl cis(±)-[3-methoxypiperidin-4-yl]carbamate hydrochloride obtained in Example (160a) (832 mg, 2.76 mmol), ethyl 5-bromopyridine-3-carboxylate (530 mg, 2.3 mmol), palladium acetate (51.72 mg, 0.23 mmol), BINAP (286.89 mg, 0.46 mmol), and cesium carbonate (2.25 g, 6.91 mmol), to obtain 487 mg of the title compound as a yellow oily substance.

$^1$H NMR spectrum (400 MHz, CDCl$_3$) δ ppm: 1.38-1.43 (3H, m), 1.87-2.04 (2H, m), 2.94-3.02 (2H, m), 3.40 (3H, s), 3.50-3.55 (1H, m), 3.68-3.70 (1H, m), 3.90-3.94 (2H, m), 4.37-4.42 (2H, m), 5.12 (2H, s), 5.22-5.30 (1H, m), 7.26-7.27 (1H, m), 7.33-7.45 (7H, m).

(162b) Ethyl cis(±)-5-(4-amino-3-methoxypiperidin-1-yl)pyridine-3-carboxylate

The same operation as in Example (160c) was performed using methyl cis(±)-4-(4-{[(benzyloxy)carbonyl]amino}-3-methoxypiperidin-1-yl)pyridine-2-carboxylate obtained in Example (162a) (436 mg) and a 10% palladium-carbon catalyst (500 mg), to obtain 137.5 mg of the title compound as a colorless oily substance. The resulting compound was used for the next reaction without purification.

(162c) Ethyl cis(±)-5-(4-{[(4-chloro-5-ethyl-1H-imidazol-2-yl)carbonyl]amino}-3-methoxypiperidin-1-yl)pyridine-3-carboxylate The same operation as in Example (1g) was performed using ethyl cis(±)-5-(4-amino-3-methoxypiperidin-1-yl)pyridine-3-carboxylate obtained in Example (162b) (137.5 mg, 0.49 mmol), 4-chloro-5-ethyl-1H-imidazole-2-carboxylic acid obtained by the method described in Example (1d) (82 mg, 0.47 mmol), WSC hydrochloride (270 mg, 1.41 mmol) and HOBt (63.4 mg, 0.47 mmol), to obtain 132 mg of the title compound as a pale yellow oily substance (65%).

$^1$H NMR spectrum (400 MHz, CDCl$_3$) δ ppm: 1.27 (3H, t, J=7.57 Hz), 1.41 (3H, t, J=7.11 Hz), 1.86-1.90 (1H, m), 2.09-2.19 (1H, m), 2.70 (2H, q, J=7.57 Hz), 2.93-3.05 (2H, m), 3.44 (3H, s), 3.57 (1H, brs), 3.74-3.77 (1H, m), 4.00-4.03 (1H, m), 4.22-4.29 (1H, m), 4.41 (2H, q, J=7.11 Hz), 7.48 (1H, d, J=8.79 Hz), 7.77-7.80 (1H, m), 8.48 (1H, d, J=2.93 Hz), 8.66-8.69 (1H, m), 11.00 (1H, br s).

(162d) cis(±)-5-(4-{[(4-Chloro-5-ethyl-1H-imidazol-2-yl)carbonyl]amino}-3-methoxypiperidin-1-yl)pyridine-3-carboxylic acid The same operation as in Example (1i) was performed using ethyl cis(±)-5-(4-{[(4-chloro-5-ethyl-1H-imidazol-2-yl)carbonyl]amino}-3-methoxypiperidin-1-yl)pyridine-3-carboxylate obtained in Example (162c) (132 mg, 0.3 mmol) and a 2 N aqueous lithium hydroxide solution (3 mL), to obtain 59.6 mg of the title compound as a white solid (48%).

$^1$H NMR spectrum (400 MHz, DMSO-d$_6$) δ ppm: 1.14 (3H, t, J=7.57 Hz), 1.67-1.76 (1H, m), 1.86-2.01 (1H, m), 2.52-2.59 (2H, m), 3.00-3.13 (2H, m), 3.31 (3H, s), 3.53-3.58 (1H, m), 3.70-3.81 (1H, m), 4.05-4.21 (2H, m), 7.60 (1H, d, J=8.30 Hz), 7.65-7.69 (1H, m), 8.43 (1H, d, J=1.46 Hz), 8.55 (1H, d, J=2.93 Hz), 13.37 (1H, br s).

mass spectrum (ESI): m/z 408 (M+H)$^+$.

Example 163 cis(±)-{(5Z)-5-[2-(4-{[(4-Chloro-5-ethyl-1H-imidazol-2-yl)carbonyl]amino}-3-methoxypiperidin-1-yl)-2-oxoethylidene]-2,4-dioxo-1,3-thiazolidin-3-yl}acetic acid (Exemplified Compound No. 163)

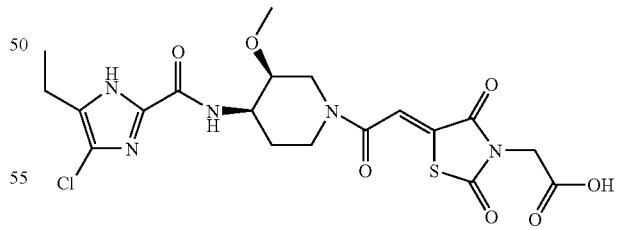

(163a) tert-Butyl cis(±)-{(5Z)-5-[2-(4-{[(4-chloro-5-ethyl-1H-imidazol-2-yl)carbonyl]amino}-3-methoxypiperidin-1-yl)-2-oxoethylidene]-2,4-dioxo-1,3-thiazolidin-3-yl}acetate cis(±)-4-Chloro-N-{1-[(2Z)-2-(2,4-dioxo-1,3-thiazolidin-5-ylidene)acetyl]-3-methoxypiperidin-4-yl}-5-ethyl-1H-imidazole-2-carboxamide obtained in Example (156) (28 mg, 0.06 mmol) was dissolved in DMF (5 mL). Ethyl bromoacetate (12.4 mg, 0.06 mmol) and sodium carbonate (6.72 mg, 0.06 mmol) were added, and the mixture was stirred at room temperature. Ethyl acetate was added to the reaction solution, and the organic layer was washed with brine and dried over anhydrous sodium sulfate. Following concentration under reduced pressure, the residue was purified by silica gel column chromatography (elution solvent: dichloromethane/methanol=40/1, 20/1, 10/1) to obtain 21.4 mg of the title compound as a white solid (61%).

mass spectrum (ESI): m/z 556 (M+H)$^+$.

(163b) cis(±)-{(5Z)-5-[2-(4-{[(4-Chloro-5-ethyl-1H-imidazol-2-yl)carbonyl]amino}-3-methoxypiperidin-1-yl)-2-oxo-ethylidene]-2,4-dioxo-1,3-thiazolidin-3-yl}acetic acid tert-Butyl cis(±)-{(5Z)-5-[2-(4-{[(4-chloro-5-ethyl-1H-imidazol-2-yl)carbonyl]amino}-3-methoxypiperidin-1-yl)-2-oxoethylidene]-2,4-dioxo-1,3-thiazolidin-3-yl}acetate obtained in Example (163a) (20.4 mg, 0.04 mmol) was dissolved in methanol (4 mL). A 20% trifluoroacetic acid-dichloromethane solution (5 ml) was added, and the mixture was stirred at room temperature. The organic solvent was evaporated under reduced pressure, and then the residue was washed with ether. The solid was collected by filtration to obtain 7.79 mg of the title compound as a white solid (43%).

$^1$H NMR spectrum (400 MHz, DMSO-d$_6$) δ ppm: 1.11-1.18 (3H, m), 1.70-1.72 (2H, m), 2.52-2.57 (2H, m), 2.91-2.99 (1H, m), 3.31 (3H, s), 3.49-3.59 (2H, m), 4.14-4.40 (4H, m), 4.45-4.83 (2H, m), 7.57-7.71 (2H, m), 13.32-13.40 (1H, m).

mass spectrum (ESI): m/z 500 (M+H)$^+$.

Example 164 cis(±)-3-(4-{[(4-Chloro-5-ethyl-1H-imidazol-2-yl)carbonyl]amino}-3-methoxypiperidin-1-yl)benzoic acid (Exemplified Compound No. 164)

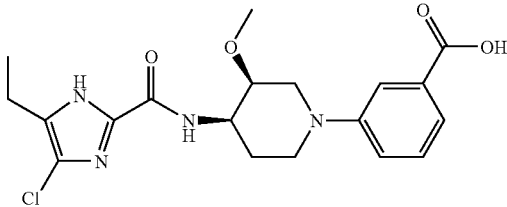

(164a) Methyl cis(±)-3-(4-amino-3-methoxypiperidin-1-yl)benzoate

The same operation as in Example (160c) was performed using methyl cis(±)-3-(4-{[(benzyloxy)carbonyl]amino}-3-methoxypiperidin-1-yl)benzoate obtained in Example (42a) (180 mg) and a 10% palladium-carbon catalyst (150 mg), to obtain 104.5 mg of the title compound as a white solid. The resulting compound was used for the next reaction without purification.

(164b) Methyl cis(±)-3-(4-{[(4-chloro-5-ethyl-1H-imidazol-2-yl)carbonyl]amino}-3-methoxypiperidin-1-yl)benzoate The same operation as in Example (1g) was performed using methyl cis(±)-3-(4-amino-3-methoxypiperidin-1-yl)benzoate obtained in Example (164a) (116.41 mg, 0.44 mmol), 4-chloro-5-ethyl-1H-imidazole-2-carboxylic acid obtained by the method described in Example (1d) (73 mg, 0.42 mmol), WSC hydrochloride (241.23 mg, 1.26 mmol) and HOBt (56.72 mg, 0.42 mmol), to obtain 148.3 mg of the title compound as a pale yellow oily substance (81%).

$^1$H NMR spectrum (400 MHz, CDCl$_3$) δ ppm: 1.27 (3H, t, J=7.56 Hz), 1.83-1.94 (1H, m), 2.09-2.21 (1H, m), 2.70 (2H, q, J=7.56 Hz), 2.89-2.98 (2H, m), 3.45 (3H, s), 3.57 (1H, brs), 3.64-3.73 (1H, m), 3.91 (3H, s), 3.91-4.00 (1H, m), 4.20-4.28 (1H, m), 7.14-7.16 (1H, m), 7.29-7.35 (1H, m), 7.47-7.54 (2H, m), 7.61-7.63 (1H, m), 11.01 (1H, br s).

(164c) cis(±)-3-(4-{[(4-Chloro-5-ethyl-1H-imidazol-2-yl)carbonyl]amino}-3-methoxypiperidin-1-yl)benzoic acid The same operation as in Example (1i) was performed using methyl cis(±)-3-(4-{[(4-chloro-5-ethyl-1H-imidazol-2-yl)carbonyl]amino}-3-methoxypiperidin-1-yl)benzoate obtained in Example (164b) (148.3 mg, 0.35 mmol) and a 2 N aqueous lithium hydroxide solution (3 mL), to obtain 27.2 mg of the title compound as a white solid (19%).

mass spectrum (ESI): m/z 407 (M+H)$^+$.

Example 165 cis(±)-2-(4-{[(4-Chloro-5-ethyl-1H-imidazol-2-yl)carbonyl]amino}-3-methoxypiperidin-1-yl)pyridine-3-carboxylic acid (Exemplified Compound No. 165)

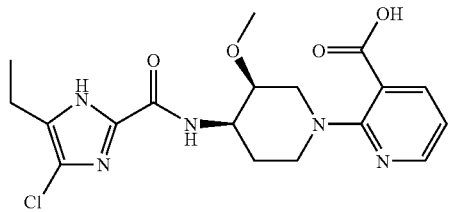

(165a) Methyl cis(±)-2-(4-{[(4-chloro-5-ethyl-1H-imidazol-2-yl)carbonyl]amino}-3-methoxypiperidin-1-yl)pyridine-3-carboxylate The same operation as in Example (158a) was performed using cis(±)-4-chloro-5-ethyl-N-(3-methoxypiperidin-4-yl)-1H-imidazole-2-carboxamide hydrochloride obtained in Example (159a) (62.51 mg, 0.19 mmol), methyl 2-fluoropyridine-3-carboxylate (68 mg, 0.39 mmol) and diisopropylethylamine (75 mg, 0.58 mmol), to obtain 65.2 mg of the title compound as a yellow brown oily substance (80%).

$^1$H NMR spectrum (400 MHz, CDCl$_3$) δ ppm: 1.26 (3H, t, J=7.56 Hz), 1.74-1.76 (1H, m), 2.10-2.12 (1H, m), 2.65-2.74 (2H, m), 3.10-3.20 (1H, m), 3.29 (3H, s), 3.37-3.50 (2H, m), 3.80-3.83 (1H, m), 3.90 (3H, s), 4.23-4.26 (2H, m), 6.69-6.75 (1H, m), 7.46 (1H, d, J=7.80 Hz), 7.93-8.00 (1H, m), 8.22-8.29 (1H, m), 10.99 (1H, br s).

(165b) cis(±)-2-(4-{[(4-Chloro-5-ethyl-1H-imidazol-2-yl)carbonyl]amino}-3-methoxypiperidin-1-yl)pyridine-3-carboxylic acid The same operation as in Example (1i) was performed using methyl cis(±)-2-(4-{[(4-chloro-5-ethyl-1H-imidazol-2-yl)carbonyl]amino}-3-methoxypiperidin-1-yl)pyridine-3-carboxylate obtained in Example (165a) (65.2 mg, 0.15 mmol) and a 2 N aqueous lithium hydroxide solution (2 mL), to obtain 27.6 mg of the title compound as a white solid (44%).

$^1$H NMR spectrum (400 MHz, DMSO-d$_6$) δ ppm: 1.14 (3H, t, J=7.44 Hz), 1.64-1.67 (1H, m), 1.93-1.98 (1H, m), 2.52-2.58 (2H, m), 3.10-3.22 (5H, m), 3.49 (1H, br s), 3.74-3.77 (1H, m), 3.95-3.99 (1H, m), 4.16-4.23 (1H, m), 6.86 (1H, dd, J=7.50, 4.70 Hz), 7.51 (1H, d, J=8.54 Hz), 7.95 (1H, dd, J=7.50, 1.95 Hz), 8.28 (1H, dd, J=4.70, 1.95 Hz), 13.35 (1H, br s).

mass spectrum (ESI): m/z 408 (M+H)+.

Example 166 cis(±)-2-(4-{[(4-Chloro-5-ethyl-1H-imidazol-2-yl)carbonyl]amino}-3-methoxypiperidin-1-yl)-6-methylpyridine-4-carboxylic acid (Exemplified Compound No. 166)

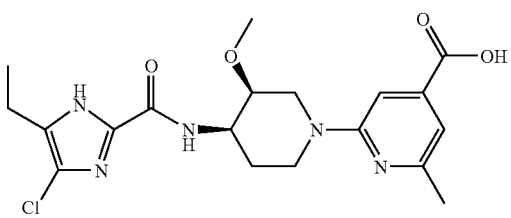

(166a) Methyl cis(±)-2-(4-{[(benzyloxy)carbonyl]amino}-3-methoxypiperidin-1-yl)-6-methylpyridine-4-carboxylate The same operation as in Example (42a) was performed using benzyl cis(±)-[3-methoxypiperidin-4-yl]carbamate hydrochloride obtained in Example (160a) (384 mg, 1.45 mmol), methyl 2-chloro-6-methylpyridine-4-carboxylate (243 mg, 1.31 mmol), palladium acetate (32.7 mg, 0.15 mmol), BINAP (181 mg, 0.29 mmol) and cesium carbonate (1.42 g, 4.36 mmol), to obtain 40.1 mg of the title compound as a yellow oily substance (6.7%).

mass spectrum (ESI): m/z 414 (M+H)+.

(166b) Methyl cis(±)-2-(4-amino-3-methoxypiperidin-1-yl)-6-methylpyridine-4-carboxylate The same operation as in Example (160c) was performed using methyl cis(±)-2-(4-{[(benzyloxy)carbonyl]amino}-3-methoxypiperidin-1-yl)-6-methylpyridine-4-carboxylate obtained in Example (166a) (38.8 mg) and a 10% palladium-carbon catalyst (40 mg), to obtain 23.9 mg of the title compound as a colorless oily substance. The resulting compound was used for the next reaction without purification.

(166c) Methyl cis(±)-2-(4-{[(4-chloro-5-ethyl-1H-imidazol-2-yl)carbonyl]amino}-3-methoxypiperidin-1-yl)-6-methylpyridine-4-carboxylate The same operation as in Example (1g) was performed using methyl cis(±)-2-(4-amino-3-methoxypiperidin-1-yl)-6-methylpyridine-4-carboxylate obtained in Example (166b) (23.9 mg, 0.44 mmol), 4-chloro-5-ethyl-1H-imidazole-2-carboxylic acid obtained by the method described in Example (1d) (14 mg, 0.08 mmol), WSC hydrochloride (46.8 mg, 0.24 mmol) and HOBt (11 mg, 0.08 mmol), to obtain 30.4 mg of the title compound as a pale yellow oily substance (86%).

mass spectrum (ESI): m/z 436 (M+H)+.

(166d) cis(±)-2-(4-{[(4-Chloro-5-ethyl-1H-imidazol-2-yl)carbonyl]amino}-3-methoxypiperidin-1-yl)-6-methylpyridine-4-carboxylic acid The same operation as in Example (1i) was performed by adding methyl cis(±)-2-(4-{[(4-chloro-5-ethyl-1H-imidazol-2-yl)carbonyl]amino}-3-methoxypiperidin-1-yl)-6-methylpyridine-4-carboxylate obtained in Example (166c) (30.4 mg, 0.07 mmol) and a 2 N aqueous lithium hydroxide solution, to obtain the title compound as a white solid.

Example 167 cis(±)-6-(4-{[(4-Chloro-5-ethyl-1H-imidazol-2-yl)carbonyl]amino}-3-methoxypiperidin-1-yl)pyridine-3-carboxylic acid (Exemplified Compound No. 167)

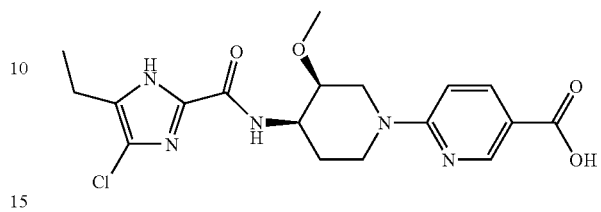

(167a) Methyl cis(±)-6-(4-{[(4-chloro-5-ethyl-1H-imidazol-2-yl)carbonyl]amino}-3-methoxypiperidin-1-yl)pyridine-3-carboxylate The same operation as in Example (158a) was performed using cis(±)-4-chloro-5-ethyl-N-(3-methoxypiperidin-4-yl)-1H-imidazole-2-carboxamide hydrochloride obtained in Example (159a) (104 mg, 0.32 mmol), methyl 6-fluoropyridine-3-carboxylate (50 mg, 0.32 mmol) and diisopropylethylamine (125 mg, 0.97 mmol), to obtain 130 mg of the title compound as a yellow brown oily substance (96%).

$^1$H NMR spectrum (400 MHz, CDCl$_3$) δ ppm: 1.26 (3H, t, J=7.56 Hz), 1.81-2.06 (2H, m), 2.66-2.72 (2H, m), 2.93-3.16 (2H, m), 3.34-3.53 (4H, m), 3.87 (3H, s), 4.22-4.34 (2H, m), 5.03-5.12 (1H, m), 6.61 (1H, d, J=9.09 Hz), 7.40-7.47 (1H, m), 8.01 (1H, dd, J=9.09, 2.26 Hz), 8.78 (1H, d, J=2.26 Hz), 10.82 (1H, br s).

(167b) cis(±)-6-(4-{[(4-Chloro-5-ethyl-1H-imidazol-2-yl)carbonyl]amino}-3-methoxypiperidin-1-yl)pyridine-3-carboxylic acid The same operation as in Example (1i) was performed using methyl cis(±)-6-(4-{[(4-chloro-5-ethyl-1H-imidazol-2-yl)carbonyl]amino}-3-methoxypiperidin-1-yl)pyridine-3-carboxylate obtained in Example (167a) (128 mg, 0.3 mmol) and a 2 N aqueous lithium hydroxide solution (5 mL), to obtain 76.5 mg of the title compound as a white solid (62%).

$^1$H NMR spectrum (400 MHz, DMSO-d$_6$) δ ppm: 1.14 (3H, t, J=7.56 Hz), 1.71-1.76 (2H, m), 2.52-2.59 (2H, m), 3.08-3.18 (2H, m), 3.29 (3H, s), 3.53 (1H, br s), 4.16-4.26 (1H, m), 4.35-4.41 (1H, m), 4.79-4.83 (1H, m), 6.90 (1H, d, J=9.02 Hz), 7.56 (1H, d, J=8.54 Hz), 7.89 (1H, dd, J=9.02, 2.44 Hz), 8.60 (1H, d, J=2.44 Hz), 12.43 (1H, br s), 13.36 (1H, br s).

mass spectrum (ESI): m/z 408 (M+H)+.

Example 168 cis(±)-4-(4-{[(4-Chloro-5-ethyl-1H-imidazol-2-yl)carbonyl]amino}-3-methoxypiperidin-1-yl)-6-methylpyridine-2-carboxylic acid (Exemplified Compound No. 168)

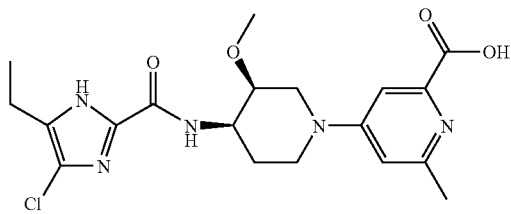

(168a) Methyl cis(±)-4-(4-{[(benzyloxy)carbonyl]amino}-3-methoxypiperidin-1-yl)-6-methylpyridine-2-carboxylate The same operation as in Example (42a) was performed using benzyl cis(±)-[3-methoxypiperidin-4-yl]carbamate hydrochloride obtained in Example (160a) (409 mg, 1.36 mmol), ethyl 4-chloro-6-methylpyridine-2-carboxylate (272 mg, 1.36 mmol), palladium acetate (30.6 mg, 0.14 mmol), BINAP (169 mg, 0.27 mmol) and cesium carbonate (1.33 g, 4.08 mmol), to obtain 194 mg of the title compound as a yellow oily substance.

$^1$H NMR spectrum (400 MHz, CDCl$_3$) δ ppm: 1.42 (3H, t, J=7.11 Hz), 1.86-1.88 (2H, m), 2.53 (3H, s), 2.94-3.02 (2H, m), 3.35 (3H, s), 3.48-3.50 (1H, m), 3.86-3.89 (2H, m), 4.10-4.12 (1H, m), 4.45 (2H, q, J=7.11 Hz), 5.12 (2H, s), 5.20-5.23 (1H, m), 6.63-6.66 (1H, m), 7.34-7.43 (5H, m), 8.01-8.04 (1H, m).

(168b) Methyl cis(±)-4-(4-amino-3-methoxypiperidin-1-yl)-6-methylpyridine-2-carboxylate The same operation as in Example (160c) was performed using methyl cis(±)-4-(4-{[benzyloxy)carbonyl]amino}-3-methoxypiperidin-1-yl)-6-methylpyridine-2-carboxylate obtained in Example (168a) (190 mg) and a 10% palladium-carbon catalyst (200 mg), to obtain 129 mg of the title compound as a colorless oily substance. The resulting compound was used for the next reaction without purification.

(168c) Methyl cis(±)-4-(4-{[(4-chloro-5-ethyl-1H-imidazol-2-yl)carbonyl]amino}-3-methoxypiperidin-1-yl)-6-methylpyridine-2-carboxylate The same operation as in Example (1g) was performed using methyl cis(±)-4-(4-amino-3-methoxypiperidin-1-yl)-6-methylpyridine-2-carboxylate obtained in Example (168b) (129 mg, 0.44 mmol), 4-chloro-5-ethyl-1H-imidazole-2-carboxylic acid obtained by the method described in Example (1d) (64 mg, 0.37 mmol), WSC hydrochloride (211 mg, 1.1 mmol) and HOBt (49.7 mg, 0.37 mmol), to obtain 174 mg of the title compound as a pale yellow oily substance.

mass spectrum (ESI): m/z 450 (M+H)$^+$.

(168d) cis(±)-4-(4-{[(4-Chloro-5-ethyl-1H-imidazol-2-yl)carbonyl]amino}-3-methoxypiperidin-1-yl)-6-methylpyridine-2-carboxylic acid The same operation as in Example (1i) was performed using methyl cis(±)-4-(4-{[(4-chloro-5-ethyl-1H-imidazol-2-yl)carbonyl]amino}-3-methoxypiperidin-1-yl)-6-methylpyridine-2-carboxylate obtained in Example (168c) (168 mg, 0.37 mmol) and a 2 N aqueous lithium hydroxide solution (4 mL), to obtain 3.1 mg of the title compound as a white solid (2%).

$^1$H NMR spectrum (400 MHz, DMSO-d$_6$) δ ppm: 1.14 (3H, t, J=7.56 Hz), 1.78-1.81 (2H, m), 2.48-2.52 (3H, m), 2.52-2.58 (2H, m), 3.32-3.36 (5H, m), 3.61 (1H, br s), 4.15-4.31 (2H, m), 4.47-4.54 (1H, m), 7.10 (1H, s), 7.36 (1H, s), 7.69 (1H, d, J=8.05 Hz), 13.36 (1H, br s).

mass spectrum (ESI): m/z 422 (M+H)$^+$.

Example 169 cis(±)-2-(4-{[(4-Chloro-5-ethyl-1H-imidazol-2-yl)carbonyl]amino}-3-methoxypiperidin-1-yl)-6-methylpyrimidine-4-carboxylic acid (Exemplified Compound No. 169)

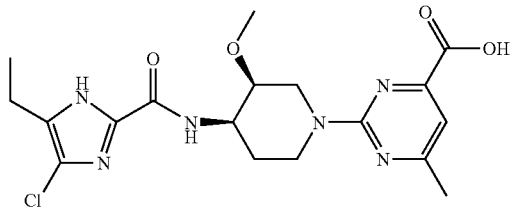

(169a) Methyl cis(±)-2-(4-{[(4-chloro-5-ethyl-1H-imidazol-2-yl)carbonyl]amino}-3-methoxypiperidin-1-yl)-6-methylpyrimidine-4-carboxylate The same operation as in Example (158a) was performed using cis(±)-4-chloro-5-ethyl-N-(3-methoxypiperidin-4-yl)-1H-imidazole-2-carboxamide hydrochloride obtained in Example (159a) (90.9 mg, 0.28 mmol), methyl 2-chloro-6-methylpyrimidine 4-carboxylate (50 mg, 0.27 mmol) and diisopropylethylamine (104 mg, 0.8 mmol), to obtain 58.4 mg of the title compound as a yellow brown oily substance (50%).

$^1$H NMR spectrum (400 MHz, CDCl$_3$) δ ppm: 1.27 (3H, t, J=7.56 Hz), 1.77-1.95 (2H, m), 2.41 (3H, s), 2.70 (2H, q, J=7.56 Hz), 2.94-3.04 (2H, m), 3.40 (3H, s), 3.50 (1H, brs), 3.93 (3H, s), 4.23-4.32 (1H, m), 4.91-4.98 (1H, m), 5.29-5.35 (1H, m), 7.01 (1H, s), 7.50 (1H, d, J=8.54 Hz), 11.23 (1H, br s).

(169b) cis(±)-2-(4-{[(4-Chloro-5-ethyl-1H-imidazol-2-yl)carbonyl]amino}-3-methoxypiperidin-1-yl)-6-methylpyrimidine-4-carboxylic acid The same operation as in Example (1i) was performed using methyl cis(±)-2-(4-{[(4-chloro-5-ethyl-1H-imidazol-2-yl)carbonyl]amino}-3-methoxypiperidin-1-yl)-6-methylpyrimidine-4-carboxylate obtained in Example (169a) (58.4 mg, 0.13 mmol) and a 2 N aqueous lithium hydroxide solution (2 mL), to obtain 9.6 mg of the title compound as a pale yellow solid (17%).

$^1$H NMR spectrum (400 MHz, DMSO-d$_6$) δ ppm: 1.14 (3H, t, J=7.56 Hz), 1.62-1.78 (2H, m), 2.36 (3H, s), 2.53-2.59 (2H, m), 3.30-3.40 (6H, m), 4.19-4.22 (1H, m), 4.70-4.74 (1H, m), 5.07-5.11 (1H, m), 6.95 (1H, s), 7.52 (1H, d, J=8.54 Hz).

mass spectrum (ESI): m/z 423 (M+H)$^+$.

Example 170 cis(±)-6-(4-{[(4-Chloro-5-ethyl-1H-imidazol-2-yl)carbonyl]amino}-3-methoxypiperidin-1-yl)-2-methylpyrimidine-4-carboxylic acid (Exemplified Compound No. 170)

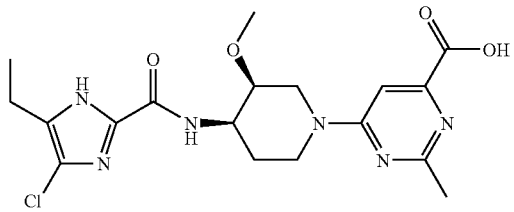

(170a) Ethyl cis(±)-6-(4-{[(4-chloro-5-ethyl-1H-imidazol-2-yl)carbonyl]amino}-3-methoxypiperidin-1-yl)-2-methylpyrimidine-4-carboxylate The same operation as in Example (158a) was performed using cis(±)-4-chloro-5-ethyl-N-(3-methoxypiperidin-4-yl)-1H-imidazole-2-carboxamide hydrochloride obtained in Example (159a) (94.7 mg, 0.29 mmol), ethyl 6-chloro-2-methylpyrimidine-4-carboxylate (56 mg, 0.28 mmol) (reference: Bioorganic and Medicinal Chemistry Letters; 14; 15; 2004; 3869-3874) and diisopropylethylamine (108 mg, 0.84 mmol), to obtain 27 mg of the title compound as a yellow brown oily substance (22%).

mass spectrum (ESI): m/z 451 (M+H)$^+$.

(170b) cis(±)-6-(4-{[(4-Chloro-5-ethyl-1H-imidazol-2-yl)carbonyl]amino}-3-methoxypiperidin-1-yl)-2-methylpyrimidine-4-carboxylic acid The same operation as in (11) was performed using ethyl cis(±)-6-(4-{[(4-chloro-5-ethyl-1H-imidazol-2-yl)carbonyl]amino}-3-methoxypiperidin-1-yl)-2-methylpyrimidine-4-carboxylate obtained in Example (170a) (27 mg, 0.06 mmol) and a 2 N aqueous lithium hydroxide solution (2 mL), to obtain 3.2 mg of the title compound as a white solid (13%).

$^1$H NMR spectrum (400 MHz, DMSO-$d_6$) δ ppm: 1.14 (3H, t, J=7.56 Hz), 1.62-1.78 (2H, m), 2.36 (3H, s), 2.53-2.59 (2H, m), 3.30-3.40 (6H, m), 4.19-4.22 (1H, m), 4.70-4.74 (1H, m), 5.07-5.11 (1H, m), 6.95 (1H, s), 7.52 (1H, d, J=8.54 Hz).

mass spectrum (ESI): m/z 423 (M+H)$^+$.

Example 171 cis(±)-5-(4-{[(4-Chloro-5-ethyl-1H-imidazol-2-yl)carbonyl]amino}-3-methoxypiperidin-1-yl)-2-methylpyridine-3-carboxylic acid

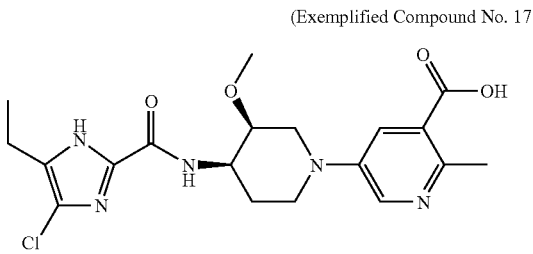

(Exemplified Compound No. 171)

(171a) Methyl cis(±)-5-(4-{[(benzyloxy)carbonyl]amino}-3-methoxypiperidin-1-yl)-2-methylpyridine-3-carboxylate The same operation as in Example (42a) was performed using benzyl cis(±)-[3-methoxypiperidin-4-yl]carbamate hydrochloride obtained in Example (160a) (190 mg, 0.63 mmol), methyl 5-chloro-2-methylpyridine-3-carboxylate (117 mg, 0.63 mmol), palladium acetate (14.2 mg, 0.06 mmol), BINAP (78.6 mg, 0.13 mmol) and cesium carbonate (617 mg, 1.89 mmol), to obtain 225 mg of the title compound as a brown oily substance (86%).

mass spectrum (ESI): m/z 414 (M+H)$^+$.

(171b) Methyl cis(±)-5-(4-amino-3-methoxypiperidin-1-yl)-2-methylpyridine-3-carboxylate The same operation as in Example (160c) was performed using methyl cis(±)-5-(4-{[(benzyloxy)carbonyl]amino}-3-methoxypiperidin-1-yl)-2-methylpyridine-3-carboxylate obtained in Example (171a) (225 mg) and a 10% palladium-carbon catalyst (250 mg), to obtain 113 mg of the title compound as a yellow oily substance. The resulting compound was used for the next reaction without purification.

(171c) Methyl cis(±)-5-(4-{[(4-chloro-5-ethyl-1H-imidazol-2-yl)carbonyl]amino}-3-methoxypiperidin-1-yl)-2-methylpyridine-3-carboxylate The same operation as in Example (1g) was performed using methyl cis(±)-5-(4-amino-3-methoxypiperidin-1-yl)-2-methylpyridine-3-carboxylate obtained in Example (171b) (113 mg, 0.4 mmol), 4-chloro-5-ethyl-1H-imidazole-2-carboxylic acid obtained by the method described in Example (1d) (64 mg, 0.37 mmol), WSC hydrochloride (211 mg, 1.1 mmol) and HOBt (49.7 mg, 0.37 mmol), to obtain 18.0 mg of the title compound as a pale yellow oily substance (11%).

mass spectrum (ESI): m/z 436 (M+H)$^+$.

(171d) cis(±)-5-(4-{[(4-Chloro-5-ethyl-1H-imidazol-2-yl)carbonyl]amino}-3-methoxypiperidin-1-yl)-2-methylpyridine-3-carboxylic acid The same operation as in Example (1i) was performed using methyl cis(±)-5-(4-{[(4-chloro-5-ethyl-1H-imidazol-2-yl)carbonyl]amino}-3-methoxypiperidin-1-yl)-2-methylpyridine-3-carboxylate obtained in Example (171c) (17.0 mg, 0.04 mmol) and a 2 N aqueous lithium hydroxide solution (2 mL), to obtain 2.1 mg of the title compound as a white solid (13%).

mass spectrum (ESI): m/z 422 (M+H)$^+$.

Example 172 cis(±)-5-(4-{[(4-Chloro-5-ethyl-1H-imidazol-2-yl)carbonyl]amino}-3-methoxypiperidin-1-yl)-2-methylbenzoic acid

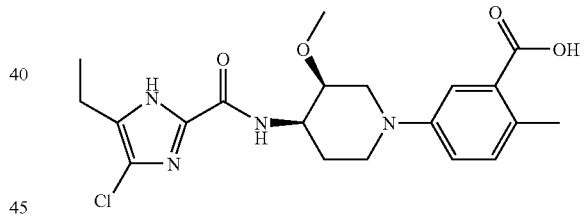

(Exemplified Compound No. 172)

(172a) Methyl cis(±)-5-(4-{[(benzyloxy)carbonyl]amino}-3-methoxypiperidin-1-yl)-2-methylbenzoate The same operation as in Example (42a) was performed using benzyl cis(±)-[3-methoxypiperidin-4-yl]carbamate hydrochloride obtained in Example (160a) (165 mg, 0.55 mmol), methyl 5-chloro-2-benzoate (101 mg, 0.55 mmol), palladium acetate (12.3 mg, 0.05 mmol), BINAP (68.3 mg, 0.11 mmol) and cesium carbonate (536 mg, 1.65 mmol), to obtain 40 mg of the title compound as a yellow oily substance (18%).

mass spectrum (ESI): m/z 413 (M+H)$^+$.

(172b) Methyl cis(±)-5-(4-amino-3-methoxypiperidin-1-yl)-2-methylbenzoate

The same operation as in Example (160c) was performed using methyl cis(±)-5-(4-{[(benzyloxy)carbonyl]amino}-3-methoxypiperidin-1-yl)-2-methylbenzoate obtained in Example (172a) (39 mg, 0.09 mmol) and a 10% palladium-carbon catalyst (50 mg), to obtain the title compound. The resulting compound was used for the next reaction without purification.

(172c) Methyl cis(±)-5-(4-{[(4-chloro-5-ethyl-1H-imidazol-2-yl)carbonyl]amino}-3-methoxypiperidin-1-yl)-2-methylbenzoate The same operation as in Example (1g) was performed using methyl cis(±)-5-(4-amino-3-methoxypiperidin-1-yl)-2-methylbenzoate obtained in Example (172b) (26.3 mg, 0.09 mmol), 4-chloro-5-ethyl-1H-imidazole-2-carboxylic acid obtained by the method described in Example (1d) (15 mg, 0.09 mmol), WSC hydrochloride (49.4 mg, 0.26 mmol) and HOBt (11.6 mg, 0.09 mmol), to obtain 33.0 mg of the title compound as a pale yellow oily substance (88%).

$^1$H NMR spectrum (400 MHz, CDCl$_3$) δ ppm: 1.24-1.31 (3H, m), 1.86-1.89 (1H, m), 2.09-2.15 (1H, m), 2.50 (3H, s), 2.65-2.75 (2H, m), 2.84-2.88 (1H, m), 3.45 (3H, s), 3.56-3.61 (2H, m), 3.82-3.86 (1H, m), 3.89 (3H, s), 3.95-3.96 (1H, m), 4.21-4.23 (1H, m), 7.00-7.05 (1H, m), 7.11-7.16 (1H, m), 7.47-7.49 (2H, m), 10.79 (1H, br s).

(172d) cis(±)-5-(4-{[(4-Chloro-5-ethyl-1H-imidazol-2-yl)carbonyl]amino}-3-methoxypiperidin-1-yl)-2-methylbenzoic acid The same operation as in Example (1i) was performed using methyl cis(±)-5-(4-{[(4-chloro-5-ethyl-1H-imidazol-2-yl)carbonyl]amino}-3-methoxypiperidin-1-yl)-2-methylbenzoate obtained in Example (172c) (33.0 mg, 0.08 mmol) and a 2 N aqueous lithium hydroxide solution (2 mL), to obtain 5.4 mg of the title compound as a pale yellow solid (17%).

$^1$H NMR spectrum (400 MHz, DMSO-d$_6$) δ ppm: 1.14 (3H, t, J=7.56 Hz), 1.70-1.72 (1H, m), 1.92-1.97 (1H, m), 2.40 (3H, s), 2.52-2.59 (2H, m), 2.87-2.90 (2H, m), 3.33 (3H, s), 3.52-3.55 (2H, m), 3.83-3.86 (1H, m), 4.09-4.12 (1H, m), 7.08-7.12 (2H, m), 7.34-7.36 (1H, m), 7.55 (1H, d, J=8.05 Hz), 13.37 (1H, br s).

mass spectrum (ESI): m/z 422 (M+H)$^+$.

Example 173 cis(±)-4-Chloro-5-ethyl-N-{1-[(2E)-4-(methoxyamino)-4-oxobuten-2-oyl]-3-(3-methylbutoxy)piperidin-4-yl}-1H-imidazole-2-carboxamide (Exemplified Compound No. 173)

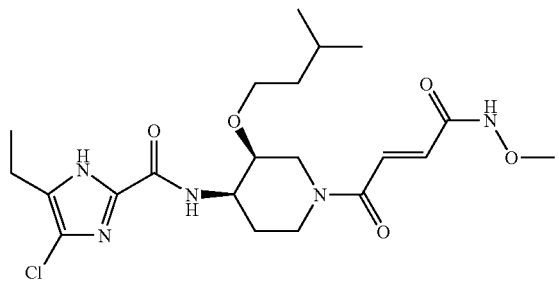

(173a) Ethyl cis(±)-(2E)-4-[4-{[(4-chloro-5-ethyl-1H-imidazol-2-yl)carbonyl]amino}-3-(3-methylbutoxy)piperidin-1-yl]-4-oxo-2-butenoate The same operation as in Example (152a) was performed using tert-butyl cis(±)-4-{[(4-chloro-5-ethyl-1H-imidazol-2-yl)carbonyl]amino}-3-(3-methylbutoxy)piperidine-1-carboxylate obtained by the method described in Example (117e) (210 mg, 0.47 mmol), a 4 N hydrochloric acid/ethyl acetate solution (4 mL), fumaric acid monoethyl ester (64.9 mg, 0.45 mmol), WSC hydrochloride (273 mg, 1.42 mmol) and DMAP (57.9 mg, 0.47 mmol), to obtain 203 mg of the title compound as a yellow solid (91%).

mass spectrum (ESI): m/z 468 (M+H)$^+$.

(173b) cis(±)-(2E)-4-[4-{[(4-Chloro-5-ethyl-1H-imidazol-2-yl)carbonyl]amino}-3-(3-methylbutoxy)piperidin-1-yl]-4-oxo-2-butenoic acid The same operation as in Example (1i) was performed using ethyl cis(±)-(2E)-4-[4-{[(4-chloro-5-ethyl-1H-imidazol-2-yl)carbonyl]amino}-3-(3-methylbutoxy)piperidin-1-yl]-4-oxo-2-butenoate obtained in Example (173a) (203 mg, 0.43 mmol) and a 2 N aqueous lithium hydroxide solution (4 mL), to obtain 152 mg of the title compound as a white solid (80%). This compound is estimated to be an about 1:1 rotamer mixture according to NMR.

$^1$H NMR spectrum (400 MHz, DMSO-d$_6$) δ ppm: 0.75-0.89 (6H, m), 1.10-1.17 (3H, m), 1.24-1.38 (2H, m), 1.65-1.72 (3H, m), 2.50-2.57 (2H, m), 2.82-2.91 (1H, m), 3.26-3.36 (2H, m), 3.47-3.64 (2H, m), 3.96-4.16 (2H, m), 4.36-4.39 (1×1/2H, m), 4.65-4.68 (1×1/2H, m), 6.46-6.50 (1H, m), 7.37-7.40 (1H, m), 7.55-7.57 (1H, m), 13.35 (1H, br s).

Example 173c cis(±)-4-Chloro-5-ethyl-N-{1-[(2E)-4-(methoxyamino)-4-oxobuten-2-oyl]-3-(3-methylbutoxy)piperidin-4-yl}-1H-imidazole-2-carboxamide The same operation as in Example (1g) was performed using cis(±)-(2E)-4-[4-{[(4-chloro-5-ethyl-1H-imidazol-2-yl)carbonyl]amino}-3-(3-methylbutoxy)piperidin-1-yl]-4-oxo-2-butenoic acid obtained in Example (173b) (150 mg, 0.34 mmol), O-methylhydroxylamine hydrochloride (56.9 mg, 0.68 mmol), WSC hydrochloride (156 mg, 1.02 mmol) and DMAP (41.6 mg, 0.34 mmol), to obtain 72.4 mg of the title compound as a pale yellow solid (45%). This compound is estimated to be an about 1:1 rotamer mixture according to NMR.

$^1$H NMR spectrum (400 MHz, DMSO-d$_6$) δ ppm: 0.76-0.85 (6H, m), 1.08-1.18 (3H, m), 1.21-1.40 (2H, m), 1.63-1.71 (3H, m), 2.53-2.58 (2H, m), 2.82-2.87 (1H, m), 3.30-3.35 (2H, m), 3.50-3.59 (2H, m), 3.65 (3H, s), 4.02-4.16 (2H, m), 4.36-4.39 (1H, m), 4.66-4.69 (1H, m), 6.59-6.62 (1H, m), 7.32-7.36 (1H, m), 7.55-7.56 (1H, m), 11.58 (1H, brs), 13.34 (1H, br s).

mass spectrum (ESI): m/z 470 (M+H)$^+$.

Example 174 cis(±)-6-(4-{[(4-Chloro-5-ethyl-1H-imidazol-2-yl)carbonyl]amino}-3-methoxypiperidin-1-yl)pyrimidine-4-carboxylic acid (Exemplified Compound No. 174)

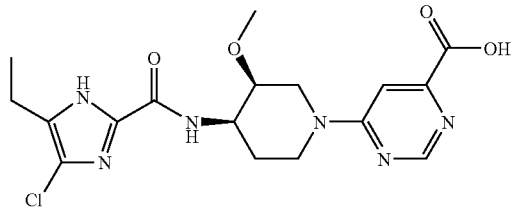

(174a) Benzyl cis(±)-[3-methoxy-1-(6-methylpyrimidin-4-yl)piperidin-4-yl]carbamate The same operation as in Example (158a) was performed using benzyl cis(±)-[3-methoxypiperidin-4-yl]carbamate hydrochloride obtained in Example (160a) (549 mg, 1.83 mmol), 4-chloro-6-methylpyrimidine (235 mg, 1.83 mmol) and diisopropylethylamine (709 mg, 5.48 mmol), to obtain the title compound.

mass spectrum (ESI): m/z 357 (M+H)$^+$.

(174b) cis(±)-6-(4-{[(Benzyloxy)carbonyl]amino}-3-methoxypiperidin-1-yl)pyrimidine-4-carboxylic acid Benzyl cis(±)-[3-methoxy-1-(6-methylpyrimidin-4-yl)piperidin-4-yl]carbamate obtained in Example (174a) (387 mg, 1.09 mmol) was dissolved in pyridine (8 mL). Selenium dioxide (181 mg, 1.63 mmol) was added, and the mixture was stirred at 120° C. for five hours. The reaction solution was diluted with water, filtered through celite and then made acidic with 1 N hydrochloric acid, followed by extraction with ethyl acetate. The organic layer was washed with water and then dried over anhydrous sodium sulfate. Following concentration under reduced pressure, 420 mg of the title compound was obtained as a pale yellow oily substance. The resulting compound was used for the next reaction without purification.

mass spectrum (ESI): m/z 387 (M+H)⁺.

(174c) Methyl cis(±)-6-(4-{[(benzyloxy)carbonyl]amino}-3-methoxypiperidin-1-yl)pyrimidine-4-carboxylate cis(±)-6-(4-{[(Benzyloxy)carbonyl]amino}-3-methoxypiperidin-1-yl)pyrimidine-4-carboxylic acid obtained in Example (174b) (420 mg, 1.09 mmol) was dissolved in DMF (10 mL). Potassium carbonate (180 mg, 1.3 mmol) and methyl iodide (185 mg, 1.3 mmol) were added, and the mixture was stirred at room temperature overnight. Potassium carbonate (180 mg, 1.3 mmol) and methyl iodide (185 mg, 1.3 mmol) were further added, and the mixture was stirred at room temperature overnight. The reaction solution was diluted with ethyl acetate, washed with water and brine, and then dried over anhydrous sodium sulfate. Following concentration under reduced pressure, the residue was purified by silica gel column chromatography (elution solvent: dichloromethane/methanol=40/1, 20/1, 10/1) to obtain 112 mg of the title compound as a brown oily substance (26%).

¹H NMR spectrum (400 MHz, DMSO-d₆) δ ppm: 1.77-1.82 (2H, m), 3.07-3.09 (2H, m), 3.35 (3H, s), 3.46-3.49 (2H, m), 3.91-3.94 (2H, m), 3.98 (3H, s), 5.12 (2H, s), 5.23-5.25 (1H, m), 7.32-7.36 (5H, m), 8.02 (1H, s), 8.67 (1H, s).

(174d) Methyl cis(±)-6-(4-amino-3-methoxypiperidin-1-yl)pyrimidine-4-carboxylate The same operation as in Example (160c) was performed using methyl cis(±)-6-(4-{[(benzyloxy)carbonyl]amino}-3-methoxypiperidin-1-yl)pyrimidine-4-carboxylate obtained in Example (174c) (111 mg, 0.28 mmol) and a 10% palladium-carbon catalyst (130 mg), to obtain 53.5 mg of the title compound as a pale yellow oily substance. The resulting compound was used for the next reaction without purification.

(174e) Methyl cis(±)-6-(4-{[(4-chloro-5-ethyl-1H-imidazol-2-yl)carbonyl]amino}-3-methoxypiperidin-1-yl)pyrimidine-4-carboxylate The same operation as in Example (1g) was performed using methyl cis(±)-6-(4-amino-3-methoxypiperidin-1-yl)pyrimidine-4-carboxylate obtained in Example (174d) (53.5 mg, 0.2 mmol), 4-chloro-5-ethyl-1H-imidazole-2-carboxylic acid obtained by the method described in Example (1d) (32 mg, 0.18 mmol), WSC hydrochloride (105 mg, 0.55 mmol) and HOBt (24.7 mg, 0.18 mmol), to obtain 62.2 mg of the title compound as a yellow oily substance (81%).

(174f) cis(±)-6-(4-{[(4-Chloro-5-ethyl-1H-imidazol-2-yl)carbonyl]amino}-3-methoxypiperidin-1-yl)pyrimidine-4-carboxylic acid The same operation as in Example (1i) was performed using methyl cis(±)-6-(4-{[(4-chloro-5-ethyl-1H-imidazol-2-yl)carbonyl]amino}-3-methoxypiperidin-1-yl)pyrimidine-4-carboxylate obtained in Example (174e) (61.8 mg, 0.15 mmol) and a 2 N aqueous lithium hydroxide solution (3 mL), to obtain 29.3 mg of the title compound as a pale yellow solid (49%).

¹H NMR spectrum (400 MHz, DMSO-d₆) δ ppm: 1.14 (3H, t, J=7.56 Hz), 1.74-1.77 (2H, m), 2.52-2.59 (2H, m), 3.26-3.32 (5H, m), 3.56-3.58 (3H, m), 4.24-4.26 (1H, m), 7.35 (1H, s), 7.62 (1H, d, J=8.54 Hz), 8.57 (1H, s), 13.36 (1H, br s).

Example 175 cis(±)-3-(4-{[(4-Chloro-5-ethyl-1H-imidazol-2-yl)carbonyl]amino}-3-methoxypiperidin-1-yl)-5-fluorobenzoic acid (Exemplified Compound No. 175)

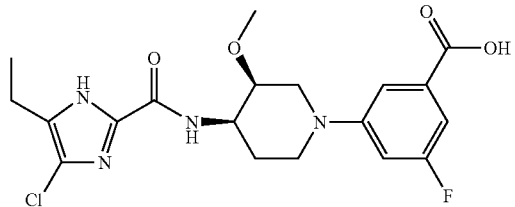

(175a) Methyl cis(±)-3-(4-{[(benzyloxy)carbonyl]amino}-3-methoxypiperidin-1-yl)-5-fluorobenzoate The same operation as in Example (42a) was performed using benzyl cis(±)-[3-methoxypiperidin-4-yl]carbamate hydrochloride obtained in Example (160a) (165 mg, 0.55 mmol), methyl 3-chloro-5-fluorobenzoate (103 mg, 0.55 mmol), palladium acetate (12.3 mg, 0.05 mmol), BINAP (68.3 mg, 0.11 mmol) and cesium carbonate (536 mg, 1.65 mmol), to obtain 79 mg of the title compound as a yellow oily substance (35%).

(175b) Methyl cis(±)-3-(4-amino-3-methoxypiperidin-1-yl)-5-fluorobenzoate

The same operation as in Example (160c) was performed using methyl cis(±)-3-(4-{[(benzyloxy)carbonyl]amino}-3-methoxypiperidin-1-yl)-5-fluorobenzoate obtained in Example (175a) (78 mg, 0.19 mmol) and a 10% palladium-carbon catalyst (100 mg), to obtain the title compound as a yellow oily substance. The resulting compound was used for the next reaction without purification.

(175c) Methyl cis(±)-3-(4-{[(4-chloro-5-ethyl-1H-imidazol-2-yl)carbonyl]amino}-3-methoxypiperidin-1-yl)-5-fluorobenzoate The same operation as in Example (1g) was performed using methyl cis(±)-3-(4-amino-3-methoxypiperidin-1-yl)-5-fluorobenzoate obtained in Example (175b) (50.6 mg, 0.18 mmol), 4-chloro-5-ethyl-1H-imidazole-2-carboxylic acid obtained by the method described in Example (1d) (28 mg, 0.16 mmol), WSC hydrochloride (93.7 mg, 0.49 mmol) and HOBt (22 mg, 0.16 mmol), to obtain 56 mg of the title compound as a pale yellow solid (78%).

¹H NMR spectrum (400 MHz, CDCl₃) δ ppm: 1.24-1.31 (3H, m), 1.86-1.90 (1H, m), 2.08-2.14 (1H, m), 2.70 (2H, q, J=7.56 Hz), 2.91-2.99 (1H, m), 3.43 (3H, s), 3.53-3.58 (1H, m), 3.67-3.76 (1H, m), 3.88-4.00 (5H, m), 4.20-4.27 (1H, m), 6.77-6.80 (1H, m), 7.15-7.17 (1H, m), 7.38-7.42 (1H, m), 7.52 (1H, d, J=8.78 Hz), 11.68 (1H, br s).

(175d) cis(±)-3-(4-{[(4-Chloro-5-ethyl-1H-imidazol-2-yl)carbonyl]amino}-3-methoxypiperidin-1-yl)-5-fluorobenzoic acid The same operation as in Example (1i) was performed using methyl cis(±)-3-(4-{[(4-chloro-5-ethyl-1H-imidazol-2-yl)carbonyl]amino}-3-methoxypiperidin-1-yl)-5-fluorobenzoate obtained in Example (175c) (51.1 mg, 0.12 mmol) and a 2 N aqueous lithium hydroxide solution (2 mL), to obtain 12.1 mg of the title compound as a white solid (49%).

$^1$H NMR spectrum (400 MHz, DMSO-$d_6$) δ ppm: 1.14 (3H, t, J=7.56 Hz), 1.69-1.72 (1H, m), 1.90-1.92 (1H, m), 2.52-2.59 (2H, m), 2.99-3.02 (2H, m), 3.31 (3H, s), 3.53 (1H, br s), 3.70-3.73 (1H, m), 4.02-4.05 (1H, m), 4.14-4.17 (1H, m), 6.95 (1H, d, J=8.78 Hz), 7.01-7.08 (1H, m), 7.28 (1H, s), 7.59 (1H, d, J=8.54 Hz), 13.37 (1H, br s).

mass spectrum (ESI): m/z 425 (M+H)$^+$.

Example 176 cis(±)-5-(4-{[(4-Chloro-5-ethyl-1H-imidazol-2-yl)carbonyl]amino}-3-methoxypiperidin-1-yl)-2-fluorobenzoic acid (Exemplified Compound No. 176)

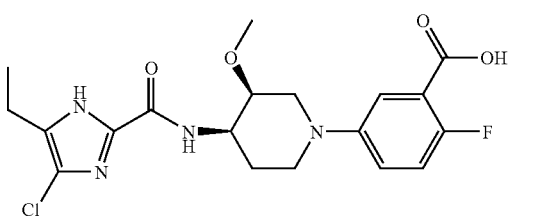

(176a) Methyl cis(±)-5-(4-{[(benzyloxy)carbonyl]amino}-3-methoxypiperidin-1-yl)-2-fluorobenzoate The same operation as in Example (42a) was performed using benzyl cis(±)-[3-methoxypiperidin-4-yl]carbamate hydrochloride obtained in Example (160a) (165 mg, 0.55 mmol), methyl 5-bromo-2-fluorobenzoate (128 mg, 0.55 mmol), palladium acetate (12.3 mg, 0.05 mmol), BINAP (68.3 mg, 0.11 mmol) and cesium carbonate (536 mg, 1.65 mmol), to obtain 33 mg of the title compound as a yellow oily substance (14%).

mass spectrum (ESI): m/z 417 (M+H)$^+$.

(176b) Methyl cis(±)-5-(4-amino-3-methoxypiperidin-1-yl)-2-fluorobenzoate

The same operation as in Example (160c) was performed using methyl cis(±)-5-(4-{[(benzyloxy)carbonyl]amino}-3-methoxypiperidin-1-yl)-2-fluorobenzoate obtained in Example (176a) (32 mg, 0.08 mmol) and a 10% palladium-carbon catalyst (50 mg), to obtain the title compound as an oily substance. The resulting compound was used for the next reaction without purification.

(176c) Methyl cis(±)-5-(4-{[(4-chloro-5-ethyl-1H-imidazol-2-yl)carbonyl]amino}-3-methoxypiperidin-1-yl)-2-fluorobenzoate The same operation as in Example (1g) was performed using methyl cis(±)-5-(4-amino-3-methoxypiperidin-1-yl)-2-fluorobenzoate obtained in Example (176b) (20.1 mg, 0.07 mmol), 4-chloro-5-ethyl-1H-imidazole-2-carboxylic acid obtained by the method described in Example (1d) (11.3 mg, 0.06 mmol), WSC hydrochloride (37.2 mg, 0.19 mmol) and HOBt (8.7 mg, 0.06 mmol), to obtain 11 mg of the title compound as a pale yellow solid (39%).

$^1$H NMR spectrum (400 MHz, CDCl$_3$) δ ppm: 1.24-1.30 (3H, m), 1.56-1.59 (1H, m), 1.85-1.88 (1H, m), 2.10-2.17 (2H, m), 2.65-2.73 (2H, m), 3.45 (3H, s), 3.53-3.60 (2H, m), 3.73-3.95 (5H, m), 4.21-4.23 (1H, m), 6.99-7.15 (2H, m), 7.40-7.54 (2H, m), 10.57 (1H, br s).

(176d) cis(±)-5-(4-{[(4-Chloro-5-ethyl-1H-imidazol-2-yl)carbonyl]amino}-3-methoxypiperidin-1-yl)-2-fluorobenzoic acid The same operation as in Example (1i) was performed using methyl cis(±)-5-(4-{[(4-chloro-5-ethyl-1H-imidazol-2-yl)carbonyl]amino}-3-methoxypiperidin-1-yl)-2-fluorobenzoate obtained in Example (176c) (11.1 mg, 0.03 mmol) and a 2 N aqueous lithium hydroxide solution (1 mL), to obtain 5.4 mg of the title compound as a white solid.

mass spectrum (ESI): m/z 417 (M+H)$^+$.

Example 177 cis(±)-3-(4-{[(4-Chloro-5-ethyl-1H-imidazol-2-yl)carbonyl]amino}-3-ethoxypiperidin-1-yl)benzoic acid (Exemplified Compound No. 177)

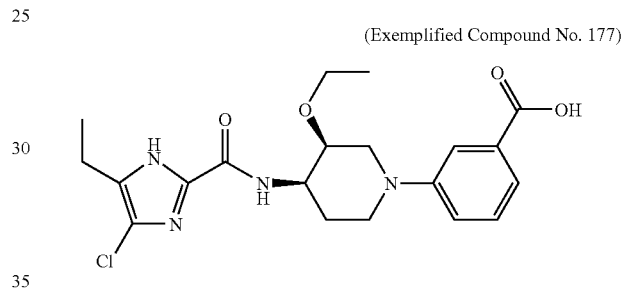

(177a) Methyl cis(±)-3-(4-amino-3-ethoxypiperidin-1-yl)benzoate

The same operation as in Example (160c) was performed using methyl cis(±)-3-(4-{[(benzyloxy)carbonyl]amino}-3-ethoxypiperidin-1-yl)benzoate obtained in Example (48c) (155 mg, 0.38 mmol) and a 10% palladium-carbon catalyst (200 mg), to obtain 24 mg of the title compound as a pale yellow oily substance. The resulting compound was used for the next reaction without purification.

(177b) Methyl cis(±)-3-(4-{[(4-chloro-5-ethyl-1H-imidazol-2-yl)carbonyl]amino}-3-ethoxypiperidin-1-yl)benzoate The same operation as in Example (1g) was performed using methyl cis(±)-3-(4-amino-3-ethoxypiperidin-1-yl)benzoate obtained in Example (177a) (24 mg, 0.09 mmol), 4-chloro-5-ethyl-1H-imidazole-2-carboxylic acid obtained by the method described in Example (1d) (15.1 mg, 0.09 mmol), WSC hydrochloride (49.7 mg, 0.26 mmol) and HOBt (11.7 mg, 0.09 mmol), to obtain 17.1 mg of the title compound as a yellow oily substance (46%).

$^1$H NMR spectrum (400 MHz, CDCl$_3$) δ ppm: 1.18-1.29 (6H, m), 1.85-1.88 (1H, m), 2.15-2.17 (1H, m), 2.69 (2H, q, J=7.64 Hz), 2.96-2.98 (2H, m), 3.48-3.52 (1H, m), 3.65-3.73 (3H, m), 3.88-3.94 (4H, m), 4.21-4.24 (1H, m), 7.12-7.13 (1H, m), 7.27-7.32 (1H, m), 7.45-7.52 (2H, m), 7.59-7.61 (1H, m), 10.75 (1H, br s).

(177c) cis(±)-3-(4-{[(4-Chloro-5-ethyl-1H-imidazol-2-yl)carbonyl]amino}-3-ethoxypiperidin-1-yl)benzoic acid The same operation as in Example (1i) was performed using methyl cis(±)-3-(4-{[(4-chloro-5-ethyl-1H-imidazol-2-yl)carbonyl]amino}-3-ethoxypiperidin-1-yl)benzoate obtained in Example (177b) (16.4 mg, 0.04 mmol) and a 2 N aqueous lithium hydroxide solution (1 mL), to obtain 9.1 mg of the title compound as a white solid (57%).

¹H NMR spectrum (400 MHz, DMSO-d₆) δ ppm: 1.04 (3H, t, J=6.95 Hz), 1.14 (3H, t, J=7.44 Hz), 1.70-1.72 (1H, m), 1.92-1.97 (1H, m), 2.52-2.59 (2H, m), 2.96-2.99 (2H, m), 3.41-3.51 (1H, m), 3.57-3.68 (3H, m), 3.87-3.94 (1H, m), 4.08-4.18 (1H, m), 7.18-7.23 (1H, m), 7.28-7.33 (2H, m), 7.43-7.47 (1H, m), 7.55 (1H, d, J=8.54 Hz), 13.36 (1H, br s).

mass spectrum (ESI): m/z 421 (M+H)⁺.

Example 178 cis(±)-3-(4-{[(4-Chloro-5-ethyl-1H-imidazol-2-yl)carbonyl]amino}-3-propoxypiperidin-1-yl)benzoic acid (Exemplified Compound No. 178)

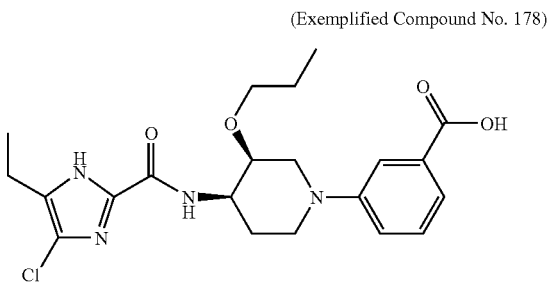 [SMILES: CCCO[C@H]1CN(c2cccc(C(=O)O)c2)CC[C@H]1NC(=O)c1nc(Cl)c(CC)[nH]1]

(178a) Methyl cis(±)-3-(4-{[(benzyloxy)carbonyl]amino}-3-propoxypiperidin-1-yl)benzoate tert-Butyl cis(±)-4-{[(benzyloxy)carbonyl]amino}-3-propoxypiperidine-1-carboxylate obtained in Example (113e) (200 mg, 0.51 mmol) was dissolved in methanol (9 mL). A 4 N hydrochloric acid/ethyl acetate solution (6 mL) was added, and the mixture was stirred at room temperature for one hour. Following concentration under reduced pressure, the same operation as in Example (42a) was performed using the resulting benzyl cis(±)-[3-propoxypiperidin-4-yl]carbamate, methyl 3-bromo-5-benzoate (132 mg, 0.61 mmol), palladium acetate (11.4 mg, 0.05 mmol), BINAP (63.5 mg, 0.1 mmol) and cesium carbonate (498 mg, 1.53 mmol), to obtain 78 mg of the title compound as a pale yellow oily substance (36%).

¹H NMR (400 MHz, CDCl₃) δ ppm: 0.85 (3H, t, J=7.44 Hz), 1.49-1.60 (2H, m), 1.83-1.86 (1H, m), 1.98-2.07 (1H, m), 2.91-2.94 (2H, m), 3.29-3.36 (1H, m), 3.52-3.61 (3H, m), 3.80-3.90 (5H, m), 5.12 (2H, s), 5.22-5.24 (1H, m), 7.07-7.12 (1H, m), 7.27-7.35 (6H, m), 7.46-7.50 (1H, m), 7.56-7.59 (1H, m).

(178b) Methyl cis(±)-3-(4-amino-3-propoxypiperidin-1-yl)benzoate

The same operation as in Example (160c) was performed using methyl cis(±)-3-(4-{[(benzyloxy)carbonyl]amino}-3-propoxypiperidin-1-yl)benzoate obtained in Example (178a) (78 mg, 0.18 mmol) and a 10% palladium-carbon catalyst (100 mg), to obtain 42.8 mg of the title compound as a pale yellow oily substance (80%). The resulting compound was used for the next reaction without purification.

(178c) Methyl cis(±)-3-(4-{[(4-chloro-5-ethyl-1H-imidazol-2-yl)carbonyl]amino}-3-propoxypiperidin-1-yl)benzoate The same operation as in Example (1g) was performed using methyl cis(±)-3-(4-amino-3-propoxypiperidin-1-yl)benzoate obtained in Example (178b) (42.4 mg, 0.14 mmol), 4-chloro-5-ethyl-1H-imidazole-2-carboxylic acid obtained by the method described in Example (1d) (24.1 mg, 0.14 mmol), WSC hydrochloride (79.4 mg, 0.41 mmol) and HOBt (18.7 mg, 0.14 mmol), to obtain 35.5 mg of the title compound as a yellow oily substance (67%).

¹H NMR spectrum (400 MHz, CDCl₃) δ ppm: 0.89 (3H, t, J=7.32 Hz), 1.27 (3H, t, J=7.62 Hz), 1.54-1.63 (2H, m), 1.81-1.89 (1H, m), 2.11-2.21 (1H, m), 2.69 (2H, q, J=7.62 Hz), 2.96-2.99 (2H, m), 3.35-3.41 (1H, m), 3.56-3.68 (3H, m), 3.89-3.93 (4H, m), 4.19-4.26 (1H, m), 7.10-7.14 (1H, m), 7.26-7.33 (1H, m), 7.45-7.52 (2H, m), 7.60 (1H, s), 10.55 (1H, br s).

(178d) cis(±)-3-(4-{[(4-Chloro-5-ethyl-1H-imidazol-2-yl)carbonyl]amino}-3-propoxypiperidin-1-yl)benzoic acid The same operation as in Example (1i) was performed using methyl cis(±)-3-(4-{[(4-chloro-5-ethyl-1H-imidazol-2-yl)carbonyl]amino}-3-propoxypiperidin-1-yl)benzoate obtained in Example (178c) (36.3 mg, 0.04 mmol) and a 2 N aqueous lithium hydroxide solution (1 mL), to obtain 27.4 mg of the title compound as a white solid (78%).

¹H NMR spectrum (400 MHz, DMSO-d₆) δ ppm: 0.81 (3H, t, J=7.44 Hz), 1.14 (3H, t, J=7.56 Hz), 1.38-1.48 (2H, m), 1.68-1.76 (1H, m), 1.90-2.00 (1H, m), 2.52-2.59 (2H, m), 2.93-3.02 (2H, m), 3.34-3.37 (1H, m), 3.49-3.54 (1H, m), 3.60-3.67 (2H, m), 3.89-3.97 (1H, m), 4.09-4.17 (1H, m), 7.18-7.21 (1H, m), 7.27-7.31 (2H, m), 7.43-7.47 (1H, m), 7.55 (1H, d, J=8.29 Hz), 13.36 (1H, br s).

mass spectrum (ESI): m/z 435 (M+H)⁺.

Example 179 cis(±)-2-Chloro-6-(4-{[(4-chloro-5-ethyl-1H-imidazol-2-yl)carbonyl]amino}-3-methoxypiperidin-1-yl)pyridine-4-carboxylic acid (Exemplified Compound No. 179)

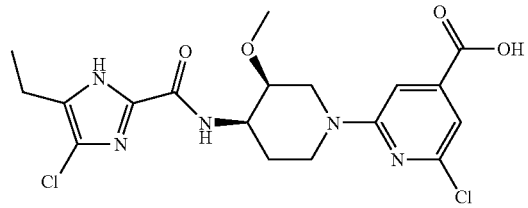

(179a) Methyl cis(±)-2-chloro-6-(4-{[(4-chloro-5-ethyl-1H-imidazol-2-yl)carbonyl]amino}-3-methoxypiperidin-1-yl)pyridine-4-carboxylate The same operation as in Example (158a) was performed using cis(±)-4-chloro-5-ethyl-N-(3-methoxypiperidin-4-yl)-1H-imidazole-2-carboxamide hydrochloride obtained in Example (159a) (107 mg, 0.33 mmol), ethyl 2,6-dichloropyridine-4-carboxylate (65 mg, 0.32 mmol) and diisopropylethylamine (122 mg, 0.95 mmol), to obtain the title compound as a yellow brown oily substance.

mass spectrum (ESI): m/z 456 (M+H)⁺.

(179b) cis(±)-2-Chloro-6-(4-{[(4-chloro-5-ethyl-1H-imidazol-2-yl)carbonyl]amino}-3-methoxypiperidin-1-yl)pyridine-4-carboxylic acid The same operation as in Example (1i) was performed using methyl cis(±)-2-chloro-6-(4-{[(4-chloro-5-ethyl-1H-imidazol-2-yl)carbonyl]amino}-3-methoxypiperidin-1-yl)pyridine-4-carboxylate obtained in Example (179a) (144 mg, 0.32 mmol) and a 2 N aqueous lithium hydroxide solution (1 mL), to obtain 3 mg of the title compound as a white solid (3%).

¹H NMR spectrum (400 MHz, DMSO-d₆) δ ppm: 1.14 (3H, t, J=7.44 Hz), 1.65-1.82 (2H, m), 2.52-2.58 (2H, m), 3.08-3.15 (2H, m), 3.29 (3H, s), 3.51-3.54 (1H, m), 4.16-4.25 (2H, m), 4.63-4.67 (1H, m), 6.89 (1H, s), 7.15 (1H, s), 7.58 (1H, d, J=8.29 Hz), 13.36 (1H, br s).

mass spectrum (ESI): m/z 442 (M+H)⁺.

Example 180 cis(±)-2-(4-{[(4-Chloro-5-ethyl-1H-imidazol-2-yl)carbonyl]amino}-3-methoxypiperidin-1-yl)-5-methylpyridine-4-carboxylic acid (Exemplified Compound No. 180)

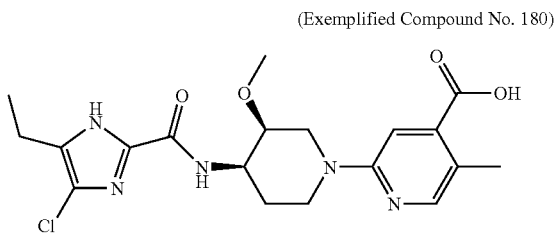 [SMILES: CCc1[nH]c(C(=O)N[C@@H]2CCN(c3cc(C(=O)O)c(C)cn3)C[C@@H]2OC)nc1Cl]

(180a) Ethyl cis(±)-2-(4-{[(benzyloxy)carbonyl]amino}-3-methoxypiperidin-1-yl)-5-methylpyridine-4-carboxylate The same operation as in Example (42a) was performed using benzyl cis(±)-[3-methoxypiperidin-4-yl]carbamate obtained in Example (160a) (320 mg, 1.21 mmol), ethyl 2-chloro-5-methylbenzoate (242 mg, 1.21 mmol), palladium acetate (27.2 mg, 0.12 mmol), BINAP (151 mg, 0.24 mmol) and cesium carbonate (1.18 g, 3.63 mmol), to obtain 207 mg of the title compound as a yellow oily substance.

(180b) Ethyl cis(±)-2-(4-amino-3-methoxypiperidin-1-yl)-5-methylpyridine-4-carboxylate The same operation as in Example (160c) was performed using ethyl cis(±)-2-(4-{[(benzyloxy)carbonyl]amino}-3-methoxypiperidin-1-yl)-5-methylpyridine-4-carboxylate obtained in Example (180a) (207 mg, 0.48 mmol) and a 10% palladium-carbon catalyst (200 mg), to obtain 26.1 mg of the title compound as a yellow oily substance.

(180c) Ethyl cis(±)-2-(4-{[(4-chloro-5-ethyl-1H-imidazol-2-yl)carbonyl]amino}-3-methoxypiperidin-1-yl)-5-methylpyridine-4-carboxylate The same operation as in Example (1g) was performed using ethyl cis(±)-2-(4-amino-3-methoxypiperidin-1-yl)-5-methylpyridine-4-carboxylate obtained in Example (180b) (26.1 mg, 0.09 mmol), 4-chloro-5-ethyl-1H-imidazole-2-carboxylic acid obtained by the method described in Example (1d) (14.8 mg, 0.08 mmol), WSC hydrochloride (48.8 mg, 0.25 mmol) and HOBt (11.5 mg, 0.08 mmol), to obtain 28.8 mg of the title compound as a yellow oily substance (76%).

mass spectrum (ESI): m/z 450 (M+H)⁺.

(180d) cis(±)-2-(4-{[(4-Chloro-5-ethyl-1H-imidazol-2-yl)carbonyl]amino}-3-methoxypiperidin-1-yl)-5-methylpyridine-4-carboxylic acid The same operation as in Example (1i) was performed using ethyl cis(±)-2-(4-{[(4-chloro-5-ethyl-1H-imidazol-2-yl)carbonyl]amino}-3-methoxypiperidin-1-yl)-5-methylpyridine-4-carboxylate obtained in Example (180c) (28.7 mg, 0.06 mmol) and a 2 N aqueous lithium hydroxide solution (1 mL), to obtain 6.3 mg of the title compound as a yellow solid (23%).

¹H NMR spectrum (400 MHz, DMSO-d₆) δ ppm: 1.12-1.18 (3H, m), 1.59-1.69 (1H, m), 1.74-1.83 (1H, m), 2.48-2.52 (3H, m), 2.53-2.57 (2H, m), 2.99-3.08 (1H, m), 3.31-3.35 (5H, m), 3.49-3.51 (1H, m), 4.11-4.20 (1H, m), 4.57-4.65 (1H, m), 7.08-7.13 (1H, m), 7.53 (1H, d, J=8.78 Hz), 8.02-8.09 (1H, m), 13.22-13.36 (1H, m).

mass spectrum (ESI): m/z 422 (M+H)⁺.

Example 181 cis(±)-3-(4-{[(4-Chloro-5-ethyl-1H-imidazol-2-yl)carbonyl]amino}-3-methoxypiperidin-1-yl)-4-fluorobenzoic acid (Exemplified Compound No. 181)

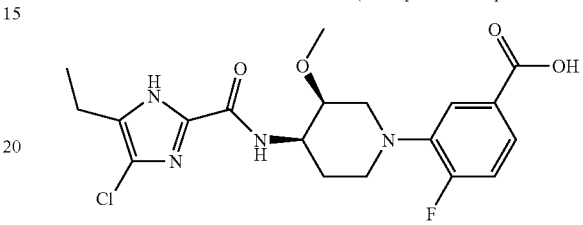

(181a) Methyl cis(±)-3-(4-{[(benzyloxy)carbonyl]amino}-3-methoxypiperidin-1-yl)-4-fluorobenzoate The same operation as in Example (42a) was performed using benzyl cis(±)-[3-methoxypiperidin-4-yl]carbamate obtained in Example (160a) (100 mg, 0.38 mmol), methyl 3-bromo-4-fluorobenzoate (264 mg, 1.13 mmol), palladium acetate (25.5 mg, 0.11 mmol), BINAP (141 mg, 0.23 mmol) and cesium carbonate (370 mg, 1.13 mmol), to obtain 97.4 mg of the title compound as a yellow oily substance. mass spectrum (ESI): m/z 417 (M+H)⁺.

(181b) Methyl cis(±)-3-(4-amino-3-methoxypiperidin-1-yl)-4-fluorobenzoate

The same operation as in Example (160c) was performed using methyl cis(±)-3-(4-{[(benzyloxy)carbonyl]amino}-3-methoxypiperidin-1-yl)-4-fluorobenzoate obtained in Example (181a) (101 mg, 0.24 mmol) and a 10% palladium-carbon catalyst (100 mg), to obtain 18 mg of the title compound as a colorless oily substance (26%). The resulting compound was used for the next reaction without purification.

(181c) Methyl cis(±)-3-(4-{[(4-chloro-5-ethyl-1H-imidazol-2-yl)carbonyl]amino}-3-methoxypiperidin-1-yl)-4-fluorobenzoate The same operation as in Example (1g) was performed using methyl cis(±)-3-(4-amino-3-methoxypiperidin-1-yl)-4-fluorobenzoate obtained in Example (181b) (18 mg, 0.06 mmol), 4-chloro-5-ethyl-1H-imidazole-2-carboxylic acid obtained by the method described in Example (1d) (10.6 mg, 0.06 mmol), WSC hydrochloride (34.9 mg, 0.18 mmol) and HOBt (8.2 mg, 0.06 mmol), to obtain 22.7 mg of the title compound as a pale yellow solid (85%).

mass spectrum (ESI): m/z 439 (M+H)⁺.

(181d) cis(±)-3-(4-{[(4-Chloro-5-ethyl-1H-imidazol-2-yl)carbonyl]amino}-3-methoxypiperidin-1-yl)-4-fluorobenzoic acid The same operation as in Example (1i) was performed using methyl cis(±)-3-(4-{[(4-chloro-5-ethyl-1H-imidazol-2-yl)carbonyl]amino}-3-methoxypiperidin-1-yl)-4-fluorobenzoate obtained in Example (181c) (22 mg, 0.05 mmol) and a 2 N aqueous lithium hydroxide solution (1 mL), to obtain 9.2 mg of the title compound as a white solid (43%). This compound is estimated to be an about 1:1 rotamer mixture according to NMR.

¹H NMR spectrum (400 MHz, DMSO-d₆) δ ppm: 1.12-1.17 (3H, m), 1.72-2.06 (2H, m), 2.52-2.60 (2H, m), 2.85-3.01 (1H, m), 3.30-3.33 (2H, m), 3.34 (3H, s), 3.53-3.73 (2H, m), 3.82-3.92 (1×½H, m), 4.10-4.18 (1×½H, m), 7.20-7.29 (1H, m), 7.56-7.59 (2H+1×½H, m), 8.56 (1×½H, d, J=8.79 Hz), 13.23 (1×½H, s), 13.36 (1×1/2H, s).

mass spectrum (ESI): m/z 425 (M+H)⁺.

Example 182

4-Chloro-5-ethyl-N-(4-methyl-2-oxo-2H-chromen-7-yl)-1H-imidazole-2-carboxamide (Exemplified Compound No. 182)

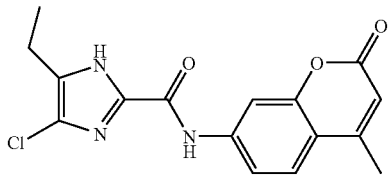

Thionyl chloride (3 ml) was added to 4-chloro-5-ethyl-1H-imidazole-2-carboxylic acid obtained in Example (1d) (110 mg), and the mixture was stirred at 80° C. for two hours. The reaction solution was concentrated under reduced pressure and then azeotropically dehydrated by adding toluene. A solution of 7-amino-4-methyl-2H-chromen-2-one (80 mg) in pyridine (2 ml) was added to the generated acid chloride, and the mixture was stirred at room temperature for two hours. Water was added to the reaction solution and the resulting solid was collected by filtration. The resulting residue was purified by silica gel column chromatography (elution solvent: THF) and recrystallized from THF/ethyl acetate to obtain 46 mg of the title compound as crystals.

¹H NMR spectrum (DMSO-D₆) δ: 13.61 (1H, s), 10.85 (1H, s), 8.01 (1H, d, J=2.20 Hz), 7.88 (1H, dd, J=8.79, 1.95 Hz), 7.75 (1H, d, J=8.79 Hz), 6.29 (1H, d, J=1.22 Hz), 2.61 (2H, q, J=7.57 Hz), 2.42 (3H, d, J=1.22 Hz), 1.19 (3H, t, J=7.57 Hz).

mass spectrum (ESI): m/z 332 (M+H)⁺.

Example 183

6-{[(4-Chloro-5-ethyl-1H-imidazol-2-yl)carbonyl]amino}-3-ethyl-1-benzothiophene-2-carboxylic acid (Exemplified Compound No. 183)

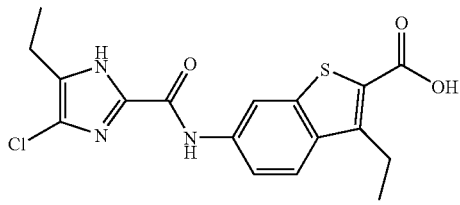

(183a) Ethyl 3-amino-6-nitro-1-benzothiophene-2-carboxylate 2,4-Dinitrobenzonitrile (5.08 g, 26.3 mmol) was dissolved in DMF (55 ml). Potassium carbonate (4.36 g, 31.6 mmol) and ethyl thioglycolate (3.17 g, 26.3 mmol) were added, and the mixture was stirred at room temperature for three days. The reaction solution was concentrated under reduced pressure, diluted with ethyl acetate, washed with water, and dried over anhydrous sodium sulfate. Following concentration under reduced pressure, the residue was recrystallized from ethyl acetate/hexane to obtain 2.27 g of the title compound as crystals (32%).

¹H NMR spectrum (DMSO-D₆) δ: 8.90 (1H, d, J=2.20 Hz), 8.37 (1H, d, J=9.02 Hz), 8.20 (1H, dd, J=8.78, 2.20 Hz), 7.28 (2H, s), 4.31 (2H, q, J=7.07 Hz), 1.31 (3H, t, J=7.07 Hz).

(183b) Ethyl 3-bromo-6-nitro-1-benzothiophene-2-carboxylate

Ethyl 3-amino-6-nitro-1-benzothiophene 2-carboxylate obtained in Example (183a) (2 g, 7.52 mmol) was dissolved in acetonitrile (150 ml). Copper (II) bromide (2.52 g, 11.3 mmol) and tert-butyl nitrite (117 g, 11.3 mmol) were added, and the mixture was stirred at room temperature overnight and at 55° C. for 2.5 hours. The reaction solution was concentrated under reduced pressure, diluted with an ethyl acetate/THF mixed solution, washed with dilute hydrochloric acid and brine, and dried over anhydrous sodium sulfate. Following concentration under reduced pressure, the residue was recrystallized from ethyl acetate/hexane to obtain 1.46 g of the title compound as crystals (59%).

(183c) Ethyl 6-nitro-3-[(trimethylsilyl)ethynyl]-1-benzothiophene-2-carboxylate

DMF (20 ml), (trimethylsilyl)acetylene (5 ml), triethylamine (10 ml) and bis(triphenylphosphine)palladium (II) dichloride (420 mg, 0.6 mmol) were added to ethyl 3-bromo-6-nitro-1-benzothiophene-2-carboxylate obtained in Example (183b) (794 mg, 2.41 mmol) and copper (I) iodide (12 mg, 0.63 mmol), and the mixture was stirred at 80° C. for one hour. The reaction solution was concentrated under reduced pressure, diluted with ethyl acetate, washed with dilute hydrochloric acid and brine, and dried over anhydrous sodium sulfate. Following concentration under reduced pressure, the residue was purified by silica gel column chromatography (elution solvent: ethyl acetate/hexane=1/10) and recrystallized from an ethyl acetate/hexane solvent, to obtain 110 mg of the title compound as crystals.

¹H NMR spectrum (CDCl₃) δ: 8.75 (1H, d, J=2.20 Hz), 8.32 (1H, dd, J=8.90, 2.07 Hz), 8.12 (1H, d, J=8.78 Hz), 4.48 (2H, q, J=7.15 Hz), 1.46 (3H, t, J=7.07 Hz), 0.36 (9H, s).

(183d) Ethyl 3-ethynyl-6-nitro-1-benzothiophene-2-carboxylate

Ethyl 6-nitro-3-[(trimethylsilyl)ethynyl]-1-benzothiophene-2-carboxylate obtained in Example (183c) (110 mg, 0.32 mmol) was dissolved in ethanol (8 mL) and THF (8 ml). Potassium carbonate (13 mg, 0.1 mmol) was added, and the mixture was stirred at room temperature for four hours. The reaction solution was concentrated under reduced pressure and the residue was purified by silica gel column chromatography (elution solvent: ethyl acetate) to obtain the title compound.

¹H NMR spectrum (CDCl₃) δ: 8.78 (1.0H, d, J=1.95 Hz), 8.33 (1H, dd, J=8.90, 2.07 Hz), 8.18 (1H, d, J=8.78 Hz), 4.48 (2H, q, J=7.15 Hz), 3.81 (1H, s), 1.46 (3H, t, J=7.07 Hz).

(183e) Ethyl 6-amino-3-ethyl-1-benzothiophene-2-carboxylate

Ethyl 3-ethynyl-6-nitro-1-benzothiophene-2-carboxylate obtained in Example (183d) was dissolved in methanol (16 mL) and THF (24 ml). A 10% palladium-carbon catalyst (120 mg) was added, and the mixture was stirred in a hydrogen atmosphere throughout the day. The reaction solution was filtered through celite and then concentrated under reduced pressure to obtain the title compound. The resulting compound was used for the next reaction without purification.

¹H NMR spectrum (CDCl₃) δ: 7.62 (1H, d, J=8.78 Hz), 7.04 (1H, d, J=2.20 Hz), 6.78 (1H, dd, J=8.66, 2.07 Hz), 4.36 (2H, q, J=7.15 Hz), 3.91 (2H, s), 3.22 (2H, q, J=7.48 Hz), 1.39 (3H, t, J=7.07 Hz), 1.26 (3H, t, J=7.56 Hz).

mass spectrum (ESI): m/z 250 (M+H)⁺.

(183f) Ethyl 6-{[(4-chloro-5-ethyl-1H-imidazol-2-yl)carbonyl]amino}-3-ethyl-1-benzothiophene-2-carboxylate Thionyl chloride (3 ml) was added to 4-chloro-5-ethyl-1H-imidazole-2-carboxylic acid obtained in Example (1d) (110 mg), and the mixture was stirred at 80° C. for 1.5 hours. The reaction solution was concentrated under reduced pressure and then azeotropically dehydrated by adding toluene. A solution of ethyl 6-amino-3-ethyl-1-benzothiophene-2-carboxylate obtained in Example (183e) in methylene chloride (3 ml) as well as pyridine (1 ml) were added to the generated acid chloride, and the mixture was stirred at room temperature for two hours. The reaction solution was concentrated under reduced pressure, diluted with ethyl acetate, washed with dilute hydrochloric acid and brine, and dried over anhydrous sodium sulfate. Following concentration under reduced pressure, the residue was purified by silica gel column chromatography (elution solvent: ethyl acetate) and recrystallized from an ethyl acetate/hexane solvent to obtain 51 mg of the title compound as crystals.

$^1$H NMR spectrum (DMSO-D$_6$) δ: 13.53 (1H, s), 10.70 (1H, s), 8.55 (1H, d, J=1.46 Hz), 7.94 (2H, dt, J=16.36, 6.84 Hz), 4.33 (2H, q, J=7.08 Hz), 3.24 (2H, d, J=7.57 Hz), 2.62 (2H, q, J=7.57 Hz), 1.33 (3H, t, J=7.08 Hz), 1.19 (6H, m).

mass spectrum (ESI): m/z 406 (M+H)$^+$.

(183g) 6-{[(4-Chloro-5-ethyl-1H-imidazol-2-yl)carbonyl]amino}-3-ethyl-1-benzothiophene-2-carboxylic acid Ethyl 6-{[(4-chloro-5-ethyl-1H-imidazol-2-yl)carbonyl]amino}-3-ethyl-1-benzothiophene-2-carboxylate obtained in Example (183f) (49 mg) was dissolved in methanol (2 ml) and THF (2 ml). A 2 N aqueous lithium hydroxide solution (2 ml) was added, and the mixture was stirred at 50° C. for 30 minutes. The organic solvent was evaporated under reduced pressure, followed by neutralization with 1 N hydrochloric acid. The resulting solid was collected by filtration, washed with distilled water and ethyl acetate, and dried under reduced pressure at 45° C. to obtain 40 mg of the title compound as a solid.

$^1$H NMR spectrum (DMSO-D$_6$) δ: 13.53 (1H, s), 10.66 (1H, s), 8.51 (1H, s), 7.89 (2H, d, J=1.71 Hz), 3.24 (3H, d, J=7.57 Hz), 2.62 (2H, q, J=7.57 Hz), 1.19 (6H, t, J=7.45 Hz).

mass spectrum (ESI): m/z 378 (M+H)$^+$.

Example 184

6-{[(4-Chloro-5-ethyl-1H-imidazol-2-yl)carbonyl]amino}-1-benzothiophene-2-carboxylic acid (Exemplified Compound No. 184)

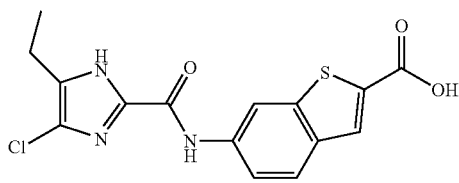

(184a) Ethyl 6-{[(4-chloro-5-ethyl-1H-imidazol-2-yl)carbonyl]amino}-1-benzothiophene-2-carboxylate Thionyl chloride (3 ml) was added to 4-chloro-5-ethyl-1H-imidazole-2-carboxylic acid obtained in Example (1d) (110 mg), and the mixture was stirred at 85° C. for two hours. The reaction solution was concentrated under reduced pressure and then azeotropically dehydrated by adding toluene. A solution of ethyl 6-amino-1-benzothiophene-2-carboxylate (110 mg) (reference: Chemical & Pharmaceutical Bulletin; 47; 12; 1999; 1694-1712) in pyridine (2 ml) was added to the generated acid chloride, and the mixture was stirred at room temperature for one hour. The reaction solution was concentrated under reduced pressure. Then, THF and water were added to the residue, and the resulting solid was collected by filtration. The resulting solid was dissolved in a THF/hexane solution and the insoluble matter was removed, followed by concentration under reduced pressure. The residue was recrystallized from ethyl acetate to obtain 74.4 g of the title compound as pink crystals.

$^1$H NMR spectrum (DMSO-D$_6$) δ: 10.69 (1H, s), 8.60 (1H, s), 8.13 (1H, d, J=0.73 Hz), 7.97 (1H, d, J=8.79 Hz), 7.89 (1H, dd, J=8.79, 1.71 Hz), 4.34 (2H, q, J=7.08 Hz), 2.62 (2H, d, J=7.57 Hz), 1.34 (3H, t, J=7.08 Hz), 1.19 (3H, t, J=7.57 Hz).

mass spectrum (ESI): m/z 378 (M+H)$^+$.

(184b) 6-{[(4-Chloro-5-ethyl-1H-imidazol-2-yl)carbonyl]amino}-1-benzothiophene-2-carboxylic acid Ethyl 6-{[(4-chloro-5-ethyl-1H-imidazol-2-yl)carbonyl]amino}-1-benzothiophene-2-carboxylate obtained in Example (184a) (74.4 mg) was dissolved in methanol (3 ml) and THF (6 ml). A 2 N aqueous lithium hydroxide solution (4 ml) was added, and the mixture was stirred at 50° C. for two hours. The organic solvent was evaporated under reduced pressure, followed by neutralization with 1 N hydrochloric acid. The resulting solid was collected by filtration, washed with distilled water, and dried under reduced pressure at 45° C. to obtain 64 mg of the title compound as a solid.

$^1$H NMR spectrum (DMSO-D$_6$) δ: 13.53 (1H, s), 13.47-13.26 (1H, brs), 10.67 (1H, s), 8.58 (1H, s), 8.03 (1H, s), 7.94 (1H, d, J=8.78 Hz), 7.88 (1H, dd, J=8.66, 1.83 Hz), 2.62 (2H, q, J=7.56 Hz), 1.19 (3H, t, J=7.56 Hz).

mass spectrum (ESI): m/z 350 (M+H)$^+$.

Example 185 cis(±)-2-(Acetylamino)-5-(4-{[(4-chloro-5-ethyl-1H-imidazol-2-yl)carbonyl]amino}-3-methoxypiperidin-1-yl)benzoic acid (Exemplified Compound No. 185)

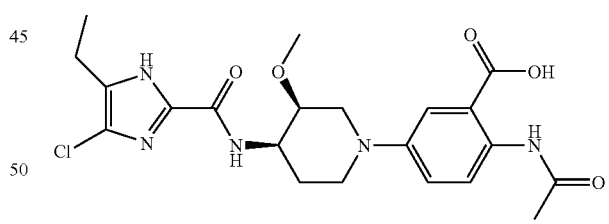

(185a) Methyl cis(±)-5-(4-{[(benzyloxy)carbonyl]amino}-3-methoxypiperidin-1-yl)-2-nitrobenzoate Methanol (15 ml) and a 4 N hydrochloric acid/ethyl acetate solution (30 mL) were added to tert-butyl cis(±)-4-{[(benzyloxy)carbonyl]amino}-3-methoxypiperidine-1-carboxylate obtained in Example (40a) (1.5 g, 4.12 mmol), and the mixture was stirred at room temperature for two hours. The reaction solution was concentrated under reduced pressure, azeotropically dehydrated by adding toluene, and dissolved in DMF (10 ml). Methyl 5-chloro-2-nitrobenzoate (900 mg, 4.17 mmol) and potassium carbonate (2.1 g, 15.2 mmol) were added, and the mixture was stirred at 175° C. for 24 hours. The reaction solution was diluted with ethyl acetate, washed with water, and concentrated under reduced pressure. Thereafter, the residue was purified by silica gel column chromatography (elution solvent: ethyl acetate/hexane) to obtain the title compound. The total resulting compound was used for the next reaction.

$^1$H NMR spectrum (DMSO-D$_6$) δ: 7.97 (1H, d, J=9.52 Hz), 7.40-7.28 (5H, m), 7.27-7.22 (1H, m), 7.10-7.06 (1H, m), 7.06-7.04 (1H, m), 5.04 (2H, s), 4.23-4.14 (1H, m), 3.95-3.84 (2H, m), 3.82 (3H, s), 3.49-3.42 (1H, m), 3.31 (3H, s), 3.30-3.17 (2H, m), 1.78-1.65 (1H, m), 1.64-1.55 (1H, m).

mass spectrum (ESI): m/z 444 (M+H)$^+$.

(185b) Methyl cis(±)-2-amino-5-(4-{[(benzyloxy)carbonyl]amino}-3-methoxypiperidin-1-yl)benzoate Methyl cis(±)-5-(4-{[(benzyloxy)carbonyl]amino}-3-methoxypiperidin-1-yl)-2-nitrobenzoate obtained in Example (185a) was dissolved in ethanol (20 ml) and THF (20 ml). Tin (II) chloride dihydrate (4.4 g, 19.6 mmol) was added, and the mixture was stirred at 75° C. overnight. The reaction solution was concentrated under reduced pressure, diluted with ethyl acetate, washed with aqueous sodium bicarbonate and brine, and dried over anhydrous sodium sulfate. Following concentration under reduced pressure, 900 mg of the title compound was obtained as an oily substance.

$^1$H NMR spectrum (CDCl$_3$) δ: 7.42 (1H, d, J=2.68 Hz), 7.41-7.29 (5H, m), 7.06 (1H, dd, J=8.90, 2.80 Hz), 6.62 (1H, d, J=8.78 Hz), 5.68-5.17 (3H, m), 5.12 (2H, s), 3.86 (3H, s), 3.85-3.76 (1H, m), 3.58-3.52 (1H, m), 3.52-3.47 (1H, m), 3.43 (3H, s), 3.35-3.27 (1H, m), 2.82-2.66 (2H, m), 2.04-1.94 (1H, m), 1.91-1.82 (1H, m).

mass spectrum (ESI): m/z 414 (M+H)$^+$.

(185c) Methyl cis(±)-2-(acetylamino)-5-(4-{[(benzyloxy)carbonyl]amino}-3-methoxypiperidin-1-yl)benzoate Methyl cis(±)-2-amino-5-(4-{[(benzyloxy)carbonyl]amino}-3-methoxypiperidin-1-yl)benzoate obtained in Example (185b) (300 mg) was dissolved in methylene chloride (25 ml). Acetyl chloride (0.1 ml) and triethylamine (0.2 ml) were added, and the mixture was stirred at room temperature for one hour. Methanol was added to the reaction solution, followed by concentration under reduced pressure. Then, the residue was diluted with ethyl acetate, washed with water, and then concentrated under reduced pressure to obtain the title compound. The resulting compound was used for the next reaction without purification.

$^1$H NMR spectrum (CDCl$_3$) δ: 8.57 (1H, d, J=9.28 Hz), 7.54 (1H, d, J=2.93 Hz), 7.41-7.30 (6H, m), 7.17 (1H, dd, J=9.52, 4.76 Hz), 5.32-5.21 (1H, m), 5.12 (2H, s), 3.92 (3H, s), 3.90-3.79 (1H, m), 3.78-3.69 (1H, m), 3.56-3.47 (2H, m), 3.42 (3H, s), 2.92-2.77 (2H, m), 2.20 (3H, s), 2.04-1.94 (1H, m), 1.91-1.83 (1H, m).

mass spectrum (ESI): m/z 456 (M+H)$^+$.

(185d) Methyl cis(±)-2-(acetylamino)-5-(4-amino-3-methoxypiperidin-1-yl)benzoate Methyl cis(±)-2-(acetylamino)-5-(4-{[(benzyloxy)carbonyl]amino}-3-methoxypiperidin-1-yl)benzoate obtained in Example (185c) was dissolved in ethanol (25 mL). A 10% palladium-carbon catalyst (180 mg) was added, and the mixture was stirred in a hydrogen atmosphere overnight. The reaction solution was filtered through celite and then concentrated under reduced pressure to obtain 210 mg of the title compound. The resulting compound was used for the next reaction without purification.

mass spectrum (ESI): m/z 322 (M+H)$^+$.

(185e) Methyl cis(±)-2-(acetylamino)-5-(4-{[(4-chloro-5-ethyl-1H-imidazol-2-yl)carbonyl]amino}-3-methoxypiperidin-1-yl)benzoate Methyl cis(±)-2-(acetylamino)-5-(4-amino-3-methoxypiperidin-1-yl)benzoate obtained in Example (185d) (210 mg, 0.65 mmol) and 4-chloro-5-ethyl-1H-imidazole-2-carboxylic acid obtained in Example (1d) (113 mg, 0.65 mmol) were dissolved in DMA (3 ml). WSC hydrochloride (500 mg, 2.6 mmol) and HOBt (88 mg, 0.65 mmol) were added, and the mixture was stirred at room temperature overnight. The reaction solution was diluted with ethyl acetate, washed with water and brine, and dried over anhydrous sodium sulfate. Following concentration under reduced pressure, the residue was recrystallized from an ethyl acetate/hexane solvent to obtain 120 mg of the title compound as crystals.

$^1$H NMR spectrum (DMSO-D$_6$) δ: 13.35 (1H, s), 10.11 (1H, s), 7.92 (1H, d, J=9.02 Hz), 7.55 (1H, d, J=8.29 Hz), 7.34 (1H, d, J=2.93 Hz), 7.25 (1H, dd, J=9.02, 2.93 Hz), 4.17-4.08 (1H, m), 3.88-3.84 (1H, m), 3.83 (3H, s), 3.58-3.50 (2H, m), 3.33 (3H, s), 2.96-2.85 (2H, m), 2.55 (2H, q, J=7.56 Hz), 2.05 (3H, s), 2.01-1.88 (1H, m), 1.76-1.67 (1H, m), 1.14 (3H, t, J=7.56 Hz).

mass spectrum (ESI): m/z 478 (M+H)$^+$.

(185f) cis(±)-2-(Acetylamino)-5-(4-{[(4-chloro-5-ethyl-1H-imidazol-2-yl)carbonyl]amino}-3-methoxypiperidin-1-yl)benzoic acid Methyl cis(±)-2-(acetylamino)-5-(4-{[(4-chloro-5-ethyl-1H-imidazol-2-yl)carbonyl]amino}-3-methoxypiperidin-1-yl)benzoate obtained in Example (185e) (120 mg) was dissolved in methanol (4 ml) and THF (4 ml). A 2 N aqueous lithium hydroxide solution (2 ml) was added, and the mixture was stirred at 70° C. for one hour. The organic solvent was evaporated under reduced pressure, followed by neutralization with 1 N hydrochloric acid and extraction with ethyl acetate. The organic layer was dried over anhydrous sodium sulfate. Following concentration under reduced pressure, the residue was recrystallized from an ethyl acetate/methanol/hexane solvent to obtain 90 mg of the title compound as crystals.

$^1$H NMR spectrum (DMSO-D$_6$) δ: 13.44 (1H, br s), 13.35 (1H, s), 10.68 (1H, br s), 8.23 (1H, d, J=9.51 Hz), 7.55 (1H, d, J=8.54 Hz), 7.44 (1H, d, J=2.93 Hz), 7.24 (1H, dd, J=9.02, 4.51 Hz), 4.16-4.08 (1H, m), 3.86-3.78 (1H, m), 3.57-3.49 (2H, m), 3.33 (3H, s), 2.94-2.84 (2H, m), 2.55 (2H, q, J=7.56 Hz), 2.07 (3H, s), 2.01-1.90 (1H, m), 1.75-1.67 (1H, m), 1.14 (3H, t, J=7.56 Hz).

mass spectrum (ESI): m/z 464 (M+H)$^+$.

Example 186 cis(±)-2-(4-{[(4-Chloro-5-ethyl-1H-imidazol-2-yl)carbonyl]amino}-3-methoxypiperidin-1-yl)-1H-benzimidazole-4-carboxylic acid (Exemplified Compound No. 186)

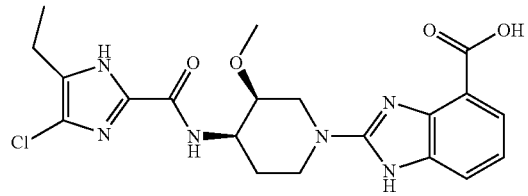

Methyl cis(±)-2-(4-{[(4-chloro-5-ethyl-1H-imidazol-2-yl)carbonyl]amino}-3-methoxypiperidin-1-yl)-1H-benzimidazole-4-carboxylate obtained in Example (187d) (190 mg, 0.41 mmol) was dissolved in methanol (5 ml) and THF (5 ml). A 2 N aqueous lithium hydroxide solution (5 ml) was added, and the mixture was stirred at 50 to 70° C. for one hour. The organic solvent was evaporated under reduced pressure, followed by neutralization with 1 N hydrochloric acid. The resulting solid was collected by filtration, washed with distilled water, and dried under reduced pressure at 45° C. to obtain the title compound as a solid.

$^1$H NMR spectrum (DMSO-D$_6$) δ: 13.37 (1H, s), 7.68 (1H, d, J=8.54 Hz), 7.61 (1H, d, J=7.80 Hz), 7.50 (1H, d, J=7.56 Hz), 7.17 (1H, t, J=8.78 Hz), 4.59-4.45 (1H, m), 4.31-4.12 (2H, m), 3.67-3.58 (1H, m), 3.49-3.35 (2H, m), 3.34 (3H, s), 2.55 (2.H, q, J=7.80 Hz), 2.02-1.87 (1H, m), 1.79-1.69 (1H, m), 1.14 (3H, t, J=7.56 Hz).

mass spectrum (ESI): m/z 447 (M+H)$^+$.

Example 187

Methyl cis(±)-2-(4-{[(4-chloro-5-ethyl-1H-imidazol-2-yl)carbonyl]amino}-3-methoxypiperidin-1-yl)-1H-benzimidazole-4-carboxylate (Exemplified Compound No. 187)

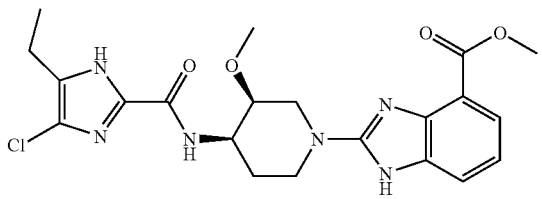

(187a) Methyl 2-chloro-1H-benzimidazole-4-carboxylate

Phosphorus oxychloride (8.5 g, 55.6 mmol) was added to methyl 2-oxo-2,3-dihydro-1H-benzimidazole-4-carboxylate (1.03 g, 5.36 mmol) (reference: WO 2006/116412 A2), and the mixture was stirred at 85° C. for four hours. The reaction solution was diluted with ethyl acetate and THF, slowly added to cold water and neutralized with sodium bicarbonate. The separated organic layer was washed with brine and dried over anhydrous sodium sulfate. Following concentration under reduced pressure, the residue was dissolved in toluene and the insoluble matter was removed. Concentration under reduced pressure gave 800 mg of the title compound as an oily substance. The resulting compound was used for the next reaction without purification.

$^1$H NMR spectrum (CDCl$_3$) δ: 7.93-7.88 (2H, m), 7.32 (1H, t, J=7.93 Hz), 4.01 (3H, s).

(187b) Methyl cis(±)-2-(4-{[(benzyloxy)carbonyl]amino}-3-methoxypiperidin-1-yl)-1H-benzimidazole-4-carboxylate Methanol (4 ml) and a 4 N hydrochloric acid/ethyl acetate solution (6 mL) were added to tert-butyl cis(±)-4-{[(benzyloxy)carbonyl]amino}-3-methoxypiperidine-1-carboxylate obtained in Example (40a) (370 mg), and the mixture was stirred at room temperature for two hours. The reaction solution was concentrated under reduced pressure, azeotropically dehydrated by adding toluene, and dissolved in n-butanol (5 ml). Methyl 2-chloro-1H-benzimidazole-4-carboxylate obtained in Example (187a) (210 mg) and diisopropylethylamine (1 ml) were added, and the mixture was stirred at 125° C. for three days. The reaction solution was concentrated under reduced pressure, diluted with ethyl acetate, washed with brine, and dried over anhydrous sodium sulfate. Following concentration under reduced pressure, the residue was purified by silica gel column chromatography (elution solvent: ethyl acetate) to obtain 330 mg of the title compound. $^1$H NMR spectrum (CDCl$_3$) δ: 9.47 (1H, s), 7.58 (2H, d, J=7.80 Hz), 7.41-7.29 (5H, m), 7.12 (1H, t, J=7.93 Hz), 5.32-5.20 (1H, m), 5.12 (2H, s), 4.50-4.41 (1H, m), 4.05-3.97 (1H, m), 3.96 (3H, s), 3.94-3.84 (1H, m), 3.56-3.50 (1H, m), 3.41 (3H, s), 3.27-3.10 (2H, m), 2.04-1.91 (1H, m), 1.91-1.83 (1H, m).

mass spectrum (ESI): m/z 439 (M+H)$^+$.

(187c) Methyl cis(±)-2-(4-amino-3-methoxypiperidin-1-yl)-1H-benzimidazole-4-carboxylate Methyl cis(±)-2-(4-{[(benzyloxy)carbonyl]amino}-3-methoxypiperidin-1-yl)-1H-benzimidazole-4-carboxylate obtained in Example (187b) (330 mg) was dissolved in ethanol (15 mL). A 10% palladium-carbon catalyst (160 mg) was added, and the mixture was stirred in a hydrogen atmosphere throughout the day. The reaction solution was filtered through celite and then concentrated under reduced pressure to obtain 220 mg of the title compound as a colorless oily substance. The resulting compound was used for the next reaction without purification.

mass spectrum (ESI): m/z 305 (M+H)$^+$.

(187d) Methyl cis(±)-2-(4-{[(4-chloro-5-ethyl-1H-imidazol-2-yl)carbonyl]amino}-3-methoxypiperidin-1-yl)-1H-benzimidazole-4-carboxylate Methyl cis(±)-2-(4-amino-3-methoxypiperidin-1-yl)-1H-benzimidazole-4-carboxylate obtained in Example (187c) (220 mg, 0.75 mmol) and 4-chloro-5-ethyl-1H-imidazole-2-carboxylic acid obtained in Example (1d) (130 mg, 0.75 mmol) were dissolved in DMA (5 ml). WSC hydrochloride (580 mg, 3 mmol) and HOBt (100 mg, 0.75 mmol) were added, and the mixture was stirred at room temperature overnight. The reaction solution was diluted with ethyl acetate, washed with water and brine, and dried over anhydrous sodium sulfate. Following concentration under reduced pressure, the residue was recrystallized from an ethyl acetate/hexane solvent to obtain the title compound as crystals.

$^1$H NMR spectrum (DMSO-D$_6$) δ: 13.37 (1H, s), 10.79 (1H, s), 7.58 (1H, d, J=9.02 Hz), 7.45 (2H, t, J=6.46 Hz), 7.06 (1H, t, J=9.27 Hz), 4.61-4.53 (1H, m), 4.29-4.15 (2H, m), 3.91 (3H, s), 3.58-3.52 (1H, m), 3.32 (3H, s), 3.30-3.16 (2H, m), 2.55 (2H, q, J=7.56 Hz), 1.98-1.85 (1H, m), 1.74-1.62 (1H, m), 1.14 (3H, t, J=7.07 Hz).

mass spectrum (ESI): m/z 461 (M+H)$^+$.

Example 188

6-{[(4-Chloro-5-ethyl-1H-imidazol-2-yl)carbonyl]amino}-1-benzothiophene-2-carboxylic acid (Exemplified Compound No. 188)

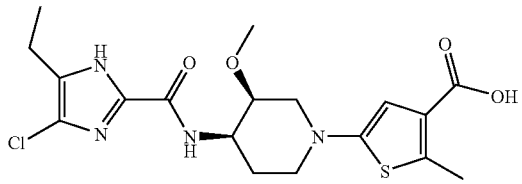

(188a) Benzyl cis(±)-[1-(chloroacetyl)-3-methoxypiperidin-4-yl]carbamate

Methanol (10 ml), ethyl acetate (10 ml) and a 4 N hydrochloric acid/ethyl acetate solution (30 mL) were added to tert-butyl cis(±)-4-{[(benzyloxy)carbonyl]amino}-3-methoxypiperidine-1-carboxylate obtained in Example (40a) (1.88 g, 5.16 mmol), and the mixture was stirred at room temperature overnight. The reaction solution was concentrated under reduced pressure, azeotropically dehydrated by adding toluene, and dissolved in methylene chloride (100 ml), followed by adding diisopropylethylamine (2.1 g). Chloroacetyl chloride (640 mg, 5.68 mmol) was dissolved in methylene chloride (50 ml), and the solution was added dropwise at 0° C. Following the dropwise addition, the mixture was stirred at 0° C. to room temperature overnight. The reaction solution was washed with water and aqueous sodium bicarbonate, concentrated under reduced pressure, and then azeotropically dehydrated by adding toluene to obtain the title compound. Half of the resulting compound was used for the next reaction without purification.

mass spectrum (ESI): m/z 341 (M+H)$^+$.

(188b) Methyl cis(±)-2-acetyl-4-(4-{[(benzyloxy)carbonyl]amino}-3-methoxypiperidin-1-yl)-4-oxobutanoate Methyl acetoacetate (510 mg, 4.4 mmol) was dissolved in methanol (15 ml). Sodium methoxide (210 mg, 3.9 mmol) was added, and the mixture was stirred at room temperature for 30 minutes. Further, benzyl cis(±)-[1-(chloroacetyl)-3-methoxypiperidin-4-yl]carbamate obtained in Example (188a) was dissolved in methanol (10 ml). The solution was added to the reaction solution, and the mixture was stirred at 70° C. overnight. The reaction solution was diluted with ethyl acetate, neutralized with 1 N hydrochloric acid, washed with brine, and dried over anhydrous sodium sulfate. Following concentration under reduced pressure, the title compound was obtained. The resulting compound was used for the next reaction without purification.

mass spectrum (ESI): m/z 421 (M+H)$^+$.

(188c) Methyl cis(±)-5-(4-{[(benzyloxy)carbonyl]amino}-3-methoxypiperidin-1-yl)-2-methylthiophene-3-carboxylate Methyl cis(±)-2-acetyl-4-(4-{[(benzyloxy)carbonyl]amino}-3-methoxypiperidin-1-yl)-4-oxobutanoate obtained in Example (188b) (1.1 g) was dissolved in toluene. Lawesson's reagent (660 mg) was added, and the mixture was stirred at 110° C. for two hours. Further, Lawesson's reagent (330 mg) was added, and the mixture was stirred at 110° C. for two hours. The reaction solution was concentrated under reduced pressure, and then the residue was purified by silica gel column chromatography (elution solvent: ethyl acetate/hexane=1/10) and recrystallized from methylene chloride/hexane, to obtain 50 mg of the title compound as crystals.

$^1$H NMR spectrum (DMSO-D$_6$) δ: 7.45-7.25 (5H, m), 6.30 (1H, s), 5.03 (2H, s), 3.73 (3H, s), 3.66-3.58 (1H, m), 3.49-3.36 (1H, m), 3.33 (3H, s), 3.30-3.27 (1H, m), 3.27-3.17 (1H, m), 2.86-2.76 (1H, m), 2.64-2.56 (1H, m), 2.53 (3H, s), 1.89-1.79 (1H, m), 1.61-1.47 (1H, m).

mass spectrum (ESI): m/z 419 (M+H)$^+$.

(188d) Methyl cis(±)-5-(4-amino-3-methoxypiperidin-1-yl)-2-methylthiophene-3-carboxylate Methyl cis(±)-5-(4-{[(benzyloxy)carbonyl]amino}-3-methoxypiperidin-1-yl)-2-methylthiophene-3-carboxylate obtained in Example (188c) (50 mg) was dissolved in acetic acid (1 mL). A hydrobromic acid-acetic acid solution (1 ml) was added, and the mixture was stirred at room temperature for one hour. The reaction solution was diluted with ethyl acetate, washed with water and brine, and dried over anhydrous sodium sulfate. Following concentration under reduced pressure, the residue was purified by silica gel column chromatography (elution solvent: methanol/ethyl acetate=0, 10%) to obtain 20 mg of the title compound as a glassy solid (59%).

mass spectrum (ESI): m/z 285 (M+H)$^+$.

(188e) Methyl cis(±)-5-(4-{[(4-chloro-5-ethyl-1H-imidazol-2-yl)carbonyl]amino}-3-methoxypiperidin-1-yl)-2-methylthiophene-3-carboxylate Methyl cis(±)-5-(4-amino-3-methoxypiperidin-1-yl)-2-methylthiophene-3-carboxylate obtained in Example (188d) (20 mg, 0.07 mmol) and 4-chloro-5-ethyl-1H-imidazole-2-carboxylic acid obtained in Example (1d) (15 mg, 0.07 mmol) were dissolved in DMA (2 ml). WSC hydrochloride (40 mg, 0.21 mmol) and HOBt (10 mg, 0.07 mmol) were added, and the mixture was stirred at 70° C. for one hour and at room temperature overnight. The reaction solution was diluted with ethyl acetate, washed with water, and dried over anhydrous sodium sulfate. Following concentration under reduced pressure, the residue was purified by silica gel column chromatography (elution solvent: ethyl acetate/hexane=0, 9, 17%) to obtain 16 mg of the title compound as a glassy solid. mass spectrum (ESI): m/z 441 (M+H)$^+$.

(188f) cis(±)-5-(4-{[(4-Chloro-5-ethyl-1H-imidazol-2-yl)carbonyl]amino}-3-methoxypiperidin-1-yl)-2-methylthiophene-3-carboxylic acid Methyl cis(±)-5-(4-{[(4-chloro-5-ethyl-1H-imidazol-2-yl)carbonyl]amino}-3-methoxypiperidin-1-yl)-2-methylthiophene-3-carboxylate obtained in Example (188e) (16 mg) was dissolved in methanol (1 ml) and THF (1 ml). A 2 N aqueous lithium hydroxide solution (1 ml) was added, and the mixture was stirred at room temperature overnight. The organic solvent was evaporated under reduced pressure. Then, the residue was neutralized with 1 N hydrochloric acid, diluted with ethyl acetate, washed with brine, and dried over anhydrous sodium sulfate. Following concentration under reduced pressure, the residue was recrystallized from an ethyl acetate/hexane solvent to obtain the title compound as crystals.

$^1$H NMR spectrum (DMSO-D$_6$) δ: 13.23 (1H, br s), 12.43 (1H, br s), 8.51 (1H, d, J=9.03 Hz), 6.31 (1H, s), 3.90-3.77 (1H, m), 3.74-3.66 (1H, m), 3.60-3.47 (1H, m), 3.39-3.34 (1H, m), 3.33 (3H, s), 2.85-2.74 (1H, m), 2.59-2.54 (3H, m), 2.53 (3H, s), 1.83-1.70 (2H, m), 1.14 (3H, t, J=7.57 Hz).

mass spectrum (ESI): m/z 427 (M+H)$^+$.

Example 189

Mixture of cis(±)-2-(4-{[(4-chloro-5-ethyl-1H-imidazol-2-yl)carbonyl]amino}-3-methoxypiperidin-1-yl)-5-[(1E)-N-methoxyethanimidoyl]-1,3-thiazole-4-carboxylic acid and cis(±)-2-(4-{[(4-chloro-5-ethyl-1H-imidazol-2-yl)carbonyl]amino}-3-methoxypiperidin-1-yl)-5-[(1Z)—N-methoxyethanimidoyl]-1,3-thiazole-4-carboxylic acid (Exemplified Compound No. 189)

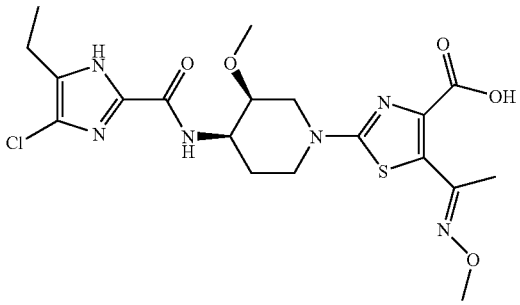

-continued

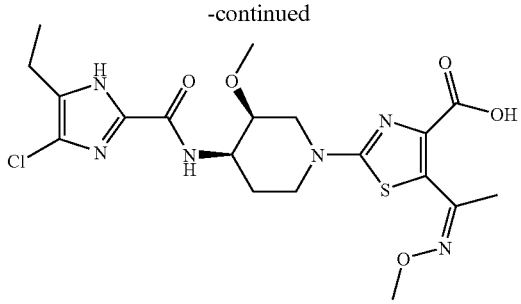

(189a) Mixture of ethyl cis(±)-2-(4-{[(4-chloro-5-ethyl-1H-imidazol-2-yl)carbonyl]amino}-3-methoxypiperidin-1-yl)-5-[(1E)-N-methoxyethanimidoyl]-1,3-thiazole-4-carboxylate and ethyl cis(±)-2-(4-{[(4-chloro-5-ethyl-1H-imidazol-2-yl)carbonyl]amino}-3-methoxypiperidin-1-yl)-5-[(1Z)—N-methoxyethanimidoyl]-1,3-thiazole-4-carboxylate Ethyl cis(±)-5-acetyl-2-(4-{[(4-chloro-5-ethyl-1H-imidazol-2-yl)carbonyl]amino}-3-methoxypiperidin-1-yl)-1,3-thiazole-4-carboxylate obtained in Example (190b) (74 mg, 0.15 mmol) was dissolved in THF (5 ml), ethanol (5 ml) and water (5 ml). O-methylhydroxylamine hydrochloride (185 mg, 2.23 mmol) was added, and the mixture was stirred at 70° C. for three hours. Following concentration under reduced pressure, the residue was diluted with ethyl acetate, washed with saturated aqueous sodium bicarbonate and brine, and dried over anhydrous sodium sulfate. Following concentration under reduced pressure, the title compound was obtained as an oily substance. The compound was not resolved and was used for the next reaction as an about 3:1 geometric isomer mixture.

$^1$H NMR spectrum (CDCl$_3$) δ: 7.52-7.39 (1H, m), 4.52-4.42 (1H, m), 4.40-4.30 (2H, m), 4.29-4.19 (1H, m), 4.02-3.95 (1H, m), 3.94 (2.2H, s), 3.87 (0.8H, s), 3.55-3.46 (1H, m), 3.43 (3H, d, J=1.46 Hz), 3.26-3.14 (1H, m), 3.13-3.06 (1H, m), 2.69 (2H, q, J=7.56 Hz), 2.19 (0.8H, s), 2.16 (2.2H, s), 2.12-1.96 (1H, m), 1.84-1.72 (1H, m), 1.39-1.33 (3H, m), 1.26 (3H, t, J=7.68 Hz).

mass spectrum (ESI): m/z 513 (M+H)$^+$.

(189b) Mixture of cis(±)-2-(4-{[(4-chloro-5-ethyl-1H-imidazol-2-yl)carbonyl]amino}-3-methoxypiperidin-1-yl)-5-[(1E)-N-methoxyethanimidoyl]-1,3-thiazole-4-carboxylic acid and cis(±)-2-(4-{[(4-chloro-5-ethyl-1H-imidazol-2-yl)carbonyl]amino}-3-methoxypiperidin-1-yl)-5-[(1Z)—N-methoxyethanimidoyl]-1,3-thiazole-4-carboxylic acid The mixture of ethyl cis(±)-2-(4-{[(4-chloro-5-ethyl-1H-imidazol-2-yl)carbonyl]amino}-3-methoxypiperidin-1-yl)-5-[(1E)-N-methoxyethanimidoyl]-1,3-thiazole-4-carboxylate and ethyl cis(±)-2-(4-{[(4-chloro-5-ethyl-1H-imidazol-2-yl)carbonyl]amino}-3-methoxypiperidin-1-yl)-5-[(1Z)—N-methoxyethanimidoyl]-1,3-thiazole-4-carboxylate obtained in Example (189a) was dissolved in methanol (1 ml) and THF (1 ml). A 2 N aqueous lithium hydroxide solution (1 ml) was added, and the mixture was stirred at room temperature overnight. The organic solvent was evaporated under reduced pressure, followed by neutralization with 1 N hydrochloric acid. The resulting solid was collected by filtration and washed with distilled water, to obtain the title compound as a solid. The compound was an about 15:2 geometric isomer mixture.

$^1$H NMR spectrum (DMSO-D$_6$) δ: 13.37 (1H, s), 13.17 (1H, br s), 7.69-7.63 (1H, m), 4.29-4.14 (2H, m), 3.95-3.86 (1H, m), 3.84 (2.6H, s), 3.78 (0.4H, s), 3.58-3.53 (1H, m), 3.34 (3H, s), 3.31-3.19 (2H, m), 2.55 (2H, q, J=7.56 Hz), 2.11 (0.4H, s), 2.08 (2.6H, s), 1.94-1.79 (1H, m), 1.72-1.62 (1H, m), 1.14 (3.H, t, J=7.32 Hz).

mass spectrum (ESI): m/z 485 (M+H)$^+$.

Example 190 cis(±)-5-Acetyl-2-(4-{[(4-chloro-5-ethyl-1H-imidazol-2-yl)carbonyl]amino}-3-methoxypiperidin-1-yl)-1,3-thiazole-4-carboxylic acid (Exemplified Compound No. 190)

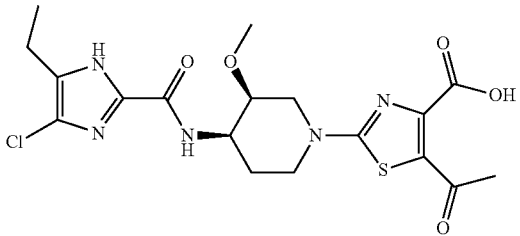

(190a) Ethyl 5-acetyl-2-bromo-1,3-thiazole-4-carboxylate

Ethyl 5-acetyl-2-amino-1,3-thiazole-4-carboxylate (218 mg, 1 mmol) (reference: U.S. Pat. No. 4,649,146 A1) was dissolved in acetonitrile (30 ml). Copper (II) bromide (345 mg, 1.55 mmol) and tert-butyl nitrite (155 mg, 1.5 mmol) were added, and the mixture was stirred at room temperature for two hours and at 70° C. for three hours. The reaction solution was concentrated under reduced pressure, diluted with ethyl acetate, washed with dilute hydrochloric acid, saturated aqueous sodium bicarbonate and brine, and dried over anhydrous sodium sulfate. Following concentration under reduced pressure, the title compound was obtained as a residue and as a brown oily substance. The resulting compound was used for the next reaction without purification.

$^1$H NMR spectrum (CDCl$_3$) δ: 4.47 (2H, q, J=7.07 Hz), 2.63 (3H, s), 1.43 (3H, t, J=7.19 Hz). (190b) Ethyl cis(±)-5-acetyl-2-(4-{[(4-chloro-5-ethyl-1H-imidazol-2-yl)carbonyl]amino}-3-methoxypiperidin-1-yl)-1,3-thiazole-4-carboxylate Methanol (4 ml) and a 4 N hydrochloric acid/ethyl acetate solution (6 mL) were added to tert-butyl cis(±)-4-{[(4-chloro-5-ethyl-1H-imidazol-2-yl)carbonyl]amino}-3-methoxypiperidine-1-carboxylate obtained in Example (1g) (130 mg, 0.34 mmol), and the mixture was stirred at room temperature for two hours. Following concentration under reduced pressure, the residue was dissolved in DMF (1 mL). Ethyl 5-acetyl-2-bromo-1,3-thiazole-4-carboxylate obtained in Example (190a) (130 mg) and diisopropylethylamine (0.4 ml) were added. and the mixture was stirred at 85° C. for four hours. Ethyl acetate was added to the reaction solution, and the organic layer was washed with water and brine, and dried over anhydrous sodium sulfate. Following concentration under reduced pressure, the residue was recrystallized from an ethyl acetate/hexane solvent to obtain 128 mg of the title compound as crystals. mass spectrum (ESI): m/z 484 (M+H)$^+$.

(190c) cis(±)-5-Acetyl-2-(4-{[(4-chloro-5-ethyl-1H-imidazol-2-yl)carbonyl]amino}-3-methoxypiperidin-1-yl)-1,3-thiazole-4-carboxylic acid Ethyl cis(±)-5-acetyl-2-(4-{[(4-chloro-5-ethyl-1H-imidazol-2-yl)carbonyl]amino}-3-methoxypiperidin-1-yl)-1,3-thiazole-4-carboxylate obtained in Example (190b) (54 mg, 0.11 mmol) was dissolved in methanol (2 ml) and THF (2 ml). A 2 N aqueous lithium hydroxide solution (2 ml) was added, and the mixture was stirred at room temperature overnight. The organic solvent was evaporated under reduced pressure, followed by neutralization with 1 N hydrochloric acid. The resulting solid was collected by filtration and washed with distilled water, to obtain the title compound as a solid.

$^1$H NMR spectrum (DMSO-D$_6$) δ: 14.13-13.80 (1H, br s), 13.37 (1H, s), 7.68 (1H, d, J=8.54 Hz), 4.44-4.11 (2H, m), 4.08-3.82 (1H, m), 3.63-3.56 (1H, m), 3.45-3.35 (2.0H, m), 3.34 (3H, s), 2.55 (2H, q, J=7.56 Hz), 2.36 (3H, s), 1.94-1.80 (1H, m), 1.74-1.65 (1H, m), 1.14 (3H, t, J=7.56 Hz).

mass spectrum (ESI): m/z 456 (M+H)$^+$.

Example 191 cis(±)-2-(4-{[(4-Chloro-5-ethyl-1H-imidazol-2-yl)carbonyl]amino}-3-methoxypiperidin-1-yl)-1,3-benzoxazole-7-carboxylic acid (Exemplified Compound No. 191)

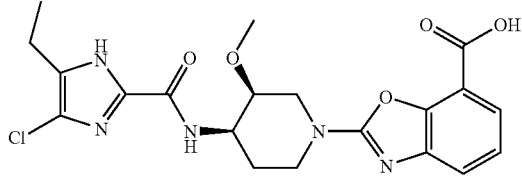

(191a) Methyl cis(±)-2-(4-{[(4-chloro-5-ethyl-1H-imidazol-2-yl)carbonyl]amino}-3-methoxypiperidin-1-yl)-1,3-benzoxazole-7-carboxylate Methanol (2 ml) and a 4 N hydrochloric acid/ethyl acetate solution (2 mL) were added to tert-butyl cis(±)-4-{[(4-chloro-5-ethyl-1H-imidazol-2-yl)carbonyl]amino}-3-methoxypiperidine-1-carboxylate obtained in Example (1g) (60 mg, 0.16 mmol), and the mixture was stirred at room temperature for two hours. Following concentration under reduced pressure, the residue was dissolved in DMF (4 mL). Methyl 2-chloro-1,3-benzooxazole-7-carboxylate (34 mg, 0.16 mmol) (reference: U.S. Pat. No. 6,166,011 A1) and diisopropylethylamine (1 ml) were added, and the mixture was stirred at 80° C. for six hours. Ethyl acetate was added to the reaction solution, and the organic layer was washed with water and dried over anhydrous sodium sulfate. Following concentration under reduced pressure, the residue was recrystallized from an ethyl acetate/hexane solvent to obtain 75 mg of the title compound as crystals. mass spectrum (ESI): m/z 462 (M+H)$^+$.

(1b) cis(±)-2-(4-{[(4-Chloro-5-ethyl-1H-imidazol-2-yl)carbonyl]amino}-3-methoxypiperidin-1-yl)-1,3-benzoxazole-7-carboxylic acid Methyl cis(±)-2-(4-{[(4-chloro-5-ethyl-1H-imidazol-2-yl)carbonyl]amino}-3-methoxypiperidin-1-yl)-1,3-benzoxazole-7-carboxylate obtained in Example (191a) (75 mg, 0.16 mmol) was dissolved in methanol (1 ml) and THF (1 ml). A 2 N aqueous lithium hydroxide solution (1 ml) was added, and the mixture was stirred at room temperature overnight. The organic solvent was evaporated under reduced pressure, followed by neutralization with 1 N hydrochloric acid. The resulting solid was collected by filtration, washed with distilled water, and dried under reduced pressure at 50° C. to obtain the title compound as a solid.

$^1$H NMR spectrum (DMSO-D$_6$) δ: 13.37 (1H, s), 13.16 (1H, s), 7.64 (1H, d, J=8.54 Hz), 7.49 (2H, d, J=7.81 Hz), 7.24 (1H, t, J=7.81 Hz), 4.51-4.41 (1H, m), 4.30-4.13 (2H, m), 3.62-3.57 (1H, m), 3.41-3.35 (2H, m), 3.35 (3H, s), 2.59-2.52 (2H, m), 1.98-1.83 (1H, m), 1.76-1.64 (1H, m), 1.14 (3H, t, J=7.57 Hz).

mass spectrum (ESI): m/z 448 (M+H)$^+$.

Example 192

3-{4-[(4-Chloro-5-ethyl-1H-imidazole-2-carbonyl)amino]piperidine-1-yl}benzoic acid (Exemplified Compound No. 192)

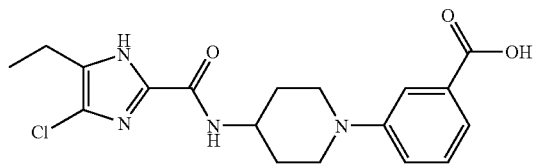

(192a) tert-Butyl 4-benzyloxycarbonylaminopiperidine-1-carboxylate

A solution of tert-butyl 4-aminopiperidine-1-carboxylate (1.2 g, 6 mmol) in dichloromethane (20 mL) was cooled to 0° C. Carbobenzoxy chloride (1.03 mL, 7.2 mmol) and diisopropylethylamine (3.15 mL, 18 mmol) were added at the same temperature, and the solution was stirred at 0° C. for one hour. The reaction solution was neutralized with saturated aqueous potassium carbonate solution, diluted with ethyl acetate, washed with brine, and dried over magnesium sulfate. Thereafter, the solvent was evaporated under reduced pressure. The resulting residue was purified by silica gel column chromatography (elution solvent: hexane/ethyl acetate=3/1) to obtain 1.5 g of the title compound as a yellow oily substance (75%).

$^1$H NMR spectrum (400 MHz, CDCl$_3$) δ ppm: 1.23-1.34 (2H, m), 1.42 (9H, s), 1.81-1.92 (2H, m), 2.75-2.86 (2H, m), 3.56-3.68 (1H, m), 3.91-4.04 (2H, m), 4.99-5.03 (1H, m), 5.05 (2H, s), 7.26-7.33 (5H, m).

(192b) Benzyl piperidin-4-yl-carbamate

A 4 N hydrochloric acid/1,4-dioxane solution (20 mL) was added to tert-butyl 4-benzyloxycarbonylaminopiperidine-1-carboxylate obtained in Example (192a) (1.5 g, 4.49 mmol). The mixture was stirred at room temperature for one hour, and the solvent was evaporated under reduced pressure. The resulting residue was dissolved in methanol. Amberlite IRA-400(Cl) ion exchange resin (20 g) was added, and the mixture was stirred at room temperature for one hour. Amberlite was filtered off, and then the solution was concentrated under reduced pressure to obtain 910 mg of the title compound as a colorless oily substance.

$^1$H NMR spectrum (400 MHz, CD$_3$OD) δ ppm: 1.30-1.42 (2H, m), 1.82-1.89 (2H, m), 2.54-2.63 (2H, m), 2.96-3.04 (2H, m), 3.30-3.31 (1H, m), 3.43-3.53 (1H, m), 5.06 (2H, s), 7.26-7.36 (5H, m).

(192c) Methyl 3-(4-benzyloxycarbonylaminopiperidin-1-yl)benzoate

Methyl 3-bromobenzoate (230 mg, 1.07 mmol), palladium acetate (12 mg, 0.054 mmol), BINAP (133 mg, 0.214 mmol) and cesium carbonate (767 mg, 2.35 mmol) were added to a solution of benzyl piperidin-4-yl-carbamate obtained in Example (192b) (248 mg, 0.817 mmol) in 1,4-dioxane (10 mL) and N,N-dimethylformamide (2.5 mL), and the mixture was stirred at 100° C. for 20 hours. The reaction solution was cooled, diluted with ethyl acetate, and washed with brine. The organic layer was dried over magnesium sulfate, and then the solvent was evaporated under reduced pressure. The resulting residue was purified by silica gel column chromatography (elution solvent: hexane/ethyl acetate=3/1) to obtain 80 mg of the title compound as a colorless oily substance (20%).

mass spectrum (ESI): m/z 369 (M+1)$^+$.

(192d) Methyl 3-{4-[(4-chloro-5-ethyl-1H-imidazole-2-carbonyl)amino]piperidin-1-yl}benzoate 10% palladium-carbon (wet, 200 mg) was added to a mixed solution of methyl 3-(4-benzyloxycarbonylaminopiperidin-1-yl)benzoate obtained in Example (192c) (120 mg, 0.345 mmol) in tetrahydrofuran/methanol=1/1 (10 mL), and the mixture was catalytically hydrogenated at room temperature for three hours. The catalyst was filtered off, and the filtrate was evaporated under reduced pressure to obtain methyl 3-(4-aminopiperidin-1-yl)benzoate as a colorless oily substance. The resulting amine was dissolved in a mixed solution of N,N-dimethylacetamide/dichloromethane=1/1 (8 mL). 4-Chloro-5-ethyl-1H-imidazole-2-carboxylic acid (described in Example 1d, 190 mg, 1.1 mmol), 1-hydroxybenzotriazole (220 mg, 1.63 mmol), 1-ethyl-3-(3-dimethylaminopropyl)-carbodiimide hydrochloride (312 mg, 1.63 mmol) and triethylamine (227 µL, 1.63 mmol) were added, and the mixture was stirred at room temperature overnight. The reaction solution was diluted with ethyl acetate, washed with brine, and then dried over magnesium sulfate. The solvent was evaporated under reduced pressure. The resulting residue was purified by silica gel column chromatography (elution solvent: hexane/ethyl acetate=1/1) to obtain 88 mg of the title compound as a colorless solid (41%).

$^1$H NMR spectrum (400 MHz, CDCl$_3$) δ ppm: 1.25-1.30 (3H, m), 1.69-1.88 (3H, m), 2.07-2.16 (2H, m), 2.68-2.75 (2H, m), 2.86-2.95 (2H, m), 3.69-3.77 (2H, m), 3.91 (3H, s), 4.01-4.10 (1H, m), 7.01-7.15 (1H, m), 7.23-7.34 (2H, m), 7.51-7.55 (1H, m), 7.60-7.63 (1H, m), 12.35 (1H, s).

mass spectrum (ESI): m/z 391 (M+1)$^+$.

(192e) 3-{4-[(4-Chloro-5-ethyl-1H-imidazole-2-carbonyl)amino]piperidine-1-yl}benzoic acid The same operation as in Example (1i) was performed using methyl 3-{4-[(4-chloro-5-ethyl-1H-imidazole-2-carbonyl)amino]piperidin-1-yl}benzoate obtained in Example (192d) (87.5 mg, 0.224 mmol) and lithium hydroxide monohydrate (47 mg, 1.12 mmol), to obtain 53 mg of the title compound as a white solid (63%).

$^1$H NMR spectrum (400 MHz, DMSO-D6) δ ppm: 1.10 (3H, t, J=7.57 Hz), 1.64-1.84 (4H, m), 2.50-2.55 (2H, m), 2.74-2.83 (2H, m), 3.97-4.05 (2H, m), 7.16-7.20 (1H, m), 7.28-7.32 (2H, m), 7.42-7.45 (1H, m), 8.26-8.31 (1H, m), 13.17 (1H, s).

mass spectrum (ESI): m/z 377 (M+1)$^+$.

Example 193 trans-3-{4-[(4-Chloro-5-ethyl-1H-imidazole-2-carbonyl)amino]cyclohexyl}benzoic acid (Exemplified Compound No. 193)

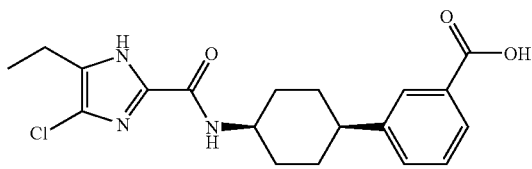

(193a) Ethyl trans-3-(4-aminocyclohexyl)benzoate

The compound was synthesized according to the method described in the following document.

WO 2006/087548 A2

(193b) Ethyl trans-3-{4-[(4-chloro-5-ethyl-1H-imidazole-2-carbonyl)amino]cyclohexyl}benzoate Ethyl trans-3-(4-aminocyclohexyl)benzoate obtained in Example (193a) (50 mg, 0.202 mmol) was dissolved in a mixed solution of N,N-dimethylacetamide/dichloromethane=1/1 (8 mL). 4-Chloro-5-ethyl-1H-imidazole-2-carboxylic acid (described in Example 1d, 71 mg, 0.404 mmol), 1-hydroxybenzotriazole (109 mg, 0.808 mmol), 1-ethyl-3-(3-dimethylaminopropyl)-carbodiimide hydrochloride (155 mg, 0.808 mmol) and triethylamine (112 µL, 0.808 mmol) were added, and the mixture was stirred at room temperature overnight. The reaction solution was diluted with ethyl acetate, washed with brine, and then dried over magnesium sulfate. The solvent was evaporated under reduced pressure. The resulting residue was purified by silica gel column chromatography (elution solvent: hexane/ethyl acetate=1/1) to obtain 43 mg of the title compound as a white solid (53%).

$^1$H NMR spectrum (400 MHz, CDCl$_3$) δ ppm: 1.27-1.32 (3H, m), 1.37-1.43 (3H, m), 1.42-1.53 (2H, m), 1.58-1.70 (2H, m), 1.98-2.05 (2H, m), 2.15-2.22 (2H, m), 2.56-2.66 (1H, m), 2.67-2.76 (2H, m), 3.92-4.01 (1H, m), 4.35-4.41 (2H, m), 7.11-7.16 (1H, m), 7.35-7.42 (2H, m), 7.87-7.91 (2H, m), 12.25 (1H, br s).

mass spectrum (ESI): m/z 404 (M+1)$^+$.

(193c) trans-3-{4-[(4-Chloro-5-ethyl-1H-imidazole-2-carbonyl)amino]cyclohexyl}benzoic acid The same operation as in Example (1i) was performed using ethyl trans-3-{4-[(4-chloro-5-ethyl-1H-imidazole-2-carbonyl)amino]cyclohexyl}benzoate obtained in Example (193b) (43 mg, 0.106 mmol) and lithium hydroxide monohydrate (44 mg, 1.06 mmol), to obtain 23 mg of the title compound as a white solid (58%).

$^1$H NMR spectrum (400 MHz, DMSO-D6) δ ppm: 1.07-1.13 (3H, m), 1.50-1.58 (4H, m), 1.78-1.90 (4H, m), 2.49-2.55 (3H, m), 4.20-4.23 (1H, m), 7.37-7.43 (1H, m), 7.47-7.52 (2H, m), 7.72-7.80 (2H, m), 8.13-8.18 (1H, m), 13.16 (1H, brs).

mass spectrum (ESI): m/z 376 (M+1)$^+$.

Example 194 cis-3-{4-[(4-Chloro-5-ethyl-1H-imidazole-2-carbonyl)amino]cyclohexyl}benzoic acid (Exemplified Compound No. 194)

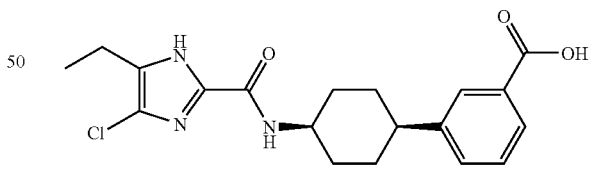

(194a) Ethyl cis-3-(4-aminocyclohexyl)benzoate

The compound was synthesized according to the method described in the following document.

WO 2006/087548 A2

(194b) Ethyl cis-3-{4-[(4-chloro-5-ethyl-1H-imidazole-2-carbonyl)amino]cyclohexyl}benzoate Ethyl cis-3-(4-aminocyclohexyl)benzoate obtained in Example (194a) (57 mg, 0.23 mmol) was dissolved in a mixed solution of N,N-dimethylacetamide/dichloromethane=1/1 (10 mL). 4-Chloro-5-ethyl-1H-imidazole-2-carboxylic acid (described in Example 1d, 60 mg, 0.345 mmol), 1-hydroxybenzotriazole (64 mg, 0.472 mmol), 1-ethyl-3-(3-dimethylaminopropyl)-carbodiimide hydrochloride (90 mg, 0.472 mmol) and triethylamine (66 μL, 0.472 mmol) were added, and the mixture was stirred at room temperature overnight. The reaction solution was diluted with ethyl acetate, washed with brine, and then dried over magnesium sulfate. The solvent was evaporated under reduced pressure. The resulting residue was purified by silica gel column chromatography (elution solvent: hexane/ethyl acetate=1/1) to obtain 50 mg of the title compound as a white solid (53%).

$^1$H NMR spectrum (400 MHz, CDCl$_3$) δ ppm: 1.23-1.33 (3H, m), 1.35-1.43 (5H, m), 1.77-1.90 (5H, m), 1.96-2.10 (3H, m), 2.68-2.77 (2H, m), 4.28-4.45 (2H, m), 7.36-7.49 (2H, m), 7.86-7.97 (2H, m), 12.45 (1H, br s).

mass spectrum (ESI): m/z 404 (M+1)$^+$.

(194c) cis-3-{4-[(4-Chloro-5-ethyl-1H-imidazole-2-carbonyl)amino]cyclohexyl}benzoic acid The same operation as in Example (1i) was performed using ethyl cis-3-{4-[(4-chloro-5-ethyl-1H-imidazole-2-carbonyl)amino]cyclohexyl}benzoate obtained in Example (194b) (50 mg, 0.124 mmol) and lithium hydroxide monohydrate (44 mg, 0.124 mmol), to obtain 23 mg of the title compound as a white solid (49%).

$^1$H NMR spectrum (400 MHz, DMSO-D6) δ ppm: 1.10 (3H, t, J=7.56 Hz), 1.60-1.86 (8H, m), 2.53 (2H, q, J=7.56 Hz), 2.61-2.70 (1H, m), 4.07-4.13 (1H, m), 7.38-7.43 (1H, m), 7.54 (1H, d, J=7.80 Hz), 7.74 (1H, d, J=7.80 Hz), 7.83 (1H, s), 7.98-8.03 (1H, m).

mass spectrum (ESI): m/z 376 (M+1)$^+$.

Example 195

3-{4-[(4-Chloro-5-ethyl-1H-imidazole-2-carbonyl)amino]cyclohex-1-enyl)benzoic acid (Exemplified Compound No. 195)

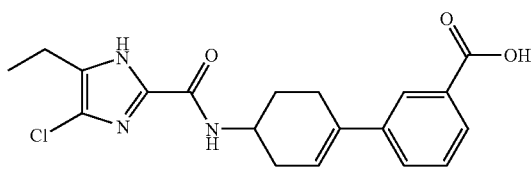

(195a) Ethyl (4-hydroxycyclohex-1-enyl)benzoate

The compound was synthesized according to the method described in the following document.

WO 2006/087548 A2

(195b) Ethyl 3-(4-tert-butoxycarbonylaminocyclohex-1-enyl)benzoate

A solution of ethyl (4-hydroxycyclohex-1-enyl)benzoate obtained in Example (195a) (1 g, 4.06 mmol) in pyridine (20 mL) was cooled to 0° C. Methanesulfonyl chloride (628 μL, 8.12 mmol) was added at the same temperature, and the mixture was stirred at 0° C. for two hours. The reaction solution was diluted with ethyl acetate, washed with 1 N hydrochloric acid and brine, and dried over magnesium sulfate. Thereafter, the solvent was evaporated under reduced pressure. The resulting residue was dissolved in N,N-dimethylformamide (30 mL). Sodium azide (1.32 g, 20.3 mmol) was added at room temperature, and the mixture was stirred at 70° C. for 18 hours. The reaction solution was diluted with ethyl acetate, washed with brine, and dried over magnesium sulfate. Thereafter, the solvent was evaporated under reduced pressure. The resulting residue was dissolved in tetrahydrofuran (30 mL). Water (109 μL, 6.09 mmol) and triphenylphosphine (1.17 g, 4.47 mmol) were added at room temperature, and the mixture was stirred at room temperature for 18 hours. After 18 hours, di-tert-butyl dicarbonate (975 mg, 4.47 mmol) was added, and the mixture was stirred at room temperature for five hours. The reaction solution was diluted with ethyl acetate, washed with brine, and dried over magnesium sulfate. Thereafter, the solvent was evaporated under reduced pressure. The resulting residue was purified by silica gel column chromatography (elution solvent: hexane/ethyl acetate=2/1) to obtain 510g of the title compound as a yellow oily substance (32%).

$^1$H NMR spectrum (400 MHz, CDCl$_3$) δ ppm: 1.36-1.42 (3H, m), 1.46 (9H, s), 1.68-1.82 (2H, m), 1.99-2.13 (2H, m), 2.51-2.64 (2H, m), 3.82-3.93 (1H, m), 4.38 (2H, q, J=7.08 Hz), 6.08 (1H, s), 7.33-7.39 (1H, m), 7.52-7.57 (1H, m), 7.87-7.93 (1H, m), 8.04 (1H, s).

(195c) Ethyl 3-(4-aminocyclohex-1-enyl)benzoate

A 4 N hydrochloric acid/1,4-dioxane solution (20 mL) was added to ethyl 3-(4-tert-butoxycarbonylaminocyclohex-1-enyl)benzoate obtained in Example (195b) (510 mg, 1.48 mmol). The mixture was stirred at room temperature for one hour, and the solvent was evaporated under reduced pressure. The resulting residue was dissolved in methanol. Amberlite IRA-400(Cl) ion exchange resin (20 g) was added, and the mixture was stirred at room temperature for one hour. Amberlite was filtered off, and then the solution was concentrated under reduced pressure to obtain 210 mg of the title compound as a colorless oily substance.

(195d) Ethyl 3-{4-[(4-chloro-5-ethyl-1H-imidazole-2-carbonyl)amino]cyclohex-1-enyl)benzoate Ethyl 3-(4-aminocyclohex-1-enyl)benzoate obtained in Example (951c) (120 mg, 0.49 mmol) was dissolved in a mixed solution of N,N-dimethylacetamide/dichloromethane=1/1 (10 mL). 4-Chloro-5-ethyl-1H-imidazole-2-carboxylic acid (described in Example 1d, 86 mg, 0.49 mmol), 1-hydroxybenzotriazole (100 mg, 0.735 mmol), 1-ethyl-3-(3-dimethylaminopropyl)-carbodiimide hydrochloride (141 mg, 0.735 mmol) and triethylamine (102 μL, 0.735 mmol) were added, and the mixture was stirred at room temperature overnight. The reaction solution was diluted with ethyl acetate, washed with brine, and then dried over magnesium sulfate. The solvent was evaporated under reduced pressure. The resulting residue was purified by silica gel column chromatography (elution solvent: hexane/ethyl acetate=1/1) to obtain 150 mg of the title compound as a white solid (76%).

$^1$H NMR spectrum (400 MHz, CDCl$_3$) δ ppm: 1.27 (3H, t, J=7.56 Hz), 1.37-1.42 (3H, m), 1.78 (2H, s), 1.84-1.94 (1H, m), 2.10-2.19 (1H, m), 2.22-2.32 (1H, m), 2.60-2.66 (2H, m), 2.71 (2H, q, J=7.56 Hz), 4.25-4.34 (1H, m), 4.39 (2H, q, J=7.56 Hz), 6.13 (1H, s), 7.27-7.29 (1H, m), 7.37-7.42 (1H, m), 7.55-7.59 (1H, m), 7.91-7.95 (1H, m), 8.06 (1H, s), 12.33 (1H, br s).

mass spectrum (ESI): m/z 402 (M+1)$^+$.

(195e) 3-{4-[(4-Chloro-5-ethyl-1H-imidazole-2-carbonyl)amino]cyclohex-1-enyl)benzoic acid The same operation as in Example (1i) was performed using ethyl 3-{4-[(4-chloro-5-ethyl-1H-imidazole-2-carbonyl)amino]cyclohex-1-enyl)benzoate obtained in Example (195d) (150 mg, 0.373 mmol) and lithium hydroxide monohydrate (156 mg, 3.73 mmol), to obtain 28 mg of the title compound as a white solid (20%).

$^1$H NMR spectrum (400 MHz, DMSO-D6) δ ppm: 1.10 (3H, t, J=7.57 Hz), 1.73-1.97 (2H, m), 2.49-2.55 (4H, m), 6.14 (1H, s), 4.20-4.25 (1H, m), 7.42-7.47 (1H, m), 7.64-7.67 (1H, m), 7.79 (1H, d, J=7.57 Hz), 7.92 (1H, s), 8.19-8.24 (1H, m), 13.17 (1H, br s).

mass spectrum (ESI): m/z 374 (M+1)$^+$.

Example 196 cis(±)-2-(4-{[(4-Chloro-5-ethyl-1H-imidazol-2-yl)carbonyl]amino}-3-fluoropiperidin-1-yl)-4-methyl-1,3-thiazole-5-carboxylic acid (Exemplified Compound No. 196)

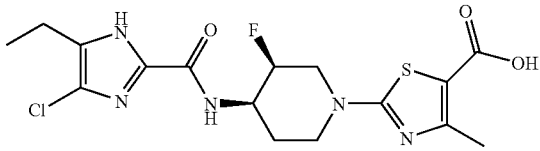

(196a) tert-Butyl cis(±)-4-amino-3-fluoropiperidine-1-carboxylate

The compound was synthesized according to the method described in the following document.

WO 2006/087543 A1

(196b) tert-Butyl cis(±)-4-{[(4-chloro-5-ethyl-1H-imidazol-2-yl)carbonyl]amino}-3-fluoropiperidine-1-carboxylate 1-Hydroxybenzotriazole hydrate (114 mg, 0.845 mmol), WSC hydrochloride (162 mg, 0.845 mmol) and triethylamine (118 µL, 0.845 mmol) were added to a solution of tert-butyl cis(±)-4-amino-3-fluoropiperidine-1-carboxylate obtained in Example (196a) (123 mg, 0.564 mmol) and 4-chloro-5-ethyl-1H-imidazole 2-carboxylic acid obtained in Example (1d) (118 mg, 0.676 mmol) in DMA (3 mL) at room temperature, and the mixture was stirred at 70° C. for two hours. Water was added to the reaction solution, followed by extraction with ethyl acetate. The resulting organic layer was washed with water and brine, and dried over anhydrous sodium sulfate, and then the insoluble matter was separated by filtration. The filtrate was concentrated under reduced pressure, and the resulting residue was purified by silica gel column chromatography (eluent: hexane:ethyl acetate=1:1 v/v) to obtain 159 mg of the title compound (75%) as a pale yellow foamy substance.

$^1$H NMR spectrum (400 MHz, CDCl$_3$) δ ppm: 1.26 (3H, t, J=7.6 Hz), 1.47 (9H, s), 1.73-1.80 (1H, m), 1.83-1.95 (1H, m), 2.69 (2H, q, J=7.6 Hz), 2.74-3.10 (2H, m), 4.12-4.36 (2H, m), 4.38-4.81 (2H, m), 7.31 (1H, d, J=9.0 Hz), 10.85 (1H, s).

mass spectrum (ESI): m/z 319, 321 (M-55 (tBu))$^+$.

(196c) Ethyl cis(±)-2-(4-{[(4-chloro-5-ethyl-1H-imidazol-2-yl)carbonyl]amino}-3-fluoropiperidin-1-yl)-4-methyl-1,3-thiazole-5-carboxylate A 4 N hydrochloric acid/1,4-dioxane solution (3 mL) was added to tert-butyl cis(±)-4-{[(4-chloro-5-ethyl-1H-imidazol-2-yl)carbonyl]amino}-3-fluoropiperidine-1-carboxylate obtained in Example (196b) (159 mg, 0.424 mmol) under ice-cooling, and the mixture was stirred at room temperature for 30 minutes. The reaction solution was concentrated under reduced pressure, and DMF (4 mL) was added. Ethyl 2-bromo-4-methyl-1,3-thiazole-5-carboxylate (117 mg, 0.467 mmol) and sodium carbonate (225 mg, 2.12 mmol) were added, and the mixture was stirred at 90° C. for three hours. Water was added to the reaction solution, followed by extraction with ethyl acetate. The resulting organic layer was washed with water and brine, and dried over anhydrous sodium sulfate, and then the insoluble matter was separated by filtration. The filtrate was concentrated under reduced pressure, and the resulting residue was purified by silica gel column chromatography (eluent: hexane:ethyl acetate=1:1 v/v) to obtain 106 mg of the title compound (56%) as a colorless solid.

$^1$H NMR spectrum (400 MHz, DMSO-d$_6$) δ ppm: 1.14 (3H, t, J=7.4 Hz), 1.24 (3H, t, J=7.1 Hz), 1.69-1.77 (1H, m), 2.00-2.11 (1H, m), 2.44 (3H, s), 2.51-2.59 (2H, m), 3.24-3.42 (1H, m), 3.52 (1H, dd, J=39.8, 14.9 Hz), 3.95-4.06 (1H, m), 4.15-4.35 (4H, m), 4.91 (1H, d, J=48.6 Hz), 8.24 (1H, d, J=6.8 Hz).

mass spectrum (ESI): m/z 444, 446 (M+H)$^+$.

(196d) cis(±)-2-(4-{[(4-Chloro-5-ethyl-1H-imidazol-2-yl)carbonyl]amino}-3-fluoropiperidin-1-yl)-4-methyl-1,3-thiazole-5-carboxylic acid A 2 N aqueous lithium hydroxide solution (1.18 mL, 2.37 mmol) was added to a mixed solution of ethyl cis(±)-2-(4-{[(4-chloro-5-ethyl-1H-imidazol-2-yl)carbonyl]amino}-3-fluoropiperidin-1-yl)-4-methyl-1,3-thiazole-5-carboxylate obtained in Example (196c) (105 mg, 0.237 mmol) in methanol (3 mL) and tetrahydrofuran (3 mL) at room temperature, and the mixture was stirred at 70° C. for two hours. The reaction solution was concentrated under reduced pressure. A 1 N aqueous hydrochloric acid solution (2.37 mL, 2.37 mmol) and water were added to the resulting residue, followed by extraction with ethyl acetate. The resulting organic layer was washed with water and brine, and dried over anhydrous sodium sulfate, and then the insoluble matter was separated by filtration. The filtrate was concentrated under reduced pressure to obtain 72 mg of the title compound (73%) as a colorless solid.

$^1$H NMR spectrum (400 MHz, DMSO-d$_6$) δ ppm: 1.14 (3H, t, J=7.6 Hz), 1.68-1.78 (1H, m), 1.98-2.12 (1H, m), 2.41 (3H, s), 2.49-2.60 (2H, m), 3.27-3.58 (2H, m), 3.99 (1H, d, J=12.0 Hz), 4.17-4.36 (2H, m), 4.91 (1H, d, J=48.8 Hz), 8.26 (1H, d, J=7.8 Hz), 13.36 (1H, s).

mass spectrum (ESI): m/z 416, 418 (M+H)$^+$.

Example 197 trans(±)-2-(4-{[(4-Chloro-5-ethyl-1H-imidazol-2-yl)carbonyl]amino}-3-fluoropiperidin-1-yl)-4-methyl-1,3-thiazole-5-carboxylic acid (Exemplified Compound No. 197)

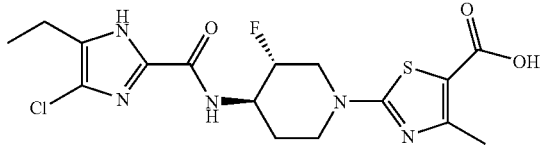

(197a) tert-Butyl trans(±)-4-amino-3-fluoropiperidine-1-carboxylate

The compound was synthesized according to the method described in the following document.

WO 2006/087543 A1

(197b) tert-Butyl trans(±)-4-{[(4-chloro-5-ethyl-1H-imidazol-2-yl)carbonyl]amino}-3-fluoropiperidine-1-carboxylate The same operation as in Example (196d) was performed using tert-butyl trans(±)-4-amino-3-fluoropiperidine-1-carboxylate obtained in Example (197a) (30.0 mg, 0.137 mmol), 4-chloro-5-ethyl-1H-imidazole-2-carboxylic acid obtained in Example (1d) (28.8 mg, 0.165 mmol), 1-hydroxybenzotriazole hydrate (27.9 mg, 0.206 mmol), WSC hydrochloride (39.5 mg, 0.206 mmol) and triethylamine (28.7 µL, 0.206 mmol), to obtain 37.0 mg of the title compound (72%) as a pale yellow foamy substance.

$^1$H NMR spectrum (400 MHz, CDCl$_3$) δ ppm: 1.22-1.60 (13H, m), 2.06-2.11 (1H, m), 2.65-2.72 (2H, m), 2.91-3.07 (2H, m), 3.93-4.02 (1H, m), 4.16-4.42 (3H, m), 7.08 (1H, d, J=8.6 Hz), 10.66 (1H, s).

mass spectrum (ESI): m/z 375 (M+H)$^+$.

(197c) Ethyl trans(±)-2-(4-{[(4-chloro-5-ethyl-1H-imidazol-2-yl)carbonyl]amino}-3-fluoropiperidin-1-yl)-4-methyl-1,3-thiazole-5-carboxylate The same operation as in Example (196c) was performed using tert-butyl trans(±)-4-{[(4-chloro-5-ethyl-1H-imidazol-2-yl)carbonyl]amino}-3-fluoropiperidine-1-carboxylate obtained in Example (197b) (37.0 mg, 0.099 mmol), 4 N hydrochloric acid/1,4-dioxane (1 mL), ethyl 2-bromo-4-methyl-1,3-thiazole-5-carboxylate (29.6 mg, 0.118 mmol) and sodium carbonate (105 mg, 0.987 mmol), to obtain 36 mg of the title compound (82%) as a colorless solid.

$^1$H NMR spectrum (400 MHz, CDCl$_3$) δ ppm: 1.26 (3H, t, J=7.6 Hz), 1.33 (3H, t, J=7.2 Hz), 1.68-1.78 (1H, m), 2.19-2.27 (1H, m), 2.55 (3H, s), 2.69 (2H, q, J=7.7 Hz), 3.25-3.34 (2H, m), 3.88-3.94 (1H, m), 4.23-4.38 (4H, m), 4.44-4.62 (1H, m), 7.13 (1H, d, J=8.0 Hz), 10.61 (1H, s).

mass spectrum (ESI): m/z 444, 446 (M+H)$^+$.

(197d) trans(±)-2-(4-{[(4-Chloro-5-ethyl-1H-imidazol-2-yl)carbonyl]amino}-3-fluoropiperidin-1-yl)-4-methyl-1,3-thiazole-5-carboxylic acid The same operation as in Example (196d) was performed using ethyl trans(±)-2-(4-{[(4-chloro-5-ethyl-1H-imidazol-2-yl)carbonyl]amino}-3-fluoropiperidin-1-yl)-4-methyl-1,3-thiazole-5-carboxylate obtained in Example (197c) (36 mg, 0.081 mmol) and a 2 N aqueous lithium hydroxide solution (406 μL, 0.811 mmol), to obtain 27 mg of the title compound (80%) as a colorless solid.

$^1$H NMR spectrum (400 MHz, DMSO-d$_6$) δ ppm: 1.13 (3H, t, J=7.6 Hz), 1.70-1.90 (2H, m), 2.42 (3H, s), 2.50-2.58 (2H, m), 3.21-3.48 (2H, m), 3.78 (1H, d, J=13.2 Hz), 4.20-4.30 (2H, m), 4.59-4.79 (1H, m), 8.67 (1H, d, J=9.0 Hz), 13.29 (1H, s).

mass spectrum (ESI): m/z 416, 418 (M+H)$^+$.

Example 198 cis(±)-2-(3-Chloro-4-{[(4-chloro-5-ethyl-1H-imidazol-2-yl)carbonyl]amino}piperidin-1-yl)-4-methyl-1,3-thiazole-5-carboxylic acid (Exemplified Compound No. 198)

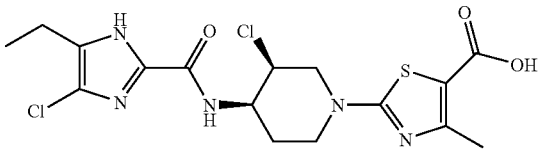

(198a) tert-Butyl cis(±)-4-amino-3-chloropiperidine-1-carboxylate

The compound was synthesized according to the method described in the following document.
WO 2006/087543 A1

(198b) tert-Butyl cis(±)-3-chloro-4-{[(4-chloro-5-ethyl-1H-imidazol-2-yl)carbonyl]amino}piperidine-1-carboxylate The same operation as in Example (196b) was performed using tert-butyl cis(±)-4-amino-3-chloropiperidine-1-carboxylate obtained in Example (198a) (134 mg, 0.571 mmol), 4-chloro-5-ethyl-1H-imidazole-2-carboxylic acid obtained in Example (1d) (99.7 mg, 0.571 mmol), 1-hydroxybenzotriazole hydrate (116 mg, 0.856 mmol), WSC hydrochloride (164 mg, 0.856 mmol) and triethylamine (119 μL, 0.856 mmol), to obtain 164 mg of the title compound (73%) as a colorless solid.

$^1$H NMR spectrum (400 MHz, DMSO-d$_6$) δ ppm: 1.14 (3H, t, J=7.6 Hz), 1.40 (9H, s), 1.52-1.60 (1H, m), 1.83-1.95 (1H, m), 2.56 (2H, q, J=7.6 Hz), 2.77-3.46 (2H, m), 3.89-4.30 (3H, m), 4.54-4.62 (1H, m), 7.98 (1H, d, J=7.3 Hz), 13.35 (1H, s).

mass spectrum (ESI): m/z 335, 337 (M-55 (tBu))$^+$.

(198c) Ethyl cis(±)-2-(3-chloro-4-{[(4-chloro-5-ethyl-1H-imidazol-2-yl)carbonyl]amino}piperidin-1-yl)-4-methyl-1,3-thiazole-5-carboxylate The same operation as in Example (196c) was performed using tert-butyl cis(±)-3-chloro-4-{[(4-chloro-5-ethyl-1H-imidazol-2-yl)carbonyl]amino}piperidine-1-carboxylate obtained in Example (198b) (101 mg, 0.258 mmol), 4 N hydrochloric acid/1,4-dioxane (2 mL), ethyl 2-bromo-4-methyl-1,3-thiazole-5-carboxylate (71.0 mg, 0.284 mmol) and sodium carbonate (547 mg, 5.16 mmol), to obtain 48 mg of the title compound (40%) as a pale yellow solid.

$^1$H NMR spectrum (400 MHz, CDCl$_3$) δ ppm: 1.27 (3H, t, J=7.3 Hz), 1.33 (3H, t, J=7.1 Hz), 1.81-1.88 (1H, m), 2.16-2.26 (1H, m), 2.55 (3H, s), 2.70 (2H, q, J=7.6 Hz), 3.16-3.23 (1H, m), 3.56 (1H, dd, J=14.4, 2.0 Hz), 4.18-4.30 (3H, m), 4.36-4.51 (3H, m), 7.47 (1H, d, J=8.3 Hz), 11.90 (1H, s).

(198d) cis(±)-2-(3-Chloro-4-{[(4-chloro-5-ethyl-1H-imidazol-2-yl)carbonyl]amino}piperidin-1-yl)-4-methyl-1,3-thiazole-5-carboxylic acid The same operation as in Example (2652d) was performed using ethyl cis(±)-2-(3-chloro-4-{[(4-chloro-5-ethyl-1H-imidazol-2-yl)carbonyl]amino}piperidin-1-yl)-4-methyl-1,3-thiazole-5-carboxylate obtained in Example (198c) (78 mg, 0.169 mmol) and a 2 N aqueous lithium hydroxide solution (848 μL). The resulting pale yellow solid was purified by thin layer silica gel chromatography (eluent: chloroform:tetrahydrofuran=3:2 v/v) to obtain 25 mg of the title compound (34%) as a colorless solid from the more polar elution fraction.

$^1$H NMR spectrum (400 MHz, DMSO-d$_6$) δ ppm: 1.15 (3H, t, J=7.6 Hz), 1.66-1.75 (1H, m), 2.02-2.14 (1H, m), 2.41 (3H, s), 2.56 (2H, q, J=7.6 Hz), 3.22-3.36 (1H, m), 3.71-3.80 (1H, m), 3.96-4.07 (1H, m), 4.17-4.26 (1H, m), 4.33-4.45 (1H, m), 4.69-4.75 (1H, m), 8.17 (1H, d, J=7.3 Hz), 13.37 (1H, brs).

mass spectrum (ESI): m/z 432, 434 (M+H)$^+$.

Example 199

(±)-2-[4-{[(4-Chloro-5-ethyl-1H-imidazol-2-yl)carbonyl]amino}-3,4-dihydropyridin-1(2H)-yl]-4-methyl-1,3-thiazole-5-carboxylic acid (Exemplified Compound No. 199)

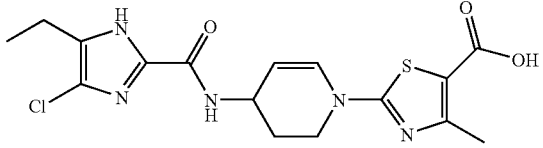

(199a) (±)-2-[4-{[(4-Chloro-5-ethyl-1H-imidazol-2-yl)carbonyl]amino}-3,4-dihydropyridin-1(2H)-yl]-4-methyl-1,3-thiazole-5-carboxylic acid 17 mg of the title compound (25%) was obtained as a colorless solid from the less polar elution fraction in Example (198d).

$^1$H NMR spectrum (400 MHz, DMSO-d$_6$) δ ppm: 1.13 (3H, t, J=7.4 Hz), 1.92-2.09 (2H, m), 2.45 (3H, s), 2.48-2.58 (2H, m), 3.60-3.84 (2H, m), 4.56-4.65 (1H, m), 4.93-5.02 (1H, m), 6.94 (1H, d, J=7.8 Hz), 8.45 (1H, d, J=7.6 Hz), 13.26 (1H, br s).

mass spectrum (ESI): m/z 396, 398 (M+H)$^+$.

Example 200 cis(±)-2-(4-{[(4-Chloro-5-ethyl-1H-imidazol-2-yl)carbonyl]amino}-3-(dimethylamino)piperidin-1-yl)-4-methyl-1,3-thiazole-5-carboxylic acid (Exemplified Compound No. 200)

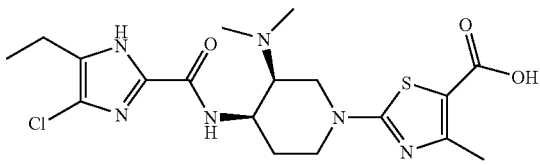

(200a) tert-Butyl cis(±)-3-amino-4-{[(benzyloxy)carbonyl]amino}piperidine-1-carboxylate The compound was synthesized according to the method described in the following document.

Bioorg. Med. Chem. Lett., 18(18), 2008, 5063-5065

(200b) tert-Butyl cis(±)-4-{[(benzyloxy)carbonyl]amino}-3-(dimethylamino)piperidine-1-carboxylate A 37% aqueous formaldehyde solution (346 μL, 4.26 mmol), acetic acid (110 μL, 1.92 mmol) and sodium cyanoborohydride (67 mg, 1.07 mmol) were added to a mixed solution of tert-butyl cis(±)-3-amino-4-{[(benzyloxy)carbonyl]amino}piperidine-1-carboxylate obtained in Example (200a) (149 mg, 0.43 mmol) in tetrahydrofuran (2 mL) and methanol (2 mL) under ice-cooling, and the mixture was stirred at room temperature for two hours. The reaction solution was concentrated under reduced pressure, and aqueous saturated sodium bicarbonate solution was added to the residue, followed by extraction with chloroform. The resulting organic layer was dried over anhydrous sodium sulfate, and then the insoluble matter was separated by filtration. The filtrate was concentrated under reduced pressure, and the resulting residue was purified by silica gel column chromatography (eluent: chloroform:methanol=10:1 v/v) to obtain 152 mg of the title compound (94%) as a colorless oily substance.

$^1$H NMR spectrum (400 MHz, CDCl$_3$) δ ppm: 1.46 (9H, s), 1.49-1.60 (1H, m), 2.08-2.16 (1H, m), 2.18-2.33 (1H, m), 2.25 (6H, s), 2.55-2.87 (1H, m), 2.92-3.01 (1H, m), 3.66-3.80 (1H, m), 3.89-3.96 (1H, m), 3.99-4.27 (1H, m), 5.10 (2H, s), 5.47 (1H, s), 7.28-7.70 (5H, m).

mass spectrum (ESI): m/z 378 (M+H)$^+$.

(200c) tert-Butyl cis(±)-4-amino-3-(dimethylamino)piperidine-1-carboxylate

20% Palladium hydroxide (15 mg) was added to a solution of tert-butyl cis(±)-4-{[(benzyloxy)carbonyl]amino}-3-(dimethylamino)piperidine-1-carboxylate obtained in Example (200b) (144 mg, 0.381 mmol) in methanol (4 mL) at room temperature, and the mixture was stirred in a hydrogen atmosphere at 50° C. for six hours. The insoluble matter was separated by filtration, and the filtrate was concentrated under reduced pressure to obtain 93 mg of the title compound (100%) as a colorless oily substance.

$^1$H NMR spectrum (400 MHz, CDCl$_3$) δ ppm: 1.46 (9H, s), 1.60-1.66 (2H, m), 1.87-1.98 (1H, m), 2.28 (6H, s), 2.71-2.98 (1H, m), 2.99-3.14 (1H, m), 3.43 (1H, q, J=3.4 Hz), 3.67-3.92 (1H, m), 3.94-4.27 (1H, m).

mass spectrum (ESI): m/z 244 (M+H)$^+$.

(200d) tert-Butyl cis(±)-4-{[(4-chloro-5-ethyl-1H-imidazol-2-yl)carbonyl]amino}-3-(dimethylamino)-piperidine-1-carboxylate The same operation as in Example (196b) was performed using tert-butyl cis(±)-4-amino-3-(dimethylamino)piperidine-1-carboxylate obtained in Example (200c) (93 mg, 0.382 mmol), 4-chloro-5-ethyl-1H-imidazole-2-carboxylic acid obtained in Example (1d) (80.1 mg, 0.459 mmol), 1-hydroxybenzotriazole hydrate (77.5 mg, 0.573 mmol), WSC hydrochloride (110 mg, 0.573 mmol) and triethylamine (79.9 μL, 0.573 mmol), to obtain 106 mg of the title compound (69%) as a colorless solid.

$^1$H NMR spectrum (400 MHz, CDCl$_3$) δ ppm: 1.25 (3H, t, J=7.6 Hz), 1.47 (9H, s), 1.56-1.69 (1H, m), 2.17-2.32 (8H, m), 2.68 (2H, q, J=7.6 Hz), 2.80-3.01 (3H, m), 3.71-3.81 (1H, m), 4.25-4.31 (1H, m), 7.51-7.54 (1H, m), 10.57 (1H, br s).

mass spectrum (ESI): m/z 400, 402 (M+H)$^+$.

(200e) Ethyl cis(±)-2-(4-{[(4-Chloro-5-ethyl-1H-imidazol-2-yl)carbonyl]amino}-3-(dimethylamino)piperidin-1-yl)-4-methyl-1,3-thiazole-5-carboxylate The same operation as in Example (196c) was performed using tert-butyl cis(±)-4-{[(4-chloro-5-ethyl-1H-imidazol-2-yl)carbonyl]amino}-3-(dimethylamino)-piperidine-1-carboxylate obtained in Example (200d) (104 mg, 0.260 mmol), 4 N hydrochloric acid/1,4-dioxane (2 mL), ethyl 2-bromo-4-methyl-1,3-thiazole-5-carboxylate (71.6 mg, 0.286 mmol) and sodium carbonate (551 mg, 5.20 mmol), to obtain 110 mg of the title compound (90%) as a pale yellow solid.

$^1$H NMR spectrum (400 MHz, CDCl$_3$) δ ppm: 1.26 (3H, t, J=7.6 Hz), 1.33 (3H, t, J=7.1 Hz), 1.75-1.85 (1H, m), 2.32 (6H, s), 2.36-2.48 (2H, m), 2.55 (3H, s), 2.69 (2H, q, J=7.6 Hz), 3.22-3.33 (2H, m), 3.69-3.77 (1H, m), 4.14-4.20 (1H, m), 4.26 (2H, q, J=7.1 Hz), 4.31-4.35 (1H, m), 7.58 (1H, d, J=4.6 Hz), 10.71 (1H, s).

mass spectrum (ESI): m/z 469, 471 (M+H)$^+$.

(200f) cis(±)-2-(4-{[(4-Chloro-5-ethyl-1H-imidazol-2-yl)carbonyl]amino}-3-(dimethylamino)piperidin-1-yl)-4-methyl-1,3-thiazole-5-carboxylic acid The same operation as in Example (196d) was performed using ethyl cis(±)-2-(4-{[(4-chloro-5-ethyl-1H-imidazol-2-yl)carbonyl]amino}-3-(dimethylamino)piperidin-1-yl)-4-methyl-1,3-thiazole-5-carboxylate obtained in Example (200e) (109 mg, 0.232 mmol) and a 2 N aqueous lithium hydroxide solution (1.24 mL, 2.47 mmol), to obtain 60 mg of the title compound (59%) as a colorless solid.

$^1$H NMR spectrum (400 MHz, CDCl$_3$) δ ppm: 1.27 (3H, t, J=7.6 Hz), 1.77-1.88 (1H, m), 2.34 (6H, s), 2.37-2.46 (2H, m), 2.56 (3H, s), 2.69 (2H, q, J=7.6 Hz), 3.26-3.36 (2H, m), 3.70-3.79 (1H, m), 4.21 (1H, d, J=9.5 Hz), 4.39-4.45 (1H, m), 7.73 (1H, d, J=5.6 Hz).

mass spectrum (ESI): m/z 441, 443 (M+H)$^+$.

Example 201 cis(±)-2-(4-{[(4-Chloro-5-ethyl-1H-imidazol-2-yl)carbonyl]amino}-3-pyrrolidin-1-ylpiperidin-1-yl)-1,3-benzothiazole-7-carboxylic acid (Exemplified Compound No. 201)

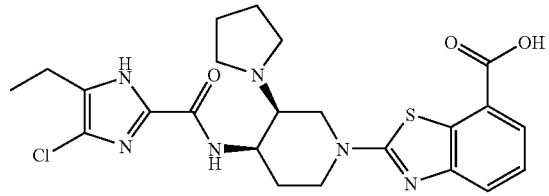

(201a) tert-Butyl trans(±)-4-amino-3-hydroxypiperidine-1-carboxylate

The compound was synthesized according to the method described in the following document.

J. Med. Chem., 41(19), 1998, 3563-3567 (201b) tert-Butyl trans(±)-4-{[(4-chloro-5-ethyl-1H-imidazol-2-yl)carbonyl]amino}-3-hydroxypiperidine-1-carboxylate The same operation as in Example (196b) was performed using tert-butyl trans(±)-4-amino-3-hydroxypiperidine-1-carboxylate synthesized in Example (201a) (600 mg, 2.77 mmol), 4-chloro-5-ethyl-1H-imidazole-2-carboxylic acid obtained in Example (2405d) (484 mg, 2.77 mmol), 1-hydroxybenzotriazole hydrate (562 mg, 4.16 mmol), WSC hydrochloride (798 mg, 4.16 mmol) and triethylamine (580 µL, 4.16 mmol), to obtain 950 mg of the title compound (92%) as a colorless solid.

$^1$H NMR spectrum (400 MHz, DMSO-d$_6$) δ ppm: 1.14 (3H, t, J=7.6 Hz), 1.35-1.53 (10H, m), 1.68-1.74 (1H, m), 2.44-3.49 (5H, m), 3.67-4.04 (3H, m), 5.02 (1H, d, J=5.1 Hz), 8.21 (1H, d, J=8.8 Hz), 13.20 (1H, s).

mass spectrum (ESI): m/z 317, 319 (M-55 (-tBu))$^+$.

(201c) tert-Butyl 4-{[(4-chloro-5-ethyl-1H-imidazol-2-yl)carbonyl]amino}-3-oxopiperidine-1-carboxylate Triethylamine (374 µL, 2.68 mmol) and sulfur trioxide-pyridine complex (256 mg, 1.61 mmol) were added to a mixed solution of tert-butyl trans(±)-4-{[(4-chloro-5-ethyl-1H-imidazol-2-yl)carbonyl]amino}-3-hydroxypiperidine-1-carboxylate synthesized in Example (201b) (100 mg, 0.268 mmol) in dimethyl sulfoxide (1 mL) and dichloromethane (1 mL) at room temperature, and the mixture was stirred at room temperature for 15 hours. Water was added to the reaction solution, followed by extraction with ethyl acetate. The organic layer was washed with water and brine, and dried over anhydrous sodium sulfate. The insoluble matter was separated by filtration, and the filtrate was concentrated under reduced pressure to obtain 120 mg of the title compound as an orange foamy substance, which was used for the next reaction without purification.

$^1$H NMR spectrum (400 MHz, CDCl$_3$) δ ppm: 1.24-1.28 (3H, m), 1.48 (9H, s), 1.75-1.85 (1H, m), 2.58-2.71 (3H, m), 3.43-3.60 (1H, m), 3.91-4.10 (2H, m), 4.34 (1H, d, J=17.4 Hz), 4.68-4.74 (1H, m), 7.62-7.67 (1H, m), 10.77 (1H, s).

mass spectrum (ESI): m/z 315, 317 (M-55 (-tBu))$^+$.

(201d) tert-Butyl cis(±)-4-{[(4-chloro-5-ethyl-1H-imidazol-2-yl)carbonyl]amino}-3-pyrrolidin-1-ylpiperidine-1-carboxylate tert-Butyl trans(±)-4-{[(4-chloro-5-ethyl-1H-imidazol-2-yl)carbonyl]amino}-3-pyrrolidin-1-ylpiperidine-1-carboxylate Pyrrolidine (45 µL, 0.539 mmol) and 3 Å molecular sieves (100 mg) were added to a solution of tert-butyl 4-{[(4-chloro-5-ethyl-1H-imidazol-2-yl)carbonyl]amino}-3-oxopiperidine-1-carboxylate obtained in Example (201c) (100 mg, 0.270 mmol) in tetrahydrofuran (3 mL), and the mixture was heated at 50° C. for four hours. Methanol (3 mL), pyrrolidine (45.0 µL, 0.539 mmol), sodium cyanoborohydride (51 mg, 0.809 mmol) and acetic acid (154 µL, 2.70 mmol) were added to the reaction solution, and the mixture was stirred at room temperature for 15 hours. The reaction solution was concentrated under reduced pressure. Saturated aqueous sodium bicarbonate solution was added to the residue, followed by extraction with ethyl acetate. The resulting organic layer was washed with brine and dried over anhydrous sodium sulfate, and then the insoluble matter was separated by filtration. The filtrate was concentrated under reduced pressure, and the resulting residue was purified by silica gel column chromatography and preparative TLC (eluent: chloroform:methanol=10:1 v/v) to obtain two isomers of the title compound, 21 mg of the cis isomer (18%) and 9 mg of the trans isomer (8%), as pale yellow oily substances.

cis-form mass spectrum (ESI): m/z 426, 428 (M+H)$^+$.

trans-form mass spectrum (ESI): m/z 426, 428 (M+H)$^+$.

(201e) Ethyl cis(±)-2-(4-{[(4-chloro-5-ethyl-1H-imidazol-2-yl)carbonyl]amino}-3-pyrrolidin-1-ylpiperidin-1-yl)-1,3-benzothiazole-7-carboxylate The same operation as in Example (196c) was performed using tert-butyl cis(±)-4-{[(4-chloro-5-ethyl-1H-imidazol-2-yl)carbonyl]amino}-3-pyrrolidin-1-ylpiperidine-1-carboxylate obtained in Example (201d) (21.0 mg, 0.049 mmol), 4 N hydrochloric acid/1,4-dioxane (2 mL), ethyl 2-bromo-1,3-benzothiazole-7-carboxylate obtained in Example (1f) (16 mg, 0.054 mmol) and sodium carbonate (52 mg, 0.493 mmol), to obtain 14 mg of the title compound (54%) as a pale yellow oily substance.

$^1$H NMR spectrum (400 MHz, CDCl$_3$) δ ppm: δ: 1.27 (3H, t, J=7.6 Hz), 1.43 (3H, q, J=7.0 Hz), 1.62-1.93 (6H, m), 2.47-2.74 (7H, m), 3.32-3.43 (2H, m), 3.98-4.05 (1H, m), 4.28-4.39 (2H, m), 4.45 (2H, q, J=7.2 Hz), 7.37 (1H, t, J=7.8 Hz), 7.71 (1H, dd, J=8.0, 1.2 Hz), 7.73 (1H, br s), 7.79 (1H, dd, J=7.8, 1.2 Hz).

mass spectrum (ESI): m/z 531, 533 (M+H)$^+$.

(201f) cis(±)-2-(4-{[(4-Chloro-5-ethyl-1H-imidazol-2-yl)carbonyl]amino}-3-pyrrolidin-1-ylpiperidin-1-yl)-1,3-benzothiazole-7-carboxylic acid The same operation as in Example (196d) was performed using ethyl cis(±)-2-(4-{[(4-chloro-5-ethyl-1H-imidazol-2-yl)carbonyl]amino}-3-pyrrolidin-1-ylpiperidin-1-yl)-1,3-benzothiazole-7-carboxylate obtained in Example (201e) (14.0 mg, 0.026 mmol) and a 2 N aqueous lithium hydroxide solution (132 µL), to obtain 6 mg of the title compound (45%) as a pale yellow solid.

$^1$H NMR spectrum (400 MHz, DMSO-d$_6$) δ ppm: δ: 1.10-1.16 (3H, m), 1.65-1.85 (5H, m), 2.17 (1H, d, J=13.9 Hz), 2.45-2.66 (7H, m), 3.36-3.57 (2H, m), 3.80-3.90 (1H, m), 4.12-4.33 (2H, m), 7.38 (1H, t, J=7.8 Hz), 7.64-7.67 (2H, m), 7.84 (1H, d, J=5.9 Hz), 13.33 (1H, br s).

mass spectrum (ESI): m/z 503, 505 (M+H)$^+$.

Example 202

2-[(3S,4R)-4-{[(4-Chloro-5-ethyl-1H-imidazol-2-yl)carbonyl]amino}-3-[(1-ethylpropyl)amino]piperidin-1-yl]-1,3-benzothiazole-7-carboxylic acid (Exemplified Compound No. 202)

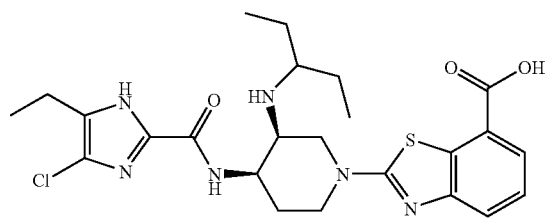

(202a) Benzyl tert-butyl (3S,4R)-piperidine-3,4-diylbiscarbamate

The compound was synthesized according to the method described in the following document.

Heterocycles, 75 (7), 2008, 1659-1671

(202b) Benzyl tert-butyl [(3S,4R)-1-(trifluoroacetyl)piperidine-3,4-diyl]biscarbamate Trifluoroacetic anhydride (124 µL, 0.88 mmol) and triethylamine (164 µL, 1.17 mmol) were added to a solution of benzyl tert-butyl (3S,4R)-piperidine-3,4-diylbiscarbamate obtained in Example (202a) (205 mg, 0.587 mmol) in dichloromethane (5 mL) under ice-cooling, and the mixture was stirred at room temperature for 18 hours. Ethyl acetate was added to the reaction solution, and the mixture was washed with water and brine. The resulting organic layer was dried over anhydrous sodium sulfate, and then the insoluble matter was separated by filtration. The filtrate was concentrated under reduced pressure, and the resulting residue was purified by silica gel column chromatography (eluent: hexane:ethyl acetate=1:1 v/v) to obtain 220 mg of the title compound (84%) as a colorless oily substance.

$^1$H NMR spectrum (400 MHz, CDCl$_3$) δ ppm: 1.43-1.55 (9H, m), 2.01-2.14 (1H, m), 2.29-2.99 (1H, m), 3.14-3.63 (2H, m), 3.86-4.16 (2H, m), 4.28-4.65 (2H, m), 5.07-5.27 (2H, m), 7.32-7.38 (5H, m).

(202c) tert-Butyl [(3S,4R)-4-{[(4-chloro-5-ethyl-1H-imidazol-2-yl)carbonyl]amino}-1-(trifluoroacetyl)piperidin-3-yl]carbamate A 10% palladium-carbon catalyst (20 mg) was added to a solution of benzyl tert-butyl [(3S,4R)-1-(trifluoroacetyl)piperidine-3,4-diyl]biscarbamate obtained in Example (202b) (220 mg, 0.494 mmol) in ethanol (5 mL), and the mixture was stirred in a hydrogen atmosphere at room temperature for two hours. The insoluble matter was separated by filtration and the filtrate was concentrated. DMA (3 mL) was added to the resulting residue. Thereafter, 4-chloro-5-ethyl-1H-imidazole-2-carboxylic acid obtained in Example (1d) (103 mg, 0.593 mmol), 1-hydroxybenzotriazole hydrate (100 mg, 0.741 mmol) and WSC hydrochloride (142 mg, 0.741 mmol) were added, and the mixture was stirred at 70° C. for three hours. Water was added to the reaction solution, followed by extraction with ethyl acetate. The resulting organic layer was washed with water and brine, and dried over anhydrous sodium sulfate, and then the insoluble matter was separated by filtration. The filtrate was concentrated under reduced pressure, and the resulting residue was purified by silica gel column chromatography (eluent: hexane:ethyl acetate=1:2 v/v) to obtain 123 mg of the title compound (53%) as a colorless solid. mass spectrum (ESI): m/z 468, 470 (M+H)$^+$.

(202d) Ethyl 2-[(3S,4R)-3-[(tert-butoxycarbonyl)amino]-4-{[(4-chloro-5-ethyl-1H-imidazol-2-yl)carbonyl]amino}piperidin-1-yl]-1,3-benzothiazole-7-carboxylate Potassium carbonate (40 mg, 0.289 mmol) was added to a solution of tert-butyl [(3S,4R)-4-{[(4-chloro-5-ethyl-1H-imidazol-2-yl)carbonyl]amino}-1-(trifluoroacetyl)piperidin-3-yl]carbamate obtained in Example (202c) (123 mg, 0.263 mmol) in methanol (5 mL), and the mixture was heated under reflux at room temperature for three hours. The reaction solution was concentrated under reduced pressure, and then the filtrate was dissolved in dimethylformamide (2 mL). Triethylamine (145 μL, 1.04 mmol) and ethyl 2-bromo-1,3-benzothiazole-7-carboxylate obtained in Example (1f) (82.1 mg, 0.287 mmol) were added at room temperature, and the mixture was stirred at 70° C. for three hours. The reaction solution was concentrated under reduced pressure, and the resulting residue was suspended in ethyl acetate and washed with water and brine. The organic layer was dried over anhydrous sodium sulfate and the filtrate was concentrated. The resulting residue was purified by silica gel column chromatography (eluent: hexane:ethyl acetate=1:3) to obtain 121 mg of the title compound (80%) as a colorless solid.

$^1$H NMR spectrum (400 MHz, CDCl$_3$) δ ppm: 1.26 (3H, t, J=7.6 Hz), 1.42 (9H, s), 1.44 (3H, t, J=0.0 Hz), 1.78-1.91 (1H, m), 2.00-2.11 (1H, m), 2.68 (2H, q, J=7.6 Hz), 3.24-3.36 (1H, m), 3.43-3.52 (1H, m), 4.20-4.35 (4H, m), 4.45 (2H, q, J=7.1 Hz), 4.99-5.09 (1H, m), 7.35-7.42 (2H, m), 7.73 (1H, d, J=7.8 Hz), 7.84 (1H, d, J=7.8 Hz), 10.60 (1H, br s).

mass spectrum (ESI): m/z 577, 579 (M+H)$^+$.

(202e) Ethyl 2-[(3S,4R)-3-amino-4-{[(4-chloro-5-ethyl-1H-imidazol-2-yl)carbonyl]amino}piperidin-1-yl]-1,3-benzothiazole-7-carboxylate A 4 N hydrochloric acid/1,4-dioxane solution (3 mL) was added to ethyl 2-[(3S,4R)-3-[(tert-butoxycarbonyl)amino]-4-{[(4-chloro-5-ethyl-1H-imidazol-2-yl)carbonyl]amino}piperidin-1-yl]-1,3-benzothiazole-7-carboxylate obtained in Example (202d) (121 mg, 0.210 mmol), and the mixture was stirred at room temperature for one hour. The reaction solution was concentrated under reduced pressure. Saturated aqueous sodium bicarbonate solution was added to the resulting residue, followed by extraction with ethyl acetate. The organic layer was washed with brine and dried over anhydrous sodium sulfate. The filtrate was concentrated. The resulting residue was purified by silica gel column chromatography (eluent: chloroform:methanol=10:1 v/v) to obtain 100 mg of the title compound (100%) as a colorless solid.

$^1$H NMR spectrum (400 MHz, CDCl$_3$) δ ppm: 1.27 (3H, t, J=7.6 Hz), 1.44 (3H, t, J=7.1 Hz), 1.82-2.01 (2H, m), 2.69 (2H, q, J=7.6 Hz), 3.23-3.31 (2H, m), 3.48 (1H, dd, J=13.4, 2.2 Hz), 4.15-4.30 (3H, m), 4.45 (2H, q, J=7.1 Hz), 7.38 (1H, t, J=7.8 Hz), 7.68-7.74 (2H, m), 7.81 (1H, dd, J=7.7, 1.1 Hz), 10.69 (1H, brs).

mass spectrum (ESI): m/z 477, 479 (M+H)$^+$.

(202f) Ethyl 2-{(3S,4R)-4-{[(4-chloro-5-ethyl-1H-imidazol-2-yl)carbonyl]amino}-3-[(1-ethylpropyl)amino]piperidin-1-yl}-1,3-benzothiazole-7-carboxylate 3-Pentanone (68.9 μL, 0.65 mmol) and sodium triacetoxyborohydride (165 mg, 0.78 mmol) were added four times every two hours to a mixed solution of ethyl 2-[(3S,4R)-3-amino-4-{[(4-chloro-5-ethyl-1H-imidazol-2-yl)carbonyl]amino}piperidin-1-yl]-1,3-benzothiazole-7-carboxylate obtained in Example (202e) (62.0 mg, 0.13 mmol) in methanol (1 mL) and tetrahydrofuran (1 mL) under ice-cooling, and the mixture was stirred at room temperature for 15 hours. Saturated aqueous sodium bicarbonate solution was added to the reaction solution, followed by extraction with ethyl acetate. The organic layer was washed with brine and dried over anhydrous sodium sulfate. The insoluble matter was separated by filtration, and the filtrate was concentrated under reduced pressure. The resulting residue was purified by silica gel column chromatography (eluate: hexane:ethyl acetate=1:1 v/v) to obtain 48 mg of the title compound (68%) as a colorless solid.

$^1$H NMR spectrum (400 MHz, CDCl$_3$) δ ppm: 0.83 (3H, t, J=7.4 Hz), 0.92 (3H, t, J=7.3 Hz), 1.25-1.52 (10H, m), 1.81-2.01 (2H, m), 2.50-2.57 (1H, m), 2.71 (2H, q, J=7.6 Hz), 2.96-3.01 (1H, m), 3.20-3.34 (2H, m), 4.15-4.31 (3H, m), 4.46 (2H, q, J=7.1 Hz), 7.38 (1H, t, J=7.9 Hz), 7.72 (1H, dd, J=8.1, 1.0 Hz), 7.82 (1H, dd, J=7.7, 1.1 Hz), 7.99 (1H, d, J=8.3 Hz), 12.36 (1H, s).

mass spectrum (ESI): m/z 547, 549 (M+H)$^+$.

(202g) 2-{(3S,4R)-4-{[(4-Chloro-5-ethyl-1H-imidazol-2-yl)carbonyl]amino}-3-[(1-ethylpropyl)amino]piperidin-1-yl}-1,3-benzothiazole-7-carboxylic acid A 2 N aqueous lithium hydroxide solution (439 μL, 0.877 mmol) was added to a mixed solution of ethyl 2-{(3S,4R)-4-{[(4-chloro-5-ethyl-1H-imidazol-2-yl)carbonyl]amino}-3-[(1-ethylpropyl)amino]piperidin-1-yl}-1,3-benzothiazole-7-carboxylate obtained in Example (202f) (48.0 mg, 0.088 mmol) in methanol (0.3 mL) and tetrahydrofuran (0.3 mL) at room temperature, and the mixture was stirred at 70° C. for two hours. The reaction solution was concentrated under reduced pressure and water was added. The aqueous layer was washed with diethyl ether. A 1 N aqueous hydrochloric acid solution (877 μL, 0.877 mmol) was added to the aqueous layer, followed by extraction with ethyl acetate. The resulting organic layer was washed with water and brine, and dried over anhydrous sodium sulfate, and then the insoluble matter was separated by filtration. The filtrate was concentrated under reduced pressure to obtain 42 mg of the title compound (92%) as a pale yellow solid.

$^1$H NMR spectrum (400 MHz, CD$_3$OD) δ ppm: 0.85-0.98 (6H, m), 1.21 (3H, t, J=7.6 Hz), 1.50-1.67 (4H, m), 1.84-2.22 (2H, m), 2.65 (2H, q, J=7.3 Hz), 2.92-3.02 (1H, m), 3.44-3.51 (1H, m), 3.58-3.75 (1H, m), 3.83 (1H, d, J=12.4 Hz), 3.88-3.99 (1H, m), 4.01-4.10 (1H, m), 4.40-4.50 (1H, m), 7.33-7.41 (1H, m), 7.61 (1H, d, J=7.8 Hz), 7.78 (1H, d, J=7.3 Hz).

mass spectrum (ESI): m/z 519, 521 (M+H)$^+$.

Example 203 cis(±)-2-[3-(Benzylamino)-4-{[(4-chloro-5-ethyl-1H-imidazol-2-yl)carbonyl]amino}piperidin-1-yl]-4-methyl-1,3-thiazole-5-carboxylic acid (Exemplified Compound No. 203)

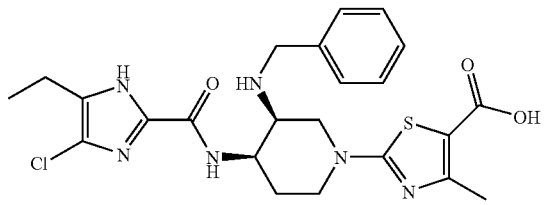

(203a) tert-Butyl cis(±)-3-(benzylamino)-4-{[(4-chloro-5-ethyl-1H-imidazol-2-yl)carbonyl]amino}piperidine-1-carboxylate tert-Butyl trans(±)-3-(benzylamino)-4-{[(4-chloro-5-ethyl-1H-imidazol-2-yl)carbonyl]amino}piperidine-1-carboxylate Benzylamine (70 µL, 0.64 mmol), acetic acid (68.7 µL, 1.20 mmol) and sodium cyanoborohydride (42 mg, 0.667 mmol) were added to a mixed solution of tert-butyl 4-{[(4-chloro-5-ethyl-1H-imidazol-2-yl)carbonyl]amino}-3-oxopiperidine-1-carboxylate obtained in Example (201c) (99 mg, 0.267 mmol) in tetrahydrofuran (3 mL) and methanol (3 mL) under ice-cooling, and the mixture was stirred at room temperature for 15 hours. The reaction solution was concentrated under reduced pressure. Saturated aqueous sodium bicarbonate solution was added to the residue, followed by extraction with ethyl acetate. The resulting organic layer was washed with brine and dried over anhydrous sodium sulfate, and then the insoluble matter was separated by filtration. The filtrate was concentrated under reduced pressure, and the resulting residue was purified by silica gel column chromatography (eluent: chloroform:methanol=10:1 v/v) to obtain 26 mg of the cis isomer of the title compound (21%) as a colorless solid and 50 mg of the trans isomer of the title compound (41%) as a colorless solid. cis-form $^1$H NMR spectrum (400 MHz, CDCl$_3$) δ ppm: 1.25 (3H, t, J=7.6 Hz), 1.48 (9H, s), 1.77-1.83 (1H, m), 2.65-2.88 (6H, m), 3.71 (1H, d, J=12.7 Hz), 3.94-4.13 (3H, m), 4.26-4.43 (1H, m), 7.19-7.32 (3H, m), 7.44 (2H, d, J=7.3 Hz), 7.90 (1H, d, J=8.0 Hz), 10.86 (1H, s).

mass spectrum (ESI): m/z 462, 464 (M+H)$^+$.

trans-form $^1$H NMR spectrum (400 MHz, CDCl$_3$) δ ppm: 1.23-1.29 (3H, m), 1.44-1.50 (9H, m), 1.94-2.06 (1H, m), 2.46-3.05 (6H, m), 3.42-4.43 (5H, m), 6.93-7.44 (5H, m).

mass spectrum (ESI): m/z 462, 464 (M+H)$^+$.

(203b) Ethyl cis(±)-2-[3-(benzylamino)-4-{[(4-chloro-5-ethyl-1H-imidazol-2-yl)carbonyl]amino}piperidin-1-yl]-4-methyl-1,3-thiazole-5-carboxylate The same operation as in Example (196c) was performed using tert-butyl cis(±)-3-(benzylamino)-4-{[(4-chloro-5-ethyl-1H-imidazol-2-yl)carbonyl]amino}piperidine-1-carboxylate obtained in Example (203a) (26.0 mg, 0.056 mmol), 4 N hydrochloric acid/1,4-dioxane (1 mL), ethyl 2-bromo-4-methyl-1,3-thiazole-5-carboxylate (17 mg, 0.068 mmol) and sodium carbonate (60 mg, 0.563 mmol), to obtain 17 mg of the title compound (57%) as a colorless solid.

$^1$H NMR spectrum (400 MHz, CDCl$_3$) δ ppm: 1.26 (3H, t, J=7.6 Hz), 1.34 (3H, t, J=7.1 Hz), 1.69-1.81 (1H, m), 1.90-1.98 (1H, m), 2.55 (3H, s), 2.69 (2H, q, J=7.6 Hz), 2.88-2.92 (1H, m), 3.13-3.22 (2H, m), 3.76 (1H, d, J=13.2 Hz), 3.96-4.04 (2H, m), 4.07-4.16 (1H, m), 4.23-4.31 (3H, m), 7.19-7.24 (1H, m), 7.25-7.31 (2H, m), 7.42 (2H, d, J=7.1 Hz), 7.85 (1H, d, J=8.5 Hz), 10.39 (1H, s).

mass spectrum (ESI): m/z 531, 533 (M+H)$^+$.

(203c) cis(±)-2-[3-(Benzylamino)-4-{[(4-chloro-5-ethyl-1H-imidazol-2-yl)carbonyl]amino}piperidin-1-yl]-4-methyl-1,3-thiazole-5-carboxylic acid The same operation as in Example (196d) was performed using ethyl cis(±)-2-[3-(benzylamino)-4-{[(4-chloro-5-ethyl-1H-imidazol-2-yl)carbonyl]amino}piperidin-1-yl]-4-methyl-1,3-thiazole-5-carboxylate obtained in Example (203b) (17 mg, 0.032 mmol) and a 2 N aqueous lithium hydroxide solution (160 µL, 0.320 mmol), to obtain 16 mg of the title compound (99%) as a colorless solid.

$^1$H NMR spectrum (400 MHz, CD$_3$OD) δ ppm: 1.23 (3H, t, J=7.6 Hz), 1.85-1.97 (2H, m), 2.49 (3H, s), 2.66 (2H, q, J=7.6 Hz), 3.00-3.06 (1H, m), 3.31-3.43 (1H, m), 3.47 (1H, dd, J=13.5, 2.8 Hz), 3.82-3.90 (2H, m), 3.98-4.09 (2H, m), 4.22-4.29 (1H, m), 7.16-7.41 (5H, m).

mass spectrum (ESI): m/z 503, 505 (M+H)$^+$.

Example 204 trans(±)-2-[3-(Benzylamino)-4-{[(4-chloro-5-ethyl-1H-imidazol-2-yl)carbonyl]amino}piperidin-1-yl]-4-methyl-1,3-thiazole-5-carboxylic acid (Exemplified Compound No. 204)

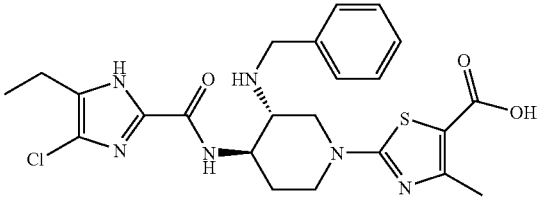

(204a) Ethyl trans(±)-2-[3-(benzylamino)-4-{[(4-chloro-5-ethyl-1H-imidazol-2-yl)carbonyl]amino}piperidin-1-yl]-4-methyl-1,3-thiazole-5-carboxylate The same operation as in Example (196c) was performed using tert-butyl trans(±)-3-(benzylamino)-4-{[(4-chloro-5-ethyl-1H-imidazol-2-yl)carbonyl]amino}piperidine-1-carboxylate obtained in Example (203a) (50.0 mg, 0.108 mmol), 4 N hydrochloric acid/1,4-dioxane (1 mL), ethyl 2-bromo-4-methyl-1,3-thiazole-5-carboxylate (32 mg, 0.130 mmol) and sodium carbonate (115 mg, 1.08 mmol), to obtain 12 mg of the title compound (21%) as a colorless solid.

$^1$H NMR spectrum (400 MHz, CDCl$_3$) δ ppm: 1.27 (3H, t, J=7.6 Hz), 1.34 (3H, t, J=7.1 Hz), 1.56-1.69 (1H, m), 2.13-2.19 (1H, m), 2.55 (3H, s), 2.65-2.72 (3H, m), 2.92 (1H, dd, J=13.2, 10.0 Hz), 3.12-3.19 (1H, m), 3.80 (1H, d, J=13.4 Hz), 3.92-4.10 (3H, m), 4.22-4.30 (3H, m), 7.01 (1H, d, J=8.3 Hz), 7.21-7.31 (5H, m), 10.49 (1H, s).

mass spectrum (ESI): m/z 531, 533 (M+H)⁺.

(204b) trans(±)-2-[3-(Benzylamino)-4-{[(4-chloro-5-ethyl-1H-imidazol-2-yl)carbonyl]amino}piperidin-1-yl]-4-methyl-1,3-thiazole-5-carboxylic acid The same operation as in Example (2652d) was performed using ethyl trans(±)-2-[3-(benzylamino)-4-{[(4-chloro-5-ethyl-1H-imidazol-2-yl)carbonyl]amino}piperidin-1-yl]-4-methyl-1,3-thiazole-5-carboxylate obtained in Example (204a) (12 mg, 0.023 mmol) and a 2 N aqueous lithium hydroxide solution (113 µL, 0.226 mmol), to obtain 11 mg of the title compound (97%) as a colorless solid.

$^1$H NMR spectrum (400 MHz, CD$_3$OD) δ ppm: 1.22 (3H, t, J=7.6 Hz), 1.73-1.86 (1H, m), 2.03-2.12 (1H, m), 2.50 (3H, s), 2.66 (2H, q, J=7.6 Hz), 2.92-3.01 (1H, m), 3.08-3.18 (1H, m), 3.21-3.33 (1H, m), 3.90-4.18 (4H, m), 4.33-4.41 (1H, m), 7.24-7.41 (5H, m).

mass spectrum (ESI): m/z 503, 505 (M+H)⁺.

Example 205 cis(±)-2-(4-{[(4-Chloro-5-ethyl-1H-imidazol-2-yl)carbonyl]amino}-3-(propylamino)piperidin-1-yl)-4-methyl-1,3-thiazole-5-carboxylic acid (Exemplified Compound No. 205)

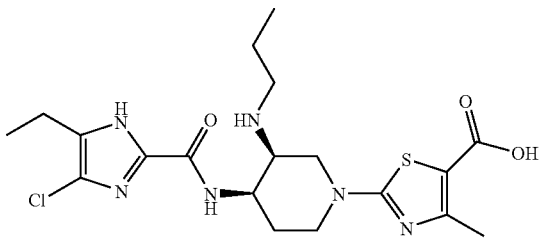

(205a) cis(±)-4-Chloro-5-ethyl-N-[3-(propylamino)piperidin-4-yl]-1H-imidazole-2-carboxamide trans(±)-4-Chloro-5-ethyl-N-[3-(propylamino)piperidin-4-yl]-1H-imidazole-2-carboxamide Propylamine (226 µL, 2.75 mmol) was added to a mixed solution of tert-butyl 4-{[(4-chloro-5-ethyl-1H-imidazol-2-yl)carbonyl]amino}-3-oxopiperidine-1-carboxylate obtained in Example (201c) (102 mg, 0.275 mmol) in tetrahydrofuran (5 mL) and methanol (5 mL) under ice-cooling, and the mixture was heated under reflux at 70° C. for three hours. The reaction solution was concentrated under reduced pressure, and then the residue was dissolved in tetrahydrofuran (5 mL) and methanol (5 mL). Acetic acid (315 µL, 5.50 mmol) and sodium cyanoborohydride (69 mg, 1.10 mmol) were added, and the mixture was stirred at room temperature for 12 hours. The reaction solution was concentrated under reduced pressure, and a 1 N aqueous hydrochloric acid solution was added. The aqueous layer was washed with diethyl ether. The aqueous layer was concentrated under reduced pressure with heating, and then saturated aqueous sodium bicarbonate solution was added to the residue, followed by extraction with chloroform. The resulting organic layer was dried over anhydrous sodium sulfate, and then the insoluble matter was separated by filtration. The filtrate was concentrated under reduced pressure, and the resulting residue was purified by NH-silica gel column chromatography (eluent: chloroform:methanol=10:1 v/v) to obtain 17 mg of the cis isomer of the title compound (20%) as a colorless oily substance and 10.0 mg of the trans isomer of the title compound (12%) as a colorless oily substance.

cis-form $^1$H NMR spectrum (400 MHz, CDCl$_3$) δ ppm: 0.95 (3H, t, J=7.4 Hz), 1.25 (3H, t, J=8.0 Hz), 1.45-1.82 (4H, m), 2.41-2.46 (1H, m), 2.54-2.75 (6H, m), 2.95-2.99 (1H, m), 3.11-3.15 (1H, m), 3.97-4.04 (1H, m), 7.83-7.88 (1H, m).

mass spectrum (ESI): m/z 314, 316 (M+H)⁺.

trans-form $^1$H NMR spectrum (400 MHz, CDCl$_3$) δ ppm: 0.86 (3H, t, J=7.4 Hz), 1.26 (3H, t, J=7.4 Hz), 1.39-1.66 (3H, m), 2.01-2.06 (1H, m), 2.39-2.43 (1H, m), 2.47-2.52 (2H, m), 2.62-2.71 (4H, m), 3.04-3.08 (1H, m), 3.37 (1H, dd, J=12.0, 3.4 Hz), 3.80-3.87 (1H, m), 7.01 (1H, d, J=8.6 Hz).

mass spectrum (ESI): m/z 314, 316 (M+H)⁺.

(205b) Ethyl cis(±)-2-(4-{[(4-chloro-5-ethyl-1H-imidazol-2-yl)carbonyl]amino}-3-(propylamino)piperidin-1-yl)-4-methyl-1,3-thiazole-5-carboxylate The same operation as in Example (196c) was performed using cis(±)-4-chloro-5-ethyl-N-[3-(propylamino)piperidin-4-yl]-1H-imidazole-2-carboxamide obtained in Example (205a) (17.0 mg, 0.054 mmol), ethyl 2-bromo-4-methyl-1,3-thiazole-5-carboxylate (15 mg, 0.060 mmol) and sodium carbonate (17 mg, 0.163 mmol), to obtain 17 mg of the title compound (65%) as a colorless solid.

$^1$H NMR spectrum (400 MHz, CDCl$_3$) δ ppm: 0.93 (3H, t, J=7.3 Hz), 1.26 (3H, t, J=7.6 Hz), 1.33 (3H, t, J=7.1 Hz), 1.40-1.61 (2H, m), 1.70-1.80 (1H, m), 1.89-1.95 (1H, m), 2.47-2.55 (1H, m), 2.54 (3H, s), 2.68 (2H, q, J=7.6 Hz), 2.75-2.82 (1H, m), 2.85-2.88 (1H, m), 3.14-3.24 (2H, m), 3.98-4.04 (1H, m), 4.10-4.20 (2H, m), 4.27 (2H, q, J=7.1 Hz), 7.81 (1H, d, J=7.8 Hz), 10.64 (1H, br s).

mass spectrum (ESI): m/z 483, 485 (M+H)⁺.

(205c) cis(±)-2-(4-{[(4-Chloro-5-ethyl-1H-imidazol-2-yl)carbonyl]amino}-3-(propylamino)piperidin-1-yl)-4-methyl-1,3-thiazole-5-carboxylic acid The same operation as in Example (196d) was performed using ethyl cis(±)-2-(4-{[(4-chloro-5-ethyl-1H-imidazol-2-yl)carbonyl]amino}-3-(propylamino)piperidin-1-yl)-4-methyl-1,3-thiazole-5-carboxylate obtained in Example (205b) (16.0 mg, 0.033 mmol) and a 2 N aqueous lithium hydroxide solution (165 µL), to obtain 11 mg of the title compound (73%) as a colorless solid.

$^1$H NMR spectrum (400 MHz, CD$_3$OD) δ ppm: 0.79-1.03 (6H, m), 1.10-1.51 (3H, m), 1.52-1.71 (1H, m), 1.95-2.06 (1H, m), 2.14-2.29 (4H, m), 2.46-2.53 (2H, m), 2.60-2.71 (2H, m), 2.95-4.98 (5H, m).

mass spectrum (ESI): m/z 455, 457 (M+H)⁺.

Example 206 trans(±)-2-(4-{[(4-Chloro-5-ethyl-1H-imidazol-2-yl)carbonyl]amino}-3-(propylamino)piperidin-1-yl)-4-methyl-1,3-thiazole-5-carboxylic acid (Exemplified Compound No. 206)

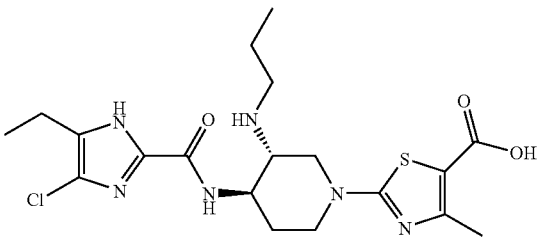

(206a) Ethyl trans(±)-2-(4-{[(4-chloro-5-ethyl-1H-imidazol-2-yl)carbonyl]amino}-3-(propylamino)piperidin-1-yl)-4-methyl-1,3-thiazole-5-carboxylate The same operation as in Example (196c) was performed using trans(±)-4-chloro-5-ethyl-N-[3-(propylamino)piperidin-4-yl]-1H-imidazole-2-carboxamide obtained in Example (205a) (10.0 mg, 0.032 mmol), ethyl 2-bromo-4-methyl-1,3-thiazole-5-carboxylate (9 mg, 0.035 mmol) and sodium carbonate (10 mg, 0.096 mmol), to obtain 13 mg of the title compound (85%) as a colorless solid.

$^1$H NMR spectrum (400 MHz, CDCl$_3$) δ ppm: 0.89 (3H, t, J=7.4 Hz), 1.26 (3H, t, J=7.6 Hz), 1.33 (3H, t, J=7.1 Hz), 1.41-1.72 (3H, m), 2.12-2.20 (1H, m), 2.52-2.59 (4H, m), 2.63-2.75 (4H, m), 2.83-2.93 (1H, m), 3.09-3.20 (1H, m), 3.88-4.00 (1H, m), 4.04-4.13 (1H, m), 4.20-4.31 (3H, m), 7.07 (1H, d, J=8.5 Hz).

mass spectrum (ESI): m/z 483, 485 (M+H)$^+$.

(206b) trans(±)-2-(4-{[(4-Chloro-5-ethyl-1H-imidazol-2-yl)carbonyl]amino}-3-(propylamino)piperidin-1-yl)-4-methyl-1,3-thiazole-5-carboxylic acid The same operation as in Example (196d) was performed using ethyl trans(±)-2-(4-{[(4-chloro-5-ethyl-1H-imidazol-2-yl)carbonyl]amino}-3-(propylamino)piperidin-1-yl)-4-methyl-1,3-thiazole-5-carboxylate obtained in Example (206a) (13.0 mg, 0.027 mmol) and a 2 N aqueous lithium hydroxide solution (135 μl), to obtain 12 mg of the title compound (98%) as a colorless solid.

mass spectrum (ESI): m/z 455, 457 (M+H)$^+$.

Example 207 cis(±)-2-(4-{[(4-Chloro-5-ethyl-1H-imidazol-2-yl)carbonyl]amino}-3-(ethylamino)piperidin-1-yl)-1,3-benzothiazole-7-carboxylic acid (Exemplified Compound No. 207)

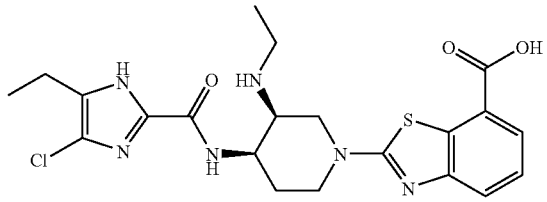

(207a) tert-Butyl cis(±)-4-{[(4-chloro-5-ethyl-1H-imidazol-2-yl)carbonyl]amino}-3-(ethylamino)piperidine-1-carboxylate tert-Butyl trans(±)-4-{[(4-chloro-5-ethyl-1H-imidazol-2-yl)carbonyl]amino}-3-(ethylamino)piperidine-1-carboxylate A 2 N ethylamine/tetrahydrofuran solution (5 mL) was added to tert-butyl 4-{[(4-chloro-5-ethyl-1H-imidazol-2-yl)carbonyl]amino}-3-oxopiperidine-1-carboxylate obtained in Example (201c) (102 mg, 0.275 mmol), and the mixture was heated under reflux at 70° C. for four hours. The reaction solution was concentrated under reduced pressure, and then tetrahydrofuran (2 mL) and methanol (2 mL) were added. A 2 N ethylamine-tetrahydrofuran solution (138 μL), sodium cyanoborohydride (86.4 mg, 1.38 mmol) and acetic acid (110 μL, 1.93 mmol) were added, and the mixture was stirred at room temperature for 15 hours. The reaction solution was concentrated under reduced pressure, and aqueous saturated sodium bicarbonate solution was added to the residue, followed by extraction with chloroform. The resulting organic layer was dried over anhydrous sodium sulfate, and then the insoluble matter was separated by filtration. The filtrate was concentrated under reduced pressure, and the resulting residue was purified by silica gel column chromatography (eluent: chloroform:methanol=10:1 v/v) to obtain 46 mg of the cis isomer of the title compound (42%) as a pale yellow oily substance and 51 mg of the trans isomer of the title compound (46%) as a pale yellow oily substance.

cis-form
  mass spectrum (ESI): m/z 400, 402 (M+H)$^+$.
trans-form
  mass spectrum (ESI): m/z 400, 402 (M+H)$^+$.

(207b) Ethyl cis(±)-2-(4-{[(4-chloro-5-ethyl-1H-imidazol-2-yl)carbonyl]amino}-3-(ethylamino)piperidin-1-yl)-1,3-benzothiazole-7-carboxylate The same operation as in Example (196c) was performed using tert-butyl cis(±)-4-{[(4-chloro-5-ethyl-1H-imidazol-2-yl)carbonyl]amino}-3-(ethylamino)piperidine-1-carboxylate obtained in Example (207a) (23.0 mg, 0.058 mmol), 4 N hydrochloric acid/1,4-dioxane (1 mL), ethyl 2-bromo-1,3-benzothiazole-7-carboxylate obtained in Example (1f) (20 mg, 0.069 mmol) and sodium carbonate (61 mg, 0.575 mmol), to obtain 13 mg of the title compound (45%) as a colorless solid.

$^1$H NMR spectrum (400 MHz, CDCl$_3$) δ ppm: 1.11 (3H, t, J=7.1 Hz), 1.27 (3H, t, J=7.3 Hz), 1.44 (3H, t, J=7.3 Hz), 1.72-1.89 (1H, m), 1.94-2.01 (1H, m), 2.59-2.74 (3H, m), 2.87-2.98 (2H, m), 3.23-3.39 (2H, m), 4.18-4.31 (3H, m), 4.43-4.48 (2H, m), 7.38 (1H, t, J=7.8 Hz), 7.69-7.73 (1H, m), 7.79-7.83 (1H, m), 7.91 (1H, d, J=6.3 Hz), 11.71 (1H, br s).

mass spectrum (ESI): m/z 505, 507 (M+H)$^+$.

(207c) cis(±)-2-(4-{[(4-Chloro-5-ethyl-1H-imidazol-2-yl)carbonyl]amino}-3-(ethylamino)piperidin-1-yl)-1,3-benzothiazole-7-carboxylic acid The same operation as in Example (196d) was performed using ethyl cis(±)-2-(4-{[(4-chloro-5-ethyl-1H-imidazol-2-yl)carbonyl]amino}-3-(ethylamino)piperidin-1-yl)-1,3-benzothiazole-7-carboxylate obtained in Example (207b) (13.0 mg, 0.025 mmol) and a 2 N aqueous lithium hydroxide solution (129 μL), to obtain 10 mg of the title compound (81%) as a colorless solid.

$^1$H NMR spectrum (400 MHz, CD$_3$OD) δ ppm: 1.18-1.30 (6H, m), 2.02-2.08 (2H, m), 2.63-2.70 (2H, m), 3.00-3.15 (2H, m), 3.30-3.33 (1H, m), 3.42-3.46 (1H, m), 3.62-3.70 (1H, m), 3.84-3.98 (2H, m), 4.03-4.09 (1H, m), 7.35-7.39 (1H, m), 7.62 (1H, d, J=8.0 Hz), 7.79 (1H, d, J=7.6 Hz).

mass spectrum (ESI): m/z 477, 479 (M+H)$^+$.

Example 208 trans(±)-2-(4-{[(4-Chloro-5-ethyl-1H-imidazol-2-yl)carbonyl]amino}-3-(ethylamino)piperidin-1-yl)-1,3-benzothiazole-7-carboxylic acid (Exemplified Compound No. 208)

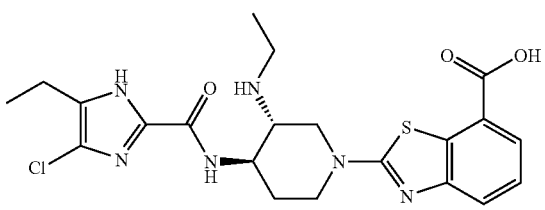

(208a) Ethyl trans(±)-2-(4-{[(4-chloro-5-ethyl-1H-imidazol-2-yl)carbonyl]amino}-3-(ethylamino)piperidin-1-yl)-1,3-benzothiazole-7-carboxylate The same operation as in Example (196c) was performed using tert-butyl trans(±)-4-{[(4-chloro-5-ethyl-1H-imidazol-2-yl)carbonyl]amino}-3-(ethylamino)piperidine-1-carboxylate obtained in Example (207a) (25.0 mg, 0.063 mmol), 4 N hydrochloric acid/1,4-dioxane (1 mL), ethyl 2-bromo-1,3-benzothiazole-7-carboxylate obtained in Example (1f) (21 mg, 0.075 mmol) and sodium carbonate (66 mg, 0.625 mmol), to obtain 15 mg of the title compound (48%) as a colorless solid.

$^1$H NMR spectrum (400 MHz, CDCl$_3$) δ ppm: 1.11 (3H, t, J=6.8 Hz), 1.26 (3H, t, J=7.3 Hz), 1.44 (3H, t, J=7.1 Hz), 1.69-1.80 (1H, m), 2.15-2.21 (1H, m), 2.63-2.73 (3H, m), 2.74-2.82 (1H, m), 2.83-2.92 (1H, m), 2.93-3.02 (1H, m), 3.20-3.28 (1H, m), 3.63-3.80 (1H, m), 3.93-4.06 (1H, m), 4.22-4.31 (1H, m), 4.41-4.51 (3H, m), 7.34-7.40 (1H, m), 7.69-7.74 (1H, m), 7.78-7.83 (1H, m).

mass spectrum (ESI): m/z 505, 507 (M+H)$^+$.

(208b) trans(±)-2-(4-{[(4-Chloro-5-ethyl-1H-imidazol-2-yl)carbonyl]amino}-3-(ethylamino)piperidin-1-yl)-1,3-benzothiazole-7-carboxylic acid The same operation as in Example (196d) was performed using ethyl trans(±)-2-(4-{[(4-chloro-5-ethyl-1H-imidazol-2-yl)carbonyl]amino}-3-(ethylamino)piperidin-1-yl)-1,3-benzothiazole-7-carboxylate obtained in Example (208a) (15.0 mg, 0.030 mmol) and a 2 N aqueous lithium hydroxide solution (149 μL), to obtain 8 mg of the title compound (57%) as a colorless solid.

$^1$H NMR spectrum (400 MHz, CD$_3$OD) δ ppm: 1.19-1.41 (6H, m), 1.53-1.84 (1H, m), 1.92-2.02 (1H, m), 2.10-2.25 (1H, m), 2.61-2.69 (2H, m), 3.12-3.21 (1H, m), 3.29-3.35 (1H, m), 3.37-3.50 (2H, m), 3.62-3.79 (1H, m), 4.07-4.21 (1H, m), 4.29-4.38 (1H, m), 7.37-7.43 (1H, m), 7.63-7.67 (1H, m), 7.77-7.83 (1H, m).

mass spectrum (ESI): m/z 477, 479 (M+H)$^+$.

Example 209 cis(±)-2-(4-{[(4-Chloro-5-ethyl-1H-imidazol-2-yl)carbonyl]amino}-3-(ethylamino)piperidin-1-yl)-4-methyl-1,3-thiazole-5-carboxylic acid

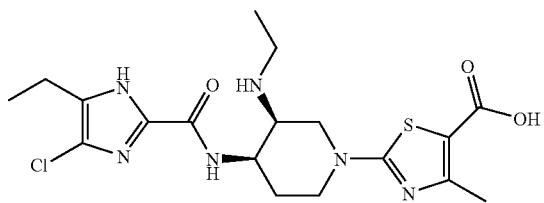

(Exemplified Compound No. 209)

(209a) Ethyl cis(±)-2-(4-{[(4-chloro-5-ethyl-1H-imidazol-2-yl)carbonyl]amino}-3-(ethylamino)piperidin-1-yl)-4-methyl-1,3-thiazole-5-carboxylate The same operation as in Example (196c) was performed using tert-butyl cis(±)-4-{[(4-chloro-5-ethyl-1H-imidazol-2-yl)carbonyl]amino}-3-(ethylamino)piperidine-1-carboxylate obtained in Example (207a) (22.0 mg, 0.055 mmol), 4 N hydrochloric acid/1,4-dioxane (1 mL), ethyl 2-bromo-4-methyl-1,3-thiazole-5-carboxylate (17 mg, 0.066 mmol) and sodium carbonate (58 mg, 0.55 mmol), to obtain 6 mg of the title compound (23%) as a colorless solid.

$^1$H NMR spectrum (400 MHz, CDCl$_3$) δ ppm: 1.11 (3H, t, J=7.0 Hz), 1.26 (3H, t, J=7.6 Hz), 1.33 (3H, t, J=7.1 Hz), 1.68-1.94 (2H, m), 2.54 (3H, s), 2.57-2.72 (3H, m), 2.82-2.93 (2H, m), 3.12-3.27 (1H, m), 3.92-4.30 (6H, m), 7.85 (1H, br s).

mass spectrum (ESI): m/z 469, 471 (M+H)$^+$.

(209b) cis(±)-2-(4-{[(4-Chloro-5-ethyl-1H-imidazol-2-yl)carbonyl]amino}-3-(ethylamino)piperidin-1-yl)-4-methyl-1,3-thiazole-5-carboxylic acid The same operation as in Example (196d) was performed using ethyl cis(±)-2-(4-{[(4-chloro-5-ethyl-1H-imidazol-2-yl)carbonyl]amino}-3-(ethylamino)piperidin-1-yl)-4-methyl-1,3-thiazole-5-carboxylate obtained in Example (209a) (6.00 mg, 0.013 mmol) and a 2 aqueous N lithium hydroxide solution (64 μL), to obtain 5 mg of the title compound (89%) as a pale yellow solid.

$^1$H NMR spectrum (400 MHz, CD$_3$OD) δ ppm: 1.18-1.25 (3H, m), 1.25-1.32 (3H, m), 1.94-2.09 (2H, m), 2.46-2.52 (4H, m), 2.61-2.70 (3H, m), 3.10-3.20 (1H, m), 3.47-3.65 (2H, m), 3.69-3.80 (1H, m), 3.87-3.92 (1H, m), 4.51-4.62 (1H, m).

mass spectrum (ESI): m/z 441, 443 (M+H)$^+$.

Example 210 trans(±)-2-(4-{[(4-Chloro-5-ethyl-1H-imidazol-2-yl)carbonyl]amino}-3-(ethylamino)piperidin-1-yl)-4-methyl-1,3-thiazole-5-carboxylic acid

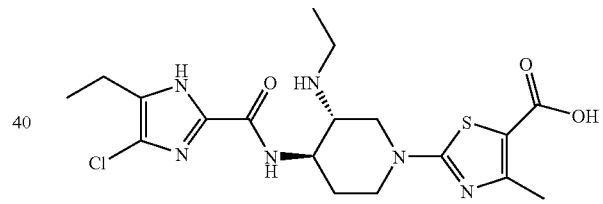

(Exemplified Compound No. 210)

(210a) Ethyl trans(±)-2-(4-{[(4-chloro-5-ethyl-1H-imidazol-2-yl)carbonyl]amino}-3-(ethylamino)piperidin-1-yl)-4-methyl-1,3-thiazole-5-carboxylate The same operation as in Example (196c) was performed using tert-butyl trans(±)-4-{[(4-chloro-5-ethyl-1H-imidazol-2-yl)carbonyl]amino}-3-(ethylamino)piperidine-1-carboxylate obtained in Example (207a) (25.0 mg, 0.063 mmol), 4 N hydrochloric acid/1,4-dioxane (1 mL), ethyl 2-bromo-4-methyl-1,3-thiazole-5-carboxylate (19 mg, 0.075 mmol) and sodium carbonate (66 mg, 0.625 mmol), to obtain 12 mg of the title compound (41%) as a colorless solid.

$^1$H NMR spectrum (400 MHz, CDCl$_3$) δ ppm: 1.09 (3H, t, J=6.8 Hz), 1.26 (3H, t, J=7.6 Hz), 1.33 (3H, t, J=7.2 Hz), 1.63-1.76 (1H, m), 2.09-2.17 (1H, m), 2.55 (3H, s), 2.62-2.74 (3H, m), 2.78-2.96 (2H, m), 3.09-3.19 (1H, m), 3.61-4.33 (6H, m).

mass spectrum (ESI): m/z 469, 471 (M+H)$^+$.

(210b) trans(±)-2-(4-{[(4-Chloro-5-ethyl-1H-imidazol-2-yl)carbonyl]amino}-3-(ethylamino)piperidin-1-yl)-4-methyl-1,3-thiazole-5-carboxylic acid The same operation as in Example (196d) was performed using ethyl trans(±)-2-(4-{[(4-chloro-5-ethyl-1H-imidazol-2-yl)carbonyl]amino}-3-(ethylamino)piperidin-1-yl)-4-methyl-1,3-thiazole-5-carboxylate obtained in Example (210a) (12.0 mg, 0.026 mmol) and a 2 N lithium aqueous hydroxide solution (128 μL), to obtain 9 mg of the title compound (80%) as a pale yellow solid.

$^1$H NMR spectrum (400 MHz, CD$_3$OD) δ ppm: 1.22 (3H, t, J=7.4 Hz), 1.28-1.34 (3H, m), 1.85-1.99 (1H, m), 2.05-2.18 (1H, m), 2.48-2.51 (4H, m), 2.61-2.70 (3H, m), 3.06-3.15 (1H, m), 3.60-3.73 (1H, m), 3.85-4.03 (2H, m), 4.15-4.33 (1H, m), 4.48-4.61 (1H, m).

mass spectrum (ESI): m/z 441, 443 (M+H)$^+$.

Example 211 cis(±)-2-(4-{[(4-Chloro-5-ethyl-1H-imidazol-2-yl)carbonyl]amino}-3-(isopropylamino)piperidin-1-yl)-1,3-benzothiazole-7-carboxylic acid (Exemplified Compound No. 211)

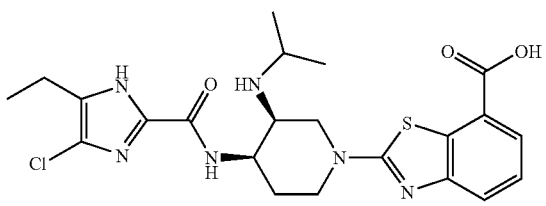

(211a) tert-Butyl cis(±)-4-{[(4-chloro-5-ethyl-1H-imidazol-2-yl)carbonyl]amino}-3-(isopropylamino)piperidine-1-carboxylate tert-Butyl trans(±)-4-{[(4-chloro-5-ethyl-1H-imidazol-2-yl)carbonyl]amino}-3-(isopropylamino)piperidine-1-carboxylate Isopropylamine (372 μL, 4.37 mmol) was added to a solution of tert-butyl 4-{[(4-chloro-5-ethyl-1H-imidazol-2-yl)carbonyl]amino}-3-oxopiperidine-1-carboxylate obtained in Example (201c) (162 mg, 0.437 mmol) in tetrahydrofuran (4 mL), and the mixture was heated under reflux at 50° C. for four hours. The reaction solution was concentrated under reduced pressure, and then tetrahydrofuran (3 mL) and methanol (3 mL) were added. Isopropylamine (37.2 μL, 0.437 mmol), sodium cyanoborohydride (82.4 mg, 1.31 mmol) and acetic acid (150 μL, 2.62 mmol) were added, and the mixture was stirred at room temperature for 15 hours. The reaction solution was concentrated under reduced pressure, and saturated aqueous sodium bicarbonate solution was added to the residue, followed by extraction with chloroform. The resulting organic layer was dried over anhydrous sodium sulfate, and then the insoluble matter was separated by filtration. The filtrate was concentrated under reduced pressure, and the resulting residue was purified by silica gel column chromatography and preparative TLC (eluent: chloroform:methanol=10:1 v/v) to obtain 24 mg of the cis isomer of the title compound (15%) as a pale yellow oily substance and 20 mg of the trans isomer of the title compound (12%) as a pale yellow oily substance.

cis-form
mass spectrum (ESI): m/z 414, 416 (M+H)$^+$.
trans-form
mass spectrum (ESI): m/z 414, 416 (M+H)$^+$.

(211b) Ethyl cis(±)-2-(4-{[(4-chloro-5-ethyl-1H-imidazol-2-yl)carbonyl]amino}-3-(isopropylamino)piperidin-1-yl)-1,3-benzothiazole-7-carboxylate The same operation as in Example (196c) was performed using tert-butyl cis(±)-4-{[(4-chloro-5-ethyl-1H-imidazol-2-yl)carbonyl]amino}-3-(isopropylamino)piperidine-1-carboxylate obtained in Example (211a) (24.0 mg, 0.058 mmol), 4 N hydrochloric acid/1,4-dioxane (2 mL), ethyl 2-bromo-1,3-benzothiazole-7-carboxylate obtained in Example (1f) (18 mg, 0.064 mmol) and sodium carbonate (61 mg, 0.580 mmol), to obtain 10 mg of the title compound (33%) as a colorless solid.

$^1$H NMR spectrum (400 MHz, CD$_3$OD) δ ppm: 1.04-1.46 (12H, m), 1.90-1.99 (2H, m), 2.66 (2H, q, J=7.6 Hz), 3.00-3.14 (2H, m), 3.45-3.62 (2H, m), 4.00-4.14 (2H, m), 4.22-4.31 (1H, m), 4.41-4.48 (2H, m), 7.40 (1H, t, J=7.9 Hz), 7.68 (1H, dd, J=8.1, 1.0 Hz), 7.77-7.83 (1H, m).

mass spectrum (ESI): m/z 519, 521 (M+H)$^+$.

(211c) cis(±)-2-(4-{[(4-Chloro-5-ethyl-1H-imidazol-2-yl)carbonyl]amino}-3-(isopropylamino)piperidin-1-yl)-1,3-benzothiazole-7-carboxylic acid The same operation as in Example (196d) was performed using ethyl cis(±)-2-(4-{[(4-chloro-5-ethyl-1H-imidazol-2-yl)carbonyl]amino}-3-(isopropylamino)piperidin-1-yl)-1,3-benzothiazole-7-carboxylate obtained in Example (211b) (10.0 mg, 0.019 mmol) and a 2 N aqueous lithium hydroxide solution (96 μL), to obtain 9 mg of the title compound (95%) as a colorless solid.

$^1$H NMR spectrum (400 MHz, CD$_3$OD) δ ppm: 1.19-1.31 (9H, m), 1.97-2.13 (2H, m), 2.66 (2H, q, J=7.6 Hz), 3.46-3.54 (1H, m), 3.59-3.65 (1H, m), 3.66-3.75 (1H, m), 3.89-4.02 (3H, m), 4.51-4.56 (1H, m), 7.37 (1H, t, J=7.4 Hz), 7.59 (1H, d, J=8.1 Hz), 7.78 (1H, d, J=7.6 Hz).

mass spectrum (ESI): m/z 491, 493 (M+H)$^+$.

Example 212 trans(±)-2-(4-{[(4-Chloro-5-ethyl-1H-imidazol-2-yl)carbonyl]amino}-3-(isopropylamino)piperidin-1-yl)-1,3-benzothiazole-7-carboxylic acid (Exemplified Compound No. 212)

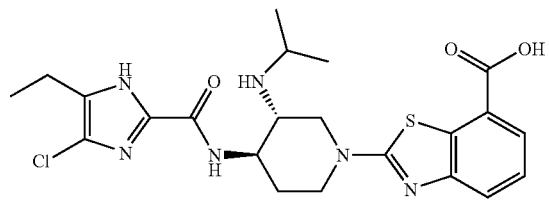

(212a) Ethyl trans(±)-2-(4-{[(4-chloro-5-ethyl-1H-imidazol-2-yl)carbonyl]amino}-3-(isopropylamino)piperidin-1-yl)-1,3-benzothiazole-7-carboxylate The same operation as in Example (196c) was performed using tert-butyl trans(±)-4-{[(4-chloro-5-ethyl-1H-imidazol-2-yl)carbonyl]amino}-3-(isopropylamino)piperidine-1-carboxylate obtained in Example (211a) (20.0 mg, 0.048 mmol), 4 N hydrochloric acid/1,4-dioxane (2 mL), ethyl 2-bromo-1,3-benzothiazole-7-carboxylate obtained in Example (1f) (15 mg, 0.053 mmol) and sodium carbonate (51 mg, 0.483 mmol), to obtain 7 mg of the title compound (28%) as a colorless solid.

$^1$H NMR spectrum (400 MHz, CD$_3$OD) δ ppm: 1.09 (3H, d, J=6.1 Hz), 1.13 (3H, d, J=6.1 Hz), 1.21 (3H, t, J=7.1 Hz), 1.43 (3H, t, J=6.8 Hz), 1.74-1.93 (1H, m), 2.05-2.26 (1H, m), 2.65 (2H, q, J=6.8 Hz), 2.85-2.94 (1H, m), 3.01-3.19 (1H, m), 3.27-3.41 (1H, m), 3.42-3.80 (1H, m), 3.95-4.07 (1H, m), 4.12-4.23 (1H, m), 4.29-4.47 (3H, m), 7.40 (1H, t, J=7.7 Hz), 7.67 (1H, d, J=8.1 Hz), 7.78 (1H, d, J=7.8 Hz).

mass spectrum (ESI): m/z 519, 521 (M+H)$^+$.

(212b) trans(±)-2-(4-{[(4-Chloro-5-ethyl-1H-imidazol-2-yl)carbonyl]amino}-3-(isopropylamino)piperidin-1-yl)-1,3-benzothiazole-7-carboxylic acid The same operation as in Example (196d) was performed using ethyl trans(±)-2-(4-{[(4-chloro-5-ethyl-1H-imidazol-2-yl)carbonyl]amino}-3-(isopropylamino)piperidin-1-yl)-1,3-benzothiazole-7-carboxylate obtained in Example (212a) (7.0 mg, 0.013 mmol) and a 2 N aqueous lithium hydroxide solution (67 μL), to obtain 6 mg of the title compound (91%) as a colorless solid.

¹H NMR spectrum (400 MHz, CD₃OD) δ ppm: 1.09-1.45 (9H, m), 1.95-2.28 (2H, m), 2.61-2.69 (2H, m), 3.27-3.75 (4H, m), 3.95-4.20 (1H, m), 4.28-4.40 (1H, m), 4.71-4.82 (1H, m), 7.33-7.47 (1H, m), 7.60-7.86 (2H, m).

mass spectrum (ESI): m/z 491, 493 (M+H)⁺.

Example 213 cis(±)-2-(4-{[(4-Chloro-5-ethyl-1H-imidazol-2-yl)carbonyl]amino}-3-(cyclopropylamino)piperidin-1-yl)-1,3-benzothiazole-7-carboxylic acid (Exemplified Compound No. 213)

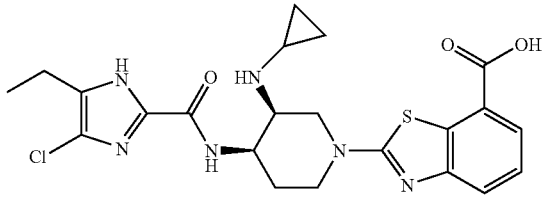

(213a) tert-Butyl cis(±)-4-{[(4-chloro-5-ethyl-1H-imidazol-2-yl)carbonyl]amino}-3-(cyclopropylamino)piperidine-1-carboxylate tert-Butyl trans(±)-4-{[(4-chloro-5-ethyl-1H-imidazol-2-yl)carbonyl]amino}-3-(cyclopropylamino)piperidine-1-carboxylate Cyclopropylamine (249 μL, 3.59 mmol) was added to a solution of tert-butyl 4-{[(4-chloro-5-ethyl-1H-imidazol-2-yl)carbonyl]amino}-3-oxopiperidine-1-carboxylate obtained in Example (201c) (190 mg, 0.512 mmol) in tetrahydrofuran (6 mL), and the mixture was heated under reflux at 50° C. for four hours. The reaction solution was concentrated under reduced pressure, and then tetrahydrofuran (3 mL) and methanol (3 mL) were added. Cyclopropylamine (71.0 μL, 0.102 mmol), sodium cyanoborohydride (97.0 mg, 1.54 mmol) and acetic acid (293 μL, 5.12 mmol) were added, and the mixture was stirred at room temperature for 15 hours. The reaction solution was concentrated under reduced pressure. Saturated aqueous sodium bicarbonate solution was added to the residue, followed by extraction with ethyl acetate. The resulting organic layer was washed with brine, and dried over anhydrous sodium sulfate, and then the insoluble matter was separated by filtration. The filtrate was concentrated under reduced pressure, and the resulting residue was purified by silica gel column chromatography and preparative TLC (eluent: chloroform:methanol=10:1 v/v) to obtain 34 mg of the cis isomer of the title compound (16%) as a pale yellow oily substance and 32 mg of the trans isomer of the title compound (15%) as a pale yellow oily substance.

cis-form mass spectrum (ESI): m/z 412, 414 (M+H)⁺.

trans-form mass spectrum (ESI): m/z 412, 414 (M+H)⁺.

(213b) Ethyl cis(±)-2-(4-{[(4-chloro-5-ethyl-1H-imidazol-2-yl)carbonyl]amino}-3-(cyclopropylamino)piperidin-1-yl)-1,3-benzothiazole-7-carboxylate The same operation as in Example (196c) was performed using tert-butyl cis(±)-4-{[(4-chloro-5-ethyl-1H-imidazol-2-yl)carbonyl]amino}-3-(cyclopropylamino)piperidine-1-carboxylate obtained in Example (213a) (34.0 mg, 0.083 mmol), 4 N hydrochloric acid/1,4-dioxane (2 mL), ethyl 2-bromo-1,3-benzothiazole-7-carboxylate obtained in Example (1f) (26 mg, 0.091 mmol) and sodium carbonate (87 mg, 0.825 mmol), to obtain 11 mg of the title compound (26%) as a pale yellow oily substance.

¹H NMR spectrum (400 MHz, CDCl₃) δ ppm: 0.28-0.87 (4H, m), 1.28 (3H, t, J=7.6 Hz), 1.44 (3H, t, J=7.1 Hz), 2.34-2.39 (1H, m), 2.66-2.75 (3H, m), 2.82-2.89 (1H, m), 3.07-3.12 (1H, m), 3.22-3.31 (1H, m), 3.39 (1H, dd, J=13.4, 2.2 Hz), 4.16-4.30 (2H, m), 4.35-4.41 (1H, m), 4.46 (2H, q, J=7.1 Hz), 7.39 (1H, t, J=7.8 Hz), 7.72 (1H, dd, J=8.0, 1.0 Hz), 7.82 (1H, dd, J=7.8, 1.0 Hz).

mass spectrum (ESI): m/z 517, 519 (M+H)⁺.

(213c) cis(±)-2-(4-{[(4-Chloro-5-ethyl-1H-imidazol-2-yl)carbonyl]amino}-3-(cyclopropylamino)piperidin-1-yl)-1,3-benzothiazole-7-carboxylic acid The same operation as in Example (196d) was performed using ethyl cis(±)-2-(4-{[(4-chloro-5-ethyl-1H-imidazol-2-yl)carbonyl]amino}-3-(cyclopropylamino)piperidin-1-yl)-1,3-benzothiazole-7-carboxylate obtained in Example (213b) (11.0 mg, 0.021 mmol) and a 2 N aqueous lithium hydroxide solution (106 μL), to obtain 10 mg of the title compound (96%) as a pale yellow solid.

¹H NMR spectrum (400 MHz, CD₃OD) δ ppm: 0.59-0.92 (4H, m), 1.18-1.27 (3H, m), 1.85-2.14 (2H, m), 2.60-2.70 (2H, m), 2.71-2.81 (1H, m), 3.60-3.73 (2H, m), 3.90-4.01 (2H, m), 4.20-4.28 (1H, m), 4.52-4.58 (1H, m), 7.43 (1H, t, J=7.8 Hz), 7.71 (1H, d, J=8.1 Hz), 7.83 (1H, d, J=7.6 Hz).

mass spectrum (ESI): m/z 489, 491 (M+H)⁺.

Example 214 trans(±)-2-(4-{[(4-Chloro-5-ethyl-1H-imidazol-2-yl)carbonyl]amino}-3-(cyclopropylamino)piperidin-1-yl)-1,3-benzothiazole-7-carboxylic acid (Exemplified Compound No. 214)

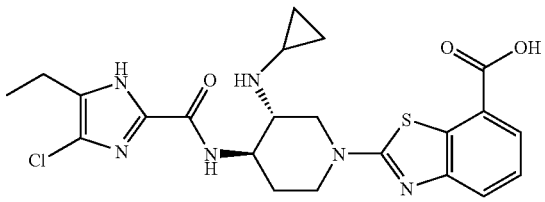

(214a) Ethyl trans(±)-2-(4-{[(4-chloro-5-ethyl-1H-imidazol-2-yl)carbonyl]amino}-3-(cyclopropylamino)piperidin-1-yl)-1,3-benzothiazole-7-carboxylate The same operation as in Example (196c) was performed using tert-butyl trans(±)-4-{[(4-chloro-5-ethyl-1H-imidazol-2-yl)carbonyl]amino}-3-(cyclopropylamino)piperidine-1-carboxylate obtained in Example (213a) (32.0 mg, 0.078 mmol), 4 N hydrochloric acid-1,4-dioxane (2 mL), ethyl 2-bromo-1,3-benzothiazole-7-carboxylate obtained in Example (1f) (24 mg, 0.085 mmol) and sodium carbonate (82 mg, 0.777 mmol), to obtain 29 mg of the title compound (72%) as a colorless solid.

¹H NMR spectrum (400 MHz, CDCl₃) δ ppm: 0.28-0.62 (4H, m), 1.26 (3H, t, J=7.6 Hz), 1.44 (3H, t, J=7.2 Hz), 1.62-1.76 (1H, m), 2.15-2.22 (2H, m), 2.69 (2H, q, J=7.6 Hz), 2.83-2.91 (1H, m), 2.99-3.08 (1H, m), 3.19-3.28 (1H, m), 3.94-4.04 (1H, m), 4.28-4.36 (1H, m), 4.45 (2H, q, J=7.1 Hz), 4.52-4.60 (1H, m), 7.11 (1H, d, J=8.0 Hz), 7.38 (1H, t, J=7.8 Hz), 7.72 (1H, dd, J=7.8, 1.2 Hz), 7.81 (1H, dd, J=7.7, 1.1 Hz).

mass spectrum (ESI): m/z 517, 519 (M+H)⁺.

(214b) trans(±)-2-(4-{[(4-Chloro-5-ethyl-1H-imidazol-2-yl)carbonyl]amino}-3-(cyclopropylamino)piperidin-1-yl)-1,3-benzothiazole-7-carboxylic acid The same operation as in Example (196d) was performed using ethyl trans(±)-2-(4-{[(4-chloro-5-ethyl-1H-imidazol-2-yl)carbonyl]amino}-3-(cyclopropylamino)piperidin-1-yl)-1,3-benzothiazole-7-carboxylate obtained in Example (214a) (28.0 mg, 0.054 mmol) and a 2 N aqueous lithium hydroxide solution (271 µL), to obtain 10 mg of the title compound (38%) as a pale yellow solid.

$^1$H NMR spectrum (400 MHz, CD$_3$OD) δ ppm: 0.52-0.80 (4H, m), 1.21 (3H, t, J=7.3 Hz), 1.80-1.92 (1H, m), 2.11-2.18 (1H, m), 2.49-2.54 (1H, m), 2.65 (2H, q, J=7.3 Hz), 3.12-3.50 (3H, m), 4.12-4.22 (2H, m), 4.62-4.70 (1H, m), 7.41 (1H, t, J=7.9 Hz), 7.67 (1H, d, J=8.1 Hz), 7.80 (1H, d, J=7.6 Hz).

mass spectrum (ESI): m/z 489, 491 (M+H)$^+$.

Example 215 cis(±)-2-(4-{[(4-Chloro-5-ethyl-1H-imidazol-2-yl)carbonyl]amino}-3-[(1-ethylpropyl)amino]piperidin-1-yl)-1,3-benzothiazole-7-carboxylic acid (Exemplified Compound No. 215)

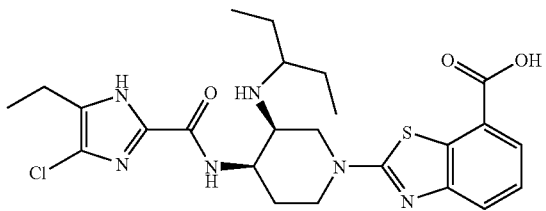

(215a) tert-Butyl cis(±)-4-{[(4-chloro-5-ethyl-1H-imidazol-2-yl)carbonyl]amino}-3-[(1-ethylpropyl)amino]piperidine-1-carboxylate tert-Butyl trans(±)-4-{[(4-chloro-5-ethyl-1H-imidazol-2-yl)carbonyl]amino}-3-[(1-ethylpropyl)amino]piperidine-1-carboxylate 1-Ethylpropylamine (124 µL, 1.06 mmol) was added to a solution of tert-butyl 4-{[(4-chloro-5-ethyl-1H-imidazol-2-yl)carbonyl]amino}-3-oxopiperidine-1-carboxylate obtained in Example (201c) (197 mg, 0.531 mmol) in tetrahydrofuran (4 mL), and the mixture was heated under reflux at 50° C. for four hours. Methanol (3 mL) was added to the reaction solution. Sodium cyanoborohydride (100 mg, 1.59 mmol) and acetic acid (304 µL, 5.31 mmol) were added, and the mixture was stirred at room temperature for 15 hours. The reaction solution was concentrated under reduced pressure. Saturated aqueous sodium bicarbonate solution was added to the residue, followed by extraction with ethyl acetate. The resulting organic layer was washed with brine, and dried over anhydrous sodium sulfate, and then the insoluble matter was separated by filtration. The filtrate was concentrated under reduced pressure, and the resulting residue was purified by silica gel column chromatography and preparative TLC (eluent: chloroform:methanol=10:1 v/v) to obtain 49 mg of the cis isomer of the title compound (21%) as a pale yellow oily substance and 16 mg of the trans isomer of the title compound (7%) as a pale yellow oily substance.
cis-form
mass spectrum (ESI): m/z 442, 444 (M+H)$^+$.
trans-form
mass spectrum (ESI): m/z 442, 444 (M+H)$^+$.

(215b) Ethyl cis(±)-2-(4-{[(4-chloro-5-ethyl-1H-imidazol-2-yl)carbonyl]amino}-3-[(1-ethylpropyl)amino]piperidin-1-yl)-1,3-benzothiazole-7-carboxylate The same operation as in Example (196c) was performed using tert-butyl cis(±)-4-{[(4-chloro-5-ethyl-1H-imidazol-2-yl)carbonyl]amino}-3-[(1-ethylpropyl)amino]piperidine-1-carboxylate obtained in Example (215a) (49.0 mg, 0.111 mmol), 4 N hydrochloric acid/1,4-dioxane (2 mL), ethyl 2-bromo-1,3-benzothiazole-7-carboxylate obtained in Example (1f) (35 mg, 0.122 mmol) and sodium carbonate (118 mg, 1.11 mmol), to obtain 11 mg of the title compound (18%) as a pale yellow oily substance.

$^1$H NMR spectrum (400 MHz, CDCl$_3$) δ ppm: 0.82 (3H, t, J=7.4 Hz), 0.91 (3H, t, J=7.4 Hz), 1.21-1.52 (10H, m), 1.78-1.99 (2H, m), 2.49-2.57 (1H, m), 2.69 (2H, q, J=7.6 Hz), 2.95-3.01 (1H, m), 3.21-3.34 (2H, m), 4.14-4.29 (3H, m), 4.45 (2H, q, J=7.0 Hz), 7.38 (1H, t, J=7.9 Hz), 7.71 (1H, dd, J=8.1, 1.0 Hz), 7.81 (1H, dd, J=7.8, 1.0 Hz), 7.90 (1H, d, J=8.8 Hz), 11.14 (1H, br s).

mass spectrum (ESI): m/z 547, 549 (M+H)$^+$.

(215c) cis(±)-2-(4-{[(4-Chloro-5-ethyl-1H-imidazol-2-yl)carbonyl]amino}-3-[(1-ethylpropyl)amino]piperidin-1-yl)-1,3-benzothiazole-7-carboxylic acid The same operation as in Example (196d) was performed using ethyl cis(±)-2-(4-{[(4-chloro-5-ethyl-1H-imidazol-2-yl)carbonyl]amino}-3-[(1-ethylpropyl)amino]piperidin-1-yl)-1,3-benzothiazole-7-carboxylate obtained in Example (215b) (10.0 mg, 0.018 mmol) and a 2 N aqueous lithium hydroxide solution (91 µL), to obtain 9 mg of the title compound (95%) as a pale yellow solid.

$^1$H NMR spectrum (400 MHz, CD$_3$OD) δ ppm: 0.88-0.95 (6H, m), 1.22 (3H, t, J=7.7 Hz), 1.51-1.63 (4H, m), 1.97-2.07 (2H, m), 2.65 (2H, q, J=7.4 Hz), 2.87-2.96 (1H, m), 3.39-3.46 (1H, m), 3.56-3.66 (1H, m), 3.78 (1H, d, J=12.0 Hz), 3.92-4.01 (1H, m), 4.02-4.11 (1H, m), 4.39-4.46 (1H, m), 7.38 (1H, t, J=8.0 Hz), 7.62 (1H, d, J=6.9 Hz), 7.76-7.80 (1H, m).

mass spectrum (ESI): m/z 519, 521 (M+H)$^+$.

Example 216 trans(±)-2-(4-{[(4-Chloro-5-ethyl-1H-imidazol-2-yl)carbonyl]amino}-3-[(1-ethylpropyl)amino]piperidin-1-yl)-1,3-benzothiazole-7-carboxylic acid (Exemplified Compound No. 216)

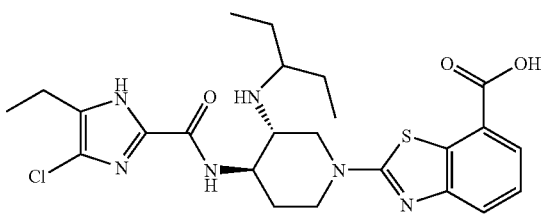

(216a) Ethyl trans(±)-2-(4-{[(4-chloro-5-ethyl-1H-imidazol-2-yl)carbonyl]amino}-3-[(1-ethylpropyl)amino]piperidin-1-yl)-1,3-benzothiazole-7-carboxylate The same operation as in Example (196c) was performed using tert-butyl trans(±)-4-{[(4-chloro-5-ethyl-1H-imidazol-2-yl)carbonyl]amino}-3-[(1-ethylpropyl)amino]piperidine-1-carboxylate obtained in Example (215a) (16.0 mg, 0.036 mmol), 4 N hydrochloric acid/1,4-dioxane (1 mL), ethyl 2-bromo-1,3-benzothiazole-7-carboxylate obtained in Example (1f) (11 mg, 0.040 mmol) and sodium carbonate (38 mg, 0.362 mmol), to obtain 11 mg of the title compound (56%) as a pale yellow oily substance.

$^1$H NMR spectrum (400 MHz, CDCl$_3$) δ ppm: 0.79 (3H, t, J=7.4 Hz), 0.91 (3H, t, J=7.3 Hz), 1.23-1.52 (10H, m), 1.65-1.80 (1H, m), 2.16-2.26 (1H, m), 2.49-2.57 (1H, m), 2.65-2.77 (3H, m), 2.93-3.02 (1H, m), 3.22-3.31 (1H, m), 3.90-4.00 (1H, m), 4.25-4.35 (2H, m), 4.45 (2H, q, J=7.1 Hz), 7.15 (1H, d, J=8.1 Hz), 7.37 (1H, t, J=7.9 Hz), 7.72 (1H, dd, J=8.1, 1.0 Hz), 7.81 (1H, dd, J=7.8, 1.0 Hz), 11.03 (1H, br s).

mass spectrum (ESI): m/z 547, 549 (M+H)$^+$.

(216b) trans(±)-2-(4-{[(4-Chloro-5-ethyl-1H-imidazol-2-yl)carbonyl]amino}-3-[(1-ethylpropyl)amino]piperidin-1-yl)-1,3-benzothiazole-7-carboxylic acid The same operation as in Example (196d) was performed using ethyl trans(±)-2-(4-{[(4-chloro-5-ethyl-1H-imidazol-2-yl)carbonyl]amino}-3-[(1-ethylpropyl)amino]piperidin-1-yl)-1,3-benzothiazole-7-carboxylate obtained in Example (216a) (3.0 mg, 0.005 mmol) and a 2 N aqueous lithium hydroxide solution (27 μL), to obtain 2 mg of the title compound (70%) as a pale yellow solid.

$^1$H NMR spectrum (400 MHz, CD$_3$OD) δ ppm: 0.92 (3H, t, J=7.4 Hz), 1.02 (3H, t, J=7.4 Hz), 1.21 (3H, t, J=7.4 Hz), 1.57-1.74 (4H, m), 1.85-1.98 (1H, m), 2.09-2.17 (1H, m), 2.61-2.69 (2H, m), 2.99-3.07 (1H, m), 3.32-3.45 (1H, m), 3.54-3.68 (1H, m), 4.12-4.26 (2H, m), 4.26-4.42 (1H, m), 4.50-4.58 (1H, m), 7.39 (1H, t, J=7.7 Hz), 7.63 (1H, d, J=6.9 Hz), 7.79 (1H, d, J=7.4 Hz).

mass spectrum (ESI): m/z 519, 521 (M+H)$^+$.

Example 217

2-(3-{[(4-Chloro-5-ethyl-1H-imidazol-2-yl)carbonyl]amino}azetidin-1-yl)-1,3-thiazole-5-carboxylic acid (Exemplified Compound No. 217)

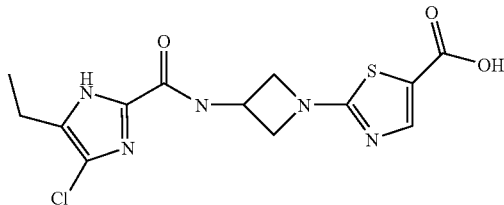

(217a) Ethyl 2-{3-[(tert-butoxycarbonyl)amino]azetidin-1-yl}-1,3-thiazole-5-carboxylate A solution of 3-tert-butoxycarbonylaminoazetidine (300 mg, 1.74 mmol), ethyl 2-bromothiazole-5-carboxylate (0.29 mL, 1.92 mmol) and diisopropylethylamine (0.61 mL, 3.48 mmol) in DMF (17 mL) was stirred at 70° C. for 10.5 hours. The reaction solution was diluted with ethyl acetate, and then the mixture was washed with brine and dried over anhydrous magnesium sulfate. Following filtration, the solvent was evaporated under reduced pressure. The resulting residue was purified by silica gel column chromatography (elution solvent: hexane/ethyl acetate=2/1) to obtain 341 mg of the title compound as a pale yellow solid (60%).

$^1$H NMR spectrum (400 MHz, CDCl$_3$) δ ppm: 1.34 (3H, t, J=7.07 Hz), 1.45 (9H, s), 3.98 (2H, dd, J=9.02, 5.37 Hz), 4.29 (2H, q, J=7.07 Hz), 4.40-4.48 (2H, m), 4.71 (1H, br s), 5.12 (1H, br s), 7.84 (1H, s).

mass spectrum (ESI): m/z 328 (M+H)$^+$.

(217b) Ethyl 2-(3-aminoazetidin-1-yl)-1,3-thiazole-5-carboxylate

A 4 N hydrochloric acid/ethyl acetate solution (1.27 mL, 5.09 mmol) was added to a solution of ethyl 2-{3-[(tert-butoxycarbonyl)amino]azetidin-1-yl}-1,3-thiazole-5-carboxylate obtained in Example (217a) (333 mg, 1.02 mmol) in 1,4-dioxane (10 mL) at 0° C., and the mixture was stirred at room temperature for 7.5 hours. Thereafter, a 4 N hydrochloric acid/ethyl acetate solution (1.27 mL, 5.09 mmol), THF (8 mL) and methanol (5 mL) were added, and the mixture was further stirred for 23 hours. The reaction solution was concentrated, and saturated aqueous sodium bicarbonate solution was added to the resulting residue. Thereafter, the mixture was extracted with ethyl acetate, and the combined organic layers were dried over anhydrous magnesium sulfate. Following filtration, the solvent was evaporated under reduced pressure to obtain 180 mg of the title compound as a pale yellow oily substance (78%).

$^1$H NMR spectrum (400 MHz, CDCl$_3$) δ ppm: 1.34 (3H, t, J=7.16 Hz), 3.81 (2H, dd, J=9.77, 5.37 Hz), 4.05-4.12 (1H, m), 4.29 (2H, q, J=7.16 Hz), 4.35-4.41 (2H, m), 7.85 (1H, s).

mass spectrum (ESI): m/z 228 (M+H)$^+$.

(217c) Ethyl 2-(3-{[(4-chloro-5-ethyl-1H-imidazol-2-yl)carbonyl]amino}azetidin-1-yl)-1,3-thiazole-5-carboxylate WSC hydrochloride (62 mg, 0.32 mmol), 1-hydroxybenzotriazole (36 mg, 0.27 mmol) and N-methylmorpholine (0.06 mL, 0.54 mmol) were added to a mixed solution of ethyl 2-(3-aminoazetidin-1-yl)-1,3-thiazole-5-carboxylate obtained in Example (217b) (61 mg, 0.27 mmol) and 4-chloro-5-ethyl-1H-imidazole-2-carboxylic acid obtained in Example (1d) (47 mg, 0.27 mmol) in DMA/dichloromethane (2 mL/2 mL), and the mixture was stirred at room temperature for 19 hours. The reaction solution was diluted with ethyl acetate, and then the mixture was washed with brine and dried over anhydrous magnesium sulfate. Following filtration, the solvent was evaporated under reduced pressure. The resulting residue was purified by silica gel column chromatography (elution solvent: dichloromethane/methanol=20/1) to obtain 66 mg of the title compound as a white solid (64%).

$^1$H NMR spectrum (400 MHz, CDCl$_3$) δ ppm: 1.27 (3H, t, J=7.57 Hz), 1.31-1.37 (3H, m), 2.70 (2H, q, J=7.57 Hz), 4.12 (2H, dd, J=9.28, 5.37 Hz), 4.26-4.34 (2H, m), 4.50 (2H, t, J=8.54 Hz), 4.99-5.08 (1H, m), 7.71 (1H, d, J=8.30 Hz), 7.87 (1H, s), 11.19 (1H, br s).

mass spectrum (ESI): m/z 384, 386 (M+H)$^+$.

(217d) 2-(3-{[(4-Chloro-5-ethyl-1H-imidazol-2-yl)carbonyl]amino}azetidin-1-yl)-1,3-thiazole-5-carboxylic acid Ethyl 2-(3-{[(4-chloro-5-ethyl-1H-imidazol-2-yl)carbonyl]amino}azetidin-1-yl)-1,3-thiazole-5-carboxylate obtained in Example (217c) (65 mg, 0.17 mmol) was dissolved in methanol (2 mL). A 2 N aqueous lithium hydroxide solution (0.85 mL, 1.69 mmol) was added, and the mixture was stirred at room temperature for 29 hours. Water was added to the reaction solution, and then the mixture was washed with ethyl acetate. A 1 N aqueous hydrochloric acid solution (1 mL) was added to the aqueous layer, followed by extraction with ethyl acetate. The combined organic layers were dried over anhydrous magnesium sulfate and then filtered, and the filtrate was concentrated under reduced pressure. The resulting solid was suspended and washed in diethyl ether to obtain 32 mg of the title compound as a white solid (53%).

$^1$H NMR spectrum (400 MHz, DMSO-d$_6$) δ ppm: 1.14 (3H, t, J=7.57 Hz), 2.55 (2H, q, J=7.57 Hz), 4.15 (2H, dd, J=8.42, 5.74 Hz), 4.35 (2H, t, J=8.42 Hz), 4.88-4.98 (1H, m), 7.75 (1H, d, J=1.22 Hz), 9.31 (1H, d, J=7.81 Hz), 12.70 (1H, br s), 13.33 (1H, s).

mass spectrum (ESI): m/z 356, 358 (M+H)⁺.

Example 218

2-(3-{[(4-Chloro-5-ethyl-1H-imidazol-2-yl)carbonyl]amino}azetidin-1-yl)-4-methyl-1,3-thiazole-5-carboxylic acid (Exemplified Compound No. 218)

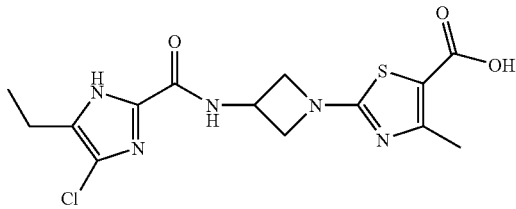

(218a) Ethyl 2-{3-[(tert-butoxycarbonyl)amino]azetidin-1-yl}-4-methyl-1,3-thiazole-5-carboxylate The same operation as in Example (217a) was performed using 3-tert-butoxycarbonylaminoazetidine (300 mg, 1.74 mmol), ethyl 2-bromo-4-methylthiazole-5-carboxylate (479 mg, 1.92 mmol) and diisopropylethylamine (0.61 mL, 3.48 mmol), to obtain 265 mg of the title compound as a pale yellow solid (45%).

¹H NMR spectrum (400 MHz, CDCl₃) δ ppm: 1.32 (3H, t, J=7.07 Hz), 1.45 (9H, s), 2.55 (3H, s), 3.94 (2H, dd, J=9.27, 5.37 Hz), 4.26 (2H, q, J=7.07 Hz), 4.35-4.45 (2H, m), 4.69 (1H, br s), 5.03 (1H, br s).

mass spectrum (ESI): m/z 342 (M+H)⁺.

(218b) Ethyl 2-(3-aminoazetidin-1-yl)-4-methyl-1,3-thiazole-5-carboxylate

A 4 N hydrochloric acid/ethyl acetate solution (0.96 mL, 3.82 mmol) was added to a solution of ethyl 2-{3-[(tert-butoxycarbonyl)amino]azetidin-1-yl}-4-methyl-1,3-thiazole-5-carboxylate obtained in Example (218a) (261 mg, 0.76 mmol) in 1,4-dioxane (8 mL) at 0° C., and the mixture was stirred at room temperature for 7.5 hours. Then, a 4 N hydrochloric acid/ethyl acetate solution (0.96 mL, 3.82 mmol) was added, and the mixture was further stirred for 45 hours. The reaction solution was concentrated, and saturated aqueous sodium bicarbonate solution was added to the resulting residue. Thereafter, the mixture was extracted with ethyl acetate, and the combined organic layers were dried over anhydrous magnesium sulfate. Following filtration, the solvent was evaporated under reduced pressure to obtain 146 mg of the title compound as a pale yellow oily substance (79%).

¹H NMR spectrum (400 MHz, CDCl₃) δ ppm: 1.32 (3H, t, J=7.32 Hz), 2.56 (3H, s), 3.78 (2H, dd, J=9.64, 5.25 Hz), 4.02-4.09 (1H, m), 4.25 (2H, q, J=7.32 Hz), 4.32-4.38 (2H, m).

mass spectrum (ESI): m/z 242 (M+H)⁺.

(218c) Ethyl 2-(3-{[(4-chloro-5-ethyl-1H-imidazol-2-yl)carbonyl]amino}azetidin-1-yl)-4-methyl-1,3-thiazole-5-carboxylate The same operation as in Example (217c) was performed using ethyl 2-(3-aminoazetidin-1-yl)-4-methyl-1,3-thiazole-5-carboxylate obtained in Example (218b) (144 mg, 0.60 mmol), 4-chloro-5-ethyl-1H-imidazole-2-carboxylic acid obtained in Example (1d) (104 mg, 0.60 mmol), WSC hydrochloride (343 mg, 1.79 mmol), 1-hydroxybenzotriazole (81 mg, 0.60 mmol) and N-methylmorpholine (0.13 mL, 1.19 mmol), to obtain 151 mg of the title compound as a white solid (64%).

¹H NMR spectrum (400 MHz, CDCl₃) δ ppm: 1.26 (3H, t, J=7.57 Hz), 1.33 (3H, t, J=7.08 Hz), 2.57 (3H, s), 2.70 (2H, q, J=7.57 Hz), 4.10 (2H, dd, J=9.16, 5.25 Hz), 4.27 (2H, q, J=7.08 Hz), 4.46 (2H, t, J=8.42 Hz), 4.96-5.07 (1H, m), 7.87 (1H, d, J=8.06 Hz), 11.83 (1H, br s).

mass spectrum (ESI): m/z 398, 400 (M+H)⁺.

(218d) 2-(3-{[(4-Chloro-5-ethyl-1H-imidazol-2-yl)carbonyl]amino}azetidin-1-yl)-4-methyl-1,3-thiazole-5-carboxylic acid Ethyl 2-(3-{[(4-chloro-5-ethyl-1H-imidazol-2-yl)carbonyl]amino}azetidin-1-yl)-4-methyl-1,3-thiazole-5-carboxylate obtained in Example (218c) (145 mg, 0.36 mmol) was dissolved in methanol (3.6 mL). A 2 N aqueous lithium hydroxide solution (1.82 mL, 3.64 mmol) was added, and the mixture was stirred at room temperature for 27 hours. THF (2 mL) was added, followed by further stirring for 22 hours. Water was added to the reaction solution, and then the mixture was washed with ethyl acetate. A 1 N aqueous hydrochloric acid solution (4 mL) was added to the aqueous layer, followed by extraction with a chloroform/methanol mixed solvent. The combined organic layers were dried over anhydrous magnesium sulfate and then filtered, and the filtrate was concentrated under reduced pressure. The resulting solid was suspended and washed in diethyl ether to obtain 123 mg of the title compound as a white solid (91%).

¹H NMR spectrum (400 MHz, DMSO-d₆) δ ppm: 1.14 (3H, t, J=7.57 Hz), 2.42 (3H, s), 2.55 (2H, q, J=7.57 Hz), 4.11 (2H, dd, J=8.54, 5.86 Hz), 4.31 (2H, t, J=8.18 Hz), 4.85-4.96 (1H, m), 9.30 (1H, d, J=7.57 Hz), 13.33 (1H, br s).

mass spectrum (ESI): m/z 370, 372 (M+H)⁺.

Example 219

2-(3-{[(4-Chloro-5-ethyl-1H-imidazol-2-yl)carbonyl]amino}azetidin-1-yl)-4-n-propyl-1,3-thiazole-5-carboxylic acid (Exemplified Compound No. 219)

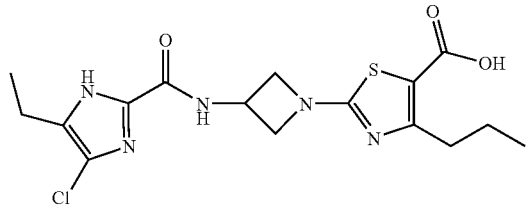

(219a) Ethyl 2-bromo-4-n-propyl-1,3-thiazole-5-carboxylate

The compound was synthesized according to the method described in the following document.

J. Chem. Soc., Perkin Trans. 1, 1982, 159-164 (219b) Ethyl 2-{3-[(tert-butoxycarbonyl)amino]azetidin-1-yl}-4-n-propyl-1,3-thiazole-5-carboxylate The same operation as in Example (217a) was performed using 3-tert-butoxycarbonylaminoazetidine (161 mg, 0.94 mmol), ethyl 2-bromo-4-n-propyl-1,3-thiazole-5-carboxylate obtained in Example (219a) (217 mg, 0.78 mmol) and diisopropylethylamine (0.27 mL, 1.56 mmol), to obtain 204 mg of the title compound as a white solid (71%).

¹H NMR spectrum (400 MHz, CDCl₃) δ ppm: 0.96 (3H, t, J=7.32 Hz), 1.32 (3H, t, J=7.32 Hz), 1.45 (9H, s), 1.60-1.72 (2H, m), 2.91-2.97 (2H, m), 3.93 (2H, dd, J=8.90, 5.49 Hz), 4.25 (2H, q, J=7.15 Hz), 4.38-4.45 (2H, m), 4.69 (1H, br s), 5.01 (1H, br s).

mass spectrum (ESI): m/z 370 (M+H)⁺.

(219c) Ethyl 2-(3-{[(4-chloro-5-ethyl-1H-imidazol-2-yl)carbonyl]amino}azetidin-1-yl)-4-n-propyl-1,3-thiazole-5-carboxylate A 4 N hydrochloric acid/ethyl acetate solution (1.37 mL, 5.47 mmol) was added to a solution of ethyl 2-{3-[(tert-butoxycarbonyl)amino]azetidin-1-yl}-4-n-propyl-1,3-thiazole-5-carboxylate obtained in Example (219b) (202 mg, 0.55 mmol) in 1,4-dioxane (6 mL), and the mixture was stirred at room temperature for 21 hours. The reaction solution was concentrated, and saturated aqueous sodium bicarbonate solution was added to the resulting residue. Thereafter, the mixture was extracted with ethyl acetate, and the combined organic layers were dried over anhydrous magnesium sulfate. Following filtration, the solvent was evaporated under reduced pressure to obtain an oily substance.

The same operation as in Example (217c) was performed using the oily substance obtained by the above operation, 4-chloro-5-ethyl-1H-imidazole-2-carboxylic acid obtained in Example (1d) (96 mg, 0.55 mmol), WSC hydrochloride (315 mg, 1.64 mmol), 1-hydroxybenzotriazole (74 mg, 0.55 mmol) and N-methylmorpholine (0.12 mL, 1.09 mmol), to obtain 218 mg of the title compound as a milk white solid (94%).

$^1$H NMR spectrum (400 MHz, CDCl$_3$) δ ppm: 0.97 (3H, t, J=7.32 Hz), 1.27 (3H, t, J=7.56 Hz), 1.33 (3H, t, J=7.56 Hz), 1.63-1.74 (2H, m), 2.70 (2H, q, J=7.56 Hz), 2.92-2.99 (2H, m), 4.09 (2H, dd, J=9.02, 5.37 Hz), 4.26 (2H, q, J=7.56 Hz), 4.47 (2H, t, J=8.41 Hz), 4.96-5.07 (1H, m), 7.70 (1H, d, J=8.05 Hz), 11.43 (1H, br s).

mass spectrum (ESI): m/z 426, 428 (M+H)$^+$.

(219d) 2-(3-{[(4-Chloro-5-ethyl-1H-imidazol-2-yl)carbonyl]amino}azetidin-1-yl)-4-n-propyl-1,3-thiazole-5-carboxylic acid Ethyl 2-(3-{[(4-chloro-5-ethyl-1H-imidazol-2-yl)carbonyl]amino}azetidin-1-yl)-4-n-propyl-1,3-thiazole-5-carboxylate obtained in Example (219c) (214 mg, 0.50 mmol) was dissolved in methanol (5 mL). A 2 N aqueous lithium hydroxide solution (2.51 mL, 5.02 mmol) and THF (1 mL) were added, and then the mixture was stirred at room temperature for 17 hours. Water was added to the reaction solution, and then the mixture was washed with ethyl acetate. A 1 N aqueous hydrochloric acid solution (4.5 mL) was added to the aqueous layer. The precipitated solid was collected by filtration to obtain 141 mg of the title compound as a white solid (71%).

$^1$H NMR spectrum (400 MHz, DMSO-d$_6$) δ ppm: 0.88 (3H, t, J=7.32 Hz), 1.14 (3H, t, J=7.56 Hz), 1.53-1.65 (2H, m), 2.55 (2H, q, J=7.56 Hz), 2.84 (2H, t, J=7.56 Hz), 4.11 (2H, dd, J=8.41, 5.98 Hz), 4.31 (2H, t, J=8.17 Hz), 4.85-4.97 (1H, m), 9.29 (1H, d, J=7.80 Hz), 12.46 (1H, br s), 13.32 (1H, s).

mass spectrum (ESI): m/z 398, 400 (M+H)$^+$.

Example 220

4-n-Butyl-2-(3-{[(4-chloro-5-ethyl-1H-imidazol-2-yl)carbonyl]amino}azetidin-1-yl)-1,3-thiazole-5-carboxylic acid (Exemplified Compound No. 220)

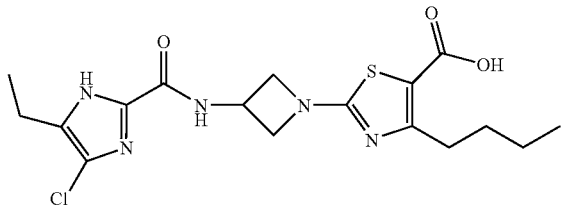

(220a) Ethyl 2-amino-4-n-butyl-1,3-thiazole-5-carboxylate

Sulfuryl chloride (0.89 mL, 11.0 mmol) was added to a solution of ethyl 3-oxoheptanoate (2.00 g, 11.6 mmol) in chloroform (40 mL) at 0° C., and the mixture was stirred at room temperature for 80 minutes. Saturated sodium bicarbonate solution was added to the reaction solution, and then the mixture was extracted with chloroform. The combined organic layers were dried over anhydrous magnesium sulfate and then filtered, and the filtrate was concentrated under reduced pressure to obtain an oily substance.

A solution of the oily substance obtained by the above operation and thiourea (839 mg, 11.0 mmol) in ethanol (58 mL) was heated under reflux for 14 hours. The reaction solution was concentrated under reduced pressure, and then the resulting residue was purified by silica gel column chromatography (elution solvent: hexane/ethyl acetate=2/1) to obtain 444 mg of the title compound as a white solid (18%).

mass spectrum (ESI): m/z 229 (M+H)$^+$.

(220b) Ethyl 2-bromo-4-n-butyl-1,3-thiazole-5-carboxylate tert-Butyl nitrite (0.35 mL, 2.92 mmol) and copper (II) bromide (650 mg, 2.91 mmol) were added to a solution of ethyl 2-amino-4-n-butyl-1,3-thiazole-5-carboxylate obtained in Example (220a) (444 mg, 1.94 mmol) in acetonitrile (19 mL) at room temperature, followed by stirring for one hour. The reaction solution was concentrated under reduced pressure, and then ethyl acetate was added to the resulting residue. The solution was washed with a 1 N aqueous hydrochloric acid solution and brine, and then dried over anhydrous magnesium sulfate. Following filtration, the filtrate was concentrated under reduced pressure. The resulting residue was purified by silica gel column chromatography (elution solvent: hexane/ethyl acetate=5/1) to obtain 548 mg of the title compound as a white solid (97%).

$^1$H NMR spectrum (400 MHz, CDCl$_3$) δ ppm: 0.94 (3H, t, J=7.32 Hz), 1.33-1.44 (5H, m), 1.64-1.73 (2H, m), 3.11 (2H, t, J=7.80 Hz), 4.33 (2H, q, J=7.07 Hz).

mass spectrum (ESI): m/z 292, 294 (M+H)$^+$.

(220c) Ethyl 2-{3-[(tert-butoxycarbonyl)amino]azetidin-1-yl}-4-n-butyl-1,3-thiazole-5-carboxylate The same operation as in Example (217a) was performed using 3-tert-butoxycarbonylaminoazetidine (212 mg, 1.23 mmol), ethyl 2-bromo-4-n-butyl-1,3-thiazole-5-carboxylate obtained in Example (220b) (300 mg, 1.03 mmol) and diisopropylethylamine (0.36 mL, 2.06 mmol), to obtain 294 mg of the title compound as a white solid (74%).

$^1$H NMR spectrum (400 MHz, CDCl$_3$) δ ppm: 0.92 (3H, t, J=7.32 Hz), 1.32 (3H, t, J=7.07 Hz), 1.35-1.42 (2H, m), 1.45 (9H, s), 1.57-1.66 (2H, m), 2.92-2.98 (2H, m), 3.90-3.96 (2H, m), 4.25 (2H, q, J=7.32 Hz), 4.40 (2H, t, J=8.05 Hz), 4.68 (1H, br s), 5.01 (1H, br s).

mass spectrum (ESI): m/z 384 (M+H)$^+$.

(220d) Ethyl 4-n-butyl-2-(3-{[(4-chloro-5-ethyl-1H-imidazol-2-yl)carbonyl]amino}azetidin-1-yl)-1,3-thiazole-5-carboxylate A 4 N hydrochloric acid/ethyl acetate solution (1.87 mL, 7.48 mmol) was added to a solution of ethyl 2-{3-[(tert-butoxycarbonyl)amino]azetidin-1-yl}-4-n-butyl-1,3-thiazole-5-carboxylate obtained in Example (220c) (287 mg, 0.75 mmol) in 1,4-dioxane (8 mL), and the mixture was stirred at room temperature for 16.5 hours. THF (8 mL) and methanol (4 mL) were added, followed by further stirring for 2.5 hours. The reaction solution was concentrated, and saturated aqueous sodium bicarbonate solution was added to the resulting residue. Thereafter, the mixture was extracted with ethyl acetate, and the combined organic layers were dried over anhydrous magnesium sulfate. Following filtration, the solvent was evaporated under reduced pressure to obtain an oily substance.

The same operation as in Example (217c) was performed using the oily substance obtained by the above operation, 4-chloro-5-ethyl-1H-imidazole-2-carboxylic acid obtained in Example (1d) (131 mg, 0.75 mmol), WSC hydrochloride (430 mg, 2.24 mmol), 1-hydroxybenzotriazole (101 mg, 0.75 mmol) and N-methylmorpholine (0.16 mL, 1.50 mmol), to obtain the crude title compound, which was suspended and washed in diethyl ether to obtain 137 mg of the title compound as a milk white solid (42%).

$^1$H NMR spectrum (400 MHz, CDCl$_3$) δ ppm: 0.93 (3H, t, J=7.32 Hz), 1.27 (3H, t, J=7.56 Hz), 1.33 (3H, t, J=7.15 Hz), 1.35-1.44 (2H, m), 1.58-1.68 (2H, m), 2.70 (2H, q, J=7.56 Hz), 2.94-3.02 (2H, m), 4.08 (2H, dd, J=9.02, 5.37 Hz), 4.26 (2H, q, J=7.15 Hz), 4.48 (2H, t, J=8.41 Hz), 4.96-5.07 (1H, m), 7.62 (1H, d, J=8.05 Hz), 11.06 (1H, br s).

mass spectrum (ESI): m/z 440, 442 (M+H)$^+$.

(220e) 2-(3-{[(4-Chloro-5-ethyl-1H-imidazol-2-yl)carbonyl]amino}azetidin-1-yl)-4-n-propyl-1,3-thiazole-5-carboxylic acid A 2 N aqueous lithium hydroxide solution (1.53 mL, 3.07 mmol) was added to a mixed solution of ethyl 4-n-butyl-2-(3-{[(4-chloro-5-ethyl-1H-imidazol-2-yl)carbonyl]}amino}azetidin-1-yl-1,3-thiazole-5-carboxylate obtained in Example (220d) (214 mg, 0.50 mmol) in methanol/THF (3 mL/0.5 mL) at room temperature, followed by stirring for 18 hours. Water was added to the reaction solution, and then the mixture was washed with ethyl acetate. A 1 N aqueous hydrochloric acid solution (2.5 mL) was added to the aqueous layer. The precipitated solid was collected by filtration to obtain 72 mg of the title compound as a white solid (57%).

mass spectrum (ESI): m/z 412, 414 (M+H)$^+$.

Example 221

2-(3-{[(4-Chloro-5-ethyl-1H-imidazol-2-yl)carbonyl]amino}azetidin-1-yl)-4-isopropyl-1,3-thiazole-5-carboxylic acid (Exemplified Compound No. 221)

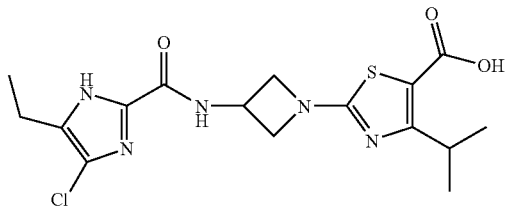

(221a) Ethyl 2-{3-[(tert-butoxycarbonyl)amino]azetidin-1-yl}-4-isopropyl-1,3-thiazole-5-carboxylate A solution of 3-tert-butoxycarbonylaminoazetidine (136 mg, 0.79 mmol), ethyl 2-bromo-4-isopropyl-1,3-thiazole-5-carboxylate obtained in Example (23b) (200 mg, 0.72 mmol) and diisopropylethylamine (0.25 mL, 1.44 mmol) in DMF (8 mL) was stirred at 90° C. for 11 hours. The reaction solution was diluted with ethyl acetate, and then the mixture was washed with 10% saline and dried over anhydrous magnesium sulfate. Following filtration, the solvent was evaporated under reduced pressure. The resulting residue was purified by silica gel column chromatography (elution solvent: hexane/ethyl acetate=4/1) to obtain 175 mg of the title compound as a white solid (66%).

mass spectrum (ESI): m/z 370 (M+H)$^+$.

(221b) Ethyl 2-(3-aminoazetidin-1-yl)-4-isopropyl-1,3-thiazole-5-carboxylate

85% phosphoric acid (0.14 mL, 1.18 mmol) was added to a solution of ethyl 2-{3-[(tert-butoxycarbonyl)amino]azetidin-1-yl}-4-isopropyl-1,3-thiazole-5-carboxylate obtained in Example (221a) (175 mg, 0.47 mmol) in dichloromethane (1 mL) at room temperature, followed by stirring for 15.5 hours. Water and a 50% aqueous sodium hydroxide solution were added to the reaction solution, and then the mixture was extracted with a chloroform/methanol mixed solvent. The combined organic layers were dried over anhydrous magnesium sulfate and filtered. Thereafter, the solvent was evaporated under reduced pressure to obtain 95 mg of the title compound as a colorless oily substance (74%).

mass spectrum (ESI): m/z 270 (M+H)$^+$.

(221c) Ethyl 2-(3-{[(4-chloro-5-ethyl-1H-imidazol-2-yl)carbonyl]amino}azetidin-1-yl)-4-isopropyl-1,3-thiazole-5-carboxylate WSC hydrochloride (203 mg, 1.06 mmol), 1-hydroxybenzotriazole (48 mg, 0.35 mmol) and N-methylmorpholine (0.08 mL, 0.71 mmol) were added to a mixed solution of ethyl 2-(3-aminoazetidin-1-yl)-4-isopropyl-1,3-thiazole-5-carboxylate obtained in Example (221b) (95 mg, 0.35 mmol) and 4-chloro-5-ethyl-1H-imidazole-2-carboxylic acid obtained in Example (1d) (62 mg, 0.35 mmol) in DMA/dichloromethane (4 mL/2 mL), and the mixture was stirred at room temperature for 14 hours. The reaction solution was diluted with ethyl acetate, and then the mixture was washed with 10% saline and dried over anhydrous magnesium sulfate. Following filtration, the solvent was evaporated under reduced pressure. The resulting residue was purified by silica gel column chromatography (elution solvent: hexane/ethyl acetate=2/1) to obtain 61 mg of the title compound as a white solid (41%).

mass spectrum (ESI): m/z 426, 428 (M+H)$^+$.

(221d) 2-(3-{[(4-Chloro-5-ethyl-1H-imidazol-2-yl)carbonyl]amino}azetidin-1-yl)-4-isopropyl-1,3-thiazole-5-carboxylic acid A 2 N aqueous lithium hydroxide solution (0.72 mL, 1.43 mmol) was added to a mixed solution of ethyl 2-(3-{[(4-chloro-5-ethyl-1H-imidazol-2-yl)carbonyl]amino}azetidin-1-yl)-4-isopropyl-1,3-thiazole-5-carboxylate obtained in Example (221c) (61 mg, 0.14 mmol) in methanol/THF (1.5 mL/1 mL) at room temperature, and the mixture was stirred at 40° C. for 70 minutes. Water was added to the reaction solution, and then the mixture was washed with ethyl acetate. A 1 N aqueous hydrochloric acid solution (1 mL) was added to the aqueous layer, followed by extraction with ethyl acetate. The combined organic layers were dried over anhydrous magnesium sulfate and then filtered, and the filtrate was concentrated under reduced pressure. The resulting solid was suspended and washed in diethyl ether to obtain 45 mg of the title compound as a white solid (79%).

$^1$H NMR spectrum (400 MHz, DMSO-d$_6$) δ ppm: 1.11-1.18 (9H, m), 2.56 (2H, q, J=7.56 Hz), 3.77-3.88 (1H, m), 4.09-4.16 (2H, m), 4.32 (2H, t, J=8.17 Hz), 4.85-4.97 (1H, m), 9.28 (1H, d, J=7.80 Hz), 12.24 (1H, br s), 13.31 (1H, br s).

mass spectrum (ESI): m/z 398, 400 (M+H)$^+$.

Example 222

2-(3-{[(4-Chloro-5-ethyl-1H-imidazol-2-yl)carbonyl]amino}azetidin-1-yl)-4-ethyl-1,3-thiazole-5-carboxylic acid (Exemplified Compound No. 222)

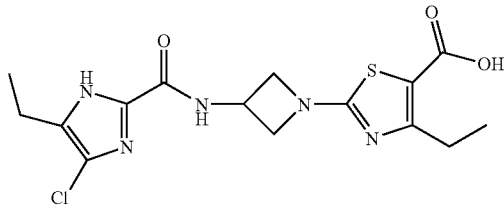

(222a) Methyl 2-{3-[(tert-butoxycarbonyl)amino]azetidin-1-yl}-4-ethyl-1,3-thiazole-5-carboxylate The same operation as in Example (217a) was performed using 3-tert-butoxycarbonylaminoazetidine (124 mg, 0.72 mmol), methyl 2-bromo-4-ethyl-1,3-thiazole-5-carboxylate obtained in Example (22c) (158 mg, 0.63 mmol) and diisopropylethylamine (0.21 mL, 1.20 mmol), to obtain 143 mg of the title compound as a white solid (66%).

$^1$H NMR spectrum (400 MHz, CDCl$_3$) δ ppm: 1.22 (3H, t, J=7.56 Hz), 1.45 (9H, s), 2.98 (2H, q, J=7.56 Hz), 3.79 (3H, s), 3.95 (2H, dd, J=8.90, 5.49 Hz), 4.38-4.45 (2H, m), 4.69 (1H, br s), 5.03 (1H, br s).

mass spectrum (ESI): m/z 342 (M+H)$^+$.

(222b) Methyl 2-(3-aminoazetidin-1-yl)-4-ethyl-1,3-thiazole-5-carboxylate

A 4 N hydrochloric acid/ethyl acetate solution (1.02 mL, 4.07 mmol) was added to a solution of methyl 2-{3-[(tert-butoxycarbonyl)amino]azetidin-1-yl}-4-ethyl-1,3-thiazole-5-carboxylate obtained in Example (222a) (139 mg, 0.41 mmol) in 1,4-dioxane (4 mL) at room temperature, and the mixture was stirred at room temperature for 13 hours. Then, methanol (2 mL) was added, and the mixture was further stirred for 5.5 hours. The reaction solution was concentrated, and saturated aqueous sodium bicarbonate solution was added to the resulting residue. Thereafter, the mixture was extracted with ethyl acetate, and the combined organic layers were dried over anhydrous magnesium sulfate. Following filtration, the solvent was evaporated under reduced pressure to obtain 94 mg of the title compound as a pale yellow oily substance (96%).

mass spectrum (ESI): m/z 242 (M+H)$^+$.

(222c) Methyl 2-(3-{[(4-chloro-5-ethyl-1H-imidazol-2-yl)carbonyl]amino}azetidin-1-yl)-4-ethyl-1,3-thiazole-5-carboxylate The same operation as in Example (217c) was performed using methyl 2-(3-aminoazetidin-1-yl)-4-ethyl-1,3-thiazole-5-carboxylate obtained in Example (222b) (94 mg, 0.39 mmol), 4-chloro-5-ethyl-1H-imidazole-2-carboxylic acid obtained in Example (1d) (68 mg, 0.39 mmol), WSC hydrochloride (224 mg, 1.17 mmol), 1-hydroxybenzotriazole (53 mg, 0.39 mmol) and N-methylmorpholine (0.09 mL, 0.78 mmol), to obtain 153 mg of the title compound as a milk white solid (99%).

$^1$H NMR spectrum (400 MHz, CDCl$_3$) δ ppm: 1.23 (3H, t, J=7.56 Hz), 1.26 (3H, t, J=7.56 Hz), 2.70 (2H, q, J=7.56 Hz), 3.00 (2H, q, J=7.56 Hz), 3.80 (3H, s), 4.10 (2H, dd, J=9.15, 5.24 Hz), 4.48 (2H, t, J=8.41 Hz), 4.96-5.06 (1H, m), 7.77 (1H, d, J=8.05 Hz), 11.65 (1H, br s).

mass spectrum (ESI): m/z 398, 400 (M+H)$^+$.

(222d) 2-(3-{[(4-Chloro-5-ethyl-1H-imidazol-2-yl)carbonyl]amino}azetidin-1-yl)-4-ethyl-1,3-thiazole-5-carboxylic acid Methyl 2-(3-{[(4-chloro-5-ethyl-1H-imidazol-2-yl)carbonyl]amino}azetidin-1-yl)-4-ethyl-1,3-thiazole-5-carboxylate obtained in Example (222c) (143 mg, 0.36 mmol) was dissolved in methanol (3.6 mL). A 2 N aqueous lithium hydroxide solution (1.80 mL, 3.59 mmol) was added, and the mixture was stirred at room temperature for 18.5 hours. Water was added to the reaction solution, and then the mixture was washed with ethyl acetate. A 1 N aqueous hydrochloric acid solution (3 mL) was added to the aqueous layer. The precipitated solid was collected by filtration to obtain 46 mg of the title compound as a white solid (33%).

$^1$H NMR spectrum (400 MHz, DMSO-d$_6$) δ ppm: 1.10-1.17 (6H, m), 2.55 (2H, q, J=7.48 Hz), 2.87 (2H, q, J=7.40 Hz), 4.09-4.16 (2H, m), 4.32 (2H, t, J=8.17 Hz), 4.86-4.97 (1H, m), 9.29 (1H, d, J=7.80 Hz), 12.46 (1H, br s), 13.32 (1H, br s).

mass spectrum (ESI): m/z 384, 386 (M+H)$^+$.

Example 223

3-(3-{[(4-Chloro-5-ethyl-1H-imidazol-2-yl)carbonyl]amino}azetidin-1-yl)benzoic acid (Exemplified Compound No. 223)

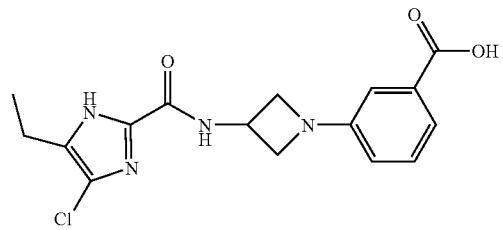

(223a) Ethyl 3-{3-[(tert-butoxycarbonyl)amino]azetidin-1-yl}benzoate

A suspension of 3-tert-butoxycarbonylaminoazetidine (300 mg, 1.74 mmol), ethyl 3-iodobenzoate (721 mg, 2.61 mmol) and copper (I) iodide (66 mg, 0.35 mmol), proline (80 mg, 0.70 mmol) and potassium carbonate (721 mg, 5.22 mmol) in DMSO was stirred at 120° C. for two hours. The reaction solution was diluted with ethyl acetate and then filtered. The filtrate was washed with brine and then dried over anhydrous magnesium sulfate. Following filtration, the solvent was evaporated under reduced pressure. The resulting residue was purified by silica gel column chromatography (elution solvent: hexane/ethyl acetate=4/1) to obtain 319 mg of the title compound as a milk white solid (57%).

$^1$H NMR spectrum (400 MHz, CDCl$_3$) δ ppm: 1.38 (3H, t, J=7.15 Hz), 1.46 (9H, s), 3.64 (2H, t, J=6.59 Hz), 4.20-4.30 (2H, m), 4.36 (2H, q, J=7.15 Hz), 4.63 (1H, br s), 4.97 (1H, br s), 6.60-6.65 (1H, m), 7.09-7.12 (1H, m), 7.24-7.29 (1H, m), 7.44 (1H, dd, J=7.68, 1.10 Hz).

mass spectrum (ESI): m/z 320 (M+H)$^+$.

(223b) Ethyl 3-(3-aminoazetidin-1-yl)benzoate

85% phosphoric acid (0.18 mL, 1.57 mmol) was added to a solution of ethyl 3-{3-[(tert-butoxycarbonyl)amino]azetidin-1-yl}benzoate obtained in Example (223a) (200 mg, 0.62 mmol) in dichloromethane (0.8 mL) at room temperature, followed by stirring for 27 hours. Water and a 50% aqueous sodium hydroxide solution were added to the reaction solution, and then the mixture was extracted with chloroform. The combined organic layers were dried over anhydrous magnesium sulfate and filtered. Thereafter, the solvent was evaporated under reduced pressure to obtain 114 mg of the title compound as a colorless oily substance (83%).

mass spectrum (ESI): m/z 221 (M+H)$^+$.

(223c) Ethyl 3-(3-{[(4-chloro-5-ethyl-1H-imidazol-2-yl)carbonyl]amino}azetidin-1-yl)benzoate The same operation as in Example (217c) was performed using ethyl 3-(3-aminoazetidin-1-yl)benzoate obtained in Example (223b) (114 mg, 0.52 mmol), 4-chloro-5-ethyl-1H-imidazole-2-carboxylic acid obtained in Example (1d) (90 mg, 0.52 mmol), WSC hydrochloride (298 mg, 1.55 mmol), 1-hydroxybenzotriazole (70 mg, 0.52 mmol) and N-methylmorpholine (0.11 mL, 1.04 mmol), to obtain 87 mg of the title compound as a gray white solid (45%).

$^1$H NMR spectrum (400 MHz, CDCl$_3$) δ ppm: 1.27 (3H, t, J=7.56 Hz), 1.39 (3H, t, J=7.07 Hz), 2.70 (2H, q, J=7.56 Hz), 3.79-3.84 (2H, m), 4.31 (2H, t, J=7.32 Hz), 4.37 (2H, q, J=7.07 Hz), 4.91-5.01 (1H, m), 6.64 (1H, dd, J=8.05, 1.71 Hz), 7.11-7.15 (1H, m), 7.25-7.32 (1H, m), 7.47 (1H, d, J=7.80 Hz), 7.59-7.72 (1H, m), 11.33 (1H, br s).

mass spectrum (ESI): m/z 377, 379 (M+H)$^+$.

(223d) 3-(3-{[(4-Chloro-5-ethyl-1H-imidazol-2-yl)carbonyl]amino}azetidin-1-yl)benzoic acid Ethyl 3-(3-{[(4-chloro-5-ethyl-1H-imidazol-2-yl)carbonyl]amino}azetidin-1-yl)benzoate obtained in Example (223c) (84 mg, 0.22 mmol) was dissolved in methanol (2 mL). A 2 N aqueous lithium hydroxide solution (1.11 mL, 2.23 mmol) was added, and the mixture was stirred at room temperature for 20 hours. Water was added to the reaction solution, and then the mixture was washed with ethyl acetate. A 1 N aqueous hydrochloric acid solution was added to the aqueous layer, followed by extraction with a chloroform/methanol mixed solvent. The combined organic layers were dried over anhydrous magnesium sulfate and then filtered, and the filtrate was concentrated under reduced pressure. The resulting solid was suspended and washed in diethyl ether to obtain 10 mg of the title compound as a white solid (13%).

$^1$H NMR spectrum (400 MHz, DMSO-d$_6$) δ ppm: 1.14 (3H, t, J=7.56 Hz), 2.55 (2H, q, J=7.56 Hz), 3.85 (2H, t, J=6.71 Hz), 4.18 (2H, t, J=7.19 Hz), 4.78-4.88 (1H, m), 6.64-6.71 (1H, m), 6.96 (1H, br s), 7.25-7.31 (2H, m), 9.13 (1H, d, J=7.56 Hz), 13.29 (1H, br s).

mass spectrum (ESI): m/z 349, 351 (M+H)$^+$.

Example 224

2-(3-{[(4-Chloro-5-ethyl-1H-imidazol-2-yl)carbonyl]amino}azetidin-1-yl)-1,3-benzothiazole-7-carboxylic acid (Exemplified Compound No. 224)

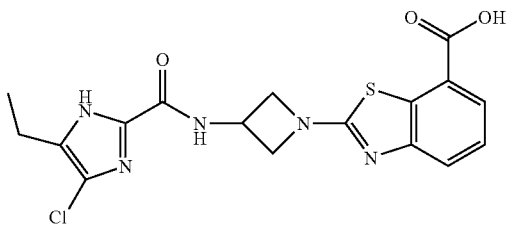

(224a) Ethyl 2-{3-[(tert-butoxycarbonyl)amino]azetidin-1-yl}-1,3-benzothiazole-7-carboxylate The same operation as in Example (217a) was performed using 3-tert-butoxycarbonylaminoazetidine (300 mg, 1.74 mmol), ethyl 2-bromo-1,3-benzothiazole-7-carboxylate obtained in Example (1f) (332 mg, 1.16 mmol) and diisopropylethylamine (0.40 mL, 2.32 mmol), to obtain 403 mg of the title compound as a pale yellow solid (92%).

$^1$H NMR spectrum (400 MHz, CDCl$_3$) δ ppm: 1.44 (3H, t, J=7.32 Hz), 1.46 (9H, s), 4.06 (2H, dd, J=8.67, 5.49 Hz), 4.45 (2H, q, J=7.16 Hz), 4.50-4.58 (2H, m), 4.76 (1H, br s), 5.06 (1H, br s), 7.36-7.43 (1H, m), 7.75-7.80 (1H, m), 7.81-7.85 (1H, m).

mass spectrum (ESI): m/z 378 (M+H)$^+$.

(224b) Ethyl 2-(3-aminoazetidin-1-yl)-1,3-benzothiazole-7-carboxylate

A 4 N hydrochloric acid/ethyl acetate solution (2.66 mL, 10.7 mmol) and methanol (5 mL) were added to a solution of ethyl 2-{3-[(tert-butoxycarbonyl)amino]azetidin-1-yl}-1,3-benzothiazole-7-carboxylate obtained in Example (224a) (402 mg, 1.07 mmol) in 1,4-dioxane (11 mL) at room temperature, followed by stirring for 17 hours. Then, THF (5 mL) was added, and the mixture was further stirred for 31 hours. The reaction solution was concentrated, and saturated aqueous sodium bicarbonate solution was added to the resulting residue. Thereafter, the mixture was extracted with ethyl acetate, and the combined organic layers were dried over anhydrous magnesium sulfate. Following filtration, the solvent was evaporated under reduced pressure to obtain 281 mg of the title compound as a pale yellow solid (95%).

$^1$H NMR spectrum (400 MHz, CDCl$_3$) δ ppm: 1.44 (3H, t, J=7.08 Hz), 3.91 (2H, dd, J=9.28, 5.37 Hz), 4.07-4.14 (1H, m), 4.41-4.50 (4H, m), 7.35-7.41 (1H, m), 7.73-7.78 (1H, m), 7.79-7.83 (1H, m).

mass spectrum (ESI): m/z 278 (M+H)$^+$.

(224c) Ethyl 2-(3-{[(4-chloro-5-ethyl-1H-imidazol-2-yl)carbonyl]amino}azetidin-1-yl)-1,3-benzothiazole-7-carboxylate The same operation as in Example (217c) was performed using ethyl 2-(3-aminoazetidin-1-yl)-1,3-benzothiazole-7-carboxylate obtained in Example (224b) (273 mg, 0.98 mmol), 4-chloro-5-ethyl-1H-imidazole-2-carboxylic acid obtained in Example (1d) (166 mg, 0.95 mmol), WSC hydrochloride (547 mg, 2.85 mmol), 1-hydroxybenzotriazole (128 mg, 0.95 mmol) and N-methylmorpholine (0.21 mL, 1.90 mmol), to obtain 352 mg of the title compound as a pale yellow solid (85%).

$^1$H NMR spectrum (400 MHz, CDCl$_3$) δ ppm: 1.27 (3H, t, J=7.57 Hz), 1.44 (3H, t, J=7.08 Hz), 2.71 (2H, q, J=7.57 Hz), 4.21 (2H, dd, J=8.79, 5.37 Hz), 4.45 (2H, q, J=7.08 Hz), 4.55-4.64 (2H, m), 5.02-5.12 (1H, m), 7.38-7.45 (1H, m), 7.76-7.86 (3H, m), 11.40-11.67 (1H, m).

mass spectrum (ESI): m/z 434, 436 (M+H)$^+$.

(224d) 2-(3-{[(4-Chloro-5-ethyl-1H-imidazol-2-yl)carbonyl]amino}azetidin-1-yl)-1,3-benzothiazole-7-carboxylic acid Ethyl 2-(3-{[(4-chloro-5-ethyl-1H-imidazol-2-yl)carbonyl]amino}azetidin-1-yl)-1,3-benzothiazole-7-carboxylate obtained in Example (224c) (350 mg, 0.81 mmol) was dissolved in methanol (8 mL). A 2 N aqueous lithium hydroxide solution (4.03 mL, 8.07 mmol) was added, and the mixture was stirred at room temperature for 18 hours. Water was added to the reaction solution, and then the mixture was washed with ethyl acetate. A 1 N aqueous hydrochloric acid solution (8 mL) was added to the aqueous layer, and then the solvent was evaporated under reduced pressure. The resulting residue was suspended and washed in methanol. Following filtration, the resulting solid was washed with water to obtain 191 mg of the title compound as a white solid (58%).

$^1$H NMR spectrum (400 MHz, CD$_3$OD) δ ppm: 1.21 (3H, t, J=7.57 Hz), 2.65 (2H, q, J=7.57 Hz), 4.57-4.64 (2H, m), 4.80-4.91 (2H, m), 5.05-5.14 (1H, m), 7.66-7.75 (2H, m), 8.04 (1H, dd, J=7.32, 1.22 Hz).

mass spectrum (ESI): m/z 406, 408 (M+H)⁺.

Example 225

2-(3-{[(4-Chloro-5-ethyl-1H-imidazol-2-yl)carbonyl]amino}azetidin-1-yl)-1,3-benzothiazole-6-carboxylic acid (Exemplified Compound No. 225)

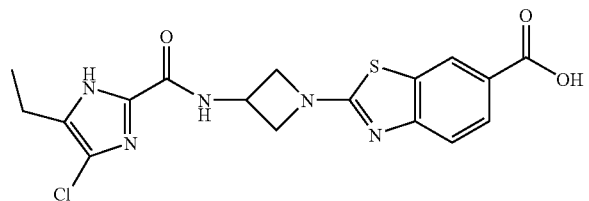

(225a) Ethyl 2-bromo-1,3-benzothiazole-6-carboxylate

The compound was synthesized according to the method described in the following document.

WO 2004/63155 A1

(225b) Ethyl 2-{3-[(tert-butoxycarbonyl)amino]azetidin-1-yl)-1,3-benzothiazole-6-carboxylate The same operation as in Example (221a) was performed using 3-tert-butoxycarbonylaminoazetidine (199 mg, 1.15 mmol), ethyl 2-bromo-1,3-benzothiazole-6-carboxylate obtained in Example (225a) (300 mg, 1.05 mmol) and diisopropylethylamine (0.37 mL, 2.10 mmol), to obtain 297 mg of the title compound as a milk white solid (75%).

¹H NMR spectrum (400 MHz, CDCl₃) δ ppm: 1.40 (3H, t, J=7.07 Hz), 1.46 (9H, s), 4.07 (2H, dd, J=9.02, 5.37 Hz), 4.37 (2H, q, J=7.07 Hz), 4.50-4.58 (2H, m), 4.74 (1H, br s), 5.05 (1H, br s), 7.57 (1H, d, J=8.54 Hz), 8.01 (1H, dd, J=8.54, 1.71 Hz), 8.32 (1H, d, J=1.71 Hz).

mass spectrum (ESI): m/z 378 (M+H)⁺.

(225c) Ethyl 2-(3-aminoazetidin-1-yl)-1,3-benzothiazole-6-carboxylate

85% phosphoric acid (0.23 mL, 1.96 mmol) was added to a solution of ethyl 2-{3-[(tert-butoxycarbonyl)amino]azetidin-1-yl)-1,3-benzothiazole-6-carboxylate obtained in Example (225b) (296 mg, 0.78 mmol) in dichloromethane (2 mL) at room temperature, followed by stirring for 27 hours. Then, THF (1 mL) and 85% phosphoric acid (0.23 mL, 1.96 mmol) were added, and the mixture was further stirred for five hours. Water was added to the reaction solution, and the mixture was washed with ethyl acetate. Then, a 1 N aqueous sodium hydroxide solution was added to the aqueous layer, followed by extraction with a chloroform/methanol mixed solvent. The combined organic layers were dried over anhydrous magnesium sulfate and filtered. Thereafter, the solvent was evaporated under reduced pressure to obtain 190 mg of the title compound as a milk white solid (87%).

mass spectrum (ESI): m/z 278 (M+H)⁺.

(225d) Ethyl 2-(3-{[(4-chloro-5-ethyl-1H-imidazol-2-yl)carbonyl]amino}azetidin-1-yl)-1,3-benzothiazole-6-carboxylate The same operation as in Example (221c) was performed using ethyl 2-(3-aminoazetidin-1-yl)-1,3-benzothiazole-6-carboxylate obtained in Example (225c) (190 mg, 0.69 mmol), 4-chloro-5-ethyl-1H-imidazole-2-carboxylic acid obtained in Example (1d) (132 mg, 0.75 mmol), WSC hydrochloride (394 mg, 2.06 mmol), 1-hydroxybenzotriazole (102 mg, 0.75 mmol) and N-methylmorpholine (0.15 mL, 1.37 mmol), to obtain 126 mg of the title compound as a milk white solid (42%).

¹H NMR spectrum (400 MHz, CDCl₃) δ ppm: 1.27 (3H, t, J=7.56 Hz), 1.40 (3H, t, J=7.07 Hz), 2.70 (2H, q, J=7.56 Hz), 4.22 (2H, dd, J=9.15, 5.49 Hz), 4.38 (2H, q, J=7.07 Hz), 4.54-4.63 (2H, m), 5.02-5.12 (1H, m), 7.59 (1H, d, J=8.54 Hz), 7.82 (1H, d, J=7.56 Hz), 8.03 (1H, dd, J=8.54, 1.71 Hz), 8.34 (1H, d, J=1.71 Hz), 11.19 (1H, br s).

mass spectrum (ESI): m/z 434, 436 (M+H)⁺.

(225e) 2-(3-{[(4-Chloro-5-ethyl-1H-imidazol-2-yl)carbonyl]amino}azetidin-1-yl)-1,3-benzothiazole-7-carboxylic acid Ethyl 2-(3-{[(4-chloro-5-ethyl-1H-imidazol-2-yl)carbonyl]amino}azetidin-1-yl)-1,3-benzothiazole-6-carboxylate obtained in Example (225d) (124 mg, 0.29 mmol) was dissolved in methanol (3 mL). A 2 N aqueous lithium hydroxide solution (1.43 mL, 2.86 mmol) was added, and the mixture was stirred at room temperature for 50 minutes. THF (1.5 mL) was added, followed by further stirring for three hours. Water was added to the reaction solution, and then the mixture was washed with ethyl acetate. A 1 N aqueous hydrochloric acid solution (2.5 mL) was added to the aqueous layer, followed by extraction with ethyl acetate. The combined organic layers were dried over anhydrous magnesium sulfate and then filtered, and the filtrate was concentrated under reduced pressure. The resulting solid was suspended and washed in diethyl ether to obtain 96 mg of the title compound as a white solid (83%).

¹H NMR spectrum (400 MHz, DMSO-d₆) δ ppm: 1.14 (3H, t, J=7.56 Hz), 2.56 (2H, q, J=7.56 Hz), 4.24 (2H, dd, J 5.85, 8.05 Hz), 4.40-4.47 (2H, m), 4.92-5.01 (1H, m), 7.44-7.50 (1H, m), 7.85 (1H, d, J=8.54 Hz), 8.33-8.37 (1H, m), 9.31-9.36 (1H, m).

mass spectrum (ESI): m/z 406, 408 (M+H)⁺.

Example 226

2-(3-{[(4-Chloro-5-ethyl-1H-imidazol-2-yl)carbonyl](methyl)amino}azetidin-1-yl)-4-methyl-1,3-thiazole-5-carboxylic acid (Exemplified Compound No. 226)

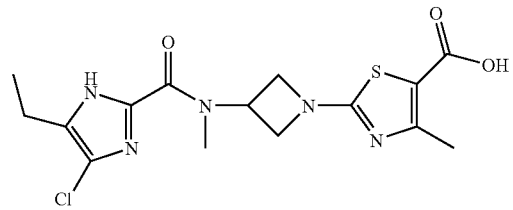

(226a) Ethyl 2-{3-[(tert-butoxycarbonyl)(methyl)amino]azetidin-1-yl}-4-methyl-1,3-thiazole-5-carboxylate The same operation as in Example (217a) was performed using 3-[(tert-butoxycarbonyl)(methyl)amino]azetidine (1.31 g, 7.03 mmol), ethyl 2-bromo-4-methylthiazole-5-carboxylate (134 mg, 0.54 mmol) and diisopropylethylamine (0.19 mL, 1.07 mmol), to obtain 136 mg of the title compound as a colorless oily substance (72%).

¹H NMR spectrum (400 MHz, CDCl₃) δ ppm: 1.33 (3H, t, J=7.08 Hz), 1.47 (9H, s), 2.56 (3H, s), 2.95 (3H, s), 4.13-4.19 (2H, m), 4.23-4.33 (4H, m), 5.16 (1H, br s).

mass spectrum (ESI): m/z 356 (M+H)⁺.

(226b) Ethyl 4-methyl-2-[3-(methylamino)azetidin-1-yl]-1,3-thiazole-5-carboxylate The same operation as in Example (222b) was performed using ethyl 2-{3-[(tert-butoxycarbonyl)(methyl)amino]azetidin-1-yl}-4-methyl-1,3-thiazole-5-carboxylate obtained in Example (226a) (170 mg, 0.48 mmol) and a 4 N hydrochloric acid/ethyl acetate solution (1.20 mL, 4.78 mmol), to obtain 116 mg of the title compound as a pale yellow oily substance (95%).

$^1$H NMR spectrum (400 MHz, CDCl$_3$) δ ppm: 1.32 (3H, t, J=7.32 Hz), 2.44 (3H, s), 2.56 (3H, s), 3.76-3.87 (3H, m), 4.22-4.31 (4H, m).

mass spectrum (ESI): m/z 256 (M+H)$^+$.

(226c) Ethyl 2-(3-{[(4-chloro-5-ethyl-1H-imidazol-2-yl)carbonyl](methyl)amino}azetidin-1-yl)-4-methyl-1,3-thiazole-5-carboxylate The same operation as in Example (217c) was performed using ethyl 4-methyl-2-[3-(methylamino)azetidin-1-yl]-1,3-thiazole-5-carboxylate obtained in Example (226b) (114 mg, 0.45 mmol), 4-chloro-5-ethyl-1H-imidazole-2-carboxylic acid obtained in Example (1d) (78 mg, 0.45 mmol), WSC hydrochloride (256 mg, 1.34 mmol), 1-hydroxybenzotriazole (60 mg, 0.45 mmol) and N-methylmorpholine (0.10 mL, 0.89 mmol), to obtain 167 mg of the title compound as a white solid (91%).

$^1$H NMR spectrum (400 MHz, CDCl$_3$) δ ppm: 1.24 (3H, t, J=7.57 Hz), 1.33 (3H, t, J=7.08 Hz), 2.58 (3H, s), 2.68 (2H, q, J=7.57 Hz), 3.26 (1.8H, s), 3.74 (1.2H, s), 4.22-4.30 (4H, m), 4.34-4.42 (0.8H, m), 4.46-4.55 (1.2H, m), 5.48-5.58 (0.4H, m), 6.91-7.01 (0.6H, m), 11.05 (0.4H, br s), 11.29 (0.6H, br s).

mass spectrum (ESI): m/z 412, 414 (M+H)$^+$.

(226d) 2-(3-{[(4-Chloro-5-ethyl-1H-imidazol-2-yl)carbonyl](methyl)amino}azetidin-1-yl)-4-methyl-1,3-thiazole-5-carboxylic acid The same operation as in Example (217d) was performed using ethyl 2-(3-{[(4-chloro-5-ethyl-1H-imidazol-2-yl)carbonyl](methyl)amino}azetidin-1-yl)-4-methyl-1,3-thiazole-5-carboxylate obtained in Example (226c) (162 mg, 0.39 mmol) and a 2 N aqueous lithium hydroxide solution (1.97 mL, 3.93 mmol), to obtain 90 mg of the title compound as a white solid (60%).

$^1$H NMR spectrum (400 MHz, DMSO-d$_6$) δ ppm: 1.14 (3H, t, J=7.57 Hz), 2.43 (3H, s), 2.56 (2H, q, J=7.57 Hz), 3.12 (1.5H, br s), 3.55 (1.5H, br s), 4.21-4.37 (4H, m), 5.31 (0.5H, br s), 6.46 (0.5H, br s), 12.50 (1H, br s), 13.21 (1H, br s).

mass spectrum (ESI): m/z 384, 386 (M+H)$^+$.

Example 227

2-(3-{[(4-Chloro-5-ethyl-1H-imidazol-2-yl)carbonyl](n-propyl)amino}azetidin-1-yl)-4-methyl-1,3-thiazole-5-carboxylic acid (Exemplified Compound No. 227)

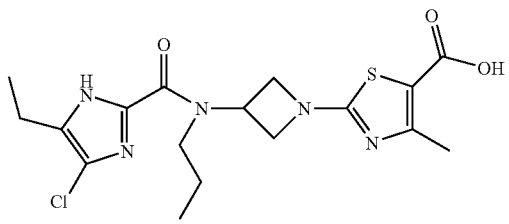

(227a) Benzyl 3-[(tert-butoxycarbonyl)amino]azetidine-1-carboxylate

Benzyl chloroformate (0.40 mL, 2.79 mmol) and triethylamine (0.65 mL, 4.64 mmol) were added to a solution of 3-[(tert-butoxycarbonyl)amino]azetidine (400 mg, 2.32 mmol) in dichloromethane (23 mL) at room temperature, followed by stirring for 40 minutes. The reaction solution was concentrated under reduced pressure, and then the resulting residue was purified by silica gel column chromatography (elution solvent: hexane/ethyl acetate=5/1) to obtain 481 mg of the title compound as a white solid (68%).

$^1$H NMR spectrum (400 MHz, CDCl$_3$) δ ppm: 1.44 (9H, s), 3.81 (2H, dd, J=9.39, 5.24 Hz), 4.25-4.33 (2H, m), 4.45 (1H, br s), 4.94 (1H, br s), 5.09 (2H, s), 7.28-7.33 (5H, m).

mass spectrum (ESI): m/z 329 (M+Na)$^+$.

(227b) Benzyl 3-[(tert-butoxycarbonyl)(n-propyl)amino]azetidine-1-carboxylate

A solution of benzyl 3-[(tert-butoxycarbonyl)amino]azetidine-1-carboxylate obtained in Example (227a) (472 mg, 1.54 mmol) in THF (5 mL) was added to a suspension of sodium hydride (55%) (134 mg, 3.08 mmol) in THF (10 mL) at 0° C. Subsequently, propyl iodide (0.75 mL, 7.70 mmol) was added at 0° C., and the mixture was stirred at room temperature for 70 minutes. THF (4 mL) and DMF (5 mL) were added, followed by further stirring for 18 hours. Water was added to the reaction solution, and the mixture was extracted with ethyl acetate. Thereafter, the combined organic layers were washed with brine and dried over anhydrous magnesium sulfate. Following filtration, the filtrate was concentrated under reduced pressure. The resulting residue was purified by silica gel column chromatography (elution solvent: hexane/ethyl acetate=2/1) to obtain 499 mg of the title compound as a colorless oily substance (93%).

$^1$H NMR spectrum (400 MHz, CDCl$_3$) δ ppm: 0.87 (3H, t, J=7.32 Hz), 1.45 (9H, s), 1.47-1.56 (2H, m), 3.19 (2H, t, J=7.56 Hz), 4.07-4.24 (4H, m), 4.33-4.64 (1H, m), 5.10 (2H, s), 7.30-7.39 (5H, m).

mass spectrum (ESI): m/z 371 (M+Na)$^+$.

(227c) Ethyl 2-{3-[(tert-butoxycarbonyl)(n-propyl)amino]azetidin-1-yl}-4-methyl-1,3-thiazole-5-carboxylate 10% Pd/C (50 mg) was added to a solution of benzyl 3-[(tert-butoxycarbonyl)(n-propyl)amino]azetidine-1-carboxylate obtained in Example (227b) (494 mg, 1.42 mmol) in methanol (7 mL), and the mixture was stirred in a hydrogen stream for three hours. The reaction solution was filtered, and then the filtrate was concentrated under reduced pressure to obtain an oily substance.

The same operation as in Example (217a) was performed using the oily substance obtained by the above operation, ethyl 2-bromo-4-methylthiazole-5-carboxylate (355 mg, 1.42 mmol) and diisopropylethylamine (0.50 mL, 2.84 mmol), to obtain 510 mg of the title compound as a pale yellow oily substance (94%).

$^1$H NMR spectrum (400 MHz, CDCl$_3$) δ ppm: 0.89 (3H, t, J=7.44 Hz), 1.33 (3H, t, J=7.07 Hz), 1.45 (9H, s), 1.49-1.58 (2H, m), 2.56 (3H, s), 3.23 (2H, t, J=7.56 Hz), 4.18-4.32 (6H, m), 4.71 (1H, br s).

mass spectrum (ESI): m/z 384 (M+H)$^+$.

(227d) Ethyl 2-(3-{[(4-chloro-5-ethyl-1H-imidazol-2-yl)carbonyl](n-propyl)amino}azetidin-1-yl)-4-methyl-1,3-thiazole-5-carboxylate The same operation as in Example (220d) was performed to obtain an oily substance from ethyl 2-{3-[(tert-butoxycarbonyl)(n-propyl)amino]azetidin-1-yl}-4-methyl-1,3-thiazole-5-carboxylate obtained in Example (227c) (505 mg, 1.32 mmol) and a 4 N hydrochloric acid/ethyl acetate solution (3.29 mL, 13.2 mmol). 313 mg of the title compound was obtained as a colorless oily substance (54%) using this oily substance, 4-chloro-5-ethyl-1H-imidazole-2-carboxylic acid obtained in Example (1d) (230 mg, 1.32 mmol), WSC hydrochloride (759 mg, 3.96 mmol), 1-hydroxybenzotriazole (178 mg, 1.32 mmol) and N-methylmorpholine (0.29 mL, 2.64 mmol).

¹H NMR spectrum (400 MHz, CDCl₃) δ ppm: 0.89-1.01 (3H, m), 1.23 (3H, t, J=7.68 Hz), 1.33 (3H, t, J=7.07 Hz), 1.59-1.79 (2H, m), 2.58 (3H, s), 2.67 (2H, q, J=7.56 Hz), 3.57-3.66 (1H, m), 4.17-4.34 (5H, m), 4.36-4.44 (1H, m), 4.48-4.56 (1H, m), 4.97 (0.5H, br s), 6.72 (0.5H, br s), 10.59 (0.5H, br s), 10.96 (0.5H, br s).

mass spectrum (ESI): m/z 440, 442 (M+H)⁺.

(227e) 2-(3-{[(4-Chloro-5-ethyl-1H-imidazol-2-yl)carbonyl](n-propyl)amino}azetidin-1-yl)-4-methyl-1,3-thiazole-5-carboxylic acid A 2 N aqueous lithium hydroxide solution (1.30 mL, 2.59 mmol) was added to a mixed solution of ethyl 2-(3-{[(4-chloro-5-ethyl-1H-imidazol-2-yl)carbonyl](n-propyl) amino}azetidin-1-yl)-4-methyl-1,3-thiazole-5-carboxylate obtained in Example (227d) (114 mg, 0.26 mmol) in methanol/THF (3 mL/0.5 mL), and the mixture was stirred at room temperature for 16 hours. Water was added to the reaction solution, and then the mixture was washed with ethyl acetate. A 1 N aqueous hydrochloric acid solution (4.5 mL) was added to the aqueous layer, followed by extraction with ethyl acetate. The combined organic layers were dried over anhydrous magnesium sulfate and then filtered, and the filtrate was concentrated under reduced pressure. The resulting solid was suspended and washed in diethyl ether to obtain 58 mg of the title compound as a white solid (54%).

¹H NMR spectrum (400 MHz, DMSO-d₆) δ ppm: 0.76-0.94 (3H, m), 1.10-1.17 (3H, m), 1.56 (2H, br s), 2.41-2.44 (3H, m), 2.55 (2H, q, J=7.56 Hz), 3.45-3.61 (1H, m), 3.96-4.39 (5H, m), 4.77 (1H, br s), 13.20 (1H, br s).

mass spectrum (ESI): m/z 412, 414 (M+H)⁺.

Example 228

2-(3-{[(4-Chloro-5-ethyl-1H-imidazol-2-yl)carbonyl](n-propyl)amino}azetidin-1-yl)-4-ethyl-1,3-thiazole-5-carboxylic acid (Exemplified Compound No. 228)

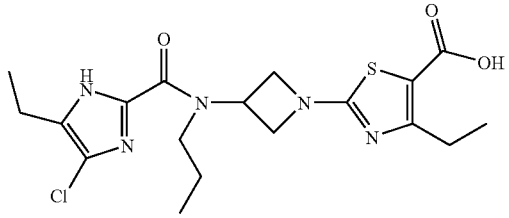

(228a) Methyl 2-{3-[(tert-butoxycarbonyl)(n-propyl)amino]azetidin-1-yl}-4-ethyl-1,3-thiazole-5-carboxylate The same operation as in Example (227c) was performed to obtain an oily substance from benzyl 3-[(tert-butoxycarbonyl)(n-propyl)amino]azetidine-1-carboxylate obtained in Example (227b) (150 mg, 0.43 mmol) and 10% Pd/C (15 mg). 118 mg of the title compound was obtained as a yellow oily substance (72%) using this oily substance, methyl 2-bromo-4-ethyl-1,3-thiazole-5-carboxylate obtained in Example (22c) (108 mg, 0.43 mmol) and diisopropylethylamine (0.15 mL, 0.86 mmol).

¹H NMR spectrum (400 MHz, CDCl₃) δ ppm: 0.89 (3H, t, J=7.32 Hz), 1.22 (3H, t, J=7.44 Hz), 1.45 (9H, s), 1.44-1.58 (2H, m), 2.93-3.04 (2H, m), 3.24 (2H, t, J=7.44 Hz), 3.79 (3H, s), 4.24-4.28 (4H, m), 4.55-4.87 (1H, m).

mass spectrum (ESI): m/z 384 (M+H)⁺.

(228b) Methyl 4-ethyl-2-[3-(n-propylamino)azetidin-1-yl]-1,3-thiazole-5-carboxylate The same operation as in Example (222b) was performed using methyl 2-{3-[(tert-butoxycarbonyl)(n-propyl)amino] azetidin-1-yl}-4-ethyl-1,3-thiazole-5-carboxylate obtained in Example (228a) (110 mg, 0.29 mmol) and a 4 N hydrochloric acid/ethyl acetate solution (0.72 mL, 2.87 mmol), to obtain 74 mg of the title compound as a pale yellow oily substance (91%).

mass spectrum (ESI): m/z 284 (M+H)⁺.

(228c) Methyl 2-(3-{[(4-chloro-5-ethyl-1H-imidazol-2-yl)carbonyl](n-propyl)amino}azetidin-1-yl)-4-ethyl-1,3-thiazole-5-carboxylate The same operation as in Example (221c) was performed using methyl 4-ethyl-2-[3-(n-propylamino)azetidin-1-yl]-1,3-thiazole-5-carboxylate obtained in Example (228b) (74 mg, 0.26 mmol), 4-chloro-5-ethyl-1H-imidazole-2-carboxylic acid obtained in Example (1d) (46 mg, 0.26 mmol), WSC hydrochloride (150 mg, 0.78 mmol), 1-hydroxybenzotriazole (35 mg, 0.26 mmol) and N-methylmorpholine (0.06 mL, 0.52 mmol), to obtain 75 mg of the title compound as a colorless oily substance (65%).

¹H NMR spectrum (400 MHz, CDCl₃) δ ppm: 0.89-1.02 (3H, m), 1.20-1.28 (6H, m), 1.59-1.79 (2H, m), 2.67 (2H, q, J=7.64 Hz), 3.00 (2H, q, J=7.56 Hz), 3.59-3.66 (1H, m), 3.80 (3H, s), 4.16-4.56 (5H, m), 4.95 (0.5H, br s), 6.73 (0.5H, br s), 10.40 (0.5H, br s), 10.67 (0.5H, br s).

mass spectrum (ESI): m/z 440, 442 (M+H)⁺.

(228d) 2-(3-{[(4-Chloro-5-ethyl-1H-imidazol-2-yl)carbonyl](n-propyl)amino}azetidin-1-yl)-4-ethyl-1,3-thiazole-5-carboxylic acid The same operation as in Example (217d) was performed using methyl 2-(3-{[(4-chloro-5-ethyl-1H-imidazol-2-yl)carbonyl](n-propyl)amino}azetidin-1-yl)-4-ethyl-1,3-thiazole-5-carboxylate obtained in Example (228c) (73 mg, 0.17 mmol) and a 2 N aqueous lithium hydroxide solution (0.83 mL, 1.66 mmol), to obtain 38 mg of the title compound as a white solid (54%).

¹H NMR spectrum (400 MHz, CDCl₃) δ ppm: 0.90-1.03 (3H, m), 1.21-1.28 (6H, m), 1.59-1.79 (2H, m), 2.68 (2H, q, J=7.56 Hz), 3.01 (2H, q, J=7.32 Hz), 3.57-3.67 (1H, m), 4.19-4.30 (2H, m), 4.36-4.47 (2H, m), 4.50-4.58 (1H, m), 4.83 (0.5H, br s), 6.74 (0.5H, br s), 11.52 (0.5H, br s), 11.72 (0.5H, br s).

mass spectrum (ESI): m/z 412, 414 (M+H)⁺.

Example 229

2-(3-{[(4-Chloro-5-ethyl-1H-imidazol-2-yl)carbonyl](n-propyl)amino}azetidin-1-yl)-4-isopropyl-1,3-thiazole-5-carboxylic acid (Exemplified Compound No. 229)

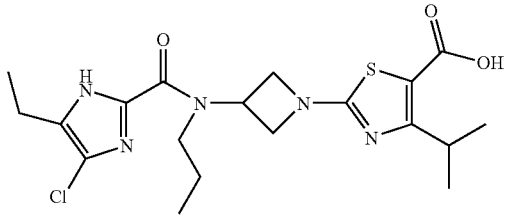

(229a) Ethyl 2-{3-[(tert-butoxycarbonyl)(n-propyl)amino]azetidin-1-yl}-4-isopropyl-1,3-thiazole-5-carboxylate The same operation as in Example (227c) was performed to obtain an oily substance from benzyl 3-[(tert-butoxycarbonyl)(n-propyl)amino]azetidine-1-carboxylate obtained in Example (227b) (154 mg, 0.44 mmol) and 10% Pd/C (15 mg). 133 mg of the title compound was obtained as a pale yellow oily substance (73%) using this oily substance, ethyl 2-bromo-4-isopropyl-1,3-thiazole-5-carboxylate obtained in Example (23b) (123 mg, 0.44 mmol) and diisopropylethylamine (0.15 mL, 0.88 mmol).

$^1$H NMR spectrum (400 MHz, CDCl$_3$) δ ppm: 0.89 (3H, t, J=7.32 Hz), 1.22 (6H, d, J=6.83 Hz), 1.32 (3H, t, J=7.32 Hz), 1.45 (9H, s), 1.49-1.61 (2H, m), 3.25 (2H, t, J=7.44 Hz), 3.81-3.92 (1H, m), 4.16-4.31 (6H, m), 4.69 (1H, br s).

mass spectrum (ESI): m/z 412 (M+H)$^+$.

(229b) Ethyl 4-isopropyl-2-[3-(n-propylamino)azetidin-1-yl]-1,3-thiazole-5-carboxylate The same operation as in Example (222b) was performed using ethyl 2-{3-[(tert-butoxycarbonyl)(n-propyl)amino]azetidin-1-yl}-4-isopropyl-1,3-thiazole-5-carboxylate obtained in Example (229a) (130 mg, 0.32 mmol) and a 4 N hydrochloric acid/ethyl acetate solution (0.79 mL, 3.16 mmol), to obtain 91 mg of the title compound as a pale yellow oily substance (93%).

mass spectrum (ESI): m/z 312 (M+H)$^+$.

(229c) Ethyl 2-(3-{[(4-chloro-5-ethyl-1H-imidazol-2-yl)carbonyl](n-propyl)amino}azetidin-1-yl)-4-isopropyl-1,3-thiazole-5-carboxylate The same operation as in Example (221c) was performed using ethyl 4-isopropyl-2-[3-(n-propylamino)azetidin-1-yl]-1,3-thiazole-5-carboxylate obtained in Example (229b) (91 mg, 0.29 mmol), 4-chloro-5-ethyl-1H-imidazole-2-carboxylic acid obtained in Example (1d) (51 mg, 0.29 mmol), WSC hydrochloride (168 mg, 0.88 mmol), 1-hydroxybenzotriazole (39 mg, 0.29 mmol) and N-methylmorpholine (0.06 mL, 0.58 mmol), to obtain 83 mg of the title compound as a colorless oily substance (61%).

$^1$H NMR spectrum (400 MHz, CDCl$_3$) δ ppm: 0.90-1.04 (3H, m), 1.21-1.27 (9H, m), 1.33 (3H, t, J=7.19 Hz), 1.58-1.80 (2H, m), 2.67 (2H, q, J=7.64 Hz), 3.64 (1H, br s), 3.83-3.93 (1H, m), 4.16-4.31 (5H, m), 4.35-4.56 (2H, m), 4.97 (0.5H, br s), 6.72 (0.5H, br s), 10.62 (0.5H, br s), 10.91 (0.5H, br s).

mass spectrum (ESI): m/z 468, 470 (M+H)$^+$.

(229d) 2-(3-{[(4-Chloro-5-ethyl-1H-imidazol-2-yl)carbonyl](n-propyl)amino}azetidin-1-yl)-4-isopropyl-1,3-thiazole-5-carboxylic acid The same operation as in Example (217d) was performed using ethyl 2-(3-{[(4-chloro-5-ethyl-1H-imidazol-2-yl)carbonyl](n-propyl)amino}azetidin-1-yl)-4-isopropyl-1,3-thiazole-5-carboxylate obtained in Example (229c) (79 mg, 0.17 mmol) and a 2 N aqueous lithium hydroxide solution (0.84 mL, 1.69 mmol), to obtain 61 mg of the title compound as an amorphous compound (82%).

$^1$H NMR spectrum (400 MHz, CDCl$_3$) δ ppm: 0.89-1.04 (3H, m), 1.19-1.30 (9H, m), 1.59-1.80 (2H, m), 2.68 (2H, q, J=7.64 Hz), 3.63 (1H, br s), 3.84-3.94 (1H, m), 4.18-4.58 (5H, m), 4.87 (0.5H, br s), 6.74 (0.5H, br s), 11.50 (0.5H, br s), 11.70 (0.5H, br s).

mass spectrum (ESI): m/z 440, 442 (M+H)$^+$.

Example 230

2-(3-{(n-Butyl)[(4-chloro-5-ethyl-1H-imidazol-2-yl)carbonyl]amino}azetidin-1-yl)-4-methyl-1,3-thiazole-5-carboxylic acid (Exemplified Compound No. 230)

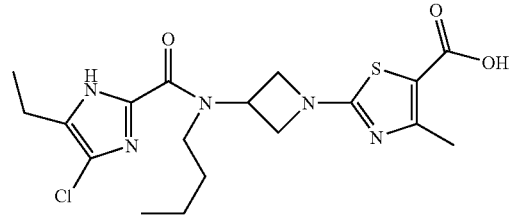

(230a) Benzyl 3-[(tert-butoxycarbonyl)(n-butyl)amino]azetidine-1-carboxylate

A solution of benzyl 3-[(tert-butoxycarbonyl)amino]azetidine-1-carboxylate obtained in Example (227a) (500 mg, 1.63 mmol) in THF (6 mL) was added to a suspension of sodium hydride (55%) (142 mg, 3.26 mmol) in THF (10 mL) at 0° C. Subsequently, butyl iodide (0.93 mL, 8.15 mmol) was added at 0° C., and the mixture was stirred at room temperature for 19 hours. DMF (2 mL) was added, followed by stirring for four hours. Then, sodium hydride (55%) (36 mg, 0.82 mmol) and butyl iodide (0.37 mL, 3.26 mmol) were added, followed by stirring for 2.5 hours. Water was added to the reaction solution, and the mixture was extracted with ethyl acetate. Thereafter, the combined organic layers were washed with brine and dried over anhydrous magnesium sulfate. Following filtration, the filtrate was concentrated under reduced pressure. The resulting residue was purified by silica gel column chromatography (elution solvent: hexane/ethyl acetate=2/1) to obtain 288 mg of the title compound as a colorless oily substance (49%).

$^1$H NMR spectrum (400 MHz, CDCl$_3$) δ ppm: 0.92 (3H, t, J=7.07 Hz), 1.23-1.34 (2H, m), 1.45 (9H, s), 1.42-1.49 (2H, m), 3.22 (2H, t, J=7.44 Hz), 4.02-4.21 (4H, m), 4.50 (1H, br s), 5.10 (2H, s), 7.30-7.39 (5H, m).

mass spectrum (ESI): m/z 385 (M+Na)$^+$.

(230b) Ethyl 2-{3-[(tert-butoxycarbonyl)(n-butyl)amino]azetidin-1-yl}-4-methyl-1,3-thiazole-5-carboxylate The same operation as in Example (227c) was performed to obtain an oily substance from benzyl 3-[(tert-butoxycarbonyl)(n-butyl)amino]azetidine-1-carboxylate obtained in Example (230a) (142 mg, 0.39 mmol) and 10% Pd/C (14 mg). 145 mg of the title compound was obtained as a pale yellow oily substance (93%) using this oily substance, ethyl 2-bromo-4-methylthiazole-5-carboxylate (98 mg, 0.39 mmol) and diisopropylethylamine (0.14 mL, 0.78 mmol).

$^1$H NMR spectrum (400 MHz, CDCl$_3$) δ ppm: 0.93 (3H, t, J=7.32 Hz), 1.24-1.35 (5H, m), 1.45 (9H, s), 1.43-1.55 (2H, m), 2.56 (3H, s), 3.27 (2H, t, J=7.56 Hz), 4.18-4.31 (6H, m), 4.72 (1H, br s).

mass spectrum (ESI): m/z 398 (M+H)$^+$.

(230c) Ethyl 2-[3-(n-butylamino)azetidin-1-yl]-4-methyl-1,3-thiazole-5-carboxylate The same operation as in Example (222b) was performed using ethyl 2-{3-[(tert-butoxycarbonyl)(n-butyl)amino]azetidin-1-yl}-4-methyl-1,3-thiazole-5-carboxylate obtained in Example (230b) (140 mg, 0.35 mmol) and a 4 N hydrochloric acid/ethyl acetate solution (0.88 mL, 3.52 mmol), to obtain 98 mg of the title compound as a pale yellow oily substance (94%).

mass spectrum (ESI): m/z 298 (M+H)$^+$.

(230d) Ethyl 2-(3-{(n-butyl)[(4-chloro-5-ethyl-1H-imidazol-2-yl)carbonyl]amino}azetidin-1-yl)-4-methyl-1,3-thiazole-5-carboxylate The same operation as in Example (221c) was performed using ethyl 2-[3-(n-butylamino)azetidin-1-yl]-4-methyl-1,3-thiazole-5-carboxylate obtained in Example (230c) (98 mg, 0.33 mmol), 4-chloro-5-ethyl-1H-imidazole-2-carboxylic acid obtained in Example (1d) (58 mg, 0.33 mmol), WSC hydrochloride (190 mg, 0.99 mmol), 1-hydroxybenzotriazole (46 mg, 0.33 mmol) and N-methylmorpholine (0.07 mL, 0.66 mmol), to obtain 119 mg of the title compound as a white solid (79%).

$^1$H NMR spectrum (400 MHz, CDCl$_3$) δ ppm: 0.89-0.99 (3H, m), 1.23 (3H, t, J=7.56 Hz), 1.28-1.43 (5H, m), 1.55-1.72 (2H, m), 2.58 (3H, s), 2.66 (2H, q, J=7.64 Hz), 3.61-3.70 (1H, m), 4.17-4.34 (5H, m), 4.36-4.56 (2H, m), 4.96 (0.5H, br s), 6.72 (0.5H, br s), 10.65 (0.5H, br s), 11.00 (0.5H, br s).

mass spectrum (ESI): m/z 454, 456 (M+H)$^+$.

(230e) 2-(3-{(n-Butyl)[(4-chloro-5-ethyl-1H-imidazol-2-yl)carbonyl]amino}azetidin-1-yl)-4-methyl-1,3-thiazole-5-carboxylic acid The same operation as in Example (217d) was performed using ethyl 2-(3-{(n-butyl)[(4-chloro-5-ethyl-1H-imidazol-2-yl)carbonyl]amino}azetidin-1-yl)-4-methyl-1,3-thiazole-5-carboxylate obtained in Example (230d) (113 mg, 0.25 mmol) and a 2 N aqueous lithium hydroxide solution (1.24 mL, 2.49 mmol), to obtain 40 mg of the title compound as a white solid (38%).

$^1$H NMR spectrum (400 MHz, DMSO-d$_6$) δ ppm: 0.81-0.94 (3H, m), 1.14 (3H, t, J=7.56 Hz), 1.19-1.42 (2H, m), 1.52 (2H, br s), 2.43 (3H, s), 2.56 (2H, q, J=7.56 Hz), 3.58 (1H, br s), 4.04-4.39 (5H, m), 4.76 (1H, br s), 12.46 (1H, br s), 13.20 (1H, br s).

mass spectrum (ESI): m/z 426, 428 (M+H)$^+$.

Example 231

2-(3-{(n-Butyl)[(4-chloro-5-ethyl-1H-imidazol-2-yl)carbonyl]amino}azetidin-1-yl)-4-ethyl-1,3-thiazole-5-carboxylic acid (Exemplified Compound No. 231)

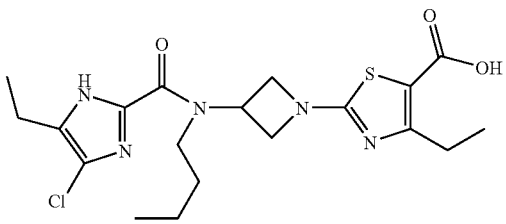

(231a) Methyl 2-{3-[(tert-butoxycarbonyl)(n-butyl)amino]azetidin-1-yl}-4-ethyl-1,3-thiazole-5-carboxylate The same operation as in Example (227c) was performed to obtain an oily substance from benzyl 3-[(tert-butoxycarbonyl)(n-butyl)amino]azetidine-1-carboxylate obtained in Example (230a) (140 mg, 0.39 mmol) and 10% Pd/C (14 mg). 127 mg of the title compound was obtained as a pale yellow oily substance (83%) using this oily substance, methyl 2-bromo-4-ethyl-1,3-thiazole-5-carboxylate obtained in Example (22c) (97 mg, 0.39 mmol) and diisopropylethylamine (0.13 mL, 0.77 mmol).

$^1$H NMR spectrum (400 MHz, CDCl$_3$) δ ppm: 0.93 (3H, t, J=7.32 Hz), 1.19-1.36 (5H, m), 1.45 (9H, s), 1.42-1.54 (2H, m), 2.99 (2H, t, J=7.32 Hz), 3.24-3.31 (2H, m), 3.79 (3H, s), 4.19-4.33 (4H, m), 4.70 (1H, brs).

mass spectrum (ESI): m/z 398 (M+H)$^+$.

(231b) Methyl 2-(3-{(n-butyl)[(4-chloro-5-ethyl-1H-imidazol-2-yl)carbonyl]amino}azetidin-1-yl)-4-ethyl-1,3-thiazole-5-carboxylate The same operation as in Example (222b) was performed using methyl 2-{3-[(tert-butoxycarbonyl)(n-butyl)amino]azetidin-1-yl}-4-ethyl-1,3-thiazole-5-carboxylate obtained in Example (231a) (123 mg, 0.31 mmol) and a 4 N hydrochloric acid/ethyl acetate solution (0.77 mL, 3.09 mmol), to obtain an oily substance.

The same operation as in Example (221c) was performed using the oily substance obtained by the above operation, 4-chloro-5-ethyl-1H-imidazole-2-carboxylic acid obtained in Example (1d) (54 mg, 0.31 mmol), WSC hydrochloride (178 mg, 0.93 mmol), 1-hydroxybenzotriazole (42 mg, 0.31 mmol) and N-methylmorpholine (0.07 mL, 0.62 mmol), to obtain 98 mg of the title compound as a colorless oily substance (70%).

$^1$H NMR spectrum (400 MHz, CDCl$_3$) δ ppm: 0.90-0.99 (3H, m), 1.21-1.27 (6H, m), 1.31-1.45 (2H, m), 1.54-1.73 (2H, m), 2.67 (2H, q, J=7.72 Hz), 3.00 (2H, q, J=7.56 Hz), 3.61-3.70 (1H, m), 3.80 (3H, s), 4.17-4.57 (5H, m), 4.94 (0.5H, br s), 6.74 (0.5H, br s), 10.39 (0.5H, br s), 10.62 (0.5H, br s).

mass spectrum (ESI): m/z 454, 456 (M+H)$^+$.

(231c) 2-(3-{(n-Butyl)[(4-chloro-5-ethyl-1H-imidazol-2-yl)carbonyl]amino}azetidin-1-yl)-4-ethyl-1,3-thiazole-5-carboxylic acid The same operation as in Example (217d) was performed using methyl 2-(3-{(n-butyl)[(4-chloro-5-ethyl-1H-imidazol-2-yl)carbonyl]amino}azetidin-1-yl)-4-ethyl-1,3-thiazole-5-carboxylate obtained in Example (231b) (94 mg, 0.21 mmol) and a 2 N aqueous lithium hydroxide solution (1.04 mL, 2.07 mmol), to obtain 64 mg of the title compound as a white solid (70%).

$^1$H NMR spectrum (400 MHz, CDCl$_3$) δ ppm: 0.91-1.00 (3H, m), 1.21-1.28 (6H, m), 1.31-1.46 (2H, m), 1.52-1.74 (2H, m), 2.67 (2H, q, J=7.64 Hz), 3.01 (2H, q, J=7.80 Hz), 3.65 (1H, br s), 4.19-4.58 (5H, m), 4.81 (0.5H, brs), 6.76 (0.5H, br s).

mass spectrum (ESI): m/z 440, 442 (M+H)$^+$.

Example 232

2-(3-{[(4-Chloro-5-ethyl-1H-imidazol-2-yl)carbonyl](2-methoxymethyl)amino}azetidin-1-yl)-4-methyl-1,3-thiazole-5-carboxylic acid (Exemplified Compound No. 232)

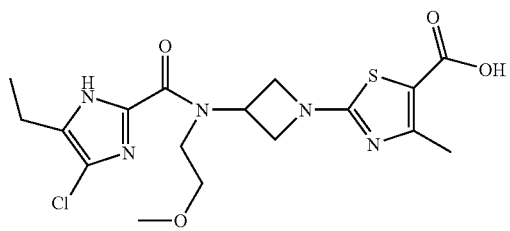

(232a) Benzyl 3-[(tert-butoxycarbonyl)(2-methoxymethyl)amino]azetidine-1-carboxylate A solution of benzyl 3-[(tert-butoxycarbonyl)amino]azetidine-1-carboxylate obtained in Example (227a) (708 mg, 2.31 mmol) in THF (8 mL) was added to a suspension of sodium hydride (55%) (202 mg, 4.62 mmol) in THF (15 mL) at room temperature, followed by stirring for 30 minutes. Then, 2-bromoethyl methyl ether (1.09 mL, 11.6 mmol) was added, and the mixture was stirred at 60° C. for 18 hours. Water was added to the reaction solution, and the mixture was extracted with ethyl acetate. Thereafter, the combined organic layers were washed with brine and dried over anhydrous magnesium sulfate. Following filtration, the filtrate was concentrated under reduced pressure. The resulting residue was purified by silica gel column chromatography (elution solvent: hexane/ethyl acetate=3/1) to obtain 255 mg of the title compound as a pale yellow oily substance (30%).

$^1$H NMR spectrum (400 MHz, CDCl$_3$) δ ppm: 1.45 (9H, s), 3.30 (3H, s), 3.39-3.47 (4H, m), 4.11-4.19 (4H, m), 5.09 (2H, s), 7.30-7.38 (5H, m).

(232b) 3-[(tert-Butoxycarbonyl)(2-methoxymethyl)amino]azetidine

10% Pd/C (25 mg) was added to a solution of benzyl 3-[(tert-butoxycarbonyl)(2-methoxymethyl)amino]azetidine-1-carboxylate obtained in Example (232a) (247 mg, 0.68 mmol) in methanol (4 mL), and the mixture was stirred in a hydrogen stream for two hours. The reaction solution was filtered, and then the filtrate was concentrated under reduced pressure to obtain 131 mg of the title compound as a colorless oily substance (84%).

mass spectrum (ESI): m/z 175 (M-tBu)$^+$.

(232c) Ethyl 2-{3-[(tert-butoxycarbonyl)(2-methoxyethyl)amino]azetidin-1-yl}-4-methyl-1,3-thiazole-5-carboxylate A solution of 3-[(tert-butoxycarbonyl)(2-methoxymethyl)amino]azetidine obtained in Example (232b) (131 mg, 0.57 mmol), ethyl 2-bromo-4-methylthiazole-5-carboxylate (142 mg, 0.57 mmol) and diisopropylethylamine (0.20 mL, 1.14 mmol) in DMF (6 mL) was stirred at 90° C. for 15.5 hours. The reaction solution was diluted with ethyl acetate, and then the mixture was washed with 5% saline and dried over anhydrous magnesium sulfate.

Following filtration, the solvent was evaporated under reduced pressure. The resulting residue was purified by silica gel column chromatography (elution solvent: hexane/ethyl acetate=2/1) to obtain 225 mg of the title compound as a pale yellow oily substance (99%).

$^1$H NMR spectrum (400 MHz, CDCl$_3$) δ ppm: 1.32 (3H, t, J=7.08 Hz), 1.45 (9H, s), 2.56 (3H, s), 3.31 (3H, s), 3.46 (4H, s), 4.21-4.31 (6H, m).

mass spectrum (ESI): m/z 400 (M+H)$^+$.

(232d) Ethyl 2-(3-{[(4-chloro-5-ethyl-1H-imidazol-2-yl)carbonyl](2-methoxymethyl)amino}azetidin-1-yl)-4-methyl-1,3-thiazole-5-carboxylate 85% phosphoric acid (0.31 mL, 2.72 mmol) was added to a solution of ethyl 2-{3-[(tert-butoxycarbonyl)(2-methoxyethyl)amino]azetidin-1-yl}-4-methyl-1,3-thiazole-5-carboxylate obtained in Example (232c) (217 mg, 0.54 mmol) in dichloromethane (1 mL) at room temperature, followed by stirring for two hours. Water was added to the reaction solution, and the mixture was washed with ethyl acetate. Then, a 1 N aqueous sodium hydroxide solution was added to the aqueous layer, followed by extraction with ethyl acetate. The combined organic layers were dried over anhydrous magnesium sulfate and filtered. Thereafter, the solvent was evaporated to obtain an oily substance.

The same operation as in Example (221c) was performed using the oily substance obtained by the above operation, 4-chloro-5-ethyl-1H-imidazole-2-carboxylic acid obtained in Example (1d) (101 mg, 0.58 mmol), WSC hydrochloride (277 mg, 1.44 mmol), 1-hydroxybenzotriazole (71 mg, 0.53 mmol) and N-methylmorpholine (0.11 mL, 0.96 mmol), to obtain 147 mg of the title compound as a pale yellow oily substance (67%).

$^1$H NMR spectrum (400 MHz, CDCl$_3$) δ ppm: 1.24 (3H, t, J=7.93 Hz), 1.33 (3H, t, J=7.07 Hz), 2.57 (3H, s), 2.67 (2H, q, J=7.40 Hz), 3.29 (3H, s), 3.56-3.68 (2H, m), 3.88 (1H, br s), 4.21-4.55 (7H, m), 4.92 (0.5H, br s), 6.79 (0.5H, br s), 10.39-10.66 (1H, m).

mass spectrum (ESI): m/z 456, 458 (M+H)$^+$.

(232e) 2-(3-{(n-Butyl)[(4-chloro-5-ethyl-1H-imidazol-2-yl)carbonyl](2-methoxymethyl)amino}azetidin-1-yl)-4-methyl-1,3-thiazole-5-carboxylic acid The same operation as in Example (217d) was performed using ethyl 2-(3-{[(4-chloro-5-ethyl-1H-imidazol-2-yl)carbonyl](2-methoxymethyl)amino}azetidin-1-yl)-4-methyl-1, 3-thiazole-5-carboxylate obtained in Example (232d) (145 mg, 0.32 mmol) and a 2 N aqueous lithium hydroxide solution (1.59 mL, 3.18 mmol), to obtain 94 mg of the title compound as a milk white solid (69%).

$^1$H NMR spectrum (400 MHz, DMSO-d$_6$) δ ppm: 1.14 (3H, t, J=7.32 Hz), 2.42 (3H, s), 2.55 (2H, q, J=7.32 Hz), 3.19 (3H, s), 3.42-3.61 (2H, m), 3.77 (1H, br s), 4.31 (5H, br s), 4.74 (0.6H, brs), 6.33 (0.4H, br s), 12.46 (1H, brs), 13.22 (1H, br s).

mass spectrum (ESI): m/z 428, 430 (M+H)$^+$.

Example 233

2-[3-({[(4-Chloro-5-ethyl-1H-imidazol-2-yl)carbonyl]amino}methyl)azetidin-1-yl]-4-methyl-1,3-thiazole-5-carboxylic acid (Exemplified Compound No. 233)

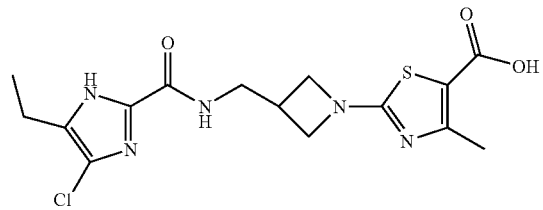

(233a) tert-Butyl 3-({[(benzyloxy)carbonyl]amino}methyl)azetidine-1-carboxylate

The compound was synthesized according to the method described in the following document.

WO 2006/17468 A2

(233b) Ethyl 2-[3-({[(benzyloxy)carbonyl]amino}methyl)azetidin-1-yl]-4-methyl-1,3-thiazole-5-carboxylate A 4 N hydrochloric acid/ethyl acetate solution (3.90 mL, 15.6 mmol) was added to a solution of tert-butyl 3-({[(benzyloxy)carbonyl]amino}methyl)azetidine-1-carboxylate obtained in Example (233a) (560 mg, 1.75 mmol) in 1,4-dioxane/methanol (8 mL/8 mL), and the mixture was stirred at room temperature for 4.5 hours. The reaction solution was concentrated to obtain 448 mg of 3-({[(benzyloxy)carbonyl]amino}methyl)azetidine hydrochloride (100%).

The same operation as in Example (223a) was performed using 3-({[(benzyloxy)carbonyl]amino}methyl)azetidine hydrochloride obtained by the above operation (342 mg, 1.33 mmol), ethyl 2-bromo-4-methylthiazole-5-carboxylate (500 mg, 2.00 mmol), copper (I) iodide (51 mg, 0.27 mmol), proline (61 mg, 0.53 mmol) and potassium carbonate (551 mg, 3.99 mmol), to obtain 309 mg of the title compound as a pale yellow solid (60%).

$^1$H NMR spectrum (400 MHz, CDCl$_3$) δ ppm: 1.32 (3H, t, J=7.07 Hz), 2.55 (3H, s), 2.95-3.08 (1H, m), 3.49 (2H, t, J=6.34 Hz), 3.78-3.86 (2H, m), 4.17 (2H, t, J=8.29 Hz), 4.25 (2H, q, J=7.07 Hz), 4.95 (1H, br s), 5.11 (2H, s), 7.35 (5H, s).

mass spectrum (ESI): m/z 390 (M+H)$^+$.

(233c) Ethyl 2-[3-(aminomethyl)azetidin-1-yl]-4-methyl-1,3-thiazole-5-carboxylate A 30% hydrogen bromide/acetic acid solution (0.64 mL, 3.29 mmol) was added to a solution of ethyl 2-[3-({[(benzyloxy)carbonyl]amino}methyl)azetidin-1-yl]-4-methyl-1,3-thiazole-5-carboxylate obtained in Example (233b) (128 mg, 0.33 mmol) in acetic acid (1 mL), and the mixture was stirred at room temperature for 100 minutes. A 1 N aqueous sodium hydroxide solution was added to the reaction solution, and the mixture was extracted with ethyl acetate. The combined organic layers were dried over anhydrous magnesium sulfate and filtered. Thereafter, the filtrate was concentrated under reduced pressure to obtain 51 mg of the title compound as a colorless oily substance (61%).

mass spectrum (ESI): m/z 256 (M+H)$^+$.

(233d) Ethyl 2-[3-({[(4-chloro-5-ethyl-1H-imidazol-2-yl)carbonyl]amino}methyl)azetidin-1-yl]-4-methyl-1,3-thiazole-5-carboxylate The same operation as in Example (221c) was performed using ethyl 2-[3-(aminomethyl)azetidin-1-yl]-4-methyl-1,3-thiazole-5-carboxylate obtained in Example (233c) (51 mg, 0.20 mmol), 4-chloro-5-ethyl-1H-imidazole-2-carboxylic acid obtained in Example (1d) (52 mg, 0.30 mmol), WSC hydrochloride (115 mg, 0.60 mmol), 1-hydroxybenzotriazole (30 mg, 0.22 mmol) and N-methylmorpholine (0.04 mL, 0.40 mmol), to obtain 46 mg of the title compound as a white solid (56%).

$^1$H NMR spectrum (400 MHz, CDCl$_3$) δ ppm: 1.26 (3H, t, J=7.56 Hz), 1.32 (3H, t, J=7.07 Hz), 2.55 (3H, s), 2.68 (2H, q, J=7.56 Hz), 3.02-3.13 (1H, m), 3.72 (2H, t, J=6.71 Hz), 3.88 (2H, dd, J=8.66, 5.24 Hz), 4.17-4.29 (4H, m), 7.28-7.33 (1H, m), 11.06 (1H, br s).

mass spectrum (ESI): m/z 412, 414 (M+H)$^+$.

(233e) 2-[3-({[(4-Chloro-5-ethyl-1H-imidazol-2-yl)carbonyl]amino}methyl)azetidin-1-yl]-4-methyl-1,3-thiazole-5-carboxylic acid The same operation as in Example (222d) was performed using ethyl 2-[3-({[(4-chloro-5-ethyl-1H-imidazol-2-yl)carbonyl]amino}methyl)azetidin-1-yl]-4-methyl-1,3-thiazole-5-carboxylate obtained in Example (233d) (42 mg, 0.10 mmol) and a 2 N aqueous lithium hydroxide solution (0.51 mL, 1.02 mmol), to obtain 18 mg of the title compound as a white solid (46%).

$^1$H NMR spectrum (400 MHz, DMSO-d$_6$) δ ppm: 1.14 (3H, t, J=7.56 Hz), 2.40 (3H, s), 2.55 (2H, q, J=7.56 Hz), 2.96-3.06 (1H, m), 3.48 (2H, t, J=6.46 Hz), 3.84 (2H, dd, J=8.29, 5.37 Hz), 4.08 (2H, t, J=8.41 Hz), 8.75-8.81 (1H, m), 12.42 (1H, br s), 13.25 (1H, br s).

mass spectrum (ESI): m/z 384, 386 (M+H)$^+$.

Example 234 trans(±)-2-(3-{[(4-Chloro-5-ethyl-1H-imidazol-2-yl)carbonyl]amino}-2-ethylazetidin-1-yl)-4-methyl-1,3-thiazole-5-carboxylic acid (Exemplified Compound No. 234)

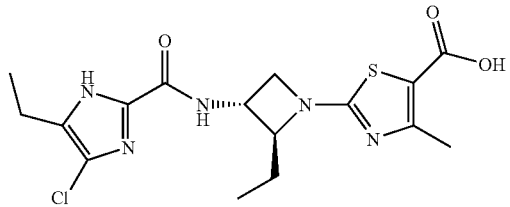

(234a) (2R*)-2-[(1R*)-1-Bromopropyl]oxirane

A solution of trans-2-penten-1-ol (2.00 g, 23.2 mmol) in chloroform (2 mL) was slowly added to a solution of bromine (3.71 g, 23.2 mmol) in chloroform (3 mL) at 0° C., and the mixture was stirred at room temperature for two hours. The reaction solution was concentrated under reduced pressure to obtain an oily substance.

A solution of potassium hydroxide (1.30 g, 23.2 mmol) in water (15 mL) was added to a solution of the oily substance obtained by the above operation in diethyl ether (12 mL) at 0° C., and the mixture was stirred at room temperature for 19 hours. The reaction solution was extracted with diethyl ether, and the combined organic layers were dried over anhydrous magnesium sulfate. Following filtration, the filtrate was concentrated under reduced pressure. The resulting residue was purified by silica gel column chromatography (elution solvent: hexane/ethyl acetate=5/1) to obtain 2.56 g of the title compound as a colorless oily substance (67%).

$^1$H NMR spectrum (400 MHz, CDCl$_3$) δ ppm: 1.09 (3H, t, J=7.32 Hz), 1.83-2.04 (2H, m), 2.75 (1H, dd, J=4.39, 2.44 Hz), 2.97 (1H, dd, J=4.39, 3.90 Hz), 3.22 (1H, ddd, J=7.32, 3.66, 2.44 Hz), 3.62 (1H, td, J=8.05, 5.12 Hz). (234b) trans(±)-1-(Diphenylmethyl)-2-ethylazetidin-3-ol Benzhydrylamine (1.04 mL, 6.06 mmol) was added to a solution of (2R*)-2-[(1R*)-1-bromopropyl]oxirane obtained in Example (234a) (1.00 g, 6.06 mmol) in methanol (6 mL), and the mixture was heated under reflux for 17 hours. The reaction solution was concentrated under reduced pressure. Saturated aqueous sodium carbonate solution was added to the resulting residue, followed by extraction with ethyl acetate. The combined organic layers were dried over anhydrous magnesium sulfate. Following filtration, the filtrate was concentrated under reduced pressure. The resulting residue was purified by silica gel column chromatography (elution solvent: hexane/ethyl acetate=2/1) to obtain 787 mg of the title compound as a colorless oily substance (49%).

$^1$H NMR spectrum (400 MHz, CDCl$_3$) δ ppm: 0.72 (3H, t, J=7.44 Hz), 0.84-0.96 (1H, m), 1.06-1.19 (1H, m), 2.54 (1H, t, J=7.19 Hz), 2.88-2.95 (1H, m), 3.64 (1H, t, J=7.07 Hz), 4.03 (1H, q, J=6.10 Hz), 4.35 (1H, s), 7.14-7.44 (10H, m).

mass spectrum (ESI): m/z 268 (M+H)$^+$.

(234c) trans(±)-1-(Diphenylmethyl)-2-ethylazetidin-3-yl methanesulfonate

Triethylamine (0.94 mL, 6.74 mmol) was added to a solution of trans(±)-1-(Diphenylmethyl)-2-ethylazetidin-3-ol obtained in Example (234b) (1.20 g, 4.49 mmol) in dichloromethane (8 mL). Then, a solution of methanesulfonyl chloride (0.45 mL, 5.83 mmol) in dichloromethane (1.5 mL) was added dropwise at room temperature, followed by stirring for four hours. The reaction solution was diluted with ethyl acetate, washed with water and brine, and then dried over anhydrous magnesium sulfate. Following filtration, the filtrate was concentrated under reduced pressure. The resulting residue was purified by silica gel column chromatography (elution solvent: hexane/ethyl acetate=5/1) to obtain 1.41 g of the title compound as a pale yellow oily substance (91%).

$^1$H NMR spectrum (400 MHz, CDCl$_3$) δ ppm: 0.73 (3H, t, J=7.56 Hz), 0.93-1.04 (1H, m), 1.04-1.17 (1H, m), 2.83-2.90 (1H, m), 2.95 (3H, s), 3.26-3.33 (1H, m), 3.69-3.76 (1H, m), 4.41 (1H, s), 4.70-4.77 (1H, m), 7.16-7.32 (6H, m), 7.35-7.44 (4H, m).

mass spectrum (ESI): m/z 346 (M+H)$^+$.

(234d) trans(±)-3-(tert-Butoxycarbonyl)amino-1-(diphenylmethyl)-2-ethylazetidine 28% aqueous ammonia (2.3 ml) was added to a solution of trans(±)-1-(diphenylmethyl)-2-ethylazetidin-3-yl methanesulfonate obtained in Example (234c) (700 mg, 2.03 mmol) in isopropanol (4 mL), and the mixture was stirred at 70° C. for 4.5 hours. The reaction solution was concentrated under reduced pressure. Then, saturated aqueous sodium bicarbonate solution was added to the resulting residue, followed by extraction with chloroform. The combined organic layers were dried over anhydrous magnesium sulfate and filtered, and then the filtrate was concentrated under reduced pressure to obtain an oily substance.

tert-Butyl dicarbonate (560 mg, 2.44 mmol) and triethylamine (0.71 mL, 5.08 mmol) were added to a solution of the oily substance obtained by the above operation in dichloromethane (10 mL) at room temperature, followed by stirring for three hours. The reaction solution was concentrated under reduced pressure, and then the resulting residue was dissolved in ethyl acetate, and the organic layer was washed with water and brine. The organic layer was dried over anhydrous magnesium sulfate. Following filtration, the filtrate was concentrated under reduced pressure. The resulting residue was purified by silica gel column chromatography (elution solvent: hexane/ethyl acetate=5/1) to obtain 536 mg of the title compound as a pale yellow oily substance (72%).

$^1$H NMR spectrum (400 MHz, CDCl$_3$) δ ppm: 0.69 (3H, t, J=7.45 Hz), 0.84-0.96 (1H, m), 1.07-1.20 (1H, m), 1.41 (9H, s), 2.41 (1H, t, J=7.57 Hz), 2.78-2.86 (1H, m), 3.60-3.68 (1H, m), 3.91-4.02 (1H, m), 4.27 (1H, s), 4.57-4.67 (1H, m), 7.14-7.30 (6H, m), 7.34-7.43 (4H, m).

mass spectrum (ESI): m/z 367 (M+H)$^+$.

(234e) trans(±)-3-(tert-Butoxycarbonyl)amino-2-ethylazetidine

10% Pd/C (100 mg) was added to a solution of trans(±)-3-(tert-butoxycarbonyl)amino-1-(diphenylmethyl)-2-ethylazetidine obtained in Example (234d) (530 mg, 1.45 mmol) in methanol (7 mL), and the mixture was stirred in a hydrogen stream at 40° C. for 13 hours. The reaction solution was filtered, and then the filtrate was concentrated under reduced pressure. A 1 N aqueous hydrochloric acid solution was added to the resulting residue. The aqueous layer was washed with ethyl acetate, and then saturated aqueous sodium bicarbonate solution was added, followed by extraction with ethyl acetate and a chloroform/methanol mixed solvent. The combined organic layers were dried over anhydrous magnesium sulfate and filtered. Thereafter, the filtrate was concentrated under reduced pressure to obtain 206 mg of the title compound as a white solid (71%).

mass spectrum (ESI): m/z 201 (M+H)$^+$.

(234f) Ethyl trans(±)-2-{3-[(tert-butoxycarbonyl)amino]-2-ethylazetidin-1-yl}-4-methyl-1,3-thiazole-5-carboxylate The same operation as in Example (232c) was performed using trans(±)-3-(tert-butoxycarbonyl)amino-2-ethylazetidine obtained in Example (234e) (110 mg, 0.55 mmol), ethyl 2-bromo-4-methylthiazole-5-carboxylate (137 mg, 0.55 mmol) and diisopropylethylamine (0.19 mL, 1.10 mmol), to obtain 156 mg of the title compound as a pale yellow oily substance (77%).

$^1$H NMR spectrum (400 MHz, CDCl$_3$) δ ppm: 1.01 (3H, t, J=7.56 Hz), 1.32 (3H, t, J=7.07 Hz), 1.45 (9H, s), 1.76-1.90 (1H, m), 2.00-2.12 (1H, m), 2.55 (3H, s), 3.70-3.79 (1H, m), 3.95-4.03 (1H, m), 4.22-4.40 (4H, m), 4.88 (1H, br s).

mass spectrum (ESI): m/z 370 (M+H)$^+$.

(234g) Ethyl trans(±)-2-(3-{[(4-chloro-5-ethyl-1H-imidazol-2-yl)carbonyl]amino}-2-ethylazetidin-1-yl)-4-methyl-1,3-thiazole-5-carboxylate The same operation as in Example (232d) was performed to obtain an oily substance from ethyl trans(±)-2-{3-[(tert-butoxycarbonyl)amino]-2-ethylazetidin-1-yl}-4-methyl-1,3-thiazole-5-carboxylate obtained in Example (234f) (152 mg, 0.41 mmol) and 85% phosphoric acid (0.24 mL, 2.06 mmol). 101 mg of the title compound was obtained as a white solid (58%) using this oily substance, 4-chloro-5-ethyl-1H-imidazole-2-carboxylic acid obtained in Example (1d) (86 mg, 0.49 mmol), WSC hydrochloride (236 mg, 1.23 mmol), 1-hydroxybenzotriazole (61 mg, 0.45 mmol) and N-methylmorpholine (0.09 mL, 0.82 mmol).

$^1$H NMR spectrum (400 MHz, CDCl$_3$) δ ppm: 1.01 (3H, t, J=7.32 Hz), 1.27 (3H, t, J=7.57 Hz), 1.33 (3H, t, J=7.08 Hz), 1.79-1.92 (1H, m), 2.03-2.15 (1H, m), 2.57 (3H, s), 2.70 (2H, q, J=7.57 Hz), 3.87-3.93 (1H, m), 4.11-4.18 (1H, m), 4.27 (2H, q, J=7.08 Hz), 4.39 (1H, t, J=8.18 Hz), 4.64-4.74 (1H, m), 7.60 (1H, d, J=8.54 Hz), 11.53 (1H, br s).

mass spectrum (ESI): m/z 426, 428 (M+H)$^+$.

(234h) trans(±)-2-(3-{[(4-Chloro-5-ethyl-1H-imidazol-2-yl)carbonyl]amino}-2-ethylazetidin-1-yl)-4-methyl-1,3-thiazole-5-carboxylic acid The same operation as in Example (217d) was performed using ethyl trans(±)-2-(3-{[(4-chloro-5-ethyl-1H-imidazol-2-yl)carbonyl]amino}-2-ethylazetidin-1-yl)-4-methyl-1,3-thiazole-5-carboxylate obtained in Example (234g) (97 mg, 0.23 mmol) and a 2 N aqueous lithium hydroxide solution (1.14 mL, 2.28 mmol), to obtain 76 mg of the title compound as a white solid (84%).

$^1$H NMR spectrum (400 MHz, DMSO-d$_6$) δ ppm: 0.89-0.96 (3H, m), 1.11-1.18 (3H, m), 1.68-1.80 (1H, m), 1.91-2.02 (1H, m), 2.42-2.45 (3H, m), 2.53-2.61 (2H, m), 3.95-4.02 (1H, m), 4.20-4.27 (2H, m), 4.55-4.64 (1H, m), 9.20-9.26 (1H, m), 12.48 (1H, br s), 13.32 (1H, br s).

mass spectrum (ESI): m/z 398, 400 (M+H)$^+$.

Example 235 cis(±)-2-(3-{[(4-Chloro-5-ethyl-1H-imidazol-2-yl)carbonyl]amino}-2-ethylazetidin-1-yl)-4-methyl-1,3-thiazole-5-carboxylic acid (Exemplified Compound No. 235)

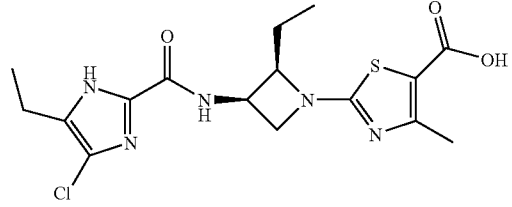

(235a) (2R*)-2-[(1S*)-1-Bromopropyl]oxirane

The same operation as in Example (234a) was performed to obtain an oily substance from cis-2-penten-1-ol (5.00 g, 58.1 mmol) and bromine (9.28 g, 58.1 mmol). 2.65 g of the title compound was obtained as a pale yellow oily substance (28%) using this oily substance and potassium hydroxide (3.26 g, 58.1 mmol).

$^1$H NMR spectrum (400 MHz, CDCl$_3$) δ ppm: 1.11 (3H, t, J=7.20 Hz), 1.88-2.00 (1H, m), 2.06-2.18 (1H, m), 2.64 (1H, dd, J=4.76, 2.56 Hz), 2.91 (1H, dd, J=4.88, 3.91 Hz), 3.15-3.21 (1H, m), 3.39-3.47 (1H, m).

(235b) cis(±)-1-(Diphenylmethyl)-2-ethylazetidin-3-ol

The same operation as in Example (234b) was performed using (2R*)-2-[(1S*)-1-bromopropyl]oxirane obtained in Example (235a) (1.50 g, 9.09 mmol) and benzhydrylamine (1.57 mL, 9.09 mmol), to obtain 699 mg of the title compound as a pale yellow solid (29%).

$^1$H NMR spectrum (400 MHz, CDCl$_3$) δ ppm: 0.57-0.68 (4H, m), 1.50-1.61 (1H, m), 2.97 (1H, dd, J=9.28, 5.86 Hz), 3.07-3.14 (1H, m), 3.22 (1H, d, J=9.28 Hz), 4.29-4.37 (2H, m), 7.15-7.31 (6H, m), 7.35-7.43 (4H, m).

mass spectrum (ESI): m/z 268 (M+H)$^+$.

(235c) cis(±)-1-(Diphenylmethyl)-2-ethylazetidin-3-yl methanesulfonate

The same operation as in Example (234c) was performed using cis(±)-1-(diphenylmethyl)-2-ethylazetidin-3-ol obtained in Example (235b) (769 mg, 2.88 mmol), triethylamine (0.60 mL, 4.32 mmol) and methanesulfonyl chloride (0.29 mL, 3.74 mmol), to obtain 321 mg of the title compound as a pale yellow oily substance (32%).

$^1$H NMR spectrum (400 MHz, CDCl$_3$) δ ppm: 0.60 (3H, t, J=7.32 Hz), 0.70-0.84 (1H, m), 1.54-1.71 (1H, m), 3.04 (3H, s), 3.09 (1H, dd, J=10.00, 5.61 Hz), 3.34-3.41 (1H, m), 3.54-3.59 (1H, m), 4.36 (1H, s), 5.20 (1H, t, J=5.98 Hz), 7.16-7.32 (6H, m), 7.37-7.44 (4H, m).

mass spectrum (ESI): m/z 346 (M+H)$^+$.

(235d) cis(±)-1-(Diphenylmethyl)-2-ethylazetidin-3-amine

28% aqueous ammonia (1.2 ml) was added to a solution of cis(±)-1-(diphenylmethyl)-2-ethylazetidin-3-yl methanesulfonate obtained in Example (235c) (315 mg, 0.91 mmol) in isopropanol (2 mL), and the mixture was stirred at 70° C. for four hours. The reaction solution was concentrated under reduced pressure. Then, saturated aqueous sodium bicarbonate solution was added to the resulting residue, followed by extraction with chloroform. The combined organic layers were dried over anhydrous magnesium sulfate and filtered. Thereafter, the filtrate was concentrated under reduced pressure to obtain 206 mg of the title compound as a pale yellow oily substance (85%).

mass spectrum (ESI): m/z 267 (M+H)$^+$.

(235e) cis(±)-3-(tert-Butoxycarbonyl)amino-1-(diphenylmethyl)-2-ethylazetidine tert-Butyl dicarbonate (202 mg, 0.93 mmol) and triethylamine (0.27 mL, 1.93 mmol) were added to a solution of cis(±)-1-(diphenylmethyl)-2-ethylazetidin-3-amine obtained in Example (235d) (206 mg, 0.77 mmol) in dichloromethane (4 mL), followed by stirring for two hours. The reaction solution was diluted with ethyl acetate, and the organic layer was washed with water and brine. The organic layer was dried over anhydrous magnesium sulfate. Following filtration, the filtrate was concentrated under reduced pressure. The resulting residue was purified by silica gel column chromatography (elution solvent: hexane/ethyl acetate=4/1) to obtain 161 mg of the title compound as a colorless oily substance (57%).

$^1$H NMR spectrum (400 MHz, CDCl$_3$) δ ppm: 0.48-0.67 (4H, m), 1.24-1.37 (1H, m), 1.44 (9H, s), 3.01-3.10 (2H, m), 3.16-3.26 (1H, m), 4.23-4.34 (2H, m), 5.25-5.35 (1H, m), 7.14-7.31 (6H, m), 7.33-7.41 (4H, m).

mass spectrum (ESI): m/z 367 (M+H)$^+$.

(235f) cis(±)-3-(tert-Butoxycarbonyl)amino-2-ethylazetidine

The same operation as in Example (234e) was performed using cis(±)-3-(tert-butoxycarbonyl)amino-1-(diphenylmethyl)-2-ethylazetidine obtained in Example (235e) (154 mg, 0.42 mmol) and 10% Pd/C (30 mg), to obtain 66 mg of the title compound as a white solid (79%).

mass spectrum (ESI): m/z 201 (M+H)$^+$.

(235g) Ethyl cis(±)-2-{3-[(tert-butoxycarbonyl)amino]-2-ethylazetidin-1-yl}-4-methyl-1,3-thiazole-5-carboxylate The same operation as in Example (232c) was performed using cis(±)-3-(tert-butoxycarbonyl)amino-2-ethylazetidine obtained in Example (235f) (66 mg, 0.33 mmol), ethyl 2-bromo-4-methylthiazole-5-carboxylate (82 mg, 0.33 mmol) and diisopropylethylamine (0.12 mL, 0.66 mmol), to obtain 102 mg of the title compound as a white solid (84%).

$^1$H NMR spectrum (400 MHz, CDCl$_3$) δ ppm: 0.97 (3H, t, J=7.44 Hz), 1.32 (3H, t, J=7.07 Hz), 1.46 (9H, s), 1.68-1.80 (1H, m), 1.89-2.01 (1H, m), 2.55 (3H, s), 3.82-3.89 (1H, m), 4.26 (2H, q, J=7.15 Hz), 4.22-4.31 (1H, m), 4.39 (1H, t, J=8.90 Hz), 4.73-4.84 (1H, m), 5.00-5.10 (1H, m).

mass spectrum (ESI): m/z 370 (M+H)$^+$.

(235h) Ethyl cis(±)-2-(3-{[(4-chloro-5-ethyl-1H-imidazol-2-yl)carbonyl]amino}-2-ethylazetidin-1-yl)-4-methyl-1,3-thiazole-5-carboxylate The same operation as in Example (232d) was performed to obtain an oily substance from ethyl cis(±)-2-{3-[(tert-butoxycarbonyl)amino]-2-ethylazetidin-1-yl}-4-methyl-1,3-thiazole-5-carboxylate obtained in Example (235g) (99 mg, 0.27 mmol) and 85% phosphoric acid (0.15 mL, 1.34 mmol). 105 mg of the title compound was obtained as a white solid (92%) using this oily substance, 4-chloro-5-ethyl-1H-imidazole-2-carboxylic acid obtained in Example (1d) (68 mg, 0.39 mmol), WSC hydrochloride (150 mg, 0.78 mmol), 1-hydroxybenzotriazole (53 mg, 0.39 mmol) and N-methylmorpholine (0.06 mL, 0.52 mmol).

$^1$H NMR spectrum (400 MHz, CDCl$_3$) δ ppm: 0.94 (3H, t, J=7.32 Hz), 1.27 (3H, t, J=7.32 Hz), 1.33 (3H, t, J=7.07 Hz), 1.73-1.86 (1H, m), 1.94-2.07 (1H, m), 2.57 (3H, s), 2.70 (2H, q, J=7.32 Hz), 4.05 (1H, dd, J=9.76, 4.88 Hz), 4.27 (2H, q, J=7.07 Hz), 4.32-4.40 (1H, m), 4.44 (1H, t, J=9.02 Hz), 5.08-5.18 (1H, m), 7.72 (1H, d, J=9.27 Hz), 11.41 (1H, br s).

mass spectrum (ESI): m/z 426, 428 (M+H)$^+$.

(235i) cis(±)-2-(3-{[(4-Chloro-5-ethyl-1H-imidazol-2-yl)carbonyl]amino}-2-ethylazetidin-1-yl)-4-methyl-1,3-thiazole-5-carboxylic acid The same operation as in Example (217d) was performed using ethyl cis(±)-2-(3-{[(4-chloro-5-ethyl-1H-imidazol-2-yl)carbonyl]amino}-2-ethylazetidin-1-yl)-4-methyl-1,3-thiazole-5-carboxylate obtained in Example (235h) (103 mg, 0.24 mmol) and a 2 N aqueous lithium hydroxide solution (1.21 mL, 2.42 mmol), to obtain 77 mg of the title compound as a white solid (80%).

$^1$H NMR spectrum (400 MHz, DMSO-d$_6$) δ ppm: 0.80 (3H, t, J=7.32 Hz), 1.15 (3H, t, J=7.08 Hz), 1.68-1.89 (2H, m), 2.41 (3H, s), 2.53-2.61 (2H, m), 4.20-4.38 (3H, m), 4.99-5.10 (1H, m), 9.20-9.26 (1H, m), 13.33 (1H, br s).

mass spectrum (ESI): m/z 398, 400 (M+H)$^+$.

Example 236

2-{(1R,5R)-2-[(4-Chloro-5-ethyl-1H-imidazol-2-yl)carbonyl]-2,6-diazabicyclo[3.2.0]hept-6-yl}-4-methyl-1,3-thiazole-5-carboxylic acid (Exemplified Compound No. 236)

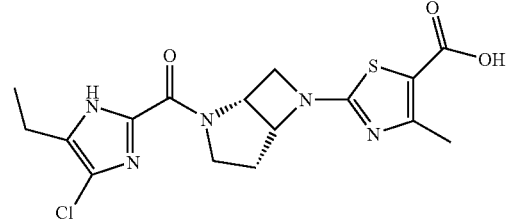

(236a) tert-Butyl (1R,5R)-2,6-diazabicyclo[3.2.0]heptane-2-carboxylate

The compound was synthesized according to the method described in the following document.

US 2005/101602 A1

(236b) tert-Butyl (1R,5R)-6-[5-(ethoxycarbonyl)-4-methyl-1,3-thiazol-2-yl]-2,6-diazabicyclo[3.2.0]heptane-2-carboxylate The same operation as in Example (217a) was performed using tert-butyl (1R,5R)-2,6-diazabicyclo[3.2.0]heptane-2-carboxylate obtained in Example (236a) (150 mg, 0.76 mmol), ethyl 2-bromo-4-methylthiazole-5-carboxylate (189 mg, 0.76 mmol) and diisopropylethylamine (0.26 mL, 1.51 mmol), to obtain 278 mg of the title compound as a yellow oily substance (100%).

$^1$H NMR spectrum (400 MHz, CDCl$_3$) δ ppm: 1.32 (3H, t, J=7.07 Hz), 1.47 (9H, s), 1.81-1.94 (1H, m), 2.34 (1H, dd, J=13.90, 6.10 Hz), 2.55 (3H, s), 3.57 (1H, br s), 3.78 (1H, br s), 3.95 (1H, br s), 4.26 (2H, q, J=7.07 Hz), 4.16-4.31 (1H, m), 4.51-4.75 (1H, m), 4.96 (1H, t, J=5.24 Hz).

mass spectrum (ESI): m/z 368 (M+H)$^+$.

(236c) Ethyl 2-[(1R,5R)-2,6-diazabicyclo[3.2.0]hept-6-yl]-4-methyl-1,3-thiazole-5-carboxylate 85% phosphoric acid (0.44 mL, 3.78 mmol) was added to a solution of tert-butyl (1R,5R)-6-[5-(ethoxycarbonyl)-4-methyl-1,3-thiazol-2-yl]-2,6-diazabicyclo[3.2.0]heptane-2-carboxylate obtained in Example (236b) (278 mg, 0.76 mmol) in dichloromethane (1 mL) at room temperature, followed by stirring for two hours. Water was added to the reaction solution, and the mixture was washed with ethyl acetate. Then, a 1 N aqueous sodium hydroxide solution was added to the aqueous layer, followed by extraction with an ethyl acetate/methanol mixed solvent. The combined organic layers were dried over anhydrous magnesium sulfate and filtered. Thereafter, the solvent was evaporated under reduced pressure to obtain 175 mg of the title compound as a pale yellow oily substance (87%).

$^1$H NMR spectrum (400 MHz, CDCl$_3$) δ ppm: 1.32 (3H, t, J=7.56 Hz), 1.42-1.53 (1H, m), 2.30 (1H, dd, J=13.66, 5.12 Hz), 2.55 (3H, s), 3.15 (1H, td, J=11.95, 5.45 Hz), 3.37 (1H, dd, J=11.95, 7.32 Hz), 3.71-3.78 (1H, m), 4.21-4.33 (4H, m), 4.87 (1H, t, J=5.00 Hz).

mass spectrum (ESI): m/z 268 (M+H)$^+$.

(236d) Ethyl 2-{(1R,5R)-2-[(4-chloro-5-ethyl-1H-imidazol-2-yl)carbonyl]-2,6-diazabicyclo[3.2.0]hept-6-yl}-4-methyl-1,3-thiazole-5-carboxylate WSC hydrochloride (377 mg, 1.97 mmol), 1-hydroxybenzotriazole (97 mg, 0.72 mmol) and N-methylmorpholine (0.14 mL, 1.31 mmol) were added to a mixed solution of ethyl 2-[(1R,5R)-2,6-diazabicyclo[3.2.0]hept-6-yl]-4-methyl-1,3-thiazole-5-carboxylate obtained in Example (236c) (175 mg, 0.66 mmol) and 4-chloro-5-ethyl-1H-imidazole-2-carboxylic acid obtained in Example (1d) (137 mg, 0.79 mmol) in DMA/dichloromethane (4 mL/4 mL), and the mixture was stirred at room temperature for 19 hours. The reaction solution was diluted with ethyl acetate, and then the mixture was washed with 5% saline and dried over anhydrous magnesium sulfate. Following filtration, the solvent was evaporated under reduced pressure. The resulting residue was purified by silica gel column chromatography (elution solvent: hexane/ethyl acetate=2/1) to obtain 192 mg of the title compound as a milk white solid (69%).

$^1$H NMR spectrum (400 MHz, CDCl$_3$) δ ppm: 1.23-1.29 (3H, m), 1.33 (3H, t, J=7.08 Hz), 1.90-2.09 (1H, m), 2.42-2.59 (1H, m), 2.57 (3H, s), 2.65-2.74 (2H, m), 3.77-3.88 (1.7H, m), 4.03-4.15 (0.3H, m), 4.23-4.34 (2.3H, m), 4.41-4.50 (1.4H, m), 4.98-5.03 (0.3H, m), 5.10 (1H, t, J=5.37 Hz), 5.35 (0.3H, dd, J=12.21, 8.30 Hz), 5.65-5.70 (0.7H, m), 11.44 (0.3H, br s), 11.58 (0.7H, br s).

mass spectrum (ESI): m/z 424, 426 (M+H)$^+$.

(236e) 2-{(1R,5R)-2-[(4-Chloro-5-ethyl-1H-imidazol-2-yl)carbonyl]-2,6-diazabicyclo[3.2.0]hept-6-yl}-4-methyl-1,3-thiazole-5-carboxylic acid The same operation as in Example (217d) was performed using ethyl 2-{(1R,5R)-2-[(4-chloro-5-ethyl-1H-imidazol-2-yl)carbonyl]-2,6-diazabicyclo[3.2.0]hept-6-yl}-4-methyl-1,3-thiazole-5-carboxylate obtained in Example (236d) (188 mg, 0.44 mmol) and a 2 N aqueous lithium hydroxide solution (2.22 mL, 4.43 mmol), to obtain 157 mg of the title compound as a white solid (90%).

$^1$H NMR spectrum (400 MHz, DMSO-d$_6$) δ ppm: 1.15 (3H, t, J=7.56 Hz), 1.88-2.02 (1H, m), 2.18-2.33 (1H, m), 2.43 (3H, s), 2.53-2.62 (2H, m), 3.61-3.71 (0.7H, m), 3.77 (1H, d, J=9.02 Hz), 3.85-3.95 (0.3H, m), 4.23-4.32 (1.6H, m), 4.94-5.00 (0.7H, m), 5.04-5.12 (1H, m), 5.38-5.44 (0.7H, m), 12.26 (1H, br s), 13.25-13.34 (1H, m).

mass spectrum (ESI): m/z 396, 398 (M+H)$^+$.

Example 237

2-[(3S)-3-{[(4-Chloro-5-ethyl-1H-imidazol-2-yl)carbonyl]amino}pyrrolidin-1-yl)-4-methyl-1,3-thiazole-5-carboxylic acid (Exemplified Compound No. 237)

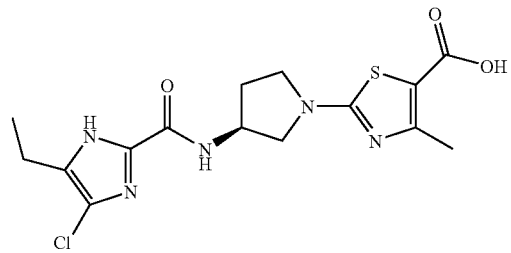

(237a) Ethyl 2-[(3S)-3-aminopyrrolidin-1-yl]-4-methyl-1,3-thiazole-5-carboxylate A solution of (3S)-3-aminopyrrolidine (0.16 mL, 1.80 mmol), ethyl 2-bromo-4-methylthiazole-5-carboxylate (300 mg, 1.20 mmol) and diisopropylethylamine (0.42 mL, 2.40 mmol) in DMF (12 mL) was stirred at 90° C. for 75 minutes. The reaction solution was diluted with ethyl acetate, and then the mixture was washed with saturated aqueous sodium bicarbonate solution, and dried over anhydrous magnesium sulfate. Following filtration, the solvent was evaporated under reduced pressure. The resulting residue was purified by silica gel column chromatography (elution solvent: dichloromethane/methanol=5/1) to obtain 257 mg of the title compound as a pale yellow solid (84%).

$^1$H NMR spectrum (400 MHz, CDCl$_3$) δ ppm: 1.33 (3H, t, J=7.08 Hz), 1.81-1.91 (1H, m), 2.19-2.29 (1H, m), 2.57 (3H, s), 3.18-3.27 (1H, m), 3.46-3.56 (1H, m), 3.61-3.71 (2H, m), 3.75-3.82 (1H, m), 4.26 (2H, q, J=7.08 Hz).

mass spectrum (ESI): m/z 256 (M+H)$^+$.

(237b) Ethyl 2-[(3S)-3-{[(4-chloro-5-ethyl-1H-imidazol-2-yl)carbonyl]amino}pyrrolidin-1-yl)-4-methyl-1,3-thiazole-5-carboxylate The same operation as in Example (217c) was performed using ethyl 2-[(3S)-3-aminopyrrolidin-1-yl]-4-methyl-1,3-thiazole-5-carboxylate obtained in Example (237a) (150 mg, 0.59 mmol), 4-chloro-5-ethyl-1H-imidazole-2-carboxylic acid obtained in Example (1d) (103 mg, 0.59 mmol), WSC hydrochloride (338 mg, 1.76 mmol), 1-hydroxybenzotriazole (79 mg, 0.59 mmol) and N-methylmorpholine (0.13 mL, 1.17 mmol), to obtain 217 mg of the title compound as a white solid (90%).

$^1$H NMR spectrum (400 MHz, CDCl$_3$) δ ppm: 1.27 (3H, t, J=7.65 Hz), 1.34 (3H, t, J=7.08 Hz), 2.13-2.23 (1H, m), 2.35-2.48 (1H, m), 2.58 (3H, s), 2.71 (2H, q, J=7.65 Hz), 3.48-3.72 (3H, m), 3.85 (1H, dd, J=10.99, 6.35 Hz), 4.27 (2H, q, J=7.08 Hz), 4.69-4.78 (1H, m), 7.29-7.35 (1H, m), 11.52 (1H, br s).

mass spectrum (ESI): m/z 412, 414 (M+H)$^+$.

(237c) 2-[(3S)-3-{[(4-Chloro-5-ethyl-1H-imidazol-2-yl)carbonyl]amino}pyrrolidin-1-yl)-4-methyl-1,3-thiazole-5-carboxylic acid Ethyl 2-[(3S)-3-{[(4-chloro-5-ethyl-1H-imidazol-2-yl)carbonyl]amino}pyrrolidin-1-yl)-4-methyl-1,3-thiazole-5-carboxylate obtained in Example (237b) (215 mg, 0.52 mmol) was dissolved in methanol (5 mL). A 2 N aqueous lithium hydroxide solution (2.61 mL, 5.22 mmol) was added, and the mixture was stirred at 40° C. for two hours. Water was added to the reaction solution, and then the mixture was washed with ethyl acetate. A 1 N aqueous hydrochloric acid solution (5 mL) was added to the aqueous layer. The precipitated solid was collected by filtration and washed with water and ethyl acetate to obtain 155 mg of the title compound as a white solid (77%).

$^1$H NMR spectrum (400 MHz, DMSO-d$_6$) δ ppm: 1.11-1.18 (3H, m), 2.09-2.31 (2H, m), 2.43 (3H, s), 2.52-2.61 (2H, m), 3.39-3.73 (4H, m), 4.55-4.65 (1H, m), 8.83-8.91 (1H, m), 12.31 (1H, br s), 13.28 (1H, br s).

mass spectrum (ESI): m/z 384, 386 (M+H)$^+$.

Example 238

2-[(3R)-3-{[(4-Chloro-5-ethyl-1H-imidazol-2-yl)carbonyl]amino}pyrrolidin-1-yl)-4-methyl-1,3-thiazole-5-carboxylic acid (Exemplified Compound No. 238)

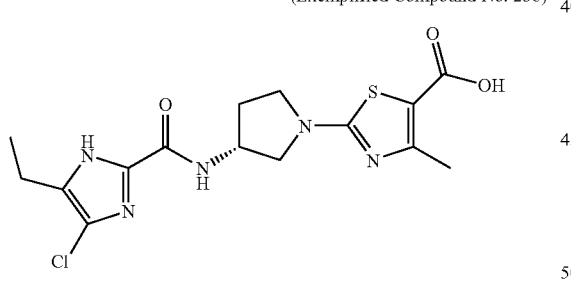

(238a) Ethyl 2-[(3R)-3-aminopyrrolidin-1-yl]-4-methyl-1,3-thiazole-5-carboxylate The same operation as in Example (237a) was performed using (3R)-3-aminopyrrolidine (0.16 mL, 1.80 mmol), ethyl 2-bromo-4-methylthiazole-5-carboxylate (300 mg, 1.20 mmol) and diisopropylethylamine (0.42 mL, 2.40 mmol), to obtain 265 mg of the title compound as a pale yellow solid (87%).

$^1$H NMR spectrum (400 MHz, CDCl$_3$) δ ppm: 1.33 (3H, t, J=7.08 Hz), 1.81-1.91 (1H, m), 2.19-2.29 (1H, m), 2.57 (3H, s), 3.20-3.26 (1H, m), 3.46-3.56 (1H, m), 3.61-3.71 (2H, m), 3.75-3.82 (1H, m), 4.26 (2H, q, J=7.08 Hz).

mass spectrum (ESI): m/z 256 (M+H)$^+$.

(238b) Ethyl 2-[(3R)-3-{[(4-chloro-5-ethyl-1H-imidazol-2-yl)carbonyl]amino}pyrrolidin-1-yl)-4-methyl-1,3-thiazole-5-carboxylate The same operation as in Example (217c) was performed using ethyl 2-[(3R)-3-aminopyrrolidin-1-yl]-4-methyl-1,3-thiazole-5-carboxylate obtained in Example (238a) (116 mg, 0.45 mmol), 4-chloro-5-ethyl-1H-imidazole-2-carboxylic acid obtained in Example (1d) (79 mg, 0.45 mmol), WSC hydrochloride (260 mg, 1.36 mmol), 1-hydroxybenzotriazole (61 mg, 0.45 mmol) and N-methylmorpholine (0.10 mL, 0.90 mmol), to obtain 155 mg of the title compound as a white solid (83%).

$^1$H NMR spectrum (400 MHz, CDCl$_3$) δ ppm: 1.27 (3H, t, J=7.65 Hz), 1.34 (3H, t, J=7.08 Hz), 2.12-2.22 (1H, m), 2.36-2.47 (1H, m), 2.58 (3H, s), 2.71 (2H, q, J=7.65 Hz), 3.49-3.71 (3H, m), 3.85 (1H, dd, J=10.99, 6.35 Hz), 4.27 (2H, q, J=7.08 Hz), 4.69-4.77 (1H, m), 7.32 (1H, d, J=7.32 Hz), 11.60 (1H, br s).

mass spectrum (ESI): m/z 412, 414 (M+H)$^+$.

(238c) 2-[(3R)-3-{[(4-Chloro-5-ethyl-1H-imidazol-2-yl)carbonyl]amino}pyrrolidin-1-yl)-4-methyl-1,3-thiazole-5-carboxylic acid The same operation as in Example (237c) was performed using ethyl 2-[(3R)-3-{[(4-chloro-5-ethyl-1H-imidazol-2-yl)carbonyl]amino}pyrrolidin-1-yl)-4-methyl-1,3-thiazole-5-carboxylate obtained in Example (238b) (154 mg, 0.37 mmol) and a 2 N aqueous lithium hydroxide solution (1.87 mL, 3.74 mmol), to obtain 98 mg of the title compound as a white solid (68%).

$^1$H NMR spectrum (400 MHz, DMSO-d$_6$) δ ppm: 1.13 (3H, t, J=7.56 Hz), 2.07-2.18 (1H, m), 2.19-2.29 (1H, m), 2.42 (3H, s), 2.55 (2H, q, J=7.56 Hz), 3.38-3.71 (4H, m), 4.54-4.64 (1H, m), 8.86 (1H, d, J=7.32 Hz), 13.29 (1H, br s).

mass spectrum (ESI): m/z 384, 386 (M+H)$^+$.

Example 239

2-(4-{[(4-Chloro-5-ethyl-1H-imidazol-2-yl)carbonyl]amino}piperidin-1-yl)-4-methyl-1,3-thiazole-5-carboxylic acid (Exemplified Compound No. 239)

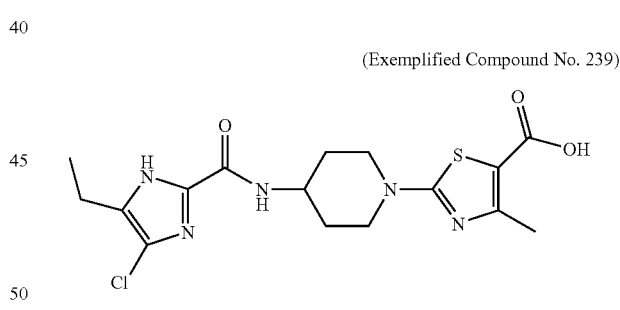

(239a) Ethyl 2-(4-aminopiperidin-1-yl)-4-methyl-1,3-thiazole-5-carboxylate

The same operation as in Example (237a) was performed using 4-aminopiperidine (0.19 mL, 1.80 mmol), ethyl 2-bromo-4-methylthiazole-5-carboxylate (300 mg, 1.20 mmol) and diisopropylethylamine (0.42 mL, 2.40 mmol), to obtain 283 mg of the title compound as a pale yellow oily substance (88%).

$^1$H NMR spectrum (400 MHz, CDCl$_3$) δ ppm: 1.32 (3H, t, J=7.08 Hz), 1.37-1.53 (2H, m), 1.88-1.95 (1H, m), 2.54 (3H, s), 2.91-3.00 (1H, m), 3.07-3.16 (2H, m), 3.97-4.05 (2H, m), 4.25 (2H, q, J=7.08 Hz).

mass spectrum (ESI): m/z 270 (M+H)$^+$.

(239b) Ethyl 2-(4-{[(4-chloro-5-ethyl-1H-imidazol-2-yl)carbonyl]amino}piperidin-1-yl)-4-methyl-1,3-thiazole-5-carboxylate The same operation as in Example (217c) was performed using ethyl 2-(4-aminopiperidin-1-yl)-4-methyl-1,3-thiazole-5-carboxylate obtained in Example (239a) (139 mg, 0.52 mmol), 4-chloro-5-ethyl-1H-imidazole-2-carboxylic acid obtained in Example (1d) (90 mg, 0.52 mmol), WSC hydrochloride (296 mg, 1.55 mmol), 1-hydroxybenzotriazole (70 mg, 0.52 mmol) and N-methylmorpholine (0.11 mL, 1.03 mmol), to obtain 205 mg of the title compound as a white solid (94%).

$^1$H NMR spectrum (400 MHz, CDCl$_3$) δ ppm: 1.27 (3H, t, J=7.57 Hz), 1.33 (3H, t, J=7.08 Hz), 1.60-1.75 (2H, m), 2.05-2.13 (2H, m), 2.55 (3H, s), 2.70 (2H, q, J=7.57 Hz), 3.14-3.24 (2H, m), 4.03-4.17 (3H, m), 4.27 (2H, q, J=7.08 Hz), 7.16 (1H, d, J=8.06 Hz), 11.80 (1H, br s).

mass spectrum (ESI): m/z 426, 428 (M+H)$^+$.

(239c) 2-(4-{[(4-Chloro-5-ethyl-1H-imidazol-2-yl)carbonyl]amino}piperidin-1-yl)-4-methyl-1,3-thiazole-5-carboxylic acid The same operation as in Example (223d) was performed using ethyl 2-(4-{[(4-chloro-5-ethyl-1H-imidazol-2-yl)carbonyl]amino}piperidin-1-yl)-4-methyl-1,3-thiazole-5-carboxylate obtained in Example (239b) (196 mg, 0.46 mmol) and a 2 N aqueous lithium hydroxide solution (2.30 mL, 4.60 mmol), to obtain 96 mg of the title compound as a white solid (53%).

$^1$H NMR spectrum (400 MHz, DMSO-d$_6$) δ ppm: 1.14 (3H, t, J=7.56 Hz), 1.62-1.74 (2H, m), 1.76-1.85 (2H, m), 2.41 (3H, s), 2.48-2.59 (2H, m), 3.12-3.23 (2H, m), 3.90-4.09 (3H, m), 8.45 (1H, d, J=8.29 Hz), 12.38 (1H, br s), 13.25 (1H, br s).

mass spectrum (ESI): m/z 398, 400 (M+H)$^+$.

Example 240

2-(4-{[(4-Chloro-5-ethyl-1H-imidazol-2-yl)carbonyl](methyl)amino}piperidin-1-yl)-4-methyl-1,3-thiazole-5-carboxylic acid (Exemplified Compound No. 240)

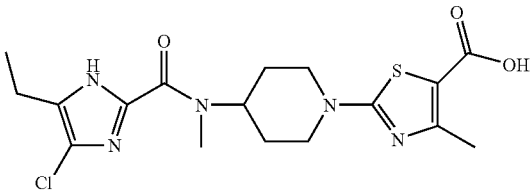

(240a) Ethyl 2-{4-[(tert-butoxycarbonyl)(methyl)amino]piperidin-1-yl}-4-methyl-1,3-thiazole-5-carboxylate The same operation as in Example (217a) was performed using 4-[(tert-butoxycarbonyl)(methyl)amino]piperidine (386 mg, 1.80 mmol), ethyl 2-bromo-4-methylthiazole-5-carboxylate (300 mg, 1.20 mmol) and diisopropylethylamine (0.42 mL, 2.40 mmol), to obtain 403 mg of the title compound as a colorless oily substance (88%).

$^1$H NMR spectrum (400 MHz, CDCl$_3$) δ ppm: 1.32 (3H, t, J=7.08 Hz), 1.47 (9H, s), 1.71-1.78 (4H, m), 2.54 (3H, s), 2.72 (3H, s), 3.04-3.15 (2H, m), 4.11-4.18 (2H, m), 4.26 (2H, q, J=7.08 Hz).

mass spectrum (ESI): m/z 384 (M+H)$^+$.

(240b) Ethyl 4-methyl-2-[4-(methylamino)piperidin-1-yl]-1,3-thiazole-5-carboxylate The same operation as in Example (222b) was performed using ethyl 2-{4-[(tert-butoxycarbonyl)(methyl)amino]piperidin-1-yl}-4-methyl-1,3-thiazole-5-carboxylate obtained in Example (240a) (396 mg, 1.03 mmol) and a 4 N hydrochloric acid/ethyl acetate solution (2.58 mL, 10.3 mmol), to obtain 256 mg of the title compound as a brown oily substance (88%).

$^1$H NMR spectrum (400 MHz, CDCl$_3$) δ ppm: 1.32 (3H, t, J=7.08 Hz), 1.38-1.52 (2H, m), 1.93-2.02 (2H, m), 2.46 (3H, s), 2.54 (3H, s), 2.59-2.68 (1H, m), 3.10-3.19 (2H, m), 3.95-4.03 (2H, m), 4.25 (2H, q, J=7.08 Hz).

mass spectrum (ESI): m/z 284 (M+H)$^+$.

(240c) Ethyl 2-(4-{[(4-chloro-5-ethyl-1H-imidazol-2-yl)carbonyl](methyl)amino}piperidin-1-yl)-4-methyl-1,3-thiazole-5-carboxylate The same operation as in Example (217c) was performed using ethyl 4-methyl-2-[4-(methylamino)piperidin-1-yl]-1,3-thiazole-5-carboxylate obtained in Example (240b) (254 mg, 0.90 mmol), 4-chloro-5-ethyl-1H-imidazole-2-carboxylic acid obtained in Example (1d) (156 mg, 0.90 mmol), WSC hydrochloride (515 mg, 2.69 mmol), 1-hydroxybenzotriazole (121 mg, 0.90 mmol) and N-methylmorpholine (0.20 mL, 1.79 mmol), to obtain 366 mg of the title compound as a white solid (93%).

$^1$H NMR spectrum (400 MHz, CDCl$_3$) δ ppm: 1.24 (3H, t, J=7.56 Hz), 1.33 (3H, t, J=7.07 Hz), 1.76-1.99 (4H, m), 2.55 (3H, s), 2.67 (2H, q, J=7.56 Hz), 2.98 (1.7H, s), 3.12-3.32 (2H, m), 3.51 (1.3H, s), 4.16-4.31 (4H, m), 4.74-4.85 (0.6H, m), 5.83-5.94 (0.4H, m), 11.20 (0.6H, br s), 11.36 (0.4H, br s).

mass spectrum (ESI): m/z 440, 442 (M+H)$^+$.

(240d) 2-(4-{[(4-Chloro-5-ethyl-1H-imidazol-2-yl)carbonyl](methyl)amino}piperidin-1-yl)-4-methyl-1,3-thiazole-5-carboxylic acid The same operation as in Example (221d) was performed using ethyl 2-(4-{[(4-chloro-5-ethyl-1H-imidazol-2-yl)carbonyl](methyl)amino}piperidin-1-yl)-4-methyl-1,3-thiazole-5-carboxylate obtained in Example (240c) (360 mg, 0.82 mmol) and a 2 N aqueous lithium hydroxide solution (4.09 mL, 8.18 mmol), to obtain 271 mg of the title compound as a white solid (80%).

$^1$H NMR spectrum (400 MHz, DMSO-d$_6$) δ ppm: 1.12 (3H, t, J=7.56 Hz), 1.66-1.90 (4H, m), 2.42 (3H, s), 2.56 (2H, q, J=7.56 Hz), 2.86 (1.3H, s), 3.06-3.40 (3.7H, m), 4.02-4.11 (2H, m), 4.59 (0.6H, br s), 5.37 (0.4H, br s), 12.37 (1H, br s), 13.09 (1H, br s).

mass spectrum (ESI): m/z 412, 414 (M+H)$^+$.

Example 241

2-(4-{[(4-Chloro-5-ethyl-1H-imidazol-2-yl)carbonyl](n-propyl)amino}piperidin-1-yl)-4-methyl-1,3-thiazole-5-carboxylic acid (Exemplified Compound No. 241)

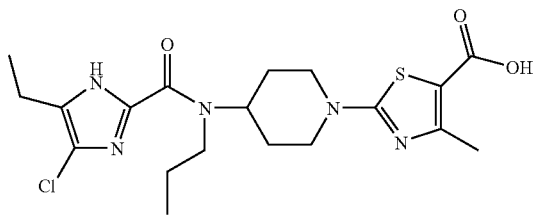

(241a) Benzyl 4-[(tert-butoxycarbonyl)amino]piperidine-1-carboxylate

The same operation as in Example (227a) was performed using 4-[(tert-butoxycarbonyl)amino]piperidine (2.00 g, 9.99 mmol), benzyl chloroformate (2.14 mL, 15.0 mmol) and triethylamine (3.48 mL, 25.0 mmol), to obtain 2.71 g of the title compound as a white solid (81%).

¹H NMR spectrum (400 MHz, CDCl₃) δ ppm: 1.23-1.36 (2H, m), 1.44 (9H, s), 1.90-2.20 (2H, m), 2.88-2.98 (2H, m), 3.60 (1H, brs), 4.10 (2H, br s), 4.44 (1H, brs), 5.12 (2H, s), 7.29-7.40 (5H, m).

mass spectrum (ESI): m/z 357 (M+Na)⁺.

(241b) Benzyl 4-[(tert-butoxycarbonyl)(n-propyl)amino]piperidine-1-carboxylate

A solution of benzyl 4-[(tert-butoxycarbonyl)amino]piperidine-1-carboxylate obtained in Example (241a) (1.00 g, 2.99 mmol) in THF (5 mL) was added to a suspension of sodium hydride (55%) (261 mg, 5.98 mmol) in THF (25 mL) at 0° C. Subsequently, propyl iodide (1.46 mL, 15.0 mmol) was added at 0° C., and the mixture was stirred at room temperature for 22 hours. Thereafter, sodium hydride (55%) (130 mg, 2.99 mmol) and propyl iodide (0.58 mL, 5.98 mmol) were added, and the mixture was heated under reflux for 22 hours. Water was added to the reaction solution, and the mixture was extracted with ethyl acetate. Thereafter, the combined organic layers were washed with brine and dried over anhydrous magnesium sulfate. Following filtration, the filtrate was concentrated under reduced pressure. The resulting residue was purified by silica gel column chromatography (elution solvent: hexane/ethyl acetate=5/1) to obtain 301 mg of the title compound as a pale yellow oily substance (27%).

¹H NMR spectrum (400 MHz, CDCl₃) δ ppm: 0.85 (3H, t, J=7.44 Hz), 1.46 (9H, s), 1.41-1.54 (4H, m), 1.62-1.72 (2H, m), 2.79 (2H, br s), 2.97 (2H, br s), 4.26 (2H, br s), 5.13 (2H, s), 7.29-7.39 (5H, m).

mass spectrum (ESI): m/z 399 (M+Na)⁺.

(241c) Ethyl 2-{4-[(tert-butoxycarbonyl)(n-propyl)amino]piperidin-1-yl}-4-methyl-1,3-thiazole-5-carboxylate The same operation as in Example (227c) was performed to obtain an oily substance from benzyl 4-[(tert-butoxycarbonyl)(n-propyl)amino]piperidine-1-carboxylate obtained in Example (241b) (295 mg, 0.78 mmol) and 10% Pd/C (30 mg). 306 mg of the title compound was obtained as a pale yellow oily substance (95%) using this oily substance, ethyl 2-bromo-4-methylthiazole-5-carboxylate (196 mg, 0.78 mmol) and diisopropylethylamine (0.27 mL, 1.57 mmol).

¹H NMR spectrum (400 MHz, CDCl₃) δ ppm: 0.85 (3H, t, J=7.44 Hz), 1.32 (3H, t, J=7.07 Hz), 1.46 (9H, s), 1.44-1.54 (2H, m), 1.78 (4H, br s), 2.54 (3H, s), 2.95-3.13 (4H, m), 4.13 (2H, d, J=13.41 Hz), 4.26 (2H, q, J=7.07 Hz).

mass spectrum (ESI): m/z 412 (M+H)⁺.

(241d) Ethyl 4-methyl-2-[4-(n-propylamino)piperidin-1-yl]-1,3-thiazole-5-carboxylate The same operation as in Example (222b) was performed using ethyl 2-{4-[(tert-butoxycarbonyl)(n-propyl)amino]piperidin-1-yl}-4-methyl-1,3-thiazole-5-carboxylate obtained in Example (241c) (302 mg, 0.73 mmol) and a 4 N hydrochloric acid/ethyl acetate solution (1.83 mL, 7.34 mmol), to obtain 206 mg of the title compound as a pale yellow oily substance (90%).

mass spectrum (ESI): m/z 312 (M+H)⁺.

(241e) Ethyl 2-(4-{[(4-chloro-5-ethyl-1H-imidazol-2-yl)carbonyl](n-propyl)amino}piperidin-1-yl)-4-methyl-1,3-thiazole-5-carboxylate The same operation as in Example (221c) was performed using ethyl 4-methyl-2-[4-(n-propylamino)piperidin-1-yl]-1,3-thiazole-5-carboxylate obtained in Example (241d) (206 mg, 0.66 mmol), 4-chloro-5-ethyl-1H-imidazole-2-carboxylic acid obtained in Example (1d) (115 mg, 0.66 mmol), WSC hydrochloride (380 mg, 1.98 mmol), 1-hydroxybenzotriazole (89 mg, 0.66 mmol) and N-methylmorpholine (0.15 mL, 1.32 mmol), to obtain 69 mg of the title compound as a white solid (22%).

mass spectrum (ESI): m/z 468, 470 (M+H)⁺.

(241f) 2-(4-{[(4-Chloro-5-ethyl-1H-imidazol-2-yl)carbonyl](n-propyl)amino}piperidin-1-yl)-4-methyl-1,3-thiazole-5-carboxylic acid The same operation as in Example (217d) was performed using ethyl 2-(4-{[(4-chloro-5-ethyl-1H-imidazol-2-yl)carbonyl](n-propyl)amino}piperidin-1-yl)-4-methyl-1,3-thiazole-5-carboxylate obtained in Example (241e) (69 mg, 0.15 mmol) and a 2 N aqueous lithium hydroxide solution (0.74 mL, 1.47 mmol), to obtain 46 mg of the title compound as a white solid (71%).

¹H NMR spectrum (400 MHz, CDCl₃) δ ppm: 0.89-0.97 (3H, m), 1.25 (3H, t, J=7.56 Hz), 1.58-1.73 (2H, m), 1.80-2.03 (4H, m), 2.57 (3H, s), 2.68 (2H, q, J=7.56 Hz), 3.13-3.33 (3H, m), 3.88-3.95 (1H, m), 4.16-4.25 (2H, m), 4.55-4.65 (0.5H, m), 5.88-5.98 (0.5H, m), 10.97 (0.5H, br s), 11.11 (0.5H, brs).

mass spectrum (ESI): m/z 440, 442 (M+H)⁺.

Example 242

2-(5-{[(4-Chloro-5-ethyl-1H-imidazol-2-yl)carbonyl]amino}-4,5,6,7-tetrahydro-1H-indazol-1-yl)-4-methyl-1,3-thiazole-5-carboxylic acid (Exemplified Compound No. 242)

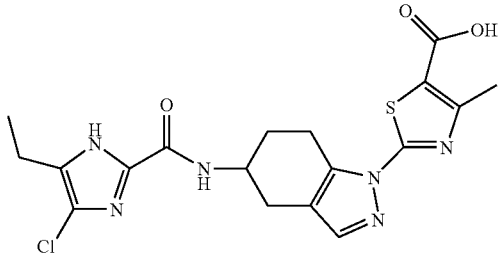

(242a) tert-Butyl {3-[(dimethylamino)methylene]-4-oxocyclohexyl}carbamate

The compound was synthesized according to the method described in the following document.

Bioorganic. Med. Chem. Lett., 2007, 2723-2727

(242b) tert-Butyl 4,5,6,7-tetrahydroindazol-5-ylcarbamate

Hydrazine monohydrate (0.11 mL, 2.35 mmol) was added to a solution of tert-butyl {3-[(dimethylamino)methylene]-4-oxocyclohexyl}carbamate obtained in Example (242a) (526 mg, 1.96 mmol) in methanol (10 mL), and the mixture was heated under reflux for 18 hours. The reaction solution was concentrated. The resulting residue was azeotropically distilled with toluene and then purified by silica gel column chromatography (elution solvent: dichloromethane/methanol=20/1) to obtain 257 mg of the title compound as an amorphous compound (55%).

¹H NMR spectrum (400 MHz, CDCl₃) δ ppm: 1.45 (9H, s), 1.81-1.92 (1H, m), 2.00-2.09 (1H, m), 2.42 (2H, dd, J=15.24, 7.44 Hz), 2.75-2.82 (2H, m), 2.85-2.96 (1H, m), 3.98 (1H, br s), 4.63 (1H, br s), 7.31 (1H, s).

mass spectrum (ESI): m/z 238 (M+H)⁺.

(242c) Ethyl 2-{5-[(tert-butoxycarbonyl)amino]-4,5,6,7-tetrahydro-1H-indazol-1-yl}-4-methyl-1,3-thiazole-5-carboxylate Ethyl 2-{5-[(tert-butoxycarbonyl)amino]-4,5,6,7-tetrahydro-2H-indazol-2-yl}-4-methyl-1,3-thiazole-5-carboxylate The same operation as in Example (223a) was performed using tert-butyl 4,5,6,7-tetrahydroindazol-5-ylcarbamate obtained in Example (242b) (246 mg, 1.04 mmol), ethyl 2-bromo-4-methylthiazole-5-carboxylate (519 mg, 2.07 mmol), copper (I) iodide (40 mg, 0.21 mmol), proline (48 mg, 0.42 mmol) and potassium carbonate (431 mg, 3.12 mmol), to obtain 96 mg of ethyl 2-{5-[(tert-butoxycarbonyl)amino]-4,5,6,7-tetrahydro-1H-indazol-1-yl}-4-methyl-1,3-thiazole-5-carboxylate as a pale yellow solid (23%).

$^1$H NMR spectrum (400 MHz, CDCl$_3$) δ ppm: 1.36 (3H, t, J=7.08 Hz), 1.45 (9H, s), 1.86-1.98 (1H, m), 2.02-2.11 (1H, m), 2.44 (1H, dd, J=15.99, 6.96 Hz), 2.67 (3H, s), 2.91 (1H, dd, J=15.62, 4.88 Hz), 3.13-3.31 (2H, m), 4.03 (1H, br s), 4.32 (2H, q, J=7.08 Hz), 4.59 (1H, br s), 7.47 (1H, s).

mass spectrum (ESI): m/z 407 (M+H)$^+$.

207 mg of ethyl 2-{5-[(tert-butoxycarbonyl)amino]-4,5,6,7-tetrahydro-2H-indazol-2-yl}-4-methyl-1,3-thiazole-5-carboxylate was obtained as an amorphous compound (49%).

$^1$H NMR spectrum (400 MHz, CDCl$_3$) δ ppm: 1.36 (3H, t, J=7.08 Hz), 1.45 (9H, s), 1.81-1.93 (1H, m), 2.03-2.13 (1H, m), 2.48 (1H, dd, J=15.99, 7.93 Hz), 2.67 (3H, s), 2.81-2.89 (2H, m), 3.00 (1H, dd, J=15.62, 4.88 Hz), 3.98 (1H, br s), 4.32 (2H, q, J=7.08 Hz), 4.59 (1H, br s), 8.02 (1H, s).

mass spectrum (ESI): m/z 407 (M+H)$^+$.

(242d) Ethyl 2-(5-amino-4,5,6,7-tetrahydro-1H-indazol-1-yl)-4-methyl-1,3-thiazole-5-carboxylate The same operation as in Example (222b) was performed using ethyl 2-{5-[(tert-butoxycarbonyl)amino]-4,5,6,7-tetrahydro-1H-indazol-1-yl}-4-methyl-1,3-thiazole-5-carboxylate obtained in Example (242c) (94 mg, 0.23 mmol) and a 4 N hydrochloric acid/ethyl acetate solution (0.58 mL, 2.31 mmol), to obtain 50 mg of the title compound as a pale yellow oily substance (71%).

mass spectrum (ESI): m/z 307 (M+H)$^+$.

(242e) Ethyl 2-(5-{[(4-chloro-5-ethyl-1H-imidazol-2-yl)carbonyl]amino}-4,5,6,7-tetrahydro-1H-indazol-1-yl)-4-methyl-1,3-thiazole-5-carboxylate The same operation as in Example (217c) was performed using ethyl 2-(5-amino-4,5,6,7-tetrahydro-1H-indazol-1-yl)-4-methyl-1,3-thiazole-5-carboxylate obtained in Example (242d) (50 mg, 0.16 mmol), 4-chloro-5-ethyl-1H-imidazole-2-carboxylic acid obtained in Example (1d) (28 mg, 0.16 mmol), WSC hydrochloride (94 mg, 0.49 mmol), 1-hydroxybenzotriazole (22 mg, 0.16 mmol) and N-methylmorpholine (0.04 mL, 0.33 mmol), to obtain 66 mg of the title compound as a white solid (88%).

$^1$H NMR spectrum (400 MHz, CDCl$_3$) δ ppm: 1.26 (3H, t, J=7.56 Hz), 1.36 (3H, t, J=7.07 Hz), 1.97-2.10 (1H, m), 2.14-2.22 (1H, m), 2.53-2.62 (1H, m), 2.67 (3H, s), 2.66-2.73 (2H, m), 2.97-3.04 (1H, m), 3.18-3.28 (1H, m), 3.33-3.42 (1H, m), 4.33 (2H, q, J=7.07 Hz), 4.29-4.46 (1H, m), 7.15 (1H, d, J=8.05 Hz), 7.49 (1H, s), 11.27 (1H, br s).

mass spectrum (ESI): m/z 463, 465 (M+H)$^+$.

(242f) 2-(5-{[(4-Chloro-5-ethyl-1H-imidazol-2-yl)carbonyl]amino}-4,5,6,7-tetrahydro-1H-indazol-1-yl)-4-methyl-1,3-thiazole-5-carboxylic acid The same operation as in Example (225e) was performed using ethyl 2-(5-{[(4-chloro-5-ethyl-1H-imidazol-2-yl)carbonyl]amino}-4,5,6,7-tetrahydro-1H-indazol-1-yl)-4-methyl-1,3-thiazole-5-carboxylate obtained in Example (242e) (64 mg, 0.14 mmol) and a 2 N aqueous lithium hydroxide solution (0.69 mL, 1.38 mmol), to obtain 36 mg of the title compound as a pale yellow solid (60%).

$^1$H NMR spectrum (400 MHz, DMSO-d$_6$) δ ppm: 1.14 (3H, t, J=7.44 Hz), 1.89-2.06 (2H, m), 2.46-2.85 (6H, m), 2.94-3.08 (1H, m), 3.27-3.36 (2H, m), 4.08-4.20 (1H, m), 7.67 (1H, s), 8.42-8.52 (1H, m), 13.19-13.38 (1H, m).

mass spectrum (ESI): m/z 435, 437 (M+H)$^+$.

Example 243

2-(5-{[(4-Chloro-5-ethyl-1H-imidazol-2-yl)carbonyl]amino}-4,5,6,7-tetrahydro-2H-indazol-2-yl)-4-methyl-1,3-thiazole-5-carboxylic acid (Exemplified Compound No. 243)

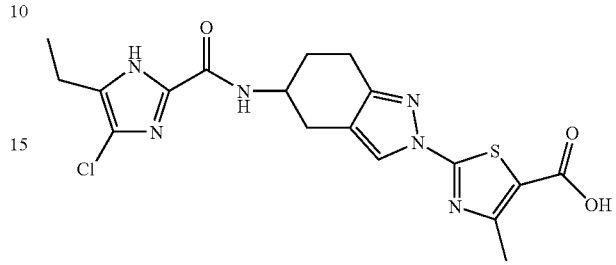

(243a) Ethyl 2-(5-amino-4,5,6,7-tetrahydro-2H-indazol-2-yl)-4-methyl-1,3-thiazole-5-carboxylate The same operation as in Example (222b) was performed using ethyl 2-{5-[(tert-butoxycarbonyl)amino]-4,5,6,7-tetrahydro-2H-indazol-2-yl}-4-methyl-1,3-thiazole-5-carboxylate obtained in Example (242c) (205 mg, 0.50 mmol) and a 4 N hydrochloric acid/ethyl acetate solution (1.26 mL, 5.04 mmol), to obtain 127 mg of the title compound as a yellow solid (82%).

mass spectrum (ESI): m/z 307 (M+H)$^+$.

(243b) Ethyl 2-(5-{[(4-chloro-5-ethyl-1H-imidazol-2-yl)carbonyl]amino}-4,5,6,7-tetrahydro-2H-indazol-2-yl)-4-methyl-1,3-thiazole-5-carboxylate The same operation as in Example (217c) was performed using ethyl 2-(5-amino-4,5,6,7-tetrahydro-2H-indazol-2-yl)-4-methyl-1,3-thiazole-5-carboxylate obtained in Example (243a) (127 mg, 0.42 mmol), 4-chloro-5-ethyl-1H-imidazole-2-carboxylic acid obtained in Example (1d) (72 mg, 0.42 mmol), WSC hydrochloride (239 mg, 1.25 mmol), 1-hydroxybenzotriazole (56 mg, 0.42 mmol) and N-methylmorpholine (0.09 mL, 0.83 mmol), to obtain 146 mg of the title compound as a pale yellow solid (76%).

$^1$H NMR spectrum (400 MHz, CDCl$_3$) δ ppm: 1.26 (3H, t, J=7.68 Hz), 1.36 (3H, t, J=7.07 Hz), 1.93-2.04 (1H, m), 2.14-2.23 (1H, m), 2.68 (3H, s), 2.58-2.73 (3H, m), 2.82-3.02 (2H, m), 3.09 (1H, dd, J=15.73, 5.49 Hz), 4.33 (2H, q, J=7.07 Hz), 4.29-4.43 (1H, m), 7.15 (1H, d, J=8.29 Hz), 8.06 (1H, s), 11.15 (1H, br s).

mass spectrum (ESI): m/z 463, 465 (M+H)$^+$.

(243c) 2-(5-{[(4-Chloro-5-ethyl-1H-imidazol-2-yl)carbonyl]amino}-4,5,6,7-tetrahydro-2H-indazol-2-yl)-4-methyl-1,3-thiazole-5-carboxylic acid The same operation as in Example (223d) was performed using ethyl 2-(5-{[(4-chloro-5-ethyl-1H-imidazol-2-yl)carbonyl]amino}-4,5,6,7-tetrahydro-2H-indazol-2-yl)-4-methyl-1,3-thiazole-5-carboxylate obtained in Example (243b) (78 mg, 0.17 mmol) and a 2 N aqueous lithium hydroxide solution (0.84 mL, 1.68 mmol), to obtain 54 mg of the title compound as a pale yellow solid (74%).

$^1$H NMR spectrum (400 MHz, DMSO-d$_6$) δ ppm: 1.15 (3H, t, J=7.32 Hz), 1.87-2.02 (2H, m), 2.56 (2H, q, J=7.32 Hz), 2.58 (3H, s), 2.65-2.90 (4H, m), 4.08-4.19 (1H, m), 8.23 (1H, s), 8.51 (1H, d, J=8.29 Hz), 13.27 (1H, s).

mass spectrum (ESI): m/z 435, 437 (M+H)$^+$.

Example 244 cis(±)-5-(4-{[(4-Chloro-5-ethyl-1H-imidazol-2-yl)carbonyl]amino}-3-methoxypiperidin-1-yl)thiophene-2-carboxylic acid (Exemplified Compound No. 244)

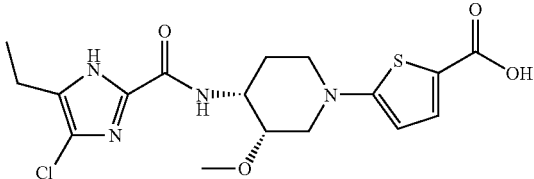

(244a) Methyl 5-bromothiophene-2-carboxylate

The compound was synthesized according to the method described in the following document.
WO 2005/79791 A1

(244b) Methyl cis(±)-5-(4-{[(benzyloxy)carbonyl]amino}-3-methoxypiperidin-1-yl)thiophene-2-carboxylate A suspension of ethyl 5-bromothiophene-2-carboxylate obtained in Example (244a) (100 mg, 0.45 mmol), benzyl cis(±)-(3-methoxypiperidin-4-yl)-carbamate obtained in Example (40b) (143 mg, 0.54 mmol), palladium acetate (10 mg, 0.05 mmol), BINAP (28 mg, 0.05 mmol) and cesium carbonate (206 mg, 0.63 mmol) in toluene was stirred at 110° C. for 39 hours. The reaction solution was diluted with ethyl acetate, washed with water and brine, and then dried over anhydrous magnesium sulfate. Following filtration, the filtrate was concentrated under reduced pressure. The resulting residue was purified by silica gel column chromatography (elution solvent: hexane/ethyl acetate=2/1) to obtain 110 mg of the title compound as a yellow oily substance (60%).

mass spectrum (ESI): m/z 405 (M+H)$^+$.

(244c) Methyl cis(±)-5-(4-amino-3-methoxypiperidin-1-yl)thiophene-2-carboxylate

The same operation as in Example (233c) was performed using methyl cis(±)-5-(4-{[(benzyloxy)carbonyl]amino}-3-methoxypiperidin-1-yl)thiophene-2-carboxylate obtained in Example (244b) (81 mg, 0.20 mmol) and a 30% hydrogen bromide/acetic acid solution (0.39 mL, 2.00 mmol), to obtain 30 mg of the title compound as a pale yellow oily substance (56%).

mass spectrum (ESI): m/z 271 (M+H)$^+$.

(244d) Methyl cis(±)-5-(4-{[(4-chloro-5-ethyl-1H-imidazol-2-yl)carbonyl]amino}-3-methoxypiperidin-1-yl) thiophene-2-carboxylate The same operation as in Example (221c) was performed using methyl cis(±)-5-(4-amino-3-methoxypiperidin-1-yl)thiophene-2-carboxylate obtained in Example (244c) (76 mg, 0.28 mmol), 4-chloro-5-ethyl-1H-imidazole-2-carboxylic acid obtained in Example (1d) (54 mg, 0.31 mmol), WSC hydrochloride (162 mg, 0.84 mmol), 1-hydroxybenzotriazole (38 mg, 0.28 mmol) and N-methylmorpholine (0.06 mL, 0.56 mmol), to obtain 60 mg of the title compound as a pale brown solid (50%).

$^1$H NMR spectrum (400 MHz, CDCl$_3$) δ ppm: 1.27 (3H, t, J=7.56 Hz), 1.79-1.87 (1H, m), 2.10-2.20 (1H, m), 2.70 (2H, q, J=7.56 Hz), 3.01-3.10 (2H, m), 3.44 (3H, s), 3.55 (1H, s), 3.63-3.70 (1H, m), 3.82 (3H, s), 3.88-3.95 (1H, m), 4.19-4.28 (1H, m), 6.04 (1H, d, J=4.15 Hz), 7.48 (1H, d, J=8.78 Hz), 7.55 (1H, br s), 11.10 (1H, br s).

mass spectrum (ESI): m/z 427, 429 (M+H)$^+$.

(244e) cis(±)-5-(4-{[(4-Chloro-5-ethyl-1H-imidazol-2-yl)carbonyl]amino}-3-methoxypiperidin-1-yl)thiophene-2-carboxylic acid The same operation as in Example (217d) was performed using methyl cis(±)-5-(4-{[(4-chloro-5-ethyl-1H-imidazol-2-yl)carbonyl]amino}-3-methoxypiperidin-1-yl)thiophene-2-carboxylate obtained in Example (244d) (59 mg, 0.14 mmol) and a 2 N aqueous lithium hydroxide solution (0.69 mL, 1.38 mmol), to obtain 29 mg of the title compound as a pale blue solid (51%).

$^1$H NMR spectrum (400 MHz, DMSO-d$_6$) δ ppm: 1.14 (3H, t, J=7.56 Hz), 1.64-1.74 (1H, m), 1.88-2.01 (1H, m), 2.48-2.59 (2H, m), 3.07-3.19 (2H, m), 3.29-3.36 (3H, m), 3.54-3.63 (2H, m), 3.84-3.92 (1H, m), 4.12-4.21 (1H, m), 6.18 (1H, d, J=4.15 Hz), 7.40-7.43 (1H, m), 7.65 (1H, d, J=8.29 Hz), 12.15 (1H, br s), 13.36 (1H, s).

mass spectrum (ESI): m/z 413, 415 (M+H)$^+$.

Example 245 cis(±)-5-(4-{[(4-Chloro-5-ethyl-1H-imidazol-2-yl)carbonyl]amino}-3-methoxypiperidin-1-yl)-3-methylthiophene-2-carboxylic acid (Exemplified Compound No. 245)

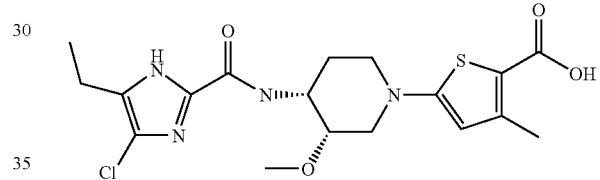

(245a) Methyl 5-bromo-3-methylthiophene-2-carboxylate

The compound was synthesized according to the method described in the following document.
WO 2007/124546 A1

(245b) Methyl cis(±)-5-(4-{[(benzyloxy)carbonyl]amino}-3-methoxypiperidin-1-yl)-3-methylthiophene-2-carboxylate The same operation as in Example (244b) was performed using methyl 5-bromo-3-methylthiophene-2-carboxylate obtained in Example (245a) (218 mg, 0.93 mmol), benzyl cis(±)-(3-methoxypiperidin-4-yl)-carbamate obtained in Example (40b) (270 mg, 1.02 mmol), palladium acetate (42 mg, 0.19 mmol), BINAP (115 mg, 0.19 mmol) and cesium carbonate (423 mg, 1.30 mmol), to obtain 92 mg of the title compound as a yellow oily substance (24%).

$^1$H NMR spectrum (400 MHz, CDCl$_3$) δ ppm: 1.76-1.85 (1H, m), 1.89-2.02 (1H, m), 2.43 (3H, s), 2.93-3.04 (2H, m), 3.40 (3H, s), 3.47 (1H, br s), 3.53-3.61 (1H, m), 3.79 (3H, s), 3.74-3.88 (2H, m), 5.11 (2H, s), 5.22 (1H, br s), 5.86 (1H, s), 7.30-7.39 (5H, m).

mass spectrum (ESI): m/z 419 (M+H)$^+$.

(245c) Methyl cis(±)-5-(4-amino-3-methoxypiperidin-1-yl)-3-methylthiophene-2-carboxylate The same operation as in Example (233c) was performed using methyl cis(±)-5-(4-{[(benzyloxy)carbonyl]amino}-3-methoxypiperidin-1-yl)-3-methylthiophene-2-carboxylate obtained in Example (245b) (88 mg, 0.21 mmol) and a 30% hydrogen bromide/acetic acid solution (0.41 mL, 2.10 mmol), to obtain 50 mg of the title compound as a yellow oily substance (84%).

mass spectrum (ESI): m/z 285 (M+H)$^+$.

(245d) Methyl cis(±)-5-(4-{[(4-chloro-5-ethyl-1H-imidazol-2-yl)carbonyl]amino}-3-methoxypiperidin-1-yl)-3-methylthiophene-2-carboxylate The same operation as in Example (221c) was performed using methyl cis(±)-5-(4-amino-3-methoxypiperidin-1-yl)-3-methylthiophene-2-carboxylate obtained in Example (245c) (50 mg, 0.18 mmol), 4-chloro-5-ethyl-1H-imidazole-2-carboxylic acid obtained in Example (1d) (46 mg, 0.26 mmol), WSC hydrochloride (101 mg, 0.53 mmol), 1-hydroxybenzotriazole (26 mg, 0.19 mmol) and N-methylmorpholine (0.04 mL, 0.35 mmol), to obtain 67 mg of the title compound as a white solid (86%).

$^1$H NMR spectrum (400 MHz, CDCl$_3$) δ ppm: 1.26 (3H, t, J=7.56 Hz), 1.77-1.85 (1H, m), 2.05-2.17 (1H, m), 2.45 (3H, s), 2.69 (2H, q, J=7.56 Hz), 2.98-3.07 (2H, m), 3.43 (3H, s), 3.53 (1H, s), 3.59-3.67 (1H, m), 3.79 (3H, s), 3.85-3.92 (1H, m), 4.17-4.26 (1H, m), 5.89 (1H, s), 7.44 (1H, d, J=8.78 Hz), 10.82 (1H, br s).

mass spectrum (ESI): m/z 441, 443 (M+H)$^+$.

(245e) cis(±)-5-(4-{[(4-Chloro-5-ethyl-1H-imidazol-2-yl)carbonyl]amino}-3-methoxypiperidin-1-yl)-3-methylthiophene-2-carboxylic acid Methyl cis(±)-5-(4-{[(4-chloro-5-ethyl-1H-imidazol-2-yl)carbonyl]amino}-3-methoxypiperidin-1-yl)-3-methylthiophene-2-carboxylate obtained in Example (245d) (65 mg, 0.15 mmol) was dissolved in methanol (1.5 mL). A 2 N aqueous lithium hydroxide solution (0.74 mL, 1.47 mmol) was added, and the mixture was stirred at room temperature for 50 minutes. THF (1 mL) was added, and the mixture was stirred for 19 hours, and then further stirred at 40° C. for 6.5 hours and at 70° C. for two hours. Water was added to the reaction solution, and then the mixture was washed with ethyl acetate. A 1 N aqueous hydrochloric acid solution (2.5 mL) was added to the aqueous layer, followed by extraction with ethyl acetate. The combined organic layers were dried over anhydrous magnesium sulfate and then filtered, and the filtrate was concentrated under reduced pressure. The resulting solid was suspended and washed in diethyl ether to obtain 23 mg of the title compound as a pale blue solid (37%).

$^1$H NMR spectrum (400 MHz, DMSO-d$_6$) δ ppm: 1.14 (3H, t, J=7.57 Hz), 1.64-1.73 (1H, m), 1.87-1.99 (1H, m), 2.33 (3H, s), 2.55 (2H, q, J=7.57 Hz), 3.03-3.15 (2H, m), 3.34 (3H, s), 3.55 (2H, br s), 3.80-3.88 (1H, m), 4.11-4.20 (1H, m), 6.06 (1H, s), 7.63 (1H, d, J=8.30 Hz), 11.95 (1H, br s), 13.35 (1H, br s).

mass spectrum (ESI): m/z 427, 429 (M+H)$^+$.

Example 246 cis(±)-3-Acetyl-5-(4-{[(4-chloro-5-ethyl-1H-imidazol-2-yl)carbonyl]amino}-3-methoxypiperidin-1-yl)thiophene-2-carboxylic acid (Exemplified Compound No. 246)

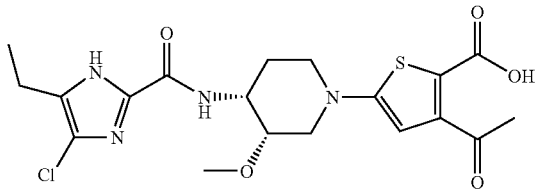

(246a) Methyl 5-bromo-3-(dibromomethyl)thiophene-2-carboxylate

A solution of methyl 5-bromo-3-methylthiophene-2-carboxylate obtained in the Example (245a) (1.18 g, 5.02 mmol), N-bromosuccinimide (2.23 g, 12.5 mmol) and AIBN (82 mg, 0.50 mmol) in carbon tetrachloride (50 mL) was stirred at 80° C. for 13.5 hours. The reaction solution was concentrated under reduced pressure, and then hexane was added to the resulting residue. The mixture was filtered. The filtrate was concentrated under reduced pressure. Thereafter, the resulting residue was purified by silica gel column chromatography (elution solvent: hexane/ethyl acetate=49/1) to obtain 1.59 g of the title compound as a pale yellow solid (81%).

$^1$H NMR spectrum (400 MHz, CDCl$_3$) δ ppm: 3.89 (3H, s), 7.58 (1H, s), 7.68 (1H, s).

(246b) Methyl 5-bromo-3-formylthiophene-2-carboxylate

Silver nitrate (1.43 g, 8.39 mmol) was added to a mixed solution of methyl 5-bromo-3-(dibromomethyl)thiophene-2-carboxylate obtained in Example (246a) (1.57 g, 4.00 mmol) in ethanol/water (30 mL/10 mL), and the mixture was stirred at 80° C. for three hours. Concentrated hydrochloric acid was added to the reaction solution at 0° C., and then the mixture was filtered. The filtrate was concentrated under reduced pressure. Then, saturated aqueous sodium bicarbonate solution was added to the resulting residue, and the aqueous layer was extracted with chloroform. The combined organic layers were dried over anhydrous magnesium sulfate, and then the filtrate was concentrated under reduced pressure to obtain 980 mg of the title compound as a pale yellow solid (98%).

$^1$H NMR spectrum (400 MHz, CDCl$_3$) δ ppm: 3.95 (3H, s), 7.55 (1H, s), 10.54 (1H, s).

(246c) Methyl cis(±)-5-(4-{[(benzyloxy)carbonyl]amino}-3-methoxypiperidin-1-yl)-3-formylthiophene-2-carboxylate The same operation as in Example (244b) was performed using methyl 5-bromo-3-formylthiophene-2-carboxylate obtained in Example (246b) (974 mg, 3.91 mmol), benzyl cis(±)-(3-methoxypiperidin-4-yl)-carbamate obtained in Example (40b) (1.10 g, 4.16 mmol), palladium acetate (176 mg, 0.78 mmol), BINAP (0.49 g, 0.78 mmol) and cesium carbonate (1.78 g, 5.47 mmol), to obtain 354 mg of the title compound as a yellow oily substance (21%).

$^1$H NMR spectrum (400 MHz, CDCl$_3$) δ ppm: 1.79-1.88 (1H, m), 1.91-2.03 (1H, m), 3.01-3.11 (2H, m), 3.39 (3H, s), 3.50 (1H, br s), 3.58-3.66 (1H, m), 3.88 (3H, s), 3.81-3.93 (2H, m), 5.12 (2H, s), 5.19-5.28 (1H, m), 6.47 (1H, s), 7.31-7.41 (5H, m), 10.56 (1H, s).

mass spectrum (ESI): m/z 433 (M+H)$^+$.

(246d) Methyl 5-((3R*,4S*)-4-{[(benzyloxy)carbonyl]amino}-3-methoxypiperidin-1-yl)-3-(1-hydroxyethyl)thiophene-2-carboxylate A solution of methylmagnesium bromide (0.97 mol/L) in THF (1.59 mL, 1.54 mmol) was added to a solution of methyl cis(±)-5-(4-{[(benzyloxy)carbonyl]amino}-3-methoxypiperidin-1-yl)-3-formylthiophene-2-carboxylate obtained in Example (246c) (333 mg, 0.77 mmol) in THF (8 mL) at 0° C., and the mixture was stirred at room temperature for five hours. Saturated ammonium chloride solution was added to the reaction solution, and the reaction solution was extracted with ethyl acetate. The combined organic layers were washed with brine and then dried over anhydrous magnesium sulfate. Following filtration, the filtrate was concentrated under reduced pressure. The resulting residue was purified by silica gel column chromatography (elution solvent: hexane/ethyl acetate=1/1) to obtain 223 mg of the title compound as a pale yellow solid (65%).

$^1$H NMR spectrum (400 MHz, CDCl$_3$) δ ppm: 1.50 (3H, d, J=6.59 Hz), 1.78-1.87 (1H, m), 1.91-2.03 (1H, m), 2.97-3.09 (2H, m), 3.39 (3H, s), 3.49 (1H, s), 3.56-3.66 (1H, m), 3.81 (3H, s), 3.78-3.93 (2H, m), 4.52 (0.5H, br s), 5.12 (2H, s), 5.06-5.35 (1.5H, m), 6.06 (1H, s), 7.31-7.42 (5H, m).

mass spectrum (ESI): m/z 449 (M+H)$^+$.

(246e) Methyl cis(±)-3-acetyl-5-(4-{[(benzyloxy)carbonyl]amino}-3-methoxypiperidin-1-yl)thiophene-2-carboxylate The Dess-Martin reagent (305 mg, 0.72 mmol) was added to a solution of methyl 5-((3R*,4S*)-4-{[(benzyloxy)carbonyl]amino}-3-methoxypiperidin-1-yl)-3-(1-hydroxyethyl)thiophene-2-carboxylate obtained in Example (246d) (215 mg, 0.48 mmol) in dichloromethane (5 mL) at room temperature, followed by stirring for one hour. Aqueous sodium thiosulfate solution was added to the reaction solution, followed by stirring at room temperature. Then, the mixture was extracted with chloroform. The combined organic layers were dried over anhydrous magnesium sulfate. Following filtration, the filtrate was concentrated under reduced pressure. The resulting residue was purified by silica gel column chromatography (elution solvent: hexane/ethyl acetate=3/1) to obtain 106 mg of the title compound as a yellow oily substance (50%).

$^1$H NMR spectrum (400 MHz, CDCl$_3$) δ ppm: 1.77-1.86 (1H, m), 1.91-2.03 (1H, m), 2.55 (3H, s), 2.99-3.09 (2H, m), 3.39 (3H, s), 3.49 (1H, br s), 3.54-3.63 (1H, m), 3.80 (3H, s), 3.76-3.88 (2H, m), 5.12 (2H, s), 5.19-5.26 (1H, m), 5.99 (1H, s), 7.33-7.40 (5H, m).

(246f) cis(±)-3-Acetyl-5-(4-{[(4-chloro-5-ethyl-1H-imidazol-2-yl)carbonyl]amino}-3-methoxypiperidin-1-yl)thiophene-2-carboxylic acid The same operation as in Example (233c) was performed using methyl cis(±)-3-acetyl-5-(4-{[(benzyloxy)carbonyl]amino}-3-methoxypiperidin-1-yl)thiophene-2-carboxylate obtained in Example (246e) (106 mg, 0.24 mmol) and a 30% hydrogen bromide/acetic acid solution (0.47 mL, 2.37 mmol), to obtain an amorphous compound.

The same operation as in Example (236d) was performed using the amorphous compound obtained by the above operation, 4-chloro-5-ethyl-1H-imidazole-2-carboxylic acid obtained in Example (1d) (41 mg, 0.24 mmol), WSC hydrochloride (90 mg, 0.47 mmol), 1-hydroxybenzotriazole (25 mg, 0.19 mmol) and N-methylmorpholine (0.04 mL, 0.31 mmol), to obtain an oily substance.

The same operation as in Example (217d) was performed using the oily substance obtained by the above operation and a 2 N aqueous lithium hydroxide solution (0.27 mL, 0.53 mmol), to obtain 13 mg of the title compound as a brown solid (54%).

$^1$H NMR spectrum (400 MHz, DMSO-d$_6$) δ ppm: 1.14 (3H, t, J=7.56 Hz), 1.63-1.73 (1H, m), 1.87-2.01 (1H, m), 2.46 (3H, s), 2.55 (2H, q, J=7.56 Hz), 3.09-3.21 (2H, m), 3.34 (3H, s), 3.53-3.64 (2H, m), 3.84-3.94 (1H, m), 4.12-4.21 (1H, m), 6.25 (1H, s), 7.65 (1H, d, J=8.78 Hz), 13.36 (1H, br s).

mass spectrum (ESI): m/z 455, 457 (M+H)$^+$.

Example 247 cis(±)-2-(4-{[(4-Chloro-5-ethyl-1H-imidazol-2-yl)carbonyl]amino}-3-ethoxypiperidin-1-yl)-4-(ethylcarbamoyl)-1,3-thiazole-5-carboxylic acid (Exemplified Compound No. 247)

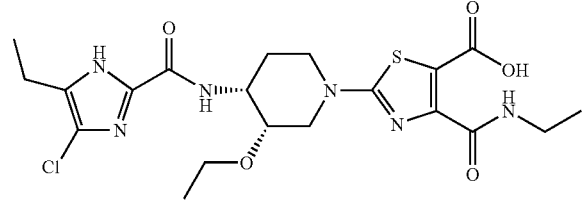

(247a) Ethyl cis(±)-2-(4-{[(4-chloro-5-ethyl-1H-imidazol-2-yl)carbonyl]amino}-3-ethoxypiperidin-1-yl)-4-(ethylcarbamoyl)-1,3-thiazole-5-carboxylate Ethylamine (2.0 M solution in THF) (0.60 mL, 1.20 mmol), WSC hydrochloride (345 mg, 1.80 mmol) and 1-hydroxybenzotriazole (8 1 mg, 0.60 mmol) were added to a mixed solution of cis(±)-2-(4-{[(4-chloro-5-ethyl-1H-imidazol-2-yl)carbonyl]amino}-3-ethoxypiperidin-1-yl)-5-(ethoxycarbonyl)-1,3-thiazole-4-carboxylic acid obtained in Example (50a) (300 mg, 0.60 mmol) in DMA/dichloromethane (6 mL/6 mL) at room temperature, followed by stirring for five hours. The reaction solution was diluted with ethyl acetate, and then the mixture was washed with a 1 N aqueous hydrochloric acid solution and 5% saline. The organic layer was dried over anhydrous magnesium sulfate. Following filtration, the filtrate was concentrated under reduced pressure. The resulting residue was suspended and washed in diethyl ether to obtain 257 mg of the title compound as a white solid (81%).

$^1$H NMR spectrum (400 MHz, CDCl$_3$) δ ppm: 1.16 (3H, t, J=7.32 Hz), 1.22-1.29 (6H, m), 1.35 (3H, t, J=7.07 Hz), 1.75-1.82 (1H, m), 2.05-2.16 (1H, m), 2.69 (2H, q, J=7.56 Hz), 3.14-3.28 (2H, m), 3.40-3.51 (3H, m), 3.62 (1H, br s), 3.70-3.80 (1H, m), 4.05-4.14 (1H, m), 4.19-4.35 (3H, m), 4.39-4.48 (1H, m), 7.45-7.51 (1H, m), 8.49 (1H, br s).

mass spectrum (ESI): m/z 527, 529 (M+H)$^+$.

(247b) cis(±)-2-(4-{[(4-Chloro-5-ethyl-1H-imidazol-2-yl)carbonyl]amino}-3-ethoxypiperidin-1-yl)-4-(ethylcarbamoyl)-1,3-thiazole-5-carboxylic acid A 2 N aqueous lithium hydroxide solution (2.41 mL, 4.82 mmol) was added to a solution of ethyl cis(±)-2-(4-{[(4-chloro-5-ethyl-1H-imidazol-2-yl)carbonyl]amino}-3-ethoxypiperidin-1-yl)-4-(ethylcarbamoyl)-1,3-thiazole-5-carboxylate obtained in Example (247a) (254 mg, 0.48 mmol) in methanol (5 mL) at room temperature, followed by stirring for 5.5 hours. The reaction solution was concentrated under reduced pressure, and then a 1 N aqueous hydrochloric acid solution was added to the resulting residue at 0° C. The precipitated solid was collected by filtration, and then washed with water and ethyl acetate to obtain 187 mg of the title compound as a white solid (78%).

$^1$H NMR spectrum (400 MHz, DMSO-d$_6$) δ ppm: 1.03 (3H, t, J=7.08 Hz), 1.11-1.18 (6H, m), 1.65-1.74 (1H, m), 1.83-1.95 (1H, m), 2.55 (2H, q, J=7.32 Hz), 3.24-3.50 (7H, m), 3.62-3.73 (2H, m), 4.21 (1H, br s), 7.66 (1H, d, J=8.30 Hz), 9.38-9.45 (1H, m), 13.36 (1H, s).

mass spectrum (ESI): m/z 499, 501 (M+H)$^+$.

Example 248 cis(±)-2-(4-{[(4-Chloro-5-ethyl-1H-imidazol-2-yl)carbonyl]amino}-3-ethoxypiperidin-1-yl)-4-(isopropylcarbamoyl)-1,3-thiazole-5-carboxylic acid (Exemplified Compound No. 248)

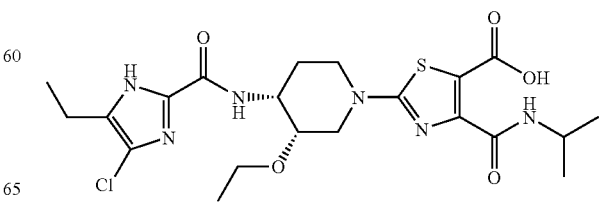

(248a) Ethyl cis(±)-2-(4-{[(4-chloro-5-ethyl-1H-imidazol-2-yl)carbonyl]amino}-3-ethoxypiperidin-1-yl)-4-(isopropylcarbamoyl)-1,3-thiazole-5-carboxylate The same operation as in Example (247a) was performed using cis(±)-2-(4-{[(4-chloro-5-ethyl-1H-imidazol-2-yl)carbonyl]amino}-3-ethoxypiperidin-1-yl)-5-(ethoxycarbonyl)-1,3-thiazole-4-carboxylic acid obtained in Example (50a) (300 mg, 0.60 mmol), isopropylamine (0.10 mL, 1.20 mmol), WSC hydrochloride (345 mg, 1.80 mmol) and 1-hydroxybenzotriazole (81 mg, 0.60 mmol), to obtain 241 mg of the title compound as a white solid (74%).

$^1$H NMR spectrum (400 MHz, CDCl$_3$) δ ppm: 1.16 (3H, t, J=7.08 Hz), 1.24-1.29 (9H, m), 1.35 (3H, t, J=7.08 Hz), 1.74-1.82 (1H, m), 2.01-2.14 (1H, m), 2.69 (2H, q, J=7.08 Hz), 3.14-3.28 (2H, m), 3.40-3.49 (1H, m), 3.62 (1H, s), 3.71-3.80 (1H, m), 4.05-4.15 (1H, m), 4.17-4.35 (4H, m), 4.39-4.48 (1H, m), 7.44 (1H, d, J=9.03 Hz), 8.35-8.40 (1H, m), 10.92 (1H, br s).

mass spectrum (ESI): m/z 541, 543 (M+H)$^+$.

(248b) cis(±)-2-(4-{[(4-Chloro-5-ethyl-1H-imidazol-2-yl)carbonyl]amino}-3-ethoxypiperidin-1-yl)-4-(isopropylcarbamoyl)-1,3-thiazole-5-carboxylic acid The same operation as in Example (247b) was performed using ethyl cis(±)-2-(4-{[(4-chloro-5-ethyl-1H-imidazol-2-yl)carbonyl]amino}-3-ethoxypiperidin-1-yl)-4-(isopropylcarbamoyl)-1,3-thiazole-5-carboxylate obtained in Example (248a) (239 mg, 0.44 mmol) and a 2 N aqueous lithium hydroxide solution (2.21 mL, 4.42 mmol), to obtain 148 mg of the title compound as a white solid (65%).

$^1$H NMR spectrum (400 MHz, CDCl$_3$) δ ppm: 1.18 (3H, t, J=7.32 Hz), 1.24-1.32 (9H, m), 1.77-1.85 (1H, m), 2.00-2.12 (1H, m), 2.70 (2H, q, J=7.57 Hz), 3.14-3.26 (2H, m), 3.42-3.52 (1H, m), 3.61-3.74 (2H, m), 4.12-4.31 (4H, m), 7.43 (1H, d, J=8.79 Hz), 7.55-7.61 (1H, m), 10.65 (1H, br s).

mass spectrum (ESI): m/z 513, 515 (M+H)$^+$.

Example 249 cis(±)-2-(4-{[(4-Chloro-5-ethyl-1H-imidazol-2-yl)carbonyl]amino}-3-ethoxypiperidin-1-yl)-4-(cyclopropylcarbamoyl)-1,3-thiazole-5-carboxylic acid (Exemplified Compound No. 249)

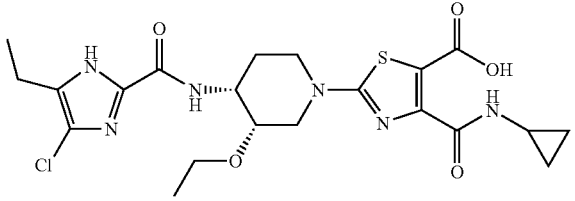

(249a) Ethyl cis(±)-2-(4-{[(4-chloro-5-ethyl-1H-imidazol-2-yl)carbonyl]amino}-3-ethoxypiperidin-1-yl)-4-(cyclopropylcarbamoyl)-1,3-thiazole-5-carboxylate The same operation as in Example (247a) was performed using cis(±)-2-(4-{[(4-chloro-5-ethyl-1H-imidazol-2-yl)carbonyl]amino}-3-ethoxypiperidin-1-yl)-5-(ethoxycarbonyl)-1,3-thiazole-4-carboxylic acid obtained in Example (50a) (300 mg, 0.60 mmol), cyclopropylamine (0.08 mL, 1.20 mmol), WSC hydrochloride (345 mg, 1.80 mmol) and 1-hydroxybenzotriazole (81 mg, 0.60 mmol), to obtain 248 mg of the title compound as a white solid (77%).

$^1$H NMR spectrum (400 MHz, CDCl$_3$) δ ppm: 0.60-0.66 (2H, m), 0.80-0.87 (2H, m), 1.15 (3H, t, J=7.32 Hz), 1.26 (3H, t, J=7.56 Hz), 1.35 (3H, t, J=7.19 Hz), 1.75-1.82 (1H, m), 2.04-2.13 (1H, m), 2.69 (2H, q, J=7.56 Hz), 2.90-2.97 (1H, m), 3.13-3.28 (2H, m), 3.40-3.49 (1H, m), 3.60-3.64 (1H, m), 3.70-3.80 (1H, m), 4.03-4.14 (1H, m), 4.19-4.34 (3H, m), 4.40-4.48 (1H, m), 7.44-7.49 (1H, m), 8.70 (1H, br s).

mass spectrum (ESI): m/z 539, 541 (M+H)$^+$.

(249b) cis(±)-2-(4-{[(4-Chloro-5-ethyl-1H-imidazol-2-yl)carbonyl]amino}-3-ethoxypiperidin-1-yl)-4-(cyclopropylcarbamoyl)-1,3-thiazole-5-carboxylic acid The same operation as in Example (247b) was performed using ethyl cis(±)-2-(4-{[(4-chloro-5-ethyl-1H-imidazol-2-yl)carbonyl]amino}-3-ethoxypiperidin-1-yl)-4-(cyclopropylcarbamoyl)-1,3-thiazole-5-carboxylate obtained in Example (249a) (246 mg, 0.46 mmol) and a 2 N aqueous lithium hydroxide solution (2.28 mL, 4.56 mmol), to obtain 161 mg of the title compound as a white solid (69%).

$^1$H NMR spectrum (400 MHz, DMSO-d$_6$) δ ppm: 0.72-0.83 (4H, m), 1.02 (3H, t, J=7.32 Hz), 1.14 (3H, t, J=7.57 Hz), 1.64-1.72 (1H, m), 1.81-1.94 (1H, m), 2.55 (2H, q, J=7.57 Hz), 2.87-2.96 (1H, m), 3.25-3.49 (5H, m), 3.61-3.71 (2H, m), 4.15-4.25 (1H, m), 7.65 (1H, d, J=8.79 Hz), 9.20 (1H, br s), 13.36 (1H, s).

mass spectrum (ESI): m/z 511, 513 (M+H)$^+$.

Example 250 cis(±)-2-(4-{[(4-Chloro-5-ethyl-1H-imidazol-2-yl)carbonyl]amino}-3-ethoxypiperidin-1-yl)-4-[(2-fluoroethyl)carbamoyl]-1,3-thiazole-5-carboxylic acid (Exemplified Compound No. 250)

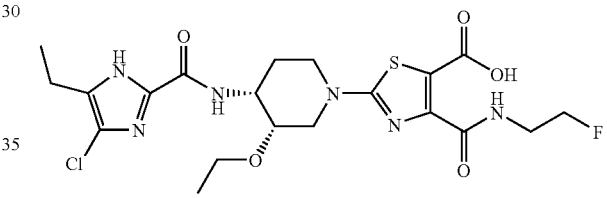

(250a) Ethyl cis(±)-2-(4-{[(4-chloro-5-ethyl-1H-imidazol-2-yl)carbonyl]amino}-3-ethoxypiperidin-1-yl)-4-[(2-fluoroethyl)carbamoyl]-1,3-thiazole-5-carboxylate The same operation as in Example (247a) was performed using cis(±)-2-(4-{[(4-chloro-5-ethyl-1H-imidazol-2-yl)carbonyl]amino}-3-ethoxypiperidin-1-yl)-5-(ethoxycarbonyl)-1,3-thiazole-4-carboxylic acid obtained in Example (50a) (250 mg, 0.50 mmol), 2-fluoroethylamine hydrochloride (100 mg, 1.00 mmol), WSC hydrochloride (288 mg, 1.50 mmol) and 1-hydroxybenzotriazole (68 mg, 0.50 mmol), to obtain 216 mg of the title compound as a white solid (79%).

$^1$H NMR spectrum (400 MHz, CDCl$_3$) δ ppm: 1.16 (3H, t, J=7.07 Hz), 1.26 (3H, t, J=7.56 Hz), 1.35 (3H, t, J=7.32 Hz), 1.60-1.83 (1H, m), 2.00-2.15 (1H, m), 2.63-2.73 (2H, m), 3.12-3.28 (2H, m), 3.38-3.49 (1H, m), 3.61 (1H, brs), 3.67-3.81 (3H, m), 4.02-4.13 (1H, m), 4.17-4.36 (3H, m), 4.37-4.48 (1H, m), 4.50-4.70 (2H, m), 7.47 (1H, br s), 8.93 (1H, br s), 11.31 (1H, br s).

mass spectrum (ESI): m/z 545, 547 (M+H)$^+$.

(250b) cis(±)-2-(4-{[(4-Chloro-5-ethyl-1H-imidazol-2-yl)carbonyl]amino}-3-ethoxypiperidin-1-yl)-4-[(2-fluoroethyl)carbamoyl]-1,3-thiazole-5-carboxylic acid A 2 N aqueous lithium hydroxide solution (1.92 mL, 3.83 mmol) was added to a solution of ethyl cis(±)-2-(4-{[(4-chloro-5-ethyl-1H-imidazol-2-yl)carbonyl]amino}-3-ethoxypiperidin-1-yl)-4-[(2-fluoroethyl)carbamoyl]-1,3-thiazole-5-carboxylate obtained in Example (250a) (209 mg, 0.38 mmol) in methanol (4 mL) at room temperature, followed by stirring for 4.5 hours. The reaction solution was concentrated under reduced pressure, and then a 1 N aqueous hydrochloric acid solution was added to the resulting residue. The aqueous layer was extracted with ethyl acetate. The combined organic layers were dried over anhydrous magnesium sulfate and filtered, and then the filtrate was concentrated under reduced pressure. The resulting solid was suspended and washed in diethyl ether to obtain 82 mg of the title compound as a milk white solid (41%).

$^1$H NMR spectrum (400 MHz, DMSO-$d_6$) δ ppm: 1.03 (3H, t, J=6.83 Hz), 1.14 (3H, t, J=7.56 Hz), 1.66-1.74 (1H, m), 1.83-1.97 (1H, m), 2.55 (2H, q, J=7.56 Hz), 3.30-3.38 (3H, m), 3.39-3.50 (2H, m), 3.57-3.74 (4H, m), 4.17-4.26 (1H, m), 4.59 (2H, dt, J=47.23, 5.00 Hz), 7.65 (1H, d, J=8.54 Hz), 9.50 (1H, br s), 13.36 (1H, s).

mass spectrum (ESI): m/z 517, 519 (M+H)$^+$.

Example 251 cis(±)-2-(4-{[(4-Chloro-5-ethyl-1H-imidazol-2-yl)carbonyl]amino}-3-ethoxypiperidin-1-yl)-4-[(2,2-difluoroethyl)carbamoyl]-1,3-thiazole-5-carboxylic acid (Exemplified Compound No. 251)

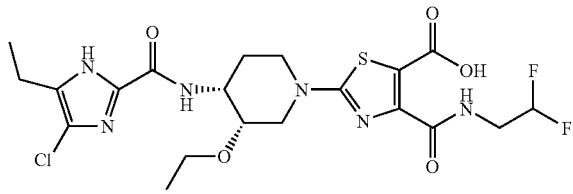

(251a) Ethyl cis(±)-2-(4-{[(4-chloro-5-ethyl-1H-imidazol-2-yl)carbonyl]amino}-3-ethoxypiperidin-1-yl)-4-[(2,2-difluoroethyl)carbamoyl]-1,3-thiazole-5-carboxylate The same operation as in Example (247a) was performed using cis(±)-2-(4-{[(4-chloro-5-ethyl-1H-imidazol-2-yl)carbonyl]amino}-3-ethoxypiperidin-1-yl)-5-(ethoxycarbonyl)-1,3-thiazole-4-carboxylic acid obtained in Example (50a) (250 mg, 0.50 mmol), 2,2-difluoroethylamine (81 mg, 1.00 mmol), WSC hydrochloride (288 mg, 1.50 mmol) and 1-hydroxybenzotriazole (68 mg, 0.50 mmol), to obtain 223 mg of the title compound as a white solid (79%).

$^1$H NMR spectrum (400 MHz, CDCl$_3$) δ ppm: 1.15 (3H, t, J=7.07 Hz), 1.27 (3H, t, J=7.56 Hz), 1.36 (3H, t, J=7.32 Hz), 1.69-1.87 (1H, m), 2.02-2.16 (1H, m), 2.69 (2H, q, J=7.56 Hz), 3.14-3.31 (2H, m), 3.40-3.50 (1H, m), 3.63 (1H, s), 3.70-3.87 (3H, m), 4.03-4.15 (1H, m), 4.20-4.38 (3H, m), 4.40-4.51 (1H, m), 5.97 (1H, tt, J=56.34, 4.39 Hz), 7.48 (1H, d, J=8.78 Hz), 9.23-9.30 (1H, m).

mass spectrum (ESI): m/z 563, 565 (M+H)$^+$.

(251b) cis(±)-2-(4-{[(4-Chloro-5-ethyl-1H-imidazol-2-yl)carbonyl]amino}-3-ethoxypiperidin-1-yl)-4-[(2,2-difluoroethyl)carbamoyl]-1,3-thiazole-5-carboxylic acid The same operation as in Example (247b) was performed using ethyl cis(±)-2-(4-{[(4-chloro-5-ethyl-1H-imidazol-2-yl)carbonyl]amino}-3-ethoxypiperidin-1-yl)-4-[(2,2-difluoroethyl)carbamoyl]-1,3-thiazole-5-carboxylate obtained in Example (251a) (220 mg, 0.39 mmol) and a 2 N aqueous lithium hydroxide solution (1.95 mL, 3.91 mmol), to obtain 180 mg of the title compound as a white solid (86%).

$^1$H NMR spectrum (400 MHz, DMSO-$d_6$) δ ppm: 1.03 (3H, t, J=7.07 Hz), 1.14 (3H, t, J=7.56 Hz), 1.66-1.75 (1H, m), 1.83-1.96 (1H, m), 2.56 (2H, q, J=7.56 Hz), 3.27-3.39 (3H, m), 3.40-3.50 (2H, m), 3.62-3.83 (4H, m), 4.17-4.27 (1H, m), 6.19 (1H, tt, J=55.49, 3.41 Hz), 7.65 (1H, d, J=8.54 Hz), 9.59 (1H, br s), 13.36 (1H, s).

mass spectrum (ESI): m/z 535 (M+H)$^+$.

Example 252 cis(±)-2-(4-{[(4-Chloro-5-ethyl-1H-imidazol-2-yl)carbonyl]amino}-3-ethoxypiperidin-1-yl)-4-[(2-ethoxyethyl)carbamoyl]-1,3-thiazole-5-carboxylic acid (Exemplified Compound No. 252)

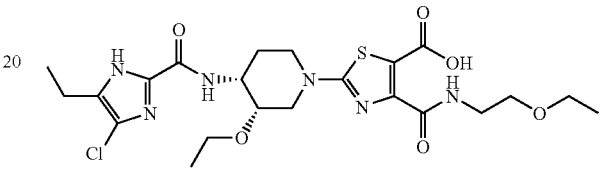

(252a) Ethyl cis(±)-2-(4-{[(4-chloro-5-ethyl-1H-imidazol-2-yl)carbonyl]amino}-3-ethoxypiperidin-1-yl)-4-[(2-ethoxyethyl)carbamoyl]-1,3-thiazole-5-carboxylate The same operation as in Example (247a) was performed using cis(±)-2-(4-{[(4-chloro-5-ethyl-1H-imidazol-2-yl)carbonyl]amino}-3-ethoxypiperidin-1-yl)-5-(ethoxycarbonyl)-1,3-thiazole-4-carboxylic acid obtained in Example (50a) (250 mg, 0.50 mmol), 2-ethoxyethylamine (0.11 mL, 1.00 mmol), WSC hydrochloride (288 mg, 1.50 mmol) and 1-hydroxybenzotriazole (68 mg, 0.50 mmol), to obtain 217 mg of the title compound as a white solid (76%).

$^1$H NMR spectrum (400 MHz, CDCl$_3$) δ ppm: 1.16 (3H, t, J=7.32 Hz), 1.21 (3H, t, J=7.07 Hz), 1.27 (3H, t, J=7.56 Hz), 1.34 (3H, t, J=7.07 Hz), 1.74-1.84 (1H, m), 2.02-2.15 (1H, m), 2.69 (2H, q, J=7.56 Hz), 3.13-3.28 (2H, m), 3.40-3.49 (1H, m), 3.54 (2H, q, J=7.07 Hz), 3.60-3.65 (5H, m), 3.70-3.80 (1H, m), 4.02-4.13 (1H, m), 4.19-4.36 (3H, m), 4.40-4.50 (1H, m), 7.49 (1H, brs), 8.52 (1H, br s).

mass spectrum (ESI): m/z 571, 573 (M+H)$^+$.

(252b) cis(±)-2-(4-{[(4-Chloro-5-ethyl-1H-imidazol-2-yl)carbonyl]amino}-3-ethoxypiperidin-1-yl)-4-[(2-ethoxyethyl)carbamoyl]-1,3-thiazole-5-carboxylic acid The same operation as in Example (247b) was performed using ethyl cis(±)-2-(4-{[(4-chloro-5-ethyl-1H-imidazol-2-yl)carbonyl]amino}-3-ethoxypiperidin-1-yl)-4-[(2-ethoxyethyl)carbamoyl]-1,3-thiazole-5-carboxylate obtained in Example (252a) (213 mg, 0.37 mmol) and a 2 N aqueous lithium hydroxide solution (1.86 mL, 3.73 mmol), to obtain 172 mg of the title compound as a white solid (85%).

$^1$H NMR spectrum (400 MHz, DMSO-$d_6$) δ ppm: 1.03 (3H, t, J=7.07 Hz), 1.10 (3H, t, J=7.32 Hz), 1.14 (3H, t, J=7.56 Hz), 1.66-1.74 (1H, m), 1.83-1.95 (1H, m), 2.55 (2H, q, J=7.32 Hz), 3.26-3.37 (3H, m), 3.38-3.56 (8H, m), 3.62-3.71 (2H, m), 4.17-4.26 (1H, m), 7.65 (1H, d, J=8.54 Hz), 9.32 (1H, brs), 13.36 (1H, s).

mass spectrum (ESI): m/z 543, 545 (M+H)$^+$.

Example 253

2-((3R*,4S*)-4-{[(4-Chloro-5-ethyl-1H-imidazol-2-yl)carbonyl]amino}-3-ethoxypiperidin-1-yl)-4-[(2-methoxy-1-methylethyl)carbamoyl]-1,3-thiazole-5-carboxylic acid (Exemplified Compound No. 253)

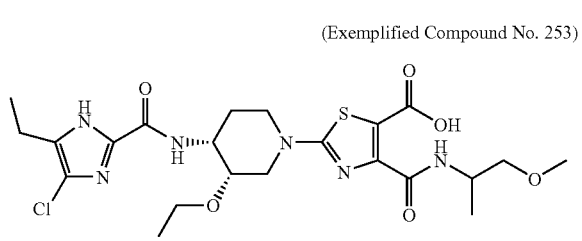 [SMILES: CCO[C@H]1CN(c2nc(C(=O)NC(C)COC)c(C(=O)O)s2)CC[C@H]1NC(=O)c1nc(Cl)c(CC)[nH]1]

(253a) Ethyl 2-((3R*,4S*)-4-{[(4-chloro-5-ethyl-1H-imidazol-2-yl)carbonyl]amino}-3-ethoxypiperidin-1-yl)-4-[(2-methoxy-1-methylethyl)carbamoyl]-1,3-thiazole-5-carboxylate The same operation as in Example (247a) was performed using cis(±)-2-(4-{[(4-chloro-5-ethyl-1H-imidazol-2-yl)carbonyl]amino}-3-ethoxypiperidin-1-yl)-5-(ethoxycarbonyl)-1,3-thiazole-4-carboxylic acid obtained in Example (50a) (250 mg, 0.50 mmol), 1-methoxy-2-propylamine (0.11 mL, 1.00 mmol), WSC hydrochloride (288 mg, 1.50 mmol) and 1-hydroxybenzotriazole (68 mg, 0.50 mmol), to obtain 228 mg of the title compound as a white solid (80%).

$^1$H NMR spectrum (400 MHz, CDCl$_3$) δ ppm: 1.16 (3H, t, J=7.07 Hz), 1.23-1.38 (9H, m), 1.75-1.83 (1H, m), 2.02-2.14 (1H, m), 2.69 (2H, q, J=7.56 Hz), 3.13-3.28 (2H, m), 3.36-3.52 (6H, m), 3.62 (1H, s), 3.70-3.80 (1H, m), 4.03-4.14 (1H, m), 4.19-4.37 (4H, m), 4.39-4.49 (1H, m), 7.41-7.50 (1H, m), 8.37.8.46 (1H, m).

mass spectrum (ESI): m/z 571, 573 (M+H)$^+$.

(253b) 2-((3R*,4S*)-4-{[(4-Chloro-5-ethyl-1H-imidazol-2-yl)carbonyl]amino}-3-ethoxypiperidin-1-yl)-4-[(2-methoxy-1-methylethyl)carbamoyl]-1,3-thiazole-5-carboxylic acid The same operation as in Example (250b) was performed using ethyl 2-((3R*,4S*)-4-{[(4-chloro-5-ethyl-1H-imidazol-2-yl)carbonyl]amino}-3-ethoxypiperidin-1-yl)-4-[(2-methoxy-1-methylethyl)carbamoyl]-1,3-thiazole-5-carboxylate obtained in Example (253a) (225 mg, 0.39 mmol) and a 2 N aqueous lithium hydroxide solution (1.97 mL, 3.94 mmol), to obtain 167 mg of the title compound as a white solid (78%).

$^1$H NMR spectrum (400 MHz, CDCl$_3$) δ ppm: 1.14-1.21 (3H, m), 1.25-1.35 (6H, m), 1.78-1.86 (1H, m), 2.00-2.14 (1H, m), 2.70 (2H, q, J=7.56 Hz), 3.15-3.27 (2H, m), 3.37-3.55 (6H, m), 3.62-3.75 (2H, m), 4.03-4.18 (1H, m), 4.20-4.39 (3H, m), 7.51 (1H, d, J=9.02 Hz), 7.93-8.03 (1H, m), 13.43 (1H, brs).

mass spectrum (ESI): m/z 543, 545 (M+H)$^+$.

Example 254

2-((3R*,4S*)-4-{[(4-Chloro-5-ethyl-1H-imidazol-2-yl)carbonyl]amino}-3-ethoxypiperidin-1-yl)-4-[(2-hydroxy-1-methylethyl)carbamoyl]-1,3-thiazole-5-carboxylic acid (Exemplified Compound No. 254)

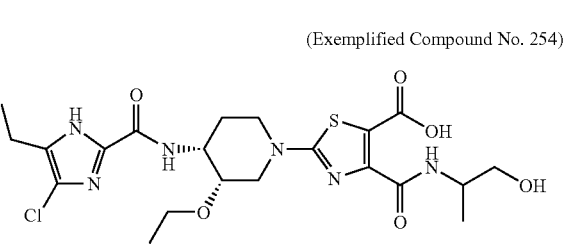 [SMILES: CCO[C@H]1CN(c2nc(C(=O)NC(C)CO)c(C(=O)O)s2)CC[C@H]1NC(=O)c1nc(Cl)c(CC)[nH]1]

(254a) Ethyl 2-((3R*,4S*)-4-{[(4-chloro-5-ethyl-1H-imidazol-2-yl)carbonyl]amino}-3-ethoxypiperidin-1-yl)-4-[(2-hydroxy-1-methylethyl)carbamoyl]-1,3-thiazole-5-carboxylate The same operation as in Example (247a) was performed using cis(±)-2-(4-{[(4-chloro-5-ethyl-1H-imidazol-2-yl)carbonyl]amino}-3-ethoxypiperidin-1-yl)-5-(ethoxycarbonyl)-1,3-thiazole-4-carboxylic acid obtained in Example (50a) (200 mg, 0.40 mmol), 2-amino-1-propanol (0.06 mL, 0.80 mmol), WSC hydrochloride (230 mg, 1.20 mmol) and 1-hydroxybenzotriazole (54 mg, 0.40 mmol), to obtain 144 mg of the title compound as a white solid (65%).

$^1$H NMR spectrum (400 MHz, CDCl$_3$) δ ppm: 1.13-1.20 (3H, m), 1.24-1.30 (6H, m), 1.34 (3H, t, J=7.32 Hz), 1.75-1.83 (1H, m), 2.01-2.15 (1H, m), 2.69 (2H, q, J=7.56 Hz), 3.14-3.32 (3H, m), 3.39-3.50 (1H, m), 3.57-3.65 (2H, m), 3.70-3.79 (1H, m), 3.83-3.90 (1H, m), 4.02-4.52 (5H, m), 7.45 (1H, d, J=8.54 Hz), 8.17-8.24 (1H, m), 11.03 (1H, br s).

mass spectrum (ESI): m/z 557, 559 (M+H)$^+$.

(254b) 2-((3R*,4S*)-4-{[(4-Chloro-5-ethyl-1H-imidazol-2-yl)carbonyl]amino}-3-ethoxypiperidin-1-yl)-4-[(2-hydroxy-1-methylethyl)carbamoyl]-1,3-thiazole-5-carboxylic acid The same operation as in Example (247b) was performed using ethyl 2-((3R*,4S*)-4-{[(4-chloro-5-ethyl-1H-imidazol-2-yl)carbonyl]amino}-3-ethoxypiperidin-1-yl)-4-[(2-hydroxy-1-methylethyl)carbamoyl]-1,3-thiazole-5-carboxylate obtained in Example (254a) (141 g, 0.25 mmol) and a 2 N aqueous lithium hydroxide solution (1.27 mL, 2.53 mmol), to obtain 108 mg of the title compound as a white solid (81%).

$^1$H NMR spectrum (400 MHz, CDCl$_3$) δ ppm: 1.16 (3H, t, J=6.84 Hz), 1.26 (3H, t, J=7.57 Hz), 1.31-1.35 (3H, m), 1.75-1.84 (1H, m), 1.95-2.11 (1H, m), 2.69 (2H, q, J=7.65 Hz), 3.14-3.25 (2H, m), 3.41-3.52 (1H, m), 3.60-3.74 (3H, m), 3.78-3.86 (1H, m), 4.09-4.31 (4H, m), 7.44 (1H, d, J=8.30 Hz), 7.93-8.01 (1H, m), 10.58 (1H, br s).

mass spectrum (ESI): m/z 529, 531 (M+H)$^+$.

Example 255 cis(±)-4-[(2-Acetamidoethyl)carbamoyl]-2-(4-{[(4-chloro-5-ethyl-1H-imidazol-2-yl)carbonyl]amino}-3-ethoxypiperidin-1-yl)-1,3-thiazole-5-carboxylic acid (Exemplified Compound No. 255)

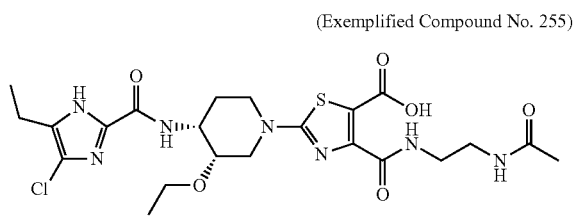 [SMILES: CCO[C@H]1CN(c2nc(C(=O)NCCNC(C)=O)c(C(=O)O)s2)CC[C@H]1NC(=O)c1nc(Cl)c(CC)[nH]1]

(255a) Ethyl cis(±)-4-[(2-acetamidoethyl)carbamoyl]-2-(4-{[(4-chloro-5-ethyl-1H-imidazol-2-yl)carbonyl]amino}-3-ethoxypiperidin-1-yl)-1,3-thiazole-5-carboxylate The same operation as in Example (247a) was performed using cis(±)-2-(4-{[(4-chloro-5-ethyl-1H-imidazol-2-yl)carbonyl]amino}-3-ethoxypiperidin-1-yl)-5-(ethoxycarbonyl)-1,3-thiazole-4-carboxylic acid obtained in Example (50a) (200 mg, 0.40 mmol), N-acetylethylenediamine (0.08 mL, 0.80 mmol), WSC hydrochloride (230 mg, 1.20 mmol) and 1-hydroxybenzotriazole (54 mg, 0.40 mmol), to obtain 134 mg of the title compound as a white solid (57%).

$^1$H NMR spectrum (400 MHz, CDCl$_3$) δ ppm: 1.16 (3H, t, J=7.08 Hz), 1.27 (3H, t, J=7.57 Hz), 1.35 (3H, t, J=7.08 Hz), 1.69-1.81 (1H, m), 1.99 (3H, s), 2.01-2.13 (1H, m), 2.69 (2H, q, J=7.65 Hz), 3.13-3.26 (2H, m), 3.39-3.63 (6H, m), 3.68-3.78 (1H, m), 4.01-4.47 (5H, m), 6.71 (1H, br s), 7.41-7.50 (1H, br s), 8.34 (1H, brs).

mass spectrum (ESI): m/z 584, 586 (M+H)$^+$.

(255b) cis(±)-4-[(2-Acetamidoethyl)carbamoyl]-2-(4-{[(4-chloro-5-ethyl-1H-imidazol-2-yl)carbonyl]amino}-3-ethoxypiperidin-1-yl)-1,3-thiazole-5-carboxylic acid The same operation as in Example (247b) was performed using ethyl cis(±)-4-[(2-acetamidoethyl)carbamoyl]-2-(4-{[(4-chloro-5-ethyl-1H-imidazol-2-yl)carbonyl]amino}-3-ethoxypiperidin-1-yl)-1,3-thiazole-5-carboxylate obtained in Example (255a) (133 mg, 0.23 mmol) and a 2 N aqueous lithium hydroxide solution (1.14 mL, 2.28 mmol), to obtain 91 mg of the title compound as a white solid (72%).

$^1$H NMR spectrum (400 MHz, DMSO-d$_6$) δ ppm: 1.04 (3H, t, J=7.07 Hz), 1.14 (3H, t, J=7.56 Hz), 1.65-1.74 (1H, m), 1.80 (3H, s), 1.83-1.95 (1H, m), 2.55 (2H, q, J=7.56 Hz), 3.19-3.51 (9H, m), 3.63-3.73 (2H, m), 4.16-4.26 (1H, m), 7.66 (1H, d, J=8.29 Hz), 8.04-8.11 (1H, m), 9.45 (1H, br s), 13.36 (1H, s).

mass spectrum (ESI): m/z 556, 558 (M+H)$^+$.

Example 256 cis(±)-4-Chloro-N-[3-ethoxy-1-(5-methyl-6-oxo-5,6-dihydro-4H-pyrrolo[3,4-d][1,3]thiazol-2-yl)piperidin-4-yl]-5-ethyl-1H-imidazole-2-carboxamide (Exemplified Compound No. 256)

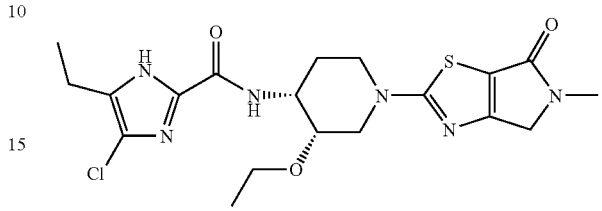

(256a) Ethyl cis(±)-2-(4-{[(4-chloro-5-ethyl-1H-imidazol-2-yl)carbonyl]amino}-3-ethoxypiperidin-1-yl)-4-[(methylamino)methyl]-1,3-thiazole-5-carboxylate 3 Å molecular sieves (500 mg) and methylamine hydrochloride (105 mg, 1.55 mmol) were added to a solution of ethyl cis(±)-2-(4-{[(4-chloro-5-ethyl-1H-imidazol-2-yl)carbonyl]amino}-3-ethoxypiperidin-1-yl)-4-formyl-1,3-thiazole-5-carboxylate obtained in Example (28a) (500 mg, 1.03 mmol) in methanol (5 mL), and the mixture was stirred at room temperature for two hours. The reaction solution was filtered, and then the filtrate was concentrated under reduced pressure. Sodium triacetoxyborohydride (437 mg, 2.06 mmol) was added to a solution of the resulting residue in dichloroethane (10 mL), and the mixture was stirred at room temperature for 20.5 hours. The reaction solution was diluted with ethyl acetate, and then the mixture was extracted with a 1 N aqueous hydrochloric acid solution. A 1 N aqueous sodium hydroxide solution was added to the aqueous layer, followed by extraction with ethyl acetate. The combined organic layers were dried over anhydrous magnesium sulfate. Following filtration, the filtrate was concentrated under reduced pressure to obtain 145 mg of the title compound as a yellow oily substance (28%).

$^1$H NMR spectrum (400 MHz, CDCl$_3$) δ ppm: 1.17 (3H, t, J=7.32 Hz), 1.26 (3H, t, J=7.57 Hz), 1.34 (3H, t, J=7.08 Hz), 1.74-1.82 (1H, m), 2.01-2.14 (1H, m), 2.45 (3H, s), 2.69 (2H, q, J=7.57 Hz), 3.09-3.24 (2H, m), 3.38-3.48 (1H, m), 3.61 (1H, br s), 3.70-3.80 (1H, m), 3.97-4.08 (3H, m), 4.18-4.31 (3H, m), 4.42 (1H, d, J=14.89 Hz), 7.48 (1H, d, J=9.03).

mass spectrum (ESI): m/z 499, 501 (M+H)$^+$.

(256b) cis(±)-4-Chloro-N-[3-ethoxy-1-(5-methyl-6-oxo-5,6-dihydro-4H-pyrrolo[3,4-d][1,3]thiazol-2-yl)piperidin-4-yl]-5-ethyl-1H-imidazole-2-carboxamide Trimethylaluminum (1.05 M solution in hexane) (0.76 mL, 0.80 mmol) was added to a solution of ethyl cis(±)-2-(4-{[(4-chloro-5-ethyl-1H-imidazol-2-yl)carbonyl]amino}-3-ethoxypiperidin-1-yl)-4-[(methylamino)methyl]-1,3-thiazole-5-carboxylate obtained in Example (256a) (80 mg, 0.16 mmol) in toluene (3 mL), and the mixture was heated under reflux for 45 minutes. A 1 N aqueous hydrochloric acid solution was added to the reaction solution, followed by stirring. Then, the mixture was extracted with ethyl acetate. The combined organic layers were dried over anhydrous magnesium sulfate and filtered, and then the filtrate was concentrated under reduced pressure. The resulting residue was purified by silica gel column chromatography (elution solvent: dichloromethane/methanol=20/1) to obtain 25 mg of the title compound as a pale yellow solid (35%).

¹H NMR spectrum (400 MHz, DMSO-d₆) δ ppm: 1.16 (3H, t, J=7.08 Hz), 1.27 (3H, t, J=7.57 Hz), 1.77-1.85 (1H, m), 2.04-2.16 (1H, m), 2.70 (2H, q, J=7.57 Hz), 3.12 (3H, s), 3.17-3.27 (2H, m), 3.41-3.50 (1H, m), 3.64 (1H, brs), 3.68-3.77 (1H, m), 4.03-4.11 (1H, m), 4.19 (2H, s), 4.22-4.30 (1H, m), 4.32-4.39 (1H, m), 7.47 (1H, d, J=9.03 Hz), 11.10 (1H, s).

mass spectrum (ESI): m/z 453, 455 (M+H)⁺.

Example 257 cis(±)-3-(4-{[(4-Chloro-5-ethyl-1H-imidazol-2-yl)carbonyl]amino}-3-methoxypiperidin-1-yl)-5-methoxybenzoic acid (Exemplified Compound No. 257)

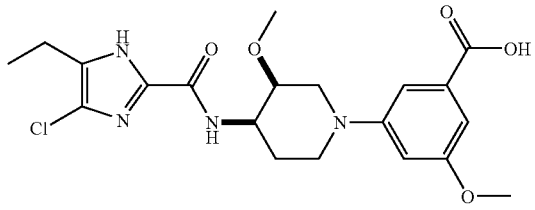

(257a) Methyl 3-bromo-5-methoxybenzoate

The compound was synthesized according to the method described in the following document.

WO 2008/9435

(257b) Methyl cis(±)-3-(4-{[(benzyloxy)carbonyl]amino}-3-methoxypiperidin-1-yl)-5-methoxybenzoate The same operation as in Example (42a) was performed using methyl 3-bromo-5-methoxybenzoate obtained in Example (257a) (371 mg, 1.51 mmol), benzyl cis(±)-(3-methoxypiperidin-4-yl)-carbamate obtained in Example (40b) (400 mg, 1.51 mmol), palladium acetate (34 mg, 0.15 mmol), (±)-BINAP (188 mg, 0.30 mmol), cesium carbonate (1.08 g, 3.33 mmol), 1,4-dioxane (15 mL) and DMF (4.5 mL), to obtain 178 mg of the title compound as a yellow oily substance (27%).

¹H-NMR spectrum (400 MHz, CDCl₃) δ ppm: 1.80-1.90 (1H, m), 1.90-2.03 (1H, m), 2.81-2.95 (2H, m), 3.40 (3H, s), 3.49 (1H, br s), 3.56-3.65 (1H, m), 3.79-3.92 (2H, m), 3.82 (3H, s), 3.89 (3H, s), 5.12 (2H, s), 5.22-5.32 (1H, m), 6.64 (1H, t, J=2.52 Hz), 7.03-7.05 (1H, m), 7.23-7.25 (1H, m), 7.31-7.42 (5H, m).

mass spectrum (ESI): m/z 429 (M+H)⁺.

(257c) Methyl cis(±)-3-(4-amino-3-methoxypiperidin-1-yl)-5-methoxybenzoate

The same operation as in Example (40e) was performed using methyl cis(±)-3-(4-{[(benzyloxy)carbonyl]amino}-3-methoxypiperidin-1-yl)-5-methoxybenzoate obtained in Example (257b) (106 mg, 0.25 mmol), a 10% palladium-carbon catalyst (42 mg), methanol (2 mL) and ethyl acetate (2 mL), to obtain the title compound. The resulting compound was used for the next reaction without purification.

(257d) Methyl cis(±)-3-(4-{[(4-chloro-5-ethyl-1H-imidazol-2-yl)carbonyl]amino}-3-methoxypiperidin-1-yl)-5-methoxybenzoate The same operation as in Example (1g) was performed using methyl cis(±)-3-(4-amino-3-methoxypiperidin-1-yl)-5-methoxybenzoate obtained in Example (257c) (about 0.25 mmol), 4-chloro-5-ethyl-1H-imidazole-2-carboxylic acid obtained in Example (1d) (48 mg, 0.22 mmol), WSC hydrochloride (139 mg, 0.73 mmol), HOBT (49 mg, 0.36 mmol), dichloromethane (2 mL) and DMA (2 mL), to obtain 87 mg of the title compound (88%).

¹H-NMR spectrum (400 MHz, CDCl₃) δ ppm: 1.27 (3H, t, J=7.34 Hz), 1.81-1.90 (1H, m), 2.09-2.20 (1H, m), 2.70 (2H, q, J=7.49 Hz), 2.85-2.94 (2H, m), 3.44 (3H, s), 3.55 (1H, brs), 3.64-3.73 (1H, m), 3.84 (3H, s), 3.91 (3H, s), 3.93-3.99 (1H, m), 4.17-4.28 (1H, m), 6.66 (1H, t, J=2.29 Hz), 7.05-7.09 (1H, m), 7.26-7.29 (1H, m), 7.57 (1H, d, J=8.71 Hz), 12.00 (1H, s).

mass spectrum (ESI): m/z 451 (M+H)⁺.

(257e) cis(±)-3-(4-{[(4-Chloro-5-ethyl-1H-imidazol-2-yl)carbonyl]amino}-3-methoxypiperidin-1-yl)-5-methoxybenzoic acid The same operation as in Example (1i) was performed using methyl cis(±)-3-(4-{[(4-chloro-5-ethyl-1H-imidazol-2-yl)carbonyl]amino}-3-methoxypiperidin-1-yl)-5-methoxybenzoate obtained in Example (257d) (40 mg, 0.09 mmol), a 2 N aqueous lithium hydroxide solution (2 mL, 4 mmol) and methanol (2 mL), to obtain 30 mg of the title compound as a white solid (77%).

¹H-NMR spectrum (400 MHz, DMSO-d₆) δ ppm: 1.15 (3H, t, J=7.49 Hz), 1.65-1.76 (1H, m), 1.86-2.00 (1H, m), 2.55 (2H, q, J=7.49 Hz), 2.90-3.00 (2H, m), 3.32 (3H, s), 3.54 (1H, br s), 3.60-3.69 (1H, m), 3.77 (3H, s), 3.90-3.98 (1H, m), 4.08-4.18 (1H, m), 6.70 (1H, t, J=2.29 Hz), 6.84-6.87 (1H, m), 7.09-7.12 (1H, m), 7.57 (1H, d, J=8.25 Hz).

mass spectrum (ESI): m/z 437 (M+H)⁺.

Example 258 cis(±)-5-(4-{[(4-Chloro-5-ethyl-1H-imidazol-2-yl)carbonyl]amino}-3-methoxypiperidin-1-yl)-2-methoxybenzoic acid (Exemplified Compound No. 258)

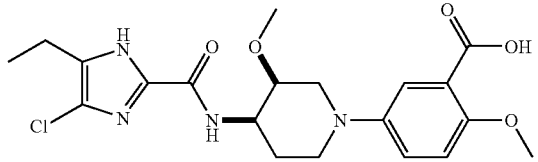

(258a) Methyl cis(±)-5-(4-{[(benzyloxy)carbonyl]amino}-3-methoxypiperidin-1-yl)-2-methoxybenzoate The same operation as in Example (42a) was performed using methyl 5-iodo-2-methoxybenzoate (442 mg, 1.51 mmol), benzyl cis(±)-(3-methoxypiperidin-4-yl)-carbamate obtained in Example (40b) (400 mg, 1.51 mmol), palladium acetate (34 mg, 0.15 mmol), (±)-BINAP (188 mg, 0.30 mmol), cesium carbonate (1.08 g, 3.33 mmol), 1,4-dioxane (15 mL) and DMF (4.5 mL), to obtain 35 mg of the title compound as a yellow oily substance (5%).

¹H-NMR spectrum (400 MHz, CDCl₃) δ ppm: 1.81-1.91 (1H, m), 1.93-2.04 (1H, m), 2.73-2.86 (2H, m), 3.46-3.39 (1H, m), 3.43 (3H, s), 3.50 (1H, br s), 3.62-3.69 (2H, m), 3.86 (3H, s), 3.89 (3H, s), 5.06-5.19 (2H, m), 5.23-5.32 (1H, m), 6.90 (1H, d, J=8.71 Hz), 7.09 (1H, dd, J=8.94, 2.98 Hz), 7.30-7.42 (6H, m).

mass spectrum (ESI): m/z 429 (M+H)⁺.

(258b) Methyl cis(±)-5-(4-amino-3-methoxypiperidin-1-yl)-2-methoxybenzoate

The same operation as in Example (40e) was performed using methyl cis(±)-5-(4-{[(benzyloxy)carbonyl]amino}-3- methoxypiperidin-1-yl)-2-methoxybenzoate obtained in Example (258a) (35 mg, 0.08 mmol), a 10% palladium-carbon catalyst (9 mg), methanol (1.5 mL) and ethyl acetate (1.5 mL), to obtain the title compound. The resulting compound was used for the next reaction without purification.

(258c) Methyl cis(±)-5-(4-{[(4-chloro-5-ethyl-1H-imidazol-2-yl)carbonyl]amino}-3-methoxypiperidin-1-yl)-2-methoxybenzoate The same operation as in Example (1g) was performed using methyl cis(±)-5-(4-amino-3-methoxypiperidin-1-yl)-2-methoxybenzoate obtained in Example (258b) (about 0.08 mmol), 4-chloro-5-ethyl-1H-imidazole-2-carboxylic acid obtained in Example (1d) (14 mg, 0.08 mmol), WSC hydrochloride (52 mg, 0.27 mmol), HOBT (18 mg, 0.14 mmol), dichloromethane (1 mL) and DMA (1 mL), to obtain 21 mg of the title compound as a colorless oily substance (57%).

$^1$H-NMR spectrum (400 MHz, CDCl$_3$) δ ppm: 1.27 (3H, t, J=7.79 Hz), 1.82-1.91 (1H, m), 2.10-2.22 (1H, m), 2.70 (2H, q, J=7.64 Hz), 2.77-2.89 (2H, m), 3.40-3.53 (1H, m), 3.46 (3H, s), 3.56 (1H, br s), 3.72-3.81 (1H, m), 3.87 (3H, s), 3.90 (3H, s), 4.16-4.25 (1H, m), 6.92 (1H, d, J=9.17 Hz), 7.12 (1H, dd, J=9.17, 3.21 Hz), 7.42 (1H, d, J=2.75 Hz), 7.53 (1H, d, J=8.71 Hz), 11.54 (1H, s).

mass spectrum (ESI): m/z 451 (M+H)$^+$.

(258d) cis(±)-5-(4-{[(4-Chloro-5-ethyl-1H-imidazol-2-yl)carbonyl]amino}-3-methoxypiperidin-1-yl)-2-methoxybenzoic acid The same operation as in Example (1i) was performed using methyl cis(±)-5-(4-{[(4-chloro-5-ethyl-1H-imidazol-2-yl)carbonyl]amino}-3-methoxypiperidin-1-yl)-2-methoxybenzoate obtained in Example (258c) (21 mg, 0.05 mmol), a 2 N aqueous lithium hydroxide solution (1.5 mL, 3 mmol) and methanol (1.5 mL), to obtain 12 mg of the title compound as a white solid (57%).

$^1$H-NMR spectrum (400 MHz, DMSO-d$_6$) δ ppm: 1.14 (3H, t, J=7.57 Hz), 1.66-1.76 (1H, m), 1.90-2.05 (1H, m), 2.55 (2H, q, J=7.49 Hz), 2.77-2.91 (2H, m), 3.34 (3H, s), 3.38-3.48 (1H, m), 3.55 (1H, br s), 3.68-3.75 (1H, m), 3.75 (3H, s), 4.04-4.18 (1H, m), 7.01 (1H, d, J=9.17 Hz), 7.11-7.26 (2H, m), 7.60-7.51 (1H, m).

mass spectrum (ESI): m/z 437 (M+H)$^+$.

Example 259 cis(±)-3-(4-{[(4-Chloro-5-ethyl-1H-imidazol-2-yl)carbonyl]amino}-3-methoxypiperidin-1-yl)-5-methylbenzoic acid (Exemplified Compound No. 259)

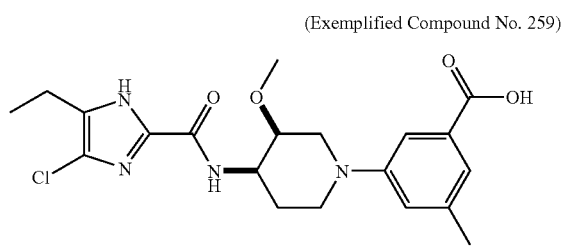 [SMILES: CCc1[nH]c(C(=O)N[C@@H]2CCN(c3cc(C)cc(C(=O)O)c3)C[C@@H]2OC)nc1Cl]

(259a) tert-Butyl cis(±)-4-benzylamino-3-methoxypiperidine-1-carboxylate

The compound was synthesized according to the method described in the following document.
WO 2006/087543

(259b) tert-Butyl cis(±)-4-{benzyl[(benzyloxy)carbonyl]amino}-3-methoxypiperidine-1-carboxylate THF (16 mL) and water (4 mL) were added to tert-butyl cis(±)-4-benzylamino-3-methoxypiperidine-1-carboxylate obtained in Example (259a) (1.00 g, 3.1 mmol). While the mixture was stirred, saturated aqueous sodium bicarbonate solution (4 mL) and benzyl chloroformate (0.96 g, 5.6 mmol) were added at room temperature, followed by stirring overnight. The reaction solution was diluted with water, followed by extraction with ethyl acetate. The organic layer was washed with brine, dried over anhydrous magnesium sulfate and then concentrated under reduced pressure. The residue was purified by silica gel column chromatography (elution solvent: ethyl acetate/hexane=1/9, 1/1) to obtain 0.66 g of the title compound as a colorless oily substance (58%).

$^1$H-NMR spectrum (400 MHz, CDCl$_3$) δ ppm: 1.24-5.21 (12H, m), 1.56 (9H, s), 3.20 (3H, s), 7.05-7.46 (10H, m).

mass spectrum (ESI): m/z 355 (M—Boc)$^+$.

(259c) Benzyl benzyl[cis(±)-3-methoxypiperidin-4-yl]carbamate

A 4 N hydrochloric acid/ethyl acetate solution (5 ml, 20 mmol) was added to a solution of tert-butyl cis(±)-4-{benzyl[(benzyloxy)carbonyl]amino}-3-methoxypiperidine-1-carboxylate obtained in Example (259b) (about 1.44 mmol) in methanol (1 mL). The mixture was stirred for one hour and the solvent was evaporated under reduced pressure. The reaction solution was diluted with ethyl acetate, washed with aqueous sodium bicarbonate solution and brine, dried over anhydrous magnesium sulfate, and then concentrated under reduced pressure. The resulting compound was used for the next reaction without purification.

(259d) Ethyl 2-amino-3-bromo-5-methylbenzoate

Ethanol (10 mL) was added to 2-amino-3-bromo-5-methylbenzoic acid (1.00 g, 4.4 mmol). While the mixture was stirred, thionyl chloride (1.03 g, 8.7 mmol) was added at room temperature, followed by stirring at 80° C. overnight. The reaction solution was concentrated, and then diluted with water under ice-cooling, followed by extraction with ethyl acetate. The organic layer was washed with aqueous sodium bicarbonate solution and brine, dried over anhydrous magnesium sulfate, and then concentrated under reduced pressure. The residue was purified by silica gel column chromatography (elution solvent: ethyl acetate/hexane=0/10, 4/6) to obtain 715 mg of the title compound as a pale yellow solid (64%).

$^1$H-NMR spectrum (400 MHz, CDCl$_3$) δ ppm: 1.38 (3H, t, J=7.34 Hz), 2.23 (3H, s), 4.34 (2H, q, J=7.03 Hz), 6.14 (2H, br s), 7.42 (1H, d, J=1.83 Hz), 7.67 (1H, d, J=1.38 Hz).

mass spectrum (ESI): m/z 258, 260 (M+H)$^+$.

(259e) Ethyl 3-bromo-5-methylbenzoate

Ethanol (20 mL) was added to ethyl 2-amino-3-bromo-5-methylbenzoate obtained in Example (259d) (715 mg, 2.8 mmol). While the mixture was stirred, trifluoroacetic acid (0.82 mL, 11.1 mmol), isopentyl nitrite (649 mg, 5.5 mmol) and hypophosphorous acid (7.3 g, 55.4 mmol) were added under ice-cooling, followed by stirring at room temperature for 30 minutes. The reaction solution was diluted and extracted with ethyl acetate and aqueous sodium bicarbonate solution. The organic layer was washed with water and brine, dried over anhydrous magnesium sulfate, and then concentrated under reduced pressure. The residue was purified by silica gel column chromatography (elution solvent: ethyl acetate/hexane=0/10, 2/8) to obtain 594 mg of the title compound as a light yellow oily substance (88%).

$^1$H-NMR spectrum (400 MHz, CDCl$_3$) δ ppm: 1.39 (3H, t, J=7.11 Hz), 4.37 (2H, q, J=7.34 Hz), 7.53-7.49 (1H, m), 7.80-7.76 (1H, m), 7.99-7.95 (1H, m).

(259f) Ethyl cis(±)-3-(4-{benzyl[(benzyloxy)carbonyl]amino}-3-methoxypiperidin-1-yl)-5-methylbenzoate The same operation as in Example (42a) was performed using benzyl benzyl[cis (±)-3-methoxypiperidin-4-yl] carbamate obtained in Example (259c) (150 mg, 0.42 mmol), ethyl 3-bromo-5-methylbenzoate obtained in Example (259e) (103 mg, 0.42 mmol), palladium acetate (10 mg, 0.04 mmol), (±)-BINAP (53 mg, 0.08 mmol), cesium carbonate (303 mg, 0.93 mmol), 1,4-dioxane (6 mL) and DMF (1.5 mL), to obtain 126 mg of the title compound as a yellow oily substance (57%).

$^1$H-NMR spectrum (400 MHz, CDCl$_3$) δ ppm: 1.33-1.41 (3H, m), 1.50-5.31 (18H, m), 4.30-4.39 (2H, m), 6.80-7.45 (13H, m).

mass spectrum (ESI): m/z 517 (M+H)$^+$.

(259g) Ethyl cis(±)-3-(4-amino-3-methoxypiperidin-1-yl)-5-methylbenzoate

The same operation as in Example (90d) was performed using ethyl cis(±)-3-(4-{benzyl[(benzyloxy)carbonyl]amino}-3-methoxypiperidin-1-yl)-5-methylbenzoate obtained in Example (259f) (126 mg, 0.24 mmol), a 10% palladium-carbon catalyst (63 mg), ammonium formate (155 mg, 2.4 mmol) and ethanol (5 mL), to obtain the title compound. The resulting compound was used for the next reaction without purification.

(259h) Ethyl cis(±)-3-(4-{[(4-chloro-5-ethyl-1H-imidazol-2-yl)carbonyl]amino}-3-methoxypiperidin-1-yl)-5-methylbenzoate The same operation as in Example (1g) was performed using ethyl cis(±)-3-(4-amino-3-methoxypiperidin-1-yl)-5-methylbenzoate obtained in Example (259g) (about 0.24 mmol), 4-chloro-5-ethyl-1H-imidazole-2-carboxylic acid obtained in Example (1d) (37 mg, 0.21 mmol), WSC hydrochloride (134 mg, 0.70 mmol), HOBT (47 mg, 0.35 mmol), dichloromethane (1.5 mL) and DMA (1.5 mL), to obtain 72 mg of the title compound as a colorless oily substance (75%).

$^1$H-NMR spectrum (400 MHz, CDCl$_3$) δ ppm: 1.23-1.33 (3H, m), 1.35-1.45 (3H, m), 1.54-4.50 (8H, m), 2.37 (3H, s), 2.64-2.77 (2H, m), 3.46 (3H, s), 4.32-4.44 (2H, m), 6.91-7.61 (4H, m), 11.73-12.09 (1H, m).

mass spectrum (ESI): m/z 449 (M+H)$^+$.

(259i) cis(±)-3-(4-{[(4-Chloro-5-ethyl-1H-imidazol-2-yl)carbonyl]amino}-3-methoxypiperidin-1-yl)-5-methylbenzoic acid The same operation as in Example (1i) was performed using ethyl cis(±)-3-(4-{[(4-chloro-5-ethyl-1H-imidazol-2-yl)carbonyl]amino}-3-methoxypiperidin-1-yl)-5-methylbenzoate obtained in Example (259h) (72 mg, 0.16 mmol), a 2 N aqueous lithium hydroxide solution (3 mL, 6 mmol) and methanol (3 mL), to obtain 67 mg of the title compound as a white solid (99%).

$^1$H-NMR spectrum (400 MHz, DMSO-d$_6$) δ ppm: 1.15 (3H, t, J=7.34 Hz), 1.69-4.16 (11H, m), 2.28-2.34 (3H, m), 2.56 (2H, q, J=7.49 Hz), 7.00-8.58 (4H, m).

mass spectrum (ESI): m/z 421 (M+H)$^+$.

Example 260 cis(±)-4-Chloro-5-ethyl-N-{3-methoxy-1-[(2H-tetrazol-5-yl)carbonyl]piperidin-4-yl}-1H-imidazole-2-carboxylic acid amide (Exemplified Compound No. 260)

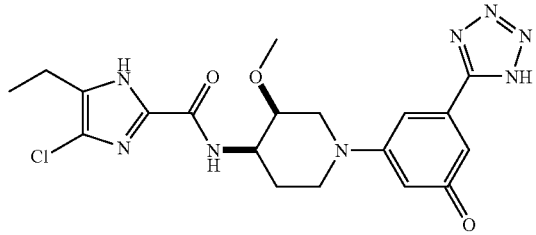

(260a) cis(±)-4-Chloro-5-ethyl-N-{3-methoxy-1-[(4-methoxybenzyl)-2H-tetrazol-5-yl]piperidin-4-yl}-1H-imidazole-2-carboxylic acid amide tert-Butyl cis(±)-4-{[(4-chloro-5-ethyl-1H-imidazol-2-yl)carbonyl]amino}-3-methoxypiperidine-1-carboxylate obtained in Example (1g) (30 mg, 0.08 mmol) was dissolved in methanol (0.5 mL). A 4 N hydrochloric acid/ethyl acetate solution (2.5 mL) was added, and the mixture was stirred at room temperature for 4.5 hours. Following concentration under reduced pressure, the same operation as in Example (1g) was performed using 2-[(4-methoxybenzyl)-2H-tetrazol-5-yl]carboxylic acid synthesized according to the method described in U.S. Pat. No. 4,442,115 A1 (16 mg, 0.07 mmol), WSC hydrochloride (43 mg, 0.22 mmol), HOBT (15 mg, 0.11 mmol), diisopropylethylamine (0.047 mL, 0.27 mmol), dichloromethane (1 mL) and DMA (1 mL), to obtain 28 mg of the title compound as a colorless oily substance (81%).

$^1$H-NMR spectrum (400 MHz, CDCl$_3$) δ ppm: 1.22-1.29 (3H, m), 1.71-1.85 (1H, m), 1.89-2.03 (1H, m), 2.62-5.21 (14H, m), 5.67-5.83 (2H, m), 6.86-7.48 (5H, m), 10.52 (1H, s).

mass spectrum (ESI): m/z 503 (M+H)$^+$.

(260b) cis(±)-4-Chloro-5-ethyl-N-{3-methoxy-1-[(2H-tetrazol-5-yl)carbonyl]piperidin-4-yl}-1H-imidazole-2-carboxylic acid amide cis(±)-4-Chloro-5-ethyl-N-{3-methoxy-1-[(4-methoxybenzyl)-2H-tetrazol-5-yl]piperidin-4-yl}-1H-imidazole-2-carboxylic acid amide obtained in Example (260a) (28 mg, 0.05 mmol) was dissolved in anisole (1 mL). Trifluoroacetic acid (2 mL) was added, and the mixture was stirred at 45° C. for 3.5 hours. Following concentration under reduced pressure, the reaction solution was diluted and extracted with dichloromethane and aqueous sodium bicarbonate solution. The organic layer was dried over anhydrous magnesium sulfate and then concentrated under reduced pressure. The residue was solidified by adding chloroform and hexane to obtain 4.1 mg of the title compound as a white solid (20%).

$^1$H-NMR spectrum (500 MHz, DMSO-d$_6$) δ ppm: 1.10-1.16 (3H, m), 4.29-4.28 (11H, m), 2.52-2.59 (2H, m), 7.63 (1H, d, J=8.02 Hz).

mass spectrum (ESI): m/z 383 (M+H)$^+$.

Example 261 cis(±)-2-(4-{[(4-Chloro-5-ethyl-1H-imidazol-2-yl)carbonyl]amino}-3-methoxypiperidin-1-yl)-N-(2-cyanoethyl)-4-methyl-1,3-thiazole-5-carboxylic acid amide (Exemplified Compound No. 261)

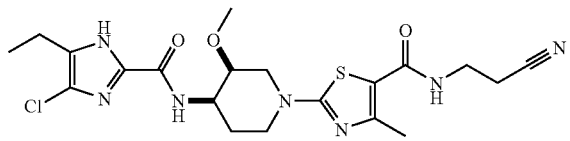

(261a) cis(±)-2-(4-{[(4-Chloro-5-ethyl-1H-imidazol-2-yl)carbonyl]amino}-3-methoxypiperidin-1-yl)-N-(2-cyanoethyl)-4-methyl-1,3-thiazole-5-carboxylic acid amide The same operation as in Example (1g) was performed using cis(±)-2-(4-{[(4-chloro-5-ethyl-1H-imidazol-2-yl)carbonyl]amino}-3-methoxypiperidin-1-yl)-4-methyl-1,3-thiazole-5-carboxylic acid obtained in Example (14a) (75 mg, 0.18 mmol), 3-aminopropionitrile (14 mg, 0.20 mmol), WSC hydrochloride (111 mg, 0.58 mmol), HOBT (39 mg, 0.29 mmol), dichloromethane (1.5 mL) and DMA (1.5 mL), to obtain 69 mg of the title compound as a white solid (82%).

$^1$H-NMR spectrum (500 MHz, CDCl$_3$) δ ppm: 1.26 (3H, t, J=7.45 Hz), 1.75-1.83 (1H, m), 1.97-2.08 (1H, m), 2.53 (3H, s), 2.65-2.74 (4H, m), 3.07-3.14 (1H, m), 3.15-3.25 (1H, m), 3.42 (3H, s), 3.51 (1H, br s), 3.61-3.67 (2H, m), 3.90-4.00 (1H, m), 4.20-4.29 (1H, m), 4.52-4.42 (1H, m), 5.86-5.92 (1H, m), 7.48 (1H, d, J=8.59 Hz), 10.83 (1H, s).

mass spectrum (ESI): m/z 480 (M+H)$^+$.

Example 262 cis(±)-4-Chloro-5-ethyl-N-{3-methoxy-1-[4-methyl-5-(1H-tetrazol-5-yl)-1,3-thiazol-2-yl]piperidin-4-yl}-1H-imidazole-2-carboxylic acid amide (Exemplified Compound No. 262)

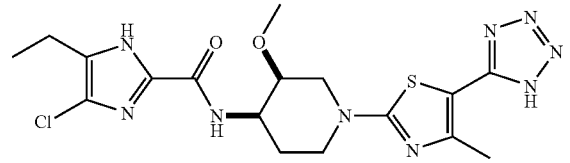

(262a) cis(±)-4-Chloro-N-(1-{5-[1-(2-cyanoethyl)-1H-tetrazol-5-yl]-4-methyl-1,3-thiazol-2-yl}-3-methoxypiperidin-4-yl)-5-ethyl-1H-imidazole-2-carboxylic acid amide THF (2 mL) was added to cis(±)-2-(4-{[(4-chloro-5-ethyl-1H-imidazol-2-yl)carbonyl]amino}-3-methoxypiperidin-1-yl)-N-(2-cyanoethyl)-4-methyl-1,3-thiazole-5-carboxylic acid amide obtained in Example (261a) (36 mg, 0.08 mmol). While the mixture was stirred, triphenylphosphine (124 mg, 0.47 mmol), diisopropyl azodicarboxylate (0.24 mL, 0.45 mmol, 1.9 M solution in toluene) and trimethylsilyl azide (7.3 g, 55.4 mmol) were added, followed by stirring at 30° C. for four days. The reaction solution was diluted with ethyl acetate. The organic layer was washed with water and brine, dried over anhydrous magnesium sulfate, and then concentrated under reduced pressure. The residue was purified by silica gel column chromatography (elution solvent: methanol/ethyl acetate=0/10, 2/8) and preparative thin layer chromatography (developing solvent: ethyl acetate/hexane=10/1) to obtain 16 mg of the title compound as a white solid (41%).

$^1$H-NMR spectrum (500 MHz, CDCl$_3$) δ ppm: 1.27 (3H, t, J=7.45 Hz), 1.80-1.88 (1H, m), 2.06-2.14 (1H, m), 2.41 (3H, s), 2.70 (2H, q, J=7.64 Hz), 3.09 (2H, t, J=7.16 Hz), 3.13-3.20 (1H, m), 3.24-3.32 (1H, m), 3.45 (3H, s), 3.55 (1H, br s), 3.90-3.98 (1H, m), 4.25-4.34 (1H, m), 4.50-4.60 (1H, m), 4.66 (2H, t, J=7.16 Hz), 7.45-7.51 (1H, m), 10.87 (1H, s).

mass spectrum (ESI): m/z 503 (M+H)$^+$.

(262b) cis(±)-4-Chloro-5-ethyl-N-{3-methoxy-1-[4-methyl-5-(1H-tetrazol-5-yl)-1,3-thiazol-2-yl]piperidin-4-yl}-1H-imidazole-2-carboxylic acid amide Dichloromethane (1.5 mL) was added to cis(±)-4-chloro-N-(1-{5-[1-(2-cyanoethyl)-1H-tetrazol-5-yl]-4-methyl-1,3-thiazol-2-yl}-3-methoxypiperidin-4-yl)-5-ethyl-1H-imidazole-2-carboxylic acid amide obtained in Example (262a) (16 mg, 0.03 mmol). While the mixture was stirred, diazabicycloundecene (15 mg, 0.10 mmol) was added, followed by stirring at room temperature overnight. The reaction solution was diluted with ethyl acetate and water. The organic layer was neutralized with 1 N hydrochloric acid, washed with brine, dried over anhydrous magnesium sulfate, and then concentrated under reduced pressure. The residue was solidified with diethyl ether and hexane to obtain 7 mg of the title compound as a white solid (47%).

$^1$H-NMR spectrum (500 MHz, DMSO-D$_6$) δ ppm: 1.14 (3H, t, J=7.45 Hz), 1.64-1.75 (1H, m), 1.83-1.96 (1H, m), 2.48 (3H, s), 2.55 (2H, q, J=7.64 Hz), 3.26-3.35 (2H, m), 3.36 (3H, s), 3.58 (1H, br s), 3.85-4.00 (1H, m), 4.17-4.32 (2H, m), 7.66 (1H, d, J=8.02 Hz).

mass spectrum (ESI): m/z 450 (M−H)$^+$.

Example 263 cis(±)-3-(4-{[(4-Chloro-5-ethyl-1H-imidazol-2-yl)carbonyl]amino}-3-methoxypiperidin-1-yl)-2-fluorobenzoic acid (Exemplified Compound No. 263)

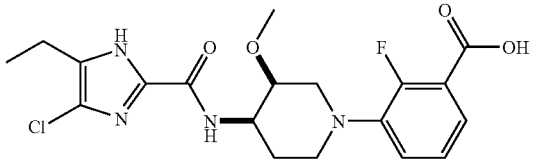

(263a) Methyl cis(±)-3-(4-{benzyl[(benzyloxy)carbonyl]amino}-3-methoxypiperidin-1-yl)-2-fluorobenzoate The same operation as in Example (42a) was performed using benzyl benzyl[cis(±)-3-methoxypiperidin-4-yl]carbamate obtained in Example (259c) (507 mg, 1.4 mmol), methyl 3-bromo-5-fluorobenzoate known in the literature (Org. Lett., 9(23), 2007, 4893-4896) (400 mg, 1.7 mmol), tris(dibenzylideneacetone)dipalladium (65 mg, 0.07 mmol), (±)-BINAP (178 mg, 0.29 mmol), cesium carbonate (1.02 g, 3.2 mmol), 1,4-dioxane (10 mL) and DMF (2.5 mL), to obtain 31 mg of the title compound as a yellow oily substance (4%).

$^1$H-NMR spectrum (400 MHz, CDCl$_3$) δ ppm: 1.77-5.33 (12H, m), 3.34 (3H, s), 3.90 (3H, s), 7.64-6.99 (13H, m).

mass spectrum (ESI): m/z 507 (M−H)$^+$.

(263b) Methyl cis(±)-3-(4-amino-3-methoxypiperidin-1-yl)-2-fluorobenzoate

The same operation as in Example (90d) was performed using methyl cis(±)-3-(4-{benzyl[(benzyloxy)carbonyl]amino}-3-methoxypiperidin-1-yl)-2-fluorobenzoate obtained in Example (263a) (31 mg, 0.06 mmol), a 10% palladium-carbon catalyst (20 mg), ammonium formate (39 mg, 0.61 mmol) and methanol (4 mL), to obtain the title compound. The resulting compound was used for the next reaction without purification.

(263c) Methyl cis(±)-3-(4-{[(4-chloro-5-ethyl-1H-imidazol-2-yl)carbonyl]amino}-3-methoxypiperidin-1-yl)-2-fluorobenzoate The same operation as in Example (1g) was performed using methyl cis(±)-3-(4-amino-3-methoxypiperidin-1-yl)-2-fluorobenzoate obtained in Example (263b) (about 0.06 mmol), 4-chloro-5-ethyl-1H-imidazole-2-carboxylic acid obtained in Example (1d) (9 mg, 0.05 mmol), WSC hydrochloride (34 mg, 0.18 mmol), HOBT (12 mg, 0.09 mmol), dichloromethane (0.75 mL) and DMA (0.75 mL), to obtain 8 mg of the title compound as a colorless oily substance (33%).

$^1$H-NMR spectrum (500 MHz, CDCl$_3$) δ ppm: 1.27 (3H, t, J=8.02 Hz), 1.83-1.93 (1H, m), 2.14-2.25 (1H, m), 2.69 (2H, q, J=7.64 Hz), 2.75-2.82 (1H, m), 2.91-3.02 (1H, m), 3.32-3.40 (1H, m), 3.48 (3H, s), 3.53 (1H, br s), 3.79-3.87 (1H, m), 3.92 (3H, s), 4.17-4.26 (1H, m), 7.10 (1H, t, J=8.02 Hz), 7.13-7.18 (1H, m), 7.47-7.52 (1H, m), 7.55 (1H, d, J=8.59 Hz), 11.42 (1H, s).

mass spectrum (ESI): m/z 439 (M+H)$^+$.

(263d) cis(±)-3-(4-{[(4-Chloro-5-ethyl-1H-imidazol-2-yl)carbonyl]amino}-3-methoxypiperidin-1-yl)-2-fluorobenzoic acid The same operation as in Example (1i) was performed using methyl cis(±)-3-(4-{[(4-chloro-5-ethyl-1H-imidazol-2-yl)carbonyl]amino}-3-methoxypiperidin-1-yl)-2-fluorobenzoate obtained in Example (263c) (8 mg, 0.02 mmol), a 2 N aqueous lithium hydroxide solution (1 mL, 2 mmol) and methanol (1 mL), to obtain 2 mg of the title compound as a white solid (31%).

$^1$H-NMR spectrum (500 MHz, DMSO-D$_6$) δ ppm: 1.14 (3H, t, J=7.64 Hz), 1.69-1.78 (1H, m), 1.94-2.07 (1H, m), 2.56 (2H, q, J=7.45 Hz), 2.79-2.95 (2H, m), 3.09-3.45 (4H, m), 3.55 (1H, br s), 3.59-3.67 (1H, m), 4.05-4.18 (1H, m), 7.03-7.41 (3H, m), 7.56 (1H, d, J=8.59 Hz).

mass spectrum (ESI): m/z 425 (M+H)$^+$.

Example 264 cis(±)-2-(4-{[(4-Chloro-5-ethyl-1H-imidazol-2-yl)carbonyl]amino}-3-methoxypiperidin-1-yl)-N-[2-(diethylamino)ethyl]-4-methyl-1,3-thiazole-5-carboxylic acid amide (Exemplified Compound No. 264)

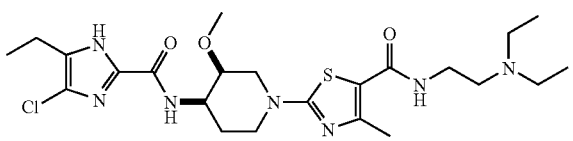

(264a) cis(±)-2-(4-{[(4-Chloro-5-ethyl-1H-imidazol-2-yl)carbonyl]amino}-3-methoxypiperidin-1-yl)-N-[2-(diethylamino)ethyl]-4-methyl-1,3-thiazole-5-carboxylic acid amide Dichloromethane (0.75 mL) and DMA (0.75 mL) were added to N,N-diethylene-1,2-diamine (6 mg, 0.05 mmol). While the mixture was stirred, cis(±)-2-(4-{[(4-chloro-5-ethyl-1H-imidazol-2-yl)carbonyl]amino}-3-methoxypiperidin-1-yl)-4-methyl-1,3-thiazole-5-carboxylic acid obtained in Example (14a) (20 mg, 0.05 mmol), WSC hydrochloride (30 mg, 0.15 mmol) and HOBT (10 mg, 0.08 mmol) were added, followed by stirring at room temperature for one day. The reaction solution was diluted with ethyl acetate and aqueous sodium bicarbonate solution. The organic layer was washed with brine, dried over anhydrous magnesium sulfate, and then concentrated under reduced pressure. The residue was solidified with diethyl ether and hexane to obtain 11 mg of the title compound as a white solid (44%).

$^1$H-NMR spectrum (500 MHz, CDCl$_3$) δ ppm: 1.06 (6H, t, J=7.16 Hz), 1.26 (3H, t, J=7.45 Hz), 1.73-1.82 (1H, m), 1.98-2.10 (1H, m), 2.50 (3H, s), 2.54-2.74 (8H, m), 3.04-3.11 (1H, m), 3.12-3.21 (1H, m), 3.40-3.47 (5H, m), 3.50 (1H, brs), 3.93-4.03 (1H, m), 4.19-4.28 (1H, m), 4.41-4.50 (1H, m), 6.53 (1H, s), 7.50 (1H, d, J=9.16 Hz).

mass spectrum (ESI): m/z 527 (M+H)$^+$.

Example 265 cis(±)-N-{[2-(4-{[(4-Chloro-5-ethyl-1H-imidazol-2-yl)carbonyl]amino}-3-methoxypiperidin-1-yl)-4-methyl-1,3-thiazol-5-yl]carbonyl}glycine (Exemplified Compound No. 265)

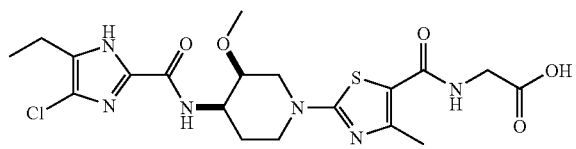

(265a) cis(±)-N-{[2-(4-{[(4-Chloro-5-ethyl-1H-imidazol-2-yl)carbonyl]amino}-3-methoxypiperidin-1-yl)-4-methyl-1,3-thiazol-5-yl]carbonyl}glycine ethyl ester The same operation as in Example (1g) was performed using cis(±)-2-(4-{[(4-chloro-5-ethyl-1H-imidazol-2-yl)carbonyl]amino}-3-methoxypiperidin-1-yl)-4-methyl-1,3-thiazole-5-carboxylic acid obtained in Example (14a) (30 mg, 0.07 mmol), hydrochloric acid glycine ethyl ester (11 mg, 0.08 mmol), WSC hydrochloride (44 mg, 0.23 mmol), HOBT (16 mg, 0.12 mmol), diisopropylethylamine (0.015 mL, 0.08 mmol), dichloromethane (0.75 mL) and DMA (0.75 mL), to obtain 31 mg of the title compound as a white solid (87%).

$^1$H-NMR spectrum (500 MHz, CDCl$_3$) δ ppm: 1.26 (3H, t, J=7.73 Hz), 1.31 (3H, t, J=7.45 Hz), 1.75-1.86 (1H, m), 1.98-2.08 (1H, m), 2.54 (3H, s), 2.69 (2H, q, J=7.64 Hz), 3.06-3.13 (1H, m), 3.14-3.23 (1H, m), 3.42 (3H, s), 3.50 (1H, br s), 3.91-4.01 (1H, m), 4.13-4.18 (2H, m), 4.19-4.29 (3H, m), 4.42-4.50 (1H, m), 6.07 (1H, t, J=5.15 Hz), 7.51 (1H, d, J=8.59 Hz), 11.31 (1H, s).

mass spectrum (ESI): m/z 514 (M+H)$^+$.

(265b) cis(±)-N-{[2-(4-{[(4-Chloro-5-ethyl-1H-imidazol-2-yl)carbonyl]amino}-3-methoxypiperidin-1-yl)-4-methyl-1,3-thiazol-5-yl]carbonyl}glycine The same operation as in Example (1i) was performed using cis(±)-N-{[2-(4-{[(4-chloro-5-ethyl-1H-imidazol-2-yl)carbonyl]amino}-3-methoxypiperidin-1-yl)-4-methyl-1,3-thiazol-5-yl]carbonyl}glycine ethyl ester obtained in Example (265a) (29 mg, 0.06 mmol), a 2 N aqueous lithium hydroxide solution (1.5 mL, 3 mmol) and methanol (1.5 mL), to obtain 16 mg of the title compound as a white solid (58%).

¹H-NMR spectrum (500 MHz, DMSO-d₆) δ ppm: 1.14 (3H, t, J=7.45 Hz), 1.62-1.72 (1H, m), 1.79-1.93 (1H, m), 2.39 (3H, s), 2.55 (2H, q, J=7.45 Hz), 3.21-3.39 (2H, m), 3.34 (3H, s), 3.56 (1H, br s), 3.74-3.82 (2H, m), 3.83-3.93 (1H, m), 4.15-4.27 (2H, m), 7.64 (1H, d, J=8.59 Hz), 7.78 (1H, t, J=5.73 Hz).

mass spectrum (ESI): m/z 485 (M+H)⁺.

Example 266 cis(±)-2-(4-{[(4-Chloro-5-ethyl-1H-imidazol-2-yl)carbonyl]amino}-3-methoxypiperidin-1-yl)-4-methyl-N-(piperidin-4-yl)-1,3-thiazole-5-carboxylic acid amide dihydrochloride (Exemplified Compound No. 266)

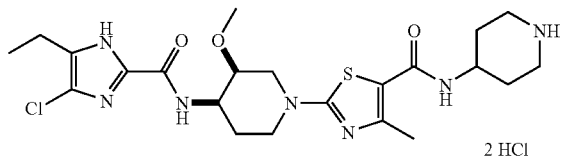

2 HCl (266a) tert-Butyl cis(±)-4-({[2-(4-{[(4-chloro-5-ethyl-1H-imidazol-2-yl)carbonyl]amino}-3-methoxypiperidin-1-yl)-4-methyl-1,3-thiazol-5-yl]carbonyl}amino)piperidine-1-carboxylate The same operation as in Example (1g) was performed using cis(±)-2-(4-{[(4-chloro-5-ethyl-1H-imidazol-2-yl)carbonyl]amino}-3-methoxypiperidin-1-yl)-4-methyl-1,3-thiazole-5-carboxylic acid obtained in Example (14a) (30 mg, 0.07 mmol), tert-butyl 4-aminopiperidine-1-carboxylate (16 mg, 0.08 mmol), WSC hydrochloride (44 mg, 0.23 mmol), HOBT (16 mg, 0.12 mmol), diisopropylethylamine (0.015 mL, 0.08 mmol), dichloromethane (0.75 mL) and DMA (0.75 mL), to obtain 31 mg of the title compound as a white solid (87%).

¹H-NMR spectrum (500 MHz, CDCl₃) δ ppm: 1.10-4.55 (17H, m), 1.27 (3H, t, J=8.02 Hz), 1.46 (9H, s), 2.50 (3H, s), 2.69 (2H, q, J=7.64 Hz), 3.42 (3H, s), 5.29 (1H, d, J=7.45 Hz), 7.44 (1H, d, J=9.16 Hz), 10.66 (1H, s).

mass spectrum (ESI): m/z 611 (M+H)⁺.

(266b) cis(±)-2-(4-{[(4-Chloro-5-ethyl-1H-imidazol-2-yl)carbonyl]amino}-3-methoxypiperidin-1-yl)-4-methyl-N-(piperidin-4-yl)-1,3-thiazole-5-carboxylic acid amide dihydrochloride A 4 N hydrochloric acid/ethyl acetate solution (2 ml, 8 mmol) was added to a solution of tert-butyl cis(±)-4-({[2-(4-{[(4-chloro-5-ethyl-1H-imidazol-2-yl)carbonyl]amino}-3-methoxypiperidin-1-yl)-4-methyl-1,3-thiazol-5-yl]carbonyl}amino)piperidine-1-carboxylate obtained in Example (266a) (30 mg, 0.05 mmol) in methanol (0.4 mL), followed by stirring for 30 minutes. The solvent was evaporated under reduced pressure. The residue was solidified by adding ethyl acetate, diethyl ether and hexane, to obtain 21 mg of the title compound as a cream-colored solid (72%).

¹H-NMR spectrum (500 MHz, DMSO-D₆) δ ppm: 1.13 (3H, t, J=7.45 Hz), 1.63-1.77 (1H, m), 1.79-1.95 (1H, m), 2.38 (3H, s), 2.55 (2H, q, J=7.64 Hz), 4.39-2.81 (15H, m), 3.56 (1H, br s), 7.65 (1H, d, J=8.59 Hz), 7.74 (1H, d, J=7.45 Hz), 8.52-8.83 (2H, m).

mass spectrum (ESI): m/z 511 (M+H)⁺.

Example 267 cis(±)-4-Chloro-5-ethyl-N-(1-formyl-3-methoxypiperidin-4-yl)-1H-imidazole-2-carboxylic acid amide (Exemplified Compound No. 267)

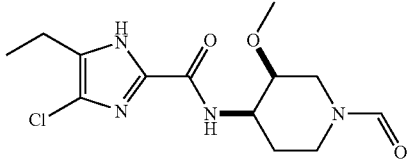

(267a) cis(±)-4-Chloro-5-ethyl-N-(1-formyl-3-methoxypiperidin-4-yl)-1H-imidazole-2-carboxylic acid amide tert-Butyl cis(±)-4-{[(4-chloro-5-ethyl-1H-imidazol-2-yl)carbonyl]amino}-3-methoxypiperidine-1-carboxylate obtained in Example (1g) (30 mg, 0.08 mmol) was dissolved in methanol (0.5 mL). A 4 N hydrochloric acid/ethyl acetate solution (2.5 mL) was added, and the mixture was stirred at room temperature for 4.5 hours. Following concentration under reduced pressure, the residue was dissolved in DMF (2 mL). Diisopropylethylamine (0.054 mL, 0.31 mmol) was added, and the mixture was stirred at 140° C. using a microwave reactor for one hour. Saline was added to the reaction solution, followed by extraction with ethyl acetate. The organic layer was washed with brine and dried over anhydrous magnesium sulfate. Following concentration under reduced pressure, the residue was purified by reverse phase high performance liquid chromatography (Develosil, 2 cm diameter×10 cm, 0.1% formic acid-containing acetonitrile/water mixed solvent) to obtain 6.6 mg of the title compound as a pale yellow solid (27%).

¹H-NMR spectrum (500 MHz, CDCl₃) δ ppm: 1.26 (3H, t, J=7.45 Hz), 1.48-4.89 (10H, m), 3.39 (1.2H, s), 3.40 (1.8H, s), 7.46 (0.4H, d, J=8.59 Hz), 7.50 (0.6H, d, J=8.59 Hz), 7.97 (0.4H, s), 8.10 (0.6H, s), 11.29 (1H, s).

mass spectrum (ESI): m/z 315 (M+H)⁺.

Example 268 cis(±)-2-(4-{[(4-Chloro-5-ethyl-1H-imidazol-2-yl)carbonyl]amino}-3-methoxypiperidin-1-yl)-N,4-dimethyl-1,3-thiazole-5-carboxylic acid amide (Exemplified Compound No. 268)

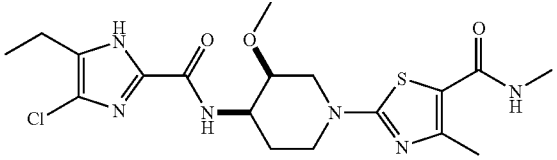

(268a) cis(±)-2-(4-{[(4-Chloro-5-ethyl-1H-imidazol-2-yl)carbonyl]amino}-3-methoxypiperidin-1-yl)-N,4-dimethyl-1,3-thiazole-5-carboxylic acid amide The same operation as in Example (1g) was performed using cis(±)-2-(4-{[(4-chloro-5-ethyl-1H-imidazol-2-yl)carbonyl]amino}-3-methoxypiperidin-1-yl)-4-methyl-1,3-thiazole-5-carboxylic acid obtained in Example (14a) (40 mg, 0.09 mmol), methylamine hydrochloride (7 mg, 0.11 mmol), WSC hydrochloride (59 mg, 0.31 mmol), HOBT (21 mg, 0.15 mmol), diisopropylethylamine (0.020 mL, 0.11 mmol), dichloromethane (0.75 mL) and DMA (0.75 mL), to obtain 30 mg of the title compound as a white solid (73%).

¹H-NMR spectrum (400 MHz, CDCl₃) δ ppm: 1.26 (3H, t, J=7.57 Hz), 1.72-1.84 (1H, m), 1.94-2.09 (1H, m), 2.51 (3H, s), 2.69 (2H, q, J=7.64 Hz), 2.94 (3H, d, J=5.04 Hz), 3.00-3.22 (2H, m), 3.41 (3H, s), 3.50 (1H, br s), 3.89-4.00 (1H, m), 4.18-4.30 (1H, m), 4.41-4.50 (1H, m), 5.40-5.53 (1H, m), 7.49 (1H, d, J=8.71 Hz), 10.95 (1H, s).

mass spectrum (ESI): m/z 441 (M+H)⁺.

Example 269 cis(±)-2-(4-{[(4-Chloro-5-ethyl-1H-imidazol-2-yl)carbonyl]amino}-3-methoxypiperidin-1-yl)-N,N,4-trimethyl-1,3-thiazole-5-carboxylic acid amide (Exemplified Compound No. 269)

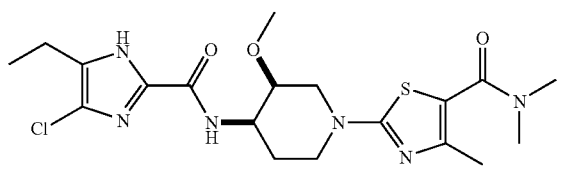

(269a) cis(±)-2-(4-{[(4-Chloro-5-ethyl-1H-imidazol-2-yl)carbonyl]amino}-3-methoxypiperidin-1-yl)-N,N,4-trimethyl-1,3-thiazole-5-carboxylic acid amide The same operation as in Example (1g) was performed using cis(±)-2-(4-{[(4-chloro-5-ethyl-1H-imidazol-2-yl)carbonyl]amino}-3-methoxypiperidin-1-yl)-4-methyl-1,3-thiazole-5-carboxylic acid obtained in Example (14a) (40 mg, 0.09 mmol), dimethylamine hydrochloride (9 mg, 0.11 mmol), WSC hydrochloride (59 mg, 0.31 mmol), HOBT (21 mg, 0.15 mmol), diisopropylethylamine (0.020 mL, 0.11 mmol), dichloromethane (0.75 mL) and DMA (0.75 mL), to obtain 27 mg of the title compound as a yellow oily substance (62%).

¹H-NMR spectrum (400 MHz, CDCl₃) δ ppm: 1.26 (3H, t, J=7.57 Hz), 1.73-1.84 (1H, m), 1.98-2.11 (1H, m), 2.26 (3H, s), 2.69 (2H, q, J=7.64 Hz), 3.04-3.11 (7H, m), 3.11-3.21 (1H, m), 3.42 (3H, s), 3.50 (1H, br s), 3.88-3.97 (1H, m), 4.19-4.29 (1H, m), 4.37-4.45 (1H, m), 7.45 (1H, d, J=8.71 Hz), 10.84 (1H, s).

mass spectrum (ESI): m/z 455 (M+H)⁺.

Example 270 cis(±)-2-(4-{[(4-Chloro-5-ethyl-1H-imidazol-2-yl)carbonyl]amino}-3-methoxypiperidin-1-yl)-4-methyl-1,3-thiazole-5-carboxylic acid amide (Exemplified Compound No. 270)

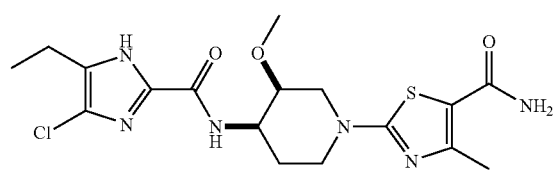

(270a) cis(±)-2-(4-{[(4-Chloro-5-ethyl-1H-imidazol-2-yl)carbonyl]amino}-3-methoxypiperidin-1-yl)-4-methyl-1,3-thiazole-5-carboxylic acid amide The same operation as in Example (1g) was performed using cis(±)-2-(4-{[(4-chloro-5-ethyl-1H-imidazol-2-yl)carbonyl]amino}-3-methoxypiperidin-1-yl)-4-methyl-1,3-thiazole-5-carboxylic acid obtained in Example (14a) (40 mg, 0.09 mmol), a 2 N ammonia/methanol solution (0.054 mL, 0.11 mmol), WSC hydrochloride (59 mg, 0.31 mmol), HOBT (21 mg, 0.15 mmol), dichloromethane (0.75 mL) and DMA (0.75 mL), to obtain 17 mg of the title compound as a yellow solid (42%).

¹H-NMR spectrum (500 MHz, DMSO-D₆) δ ppm: 1.14 (3H, t, J=7.45 Hz), 1.61-1.71 (1H, m), 1.79-1.92 (1H, m), 2.37 (3H, s), 2.55 (2H, q, J=7.45 Hz), 3.19-3.38 (5H, m), 3.55 (1H, s), 3.78-3.92 (1H, m), 4.12-4.26 (2H, m), 7.02 (2H, s), 7.64 (1H, d, J=8.59 Hz).

mass spectrum (ESI): m/z 427 (M+H)⁺.

Example 271 cis(±)-2-(4-{[(4-Chloro-5-ethyl-1H-imidazol-2-yl)carbonyl]amino}-3-methoxypiperidin-1-yl)-1,3-thiazole-5-carboxylic acid amide (Exemplified Compound No. 271)

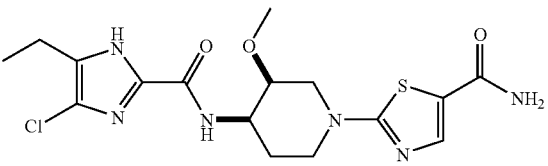

(271a) cis(±)-2-(4-{[(4-Chloro-5-ethyl-1H-imidazol-2-yl)carbonyl]amino}-3-methoxypiperidin-1-yl)-1,3-thiazole-5-carboxylic acid amide The same operation as in Example (1g) was performed using cis(±)-2-(4-{[(4-chloro-5-ethyl-1H-imidazol-2-yl)carbonyl]amino}-3-methoxypiperidin-1-yl)-1,3-thiazole-5-carboxylic acid obtained in Example (11b) (40 mg, 0.09 mmol), a 0.5 N ammonia/1,4-dioxane solution (0.22 mL, 0.11 mmol), WSC hydrochloride (61 mg, 0.32 mmol), HOBT (22 mg, 0.16 mmol), dichloromethane (0.75 mL) and DMA (0.75 mL), to obtain 17 mg of the title compound as a white solid (43%).

¹H-NMR spectrum (500 MHz, DMSO-D₆) δ ppm: 1.14 (3H, t, J=6.87 Hz), 1.63-1.72 (1H, m), 1.80-1.92 (1H, m), 2.55 (2H, q, J=7.45 Hz), 3.22-3.35 (5H, m), 3.56 (1H, brs), 3.83-3.95 (1H, m), 4.15-4.24 (1H, m), 4.24-4.33 (1H, m), 7.10 (1H, br s), 7.65 (1H, d, J=8.59 Hz), 7.74 (1H, s).

mass spectrum (ESI): m/z 413 (M+H)⁺.

Example 272 cis(±)-2-(4-{[(4-Chloro-5-ethyl-1H-imidazol-2-yl)carbonyl]amino}-3-methoxypiperidin-1-yl)-N-methyl-1,3-thiazole-5-carboxylic acid amide (Exemplified Compound No. 272)

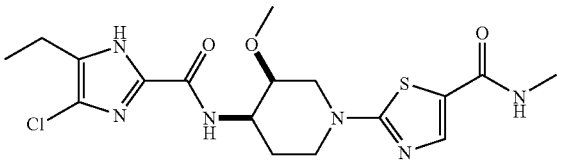

(272a) cis(±)-2-(4-{[(4-Chloro-5-ethyl-1H-imidazol-2-yl)carbonyl]amino}-3-methoxypiperidin-1-yl)-N-methyl-1,3-thiazole-5-carboxylic acid amide The same operation as in Example (1g) was performed using cis(±)-2-(4-{[(4-chloro-5-ethyl-1H-imidazol-2-yl)carbonyl]amino}-3-methoxypiperidin-1-yl)-1,3-thiazole-5-carboxylic acid obtained in Example (11b) (40 mg, 0.09 mmol), methylamine hydrochloride (8 mg, 0.11 mmol), WSC hydrochloride (61 mg, 0.32 mmol), HOBT (22 mg, 0.16 mmol), diisopropylethylamine (0.020 mL, 0.12 mmol), dichloromethane (0.75 mL) and DMA (0.75 mL), to obtain 32 mg of the title compound as a white solid (77%).

$^1$H-NMR spectrum (500 MHz, DMSO-D$_6$) δ ppm: 1.14 (3H, t, J=7.45 Hz), 1.62-1.72 (1H, m), 1.79-1.93 (1H, m), 2.55 (2H, q, J=7.64 Hz), 2.70 (3H, d, J=4.58 Hz), 3.20-3.38 (5H, m), 3.56 (1H, brs), 3.82-3.95 (1H, m), 4.14-4.33 (2H, m), 7.65 (1H, d, J=8.59 Hz), 7.69 (1H, s), 8.13 (1H, q, J=4.39 Hz).

mass spectrum (ESI): m/z 427 (M+H)$^+$.

Example 273 cis(±)-2-(4-{[(4-Chloro-5-ethyl-1H-imidazol-2-yl)carbonyl]amino}-3-methoxypiperidin-1-yl)-N,N-dimethyl-1,3-thiazole-5-carboxylic acid amide (Exemplified Compound No. 273)

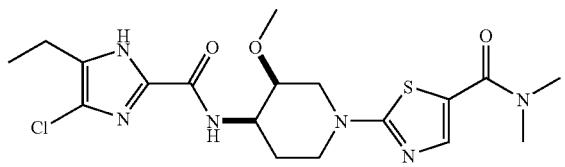

(273a) cis(±)-2-(4-{[(4-Chloro-5-ethyl-1H-imidazol-2-yl)carbonyl]amino}-3-methoxypiperidin-1-yl)-N,N-dimethyl-1,3-thiazole-5-carboxylic acid amide The same operation as in Example (1g) was performed using cis(±)-2-(4-{[(4-chloro-5-ethyl-1H-imidazol-2-yl)carbonyl]amino}-3-methoxypiperidin-1-yl)-1,3-thiazole-5-carboxylic acid obtained in Example (11b) (40 mg, 0.09 mmol), dimethylamine hydrochloride (9 mg, 0.11 mmol), WSC hydrochloride (61 mg, 0.32 mmol), HOBT (22 mg, 0.16 mmol), diisopropylethylamine (0.020 mL, 0.12 mmol), dichloromethane (0.75 mL) and DMA (0.75 mL), to obtain 37 mg of the title compound as a white solid (87%).

$^1$H-NMR spectrum (500 MHz, DMSO-D$_6$) δ ppm: 1.14 (3H, t, J=7.45 Hz), 1.63-1.72 (1H, m), 1.81-1.93 (1H, m), 2.55 (2H, q, J=7.64 Hz), 3.22-3.35 (2H, m), 3.32 (6H, s), 3.34 (3H, s), 3.56 (1H, br s), 3.85-3.96 (1H, m), 4.16-4.24 (1H, m), 4.25-4.34 (1H, m), 7.57 (1H, s), 7.65 (1H, d, J=8.59 Hz).

mass spectrum (ESI): m/z 441 (M+H)$^+$.

TEST EXAMPLES

Test Example 1

Method of Testing Inhibitory Activity of Enzymes

The ATP hydrolysis activity of GyrB and ParE was determined by correlating it with ADP production and NADH oxidation mediated by pyruvate kinase/lactate dehydrogenase. This method has been previously reported (Tamura, J. K. and Gellert, M. 1990, J. Biol. Chem. 265:21342-21349).

The ATP hydrolysis assay was carried out in a buffer solution containing final concentrations of 100 mM Tris-HCl (pH 7.5), 150 mM KCl, 1.5 mM MgCl$_2$, 0.4 mM nicotinamide adenine dinucleotide (NADH), 2.5 mM phosphoenolpyruvate, 1 mM DTT, 15 U/ml pyruvate kinase, 10.5 U/ml lactate dehydrogenase and 1 mU/ml enzyme (GyrB or ParE of Streptococcus pneumoniae or Haemophilus influenzae) (provided that the concentration of KCl was 25 mM and the concentration of MgCl$_2$ was 10 mM in the case of ParE of Haemophilus influenzae). A solution of the test compound serially four-fold diluted in DMSO:MeOH (7:3) was added at a final concentration of 5% (v/v). After mixing, the reaction solution was incubated at room temperature for five minutes. As a control with an inhibition rate of 0%, a reaction solution was also prepared by adding a DMSO:MeOH (7:3) solution to the buffer solution. ATP was added at a final concentration of 1 mM; after mixing, the absorbance at 340 nm (amount of NADH) was determined (provided that the final ATP concentration was 0.3 mM in the case of ParE of Haemophilus influenzae). The reaction solution was incubated at 30° C. for two hours, and then the absorbance at 340 nm was determined. The ATP hydrolysis inhibition rate (%) was calculated from the difference in absorbance before and after the incubation (amount of NADH oxidized). The 50% inhibition concentration (IC$_{50}$) was calculated from the reaction performed in the presence of seven different concentrations of the test compound.

The compounds of Examples generally had an IC$_{50}$ of less than 20 μg/ml for GyrB of Streptococcus pneumoniae or Haemophilus influenzae.

The compound of Example 8 (Exemplified Compound No. 8) had an IC$_{50}$ of 0.059 μg/ml for ParE of Haemophilus influenzae.

Test Example 2

Method of Testing Sensitivity of Bacteria

The antibacterial activity of the compounds of the present invention was tested by sensitivity tests by the broth microdilution method. The assay was carried out according to the latest CLSI guidelines for managing the procedures of sensitivity tests: "M7-A7 Methods for Dilution Antimicrobial Susceptibility Tests for Bacteria That Grow Aerobically; Approved Standard—Seventh Edition (2006)".

Test strains were grown on appropriate agar plates overnight. A broth containing the test compound serially two-fold diluted was dispensed at 100 μL to each well of a 96-well microplate. As a growth control, a well with a broth not containing the test compound was also prepared. Colonies grown on the plates were suspended in saline, adjusted to 0.5 McFarland (OD625=0.08 to 0.10) using a colorimeter, and then diluted ten-fold with saline. The bacterial suspension was inoculated at 4 μL into each well of the microplate using a bacterial suspension inoculation apparatus. The inoculated microplate was incubated at 35° C. overnight (about 20 hours). The growth condition was observed by the naked eye, and the minimum concentration to inhibit bacterial proliferation was defined as a minimum inhibitory concentration (MIC).

The compound of Example 8 (Exemplified Compound No. 8) had an MIC of 4 μg/ml for Haemophilus influenzae in a medium obtained by mixing a hemophilus test medium with human serum at a ratio of 1:1.

Test Example 3

Method of Testing Cytotoxicity

50 μL of a HeLa cell solution containing 80000 cells/mL was inoculated into each well of a 96-well microplate, and the mixture was incubated at 37° C. in a 5% carbon dioxide incubator for 24 hours. Thereafter, a medium containing the test compound serially four-fold diluted was added at 50 μL to each well, and the mixture was incubated at 37° C. in a 5% carbon dioxide incubator for 48 hours. As a control with an inhibition rate of 0%, a well not containing the test compound was also prepared. Following washing with phosphate buffered saline, a MTS [3-(4,5-dimethylthiazol-2-yl)-5-(3-carboxymethoxyphenyl)-2-(4-sulphophenyl)-2H-tetrazolium, inner salt]-PMS (phenazine methosulfate) coloring reagent solution was added, and the mixture was allowed to stand at 37° C. in a 5% carbon dioxide incubator for 1.5 hours. Thereafter, the absorbance at 490 nm was determined. The 50% inhibition concentration ($IC_{50}$) was calculated from the proliferation inhibition rate (%) in the presence of four different concentrations of the test compound.

The compound of Example 8 (Exemplified Compound No. 8) had an $IC_{50}$ of more than 200 μg/ml.

Test Example 4

Method of Testing Solubility in Water

A 10 mmol/L solution of the test compound in DMSO was prepared. 50 mL of the solution was dispensed to a sample tube and then lyophilized. On the other hand, the mmol/L solution in DMSO was serially diluted with a 50% aqueous DMSO solution to prepare two solutions, i.e. a 100 mmol/L solution and a 5 mmol/L solution, respectively. The solutions were analyzed by HPLC or, where necessary, LC-MS/MS. 250 mL of 1st fluid for the disintegration test of the Japanese Pharmacopoeia (hereinafter JP1 fluid) or 2nd fluid for the disintegration test of the Japanese Pharmacopoeia (hereinafter JP2 fluid) was added to the lyophilized test compound to dissolve the compound. The solution was left to stand at room temperature for four hours or more and filtered by suction. The resulting filtrate was diluted two-fold and 20-fold. The resulting samples were analyzed by HPLC. LC-MS/MS was used where necessary. The solubility of the test compound was calculated using a calibration curve prepared by the peak area value and the preparation concentration of the calibration curve sample.

The compound of Example 8 (Exemplified Compound No. 8) had a solubility in JP1 fluid of 100 μg/ml and a solubility in JP2 fluid of 720 μg/ml.

Test Example 5

Therapeutic Effect Evaluation Method Using Mouse Pulmonary Infection Model by *Streptococcus pneumoniae*

The *Streptococcus pneumoniae* strain cultured using Todd Hewitt broth was harvested by centrifugation, suspended in saline, and nasally inoculated into CBA/JNCrlj mice (three- to six-week-old, Charles River Laboratories Japan Inc.: four mice per group) under anesthesia with a ketamine-xylazine mixture. The drug was administered to this infection model twice at an interval of 6 to 10 hours. The number of bacteria in the lung was determined in the non-treated group (pre-control) immediately before initial administration of the drug and in the non-treated group (post-control) and the drug-administered group on the day after administration of the drug (infection). A variation in the number of bacteria in the lung was used as an index of therapeutic effect.

The compounds of the Examples exhibited a therapeutic effect in this test method.

Examples of the compounds included in the present invention can be further illustrated below.

| Exemplified Compound No. | Chemical structure |
|---|---|
| 274 | 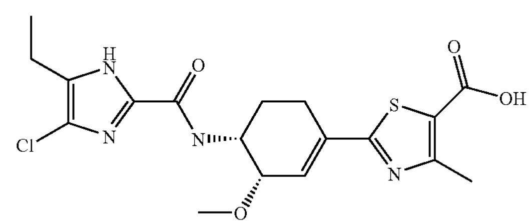 [SMILES: CCc1[nH]c(C(=O)N[C@@H]2CCC(c3nc(C)c(C(=O)O)s3)=C[C@@H]2OC)nc1Cl] |
| 275 | 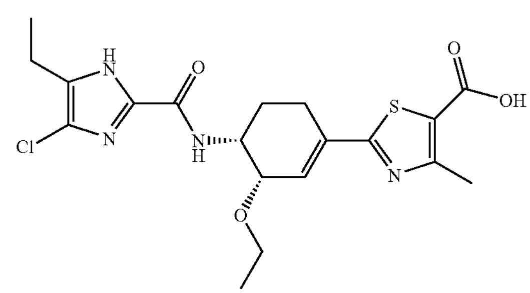 [SMILES: CCO[C@H]1C=C(c2nc(C)c(C(=O)O)s2)CC[C@H]1NC(=O)c1nc(Cl)c(CC)[nH]1] |

-continued
| Exemplified Compound No. | Chemical structure |
|---|---|
| 276 | 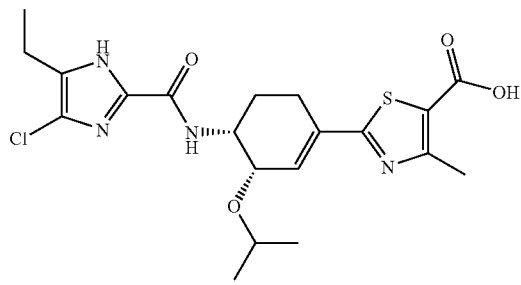 [SMILES: CCc1[nH]c(C(=O)N[C@@H]2CCC(c3nc(C)c(C(=O)O)s3)=C[C@@H]2OC(C)C)nc1Cl] |
| 277 | 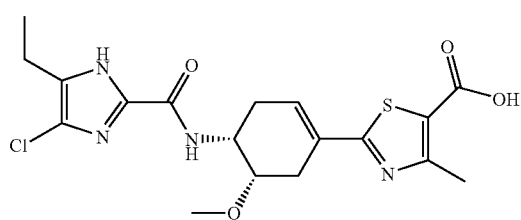 [SMILES: CCc1[nH]c(C(=O)N[C@@H]2CC=C(c3nc(C)c(C(=O)O)s3)C[C@@H]2OC)nc1Cl] |
| 278 | 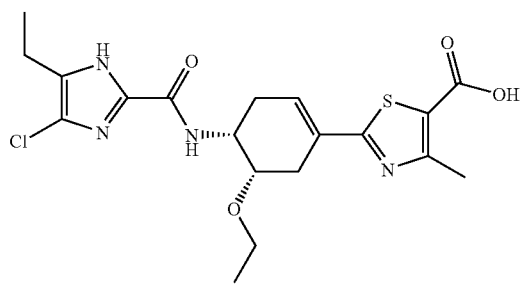 [SMILES: CCO[C@H]1CC(c2nc(C)c(C(=O)O)s2)=CC[C@H]1NC(=O)c1nc(Cl)c(CC)[nH]1] |
| 279 | 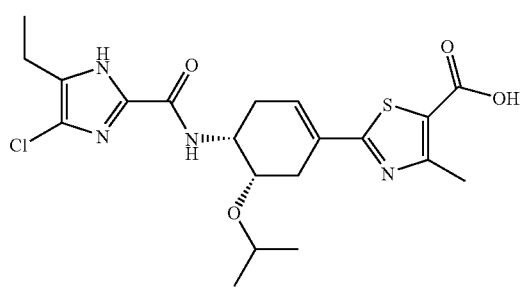 [SMILES: CCc1[nH]c(C(=O)N[C@@H]2CC=C(c3nc(C)c(C(=O)O)s3)C[C@@H]2OC(C)C)nc1Cl] |
| 280 | 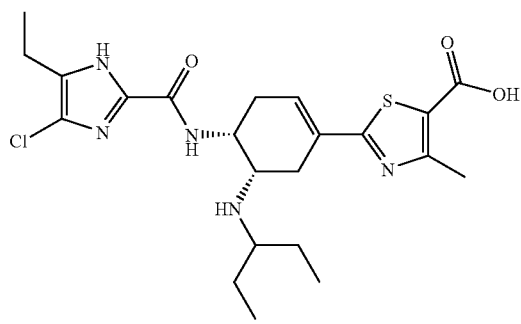 [SMILES: CCc1[nH]c(C(=O)N[C@@H]2CC=C(c3nc(C)c(C(=O)O)s3)C[C@@H]2NC(CC)CC)nc1Cl] |

| Exemplified Compound No. | Chemical structure |
|---|---|
| 281 | 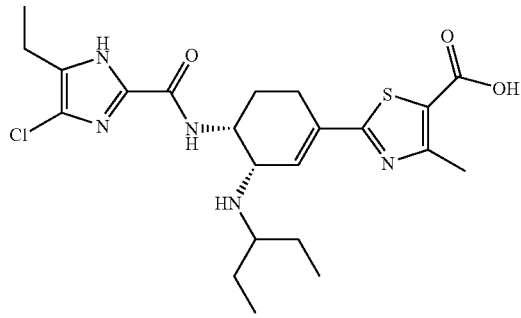 [SMILES: CCc1[nH]c(C(=O)N[C@@H]2CCC(c3nc(C)c(C(=O)O)s3)=C[C@@H]2NC(CC)CC)nc1Cl] |
| 282 | 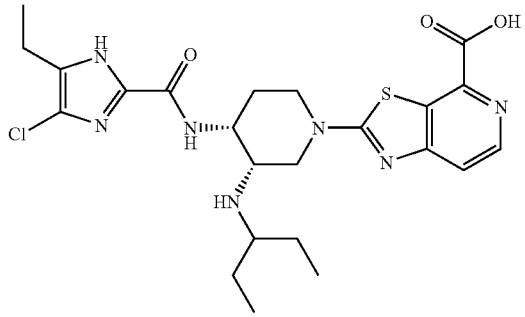 [SMILES: CCc1[nH]c(C(=O)N[C@@H]2CCN(c3nc4ccnc(C(=O)O)c4s3)C[C@@H]2NC(CC)CC)nc1Cl] |
| 283 | 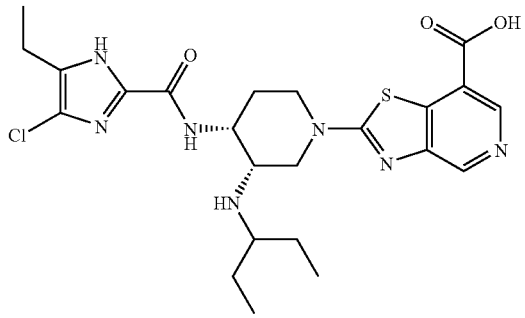 [SMILES: CCc1[nH]c(C(=O)N[C@@H]2CCN(c3nc4cncc(C(=O)O)c4s3)C[C@@H]2NC(CC)CC)nc1Cl] |
| 284 | 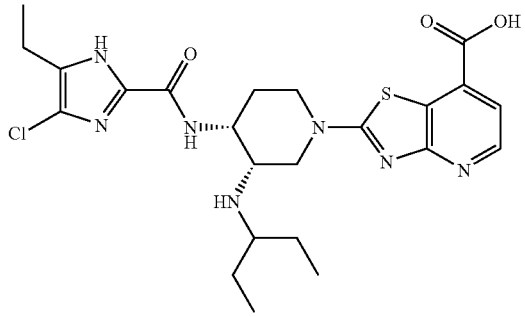 [SMILES: CCc1[nH]c(C(=O)N[C@@H]2CCN(c3nc4nccc(C(=O)O)c4s3)C[C@@H]2NC(CC)CC)nc1Cl] |

-continued
| Exemplified Compound No. | Chemical structure |
|---|---|
| 285 | 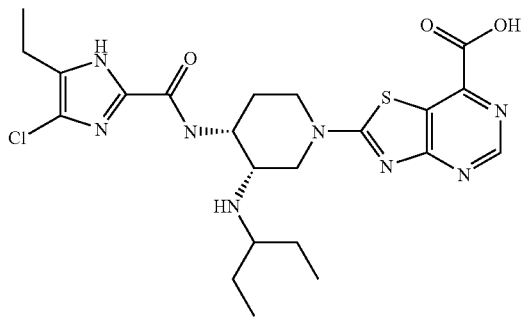 [SMILES: CCc1[nH]c(C(=O)N[C@@H]2CCN(c3nc4ncnc(C(=O)O)c4s3)C[C@@H]2NC(CC)CC)nc1Cl] |
| 286 | 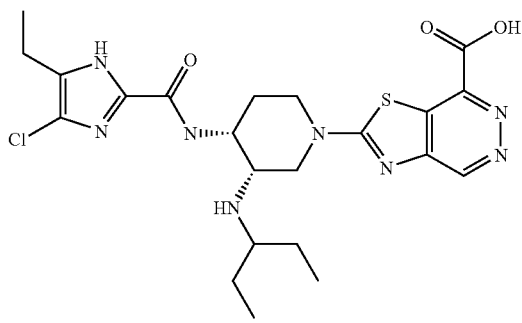 |
| 287 | 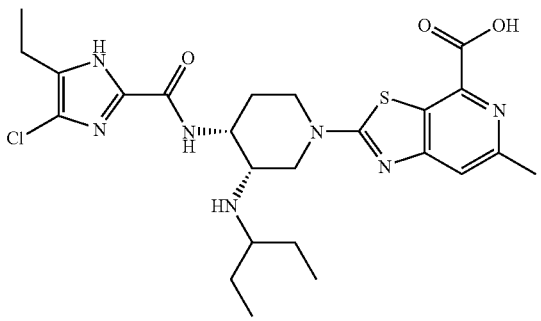 [SMILES: CCc1[nH]c(C(=O)N[C@@H]2CCN(c3nc4cc(C)nc(C(=O)O)c4s3)C[C@@H]2NC(CC)CC)nc1Cl] |
| 288 | 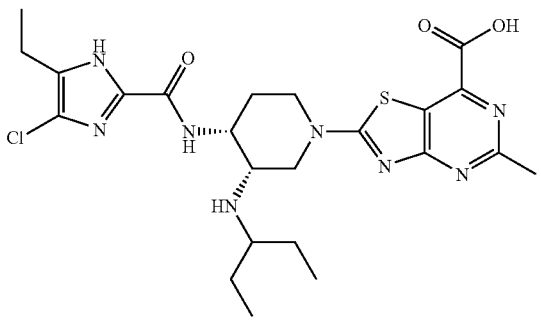 [SMILES: CCc1[nH]c(C(=O)N[C@@H]2CCN(c3nc4nc(C)nc(C(=O)O)c4s3)C[C@@H]2NC(CC)CC)nc1Cl] |
| 289 | 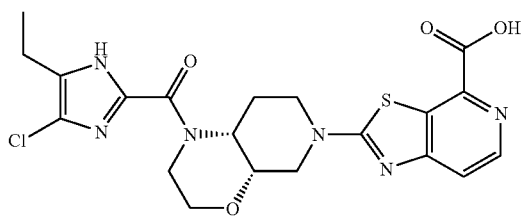 [SMILES: CCc1[nH]c(C(=O)N2CCO[C@H]3CN(c4nc5ccnc(C(=O)O)c5s4)CC[C@H]32)nc1Cl] |

-continued
| Exemplified Compound No. | Chemical structure |
|---|---|
| 290 | 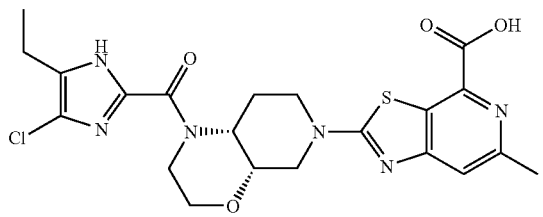 [SMILES: CCc1[nH]c(C(=O)N2CCO[C@H]3CN(c4nc5cc(C)nc(C(=O)O)c5s4)CC[C@H]32)nc1Cl] |
| 291 | 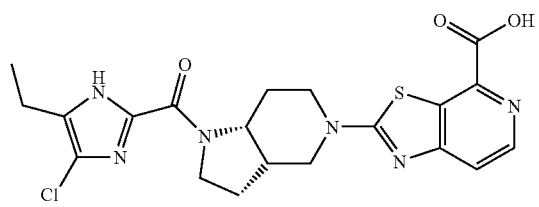 |
| 292 | 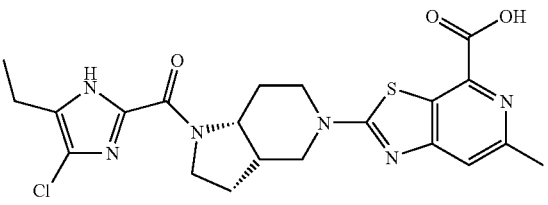 |
| 293 | 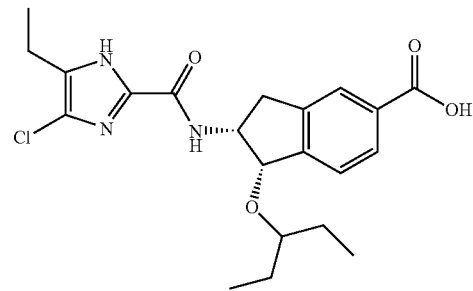 [SMILES: CCc1[nH]c(C(=O)N[C@@H]2Cc3cc(C(=O)O)ccc3[C@@H]2OC(CC)CC)nc1Cl] |
| 294 | 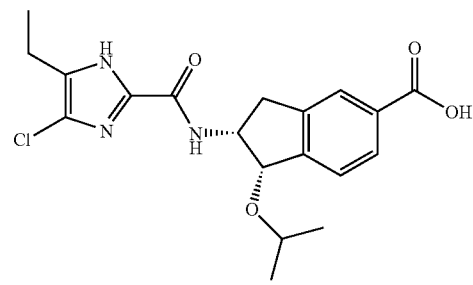 [SMILES: CCc1[nH]c(C(=O)N[C@@H]2Cc3cc(C(=O)O)ccc3[C@@H]2OC(C)C)nc1Cl] |
| 295 | 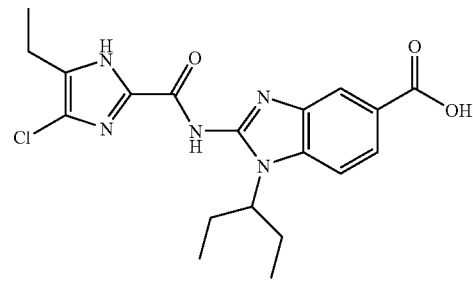 [SMILES: CCc1[nH]c(C(=O)Nc2nc3cc(C(=O)O)ccc3n2C(CC)CC)nc1Cl] |

-continued

| Exemplified Compound No. | Chemical structure |
| --- | --- |
| 296 | 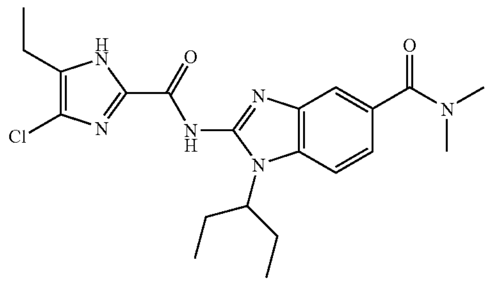 [SMILES: CCc1[nH]c(C(=O)Nc2nc3cc(C(=O)N(C)C)ccc3n2C(CC)CC)nc1Cl] |
| 297 | 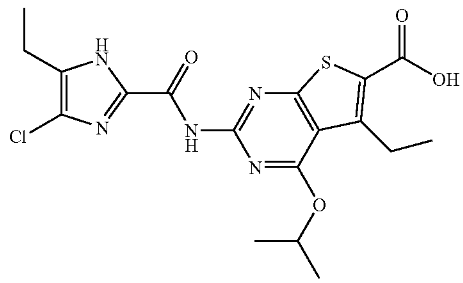 [SMILES: CCc1[nH]c(C(=O)Nc2nc(OC(C)C)c3c(CC)c(C(=O)O)sc3n2)nc1Cl] |
| 298 | 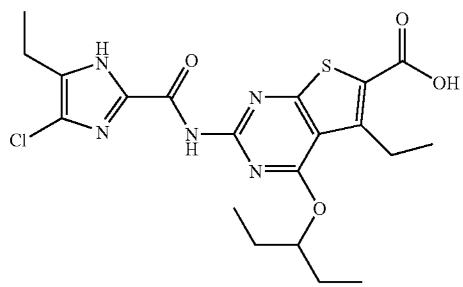 [SMILES: CCc1[nH]c(C(=O)Nc2nc(OC(CC)CC)c3c(CC)c(C(=O)O)sc3n2)nc1Cl] |
| 299 | 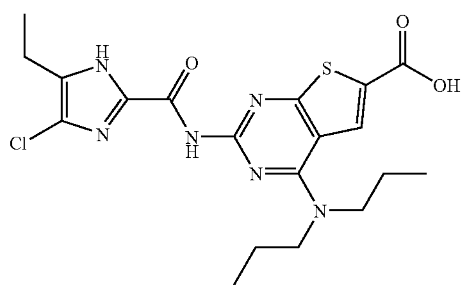 [SMILES: CCCN(CCC)c1nc(NC(=O)c2nc(Cl)c(CC)[nH]2)nc2sc(C(=O)O)cc12] |
| 300 | 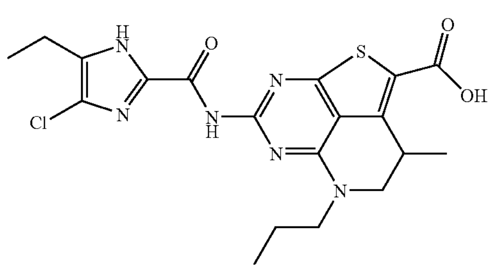 [SMILES: CCCN1CC(C)c2c(C(=O)O)sc3nc(NC(=O)c4nc(Cl)c(CC)[nH]4)nc1c23] |

Preferred compounds having the general formula (1) according to the present invention may include Exemplified Compound Nos.: 1, 8, 14, 19, 22, 23, 25, 28, 30, 31, 32, 34, 37, 38, 39, 41, 42, 44, 45, 47, 48, 52, 53, 54, 55, 56, 57, 58, 62, 63, 68, 70, 72, 73, 74, 75, 76, 77, 81, 82, 83, 84, 85, 86, 87, 88, 117, 118, 119, 120, 122, 124, 126, 129, 130, 147, 148, 149, 164, 172, 175, 177, 178, 198, 202, 203, 213, 215, 244, 246, 247, 248, 249, 250, 252, 253, 257, 11, 12, 16, 17, 20, 21, 24, 26, 29, 40, 43, 49, 59, 64, 66, 67, 71, 94, 99, 106, 110, 111, 112, 113, 114, 115, 116, 121, 125, 128, 137, 140, 150, 153, 156, 158, 159, 166, 167, 173, 176, 179, 181, 183, 188, 189, 191, 192, 195, 196, 199, 211, 214, 216, 219, 220, 221, 222, 227, 228, 229, 230, 231, 235, 236, 239, 241, 242, 251, 254, 256, 258, 259, 261, 268, 269, 270, 271, 272, 273. More preferred compounds may include Exemplified Compound Nos.: 1, 8, 14, 19, 22, 23, 25, 28, 30, 31, 32, 34, 37, 38, 39, 41, 42, 44, 45, 47, 48, 52, 53, 54, 55, 56, 57, 58, 62, 63, 68, 70, 72, 73, 74, 75, 76, 77, 81, 82, 83, 84, 85, 86, 87, 88, 117, 118, 119, 120, 122, 124, 126, 129, 130, 147, 148, 149, 164, 172, 175, 177, 178, 198, 202, 203, 213, 215, 244, 246, 247, 248, 249, 250, 252, 253, 257.

The invention claimed is:

1. A compound represented by the formula (1) or a pharmacologically acceptable salt thereof:

[Formula 1]

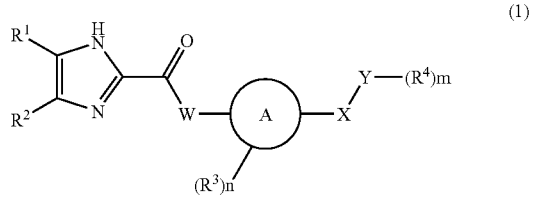

(1)

wherein $R^1$ and $R^2$ are each independently selected from a hydrogen atom, a nitro group, a hydroxy group, a halogen atom, a cyano group, a $(C_1-C_4)$ alkyl group, a $(C_1-C_4)$ alkoxy group, a $(C_2-C_4)$ alkenyl group, a $(C_2-C_4)$ alkynyl group, a —$CO(C_1-C_4)$ alkyl group, a —$S(O)_a(C_1-C_4)$ alkyl group (wherein a is 0, 1, or 2), and a $(C_3-C_6)$ cycloalkyl group, and $R^1$ and $R^2$ may each independently be substituted at their respective carbon atoms with one or more halogen atom(s), cyclopropyl group(s), cyclobutyl group(s), and/or $(C_1-C_4)$ alkoxy group(s);

W represents —$NR^5$—;

ring A represents a piperidine ring group;

X represents a single bond, —O—, —$NR^8$—, —$C(R^9)(R^{10})$—, —$C(O)$—, —$S(O)_p$— (wherein p is an integer of 0, 1, or 2), —$C(O)NR^{11}$—, —$NR^{12}C(O)$—, —$S(O)_2NR^{13}$—, or —$NR^{14}S(O)_2$—;

Y is selected from the group consisting of a benzene ring group, a cyclopropane ring group, a pyrrolidine ring group, an oxazole ring group, a benzoxazole ring group, a benzimidazole ring group, a thiazole ring group, a thiadiazole ring group, a thiophene ring group, a tetrazole ring group, a 1,4-dihydroquinoline ring group, a benzothiazole ring group, a pyrimidine ring group, a 5,6-dihydro-4H-pyrrolo[3,4-d][1,3]thiazole ring group, a 1,2-dihydropyridine ring group, and a pyridine ring group;

$R^3$ and $R^4$ are each independently selected from the following substituents: the substituents are a hydrogen atom, a halogen atom, a nitro group, a cyano group, an oxo group, a hydroxy group, a trifluoromethoxy group, an amino group, a carboxy group, a carbamoyl group, a mercapto group, a sulfamoyl group, a sulfo group, a formyl group, an ureido group, a hydroxyiminomethyl group, a $(C_1-C_4)$ alkoxyiminomethyl group, an N-hydroxyformamide group, a $(C_1-C_4)$ alkylhydrazino group, a hydrazinocarbonyl group, an N-hydroxyethanimidoyl group, a $(C_1-C_4)$ alkyl group, a $(C_2-C_4)$ alkenyl group, a $(C_2-C_4)$ alkynyl group, a $(C_1-C_4)$ alkoxy group, —$CO(C_1-C_4)$ alkyl, —$OC(O)(C_1-C_4)$ alkyl, —$NH(C_1-C_4)$ alkyl, —$N[di(C_1-C_4)$ alkyl], —$NHC(O)(C_1-C_4)$ alkyl, —$C(O)NH(C_1-C_4)$ alkyl, —$C(O)N[di(C_1-C_4)$ alkyl], —$C(O)NH(C_1-C_4)$ alkoxy, —$NHC(O)NH(C_1-C_4)$ alkyl, —$NHC(O)N[di(C1-C4)$ alkyl], —$C(O)N[(C_1-C_4)$ alkyl][$(C_1-C_4)$ alkoxy], —$S(O)a(C_1-C_4)$ alkyl (wherein a is 0, 1, or 2), —$C(O)(C_1-C_4)$ alkoxy, —$OC(O)(C_1-C_4)$ alkoxy, —$NHC(O)(C_1-C_4)$ alkoxy, —$S(O)_2NH(C_1-C_4)$ alkyl, —$S(O)_2N[di(C_1-C_4)$ alkyl], —$NHSO_2(C_1-C_4)$ alkyl, —$C(O)NHS O_2(C1-C4)$ alkyl, —$C(O)NHNH(C_1-C_4)$ alkyl, —$C(O)NHN[di(C_1-C_4)$ alkyl], =$CH(C_1-C_4)$ alkyl, =$C[di(C_1-C_4)$ alkyl], =$N(C_1-C_4)$ alkoxy, =$NN[di(C_1-C_4)$ alkyl], and $R^3$ and $R^4$ may each independently be substituted with one or more $R^{17}$ moiety/moieties;

$R^5$, $R^6$, $R^7$, $R^8$, $R^9$, $R^{10}$, $R^{11}$, $R^{12}$, $R^{13}$, and $R^{14}$ each independently represent a hydrogen atom or a $(C_1-C_4)$ alkyl group, wherein the $(C_1-C_4)$ alkyl group may be substituted with $R^{17}$;

n is an integer of 0, 1, 2, 3, or 4, wherein a plurality of $R^3$ moieties are the same or different;

m is an integer of 0, 1, 2, 3, or 4, wherein a plurality of $R^4$ moieties are the same or different;

$R^{17}$ is selected from an azide group, a halogen atom, a nitro group, a cyano group, an oxo group, a hydroxy group, a trifluoromethoxy group, an amino group, a carboxy group, a carbamoyl group, a mercapto group, a sulfamoyl group, a $(C_1-C_4)$ alkyl group, a $(C_2-C_4)$ alkenyl group, a $(C_2-C_4)$ alkynyl group, a $(C_1-C_4)$ alkoxy group, a —$CO(C_1-C_4)$ alkyl group, a —$OC(O)(C_1-C_4)$ alkyl group, —$OC(O)(C_1-C_4)$ alkoxy, a —$NH(C_1-C_4)$ alkyl group, a —$N[di(C_1-C_4)$ alkyl] group, a —$NHC(O)(C_1-C_4)$ alkyl group, —$C(O)NH(C_1-C_4)$ alkyl, —$C(O)N[di(C_1-C_4)$ alkyl], —$C(O)NH(C_1-C_4)$ alkoxy, —$NHC(O)NH(C_1-C_4)$ alkyl, —$NHC(O)N[di(C_1-C_4)$ alkyl], —$C(O)N[(C_1-C_4)$ alkyl][$(C_1-C_4)$ alkoxy], —$S(O)a(C_1-C_4)$ alkyl (wherein a is 0, 1, or 2), —$C(O)(C_1-C_4)$ alkoxy, —$S(O)_2NH(C_1-C_4)$ alkyl, —$S(O)_2N[di(C_1-C_4)$ alkyl], —$NHS(O)_2(C_1-C_4)$ alkyl, —$NHC(O)(C_1-C_4)$ alkoxy, =$CH(C_1-C_4)$ alkyl, =$C[di(C_1-C_4)$ alkyl], =$N(C_1-C_4)$ alkoxy, =$NN[di(C_1-C_4)$ alkyl].

2. The compound according to claim 1 or a pharmacologically acceptable salt thereof, wherein X is selected from a single bond and —$C(O)$—.

3. The compound according to claim 1 or a pharmacologically acceptable salt thereof, wherein Y is a benzene ring group.

4. The compound according to claim 1, a pharmacologically acceptable salt thereof, wherein Y is selected from a benzene ring group, a thiazole ring group, an oxazole ring group, a benzoxazole ring group, a benzothiazole ring group, and a thiadiazole ring group.

5. A pharmaceutical agent comprising a pharmaceutically acceptable excipient or carrier and a compound according to claim 1 or a pharmacologically acceptable salt thereof.

6. A method for producing a pharmaceutical agent, comprising combining a compound of claim 1 or a pharmacologically acceptable salt thereof, with a pharmaceutically acceptable excipient or carrier to provide a pharmaceutical agent.

7. A method for inhibiting bacterial DNA gyrase in a warm-blooded animal, comprising administering an effective amount of a compound of claim 1 or a pharmacologically acceptable salt thereof, to a subject in need thereof.

8. The method of claim 7, wherein the warm-blooded animal is a human.

9. A method for treating bacterial infection in a warm-blooded animal, comprising administering an effective amount of a compound of claim 1 or a pharmacologically acceptable salt thereof, to a subject in need thereof.

10. The method of claim 9, wherein the warm-blooded animal is a human.

11. A method for treating an infectious disease treatable by inhibiting bacterial DNA gyrase in a warm-blooded animal, comprising administering an effective amount of a compound of claim 1 or a pharmacologically acceptable salt thereof, to a subject in need thereof.

12. The method of claim 11, wherein the warm-blooded animal is a human.

* * * * *

UNITED STATES PATENT AND TRADEMARK OFFICE
CERTIFICATE OF CORRECTION

| | |
|---|---|
| PATENT NO. | : 8,536,197 B2 |
| APPLICATION NO. | : 12/811004 |
| DATED | : September 17, 2013 |
| INVENTOR(S) | : Tsuyoshi Soneda et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 177 days.

Signed and Sealed this
Twenty-first Day of April, 2015

Michelle K. Lee
*Director of the United States Patent and Trademark Office*